(12) United States Patent
Callen et al.

(10) Patent No.: US 10,047,350 B2
(45) Date of Patent: Aug. 14, 2018

(54) ENZYMES HAVING ALPHA AMYLASE ACTIVITY AND METHODS OF MAKING AND USING THEM

(71) Applicant: BASF ENZYMES LLC, San Diego, CA (US)

(72) Inventors: Walter Callen, San Diego, CA (US); Toby Richardson, San Diego, CA (US); Gerhard Frey, San Diego, CA (US); Jay M. Short, Del Mar, CA (US); Eric J. Mathur, Carlsbad, CA (US); Kevin A. Gray, San Diego, CA (US); Janne S. Kerovuo, San Diego, CA (US); Malgorzata Slupska, San Diego, CA (US)

(73) Assignee: BASF Enzymes LLC, San Diego, CA (US)

( * ) Notice: Subject to any disclaimer, the term of this patent is extended or adjusted under 35 U.S.C. 154(b) by 0 days.

(21) Appl. No.: 15/135,732

(22) Filed: Apr. 22, 2016

(65) Prior Publication Data

US 2016/0264951 A1 Sep. 15, 2016

Related U.S. Application Data

(60) Continuation of application No. 13/669,707, filed on Nov. 6, 2012, now abandoned, which is a continuation of application No. 12/567,550, filed on Sep. 25, 2009, now Pat. No. 8,334,118, which is a continuation of application No. 11/621,528, filed on Jan. 9, 2007, now Pat. No. 7,785,855, which is a division of application No. 10/081,872, filed on Feb. 21, 2002, now Pat. No. 7,407,677.

(60) Provisional application No. 60/291,122, filed on May 14, 2001, provisional application No. 60/270,495, filed on Feb. 21, 2001, provisional application No. 60/270,496, filed on Feb. 21, 2001.

(51) Int. Cl.

| | |
|---|---|
| *C12N 9/28* | (2006.01) |
| *C12P 19/14* | (2006.01) |
| *C12N 9/26* | (2006.01) |
| *A21D 8/04* | (2006.01) |
| *C12P 19/04* | (2006.01) |

(52) U.S. Cl.
CPC ........... *C12N 9/2417* (2013.01); *A21D 8/042* (2013.01); *C12N 9/2414* (2013.01); *C12P 19/04* (2013.01); *C12P 19/14* (2013.01); *C12Y 302/01001* (2013.01); *Y02E 50/16* (2013.01); *Y02E 50/17* (2013.01)

(58) Field of Classification Search
CPC ..... C12N 9/2414; C12N 9/2417; C12N 9/242
See application file for complete search history.

(56) References Cited

U.S. PATENT DOCUMENTS

| | | |
|---|---|---|
| 3,847,740 A | 11/1974 | Heady |
| 4,521,252 A | 6/1985 | Miyake |
| 4,557,927 A | 12/1985 | Miyake |
| 5,093,257 A | 3/1992 | Gray |
| 5,789,228 A | 8/1998 | Lam |
| 5,939,250 A | 8/1999 | Short |
| 6,297,037 B1 | 10/2001 | Barnett et al. |
| 6,479,258 B1 | 11/2002 | Short |
| 7,102,057 B2 | 9/2006 | Lanahan |
| 7,273,740 B2 | 9/2007 | Callen |
| 7,557,262 B2 | 7/2009 | Lanahan |
| 7,560,126 B2 | 7/2009 | Callen |
| 8,841,107 B2 | 9/2014 | Power et al. |
| 2001/0053519 A1 | 12/2001 | Fodor |
| 2003/0135885 A1 | 7/2003 | Lanahan |
| 2004/0018607 A1 | 1/2004 | Callen |
| 2004/0259222 A1 | 12/2004 | Breves |
| 2005/0176000 A1 | 8/2005 | Callen |
| 2007/0157329 A1 | 7/2007 | Callen |
| 2015/0001770 A1 | 1/2015 | Tyree |

FOREIGN PATENT DOCUMENTS

| | | |
|---|---|---|
| EP | 0252666 B1 | 6/1993 |
| EP | 0606753 A2 | 12/1993 |
| EP | 0628630 A2 | 12/1994 |
| GB | 2106912 | 4/1983 |
| JP | 62-104580 A2 | 5/1987 |
| WO | WO 1993/000426 A1 | 1/1993 |
| WO | WO 1996/038469 | 12/1996 |
| WO | 199967408 A1 | 12/1999 |
| WO | WO 1999/067406 A1 | 12/1999 |
| WO | 2002/029079 A2 | 11/2002 |

OTHER PUBLICATIONS

Y. Tachibana et al. "Cloning and expression of the α-amylase gene from the hyperthermophilic archaeon *Pyrococcus* sp. KOD1, and characterization of the enzyme", Journal of Fermentation and Bioengineering 82:224-232 (1996).*
GenBank Accession No. ASJ02053 (2017).*
AUIPO—Dec. 6, 2013—Examiner's First Report—2012238328.
CIPO—Sep. 25, 2013—Office Action—CA 2,515,340.
EPO—Oct. 14, 2013—Art. 94(3) Communication—EP07869797.6.
JPO—Aug. 7, 2013—Second Office Action and Translation—JP 2010-132602.
JPO—Feb. 5, 2014—Second Office Action—JP2011-022288.
Saponins—Discover the Wealth of Benefits Saponins Provide—Ecological Surfactants, Inc. http://www.ecologicalsurfactants.com/saponin/—Retrieved Mar. 13, 2014.
SIPO—Jun. 26, 2013—Third Office Action and Translation—CN200910224585.4.

(Continued)

*Primary Examiner* — Rebecca E Prouty

(74) *Attorney, Agent, or Firm* — BASF; Brian W. Siddons

(57) ABSTRACT

The invention relates to alpha amylases and to polynucleotides encoding the alpha amylases. In addition methods of designing new alpha amylases and methods of use thereof are also provided. The alpha amylases have increased activity and stability at acidic, neutral and alkaline pH and increased temperature.

13 Claims, 151 Drawing Sheets

(56) References Cited

OTHER PUBLICATIONS

SIPO—Sep. 11, 2013—Second Office Action and Translation—CN201210020583.5.
SIPO—Feb. 20, 2014—Third Office Action and Translation—CN201210020583.5.
SIPO—Mar. 5, 2014—Fourth Office Action and Translation—CN200910224585.4.
Surfactants: the ubiquitous amphiphiles—Royal Society of Chemistry, Chemistry World, http://www.rsc.org/chemistryworld/issues/2003/july/amphiphiles.asp (2003)—Retrieved Mar. 13, 2014.
USPTO—Mar. 20, 2014—Office Action, 892, Refs Considered—U.S. Appl. No. 13/482,919.
Ausubel—Current Protocols in Molecular Biology, Chapters 1-3, 16 and Vectors—Appendix 5, John Wiley & Sons, New York, NY (1990).
Brown—Nature Genetics (1999)—21—33-37.
Bult—Science (1996)—273—1058-1073.
Devos—Proteins: Structure, Function, and Genetics (2000)—41—98-107.
Hulsmann—J. Bacteriol. (2000)—22—6292-6301.
JPO—Dec. 20, 2012—Office Action—JP2011-022288.
SIPO—Oct. 12, 2012—Decision of Final Rejection & Translation—CN200910224585.4.
SIPO—Feb. 4, 2013—First Office Action and Translation—CN201210020583.5.
USPTO—Feb. 7, 2013—Office Action, 892, IDSs considered—U.S. Appl. No. 13/283,119.
WIPO—PCT/US2003/33150—Search Report—dated Dec. 20, 2004.
EPO—Apr. 29, 2014—94(3) Communication—10 182 415.7.
EPO—Dec. 22, 2014—94(3) Communication—10 184 415.7.
Suzuki—J. Biol. Chem. (1989) 264—32—18933-18938.
Declerck—J. Biol. Chem. (1990) 265—26—15481-15488.
Declerck—J. Mol. Biol. (2000) 301—1041-1057.
Horváthová—Gen. Physiol. Biophys. (2001) 20—7-32.
CIPO—Feb. 18, 2015—Examiner's First Requisition—CA 2,833,423.
94(3) Communication for EP09171688.6 dated Feb. 7, 2012.
94(3) Communication for EP09180956.6 dated Mar. 15, 2012.
94(3) Communication for EP10182375.5 dated Mar. 7, 2012.
94(3) Communication for EP10184415.7 dated May 2, 2012.
94(3) Communication for EP10184478.5 dated May 2, 2012.
Birren, (2006), UNIPROT Accession No. Q0C881.
Birren, (2006), UNIPROT Accession No. Q0CPK9.
Devos, (2000), Proteins: Structure, Function, and Genetics, 41:98-107.
EBI Accession No. EAU29552, (2006), Aspergillus terreus NIH2624.
Examiner's First Report for AU2009222426 dated Jul. 4, 2011.
Examiner's First Report for AU2010246342 dated Jun. 8, 2011.
Examiner's Second Report for AU2009222426 dated Aug. 22, 2011.
Examiner's Second Report for AU2010246342 dated Aug. 18, 2011.
Extended EP Search Report for EP 10182375.5 dated May 19, 2011.
Extended EP Search Report for EP10184415.7 dated Aug. 9, 2011.
Extended EP Search Report for EP10184478.5 dated Aug. 9, 2011.
Extended EP Search Report for EP12152656.0 dated May 29, 2012.
Extended EP Search Report for EP12152662.8 dated May 29, 2012.
First Examination Report for Indian Application No. 3819/KOLNP/2008 dated Jun. 7, 2012.
Genbank Accession No. CAB88152 (Apr. 19, 2000).
Gray, (1986), Journal of Bacteriology, 166, 2:635-643.
Hu, (1992), Journal of General Microbiology, 138:1647-1655.
Jiang, (2003), GENESEQ Accession No. ABB80181.
Jiang, (2003), GENESEQ Accession No. ABQ80354.
Lin, (1995), GENBANK Accession No. U22045.
Lin, (1997), Journal of Applied Microbiology, 82:325-334.
Lin, (1997), Letters in Applied Microbiology, 24:365-368.
Lin, (1996), UNIPROT Accession No. Q59222.
NCBI Accession No. EAU34822, (2006), Aspergillus terreus NIH2624 glucoamylase precursor.
Office Action for JP2008-136876 dated Jun. 2, 2011.
Office Action for CA2438205 dated Jan. 9, 2012.
Office Action for CA2515340 dated Nov. 14, 2011.
Office Action for EP07869797.9 dated Dec. 13, 2011.
Office Action for EP09171688.6 dated Jan. 21, 2011.
Office Action for JP2010-132602 dated Aug. 16, 2012.
Office Action for JP2010-135846 dated May 14, 2012.
Office Action for U.S. Appl. No. 12/822,413 dated Oct. 12, 2011.
Office Action U.S. Appl. No. 12/520,523 dated Apr. 30, 2012.
Partial EP Search Report for EP10 184 381 dated May 24, 2011.
Partial EP Search Report for EP10184415.7 dated Apr. 6, 2011.
Partial EP Search Report for EP10184478.5 dated Apr. 6, 2011.
Robyt, (2009), "Enzymes and Their Action on Starch" in *Starch: Chemistry and Technology*, 3rd ed.:237-292.
Wishart, (1995), Journal of Biological Chemistry, 270:26782-26785.
BPTO—Mar. 23, 2014—Office Action—PI0207770-1.
BPTO—Sep. 9, 2014—Office Action—PI0207770-1.
CIPO—May 28, 2014—Examiner's Requisition—CA 2, 438, 205.
EPO—Apr. 22, 2014—94(3) Communication—10 184 478.5.
EPO—May 13, 2014—94(3) Communication—09 171 688.6.
EPO—Dec. 8, 2014—94(3) Communication 12 152 662.8.
EPO—Dec. 8, 2014—94(3) Communication 12 152 656.0.
Genbank Accession No. AF032864.1—Da Silva—1997.
Genbank Accession No. M38570.1—Udaka—1993.
Robertson—Applied and Environmental Microbiology (2004)—70—2429-2436.

* cited by examiner

FIGURE 5: Residual activity of various amylases following heating to 90°C for 10 min.

FIGURE 6: Net percent starch removed vs. enzyme concentration in ADW wash test with bleach and chelators FIGURE 7: Activity of parental amylases at pH 8, 40°C (black bars) in ADW formulation at 55°C (grey bars). Values are 384 well averages; error bars represent standard deviation.

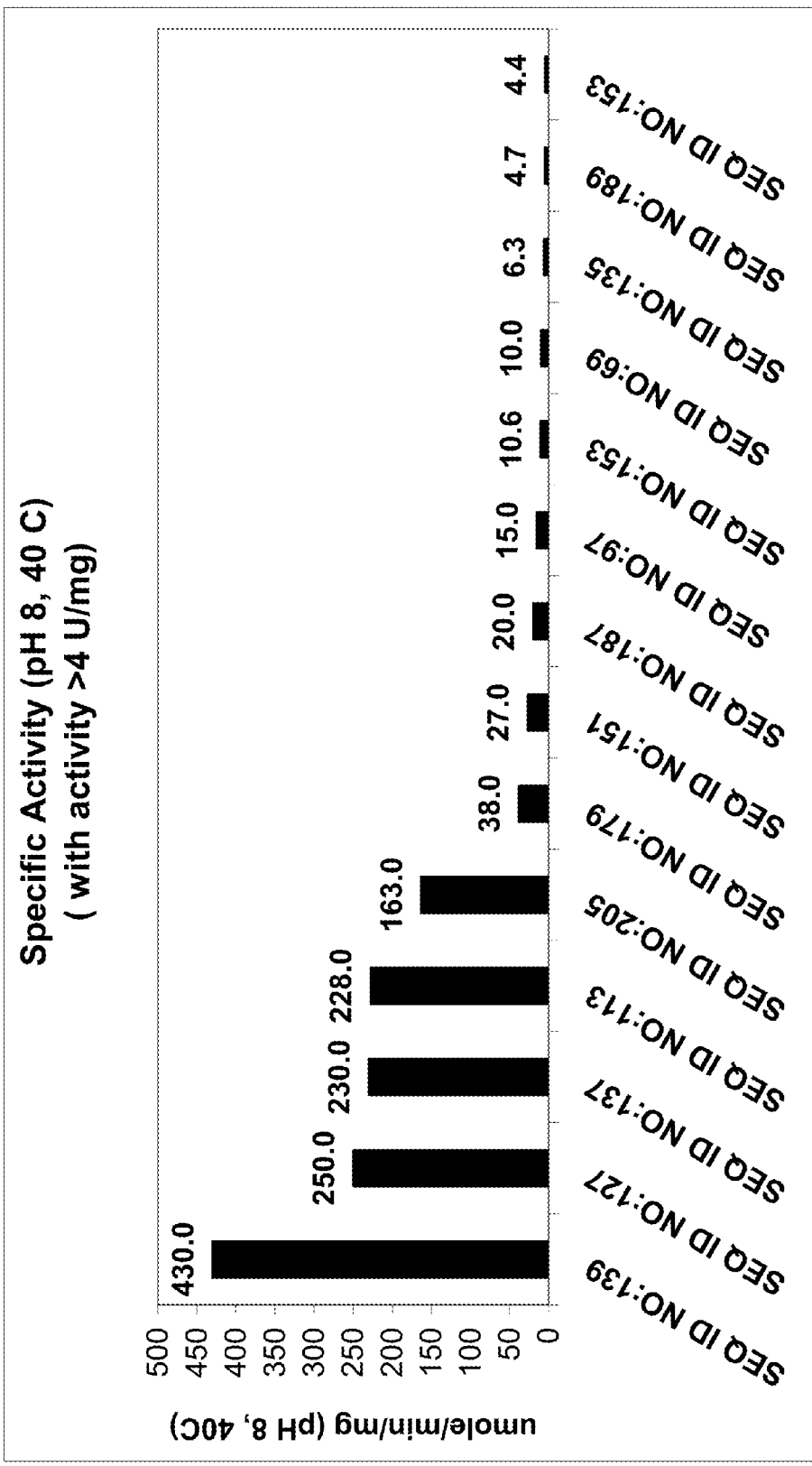
FIGURE 9A: A graph of the pH and temperature data for a selection of the amylases characterized: a) pH 8 and 40°C. b) pH 10 and 50°C

```
BD2238    (1)   ----AANLNTIKYEKMNDQHKKDQNIDSAYLAEHQITKMLIYDTS-QADVMGAILIYHTVR
BD6857    (1)   -QANTAPVNGTMQYEKDLENDTIKMTKVKNEASSLSLLITKLMLDAYKTS-QDVMGVILIYLNDSTIR
364g11    (1)   AKYSELEQGSVIKKAYDVEGQIWKDTKRQKIPEWYDAIKSIKKITSKMGGAYSKKKDPKKYFKKKKKKKTVE

BD2238   (76)   KYKTKGELQSAIKSLHSRDINVYGSVITKKGSAKATEDVTAVEVDPADRNKVISKEKRIKAWTHFHFPGRGSTYSDFK
BD6857   (79)   KYKTKTKNKQAQAAKSAGMQVYAKVFKKKALSTEWVDAVEVNPSNRNQETSKTYQIQAWTKFDFPGRGNTYSSFK
364g11   (81)   RKKSKKEELKVMKSTAHQYGIKVIAKTKKKKKFAKGKLEWNPYVGDYTKTDFSKVASKKYKAHYMDFHPN------

BD2238  (156)   WHWYHFDGTKTWDESRKLNRKYKFQG--KAKDKEVSNENGNYDYLMYADKDYDHPKVAAEKKRWGTWKANELQKKGFKLKA
BD6857  (159)   WRWYHFDGTKTWDESRKLNRKYKFRGTGKAKDKEVDKENGNYDYLMKADLDMDHPEVVTELKNWGTWKKNKTNVKGFKLKA
364g11  (150)   ----NKKSTKKKEGTFGGFPDKDHLVPFNQYKLKASNES----------------YAAKKLKRSIGKKAWKFKY

BD2238  (234)   KKKHIKTKSFLRDQKNHVREKTGKEMFTKAKYKQNDKGAKEKYKNKTNFNHSKKDKVKHYQFKAKSTQGGYDMRKLLNG---
BD6857  (239)   KKKHIKYSFFPDKLKHVRSQTRKNLFAKGKFNKSYDVNKKHKYITKTSGKMSKKLKAKHNNFYTKSKSSGYKDMRYLLNNK---
364g11  (200)   GYGAWVKKDKKLSQWGG------KAKGKYKDTNVDAKLKWAYSSG--AKVKFKKYKMDEKFDNKNIPAKVYAKONGE

BD2238  (312)   VVSKKKKKKKFDKKKKQPGQSLESTVQTKFKPLKKKTRESKYKQVKGKMYGTKGDSQ--REIPAKKHKIEPKL
BD6857  (317)   LKKDQKSLKKLKDKKKQPGQSLQSWVKPKKKFKPLAKKKTRQEKYKCVKGKYYGIPKYN-----IPGKKSKIKDPLL
364g11  (272)   VVSKRDKFKGKKFAKKKKK------IIKNKYPKKTYE-KQKVKFFKRKYEEWLNKD-----------KLNNKKI

BD2238  (390)   KARKQYKYKAQHDYFDHHKIKWGTKKKDKSVANSGLAAKITDGPGGAKRMYVKKONAGETKHDKTKNRS--EPVVINSKE
BD6857  (392)   IARRDYKYKQRDYIDHQKIIGWTKKKIDSKPNSGLAAKITDGPGGKKMYVKKHAGKVFKKDKTKNRS--DTVTINAD
364g11  (331)   WIHEHLKGSTKILKYDDKELIEMKYGDRPGL-KTYKNLGSWKEKMKNVKSKFAGYTIHKYTKNLGGWVDRKYQYD
```

FIGURE 10: Alignments of the genes proposed to be used in reassembly

```
              481                                                            560
BD2238 (468)  GEEHVN------------G--SINVQR----------------------------------
BD6857 (470)  GEFKVN------------G--SINVAKTSQVTFTVNNATTISGQNVYVVGNIPELGNWNTANAIKMTPSSYPTWKATIALP
364gl1 (410)  VRLTAPPHDPANGYYYYWSLAGVG---------------------------------------

561                                       605
BD2238 (485)  ----------------------------------------
BD6857 (541)  QGKAIEFKFIKKDQSGNVVWESIPNRTYTVPFLSTGSYTASWNVP
364gl1 (437)  ----------------------------------------
```

FIGURE 10 CONTINUED

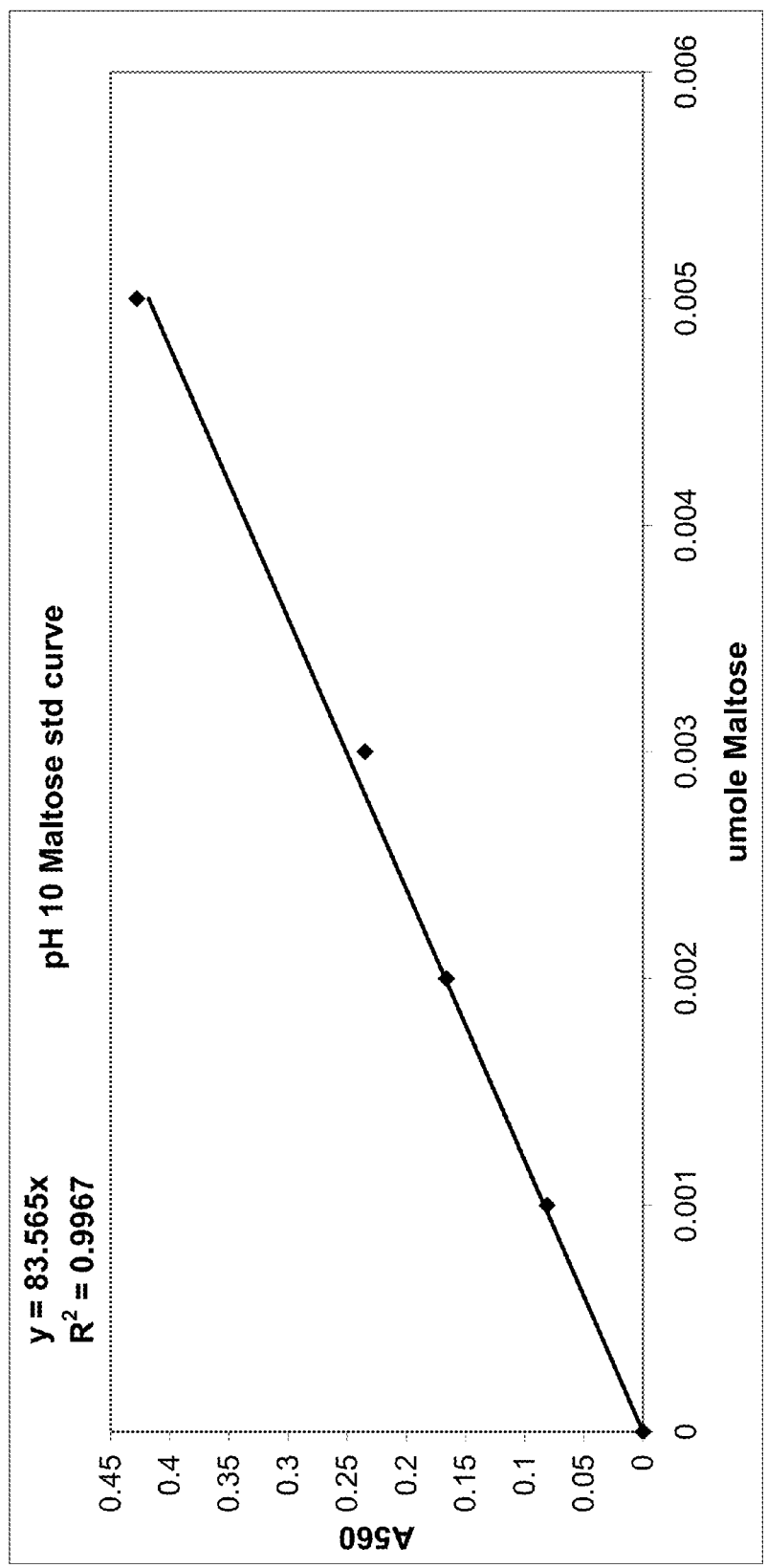
FIGURE 11: Example Standard Curve of the assay of Example 5

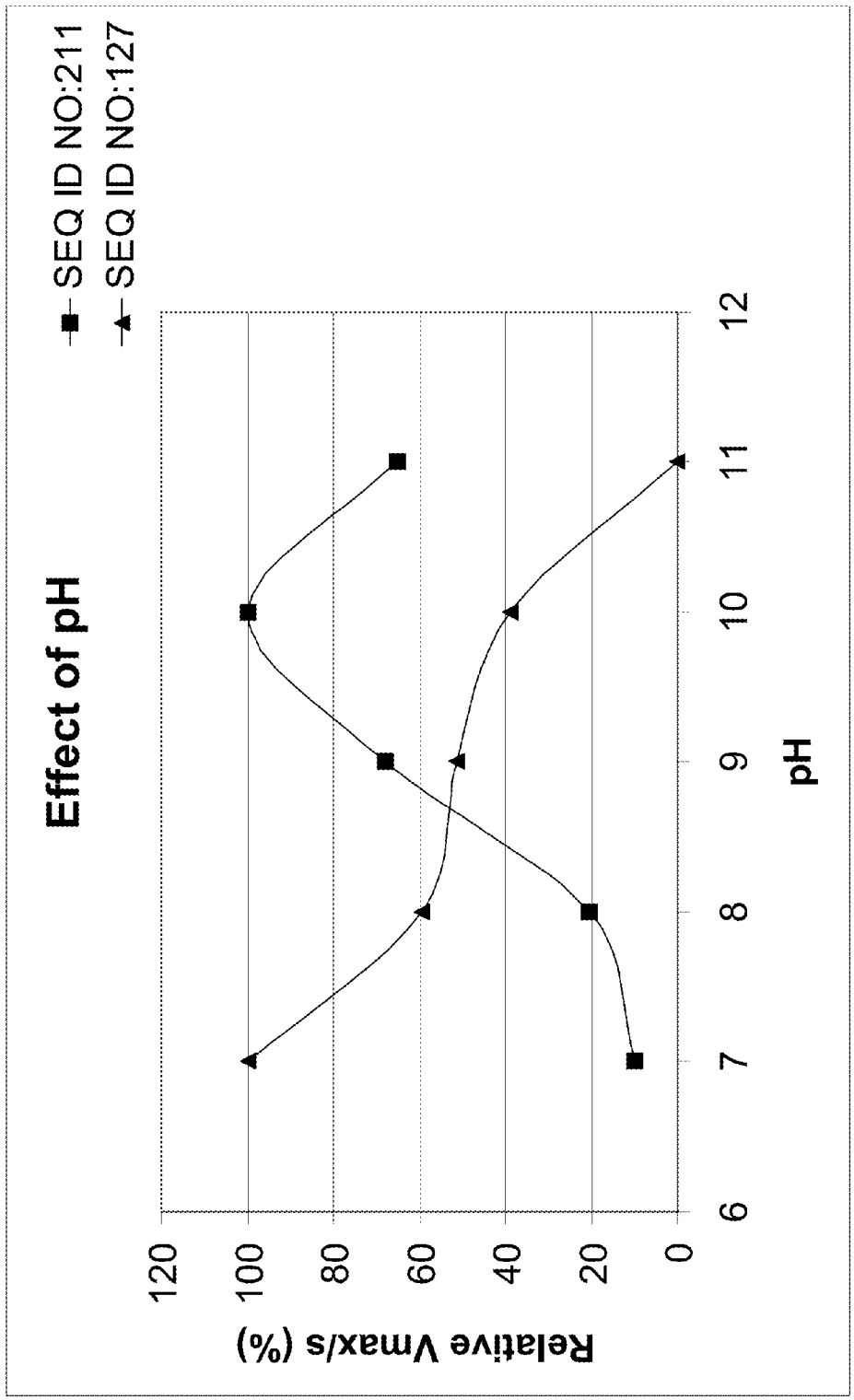
FIGURE 12: A graph of the pH rate profiles for 2 different amylases. BD7188 is a control; an enzyme that was discovered previously and has a neutral pH optimum. BD7837 is a more recently discovered amylase and has an optimum around pH 10. Pure protein was used in these assays.

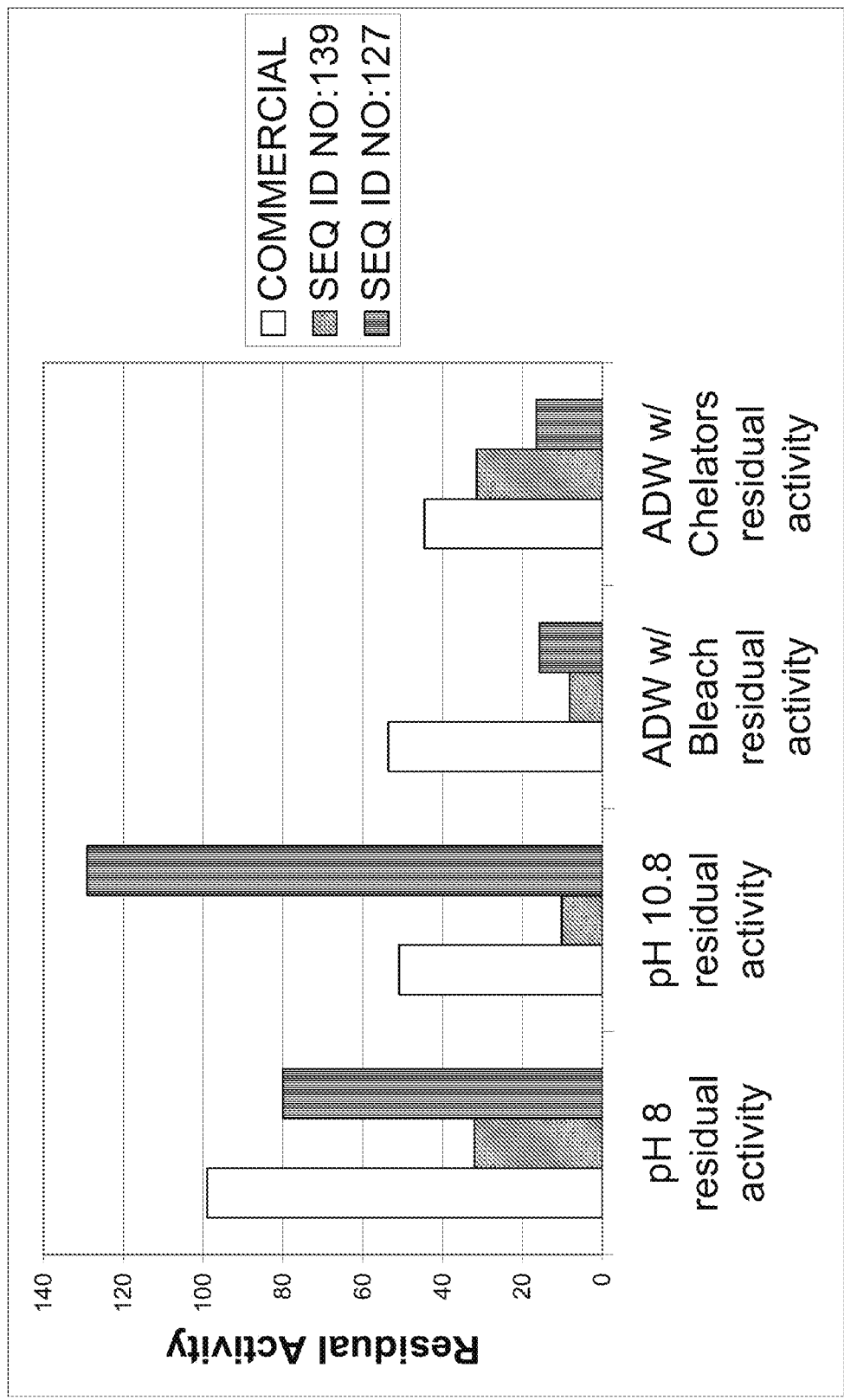
FIGURE 13: Stability of Diversa amylases vs. a commercial enzyme

```
                   1                                                      50
SEQ ID NO:81       ~~~~~~~~~~ ~~~~~~~~MKK FVALFITMFF VVSMAVV... ..AQPASAAK
       pyro        ~~~~~~~~~~ ~~~~~~~~MKK FVALLITMFF VVSMAAV... ..AQPASAAK
       pyro2       ~~~~~~~~~~ ~~~~~VNIKK LTPLLTLLLF FI...VL... ..ASPVSAAK
       thermo      SESQCTATCT WRVVYMSAKK LLALLFVLAV LVGVAVIPAR VGIAPVSAGA
       thermo2     ~~~~~~~~~~ ~~~~~~~~~~ ~~~~~~~~MA RKVLVALLVF LVVLSVSAVP
       Consensus   ~~~~~~~~~~ ~~~~~~~~~~ ---------- ---------- ------SA--

51                                                     100
SEQ ID NO:81       YS..ELEEGG VIMQAFYWDV PGGGIWWDTI RSKIPEWYEA GISAIWIPPA
       pyro        YS..ELEEGG VIMQAFYWDV PAGGIWWDTI RSKIPEWYEA GISAIWIPPA
       pyro2       YL..ELEEGG VIMQAFYWDV PGGGIWWDHI RSKIPEWYEA GISAIWLPPP
       thermo      TSRPSLEEGG VIMQAFYWDV PAGGIWWDTI RSKIPDWASA GISAIWIPPA
       thermo2     AKAETLENGG VIMQAFYWDV PGGGIWWDTI AQKIPDWASA GISAIWIPPA
       Consensus   -----LE-GG VIMQAFYWDV P-GGIWWD-I --KIP-W---A GISAIW-PP-
                        Sense primer
                   101                                                    150
SEQ ID NO:81       SKGMSGGYSM GYDPYDFFDL GEYNQKGTIE TRFGSKQELI NMINTAHAYG
       pyro        SKGMGGAYSM GYDPYDFFDL GEYNQKGTVE TRFGSKQELI NMINTAHAYG
       pyro2       SKGMGGGYSM GYDPYDYFDL GEYYQKGTVE TRFGSKEELV RLIQTAHAYG
       thermo      SKGMSGAYSM GYDPYDFFDL GEYYQKGTVE TRFGSKQELI NMINTAHSYG
       thermo2     SKGMSGGYSM GYDPYDFFDL GEYYQKGSVE TRFGSKEELV NMINTAHAHN
       Consensus   SKGM-G-YSM GYDPYD-FDL GEY-QKG--E TRFGSK-EL- ---I-TAH---

151                                                    200
SEQ ID NO:81       IKVIADIVIN HRAGGDLEWN PFVGDYTWTD FSKVASGKYT ANYLDFHPNE
       pyro        IKVIADIVIN HRAGGDLEWN PFVGDYTWTD FSKVASGKYT ANYLDFHPNE
       pyro2       IKVIADVVIN HRAGGDLEWN PFVGDYTWTD FSKVASGKYT ANYLDFHPNE
       thermo      IKVIADIVIN HRAGGDLEWN PFTNSYTWTD FSKVASGKYT ANYLDFHPNE
       thermo2     MKVIADIVIN HRAGGDLEWN PFTNSYTWTD FSKVASGKYT ANYLDFHPNE
       Consensus   -KVIAD-VIN HRAGGDLEWN PF----YTWTD FSKVASGKYT ANYLDFHPNE 201                                                    250
SEQ ID NO:81       VKCCDEGTFG GFPDIAHEKS WDQHWLWASD ESYAAYLRSI GVDAWRFDYV
       pyro        VKCCDEGTFG GFPDIAHEKE WDQHWLWASD ESYAAYLRSI GVDAWRFDYV
       pyro2       LHCCDEGTFG GFPDICHHKE WDQYWLWKSN ESYAAYLRSI GFDGWRFDYV
       thermo      VKCCDEGTFG GFPDIAHEKS WDQYWLWASQ KSYAAYLRSI GIDAWRFDYV
       thermo2     LHAGDSGTFG GYPDICHDKS WDQHWLWASN ESYAAYLRSI GIDAWRFDYV
       Consensus   ----D-GTFG G-PDI-H-K- WDQ-WLW-S- -SYAAYLRSI G-D-WRFDYV 251                                                    300
SEQ ID NO:81       KGYGAWVVKD WLNWWGGWAV GEYWDTNVDA LLNWAYSSGA KVFDFPLYYK
       pyro        KGYGAWVVKD WLNWWGGWAV GEYWDTNVDA LLNWAYSSGA KVFDFPLYYK
       pyro2       KGYGAWVVRD WLNWWGGWAV GEYWDTNVDA LLSWAYESGA KVFDFPLYYK
       thermo      KGYGAWVVKD WLKWW.ALAV GEYWDTNVDA LLNWAYSSGA KVFDFPLYYK
       thermo2     KGYAPWVVKN WLNRWGGWAV GEYWDTNVDA LLSWAYDSGA KVFDFPLYYK
       Consensus   KGY--WVV-- WL--W---AV GEYWDTNVDA LL-WAY-SGA KVFDFPLYYK 301                                                    350
SEQ ID NO:81       MDEAFDNKNI PALVSALQNG QTVVSRDPFK AVTFVANHDT DIIWNKYLAY
       pyro        MDEAFDNTNI PALVDALQNG GTVVSRDPFK AVTFVANHDT DIIWNKYPAY
       pyro2       MDEAFDNNNI PALVYALQNG QTVVSRDPFK AVTFVANHDT DIIWNKYPAY
       thermo      MDEAFDNKNI PALVSALQNG QTVVSRDPFK AVTFVANHDT DIIWNKYPAY
       thermo2     MDEAFDNNNI PALVDALKNG GTVVSRDPFK AVTFVANHDT NIIWNKYPAY
       Consensus   MDEAFDN-NI PALV-AL-NG -TVVSRDPFK AVTFVANHDT -IIWNKY-AY
```

FIGURE 14A

```
              351                                                        400
SEQ ID NO:81  AFILTYEGQP VIFYRDYEEW LNKDRLNNLI WIHDHLAGGS TSIVYYDSDE
        pyro  AFILTYEGQP VIFYRDYEEW LNKDKLNNLI WIHDHLAGGS TSIVYYDSDE
       pyro2  AFILTYEGQP VIFYRDFEEW LNKDKLINLI WIHDHLAGGS TTIVYYDNDE
       thermo AFILTYEGQP VIFYRDYEEW LNKDRLKNLI WIHNNLAGGS TSIVYYDNDE
      thermo2 AFILTYEGQP AIFYRDYEEW LNKDRLRNLI WIHDHLAGGS TDIIYYDSDE
    Consensus AFILTYEGQP -IFYRD-EEW LNKD-L-NLI WIH---LAGGS T-I-YYD-DE 401                                                        450
SEQ ID NO:81  MIFVRNGYGS KPGLITYINL GSSKVGRWVY VPKFAGACIH EYTGNLGGWV
        pyro  LIFVRNGDSK RPGLITYINL GSSKVGRWVY VPKFAGACIH EYTGNLGGWV
       pyro2  LIFVRNGDSR RPGLITYINL SPNWVGRWVY VPKFAGACIH EYTGNLGGWV
       thermo LIFVRNGYGN KPGLITYINL GSSKVGRWVY VPKFAGSCIH EYTGNLGGWV
      thermo2 LIFVRNGYGD KPGLITYINL GSSKAGRWVY VPKFAGSCIH EYTGNLGGWI
    Consensus -IFVRNG--- -PGLITYINL -----GRWVY VPKFAG-CIH EYTGNLGGW- 451                           486
SEQ ID NO:81  DKYVYSSGWV YFEAPAYDPA NGQYGYSVWS YCGVG*
        pyro  DKYVESSGWV YLEAPAYDPA SGQYGYTVWS YCGVG*
       pyro2  DKRVDSSGWV YLEAPPHDPA NGYYGYSVWS YCGVG*
       thermo DKYVGSNGWV YLEAPAHDPA KGQYGYSVWS YCGVG*
      thermo2 DKWVDSSGRV YLEAPAHDPA NGQYGYSVWS YCGVG*
    Consensus DK-V-S-G-V Y-EAP--DPA -G-YGY-VWS YCGVG*
              Antisense primer
```

FIGURE 14A cont.

```
                        1                                                        50
SEQ ID NO:81    ~~~~~~~~~~ ~~~~~~~~~~ ~~~~MKKFVA LFITMFFVVS MAVVAQPASA
        pyro    ~~~~~~~~~~ ~~~~~~~~~~ ~~~~MKKFVA LLITMFFVVS MAAVAQPASA
SEQ ID NO:73    ~~~~~~~~~~ ~~~~~~~~~~ ~~~~~~~~~~ ~~~~~~~~~~ ~~~~~~~~~~
      thermo2   ~~~~~~~~~~ ~~~~~~~~~~ ~~~~~~~~MA RKVLVALLVF LVVLSVSAVP
SEQ ID NO:75    ~~~~~~~~~~ ~~~~~~~~~~ ~~~~~~~~~~ ~~~~~~~~~~ ~~~~~~~~~~
SEQ ID NO:77    ~~~~~~~~~~ ~~~~~~~~~~ ~~~~~~~~~~ ~~~~~~~~~~ ~~~~~~~~~~
SEQ ID NO:83    ~~~~~~~~~~ ~~~~~~~~~~ ~~~~~~~~~~ ~~~~~~~~~~ ~~~~~~~~~~
SEQ ID NO:85    ~~~~~~~~~~ ~~~~~~~~~~ ~~~~~~~~~~ ~~~~~~~~~~ ~~~~~~~~~~
SEQ ID NO:79    ~~~~~~~~~~ ~~~~~~~~~~ ~~~~MKPAKL LVFVLVVSIL AGLYAQPAGA
       thermo   SESQCTATCT WRVVYMSAKK LLALLFVLAV LVGVAVIPAR VGIAPVSAGA
        pyro2   ~~~~~~~~~~ ~~~~~~~~~~ ~~~~~VNIKK LTPLLTLLLF FIVLASPVSA
      CLONE A   ~~~~~~~~~~ ~~~~~~~~~~ ~~~MRRSARV LVLIIAFFLL AGIYYPSTSA
    Consensus   ~~~~~~~~~~ ~~~~~~~~~~ ~~~~~~---- ---------- ----------

51                                                       100
SEQ ID NO:81    AKYSELEEGG VIMQAFYWDV PGGGIWWDTI RSKIPEWYEA GISAIWIPPA
        pyro    AKYSELEEGG VIMQAFYWDV PAGGIWWDTI RSKIPEWYEA GISAIWIPPA
SEQ ID NO:73    ~~~MALEEGG LIMQAFYWDV PGGGIWWDTI AQKIPDWASA GISAIWIPPA
      thermo2   AKAETLENGG VIMQAFYWDV PGGGIWWDTI AQKIPDWASA GISAIWIPPA
SEQ ID NO:75    ~~~MALEEGG LIMQAFYWDV PMGGIWWDTI AQKIPDWASA GISAIWIPPA
SEQ ID NO:77    ~~~MALEEGG LIMQAFYWDV PMGGIWWDTI AQKIPDWASA GISAIWIPPA
SEQ ID NO:83    ~~~MALEEGG LIMQAFYWDV PGGGIWWDTI AQKIPEWASA GISAIWIPPA
SEQ ID NO:85    ~~~MALEEGG LIMQAFYWDV PGGGIWWDTI AQKIPEWASA GISAIWIPPA
SEQ ID NO:79    AKYLELEEGG VIMQAFYWDV PSGGIWWDTI RQKIPEWYDA GISAIWIPPA
       thermo   TSRPSLEEGG VIMQAFYWDV PAGGIWWDTI RSKIPDWASA GISAIWIPPA
        pyro2   AKYLELEEGG VIMQAFYWDV PGGGIWWDHI RSKIPEWYEA GISAIWLPPF
      CLONE A   AKYSELEQGG VIMQAFYWDV PEGGIWWDTI RQKIPEWYDA GISAIWIPPA
    Consensus   --------GG -IMQAFYWDV P-GGIWWD-I --KIP-W--A GISAIW-PP- 101                                                      150
SEQ ID NO:81    SKGMSGGYSM GYDPYDFFDL GEYNQKGTIE TRFGSKQELI NMINTAHAYG
        pyro    SKGMGGAYSM GYDPYDFFDL GEYNQKGTVE TRFGSKQELI NMINTAHAYG
SEQ ID NO:73    SKGMSGGYSM GYDPYDFFDL GEYYQKGSVE TRFGSKEELV NMINTAHAHN
      thermo2   SKGMSGGYSM GYDPYDFFDL GEYYQKGSVE TRFGSKEELV NMINTAHAHN
SEQ ID NO:75    SKGMSGGYSM GYDPYDYFDL GEYYQKGTVE TRFGSKQELI NMINTAHAYG
SEQ ID NO:77    SKGMSGGYSM GYDPYDYFDL GEYYQKGTVE TRFGSKQELI NMINTAHAYG
SEQ ID NO:83    SKGMSGGYSM GYDPYDFFDL GEYYQKGTVE TRFGSKEELV NMINTAHSYG
SEQ ID NO:85    SKGMSGGYSM GYDPYDFFDL GEYYQKGTVE TRFGSKEELV NMINTAHSYG
SEQ ID NO:79    SKGMGGAYSM GYDPYDFFDL GEYDQKGTVE TRFGSKQELV NMINTAHAYG
       thermo   SKGMSGAYSM GYDPYDFFDL GEYYQKGTVE TRFGSKQELI NMINTAHSYG
        pyro2   SKGMSGGYSM GYDPYDYFDL GEYYQKGTVE TRFGSKEELV RLIQTAHAYG
      CLONE A   SKGMGGAYSM GYDPYDYFDL GEFYQKGTVE TRFGSKEELV NMISTAHQYG
    Consensus   SKGM-G-YSM GYDPYD-FDL GE--QKG--E TRFGSK-EL- --I-TAH---

151                                                      200
SEQ ID NO:81    IKVIADIVIN HRAGGDLEWN PFVGDYTWTD FSKVASGKYT ANYLDFHPNE
        pyro    IKVIADIVIN HRAGGDLEWN PFVGDYTWTD FSKVASGKYT ANYLDFHPNE
SEQ ID NO:73    MKVIADIVIN HRAGGDLEWN PFTNSYTWTD FSKVASGKYT ANYLDFHPNE
      thermo2   MKVIADIVIN HRAGGDLEWN PFTNSYTWTD FSKVASGKYT ANYLDFHPNE
SEQ ID NO:75    MKVIADIVIN HRAGGDLEWN PFVNDYTWTD FSKVASGKYT ANYLDFHPNE
SEQ ID NO:77    MKVIADIVIN HRAGGDLEWN PFVNDYTWTD FSKVASGKYT ANYLDFHPNE
SEQ ID NO:83    IKVIADIVIN HRAGGDLEWN PFVNDYTWTD FSKVASGKYT ANYLDFHPNE
SEQ ID NO:85    IKVIADIVIN HRAGGGLEWN PFVNDYTWTD FSKVASGKYT ANYLDFHPNE
SEQ ID NO:79    IKVIADIVIN HRAGGDLEWN PFVGDYTWTD FSKVASGKYT ANYLDFHPNE
       thermo   IKVIADIVIN HRAGGDLEWN PFTNSYTWTD FSKVASGKYT ANYLDFHPNE
        pyro2   IKVIADVVIN HRAGGDLEWN PFVGDYTWTD FSKVASGKYT ANYLDFHPNE
      CLONE A   IKVIADIVIN HRAGGDLEWN PYVGDYTWTD FSKVASGKYK AHYMDFHPNN
    Consensus   -KVIAD-VIN HRAGG-LEWN P----YTWTD FSKVASGKY- A-Y-DFHPN-
```

FIGURE 14B

```
                    201                                                         250
SEQ ID NO:81        VKCCDEGTFG GFPDIAHEKS WDQHWLWASD ESYAAYLRSI GVDAWRFDYV
        pyro        VKCCDEGTFG GFPDIAHEKE WDQHWLWASD ESYAAYLRSI GVDAWRFDYV
SEQ ID NO:73        LHAGDSGTFG GYPDICHDKS WDQHWLWASN ESYAAYLRSI GIDAWRFDYV
      thermo2       LHAGDSGTFG GYPDICHDKS WDQHWLWASN ESYAAYLRSI GIDAWRFDYV
SEQ ID NO:75        LHAGDSGTFG GYPDICHDKS WDQYWLWASQ ESYAAYLRSI GIDAWRFDYV
SEQ ID NO:77        LHAGDSGTFG GYPDICHDKS WDQYWLWASQ ESYAAYLRSI GIDAWRFDYV
SEQ ID NO:83        LHCCDEGTFG GYPDICHDKS WDQYWLWASS ESYAAYLRSI GVDAWRFDYV
SEQ ID NO:85        LHCCDEGTFG GYPDICHDKS WDQYWLWASS ESYAAYLRSI GVDAWCFDYV
SEQ ID NO:79        VKCCDEGTFG GFPDIAHEKS WDQYWLWASN ESYAAYLRSI GVDAWRFDYV
      thermo        VKCCDEGTFG GFPDIAHEKS WDQYWLWASQ KSYAAYLRSI GIDAWRFDYV
      pyro2         LHCCDEGTFG GFPDICHHKE WDQYWLWKSN ESYAAYLRSI GFDGWRFDYV
     CLONE A        YSTSDEGTFG GFPDIDHLVP FNQYWLWASN ESYAAYLRSI GIDAWRFDYV
     Consensus      ----D-GTFG G-PDI-H--- --Q-WLW-S- -SYAAYLRSI G-D-W-FDYV 251                                                         300
SEQ ID NO:81        KGYGAWVVKD WLNWWGGWAV GEYWDTNVDA LLNWAYSSGA KVFDFPLYYK
        pyro        KGYGAWVVKD WLNWWGGWAV GEYWDTNVDA LLNWAYSSGA KVFDFPLYYK
SEQ ID NO:73        KGYAPWVVKN WLNRWGGWAV GEYWDTNVDA LLSWAYDSGA KVFDFPLYYK
      thermo2       KGYAPWVVKN WLNRWGGWAV GEYWDTNVDA LLSWAYDSGA KVFDFPLYYK
SEQ ID NO:75        KGYAPWVVRD WLNWWGGWAV GEYWDTNVDA VLNWAYSSGA KVFDFALYYK
SEQ ID NO:77        KGYAPWVVKD WLNWWGGWAV GEYWDTNVDA VLNWAYSSGA KVFDFALYYK
SEQ ID NO:83        KGYGAWVVND WLSWWGGWAV GEYWDTNVDA LLNWAYSSGA KVFDFPLYYK
SEQ ID NO:85        KGYGAWVVND WLSWWGGWAV GEYWDTNVDA LLNWAYNSGA KVFDFPLYYK
SEQ ID NO:79        KGYGAWVVKD WLDWWGGWAV GEYWDTNVDA LLNWAYSSDA KVFDFPLYYK
      thermo        KGYGAWVVKD WLKWW.ALAV GEYWDTNVDA LLNWAYSSGA KVFDFPLYYK
      pyro2         KGYGAWVVRD WLNWWGGWAV GEYWDTNVDA LLSWAYESGA KVFDFPLYYK
     CLONE A        KGYGAWVVKD WLSQWGGWAV GEYWDTNVDA LLNWAYSSGA KVFDFPLYYK
     Consensus      KGY--WVV-- WL--W---AV GEYWDTNVDA -L-WAY-S-A KVFDF-LYYK 301                                                         350
SEQ ID NO:81        MDEAFDNKNI PALVSALQNG QTVVSRDPFK AVTFVANHDT DIIWNKYLAY
        pyro        MDEAFDNTNI PALVDALQNG GTVVSRDPFK AVTFVANHDT DIIWNKYPAY
SEQ ID NO:73        MDEAFDNNNI PALVDALKNG GTVVSRDPFK AVTFVANHDT NIIWNKYPAY
      thermo2       MDEAFDNNNI PALVDALKNG GTVVSRDPFK AVTFVANHDT NIIWNKYPAY
SEQ ID NO:75        MDEAFDNNNI PALVDALRYG QTVVSRDPFK AVTFVANHDT DIIWNKYPAY
SEQ ID NO:77        MDEAFDNNNI PALVDALRYG QTVVSRDPFK AVTFVANHDT DIIWNKYPAY
SEQ ID NO:83        MDEAFDNTNI PALVDALRYG QTVVSRDPFK AVTFVANHDT DIIWNKYPAY
SEQ ID NO:85        MDEAFDNTNI PALVYALKNG GTVVSRDPFK AVTFVANHDT DIIWNKYPAY
SEQ ID NO:79        MDAAFDNKNI PALVEALKNG GTVVSRDPFK AVTFVANHDT DIIWNKYPAY
      thermo        MDEAFDNKNI PALVSALQNG QTVVSRDPFK AVTFVANHDT DIIWNKYPAY
      pyro2         MDEAFDNNNI PALVYALQNG QTVVSRDPFK AVTFVANHDT DIIWNKYPAY
     CLONE A        MDEAFDNKNI PALVYAIQNG ETVVSRDPFK AVTFVANHDT NIIWNKYPAY
     Consensus      MD-AFDN-NI PALV-A---G -TVVSRDPFK AVTFVANHDT -IIWNKY-AY 351                                                         400
SEQ ID NO:81        AFILTYEGQP VIFYRDYEEW LNKDRLNNLI WIHDHLAGGS TSIVYYDSDE
        pyro        AFILTYEGQP VIFYRDYEEW LNKDKLNNLI WIHDHLAGGS TSIVYYDSDE
SEQ ID NO:73        AFILTYEGQP AIFYRDYEEW LNKDRLRNLI WIHDHLAGGS TDIIYYDSDE
      thermo2       AFILTYEGQP AIFYRDYEEW LNKDRLRNLI WIHDHLAGGS TDIIYYDSDE
SEQ ID NO:75        AFILTYEGQP TIFYRDYEEW LNKDKLKNLI WIHDNLAGGS TDIVYYDNDE
SEQ ID NO:77        AFILTYEGQP TIFYRDYEEW LNKDKLKNLI WIHDNLAGGS TDIVYYDNDE
SEQ ID NO:83        AFILTYEGQP VIFYRDYEEW LNKDKLNNLI WIHDHLAGGS TDIVYYDSDE
SEQ ID NO:85        AFILTYEGQP VIFYRDYEEW LNKDKLNNLI WIHDHLAGGS TDIVYYDSDE
SEQ ID NO:79        AFILTYEGQP TIFYRDYEEW LNKDRLKNLI WIHDHLAGGS TDIVYYDNDE
      thermo        AFILTYEGQP VIFYRDYEEW LNKDRLKNLI WIHNNLAGGS TSIVYYDNDE
      pyro2         AFILTYEGQP VIFYRDFEEW LNKDKLINLI WIHDHLAGGS TTIVYYDNDE
     CLONE A        AFILTYEGQP VIFYRDYEEW LNKDKLNNLI WIHEHLAGGS TKILYDDDDE
     Consensus      AFILTYEGQP -IFYRD-EEW LNKD-L-NLI WIH--LAGGS T-I-YYD-DE
```

FIGURE 14B cont

```
              401                                                    450
SEQ ID NO:81  MIFVRNGYGS KPGLITYINL GSSKVGRWVY V.PKFAGACI HEYTGNLGGW
       pyro   LIFVRNGDSK RPGLITYINL GSSKVGRWVY V.PKFAGACI HEYTGNLGGW
SEQ ID NO:73  LIFVRNGYGD KPGLITYINL GSSKAGRWVY V.PKFAGSCI HEYTGNLGGW
     thermo2  LIFVRNGYGD KPGLITYINL GSSKAGRWVY V.PKFAGSCI HEYTGNLGGW
SEQ ID NO:75  LIFVRNGYGS KPGLITYINL GSSKAGRWVY V.PKFAGSCI HEYTGNLGGW
SEQ ID NO:77  LIFVRNGYGS KPGLITYINL ASSKAGRWVY V.PKFAGSCI HEYTGNLGGW
SEQ ID NO:83  LIFVRNGYGT KPGLITYINL GSSKVGRWVY V.PKFAGSCI HEYTGNLGGW
SEQ ID NO:85  LIFVRNGYGT KPGLITYINL GSSKAGRWVY V.PKFAGSCI HEYTGSLGGW
SEQ ID NO:79  LIFVRNGYGD KPGLITYINL GSSKAGRWVY V.PKFAGACI HEYTGNLGGW
      thermo  LIFVRNGYGN KPGLITYINL GSSKVGRWVY V.PKFAGSCI HEYTGNLGGW
       pyro2  LIFVRNGDSR RPGLITYINL SPNWVGRWVY V.PKFAGACI HEYTGNLGGW
     CLONE A  LIFMREGYGD RPGLITYINL GSDWAERWVN VGSKFAGYTI HEYTGNLGGW
   Consensus  -IF-R-G--- -PGLITYINL -------RWV- V--KFAG---I HEYTG-LGGW 451                             487
SEQ ID NO:81  VDKYVYSSGW VYFEAPAYDP ANGQYGYSVW SYCGVG*
       pyro   VDKYVESSGW VYLEAPAYDP ASGQYGYTVW SYCGVG*
SEQ ID NO:73  IDKWVDSSGR VYLEAPAHDP ANGQYGYSVW SYCGVG*
     thermo2  IDKWVDSSGR VYLEAPAHDP ANGQYGYSVW SYCGVG*
SEQ ID NO:75  VDKWVDSSGW VYLEAPAHDP ANGQYGYSVW SYCGVG*
SEQ ID NO:77  VDKWVDSSGW VYLEAPAHDP ANGQYGYSVW SYCGVG*
SEQ ID NO:83  IDKYVSSSGW VYLEAPAHDP ANGYYGYSVW SYCGVG*
SEQ ID NO:85  IDKYVSSSGW VYLEAPAHDP ANGQYGYSVW SYCGVG*
SEQ ID NO:79  VDKWVDSSGW VYLEAPAHDP ANGYYGYSVW SYCGVG*
      thermo  VDKYVGSNGW VYLEAPAHDP AKGQYGYSVW SYCGVG*
       pyro2  VDKRVDSSGW VYLEAPPHDP ANGYYGYSVW SYCGVG*
     CLONE A  VDRYVQYDGW VKLTAPPHDP ANGYYGYSVW SYAGVG*
   Consensus  -D--V---G- V---AP--DP A-G-YGY-VW SY-GVG*
```

FIGURE 14B cont

```
                    1                                                                          50
SEQ ID NO:83        ~~~~~~~~~~ ~~~~~~~~~~ ~~~~~~~~~~ ~~~~~~~~~~ ~~~~~~~~~~
SEQ ID NO:85        ~~~~~~~~~~ ~~~~~~~~~~ ~~~~~~~~~~ ~~~~~~~~~~ ~~~~~~~~~~
SEQ ID NO:75        ~~~~~~~~~~ ~~~~~~~~~~ ~~~~~~~~~~ ~~~~~~~~~~ ~~~~~~~~~~
SEQ ID NO:77        ~~~~~~~~~~ ~~~~~~~~~~ ~~~~~~~~~~ ~~~~~~~~~~ ~~~~~~~~~~
SEQ ID NO:73        ~~~~~~~~~~ ~~~~~~~~~~ ~~~~~~~~~~ ~~~~~~~~~~ ~~~~~~~~~~
SEQ ID NO:79        ~~~ATGAAGC CTGCGAAACT CCTCGTCTTT GTGCTCGTAG TCTCTATCCT
SEQ ID NO:81        ~~~ATGAAGA AGTTTGTCGC CCTGTTCATA ACCATGTTTT TCGTAGTGAG
      CLONE A       ATGAGGAGAT CCGCAAGGGT TTTGGTTCTG ATTATAGCGT TTTTCCTCCT
      Consensus     ~~~~~~~~~~ ~~~~~~~~~~ ~~~~~~~~~~ ~~~~~~~~~~ ~~~~~~~~~~

51                                                                         100
SEQ ID NO:83        ~~~~~~~~~~ ~~~~~~~~~~ ~~~~~~~~~~ ~~~~~~~~~~ ATGGCTCTGG
SEQ ID NO:85        ~~~~~~~~~~ ~~~~~~~~~~ ~~~~~~~~~~ ~~~~~~~~~~ ATGGCTCTGG
SEQ ID NO:75        ~~~~~~~~~~ ~~~~~~~~~~ ~~~~~~~~~~ ~~~~~~~~~~ ATGGCTCTGG
SEQ ID NO:77        ~~~~~~~~~~ ~~~~~~~~~~ ~~~~~~~~~~ ~~~~~~~~~~ ATGGCTCTGG
SEQ ID NO:73        ~~~~~~~~~~ ~~~~~~~~~~ ~~~~~~~~~~ ~~~~~~~~~~ ATGGCTCTGG
SEQ ID NO:79        CGCGGGGCTC TACGCCCAGC CCGCGGGGGC GGCCAAGTAC CTGGAGCTCG
SEQ ID NO:81        CATGGCAGTC GTTGCACAGC CAGCTAGCGC CGCAAAGTAT TCCGAGCTCG
      CLONE A       GGCGGGGATT TACTACCCCT CCACGAGTGC CGCGAAGTAC TCCGAGCTGG
      Consensus     ~~~~~~~~~~ ~~~~~~~~~~ ~~~~~~~~~~ ~~~~~~~~~~ ~~~~~~~~~~

101                                                                        150
SEQ ID NO:83        AAGAGGGCGG GCTCATAATG CAGGCCTTCT ACTGGGATGT TCCTGGAGGA
SEQ ID NO:85        AAGAGGGCGG GCTTATAATG CAGGCATTCT ATTGGGACGT CCCAGGTGGA
SEQ ID NO:75        AAGAGGGCGG GCTTATAATG CAGGCATTCT ACTGGGACGT CCCCATGGGA
SEQ ID NO:77        AAGAGGGCGG GCTCATAATG CAGGCCTTCT ACTGGGACGT CCCCATGGGA
SEQ ID NO:73        TAGAGGGCGG GCTTATAATG CAGGCCTTCT ACTGGGACGT CCCAGGTGGA
SEQ ID NO:79        AAGAGGGCGG CGTCATAATG CAGGCGTTCT ACTGGGACGT GCCTTCAGGA
SEQ ID NO:81        AAGAAGGCGG CGTTATAATG CAGGCCTTCT ACTGGGACGT CCCAGGTGGA
      CLONE A       AGCAGGGCGG AGTCATAATG CAGGCCTTCT ACTGGGACGT TCCGGAGGGA
      Consensus     -----GGCGG --T-ATAATG CAGGC-TTCT A-TGGGA-GT -CC----GGA 151                                                                        200
SEQ ID NO:83        GGAATCTGGT GGGACACAAT AGCTCAAAAG ATACCCGAAT GGGCAAGTGC
SEQ ID NO:85        GGAATCTGGT GGGACACCAT AGCCCAGAAG ATACCCGAAT GGGCAAGTGC
SEQ ID NO:75        GGAATCTGGT GGGACACGAT AGCCCAGAAG ATACCCGACT GGGCAAGCGC
SEQ ID NO:77        GGAATCTGGT GGGACACGAT AGCCCAGAAG ATACCCGACT GGGCAAGCGC
SEQ ID NO:73        GGAATCTGGT GGGACACCAT AGCCCAGAAG ATACCCGACT GGGCGAGCGC
SEQ ID NO:79        GGAATATGGT GGGACACAAT ACGGCAGAAG ATACCGGAGT GGTACGATGC
SEQ ID NO:81        GGAATCTGGT GGGACACCAT CAGGAGCAAG ATACCGGAGT GGTACGAGGC
      CLONE A       GGAATCTGGT GGGACACAAT ACGGCAGAAG ATCCCTGAAT GGTACGATGC
      Consensus     GGAAT-TGGT GGGACAC-AT -------AAG AT-CC-GA-T GG------GC 201                                                                        250
SEQ ID NO:83        AGGAATCTCA GCGATATGGA TTCCACCAGC GAGTAAGGGC ATGAGCGGTG
SEQ ID NO:85        AGGAATCTCA GCGATATGGA TTCCACCAGC GAGTAAGGGA ATGAGCGGTG
SEQ ID NO:75        CGGGATTTCG GCGATATGGA TTCCCCCGC GAGCAAGGGT ATGAGCGGCG
SEQ ID NO:77        CGGGATTTCG GCGATATGGA TCCCTCCCGC GAGCAAGGGT ATGAGCGGCG
SEQ ID NO:73        CGGGATTTCG GCAATATGGA TTCCTCCCGC GAGTAAGGGC ATGAGCGGCG
SEQ ID NO:79        CGGAATCTCC GCAATATGGA TTCCCCGGC GAGCAAGGGC ATGGGCGGCG
SEQ ID NO:81        GGGAATATCC GCCATTTGGA TTCCGCCAGC CAGCAAGGGG ATGAGCGGCG
      CLONE A       AGGCATATCC GCCATCTGGA TACCCCCGGC GAGCAAGGGC ATGGGCGGGG
      Consensus     -GG-AT-TC- GC-AT-TGGA T-CC-CC-GC -AG-AAGGG- ATG-GCGG-G
```

FIGURE 14C

```
              251                                                    300
SEQ ID NO:83  GTTATTCCAT GGGCTACGAT CCCTACGATT TCTTTGACCT CGGCGAGTAC
SEQ ID NO:85  GTTATTCCAT GGGCTACGAT CCCTACGATT TCTTTGACCT CGGCGAGTAC
SEQ ID NO:75  GCTATTCGAT GGGCTACGAC CCCTACGATT ATTTTGACCT CGGTGAGTAC
SEQ ID NO:77  GCTATTCGAT GGGCTACGAC CCCTACGATT ATTTTGACCT CGGTGAGTAC
SEQ ID NO:73  GCTATTCGAT GGGCTACGAC CCCTACGATT TCTTCGACCT CGGTGAGTAC
SEQ ID NO:79  CCTATTCGAT GGGCTACGAC CCCTACGACT TCTTTGACCT CGGTGAGTAC
SEQ ID NO:81  GTTACTCGAT GGGCTACGAT CCCTACGATT TCTTTGACCT CGGCGAGTAC
    CLONE A   CCTACTCGAT GGGCTACGAC CCCTACGATT ACTTCGATCT GGGCGAGTTT
    Consensus --TA-TC-AT GGGCTACGA- CCCTACGA-T --TT-GA-CT -GG-GAGT--

301                                                    350
SEQ ID NO:83  TATCAGAAGG GGACAGTTGA GACGCGCTTC GGCTCAAAGG AAGAACTGGT
SEQ ID NO:85  TATCAGAAGG GGACAGTTGA GACGCGCTTC GGCTCAAAGG AAGAACTGGT
SEQ ID NO:75  TACCAGAAGG GAACGGTGGA AACAAGATTC GGCTCAAAGC AGGAGCTCAT
SEQ ID NO:77  TACCAGAAGG GAACGGTGGA AACGAGGTTC GGCTCAAAGC AGGAGCTCAT
SEQ ID NO:73  TACCAGAAGG GAAGCGTTGA GACCCGCTTC GGATCAAAAG AGGAGCTTGT
SEQ ID NO:79  GACCAGAAGG GAACGGTAGA GACGCGCTTT GGCTCCAAGC AGGAGCTCGT
SEQ ID NO:81  AACCATCGA GAACCATCGA AACGCGCTTT GGCTCTAAAC AGGAGCTCAT
    CLONE A   TACCAGAAGG GAACCGTTGA GACCCGCTTC GGCTCCAAGG AAGAGCTCGT
    Consensus -A-CAGAAGG G-A---T-GA -AC--G-TT- GG-TC-AA-- A-GA-CT--T 351                                                    400
SEQ ID NO:83  GAACATGATA AACACCGCAC ACTCCTACGG CATAAAGGTG ATAGCAGACA
SEQ ID NO:85  GAACATGATA AACACCGCAC ACTCCTACGG CATAAAGGTG ATAGCGGACA
SEQ ID NO:75  AAACATGATA AACACCGCCC ACGCCTATGG CATGAAGGTA ATAGCCGATA
SEQ ID NO:77  AAACATGATA AACACCGCCC ACGCCTATGG CATGAAGGTA ATAGCCGATA
SEQ ID NO:73  GAACATGATA AACACCGCCC ATGCTCACAA CATGAAGGTC ATAGCGGACA
SEQ ID NO:79  GAACATGATA AACACCGCCC ACGCCTACGG CATCAAGGTC ATCGCAGACA
SEQ ID NO:81  CAATATGATA AACACGGCCC ATGCCTACGG CATAAAGGTC ATAGCGGACA
    CLONE A   CAACATGATC TCCACGGCCC ACCAGTACGG CATCAAGGTT ATAGCGGACA
    Consensus -AA-ATGAT- --CAC-GC-C A------A--- CAT-AAGGT- AT-GC-GA-A 401                                                    450
SEQ ID NO:83  TAGTCATAAA CCACCGCGCC GGTGGAGACC TTGAGTGGAA CCCCTTCGTG
SEQ ID NO:85  TAGTCATAAA CCACCGCGCC GGTGGAGGCC TCGAGTGGAA CCCCTTCGTG
SEQ ID NO:75  TAGTCATCAA CCACCGCGCC GGCGGCGATC TGGAGTGGAA CCCCTTCGTG
SEQ ID NO:77  TAGTCATCAA CCACCGCGCC GGCGGTGACC TGGAGTGGAA CCCCTTCGTG
SEQ ID NO:73  TAGTCATCAA CCACCGCGCC GGCGGCGACC TGGAGTGGAA TCCTTTCACC
SEQ ID NO:79  TAGTAATCAA CCACCGCGCC GGAGGAGACC TTGAGTGGAA CCCCTTCGTC
SEQ ID NO:81  TCGTCATAAA CCACCGCGCA GGCGGAGACC TCGAGTGGAA CCCGTTCGTT
    CLONE A   TAGTGATAAA CCACCGCGCA GGTGGAGACC TCGAATGGAA CCCATACGTC
    Consensus T-GT-AT-AA CCACCGCGC- GG-GG-G--C T-GA-TGGAA -CC-T-C---

451                                                    500
SEQ ID NO:83  AACGACTATA CCTGGACAGA CTTCTCAAAA GTCGCCTCCG GTAAATATAC
SEQ ID NO:85  AACGACTATA CCTGGACAGA CTTCTCAAAA GTCGCCTCCG GTAAATATAC
SEQ ID NO:75  AACGACTATA CCTGGACCGA CTTCTCGAAG GTCGCGTCGG GTAAATACAC
SEQ ID NO:77  AACGACTATA CCTGGACCGA CTTCTCAAAG GTCGCGTCGG GTAAATACAC
SEQ ID NO:73  AACAGCTACA CCTGGACCGA TTTCTCGAAG GTCGCGTCGG GCAAGTACAC
SEQ ID NO:79  AATGACTACA CCTGGACGGA CTTCTCGAAG GTCGCTTCCG GCAAGTACAC
SEQ ID NO:81  GGGGACTACA CCTGGACGGA CTTCTCAAAG GTGGCCTCGG GCAAATATAC
    CLONE A   GGCGACTATA CCTGGACGGA CTTTTCTAAG GTCGCCTCCG GGAAATACAA
    Consensus -----CTA-A CCTGGAC-GA -TT-TC-AA- GT-GC-TC-G G-AA-TA-A-
```

FIGURE 14C cont

```
                    501                                                    550
SEQ ID NO:83     GGCCAACTAC CTTGACTTCC ACCCAAACGA GCTTCACTGT TGTGATGAAG
SEQ ID NO:85     AGCCAACTAC CTTGACTTCC ACCCAAACGA GCTTCACTGT TGTGATGAAG
SEQ ID NO:75     GGCCAACTAC CTCGACTTCC ACCCGAACGA GCTCCACGCG GGCGATTCCG
SEQ ID NO:77     GGCCAACTAC CTCGACTTCC ACCCGAACGA GCTCCATGCG GGCGATTCCG
SEQ ID NO:73     GGCCAACTAC CTCGACTTCC ACCCGAACGA GCTTCACGCG GGCGATTCCG
SEQ ID NO:79     GGCCAACTAC CTCGACTTCC ACCCCAACGA GGTCAAGTGC TGCGACGAGG
SEQ ID NO:81     TGCCAACTAC CTCGACTTCC ACCCCAACGA GGTCAAGTGC TGTGACGAGG
    CLONE A      GGCCCACTAC ATGGACTTCC ATCCAAACAA CTACAGCACC TCAGACGAGG
    Consensus    -GCC-ACTAC -T-GACTTCC A-CC-AAC-A ---------- ---GA----G 551                                                    600
SEQ ID NO:83     GTACCTTTGG AGGATACCCT GATATATGTC ACGACAAAAG CTGGGACCAG
SEQ ID NO:85     GTACCTTTGG AGGATACCCT GATATATGTC ACGACAAAAG CTGGGACCAG
SEQ ID NO:75     GAACATTTGG AGGCTATCCC GACATATGCC ACGACAAGAG CTGGGACCAG
SEQ ID NO:77     GAACATTTGG AGGCTATCCC GACATATGCC ACGACAAGAG CTGGGACCAG
SEQ ID NO:73     GAACATTTGG AGGCTATCCC GACATATGCC ACGACAAGAG CTGGGACCAG
SEQ ID NO:79     GCACCTTTGG AGGGTTCCCG GACATAGCCC ACGAGAAGAG CTGGGACCAG
SEQ ID NO:81     GCACATTTGG AGGCTTCCCA GACATAGCCC ACGAGAAGAG CTGGGACCAG
    CLONE A      GAACCTCGG TGGCTTCCCA GACATTGATC ACCTCGTGCC CTTCAACCAG
    Consensus    G-AC-TT-GG -GG-T---CC- GA-AT----C AC-------- CT----ACCAG 601                                                    650
SEQ ID NO:83     TACTGGCTCT GGGCGAGCAG CGAAAGCTAC GCTGCCTACC TCAGGAGCAT
SEQ ID NO:85     TACTGGCTCT GGGCGAGCAG CGAAAGCTAC GCTGCCTACC TCAGGAGCAT
SEQ ID NO:75     TACTGGCTCT GGGCCAGCCA GGAGAGCTAC GCGGCCTATC TCAGGAGCAT
SEQ ID NO:77     TACTGGCTCT GGGCCAGCCA GGAGAGCTAC GCGGCATATC TCAGGAGCAT
SEQ ID NO:73     CACTGGCTCT GGGCCAGCAA CGAAAGCTAC GCCGCCTACC TCCGGAGCAT
SEQ ID NO:79     TACTGGCTCT GGGCGAGCAA CGAGAGCTAC GCCGCCTACC TCAGGAGCAT
SEQ ID NO:81     CACTGGCTCT GGGCGAGCGA TGAGAGCTAC GCCGCCTACC TAAGGAGCAT
    CLONE A      TACTGGCTGT GGGCGAGCAA CGAGAGCTAC GCCGCCTACC TCAGGAGCAT
    Consensus    -ACTGGCT-T GGGC-AGC-- -GA-AGCTAC GC-GC-TA-C T--GGAGCAT 651                                                    700
SEQ ID NO:83     AGGGGTTGAC GCCTGGCGTT TCGACTACGT CAAGGGCTAC GGAGCATGGG
SEQ ID NO:85     AGGGGTTGAC GCCTGGTGTT TCGACTACGT CAAGGGCTAC GGAGCCTGGG
SEQ ID NO:75     CGGCATCGAC GCCTGGCGCT TCGACTACGT CAAGGGCTAT GCTCCCTGGG
SEQ ID NO:77     CGGCATCGAT GCCTGGCGCT TCGACTACGT CAAGGGCTAT GCTCCCTGGG
SEQ ID NO:73     CGGCATCGAC GCCTGGCGCT TCGACTACGT CAAGGGCTAC GCTCCCTGGG
SEQ ID NO:79     CGGCGTTGAC GCATGGCGCT TCGACTACGT CAAGGGCTAC GGAGCGTGGG
SEQ ID NO:81     CGGCGTTGAT GCCTGGCGCT TTGACTACGT GAAGGGCTAC GGAGCGTGGG
    CLONE A      AGGGATCGAT GCGTGGCGCT TTGACTACGT TAAGGGCTAC GGCGCGTGGG
    Consensus    -GG--T-GA- GC-TGG-G-T T-GACTACGT -AAGGGCTA- G---C-TGGG 701                                                    750
SEQ ID NO:83     TTGTTAACGA CTGGCTCAGC TGGTGGGGAG GCTGGGCCGT TGGAGAGTAC
SEQ ID NO:85     TTGTTAACGA CTGGCTCAGC TGGTGGGGAG GCTGGGCCGT TGGAGAGTAC
SEQ ID NO:75     TCGTCAGGGA CTGGCTGAAC TGGTGGGGAG GCTGGGCAGT TGGAGAGTAC
SEQ ID NO:77     TCGTCAAGGA CTGGCTGAAC TGGTGGGGAG GCTGGGCGGT TGGAGAGTAC
SEQ ID NO:73     TCGTTAAGAA CTGGCTGAAC CGGTGGGGCG GCTGGGCGGT TGGAGAGTAC
SEQ ID NO:79     TCGTCAAGGA CTGGCTGGAC TGGTGGGGAG GCTGGGCCGT CGGGGAGTAC
SEQ ID NO:81     TCGTCAAGGA CTGGCTCAAC TGGTGGGCG GCTGGGCCGT TGGCGAGTAC
    CLONE A      TCGTCAAGGA CTGGCTGAGT CAGTGGGGCG GCTGGGCCGT CGGCGAGTAC
    Consensus    T-GT-A---A CTGGCT---- --GTGGGG-G GCTGGGC-GT -GG-GAGTAC
```

FIGURE 14C cont

```
              751                                                    800
SEQ ID NO:83  TGGGACACGA ACGTTGATGC ACTCCTCAAC TGGGCATACA GCAGCGGCGC
SEQ ID NO:85  TGGGACACTA ACGTTGATGC ACTCCTCAAC TGGGCATACA ACAGCGGCGC
SEQ ID NO:75  TGGGACACCA ACGTCGACGC TGTTCTCAAC TGGGCATACT CGAGCGGTGC
SEQ ID NO:77  TGGGACACCA ACGTCGACGC TGTTCTCAAC TGGGCATACT CGAGCGGTGC
SEQ ID NO:73  TGGGACACCA ACGTCGATGC ACTCCTGAGC TGGGCCTACG ACAGCGGTGC
SEQ ID NO:79  TGGGACACAA ACGTTGATGC ACTGCTCAAC TGGGCCTACT CGAGCGATGC
SEQ ID NO:81  TGGGACACCA ACGTTGATGC ACTCCTCAAC TGGGCCTACT CGAGCGGCGC
    CLONE A   TGGGACACCA ACGTCGATGC GCTCCTCAAC TGGGCCTACA GCAGCGGCGC
    Consensus TGGGACAC-A ACGT-GA-GC --T-CT-A-C TGGGC-TAC- --AGCG--GC 801                                                    850
SEQ ID NO:83  CAAGGTCTTT GACTTCCCGC TCTACTACAA GATGGACGAA GCCTTCGACA
SEQ ID NO:85  CAAGGTCTTT GACTTCCCGC TCTACTACAA GATGGACGAA GCCTTCGACA
SEQ ID NO:75  CAAGGTCTTT GACTTCGCCC TCTACTACAA GATGGACGAG GCCTTCGATA
SEQ ID NO:77  CAAGGTCTTT GACTTCGCCC TCTACTACAA GATGGACGAG GCCTTCGATA
SEQ ID NO:73  TAAAGTCTTC GACTTCCCGC TCTACTACAA GATGGACGAG GCCTTCGATA
SEQ ID NO:79  AAAAGTCTTC GACTTCCCGC TCTACTACAA GATGGACGCG GCCTTTGACA
SEQ ID NO:81  CAAGGTCTTC GACTTCCCGC TCTACTACAA GATGGATGAG GCCTTTGACA
    CLONE A   CAAGGTCTTC GACTTCCCGC TCTACTACAA GATGGACGAG GCCTTTGACA
    Consensus -AA-GTCTT- GACTTC-C-C TCTACTACAA GATGGA-G-- GCCTT-GA-A 851                                                    900
SEQ ID NO:83  ACACCAACAT CCCGGCATTA GTGGATGCAC TCAGATACGG CCAGACAGTG
SEQ ID NO:85  ATACCAACAT CCCCGCTTTG GTTTACGCCC TCAAGAATGG CGGGACAGTG
SEQ ID NO:75  ACAACAACAT TCCCGCCCTG GTGGACGCCC TCAGATACGG CCAGACAGTG
SEQ ID NO:77  ACAACAACAT TCCCGCCCTG GTGGACGCCC TCAGATACGG TCAGACAGTG
SEQ ID NO:73  ACAACAACAT CCCCGCCCTC GTGGACGCCC TCAAGAACGG AGGCACGGTC
SEQ ID NO:79  ACAAGAACAT TCCCGCACTC GTCGAGGCCC TCAAGAACGG GGGCACAGTC
SEQ ID NO:81  ACAAAAACAT TCCAGCGCTC GTCTCTGCCC TTCAGAACGG CCAGACTGTT
    CLONE A   ACAAGAACAT TCCCGCCCTC GTTTACGCCA TCAGAACGG TGAAACCGTC
    Consensus A-A--AACAT -CC-GC--T- GT----GC-- T-----A-GG ----AC-GT- 901                                                    950
SEQ ID NO:83  GTCAGCCGCG ATCCCTTCAA GGCGGTAACT TTCGTTGCCA ACCACGATAC
SEQ ID NO:85  GTCAGCCGCG ACCCATTCAA GGCGGTAACT TTCGTTGCCA ACCACGATAC
SEQ ID NO:75  GTCAGCCGCG ACCCGTTCAA GGCTGTGACG TTTGTAGCCA ACCACGATAC
SEQ ID NO:77  GTCAGCCGCG ACCCGTTCAA GGCTGTGACG TTTGTAGCCA ACCACGATAC
SEQ ID NO:73  GTCAGCCGCG ACCCGTTCAA AGCCGTGACC TTCGTTGCCA ACCACGATAC
SEQ ID NO:79  GTCAGCCGCG ACCCGTTTAA GGCCGTAACC TTCGTTGCAA ACCACGACAC
SEQ ID NO:81  GTCTCCCGCG ACCCGTTCAA GGCCGTAACC TTTGTAGCAA ACCACGACAC
    CLONE A   GTCAGCAGGG ATCCCTTCAA GGCCGTTACC TTCGTGGCTA ACCACGATAC
    Consensus GTC--C-G-G A-CC-TT-AA -GC-GT-AC- TT-GT-GC-A ACCACGA-AC 951                                                    1000
SEQ ID NO:83  AGATATAATC TGGAACAAGT ATCCGGCTTA TGCATTCATC CTTACCTATG
SEQ ID NO:85  AGATATAATC TGGAACAAGT ATCCGGCTTA TGCATTCATC CTTACCTATG
SEQ ID NO:75  CGACATAATC TGGAACAAGT ATCCAGCCTA CGCGTTCATC CTCACCTACG
SEQ ID NO:77  CGACATAATC TGGAACAAGT ATCCAGCCTA CGCGTTCATC CTCACCTACG
SEQ ID NO:73  CAACATAATC TGGAACAAGT ATCCGGCCTA CGCCTTCATC CTCACCTATG
SEQ ID NO:79  GGACATAATT TGGAACAAGT ACCCGGCCTA CGCCTTCATC CTCACCTACG
SEQ ID NO:81  CGATATAATC TGGAACAAGT ACCTTGCTTA TGCTTTCATC CTCACCTACG
    CLONE A   GAACATAATC TGGAACAAGT ACCCTGCCTA TGCCTTCATC CTGACCTACG
    Consensus --A-ATAAT- TGGAACAAGT A-C--GC-TA -GC-TTCATC CT-ACCTA-G
```

FIGURE 14C cont

```
                    1001                                                    1050
SEQ ID NO:83    AGGGACAGCC TGTTATATTC TACCGCGACT ACGAGGAGTG GCTCAACAAG
SEQ ID NO:85    AGGGACAGCC TGTTATATTC TACCGCGACT ACGAGGAGTG GCTCAACAAG
SEQ ID NO:75    AGGGCCAGCC GACAATATTC TACCGCGACT ACGAGGAGTG GCTCAACAAG
SEQ ID NO:77    AGGGCCAGCC GACAATATTC TACCGCGACT ACGAGGAGTG GCTCAACAAG
SEQ ID NO:73    AGGGACAGCC GGCAATATTC TACCGCGACT ACGAGGAGTG GCTCAACAAG
SEQ ID NO:79    AGGGCCAGCC GACGATATTC TACCGCGACT ACGAGGAGTG GCTCAACAAG
SEQ ID NO:81    AAGGCCAGCC CGTCATATTT TACCGCGACT ACGAGGAGTG GCTCAACAAG
    CLONE A     AAGGTCAGCC CGTCATCTTC TACCGCGACT ACGAGGAGTG GCTCAACAAG
    Consensus   A-GG-CAGCC ----AT-TT- TACCGCGACT ACGAGGAGTG GCTCAACAAG 1051                                                    1100
SEQ ID NO:83    GATAAGCTTA ACAACCTCAT CTGGATACAC GATCACCTTG CTGGAGGGAG
SEQ ID NO:85    GATAAGCTTA ACAACCTCAT CTGGATACAC GATCACCTTG CTGGAGGGAG
SEQ ID NO:75    GACAAGCTCA AGAACCTCAT CTGGATACAT GACAACCTCG CCGGAGGGAG
SEQ ID NO:77    GATAAGCTCA AGAACCTCAT CTGGATACAT GACAACCTCG CCGGAGGGAG
SEQ ID NO:73    GACAGGCTCA GGAACCTCAT CTGGATACAC GACCACCTCG CGGGAGGAAG
SEQ ID NO:79    GACAGGCTCA AGAACCTCAT CTGGATACAC GACCACCTCG CCGGTGGAAG
SEQ ID NO:81    GACAGGTTGA ACAACCTCAT ATGGATACAC GACCACCTCG CAGGTGGAAG
    CLONE A     GACAAACTCA ACAACCTCAT ATGGATTCAC GAGCACCTGG CAGGGGGAAG
    Consensus   GA-A---T-A --AACCTCAT -TGGAT-CA- GA--ACCT-G C-GG-GG-AG 1101                                                    1150
SEQ ID NO:83    TACTGACATT GTTTACTACG ACAGCGACGA GCTTATCTTT GTGAGAAACG
SEQ ID NO:85    TACTGACATT GTTTACTACG ACAGCGACGA GCTTATCTTT GTGAGAAACG
SEQ ID NO:75    CACTGACATC GTTTACTACG ACAACGACGA GCTGATATTC GTGAGAAACG
SEQ ID NO:77    CACTGACATC GTTTACTACG ACAACGACGA GCTGATATTC GTGAGAAACG
SEQ ID NO:73    CACAGACATC ATCTACTACG ACAGCGACGA GCTTATCTTC GTGAGAAACG
SEQ ID NO:79    CACCGACATA GTCTACTACG ATAACGATGA ACTCATCTTC GTCAGGAACG
SEQ ID NO:81    CACGAGCATA GTTTACTACG ACAGCGACGA GATGATTTTC GTGAGGAACG
    CLONE A     CACCAAGATC CTCTACTACG ACGACGATGA GCTCATCTTC ATGAGGGAAG
    Consensus   -AC----AT- -T-TACTACG A---CGA-GA --T-AT-TT- -T-AG---A-G 1151                                                    1200
SEQ ID NO:83    GCTATGGCAC CAAACCAGGA CTGATAACCT ATATCAACCT CGGCTCAAGC
SEQ ID NO:85    GCTATGGCAC CAAACCAGGA CTGATAACCT ATATCAACCT CGGCTCAAGC
SEQ ID NO:75    GCTACGAAG  CAAGCCGGGA CTGATAACAT ACATCAACCT CGGCTCAAGC
SEQ ID NO:77    GCTACGAAG  CAAGCCGGGA CTGATAACAT ACATCAACCT CGCCTCAAGC
SEQ ID NO:73    GCTACGGGA  CAAGCCGGGA CTGATAACCT ACATCAACCT CGGCTCAAGC
SEQ ID NO:79    GCTACGGGA  CAAGCCGGGG CTTATAACCT ACATCAACCT AGGCTCGAGC
SEQ ID NO:81    GCTATGGAAG  CAAGCCTGGC CTTATAACTT ACATCAACCT CGGCTCGAGC
    CLONE A     GCTACGGCGA CAGGCCCGGG CTTATAACCT ACATCAACCT CGGTAGCGAC
    Consensus   GCTA-GG--- CA--CC-GG- CT-ATAAC-T A-ATCAACCT -G------C 1201                                                    1250
SEQ ID NO:83    AAAGTTGGAA GGTGGGTCTA CGTT...CCA AAGTTCGCCG GTTCATGCAT
SEQ ID NO:85    AAAGCTGGAA GGTGGGTCTA CGTT...CCA AAGTTCGCCG GTTCATGCAT
SEQ ID NO:75    AAAGCCGGAA GGTGGGTTTA CGTT...CCG AAGTTCGCAG GCTCGTGCAT
SEQ ID NO:77    AAAGCCGGAA GGTGGGTTTA CGTT...CCG AAGTTCGCAG GCTCGTGCAT
SEQ ID NO:73    AAGGCCGGAA GGTGGGTCTA CGTT...CCG AAGTTCGCAG GCTCGTGCAT
SEQ ID NO:79    AAGGCCGGGA GGTGGGTCTA CGTT...CCG AAGTTCGCGG GAGCGTGCAT
SEQ ID NO:81    AAGGTTGGAA GGTGGGTTTA TGTG...CCG AAGTTCGCGG GCGCGTGCAT
    CLONE A     TGGGCGGAGA GATGGGTGAA CGTTGGCTCA AAGTTCGCGG GCTATACAAT
    Consensus   ---G--G--A G-TGGGT--A -GT-----C- AAGTTCGC-G G-------AT
```

FIGURE 14C cont

```
                  1251                                                    1300
SEQ ID NO:83      CCACGAGTAC ACCGGCAACC TCGGCGGTTG GATAGACAAG TACGTCTCCT
SEQ ID NO:85      CCACGAGTAC ACCGGCAGCC TCGGCGGTTG GATAGACAAG TACGTCTCCT
SEQ ID NO:75      ACACGAGTAC ACCGGCAACC TCGGCGGCTG GGTGGACAAG TGGGTGGACT
SEQ ID NO:77      ACACGAGTAC ACCGGCAATC TCGGCGGCTG GGTGGACAAG TGGGTGGACT
SEQ ID NO:73      ACACGAGTAC ACCGGCAACC TCGGCGGCTG GATTGACAAG TGGGTTGACT
SEQ ID NO:79      CCACGAGTAC ACCGGCAACC TCGGCGGCTG GGTGGACAAG TGGGTGGACT
SEQ ID NO:81      CCACGAGTAT ACTGGTAACC TCGGAGGCTG GGTAGACAAG TACGTCTACT
     CLONE A      CCACGAATAC ACCGGAAACC TCGGCGGCTG GGTCGACAGG TACGTCCAGT
     Consensus    -CACGA-TA- AC-GG-A--C TCGG-GG-TG G-T-GACA-G T--GT----T 1301                                                    1350
SEQ ID NO:83      CCAGCGGCTG GGTCTATCTT GAGGCCCCAG CCCACGACCC GGCGAACGGC
SEQ ID NO:85      CCAGCGGCTG GGTCTACCTT GAGGCCCCGG CCCACGACCC GGCCAATGGC
SEQ ID NO:75      CAAGCGGCTG GGTTTACCTC GAGGCTCCTG CCCACGACCC GGCCAACGGC
SEQ ID NO:77      CAAGCGGCTG GGTCTACCTC GAGGCTCCTG CCCACGACCC GGCCAACGGC
SEQ ID NO:73      CAAGCGGTCG GGTCTACCTT GAGGCCCCCG CCCACGACCC GGCCAACGGC
SEQ ID NO:79      CAAGCGGGTG GGTGTACCTC GAGGCCCCTG CCCACGACCC GGCCAACGGC
SEQ ID NO:81      CAAGCGGCTG GGTCTATTTC GAAGCTCCAG CTTACGACCC TGCCAACGGG
     CLONE A      ACGACGGCTG GGTCAAGCTT ACCGCTCCGC CACACGATCC GGCAAACGGC
     Consensus    ----CGG---G GGT--A--T- ---GC-CC-- C--ACGA-CC -GC-AA-GG- 1351                                              1393
SEQ ID NO:83      TACTACGGCT ACTCCGTATG GAGCTACTGC GGGGTTGGGT GA~
SEQ ID NO:85      CAGTATGGCT ACTCCGTCTG GAGCTATTGC GGGGTTGGGT GA~
SEQ ID NO:75      CAGTACGGCT ACTCCGTTTG GAGCTATTGC GGTGTTGGGT GA~
SEQ ID NO:77      CAGTACGGCT ACTCCGTCTG GAGCTACTGC GGTGTTGGGT GA~
SEQ ID NO:73      CAGTACGGCT ACTCCGTATG GAGCTACTGC GGTGTTGGGT GA~
SEQ ID NO:79      TATTACGGCT ACTCCGTCTG GAGCTACTGC GGGGTGGGCT GA~
SEQ ID NO:81      CAGTATGGCT ACTCCGTGTG GAGCTATTGC GGTGTTGGGT GA~
     CLONE A      TATTACGGCT ACTCGGTCTG GAGCTACGCC GGAGTTGGAT GA~
     Consensus    -A-TA-GGCT ACTC-GT-TG GAGCTA---C GG-GT-GG-T GA~
```

FIGURE 14C cont

Neighbor-joining tree for Thermococcales

Summit & Baross, Deep-Sea Research Pt. II, in press

FIGURE 16A (all sequences are listed in 5' to 3' order)
SEQ ID NO.: 1
```
atggcaaagtattccgagctcgaagagggcgggctcataatgcaggccttctactgggacgtccc
catgggaggaatctggtgggacacgatagcccagaagataccgactgggcaagcgccgggattt
cggcgatatggattccccggcgagcaagggcatggcggcgcctattcgatgggctacgacccc
tacgacttctttgacctcggtgagtacgaccagaagggaacggtagagacgcgctttggctccaa
gcaggagctcgtgaacatgataaacaccgccacgcctatggcatgaaggtaatagccgatatag
tcatcaaccaccgcgccggcggtgacctggagtggaacccttcgtgaacgactatacctggacc
gacttctcaaaggtcgcgtcgggtaaatacacggccaactacctcgacttccacccgaacgagct
ccatgcgggcgattccggaacatttggaggctatcccgacatatgccacgacaagagctgggacc
agtactggctctggccagccaggagagctacgcggcatatctcaggagcatcggcatcgatgcc
tggcgcttcgactacgtcaagggctacggagcgtgggtcgtcaaggactggctggactggtgggg
aggctgggccgtcggggagtactgggacacaaacgttgatgcactgctcaactgggcctactcga
gcgatgcaaaagtcttcgacttcccgctctactacaagatggacgcggcctttgacaacaagaac
attcccgcactcgtcgaggccctcaagaacggggcacagtcgtcagccgcgacccgtttaaggc
cgtaaccttcgttgcaaaccacgacaccgatataatctggaacaagtatccagcctacgcgttca
tcctcacctacgagggccagccgacaatattctaccgcgactacgaggagtggctcaacaaggat
aagctcaagaacctcatctggatacatgacaacctcgccggaggaagcactgacatcgtttacta
cgacaacgacgagctgatattcgtgagaaacggctacggaagcaagccgggactgataacataca
tcaacctcgcctcaagcaaagccggaaggtgggtttacgttccgaagttcgcaggctcgtgcata
cacgagtacaccggcaatctcggcggctgggtggacaagtgggtggactcaagcggctgggtcta
cctcgaggctcctgcccacgacccggccaacggccagtacggctactccgtctggagctactgcg
gtgttgggtga
```
FIGURE 16B
SEQ ID NO.: 2
```
Met Ala Lys Tyr Ser Glu Leu Glu Glu Gly Gly Leu Ile Met Gln Ala
Phe Tyr Trp Asp Val Pro Met Gly Gly Ile Trp Trp Asp Thr Ile Ala
Gln Lys Ile Pro Asp Trp Ala Ser Ala Gly Ile Ser Ala Ile Trp Ile
Pro Pro Ala Ser Lys Gly Met Gly Gly Ala Tyr Ser Met Gly Tyr Asp
Pro Tyr Asp Phe Phe Asp Leu Gly Glu Tyr Asp Gln Lys Gly Thr Val
Glu Thr Arg Phe Gly Ser Lys Gln Glu Leu Val Asn Met Ile Asn Thr
Ala His Ala Tyr Gly Met Lys Val Ile Ala Asp Ile Val Ile Asn His
Arg Ala Gly Gly Asp Leu Glu Trp Asn Pro Phe Val Asn Asp Tyr Thr
Trp Thr Asp Phe Ser Lys Val Ala Ser Gly Lys Tyr Thr Ala Asn Tyr
Leu Asp Phe His Pro Asn Glu Leu His Ala Gly Asp Ser Gly Thr Phe
Gly Gly Tyr Pro Asp Ile Cys His Asp Lys Ser Trp Asp Gln Tyr Trp
Leu Trp Ala Ser Gln Glu Ser Tyr Ala Ala Tyr Leu Arg Ser Ile Gly
Ile Asp Ala Trp Arg Phe Asp Tyr Val Lys Gly Tyr Gly Ala Trp Val
Val Lys Asp Trp Leu Asp Trp Trp Gly Gly Trp Ala Val Gly Glu Tyr
Trp Asp Thr Asn Val Asp Ala Leu Leu Asn Trp Ala Tyr Ser Ser Asp
Ala Lys Val Phe Asp Phe Pro Leu Tyr Tyr Lys Met Asp Ala Ala Phe
Asp Asn Lys Asn Ile Pro Ala Leu Val Glu Ala Leu Lys Asn Gly Gly
Thr Val Val Ser Arg Asp Pro Phe Lys Ala Val Thr Phe Val Ala Asn
His Asp Thr Asp Ile Ile Trp Asn Lys Tyr Pro Ala Tyr Ala Phe Ile
Leu Thr Tyr Glu Gly Gln Pro Thr Ile Phe Tyr Arg Asp Tyr Glu Glu
Trp Leu Asn Lys Asp Lys Leu Lys Asn Leu Ile Trp Ile His Asp Asn
Leu Ala Gly Gly Ser Thr Asp Ile Val Tyr Tyr Asp Asn Asp Glu Leu
Ile Phe Val Arg Asn Gly Tyr Gly Ser Lys Pro Gly Leu Ile Thr Tyr
Ile Asn Leu Ala Ser Ser Lys Ala Gly Arg Trp Val Tyr Val Pro Lys
Phe Ala Gly Ser Cys Ile His Glu Tyr Thr Gly Asn Leu Gly Gly Trp
Val Asp Lys Trp Val Asp Ser Ser Gly Trp Val Tyr Leu Glu Ala Pro
Ala His Asp Pro Ala Asn Gly Gln Tyr Gly Tyr Ser Val Trp Ser Tyr
Cys Gly Val Gly
```

FIGURE 16C

SEQ ID NO.: 3 atggccaagtacctggagctcgaagagggcgggctcataatgcaggccttctactgggacgtccc
catgggaggaatctggtgggacacgatagcccagaagatacccgactgggcaagcgccgggattt
cggcgatatggattccccggcgagcaagggcatggcggcgcctattcgatgggctacgacccc
tacgacttctttgacctcggtgagtacgaccagaagggaacggtagagacgcgctttggctccaa
gcaggagctcgtgaacatgataaacaccgcccacgcctacggcatcaaggtcatcgcagacatag
taatcaaccacgcgccggaggagaccttgagtggaacccccttcgtcaatgactacacctggacg
gacttctcgaaggtcgcttccggcaagtacacggccaattacctcgacttccacccgaacgagct
ccatgcgggcgattccggaacatttggaggctatcccgacatatgccacgacaagagctgggacc
agtactggctctgggccagccaggagagctacgcggcatatctcaggagcatcggcatcgatgcc
tggcgcttcgactacgtcaagggctatgctccctgggtcgtcaaggactggctgaactggtgggg
aggctgggcggttggagagtactgggacaccaacgtcgacgctgttctcaactgggcatactcga
gcggtgccaaggtctttgacttcgccctctactacaagatggatgaggcctttgacaacaaaaac
attccagcgctcgtctctgcccttcagaacggccagactgttgtctcccgcgacccgttcaaggc
cgtaacctttgtagcaaaccacgacaccgatataatctggaacaagtatccagcctacgcgttca
tcctcacctacgagggccagccgacaatattctaccgcgactacgaggagtggctcaacaaggat
aagctcaagaacctcatctggatacatgacaacctcgccggaggaagcactgacatcgtttacta
cgacaacgacgagctgatattcgtgagaaacggctacggaagcaagccgggactgataacataca
tcaacctcgcctcaagcgaagccggaaggtgggtctacgttccgaagttcgcgggagcgtgcatc
cacgagtacaccggcaacctcggcggctgggtggacaagtgggtggactcaagcgggtgggtgta
cctcgaggcccctgcccacgaccggccaacggctattacggctactccgtctggagctattgcg
gtgttgggtga

FIGURE 16D

SEQ ID NO.: 4

Met Ala Lys Tyr Leu Glu Leu Glu Glu Gly Gly Leu Ile Met Gln Ala
Phe Tyr Trp Asp Val Pro Met Gly Gly Ile Trp Trp Asp Thr Ile Ala
Gln Lys Ile Pro Asp Trp Ala Ser Ala Gly Ile Ser Ala Ile Trp Ile
Pro Pro Ala Ser Lys Gly Met Gly Gly Ala Tyr Ser Met Gly Tyr Asp
Pro Tyr Asp Phe Phe Asp Leu Gly Glu Tyr Asp Gln Lys Gly Thr Val
Glu Thr Arg Phe Gly Ser Lys Gln Glu Leu Val Asn Met Ile Asn Thr
Ala His Ala Tyr Gly Ile Lys Val Ile Ala Asp Ile Val Ile Asn His
Arg Ala Gly Gly Asp Leu Glu Trp Asn Pro Phe Val Asn Asp Tyr Thr
Trp Thr Asp Phe Ser Lys Val Ala Ser Gly Lys Tyr Thr Ala Asn Tyr
Leu Asp Phe His Pro Asn Glu Leu His Ala Gly Asp Ser Gly Thr Phe
Gly Gly Tyr Pro Asp Ile Cys His Asp Lys Ser Trp Asp Gln Tyr Trp
Leu Trp Ala Ser Gln Glu Ser Tyr Ala Ala Tyr Leu Arg Ser Ile Gly
Ile Asp Ala Trp Arg Phe Asp Tyr Val Lys Gly Tyr Ala Pro Trp Val
Val Lys Asp Trp Leu Asn Trp Trp Gly Gly Trp Ala Val Gly Glu Tyr
Trp Asp Thr Asn Val Asp Ala Val Leu Asn Trp Ala Tyr Ser Ser Gly
Ala Lys Val Phe Asp Phe Ala Leu Tyr Tyr Lys Met Asp Glu Ala Phe
Asp Asn Lys Asn Ile Pro Ala Leu Val Ser Ala Leu Gln Asn Gly Gln
Thr Val Val Ser Arg Asp Pro Phe Lys Ala Val Thr Phe Val Ala Asn
His Asp Thr Asp Ile Ile Trp Asn Lys Tyr Pro Ala Tyr Ala Phe Ile
Leu Thr Tyr Glu Gly Gln Pro Thr Ile Phe Tyr Arg Asp Tyr Glu Glu
Trp Leu Asn Lys Asp Lys Leu Lys Asn Leu Ile Trp Ile His Asp Asn
Leu Ala Gly Gly Ser Thr Asp Ile Val Tyr Tyr Asp Asn Asp Glu Leu
Ile Phe Val Arg Asn Gly Tyr Gly Ser Lys Pro Gly Leu Ile Thr Tyr
Ile Asn Leu Ala Ser Ser Glu Ala Gly Arg Trp Val Tyr Val Pro Lys
Phe Ala Gly Ala Cys Ile His Glu Tyr Thr Gly Asn Leu Gly Gly Trp
Val Asp Lys Trp Val Asp Ser Ser Gly Trp Val Tyr Leu Glu Ala Pro
Ala His Asp Pro Ala Asn Gly Tyr Tyr Gly Tyr Ser Val Trp Ser Tyr
Cys Gly Val Gly

FIGURE 16E
SEQ ID NO.: 5
atggccaagtactccgagctggaagagggcggcgttataatgcaggccttctactgggacgtccc
aggtggaggaatctggtgggacaccatcaggagcaagataccggagtggtacgaggcgggaatat
ccgccatttggattccccggcaagcaagggcatgggcggcgcctattcgatggctacgacccc
tacgacttctttgacctcggtgagtacgaccagaagggaacggtagagacgcgctttggctccaa
gcaggagctcgtgaacatgataaacaccgccacgcctatggcatgaaggtaatagccgatatag
tcatcaaccaccgcgccggcggtgacctggagtggaaccccttcgtgaacgactatacctggacc
gacttctcaaaggtcgcgtcgggtaaatacacggccaactacctcgacttccacccgaacgagct
ccatgcgggcgattccggaacatttggaggctatcccgacatatgccacgacaagagctgggacc
agtactggctctgggccagccaggagagctacgcggcatatctcaggagcatcggcatcgatgcc
tggcgcttcgactacgtcaagggctatgctcctgggtcgtcaaggactggctgaactggtgggg
aggctgggcggttggagagtactgggacaccaacgtcgacgctgttctcaactgggcatactcga
gcggtgccaaggtctttgacttcgccctctactacaagatggatgaggcctttgacaacaaaaac
attccagcgctcgtctctgcccttcagaacggccagactgttgtctcccgcgacccgttcaaggc
cgtaacctttgtagcaaaccacgacaccgatataatctggaacaagtaccttgcttatgctttca
tcctcacctacgaaggccagcccgtcatattctaccgcgaccacgaggagtggctcaacaaggac
aggttgaacaacctcatatggatacacgaccacctcgcaggtggaagcaccgacatagtctacta
cgataacgatgaactcatcttcgtcaggaacggctacggggacaagccggggcttataacctaca
tcaacctaggctcgagcaaggccggaaggtgggtttatgtgccgaagttcgcgggcgcgtgcatc
cacgagtatactggtaacctcggaggctgggtagacaagtacgtctactcaagcggctgggtcta
tctcgaagctccagcttacgaccctgccaacgggcagtatggctactccgtgtggagctactgcg
gggtgggctga
FIGURE 16F
SEQ ID NO.: 6
Met Ala Lys Tyr Ser Glu Leu Glu Glu Gly Gly Val Ile Met Gln Ala
Phe Tyr Trp Asp Val Pro Gly Gly Gly Ile Trp Trp Asp Thr Ile Arg
Ser Lys Ile Pro Glu Trp Tyr Glu Ala Gly Ile Ser Ala Ile Trp Ile
Pro Pro Ala Ser Lys Gly Met Gly Gly Ala Tyr Ser Met Gly Tyr Asp
Pro Tyr Asp Phe Phe Asp Leu Gly Glu Tyr Asp Gln Lys Gly Thr Val
Glu Thr Arg Phe Gly Ser Lys Gln Glu Leu Val Asn Met Ile Asn Thr
Ala His Ala Tyr Gly Met Lys Val Ile Ala Asp Ile Val Ile Asn His
Arg Ala Gly Gly Asp Leu Glu Trp Asn Pro Phe Val Asn Asp Tyr Thr
Trp Thr Asp Phe Ser Lys Val Ala Ser Gly Lys Tyr Thr Ala Asn Tyr
Leu Asp Phe His Pro Asn Glu Leu His Ala Gly Asp Ser Gly Thr Phe
Gly Gly Tyr Pro Asp Ile Cys His Asp Lys Ser Trp Asp Gln Tyr Trp
Leu Trp Ala Ser Gln Glu Ser Tyr Ala Ala Tyr Leu Arg Ser Ile Gly
Ile Asp Ala Trp Arg Phe Asp Tyr Val Lys Gly Tyr Ala Pro Trp Val
Val Lys Asp Trp Leu Asn Trp Trp Gly Gly Trp Ala Val Gly Glu Tyr
Trp Asp Thr Asn Val Asp Ala Val Leu Asn Trp Ala Tyr Ser Ser Gly
Ala Lys Val Phe Asp Phe Ala Leu Tyr Tyr Lys Met Asp Glu Ala Phe
Asp Asn Lys Asn Ile Pro Ala Leu Val Ser Ala Leu Gln Asn Gly Gln
Thr Val Val Ser Arg Asp Pro Phe Lys Ala Val Thr Phe Val Ala Asn
His Asp Thr Asp Ile Ile Trp Asn Lys Tyr Leu Ala Tyr Ala Phe Ile
Leu Thr Tyr Glu Gly Gln Pro Val Ile Phe Tyr Arg Asp His Glu Glu
Trp Leu Asn Lys Asp Arg Leu Asn Asn Leu Ile Trp Ile His Asp His
Leu Ala Gly Gly Ser Thr Asp Ile Val Tyr Tyr Asp Asn Asp Glu Leu
Ile Phe Val Arg Asn Gly Tyr Gly Asp Lys Pro Gly Leu Ile Thr Tyr
Ile Asn Leu Gly Ser Ser Lys Ala Gly Arg Trp Val Tyr Val Pro Lys
Phe Ala Gly Ala Cys Ile His Glu Tyr Thr Gly Asn Leu Gly Gly Trp
Val Asp Lys Tyr Val Tyr Ser Ser Gly Trp Val Tyr Leu Glu Ala Pro
Ala Tyr Asp Pro Ala Asn Gly Gln Tyr Gly Tyr Ser Val Trp Ser Tyr
Cys Gly Val Gly

FIGURE 16G
SEQ ID NO.: 9
atggccaagtactccgagctggaagagggcgggctcataatgcaggccttctactgggacgtccc
catgggaggaatctggtgggacacgatagcccagaagatacccgactgggcaagcgccggattt
cggcgatatggattccccggcgagcaagggcatgggcggcgcctattcgatgggctacgacccc
tacgacttctttgacctcggtgagtacgaccagaagggaacggtagagacgcgctttggctccaa
gcaggagctcgtgaacatgataaacacggcccatgcctacggcataaaggtcatagcggacatcg
tcataaaccaccgcgcaggcggagacctcgagtggaacccgttcgttggggactacacctggacg
gacttctcaaaggtggcctcgggcaaatatactgccaactacctcgacttccacccgaacgagct
ccatgcgggcgattccggaacatttggaggctatcccgacatatgccacgacaagagctgggacc
agtactggctctgggccagccaggagagctacgcggcatatctcaggagcatcggcatcgatgcc
tggcgcttcgactacgtcaagggctatgctccctgggtcgtcaaggactggctgaactggtgggg
aggctggcggttggagagtactgggacaccaacgtcgacgctgttctcaactgggcatactcga
gcggtgccaaggtctttgacttcgccctctactacaagatggacgaggccttcgataacaacaac
attcccgccctggtggacgccctcagatacggtcagacagtggtcagccgcgacccgttcaaggc
tgtgacgtttgtagccaaccacgataccgatataatctggaacaagtatccagcctacgcgttca
tcctcacctacgagggccagccgacaatattctaccgcgactacgaggagtggctcaacaaggat
aagctcaagaacctcatctggatacatgacaacctcgccggaggaagcactgacatcgtttacta
cgacaacgacgagctgatattcgcgagaaacggctacggaagcaagccgggactgataacataca
tcaacctcgcctcaagcaaagccggaaggtgggtttacgttccgaagttcgcaggctcgtgcata
cacgagtacaccggcaatctcggcggctgggtggacaagtgggtggactcaagcggctggtcta
cctcgaggctcctgccacgacccggccaacggccagtacggctactccgtctggagctactgcg
gtgttgggtga

FIGURE 16H
SEQ ID NO.: 10
Met Ala Lys Tyr Ser Glu Leu Glu Glu Gly Gly Leu Ile Met Gln Ala
Phe Tyr Trp Asp Val Pro Met Gly Gly Ile Trp Trp Asp Thr Ile Ala
Gln Lys Ile Pro Asp Trp Ala Ser Ala Gly Ile Ser Ala Ile Trp Ile
Pro Pro Ala Ser Lys Gly Met Gly Gly Ala Tyr Ser Met Gly Tyr Asp
Pro Tyr Asp Phe Phe Asp Leu Gly Glu Tyr Asp Gln Lys Gly Thr Val
Glu Thr Arg Phe Gly Ser Lys Gln Glu Leu Val Asn Met Ile Asn Thr
Ala His Ala Tyr Gly Ile Lys Val Ile Ala Asp Ile Val Ile Asn His
Arg Ala Gly Gly Asp Leu Glu Trp Asn Pro Phe Val Gly Asp Tyr Thr
Trp Thr Asp Phe Ser Lys Val Ala Ser Gly Lys Tyr Thr Ala Asn Tyr
Leu Asp Phe His Pro Asn Glu Leu His Ala Gly Asp Ser Gly Thr Phe
Gly Gly Tyr Pro Asp Ile Cys His Asp Lys Ser Trp Asp Gln Tyr Trp
Leu Trp Ala Ser Gln Glu Ser Tyr Ala Ala Tyr Leu Arg Ser Ile Gly
Ile Asp Ala Trp Arg Phe Asp Tyr Val Lys Gly Tyr Ala Pro Trp Val
Val Lys Asp Trp Leu Asn Trp Trp Gly Gly Trp Ala Val Gly Glu Tyr
Trp Asp Thr Asn Val Asp Ala Val Leu Asn Trp Ala Tyr Ser Ser Gly
Ala Lys Val Phe Asp Phe Ala Leu Tyr Tyr Lys Met Asp Glu Ala Phe
Asp Asn Asn Asn Ile Pro Ala Leu Val Asp Ala Leu Arg Tyr Gly Gln
Thr Val Val Ser Arg Asp Pro Phe Lys Ala Val Thr Phe Val Ala Asn
His Asp Thr Asp Ile Ile Trp Asn Lys Tyr Pro Ala Tyr Ala Phe Ile
Leu Thr Tyr Glu Gly Gln Pro Thr Ile Phe Tyr Arg Asp Tyr Glu Glu
Trp Leu Asn Lys Asp Lys Leu Lys Asn Leu Ile Trp Ile His Asp Asn
Leu Ala Gly Gly Ser Thr Asp Ile Val Tyr Tyr Asp Asn Asp Glu Leu
Ile Phe Ala Arg Asn Gly Tyr Gly Ser Lys Pro Gly Leu Ile Thr Tyr
Ile Asn Leu Ala Ser Ser Lys Ala Gly Arg Trp Val Tyr Val Pro Lys
Phe Ala Gly Ser Cys Ile His Glu Tyr Thr Gly Asn Leu Gly Gly Trp
Val Asp Lys Trp Val Asp Ser Ser Gly Trp Val Tyr Leu Glu Ala Pro
Ala His Asp Pro Ala Asn Gly Gln Tyr Gly Tyr Ser Val Trp Ser Tyr
Cys Gly Val Gly

FIGURE 16I
SEQ ID NO.: 11
atggccaagtacctggagctcgaggagggcgggctcataatgcaggccttctactgggacgtccc
catgggaggaatctggtgggacacgatagcccagaagatacccgactgggcaagcgccgggattt
cggcgatatggattccccggcgagcaagggcatgggcggcgcctattcgatgggctacgacccc
tacgacttctttgacctcggtgagtacgaccagaagggaacggtagagacgcgctttggctccaa
gcaggagctcgtgaacatgataaacaccgcccacgcctatggcatgaaggtaatagccgatatag
tcatcaaccaccgcgccggcggtgacctggagtggaaccccttcgtgaacgactatacctggacc
gacttctcaaaggtcgcgtcgggtaaatacacggccaactacctcgacttccacccgaacgagct
ccatgcgggcgattccggaacatttggaggctatcccgacatatgccacgacaagagctgggacc
agtactggctctgggccagccaggagagctacgcggcatatctcaggagcatcggcatcgatgcc
tggcgcttcgactacgtcaaggctatgctccctgggtcgtcaaggactggctgaactggtgggg
aggctgggcggttggagagtactgggacaccaacgtcgacgctgttctcaactgggcatactcga
gcggtgccaaggtctttgacttcgccctctactacaagatggacgaggccttcgataacaacaac
attcccgccctggtggacgccctcagatacggtcagacagtggtcagccgcgacccgttcaaggc
tgtgacgtttgtagccaaccacgataccgatataatctggaacaagtatccagcctacgcgttca
tcctcacctacgagggccagccgacaatattctaccgcgactacgaggagtggctcaacaaggat
acgctcaagaacctcatctggatacatgacaacctcgccggaggaagcacgagcatagtttacta
cgacagcgacgagatgatcttcgtgaggaacggctatggaagcaagcctggccttataacttaca
tcaacctcggctcgagcaaggttggaaggtgggtctacgttccgaagttcgcgggagcgtgcatc
cacgagtacaccggcaacctcggcggctgggtggacaagtgggtggactcaagcgggtgggtgta
cctcgaggcccctgcccacgacccggccaacggctattacggctactccgtctggagctactgcg
gtgttggctga

FIGURE 16J
SEQ ID NO.: 12
Met Ala Lys Tyr Leu Glu Leu Glu Glu Gly Gly Leu Ile Met Gln Ala
Phe Tyr Trp Asp Val Pro Met Gly Gly Ile Trp Trp Asp Thr Ile Ala
Gln Lys Ile Pro Asp Trp Ala Ser Ala Gly Ile Ser Ala Ile Trp Ile
Pro Pro Ala Ser Lys Gly Met Gly Gly Ala Tyr Ser Met Gly Tyr Asp
Pro Tyr Asp Phe Phe Asp Leu Gly Glu Tyr Asp Gln Lys Gly Thr Val
Glu Thr Arg Phe Gly Ser Lys Gln Glu Leu Val Asn Met Ile Asn Thr
Ala His Ala Tyr Gly Met Lys Val Ile Ala Asp Ile Val Ile Asn His
Arg Ala Gly Gly Asp Leu Glu Trp Asn Pro Phe Val Asn Asp Tyr Thr
Trp Thr Asp Phe Ser Lys Val Ala Ser Gly Lys Tyr Thr Ala Asn Tyr
Leu Asp Phe His Pro Asn Glu Leu His Ala Gly Asp Ser Gly Thr Phe
Gly Gly Tyr Pro Asp Ile Cys His Asp Lys Ser Trp Asp Gln Tyr Trp
Leu Trp Ala Ser Gln Glu Ser Tyr Ala Ala Tyr Leu Arg Ser Ile Gly
Ile Asp Ala Trp Arg Phe Asp Tyr Val Lys Gly Tyr Ala Pro Trp Val
Val Lys Asp Trp Leu Asn Trp Trp Gly Gly Trp Ala Val Gly Glu Tyr
Trp Asp Thr Asn Val Asp Ala Val Leu Asn Trp Ala Tyr Ser Ser Gly
Ala Lys Val Phe Asp Phe Ala Leu Tyr Tyr Lys Met Asp Glu Ala Phe
Asp Asn Asn Asn Ile Pro Ala Leu Val Asp Ala Leu Arg Tyr Gly Gln
Thr Val Val Ser Arg Asp Pro Phe Lys Ala Val Thr Phe Val Ala Asn
His Asp Thr Asp Ile Ile Trp Asn Lys Tyr Pro Ala Tyr Ala Phe Ile
Leu Thr Tyr Glu Gly Gln Pro Thr Ile Phe Tyr Arg Asp Tyr Glu Glu
Trp Leu Asn Lys Asp Thr Leu Lys Asn Leu Ile Trp Ile His Asp Asn
Leu Ala Gly Gly Ser Thr Ser Ile Val Tyr Tyr Asp Ser Asp Glu Met
Ile Phe Val Arg Asn Gly Tyr Gly Ser Lys Pro Gly Leu Ile Thr Tyr
Ile Asn Leu Gly Ser Ser Lys Val Gly Arg Trp Val Tyr Val Pro Lys
Phe Ala Gly Ala Cys Ile His Glu Tyr Thr Gly Asn Leu Gly Gly Trp
Val Asp Lys Trp Val Asp Ser Ser Gly Trp Val Tyr Leu Glu Ala Pro
Ala His Asp Pro Ala Asn Gly Tyr Tyr Gly Tyr Ser Val Trp Ser Tyr
Cys Gly Val Gly

FIGURE 16K
SEQ ID NO.: 13
atggccaagtacctggagctcgaagagggcggggtcataatgcaggcgttctactgggacgtgcc
ttcaggaggaatatggtgggacacaatacggcagaagataccggagtggtacgatgccggaatct
ccgcaatatggattccccggcgagcaagggcatgggcggcgcctattcgatgggctacgacccc
tacgacttctttgacctcggtgagtatgaccagaagggaacggtagagacgcgctttggctccaa
gcaggagctcgtgaacatgataaacacggcacatgcctacggcataaaggtcatagcggacatcg
tcataaaccaccgcgcaggcggagacctcgagtggaacccgttcgttggggactacacctggacg
gacttctcaaaggtggcctcgggcaaatatactgccaactacctcgacttccaccccaacgaggt
caagtgctgtgacgagggcacatttggaggcttcccagacatagcccacgagaagagctgggacc
agcactggctctgggcgagcgatgagagctacgccgcctacctaaggagcatcggcgttgatgcc
tggcgcttcgactacgtcaagggctacggagcgtgggtcgtcaaggactggctggactggtgggg
aggctgggccgtcggggagtactgggacacaaacgttgatgcactgctcaactgggcctactcga
gcgatgcaaaagtcttcgacttcccgctctactacaagatggatgaggcctttgacaacaaaaac
attccagcgctcgtctctgcccttcagaacggccagactgttgtctcccgcgacccgttcaaggc
cgtaacctttgtagcaaaccacgacaccgatataatctggaacaagtatccagcctacgcgttca
tcctcacctacgagggccagccgacaatattctaccgcgactacgaggagtggctcaacaaggat
aagctcaagaacctcatctggatacatgacaacctcgccggaggaagcactgacatagtctacta
cgataacgatgaactcatcttcgtcaggaacggctacggggacaagccggggcttataacctaca
tcaacctaggctcgagcaaggccggaaggtgggtttatgtgccgaagttcgcgggcgcgtgcatc
cacgagtatactggtaacctcggaggctgggtagacaagtacgtctactcaagcggctgggtcta
tctcgaagctccagcttacgaccctgccaacgggcagtatggctactccgtgtggagctactgcg
gtgttggctga
FIGURE 16L
SEQ ID NO.: 14
Met Ala Lys Tyr Leu Glu Leu Glu Glu Gly Gly Val Ile Met Gln Ala
Phe Tyr Trp Asp Val Pro Ser Gly Gly Ile Trp Trp Asp Thr Ile Arg
Gln Lys Ile Pro Glu Trp Tyr Asp Ala Gly Ile Ser Ala Ile Trp Ile
Pro Pro Ala Ser Lys Gly Met Gly Gly Ala Tyr Ser Met Gly Tyr Asp
Pro Tyr Asp Phe Phe Asp Leu Gly Glu Tyr Asp Gln Lys Gly Thr Val
Glu Thr Arg Phe Gly Ser Lys Gln Glu Leu Val Asn Met Ile Asn Thr
Ala His Ala Tyr Gly Ile Lys Val Ile Ala Asp Ile Val Ile Asn His
Arg Ala Gly Gly Asp Leu Glu Trp Asn Pro Phe Val Gly Asp Tyr Thr
Trp Thr Asp Phe Ser Lys Val Ala Ser Gly Lys Tyr Thr Ala Asn Tyr
Leu Asp Phe His Pro Asn Glu Val Lys Cys Cys Asp Glu Gly Thr Phe
Gly Gly Phe Pro Asp Ile Ala His Glu Lys Ser Trp Asp Gln His Trp
Leu Trp Ala Ser Asp Glu Ser Tyr Ala Ala Tyr Leu Arg Ser Ile Gly
Val Asp Ala Trp Arg Phe Asp Tyr Val Lys Gly Tyr Gly Ala Trp Val
Val Lys Asp Trp Leu Asp Trp Trp Gly Gly Trp Ala Val Gly Glu Tyr
Trp Asp Thr Asn Val Asp Ala Leu Leu Asn Trp Ala Tyr Ser Ser Asp
Ala Lys Val Phe Asp Phe Pro Leu Tyr Tyr Lys Met Asp Glu Ala Phe
Asp Asn Lys Asn Ile Pro Ala Leu Val Ser Ala Leu Gln Asn Gly Gln
Thr Val Val Ser Arg Asp Pro Phe Lys Ala Val Thr Phe Val Ala Asn
His Asp Thr Asp Ile Ile Trp Asn Lys Tyr Pro Ala Tyr Ala Phe Ile
Leu Thr Tyr Glu Gly Gln Pro Thr Ile Phe Tyr Arg Asp Tyr Glu Glu
Trp Leu Asn Lys Asp Lys Leu Lys Asn Leu Ile Trp Ile His Asp Asn
Leu Ala Gly Gly Ser Thr Asp Ile Val Tyr Tyr Asp Asn Asp Glu Leu
Ile Phe Val Arg Asn Gly Tyr Gly Asp Lys Pro Gly Leu Ile Thr Tyr
Ile Asn Leu Gly Ser Ser Lys Ala Gly Arg Trp Val Tyr Val Pro Lys
Phe Ala Gly Ala Cys Ile His Glu Tyr Thr Gly Asn Leu Gly Gly Trp
Val Asp Lys Tyr Val Tyr Ser Ser Gly Trp Val Tyr Leu Glu Ala Pro
Ala Tyr Asp Pro Ala Asn Gly Gln Tyr Gly Tyr Ser Val Trp Ser Tyr
Cys Gly Val Gly

FIGURE 16M
SEQ ID NO.: 15
atggccaagtactccgagctggaagagggcgggctcataatgcaggccttctactgggacgtccc
catgggaggaatctggtgggacacgatagcccagaagatacccgactgggcaagcgccgggattt
cggcgatatggattccccggcgagcaaggcatggcggcgcctattcgatgggctacgacccc
tacgacttctttgacctcggtgagtacgaccagaagggaacggtagagacgcgctttggctccaa
gcaggagctcgtgaacatgataaacacggcccatgcctacggcataaaggtcatagcggacatcg
tcataaaccaccgcgcaggcggagacctcgagtggaacccgttcgttggggactacacctggacg
gacttctcaaaggtggcctcgggcaaatatactgccaactacctcgacttccacccgaacgagct
ccatgcgggcgattccggaacatttggaggctatcccgacatatgccacgacaagagctgggacc
agtactggctctgggccagccaggagagctacgcggcatatctcaggagcatcggcatcgatgcc
tggcgcttcgactacgtcaagggctacggagcgtgggtcgtcaaggactggctggactggtgggg
aggctgggccgtcggggagtactgggacacaaacgttgatgcactgctcaactgggcctactcga
gcgatgcaaaagtcttcgacttcccgctctactacaagatggatgaggcctttgacaacaaaaac
attccagcgctcgtctctgcccttcagaacggccagactgttgtctcccgcgacccgttcaaggc
cgtaacctttgtagcaaaccacgacaccgatataatttggaacaagtacccggcctacgccttca
tcctcacctacgagggccagccgacgatattctaccgcgactacgaggagtggctcaacaaggac
aggctcaagaacctcatctggatacacgaccaccttgccggtggaagcactgacatcgtttacta
cgacaacgacgagctgatattcgtgagaaacggctacggaagcaagccgggactgataaacataca
tcaacctcgcctcaagcaaagccggaaggtgggtttatgtgccgaagttcgcgggcgcgtgcatc
cacgagtatactggtaacctcggaggctgggtagacaagtacgtctactcaagcggctgggtcta
tctcgaagctccagcttacgaccctgccaacgggcagtatggctactccgtgtggagctattgcg
gtgttgggtga

FIGURE 16N
SEQ ID NO.: 16
Met Ala Lys Tyr Ser Glu Leu Glu Glu Gly Gly Leu Ile Met Gln Ala
Phe Tyr Trp Asp Val Pro Met Gly Gly Ile Trp Trp Asp Thr Ile Ala
Gln Lys Ile Pro Asp Trp Ala Ser Ala Gly Ile Ser Ala Ile Trp Ile
Pro Pro Ala Ser Lys Gly Met Gly Gly Ala Tyr Ser Met Gly Tyr Asp
Pro Tyr Asp Phe Phe Asp Leu Gly Glu Tyr Asp Gln Lys Gly Thr Val
Glu Thr Arg Phe Gly Ser Lys Gln Glu Leu Val Asn Met Ile Asn Thr
Ala His Ala Tyr Gly Ile Lys Val Ile Ala Asp Ile Val Ile Asn His
Arg Ala Gly Gly Asp Leu Glu Trp Asn Pro Phe Val Gly Asp Tyr Thr
Trp Thr Asp Phe Ser Lys Val Ala Ser Gly Lys Tyr Thr Ala Asn Tyr
Leu Asp Phe His Pro Asn Glu Leu His Ala Gly Asp Ser Gly Thr Phe
Gly Gly Tyr Pro Asp Ile Cys His Asp Lys Ser Trp Asp Gln Tyr Trp
Leu Trp Ala Ser Gln Glu Ser Tyr Ala Ala Tyr Leu Arg Ser Ile Gly
Ile Asp Ala Trp Arg Phe Asp Tyr Val Lys Gly Tyr Gly Ala Trp Val
Val Lys Asp Trp Leu Asp Trp Trp Gly Gly Trp Ala Val Gly Glu Tyr
Trp Asp Thr Asn Val Asp Ala Leu Leu Asn Trp Ala Tyr Ser Ser Asp
Ala Lys Val Phe Asp Phe Pro Leu Tyr Tyr Lys Met Asp Glu Ala Phe
Asp Asn Lys Asn Ile Pro Ala Leu Val Ser Ala Leu Gln Asn Gly Gln
Thr Val Val Ser Arg Asp Pro Phe Lys Ala Val Thr Phe Val Ala Asn
His Asp Thr Asp Ile Ile Trp Asn Lys Tyr Pro Ala Tyr Ala Phe Ile
Leu Thr Tyr Glu Gly Gln Pro Thr Ile Phe Tyr Arg Asp Tyr Glu Glu
Trp Leu Asn Lys Asp Arg Leu Lys Asn Leu Ile Trp Ile His Asp His
Leu Ala Gly Gly Ser Thr Asp Ile Val Tyr Tyr Asp Asn Asp Glu Leu
Ile Phe Val Arg Asn Gly Tyr Gly Ser Lys Pro Gly Leu Ile Thr Tyr
Ile Asn Leu Ala Ser Ser Lys Ala Gly Arg Trp Val Tyr Val Pro Lys
Phe Ala Gly Ala Cys Ile His Glu Tyr Thr Gly Asn Leu Gly Gly Trp
Val Asp Lys Tyr Val Tyr Ser Ser Gly Trp Val Tyr Leu Glu Ala Pro
Ala Tyr Asp Pro Ala Asn Gly Gln Tyr Gly Tyr Ser Val Trp Ser Tyr
Cys Gly Val Gly

FIGURE 16O

SEQ ID NO.: 17
atggccaagtactccgagctggaaggggggcgggctcataatgcaggccttctactgggacgtccc
catgggaggaatctggtgggacacgatagcccagaagatacccgactgggcaagcgccgggattt
cggcgatatggattccccggcgagcaagggcatgggcggcgcctattcgatgggctacgacccc
tacgacttctttgacctcggtgagtacgaccaggagggaacggtagagacgcgctttggctccaa
gcaggagctcgtgaacatgataaacacggcccatgcctacggcataaaggtcatagcggacatcg
tcataaaccaccgcgcaggcggagacctcgagtggaacccgttcgttggggactacacctggacg
gacttctcaaaggtggcctcgggcaaatatactgccaactacctcgacttccaccccaacgaggt
caagtgctgtgacgagggcacatttggaggcttcccagacatagcccacgagaagagctgggacc
agcactggctctgggcgagcgatgagagctacgccgcctacctaaggagcatcggcgttgatgcc
tggcgcttcgactacgtcaaggcctacggagcgtgggtcgtcaaggactggctggactggtgggg
aggctgggccgtcggggagtactgggacacaaacgttgatgcactgctcaactgggcctactcga
gcgatgcaaaagtcttcgacttcccgctctactacaagatggacgcggcctttgacaacaagaac
attcccgcactcgtcgaggccctcaagaacgggggcacagtcgtcagccgcgacccgtttaaggc
cgtaaccttcgttgcaaaccacgacaccgatataatctggaacaagtatccagcctacgcgttca
tcctcacctacgagggccagccgacaatattctaccgcgactacgaggagtggctcaacaaggat
aagctcaagaacctcatctggatacatgacaacctcgccggaggaagcacgagcatagtttacta
cgacagcgacgagatgatcttcgtgaggaacggctatggaagcaagcctggccttataacttaca
tcaacctcggctcgagcaaggttggaaggtgggtttacgttccgaagttcgcaggctcgtgcata
cacgagtacaccggcaatctcggcggctgggtggacaagtgggtggactcaagcggctgggtcta
cctcgaggctcctgcccacgaccggccaacggccagtacggctactccgtctggagctactgcg
gtgttgggtga

FIGURE 16P

SEQ ID NO.: 18
Met Ala Lys Tyr Ser Glu Leu Glu Gly Gly Gly Leu Ile Met Gln Ala
Phe Tyr Trp Asp Val Pro Met Gly Gly Ile Trp Trp Asp Thr Ile Ala
Gln Lys Ile Pro Asp Trp Ala Ser Ala Gly Ile Ser Ala Ile Trp Ile
Pro Pro Ala Ser Lys Gly Met Gly Gly Ala Tyr Ser Met Gly Tyr Asp
Pro Tyr Asp Phe Phe Asp Leu Gly Glu Tyr Asp Gln Glu Gly Thr Val
Glu Thr Arg Phe Gly Ser Lys Gln Glu Leu Val Asn Met Ile Asn Thr
Ala His Ala Tyr Gly Ile Lys Val Ile Ala Asp Ile Val Ile Asn His
Arg Ala Gly Gly Asp Leu Glu Trp Asn Pro Phe Val Gly Asp Tyr Thr
Trp Thr Asp Phe Ser Lys Val Ala Ser Gly Lys Tyr Thr Ala Asn Tyr
Leu Asp Phe His Pro Asn Glu Val Lys Cys Cys Asp Glu Gly Thr Phe
Gly Gly Phe Pro Asp Ile Ala His Glu Lys Ser Trp Asp Gln His Trp
Leu Trp Ala Ser Asp Glu Ser Tyr Ala Ala Tyr Leu Arg Ser Ile Gly
Val Asp Ala Trp Arg Phe Asp Tyr Val Lys Gly Tyr Gly Ala Trp Val
Val Lys Asp Trp Leu Asp Trp Trp Gly Gly Trp Ala Val Gly Glu Tyr
Trp Asp Thr Asn Val Asp Ala Leu Leu Asn Trp Ala Tyr Ser Ser Asp
Ala Lys Val Phe Asp Phe Pro Leu Tyr Tyr Lys Met Asp Ala Ala Phe
Asp Asn Lys Asn Ile Pro Ala Leu Val Glu Ala Leu Lys Asn Gly Gly
Thr Val Val Ser Arg Asp Pro Phe Lys Ala Val Thr Phe Val Ala Asn
His Asp Thr Asp Ile Ile Trp Asn Lys Tyr Pro Ala Tyr Ala Phe Ile
Leu Thr Tyr Glu Gly Gln Pro Thr Ile Phe Tyr Arg Asp Tyr Glu Glu
Trp Leu Asn Lys Asp Lys Leu Lys Asn Leu Ile Trp Ile His Asp Asn
Leu Ala Gly Gly Ser Thr Ser Ile Val Tyr Tyr Asp Ser Asp Glu Met
Ile Phe Val Arg Asn Gly Tyr Gly Ser Lys Pro Gly Leu Ile Thr Tyr
Ile Asn Leu Gly Ser Ser Lys Val Gly Arg Trp Val Tyr Val Pro Lys
Phe Ala Gly Ser Cys Ile His Glu Tyr Thr Gly Asn Leu Gly Gly Trp
Val Asp Lys Trp Val Asp Ser Ser Gly Trp Val Tyr Leu Glu Ala Pro
Ala His Asp Pro Ala Asn Gly Gln Tyr Gly Tyr Ser Val Trp Ser Tyr
Cys Gly Val Gly

FIGURE 16Q
SEQ ID NO.: 19
atggccaagtacctggagctcgaagagggcgggctcataatgcaggccttctactgggacgtccc
catgggaggaatctggtgggacacgatagcccagaagatacccgactgggcaagcgcgggattt
cggcgatatggattcctccgcgagcaagggtatgagcggcggctattcgatgggctacgacccc
tacgattattttgaccttggtgagtactaccagaagggaacggtggaaacgaggttcggctcaaa
gcaggagctcataaacatgataaacacggcccatgcctacggcataaaggtcatagcggacatcg
tcataaaccaccgcgcaggcggagacctcgagtggaacccgttcgttggggactacacctggacg
gacttctcaaaggtggcctcgggcaaatatactgccaactacctcgacttccacccgaacgagct
ccatgcgggcgattccggaacatttggaggctatcccgacatatgccacgacaagagctgggacc
agtactggctctgggccagccaggagagctacgcggcatatctcaggagcatcggcatcgatgcc
tggcgcttcgactacgtcaagggctatgctccctgggtcgtcaaggactggctgaactggtgggg
gggctgggcggttggagagtactgggacaccaacgtcgacgctgttctcaactgggcatactcga
gcggtgccaaggtctttgacttcgccctctactacaagatggatgaggcctttgacaacaaaaac
attccagcgctcgtctctgcccttcagaacggccagactgttgtctcccgcgacccgttcaaggc
cgtaacctttgtagcaaaccacgacaccgatataatttggaacaagtacccggcctacgccttca
tcctcacctacgagggccagccgacgatattctaccgcgactacgaggagtggctcaacaaggac
aggctcaagaacctcatctggatacacgaccacctcgccggtggaagcactgacatcgtttacta
cgacaacgacgagctgatattcgtgagaaacggctacggaagcaagccgggactgataacataca
tcaacctcgcctcaagcaaagccggaaggtgggtttatgtgccgaagttcgcgggcgcgtgcatc
cacgagcatactggtaacctcggaggctgggtagacaagtacgtctactcaagcggctgggtcta
tctcgaagctccagcttacgaccctgccaacgggcagtatggctactccgtgtggagctactgcg
gtgttggctga

FIGURE 16R
SEQ ID NO.: 20
Met Ala Lys Tyr Leu Glu Leu Glu Glu Gly Gly Leu Ile Met Gln Ala
Phe Tyr Trp Asp Val Pro Met Gly Gly Ile Trp Trp Asp Thr Ile Ala
Gln Lys Ile Pro Asp Trp Ala Ser Ala Gly Ile Ser Ala Ile Trp Ile
Pro Pro Ala Ser Lys Gly Met Ser Gly Gly Tyr Ser Met Gly Tyr Asp
Pro Tyr Asp Tyr Phe Asp Leu Gly Glu Tyr Tyr Gln Lys Gly Thr Val
Glu Thr Arg Phe Gly Ser Lys Gln Glu Leu Ile Asn Met Ile Asn Thr
Ala His Ala Tyr Gly Ile Lys Val Ile Ala Asp Ile Val Ile Asn His
Arg Ala Gly Gly Asp Leu Glu Trp Asn Pro Phe Val Gly Asp Tyr Thr
Trp Thr Asp Phe Ser Lys Val Ala Ser Gly Lys Tyr Thr Ala Asn Tyr
Leu Asp Phe His Pro Asn Glu Leu His Ala Gly Asp Ser Gly Thr Phe
Gly Gly Tyr Pro Asp Ile Cys His Asp Lys Ser Trp Asp Gln Tyr Trp
Leu Trp Ala Ser Gln Glu Ser Tyr Ala Ala Tyr Leu Arg Ser Ile Gly
Ile Asp Ala Trp Arg Phe Asp Tyr Val Lys Gly Tyr Ala Pro Trp Val
Val Lys Asp Trp Leu Asn Trp Trp Gly Gly Trp Ala Val Gly Glu Tyr
Trp Asp Thr Asn Val Asp Ala Val Leu Asn Trp Ala Tyr Ser Ser Gly
Ala Lys Val Phe Asp Phe Ala Leu Tyr Tyr Lys Met Asp Glu Ala Phe
Asp Asn Lys Asn Ile Pro Ala Leu Val Ser Ala Leu Gln Asn Gly Gln
Thr Val Val Ser Arg Asp Pro Phe Lys Ala Val Thr Phe Val Ala Asn
His Asp Thr Asp Ile Ile Trp Asn Lys Tyr Pro Ala Tyr Ala Phe Ile
Leu Thr Tyr Glu Gly Gln Pro Thr Ile Phe Tyr Arg Asp Tyr Glu Glu
Trp Leu Asn Lys Asp Arg Leu Lys Asn Leu Ile Trp Ile His Asp His
Leu Ala Gly Gly Ser Thr Asp Ile Val Tyr Tyr Asp Asn Asp Glu Leu
Ile Phe Val Arg Asn Gly Tyr Gly Ser Lys Pro Gly Leu Ile Thr Tyr
Ile Asn Leu Ala Ser Ser Lys Ala Gly Arg Trp Val Tyr Val Pro Lys
Phe Ala Gly Ala Cys Ile His Glu His Thr Gly Asn Leu Gly Gly Trp
Val Asp Lys Tyr Val Tyr Ser Ser Gly Trp Val Tyr Leu Glu Ala Pro
Ala Tyr Asp Pro Ala Asn Gly Gln Tyr Gly Tyr Ser Val Trp Ser Tyr
Cys Gly Val Gly

FIGURE 16S
SEQ ID NO.: 21
atggccaagtactccgagctggaagagggcggcgttataatgcaggccttctactgggacgtccc
aggtggaggaatctggtgggacaccatcaggagcaagataccggagtggtacgaggcgggaatat
ccgccatttggattcctcccggagcaagggtatgagcggcggctattcgatgggctacgacccc
tacgatgatttggacctggtgagtactaccagaagggaacggtggaaacgaggttcggctcaaa
gcaggagctcataaacatgataaacacggcccatgcctacggcataaaggtcatagcggacatcg
tcataaaccaccgcgcaggcggagacctcgagtggaacccgttcgttggggactacacctggacg
gacttctcaaaggtggcctcgggcaaatatactgccaactacctcgacttccacccgaacgagct
ccatgcgggcgattccggaacatttggaggctatcccgacatatgccacgacaagagctgggacc
agtactggctctgggccagccaggagagctacgcggtatatctcaggagcatcggcatcgatgcc
tggcgcttcgactacgtcaagggctacggagcgtgggtcgtcaaggactggctggactggtgggg
aggctgggccgtcggggagtactgggacacaaacgttgatgcactgctcaactgggcctactcga
gcgatgcaaaagtcttcgacttcccgctctactacaagatggatgaggcctttgacaacaaaaac
attccagcgctcgtctctgcccttcagaacggccagactgttgtctcccgcgacccgttcaaggc
cgtaacctttgtagcaaaccacgacaccgatataatttggaacaagtacccggcctacgccttca
tcctcacctacgagggccagccgacgatattctaccgcgactacgaggagtggctcaacaaggac
aggctcaagaacctcatctggatacacgactacctcgccggtggaagcactgacatcgtttacta
cgacaacgacgagctgatattcgtgagaaacggctacggaagcaagccgggactgataacataca
tcaacctcgcctcaagcaaagccggaaggtgggtttatgtgccgaagttcgcgggcgcgtgcatc
cacgagtatactggtaacctcggaggctgggtagacaagtacgtctactcaagcggctgggtcta
tctcgaagctccagcttacgaccctgccaacgggcagtatggctactccgtgtggagctattgcg
gtgttggctga

FIGURE 16T
SEQ ID NO.: 22
Met Ala Lys Tyr Ser Glu Leu Glu Glu Gly Gly Val Ile Met Gln Ala
Phe Tyr Trp Asp Val Pro Gly Gly Gly Ile Trp Trp Asp Thr Ile Arg
Ser Lys Ile Pro Glu Trp Tyr Glu Ala Gly Ile Ser Ala Ile Trp Ile
Pro Pro Gly Ser Lys Gly Met Ser Gly Gly Tyr Ser Met Gly Tyr Asp
Pro Tyr Asp Asp Leu Asp Leu Gly Glu Tyr Tyr Gln Lys Gly Thr Val
Glu Thr Arg Phe Gly Ser Lys Gln Glu Leu Ile Asn Met Ile Asn Thr
Ala His Ala Tyr Gly Ile Lys Val Ile Ala Asp Ile Val Ile Asn His
Arg Ala Gly Gly Asp Leu Glu Trp Asn Pro Phe Val Gly Asp Tyr Thr
Trp Thr Asp Phe Ser Lys Val Ala Ser Gly Lys Tyr Thr Ala Asn Tyr
Leu Asp Phe His Pro Asn Glu Leu His Ala Gly Asp Ser Gly Thr Phe
Gly Gly Tyr Pro Asp Ile Cys His Asp Lys Ser Trp Asp Gln Tyr Trp
Leu Trp Ala Ser Gln Glu Ser Tyr Ala Val Tyr Leu Arg Ser Ile Gly
Ile Asp Ala Trp Arg Phe Asp Tyr Val Lys Gly Tyr Gly Ala Trp Val
Val Lys Asp Trp Leu Asp Trp Trp Gly Gly Trp Ala Val Gly Glu Tyr
Trp Asp Thr Asn Val Asp Ala Leu Leu Asn Trp Ala Tyr Ser Ser Asp
Ala Lys Val Phe Asp Phe Pro Leu Tyr Tyr Lys Met Asp Glu Ala Phe
Asp Asn Lys Asn Ile Pro Ala Leu Val Ser Ala Leu Gln Asn Gly Gln
Thr Val Val Ser Arg Asp Pro Phe Lys Ala Val Thr Phe Val Ala Asn
His Asp Thr Asp Ile Ile Trp Asn Lys Tyr Pro Ala Tyr Ala Phe Ile
Leu Thr Tyr Glu Gly Gln Pro Thr Ile Phe Tyr Arg Asp Tyr Glu Glu
Trp Leu Asn Lys Asp Arg Leu Lys Asn Leu Ile Trp Ile His Asp Tyr
Leu Ala Gly Gly Ser Thr Asp Ile Val Tyr Tyr Asp Asn Asp Glu Leu
Ile Phe Val Arg Asn Gly Tyr Gly Ser Lys Pro Gly Leu Ile Thr Tyr
Ile Asn Leu Ala Ser Ser Lys Ala Gly Arg Trp Val Tyr Val Pro Lys
Phe Ala Gly Ala Cys Ile His Glu Tyr Thr Gly Asn Leu Gly Gly Trp
Val Asp Lys Tyr Val Tyr Ser Ser Gly Trp Val Tyr Leu Glu Ala Pro
Ala Tyr Asp Pro Ala Asn Gly Gln Tyr Gly Tyr Ser Val Trp Ser Tyr
Cys Gly Val Gly

FIGURE 16U
SEQ ID NO.: 23
atggccaagtactccgagctggaagagggcggcgttatagtgcaggccttctactgggacgtccc
aggtggaggaatctggtgggacaccatcaggagcaagataccggagtggtacgaggcgggaatat
ccgccatttggattccccggcgagcaagggcatgggcggcgcctattcgatgggctacgacccc
tacgacttctttgacctcggtgagtacgaccagaagggaacggtagagacgcgctttggctccaa
gcaggagctcgtgaacatgataaacacggcccatgcctacggcataaaggtcatagcggacatcg
tcataaaccaccgcgcaggcggagacctcgagtggaacccgttcgttggggactacacctggacg
gacttctcaaaggtggcctcgggcaaatatactgccaactacctcgacttccacccgaacgagct
ccatgcgggcgattccggaacatttggaggctatccgacatatgccacgacaagagctgggacc
agtactggctctgggccagccaggagagctacgcggcatatctcaggagcatcggcatcgatgcc
tggcgcttcgactacgtcaagggctacggagcgtgggtcgtcaaggactggctggactggtgggg
aggctgggccgtcggggagtactggacacaaacgttgatgcactgctcaactgggcctactcga
gcgatgcaaaagtcttcgacttcccgctctactacaagatggatgaggcctttgacaacaaaaac
attccagcgctcgtctctgcccttcagaacggccagactgttgtctcccgcgacccgttcaaggc
cgtaacctttgtagcaaaccacgacaccgatataatctggaacaagtatccagcctacgcgttca
tcctcacctacgagggccagccgacaatattctaccgcgactacgaggagtggctcaacaaggat
aagctcaagaacctcatctggatacatgacaacctcgccggaggaagcatgagcatagtttacta
cgacagcgacgagatgatcttcgtgaggaacggctatggaagcaagcctggccttataacttaca
tcaacctcggctcgagcaaggttggaaggtgggtctacgttccgaagttcgcgggagcgtgcatc
cacgagtacaccggcaacctcggcggctgggtggacaagtgggtggactcaagcgggtgggtgta
cctcgaggcccctgcccacgacccggccaacggctattacggctactccgtctggagctattgcg
gtgttggctga

FIGURE 16V
SEQ ID NO.: 24
Met Ala Lys Tyr Ser Glu Leu Glu Glu Gly Gly Val Ile Val Gln Ala
Phe Tyr Trp Asp Val Pro Gly Gly Gly Ile Trp Trp Asp Thr Ile Arg
Ser Lys Ile Pro Glu Trp Tyr Glu Ala Gly Ile Ser Ala Ile Trp Ile
Pro Pro Ala Ser Lys Gly Met Gly Gly Ala Tyr Ser Met Gly Tyr Asp
Pro Tyr Asp Phe Phe Asp Leu Gly Glu Tyr Asp Gln Lys Gly Thr Val
Glu Thr Arg Phe Gly Ser Lys Gln Glu Leu Val Asn Met Ile Asn Thr
Ala His Ala Tyr Gly Ile Lys Val Ile Ala Asp Ile Val Ile Asn His
Arg Ala Gly Gly Asp Leu Glu Trp Asn Pro Phe Val Gly Asp Tyr Thr
Trp Thr Asp Phe Ser Lys Val Ala Ser Gly Lys Tyr Thr Ala Asn Tyr
Leu Asp Phe His Pro Asn Glu Leu His Ala Gly Asp Ser Gly Thr Phe
Gly Gly Tyr Pro Asp Ile Cys His Asp Lys Ser Trp Asp Gln Tyr Trp
Leu Trp Ala Ser Gln Glu Ser Tyr Ala Ala Tyr Leu Arg Ser Ile Gly
Ile Asp Ala Trp Arg Phe Asp Tyr Val Lys Gly Tyr Gly Ala Trp Val
Val Lys Asp Trp Leu Asp Trp Trp Gly Gly Trp Ala Val Gly Glu Tyr
Trp Asp Thr Asn Val Asp Ala Leu Leu Asn Trp Ala Tyr Ser Ser Asp
Ala Lys Val Phe Asp Phe Pro Leu Tyr Tyr Lys Met Asp Glu Ala Phe
Asp Asn Lys Asn Ile Pro Ala Leu Val Ser Ala Leu Gln Asn Gly Gln
Thr Val Val Ser Arg Asp Pro Phe Lys Ala Val Thr Phe Val Ala Asn
His Asp Thr Asp Ile Ile Trp Asn Lys Tyr Pro Ala Tyr Ala Phe Ile
Leu Thr Tyr Glu Gly Gln Pro Thr Ile Phe Tyr Arg Asp Tyr Glu Glu
Trp Leu Asn Lys Asp Lys Leu Lys Asn Leu Ile Trp Ile His Asp Asn
Leu Ala Gly Gly Ser Met Ser Ile Val Tyr Tyr Asp Ser Asp Glu Met
Ile Phe Val Arg Asn Gly Tyr Gly Ser Lys Pro Gly Leu Ile Thr Tyr
Ile Asn Leu Gly Ser Ser Lys Val Gly Arg Trp Val Tyr Val Pro Lys
Phe Ala Gly Ala Cys Ile His Glu Tyr Thr Gly Asn Leu Gly Gly Trp
Val Asp Lys Trp Val Asp Ser Ser Gly Trp Val Tyr Leu Glu Ala Pro
Ala His Asp Pro Ala Asn Gly Tyr Tyr Gly Tyr Ser Val Trp Ser Tyr
Cys Gly Val Gly

FIGURE 16W
SEQ ID NO.: 25
atggccaagtacctggagctcgaagagggcgggctcataatgcaggccttctactgggacgtccc
catgggaggaatctggtgggacacgatagcccagaagatacccgactgggcaagcgccgggattt
cggcgatatggattcctcccgcgagcaagggtatgagcggcggctattcgatgggctacgacccc
tacgattattttgacctcggtgagtactaccagaagggaacggtggaaacgaggttcggctcaaa
gcaggagctcataaacatgataaacaccgcccacgcctatggcatgaaggtaatagccgatatag
tcatcaaccaccgcgccggcggtgacctggagtggaaccccttcgtgaacgactatacctggacc
gacttctcaaaggtcgcgtcgggtaaatacacggccaactacctcgacttccacccgaacgagct
ccatgcgggcgattccggaacatttggaggctatcccgacatatgccacgacaagagctgggacc
agtactggctctgggccagccaggagagctacgcggcatatctcaggagcatcggcatcgatgcc
tggcgcttcgactacgtcaaggctatgctccctgggtcgtcaaggactggctgaactggtgggg
aggctgggcggttggagagtactgggacaccaacgtcgacgctgttctcaactgggcatactcga
gcggtgccaaggtctttgacttcgccctctactacaagatggacgaggccttcgataacaacaac
attcccgccctggtgggcgccctcagatacggtcagacagtggtcagccgcgacccgttcaaggc
tgtgacgtttgtagccaaccacgataccgatataatctggaacaagtatccagcctacgcgttca
tcctcacctacgagggccagccgacaatattctaccgcgactacgaggagtggctcaacaaggat
aagctcaagaacctcatctggatacatgacaacctcgccggaggaagcaccgacatagtctacta
cgataacgatgaactcatcttcgtcaggcacggctacggggacaagccgggcttataacctaca
tcaacctaggctcgagcaaggccggaaggtgggtttacgttccgaagttcgcaggctcgtgcata
cacgagtacaccggcaatctcggcggctggtggacaagtgggtggactcaagcggctggtcta
cctcgaggctcctgcccacgacccggccaacggccagtacggctactccgtctggagctattgcg
gtgttgggtga

FIGURE 16X
SEQ ID NO.: 26
Met Ala Lys Tyr Leu Glu Leu Glu Glu Gly Gly Leu Ile Met Gln Ala
Phe Tyr Trp Asp Val Pro Met Gly Gly Ile Trp Trp Asp Thr Ile Ala
Gln Lys Ile Pro Asp Trp Ala Ser Ala Gly Ile Ser Ala Ile Trp Ile
Pro Pro Ala Ser Lys Gly Met Ser Gly Gly Tyr Ser Met Gly Tyr Asp
Pro Tyr Asp Tyr Phe Asp Leu Gly Glu Tyr Tyr Gln Lys Gly Thr Val
Glu Thr Arg Phe Gly Ser Lys Gln Glu Leu Ile Asn Met Ile Asn Thr
Ala His Ala Tyr Gly Met Lys Val Ile Ala Asp Ile Val Ile Asn His
Arg Ala Gly Gly Asp Leu Glu Trp Asn Pro Phe Val Asn Asp Tyr Thr
Trp Thr Asp Phe Ser Lys Val Ala Ser Gly Lys Tyr Thr Ala Asn Tyr
Leu Asp Phe His Pro Asn Glu Leu His Ala Gly Asp Ser Gly Thr Phe
Gly Gly Tyr Pro Asp Ile Cys His Asp Lys Ser Trp Asp Gln Tyr Trp
Leu Trp Ala Ser Gln Glu Ser Tyr Ala Ala Tyr Leu Arg Ser Ile Gly
Ile Asp Ala Trp Arg Phe Asp Tyr Val Lys Gly Tyr Ala Pro Trp Val
Val Lys Asp Trp Leu Asn Trp Trp Gly Gly Trp Ala Val Gly Glu Tyr
Trp Asp Thr Asn Val Asp Ala Val Leu Asn Trp Ala Tyr Ser Ser Gly
Ala Lys Val Phe Asp Phe Ala Leu Tyr Tyr Lys Met Asp Glu Ala Phe
Asp Asn Asn Asn Ile Pro Ala Leu Val Gly Ala Leu Arg Tyr Gly Gln
Thr Val Val Ser Arg Asp Pro Phe Lys Ala Val Thr Phe Val Ala Asn
His Asp Thr Asp Ile Ile Trp Asn Lys Tyr Pro Ala Tyr Ala Phe Ile
Leu Thr Tyr Glu Gly Gln Pro Thr Ile Phe Tyr Arg Asp Tyr Glu Glu
Trp Leu Asn Lys Asp Lys Leu Lys Asn Leu Ile Trp Ile His Asp Asn
Leu Ala Gly Gly Ser Thr Asp Ile Val Tyr Tyr Asp Asn Asp Glu Leu
Ile Phe Val Arg His Gly Tyr Gly Asp Lys Pro Gly Leu Ile Thr Tyr
Ile Asn Leu Gly Ser Ser Lys Ala Gly Arg Trp Val Tyr Val Pro Lys
Phe Ala Gly Ser Cys Ile His Glu Tyr Thr Gly Asn Leu Gly Gly Trp
Val Asp Lys Trp Val Asp Ser Ser Gly Trp Val Tyr Leu Glu Ala Pro
Ala His Asp Pro Ala Asn Gly Gln Tyr Gly Tyr Ser Val Trp Ser Tyr
Cys Gly Val Gly

FIGURE 16Y
SEQ ID NO.: 27
atggcaaagtattccgagctcgaagagggcggcgttataatgcaggccttctactgggacgtccc
aggtggaggaatctggtgggacaccatcaggagcaagataccggagtggtacgaggcgggaatat
ccgccatttggattcctcccgcgagcaagggtatgagcggcggctattcgatgggctacgacccc
tacgattattttgacctcggtgagtactaccagaagggaacggtggaaacgaggttcggctcaaa
gcaggagctcataaacatgataaacacggcccatgcctacggcataaaggtcatagcggacatcg
tcataaaccaccgcgcaggcggagacctcgagtggaacccgttcgttggggactacacctggacg
gacttctcaaaggtggcctcgggcaaatatactgccaactacctcgacttccacccgaacgagct
ccatgcgggcgattccggaacatttggaggctatcccgacatatgccacgacaagagctggacc
agtactggctctgggccagccaggagagctacgcggcatatctcaggagcatcggcatcgatgcc
tggcgcttcgactacgtcaagggctatgctcctgggtcgtcaaggactggctgaactggtgggg
aggctgggcggttggagagtactgggacaccaacgtcgacgctgttctcaactgggcatactcga
gcggtgccaaggtctttgacttcgccctctactacaagatggacgcggcctttgacaacaagaac
attcccgcactcgtcgaggccctcaagaacgggggcacagtcgtcagccgcgacccgtttaaggc
cgtaaccttcgttgcaaaccacgacaccgatataatctggaacaagtatccagcctacgcgttca
tcctcacctacgagggccagccgacaatattctaccgcgactacgaggagtggctcaacaaggat
aagctcaagaacctcatctggatacatgacaacctcgccggaggaagcactgacatcgtttacta
cgacaacgacgagctgatattcgtgagaaacggctacggaagcaagccgggactgataacataca
tcaacctcgcgtcaagcaaagccggaaggtgggtttacgttccgaagttcgcaggctcgtgcata
cacgagtacaccggcaatctcggcggctgggtggacaagtgggtggactcaagcggctgggtcta
cctcgaggctcctgcccacgacccggccaacggccagtacggctactccgtctggagctactgcg
gtgttgggtga

FIGURE 16Z
SEQ ID NO.: 28
Met Ala Lys Tyr Ser Glu Leu Glu Glu Gly Gly Val Ile Met Gln Ala
Phe Tyr Trp Asp Val Pro Gly Gly Gly Ile Trp Trp Asp Thr Ile Arg
Ser Lys Ile Pro Glu Trp Tyr Glu Ala Gly Ile Ser Ala Ile Trp Ile
Pro Pro Ala Ser Lys Gly Met Ser Gly Gly Tyr Ser Met Gly Tyr Asp
Pro Tyr Asp Tyr Phe Asp Leu Gly Glu Tyr Tyr Gln Lys Gly Thr Val
Glu Thr Arg Phe Gly Ser Lys Gln Glu Leu Ile Asn Met Ile Asn Thr
Ala His Ala Tyr Gly Ile Lys Val Ile Ala Asp Ile Val Ile Asn His
Arg Ala Gly Gly Asp Leu Glu Trp Asn Pro Phe Val Gly Asp Tyr Thr
Trp Thr Asp Phe Ser Lys Val Ala Ser Gly Lys Tyr Thr Ala Asn Tyr
Leu Asp Phe His Pro Asn Glu Leu His Ala Gly Asp Ser Gly Thr Phe
Gly Gly Tyr Pro Asp Ile Cys His Asp Lys Ser Trp Asp Gln Tyr Trp
Leu Trp Ala Ser Gln Glu Ser Tyr Ala Ala Tyr Leu Arg Ser Ile Gly
Ile Asp Ala Trp Arg Phe Asp Tyr Val Lys Gly Tyr Ala Pro Trp Val
Val Lys Asp Trp Leu Asn Trp Trp Gly Gly Trp Ala Val Gly Glu Tyr
Trp Asp Thr Asn Val Asp Ala Val Leu Asn Trp Ala Tyr Ser Ser Gly
Ala Lys Val Phe Asp Phe Ala Leu Tyr Tyr Lys Met Asp Ala Ala Phe
Asp Asn Lys Asn Ile Pro Ala Leu Val Glu Ala Leu Lys Asn Gly Gly
Thr Val Val Ser Arg Asp Pro Phe Lys Ala Val Thr Phe Val Ala Asn
His Asp Thr Asp Ile Ile Trp Asn Lys Tyr Pro Ala Tyr Ala Phe Ile
Leu Thr Tyr Glu Gly Gln Pro Thr Ile Phe Tyr Arg Asp Tyr Glu Glu
Trp Leu Asn Lys Asp Lys Leu Lys Asn Leu Ile Trp Ile His Asp Asn
Leu Ala Gly Gly Ser Thr Asp Ile Val Tyr Tyr Asp Asn Asp Glu Leu
Ile Phe Val Arg Asn Gly Tyr Gly Ser Lys Pro Gly Leu Ile Thr Tyr
Ile Asn Leu Ala Ser Ser Lys Ala Gly Arg Trp Val Tyr Val Pro Lys
Phe Ala Gly Ser Cys Ile His Glu Tyr Thr Gly Asn Leu Gly Gly Trp
Val Asp Lys Trp Val Asp Ser Ser Gly Trp Val Tyr Leu Glu Ala Pro
Ala His Asp Pro Ala Asn Gly Gln Tyr Gly Tyr Ser Val Trp Ser Tyr
Cys Gly Val Gly

FIGURE 16AA
SEQ ID NO.: 29
atggccaagtacctggagctcgaagagggcgggctcataatgcaggccttctactgggacgtccc
catgggaggaatctggtgggacacggtagcccagaagataccggactgggcaagcgccgggattt
cggcgatatggattccccggcgagcaagggcatgggcggcgcctattcgatgggctacgacccc
tacgacttctttgacctcggtgagtacgaccagaagggaacggtagagacgcgctttggctccaa
gcaggagctcgtgaacatgataaacacggcccatgcctacggcataaaggtcatagcggacatcg
tcataaaccaccgcgcaggcggagacctcgagtggaacccgttcgttggggactacacctggacg
gacttctcaaaggtggtctcgggcaaatatactgccaactacctcgacttccacccgaacgagct
ccatgcgggcgattccggaacatttggaggctatccgacatatgccacgacaagagctgggacc
agtactggctctgggccagccaggagagctacgcggcatatctcaggagcatcggcatcgatgcc
tggcgcttcgactacgtcaagggctatgctccctgggtcgtcaaggactggctgaactggtgggg
aggctgggcggttggagagtactgggacaccaacgtcgacgctgttctcaactgggcatactcga
gcggtgccaaggtctttgacttcgccctctactacaagatggatgaggcctttgacaacaaaaac
attccagcgctcgtctctgcccttcagaacggccagactgttgtctcccgcgacccgttcaaggc
cgtaacctttgtagcaaaccacgacaccgatataatctggaacaagtaccttgcttatgccttca
tcctcacctacgaaggccagcccgtcatattctaccgcgactacgaggagtggctcaacaaggac
aggttgaacaacctcatatggatacacgaccacctcgcagggggaagcaccgacatagtctacta
cgataacgatgaactcatcttcgtcaggaacggctacggggacaagccgggcttataacctaca
tcaacctaggctcgagcaaggccggaaggtgggtttatgtgccgaagttcgcgggcgcgtgcatc
cacgagtatactggtaacctcggaggctgggtagacaagtacgtctactcaagcggctgggtcta
tctcgaagctccagcttacgaccctgccaacgggcagtatggctactccgtgtggagctactgcg
gtgttgggtga
FIGURE 16BB
SEQ ID NO.: 30
Met Ala Lys Tyr Leu Glu Leu Glu Glu Gly Gly Leu Ile Met Gln Ala
Phe Tyr Trp Asp Val Pro Met Gly Gly Ile Trp Trp Asp Thr Val Ala
Gln Lys Ile Pro Asp Trp Ala Ser Ala Gly Ile Ser Ala Ile Trp Ile
Pro Pro Ala Ser Lys Gly Met Gly Gly Ala Tyr Ser Met Gly Tyr Asp
Pro Tyr Asp Phe Phe Asp Leu Gly Glu Tyr Asp Gln Lys Gly Thr Val
Glu Thr Arg Phe Gly Ser Lys Gln Glu Leu Val Asn Met Ile Asn Thr
Ala His Ala Tyr Gly Ile Lys Val Ile Ala Asp Ile Val Ile Asn His
Arg Ala Gly Gly Asp Leu Glu Trp Asn Pro Phe Val Gly Asp Tyr Thr
Trp Thr Asp Phe Ser Lys Val Val Ser Gly Lys Tyr Thr Ala Asn Tyr
Leu Asp Phe His Pro Asn Glu Leu His Ala Gly Asp Ser Gly Thr Phe
Gly Gly Tyr Pro Asp Ile Cys His Asp Lys Ser Trp Asp Gln Tyr Trp
Leu Trp Ala Ser Gln Glu Ser Tyr Ala Ala Tyr Leu Arg Ser Ile Gly
Ile Asp Ala Trp Arg Phe Asp Tyr Val Lys Gly Tyr Ala Pro Trp Val
Val Lys Asp Trp Leu Asn Trp Trp Gly Gly Trp Ala Val Gly Glu Tyr
Trp Asp Thr Asn Val Asp Ala Val Leu Asn Trp Ala Tyr Ser Ser Gly
Ala Lys Val Phe Asp Phe Ala Leu Tyr Tyr Lys Met Asp Glu Ala Phe
Asp Asn Lys Asn Ile Pro Ala Leu Val Ser Ala Leu Gln Asn Gly Gln
Thr Val Val Ser Arg Asp Pro Phe Lys Ala Val Thr Phe Val Ala Asn
His Asp Thr Asp Ile Ile Trp Asn Lys Tyr Leu Ala Tyr Ala Phe Ile
Leu Thr Tyr Glu Gly Gln Pro Val Ile Phe Tyr Arg Asp Tyr Glu Glu
Trp Leu Asn Lys Asp Arg Leu Asn Asn Leu Ile Trp Ile His Asp His
Leu Ala Gly Gly Ser Thr Asp Ile Val Tyr Tyr Asp Asn Asp Glu Leu
Ile Phe Val Arg Asn Gly Tyr Gly Asp Lys Pro Gly Leu Ile Thr Tyr
Ile Asn Leu Gly Ser Ser Lys Ala Gly Arg Trp Val Tyr Val Pro Lys
Phe Ala Gly Ala Cys Ile His Glu Tyr Thr Gly Asn Leu Gly Gly Trp
Val Asp Lys Tyr Val Tyr Ser Ser Gly Trp Val Tyr Leu Glu Ala Pro
Ala Tyr Asp Pro Ala Asn Gly Gln Tyr Gly Tyr Ser Val Trp Ser Tyr
Cys Gly Val Gly

FIGURE 16CC
SEQ ID NO.: 31
atggcaaagtactccgagctggaagagggcggcgttataatgcaggccttctactgggacgtccc
aggtggaggaatctggtgggacaccatcaggagcaggataccggagtggtacgaggcgggaatat
ccgccatttggattccccggcgagcaagggcatgggcggcgcctattcgatgggctacgacccc
tacgacttctttgacctcggtgagtacgaccagaagggaacggtagagacgcgctttggctccaa
gcaggagctcgtgaacatgataaacacggcccatgcctacggcataaaggtcatagcggacatcg
tcataaaccaccgcgcaggcggagacctcgagtggaacccgttcgttggggactacacctggacg
gacttctcaaaggtggcctcgggcaaatatactgccaactacctcgacttccacccgaacgagct
ccatgcgggcgattccggaacatttggaggctatcccgacatatgccacgacaagagctgggacc
agtactggctctgggccagccaggagagctacgcggcatatctcaggagcatcggcatcgatgcc
tggcgctttgactacgtgaagggctacggagcgtgggtcgtcaaggactggctcaactggtgggg
cggctgggccgttggcgagtactgggacaccaacgttgatgcactcctcaactgggcctactcga
gcggcgccaaggtcttcgacttcccgctctactacaagatggacgaggccttcgataacaacaac
attcccgccctggtggacgccctcagatacggtcagacagtggtcagccgcgacccgttcaaggc
tgtgacgtttgtagccaaccacgataccgatataatctggaacaagtatccagcctacgcgttca
tcctcacctacgagggccagccgacaatattctaccgcgactacgaggagtggctcaacaaggat
aagctcaagaacctcatctggatacatgacaacctggccggaggaagcacgagcatagtttacta
cgacagcgacgagatgatcttcgtgaggaccggctatggaagcaagcctggccttataacttaca
tcaacctcggctcgagcaaggttggaaggtgggtttatgtgccgaagttcgcgggcgcgtgcatc
cacgagtatactggtaacctcggaggctgggtagacaagtacgtctactcaagcggctgggtcta
tctcgaagctccagcttacgaccctgccaacgggcagtatggctactccgtgtggagctattgcg
gtgttggctga

FIGURE 16DD
SEQ ID NO.: 32
Met Ala Lys Tyr Ser Glu Leu Glu Glu Gly Gly Val Ile Met Gln Ala
Phe Tyr Trp Asp Val Pro Gly Gly Gly Ile Trp Trp Asp Thr Ile Arg
Ser Arg Ile Pro Glu Trp Tyr Glu Ala Gly Ile Ser Ala Ile Trp Ile
Pro Pro Ala Ser Lys Gly Met Gly Gly Ala Tyr Ser Met Gly Tyr Asp
Pro Tyr Asp Phe Phe Asp Leu Gly Glu Tyr Asp Gln Lys Gly Thr Val
Glu Thr Arg Phe Gly Ser Lys Gln Glu Leu Val Asn Met Ile Asn Thr
Ala His Ala Tyr Gly Ile Lys Val Ile Ala Asp Ile Val Ile Asn His
Arg Ala Gly Gly Asp Leu Glu Trp Asn Pro Phe Val Gly Asp Tyr Thr
Trp Thr Asp Phe Ser Lys Val Ala Ser Gly Lys Tyr Thr Ala Asn Tyr
Leu Asp Phe His Pro Asn Glu Leu His Ala Gly Asp Ser Gly Thr Phe
Gly Gly Tyr Pro Asp Ile Cys His Asp Lys Ser Trp Asp Gln Tyr Trp
Leu Trp Ala Ser Gln Glu Ser Tyr Ala Ala Tyr Leu Arg Ser Ile Gly
Ile Asp Ala Trp Arg Phe Asp Tyr Val Lys Gly Tyr Gly Ala Trp Val
Val Lys Asp Trp Leu Asn Trp Trp Gly Gly Trp Ala Val Gly Glu Tyr
Trp Asp Thr Asn Val Asp Ala Leu Leu Asn Trp Ala Tyr Ser Ser Gly
Ala Lys Val Phe Asp Phe Pro Leu Tyr Tyr Lys Met Asp Glu Ala Phe
Asp Asn Asn Asn Ile Pro Ala Leu Val Asp Ala Leu Arg Tyr Gly Gln
Thr Val Val Ser Arg Asp Pro Phe Lys Ala Val Thr Phe Val Ala Asn
His Asp Thr Asp Ile Ile Trp Asn Lys Tyr Pro Ala Tyr Ala Phe Ile
Leu Thr Tyr Glu Gly Gln Pro Thr Ile Phe Tyr Arg Asp Tyr Glu Glu
Trp Leu Asn Lys Asp Lys Leu Lys Asn Leu Ile Trp Ile His Asp Asn
Leu Ala Gly Gly Ser Thr Ser Ile Val Tyr Tyr Asp Ser Asp Glu Met
Ile Phe Val Arg Thr Gly Tyr Gly Ser Lys Pro Gly Leu Ile Thr Tyr
Ile Asn Leu Gly Ser Ser Lys Val Gly Arg Trp Val Tyr Val Pro Lys
Phe Ala Gly Ala Cys Ile His Glu Tyr Thr Gly Asn Leu Gly Gly Trp
Val Asp Lys Tyr Val Tyr Ser Ser Gly Trp Val Tyr Leu Glu Ala Pro
Ala Tyr Asp Pro Ala Asn Gly Gln Tyr Gly Tyr Ser Val Trp Ser Tyr
Cys Gly Val Gly

FIGURE 16EE
SEQ ID NO.: 33
atggccaagtactccgagctggaagagggcggggtcataatgcaggcgttctactgggacgtgcc
ttcaggaggaatatggtgggacacaatacggcagaagataccggagtggtacgatgccggaatct
ccgcaatatggattcctcccgcgagcaagggtatgagcggcggctattcgatgggctacgacccc
tacgattattttgacctcggtgagtactaccagaagggaacggtggaaacgaggttcggctcaaa
gcaggagctcataaacatgataaacacggcccatgcctacggcataaaggtcatagcggacatcg
tcataaaccaccgcgcaggcggagacctcgagtggaacccgttcgttggggactacacctggacg
gacttctcaaaggtggcctcgggcaaatatactgccaactacctcgacttccacccgaacgagct
ccatgcgggcgattccggaacatttggaggctatcccgacatatgccacgacaagagctgggacc
agtactggctctgggccagccaggagagctacgcggcatatctcaggagcatcggcatcgatgcc
tggcgctttgactacgtgaagggctacggagcgtgggtcgtcaaggactggctcaactggtgggg
cggctgggccgttggcgagtactgggacaccaacgttgatgcactcctcaactgggcctactcga
gcggcgccaaggtcttcgactttccgctctactacaagatggacgcggcctttgacaacaagaac
attcccgcactcgtcgaggccctcaagaacggggcacagtcgtcagccgcgacccgtttaaggc
cgtaaccttcgttgcaaaccacgacaccgatataatctggaccaagtaccttgcttatgctttca
tcctcacctacgaaggccagcccgtcatattctaccgcgactacgaggagtggctcaacaaggac
aggttgaacaacctcatatggatacacgaccacctcgcaggtggaagcaccgacatagtctacta
cgataacgatgaactcatcttcgtcaggaacggctacggggacaagccgggcttataacctaca
tcaacctaggctcgagcaaggccggaaggtgggtttacgttccgaagttcgcaggctcgtgcata
cacgagtacaccggcaatctcggcggctgggtggacaagtgggtggactcaagcggctgggtcta
cctcgaggctcctgcccacgacccggccaacggccagtacggctactccgtctggagctactgcg
gtgttggctga
FIGURE 16FF
SEQ ID NO.: 34
Met Ala Lys Tyr Ser Glu Leu Glu Glu Gly Gly Val Ile Met Gln Ala
Phe Tyr Trp Asp Val Pro Ser Gly Gly Ile Trp Trp Asp Thr Ile Arg
Gln Lys Ile Pro Glu Trp Tyr Asp Ala Gly Ile Ser Ala Ile Trp Ile
Pro Pro Ala Ser Lys Gly Met Ser Gly Gly Tyr Ser Met Gly Tyr Asp
Pro Tyr Asp Tyr Phe Asp Leu Gly Glu Tyr Tyr Gln Lys Gly Thr Val
Glu Thr Arg Phe Gly Ser Lys Gln Glu Leu Ile Asn Met Ile Asn Thr
Ala His Ala Tyr Gly Ile Lys Val Ile Ala Asp Ile Val Ile Asn His
Arg Ala Gly Gly Asp Leu Glu Trp Asn Pro Phe Val Gly Asp Tyr Thr
Trp Thr Asp Phe Ser Lys Val Ala Ser Gly Lys Tyr Thr Ala Asn Tyr
Leu Asp Phe His Pro Asn Glu Leu His Ala Gly Asp Ser Gly Thr Phe
Gly Gly Tyr Pro Asp Ile Cys His Asp Lys Ser Trp Asp Gln Tyr Trp
Leu Trp Ala Ser Gln Glu Ser Tyr Ala Ala Tyr Leu Arg Ser Ile Gly
Ile Asp Ala Trp Arg Phe Asp Tyr Val Lys Gly Tyr Gly Ala Trp Val
Val Lys Asp Trp Leu Asn Trp Trp Gly Gly Trp Ala Val Gly Glu Tyr
Trp Asp Thr Asn Val Asp Ala Leu Leu Asn Trp Ala Tyr Ser Ser Gly
Ala Lys Val Phe Asp Phe Pro Leu Tyr Tyr Lys Met Asp Ala Ala Phe
Asp Asn Lys Asn Ile Pro Ala Leu Val Glu Ala Leu Lys Asn Gly Gly
Thr Val Val Ser Arg Asp Pro Phe Lys Ala Val Thr Phe Val Ala Asn
His Asp Thr Asp Ile Ile Trp Thr Lys Tyr Leu Ala Tyr Ala Phe Ile
Leu Thr Tyr Glu Gly Gln Pro Val Ile Phe Tyr Arg Asp Tyr Glu Glu
Trp Leu Asn Lys Asp Arg Leu Asn Asn Leu Ile Trp Ile His Asp His
Leu Ala Gly Gly Ser Thr Asp Ile Val Tyr Tyr Asp Asn Asp Glu Leu
Ile Phe Val Arg Asn Gly Tyr Gly Asp Lys Pro Gly Leu Ile Thr Tyr
Ile Asn Leu Gly Ser Ser Lys Ala Gly Arg Trp Val Tyr Val Pro Lys
Phe Ala Gly Ser Cys Ile His Glu Tyr Thr Gly Asn Leu Gly Gly Trp
Val Asp Lys Trp Val Asp Ser Ser Gly Trp Val Tyr Leu Glu Ala Pro
Ala His Asp Pro Ala Asn Gly Gln Tyr Gly Tyr Ser Val Trp Ser Tyr
Cys Gly Val Gly

FIGURE 16GG
SEQ ID NO.: 35
atggccaagtactccgagctggaagagggcggcgttataatgcaggccttctactgggacgtccc
aggtggaggaatctggtgggacaccatcaggagcaagataccggagtggtacgaggcgggaatat
ccgccatttggattccccggcgagcaagggcatggcggcgcctattcgatgggctacgacccc
tacgacttctttgacctcggtgagtacgaccagaagggaacggtagagacgcgctttggctccaa
gcaggagctcgtgaacatgataaacaccgcccacgcctacggcatcaaggtcatcgcagacatag
taatcaaccaccgcgcggaggagaccttgagtggaaccccttcgtcaatgactacacctggacg
gacttctcgaaggtcgcttccggcaagtacacggccaactacctcgacttccaccccaacgaggt
caagtgctgtgacgagggcacatttggaggcttcccagacatagcccacgagaagagctgggacc
agcactggctctgggcgagcgatgagagctacgccgcctacctaaggagcatcggcgttgatgcc
tggcgcttcgactacgtcaagggctatgctccctgggtcgtcaaggactggctgaactggtgggg
aggctgggcggttggagagtactgggacaccaacgtcgacgctgttctcaactgggcatactcga
gcggtgccaaggtctttgacttcgccctctactacaagatggacgcggcctttgacaacaagaac
attcccgcactcgtcgaggccctcaagaacggggcacagtcgtcagccgcgacccgtttaaggc
cgtaaccttcgttgcaaccacgacaccgatataatctggaacaagtatccagcctacgcgttca
tcctcacctacgagggccagccgacaatattctaccgcgactacgaggagtggctcaacaaggat
aagctcaagaacctcatctggatacatgacaacgtcgccggaggaagcaccgacatagtctacta
cgataacgatgaactcatcttcgtcaggaacggctacggggacaagccggggcttataacctaca
tcaacctaggctcgagcaaggccggaaggtgggtttacgttccgaagttcgcaggctcgtgcata
cacgagtacaccggcaatctcggcggctgggtggacaagtgggtggactcaagcggctgggtcta
cctcgaggctcctgcccacgaccggccaacggccagtacggctactccgtctggagctactgcg
gtgttgggtga

FIGURE 16HH
SEQ ID NO.: 36
Met Ala Lys Tyr Ser Glu Leu Glu Glu Gly Gly Val Ile Met Gln Ala
Phe Tyr Trp Asp Val Pro Gly Gly Gly Ile Trp Trp Asp Thr Ile Arg
Ser Lys Ile Pro Glu Trp Tyr Glu Ala Gly Ile Ser Ala Ile Trp Ile
Pro Pro Ala Ser Lys Gly Met Gly Gly Ala Tyr Ser Met Gly Tyr Asp
Pro Tyr Asp Phe Phe Asp Leu Gly Glu Tyr Asp Gln Lys Gly Thr Val
Glu Thr Arg Phe Gly Ser Lys Gln Glu Leu Val Asn Met Ile Asn Thr
Ala His Ala Tyr Gly Ile Lys Val Ile Ala Asp Ile Val Ile Asn His
Arg Ala Gly Gly Asp Leu Glu Trp Asn Pro Phe Val Asn Asp Tyr Thr
Trp Thr Asp Phe Ser Lys Val Ala Ser Gly Lys Tyr Thr Ala Asn Tyr
Leu Asp Phe His Pro Asn Glu Val Lys Cys Cys Asp Glu Gly Thr Phe
Gly Gly Phe Pro Asp Ile Ala His Glu Lys Ser Trp Asp Gln His Trp
Leu Trp Ala Ser Asp Glu Ser Tyr Ala Ala Tyr Leu Arg Ser Ile Gly
Val Asp Ala Trp Arg Phe Asp Tyr Val Lys Gly Tyr Ala Pro Trp Val
Val Lys Asp Trp Leu Asn Trp Trp Gly Gly Trp Ala Val Gly Glu Tyr
Trp Asp Thr Asn Val Asp Ala Val Leu Asn Trp Ala Tyr Ser Ser Gly
Ala Lys Val Phe Asp Phe Ala Leu Tyr Tyr Lys Met Asp Ala Ala Phe
Asp Asn Lys Asn Ile Pro Ala Leu Val Glu Ala Leu Lys Asn Gly Gly
Thr Val Val Ser Arg Asp Pro Phe Lys Ala Val Thr Phe Val Ala Asn
His Asp Thr Asp Ile Ile Trp Asn Lys Tyr Pro Ala Tyr Ala Phe Ile
Leu Thr Tyr Glu Gly Gln Pro Thr Ile Phe Tyr Arg Asp Tyr Glu Glu
Trp Leu Asn Lys Asp Lys Leu Lys Asn Leu Ile Trp Ile His Asp Asn
Val Ala Gly Gly Ser Thr Asp Ile Val Tyr Tyr Asp Asn Asp Glu Leu
Ile Phe Val Arg Asn Gly Tyr Gly Asp Lys Pro Gly Leu Ile Thr Tyr
Ile Asn Leu Gly Ser Ser Lys Ala Gly Arg Trp Val Tyr Val Pro Lys
Phe Ala Gly Ser Cys Ile His Glu Tyr Thr Gly Asn Leu Gly Gly Trp
Val Asp Lys Trp Val Asp Ser Ser Gly Trp Val Tyr Leu Glu Ala Pro
Ala His Asp Pro Ala Asn Gly Gln Tyr Gly Tyr Ser Val Trp Ser Tyr
Cys Gly Val Gly

FIGURE 16II
SEQ ID NO.: 71
atggccaagtacctggagctcgaagagggcggggtcataatgcaggcgttctactgggacgtgcc
ttcaggaggaatatggtgggacacaatacggcagaagataccggagtggtacgatgccggaatct
ccgcaatatggattccccggcgagcaagggcatggcggcgcctattcgatgggctacgacccc
tacgacttctttgacctcggtgagtacgaccagaagggaacggtagagacgcgctttggctccaa
gcaggagctcgtgaacatgataaacacggcccatgcctacggcataaaggtcatagcggacatcg
tcataaaccaccgcgcaggcggagacctcgagtggaacccgttcgttggggactacacctggacg
gacttctcaaaggtagcctcgggcaaatatactgccaactacctcgacttccacccgaacgagct
ccatgcgggcgattccggaacatttggaggctatcccgacatatgccacgacaagagctggacc
agtactggctctgggccagccaggagagctacgcggcatatctcaggagcatcggcatcgatgcc
tggcgcttcgactacgtcaagggctatgctccctgggtcgtcaaggactggctgaactggtgggg
aggctgggcggttggagagtactgggacaccaacgtcgacgctgttctcaactgggcatactcga
gcggtgccaaggtctttgacttcgccctctactacaagatggatgaggcctttgacaacaaaaac
attccagcgctcgtctctgcccttcagaacggccagactgttgtctcccgcgacccgttcaaggc
cgtaacctttgtagcaaaccacgacaccgatataatctggaacaagtatccagcctacgcgttca
tcctcacctacgagggccagccgacaatattctaccgcgactacgaggagtggctcaacaaggat
aagctcaagaacctcatctggatacatgacaacctcgccggaggaagcactgacatcgtttacta
cgacaacgacgagctgatattcgtgagaaacggctacggaagcaagccgggactgataacataca
tcaacctcgcctcaagcaaagccggaaggtgggtttatgtgccgaagttcgcgggcgcgtgcatc
cacgagtatactggtaacctcggaggctgggtagacaagtacgtctactcaagcggctgggtcta
tctcgaagctccagcttacgaccctgccaacgggcagtatggctactccgtgtggagctactgcg
gggtgggctga

FIGURE 16JJ
SEQ ID NO.: 72
Met Ala Lys Tyr Leu Glu Leu Glu Glu Gly Gly Val Ile Met Gln Ala
Phe Tyr Trp Asp Val Pro Ser Gly Gly Ile Trp Trp Asp Thr Ile Arg
Gln Lys Ile Pro Glu Trp Tyr Asp Ala Gly Ile Ser Ala Ile Trp Ile
Pro Pro Ala Ser Lys Gly Met Gly Gly Ala Tyr Ser Met Gly Tyr Asp
Pro Tyr Asp Phe Phe Asp Leu Gly Glu Tyr Asp Gln Lys Gly Thr Val
Glu Thr Arg Phe Gly Ser Lys Gln Glu Leu Val Asn Met Ile Asn Thr
Ala His Ala Tyr Gly Ile Lys Val Ile Ala Asp Ile Val Ile Asn His
Arg Ala Gly Gly Asp Leu Glu Trp Asn Pro Phe Val Gly Asp Tyr Thr
Trp Thr Asp Phe Ser Lys Val Ala Ser Gly Lys Tyr Thr Ala Asn Tyr
Leu Asp Phe His Pro Asn Glu Leu His Ala Gly Asp Ser Gly Thr Phe
Gly Gly Tyr Pro Asp Ile Cys His Asp Lys Ser Trp Asp Gln Tyr Trp
Leu Trp Ala Ser Gln Glu Ser Tyr Ala Ala Tyr Leu Arg Ser Ile Gly
Ile Asp Ala Trp Arg Phe Asp Tyr Val Lys Gly Tyr Ala Pro Trp Val
Val Lys Asp Trp Leu Asn Trp Trp Gly Gly Trp Ala Val Gly Glu Tyr
Trp Asp Thr Asn Val Asp Ala Val Leu Asn Trp Ala Tyr Ser Ser Gly
Ala Lys Val Phe Asp Phe Ala Leu Tyr Tyr Lys Met Asp Glu Ala Phe
Asp Asn Lys Asn Ile Pro Ala Leu Val Ser Ala Leu Gln Asn Gly Gln
Thr Val Val Ser Arg Asp Pro Phe Lys Ala Val Thr Phe Val Ala Asn
His Asp Thr Asp Ile Ile Trp Asn Lys Tyr Pro Ala Tyr Ala Phe Ile
Leu Thr Tyr Glu Gly Gln Pro Thr Ile Phe Tyr Arg Asp Tyr Glu Glu
Trp Leu Asn Lys Asp Lys Leu Lys Asn Leu Ile Trp Ile His Asp Asn
Leu Ala Gly Gly Ser Thr Asp Ile Val Tyr Tyr Asp Asn Asp Glu Leu
Ile Phe Val Arg Asn Gly Tyr Gly Ser Lys Pro Gly Leu Ile Thr Tyr
Ile Asn Leu Ala Ser Ser Lys Ala Gly Arg Trp Val Tyr Val Pro Lys
Phe Ala Gly Ala Cys Ile His Glu Tyr Thr Gly Asn Leu Gly Gly Trp
Val Asp Lys Tyr Val Tyr Ser Ser Gly Trp Val Tyr Leu Glu Ala Pro
Ala Tyr Asp Pro Ala Asn Gly Gln Tyr Gly Tyr Ser Val Trp Ser Tyr
Cys Gly Val Gly

FIGURE 16KK
SEQ ID NO.: 49
gtggtttatgacgatgtccgctatgacctttatgccgtaggcatgggccgtgtttatcatgttca
cgagctcctgcttggagccaaagcgcgtctctaccgttcccttctggtcgtactcaccgaggtca
aagaagtcgtaggggtcgtagcccatcgaataggcgccgcccatgccttgctcgccgggggaat
ccatatcgccgaaatcccggcgcttgcccagtcgggtatcttctgggctatcgtgtcccaccaga
ttcctcccatggggacgtcccagtagaaggcctgcattatgagccgcctcttcgagcccggaa
tactttgccataagttacctcctactagtagattaaaattctgtttcctgtgtgaaattgtt

FIGURE 16LL
SEQ ID NO.: 50
Val Val Tyr Asp Asp Val Arg Tyr Asp Leu Tyr Ala Val Gly Met Gly
Arg Val Tyr His Val His Glu Leu Leu Leu Gly Ala Lys Ala Arg Leu
Tyr Arg Ser Leu Leu Val Val Leu Thr Glu Val Lys Glu Val Val Gly
Val Val Ala His Arg Ile Gly Ala Ala His Ala Leu Ala Arg Arg Gly
Asn Pro Tyr Arg Arg Asn Pro Gly Ala Cys Pro Val Gly Tyr Leu Leu
Gly Tyr Arg Val Pro Pro Asp Ser Ser His Gly Asp Val Pro Val Glu
Gly Leu His Tyr Glu Pro Ala Leu Phe Glu Pro Gly Ile Leu Cys His
Lys Leu Pro Pro Thr Ser Arg Leu Lys Phe Cys Phe Leu Cys Glu Ile
Val

FIGURE 16MM
SEQ ID NO.: 51
ATGGCCAAGTACCTGGAGCTCGAAGAGGGCGGGGTCATAATGCAGGCGTTCTACTGGGACGTGCC
TTCAGGAGGAATATGGTGGGACACAATACGGCAGAAGATACCGGAGTGGTACGATGCCGGAATCT
CCGCAATATGGATTCCCCCGGCGAGCAAGGGCATGGGCGGCGCCTATTCGATGGGCTACGACCCC
TACGACTTCTTTGACCTCGGTGAGTACGACCAGAAGGGAACGGTAGAGACGCGCTTTGGCTCCAA
GCAGGAGCTCGTGAACATGATAAACACCGCCCACGCCTATGGCATGAAGGTAATAGCCGATATAG
TCATCAACCACCGCGCCGGCGGTGACCTGGAGTGGAACCCCTTCGTGAACGACTATACCTGGACC
GACTTCTCAAAGGTCGCGTCGGGTAAATACACGGCCAACTACCTCGACTTCCACCCCAACGAGGT
CAAGTGCTGTGACGAGGGCACATTTGGAGGCTTCCCAGACATAGCCCACGAGAAGAGCTGGGACC
AGCACTGGCTCTGGGCGAGCGATGAGAGCTACGCCGCCTACCTAAGGAGCATCGGCGTTGATGCC
TGGCGCTTTGACTACGTGAAGGGCTACGGAGCGTGGGTCGTCAAGGACTGGCTCAACTGGTGGGG
CGGCTGGGCCGTTGGCGAGTACTGGGACACCAACGTTGATGCACTCCTCAACTGGGCCTACTCGA
GCGGCGCCAAGGTCTTCGACTTCCCGCTCTACTACAAGATGGATGAGGCCTTTGACAACAAAAAC
ATTCCAGCGCTCGTCTCTGCCCTTCAGAACGGCCAGACTGTTGTCTCCCGCGACCCGTTCAAGGC
CGTAACCTTTGTAGCAAACCACGACACCGATATAATCTGGAACAAGTATCCAGCCTACGCGTTCA
TCCTCACCTACGAGGGCCAGCCGACAATATTCTACCGCGACTACGAGGAGTGGCTCAACAAGGAT
AAGCTCAAGAACCTCATCTGGATACATGACAACCTCGCCGGAGGAAGCACTGACATCGTTTACTA
CGACAACGACGAGCTGATATTCGTGAGAAACGGCTACGGAAGCAAGCCGGGACTGATAACATACA
TCAACCTCGCCTCAAGCAAAGCCGGAAGGTGGGTTTACGTTCCGAAGTTCGCAGGCTCGTGCATA
CACGAGTACACCGGCAATCTCGGCGGCTGGGTGGACAAGTGGGTGGACTCAAGCGGCTGGGTCTA
CCTCGAGGCTCCTGCCCACGACCCGGCCAACGGCCAGTACGGCTACTCCGTCTGGAGCTATTGCG
GTGTTGGCTGA

FIGURE 16NN
SEQ ID NO.: 52
MAKYLELEEGGVIMQAFYWDVPSGGIWWDTIRQKIPEWYDAGISAIWIPPASKGMGGAYSMGYDP
YDFFDLGEYDQKGTVETRFGSKQELVNMINTAHAYGMKVIADIVINHRAGGDLEWNPFVNDYTWT
DFSKVASGKYTANYLDFHPNEVKCCDEGTFGGFPDIAHEKSWDQHWLWASDESYAAYLRSIGVDA
WRFDYVKGYGAWVVKDWLNWWGGWAVGEYWDTNVDALLNWAYSSGAKVFDFPLYYKMDEAFDNKN
IPALVSALQNGQTVVSRDPFKAVTFVANHDTDIIWNKYPAYAFILTYEGQPTIFYRDYEEWLNKD
KLKNLIWIHDNLAGGSTDIVYYDNDELIFVRNGYGSKPGLITYINLASSKAGRWVYVPKFAGSCI
HEYTGNLGGWVDKWVDSSGWVYLEAPAHDPANGQYGYSVWSYCGVG

FIGURE 16OO
SEQ ID NO.: 37
atggccaagtacctggagctcgaagagggcggggtcataatgcaggcgttctactgggacgtgcc
ttcaggaggaatatggtgggacacaatacggcagaagataccggagtggtacgatgccggaatct
ccgcaatatggattccccggcgagcaagggcatggccggcgcctattcgatggctacgacccc
tacgacttctttgacctcggtgagtacgaccagaagggaacggtagagacgcgctttggctccaa
gcaggagctcgtgaacatgataaacaccgcccacgcctatggcatgaaggtaatagccgatatag
tcatcaaccaccgcgccggcggtgacctggagtggaaccccttcgtgaacgactatacctggacc
gacttctcaaaggtcgcgtcgggtaaatacacggccaactacctcgacttccacccgaacgagct
ccatgcgggcgattccggaacatttggaggctatcccgacatatgccacgacaagagctgggacc
agtactggctctgggccagccaggagagctacgcggcatatctcaggagcatcggcatcgatgcc
tggcgctttgactacgtgaagggctacgagcgcgggtcgtcaaggactggctcaactggtgggg
cggctgggccgttggcgagtactgggacaccaacgttgatgcactcctcaactgggcctactcga
gcggcgccaaggtcttcgacttcccgctctactacaagatggatgaggcctttgacaacaaaaac
attccagcgctcgtctctgcccttcagaacggccagactgttgtctcccgcgacccgttcaaggc
cgtaacctttgtagcaaaccacgacaccgatataatctggaacaagtatccagcctacgcgttca
tcctcacctacgagggccagccgacaatattctatcgcgactacgaggagtggctcaacaaggat
aagctcaagaacctcatctggatacatgacaacctcgccggaggaagcactgacatcgtttacta
cgacaacgacgagctgatattcgtgagaaacggctacggaagcaagccgggactgataacataca
tcaacctcgcctcaagcaaagccggaaggtgggtttacgttccgaagttcgcaggctcgtgcata
cacgagtacaccggcaatctcggcggctgggtggacaagtgggtggactcaagcggctgggtcta
cctcgaggctcctgcccacgacccggccaacggccagtacggctactccgtctggagctactgcg
ggtggggtga
FIGURE 16PP
SEQ ID NO.: 38
Met Ala Lys Tyr Leu Glu Leu Glu Glu Gly Gly Val Ile Met Gln Ala
Phe Tyr Trp Asp Val Pro Ser Gly Gly Ile Trp Trp Asp Thr Ile Arg
Gln Lys Ile Pro Glu Trp Tyr Asp Ala Gly Ile Ser Ala Ile Trp Ile
Pro Pro Ala Ser Lys Gly Met Gly Gly Ala Tyr Ser Met Gly Tyr Asp
Pro Tyr Asp Phe Phe Asp Leu Gly Glu Tyr Asp Gln Lys Gly Thr Val
Glu Thr Arg Phe Gly Ser Lys Gln Glu Leu Val Asn Met Ile Asn Thr
Ala His Ala Tyr Gly Met Lys Val Ile Ala Asp Ile Val Ile Asn His
Arg Ala Gly Gly Asp Leu Glu Trp Asn Pro Phe Val Asn Asp Tyr Thr
Trp Thr Asp Phe Ser Lys Val Ala Ser Gly Lys Tyr Thr Ala Asn Tyr
Leu Asp Phe His Pro Asn Glu Leu His Ala Gly Asp Ser Gly Thr Phe
Gly Gly Tyr Pro Asp Ile Cys His Asp Lys Ser Trp Asp Gln Tyr Trp
Leu Trp Ala Ser Gln Glu Ser Tyr Ala Ala Tyr Leu Arg Ser Ile Gly
Ile Asp Ala Trp Arg Phe Asp Tyr Val Lys Gly Tyr Gly Ala Arg Val
Val Lys Asp Trp Leu Asn Trp Trp Gly Gly Trp Ala Val Gly Glu Tyr
Trp Asp Thr Asn Val Asp Ala Leu Leu Asn Trp Ala Tyr Ser Ser Gly
Ala Lys Val Phe Asp Phe Pro Leu Tyr Tyr Lys Met Asp Glu Ala Phe
Asp Asn Lys Asn Ile Pro Ala Leu Val Ser Ala Leu Gln Asn Gly Gln
Thr Val Val Ser Arg Asp Pro Phe Lys Ala Val Thr Phe Val Ala Asn
His Asp Thr Asp Ile Ile Trp Asn Lys Tyr Pro Ala Tyr Ala Phe Ile
Leu Thr Tyr Glu Gly Gln Pro Thr Ile Phe Tyr Arg Asp Tyr Glu Glu
Trp Leu Asn Lys Asp Lys Leu Lys Asn Leu Ile Trp Ile His Asp Asn
Leu Ala Gly Gly Ser Thr Asp Ile Val Tyr Tyr Asp Asn Asp Glu Leu
Ile Phe Val Arg Asn Gly Tyr Gly Ser Lys Pro Gly Leu Ile Thr Tyr
Ile Asn Leu Ala Ser Ser Lys Ala Gly Arg Trp Val Tyr Val Pro Lys
Phe Ala Gly Ser Cys Ile His Glu Tyr Thr Gly Asn Leu Gly Gly Trp
Val Asp Lys Trp Val Asp Ser Ser Gly Trp Val Tyr Leu Glu Ala Pro
Ala His Asp Pro Ala Asn Gly Gln Tyr Gly Tyr Ser Val Trp Ser Tyr
Cys Gly Val Gly

FIGURE 16QQ
SEQ ID NO.: 39
atggccaagtacctggagctcgaagagggcggggtcataatgcaggcgttctactgggacgtgcc
ttcaggaggaatatggtgggacacaatacggcagaagataccggagtggtacgatgccggaatct
ccgcaatatggattcctcccgcgagcaggggtatgagcggcggctattcgatgggctacgacccc
tacgattattttgacctcggtgagtactaccagaagggaacggtggaaacgaggttcggctcaaa
gcaggagctcataaacatgataaacaccgcccacgcctatggcatgaaggtaatagccgatatag
tcatcaaccaccgcgccggcggtgacctggagtggaacccctcgtgaacgactatacctggacc
gacttctcaaaggtcgcgtcgggtaaatacacggccaactacctcgacttccacccgaacgagct
ccatgcgggcgattccggaacatttggaggctatcccgacatatgccacgacaagagctgggacc
agtactggctctgggccagccaggagagctacgcggcatatctcaggagcatcggtatcgatgcc
tggcgctttgactacgtgaaggggctacggagcgtgggtcgtcaaggactggctcaactggtgggg
cggctgggccgttggcgagtactgggaccccaacgttgatgccctcctccctgggcctactcga
gcggcgccaaggtcttcgacttcccgctctactacaagatggatgaggcctttgacaacaaaaac
attccagcgctcgtctctgcccttcagaacggccagactgttgtctcccgcgacccgttcaaggc
cgtaacctttgtagccaaccacgataccgatataatctggaacaagtatccagcctacgcgttca
tcctcacctacgagggccagccgacaatattctaccgcgactacgaggagtggctcaacaaggat
aagctcaagaacctcatctggatacatgacaacctcgccggaggaagcaccgacatagtctacta
cgataacgatgaactcatcttcgtcaggaacggctacggggacaagccggggcttataacctaca
tcaacctaggctcgagcaaggccggaaggtgggtctacgttccgaagttcgcgggagcgtgcatc
cacgagtacaccggcaacctcggcggctgggtggacaagtgggtggactcaagcgggtgggtgta
cctcgaggcccctgcccacgacccggccaacggctattacggctactccgtctggagctactgcg
gggtgggctga

FIGURE 16RR
SEQ ID NO.: 40
Met Ala Lys Tyr Leu Glu Leu Glu Glu Gly Gly Val Ile Met Gln Ala
Phe Tyr Trp Asp Val Pro Ser Gly Gly Ile Trp Trp Asp Thr Ile Arg
Gln Lys Ile Pro Glu Trp Tyr Asp Ala Gly Ile Ser Ala Ile Trp Ile
Pro Pro Ala Ser Arg Gly Met Ser Gly Gly Tyr Ser Met Gly Tyr Asp
Pro Tyr Asp Tyr Phe Asp Leu Gly Glu Tyr Tyr Gln Lys Gly Thr Val
Glu Thr Arg Phe Gly Ser Lys Gln Glu Leu Ile Asn Met Ile Asn Thr
Ala His Ala Tyr Gly Met Lys Val Ile Ala Asp Ile Val Ile Asn His
Arg Ala Gly Gly Asp Leu Glu Trp Asn Pro Phe Val Asn Asp Tyr Thr
Trp Thr Asp Phe Ser Lys Val Ala Ser Gly Lys Tyr Thr Ala Asn Tyr
Leu Asp Phe His Pro Asn Glu Leu His Ala Gly Asp Ser Gly Thr Phe
Gly Gly Tyr Pro Asp Ile Cys His Asp Lys Ser Trp Asp Gln Tyr Trp
Leu Trp Ala Ser Gln Glu Ser Tyr Ala Ala Tyr Leu Arg Ser Ile Gly
Ile Asp Ala Trp Arg Phe Asp Tyr Val Lys Gly Tyr Gly Ala Trp Val
Val Lys Asp Trp Leu Asn Trp Trp Gly Gly Trp Ala Val Gly Glu Tyr
Trp Asp Pro Asn Val Asp Ala Leu Leu Pro Trp Ala Tyr Ser Ser Gly
Ala Lys Val Phe Asp Phe Pro Leu Tyr Tyr Lys Met Asp Glu Ala Phe
Asp Asn Lys Asn Ile Pro Ala Leu Val Ser Ala Leu Gln Asn Gly Gln
Thr Val Val Ser Arg Asp Pro Phe Lys Ala Val Thr Phe Val Ala Asn
His Asp Thr Asp Ile Ile Trp Asn Lys Tyr Pro Ala Tyr Ala Phe Ile
Leu Thr Tyr Glu Gly Gln Pro Thr Ile Phe Tyr Arg Asp Tyr Glu Glu
Trp Leu Asn Lys Asp Lys Leu Lys Asn Leu Ile Trp Ile His Asp Asn
Leu Ala Gly Gly Ser Thr Asp Ile Val Tyr Tyr Asp Asn Asp Glu Leu
Ile Phe Val Arg Asn Gly Tyr Gly Asp Lys Pro Gly Leu Ile Thr Tyr
Ile Asn Leu Gly Ser Ser Lys Ala Gly Arg Trp Val Tyr Val Pro Lys
Phe Ala Gly Ala Cys Ile His Glu Tyr Thr Gly Asn Leu Gly Gly Trp
Val Asp Lys Trp Val Asp Ser Ser Gly Trp Val Tyr Leu Glu Ala Pro
Ala His Asp Pro Ala Asn Gly Tyr Tyr Gly Tyr Ser Val Trp Ser Tyr
Cys Gly Val Gly

FIGURE 16SS
SEQ ID NO.: 41
atggccaagtacctggagctcgaagagggcggggtcataatgcaggcgttctactgggacgtgcc
ttcaggaggaatatggtgggacacaatacggcagaagataccggagtggtacgatgccggaatct
ccgcaatatggattcctcccgcgagcaagggtatgagcggcggctattcgatgggctacgacccc
tacgattattttgacctcggtgagtactaccagaagggaacggtggaaacgaggttcggctcaaa
gcaggagctcataaacatgataaacacggcccatgcctacggcataaaggtcatagcggacatcg
tcataaaccaccgcgcaggcggagacctcgagtggaacccgttcgttggggactacacctggacg
gacttctcaaaggtggcctcgggcaaatatactgccaactacctcgacttccacccgaacgagct
ccatgcgggcgattccggaacatttggaggctatcccgacatatgccacgacaagagctggacc
agtactggctctgggccagccaggagagctacgcggcatatctcaggagcatcggcatcgatgcc
tggcgctttgactacgtgaagggctacgagcgtggtcgtcaaggactggctcaactggtgggg
cggctgggccgttggcgagtactgggacaccaacgttgatgcactcctcaactgggcctactcga
gcggcgccaaggtcttcgacttcccgctctactacaagatggacgcggcctttgacaacaagaac
attcccgcactcgtcgaggccctcaagaacggggcacagtcgtcagccgcgacccgtttaaggc
cgtaaccttcgttgcaaaccacgacaccgatataatctggaacaagtatccagcctacgcgttca
tcctcacctacgagggccagccgacaatattctaccgcgactacgaggagtggctcaacaaggat
aagctcaagaacctcatctggatacatgacaacctcgccggaggaagcacgagcatagtttacta
cgacagcgacgagatgatcttcgtgaggaacggctatggaagcaagcctggccttataacttaca
tcaacctcggctcgagcaaggttggaaggtgggtttatgtgccgaagttcgcgggcgcgtgcatc
cacgagtatactggtaacctcggaggctgggtagacaagtacgtctactcaagcggctgggtcta
tctcgaagctccagcttacgaccctgccaacgggcagtatggctactccgtgtggagctactgcg
gtgttgggtga

FIGURE 16TT
SEQ ID NO.: 42
Met Ala Lys Tyr Leu Glu Leu Glu Glu Gly Gly Val Ile Met Gln Ala
Phe Tyr Trp Asp Val Pro Ser Gly Gly Ile Trp Trp Asp Thr Ile Arg
Gln Lys Ile Pro Glu Trp Tyr Asp Ala Gly Ile Ser Ala Ile Trp Ile
Pro Pro Ala Ser Lys Gly Met Ser Gly Gly Tyr Ser Met Gly Tyr Asp
Pro Tyr Asp Tyr Phe Asp Leu Gly Glu Tyr Tyr Gln Lys Gly Thr Val
Glu Thr Arg Phe Gly Ser Lys Gln Glu Leu Ile Asn Met Ile Asn Thr
Ala His Ala Tyr Gly Ile Lys Val Ile Ala Asp Ile Val Ile Asn His
Arg Ala Gly Gly Asp Leu Glu Trp Asn Pro Phe Val Gly Asp Tyr Thr
Trp Thr Asp Phe Ser Lys Val Ala Ser Gly Lys Tyr Thr Ala Asn Tyr
Leu Asp Phe His Pro Asn Glu Leu His Ala Gly Asp Ser Gly Thr Phe
Gly Gly Tyr Pro Asp Ile Cys His Asp Lys Ser Trp Asp Gln Tyr Trp
Leu Trp Ala Ser Gln Glu Ser Tyr Ala Ala Tyr Leu Arg Ser Ile Gly
Ile Asp Ala Trp Arg Phe Asp Tyr Val Lys Gly Tyr Gly Ala Trp Val
Val Lys Asp Trp Leu Asn Trp Trp Gly Gly Trp Ala Val Gly Glu Tyr
Trp Asp Thr Asn Val Asp Ala Leu Leu Asn Trp Ala Tyr Ser Ser Gly
Ala Lys Val Phe Asp Phe Pro Leu Tyr Tyr Lys Met Asp Ala Ala Phe
Asp Asn Lys Asn Ile Pro Ala Leu Val Glu Ala Leu Lys Asn Gly Gly
Thr Val Val Ser Arg Asp Pro Phe Lys Ala Val Thr Phe Val Ala Asn
His Asp Thr Asp Ile Ile Trp Asn Lys Tyr Pro Ala Tyr Ala Phe Ile
Leu Thr Tyr Glu Gly Gln Pro Thr Ile Phe Tyr Arg Asp Tyr Glu Glu
Trp Leu Asn Lys Asp Lys Leu Lys Asn Leu Ile Trp Ile His Asp Asn
Leu Ala Gly Gly Ser Thr Ser Ile Val Tyr Tyr Asp Ser Asp Glu Met
Ile Phe Val Arg Asn Gly Tyr Gly Ser Lys Pro Gly Leu Ile Thr Tyr
Ile Asn Leu Gly Ser Ser Lys Val Gly Arg Trp Val Tyr Val Pro Lys
Phe Ala Gly Ala Cys Ile His Glu Tyr Thr Gly Asn Leu Gly Gly Trp
Val Asp Lys Tyr Val Tyr Ser Ser Gly Trp Val Tyr Leu Glu Ala Pro
Ala Tyr Asp Pro Ala Asn Gly Gln Tyr Gly Tyr Ser Val Trp Ser Tyr
Cys Gly Val Gly

FIGURE 16UU
SEQ ID NO.: 43
atggccaagtactccgagctggaagagggcggcgttataatgcaggccttctactgggacgtccc
aggtggaggaatctggtgggacaccatcaggagcaagataccggagtggtacgaggcgggaatat
ccgccatttggattccccggcgagcaagggcatggcggcgcctattcgatgggctacgacccc
tacgacttctttgacctcggtgagtacgaccagaagggaacggtagagacgcgctttggctccaa
gcaggagctcgtgaacatgataaacacggcccatgcctacggcataaaggtcatagcggacatcg
tcataaaccaccgcgaggcggagacctcgagtggaacccgttcgttggggactacacctggacg
gacttctcaaaggtggcctcgggcaaatactgccaactacctcgacttccaccccaacgaggt
caagtgctgtgacgagggcacatttggaggcttcccagacatagcccacgagaagagctgggacc
agcactggctctgggcgagcgatgagagctacgccgcctacctaaggagcatcggcgttgatgcc
tggcgcttcgactacgtcaagggctacggagcgtgggtcgtcaaggactggctggactggtgggg
aggctgggccgtcggggagtactgggacacaaacgttgatgcactgctcaactgggcctactcga
gcgatgcaaaagtcttcgacttcccgctctactacaagatggatgaggcctttgacaacaaaaac
attccagcgctcgtctctgcccttcagaacggccagactgttgtctcccgcgacccgttcaaggc
cgtaacctttgtagcaaaccacgacaccgatataatctggaacaagtatccagcctacgcgttca
tcctcacctacgagggccagccgacaatattctaccgcgactacgaggagtggctcaacaaggat
aagctcaagaacctcatctggatacatgacaacctcgtcggaggaagcacgagcatagtttacta
cgacagcgacgagatgatcttcgtgaggaacggctatggaagcaagcctggcctttataacttaca
tcaacctcggctcgagcaaggttggaaggtgggtttacgttccgaagttcgcaggctcgtgcata
cacgagtacaccggcaatctcggcggctgggtggacaagtgggtggactcaagcggctgggtcta
cctcgaggctcctgcccacgacccggccaacggccagtacggctactccgtctggagctactgcg
gtgttggctga

FIGURE 16VV
SEQ ID NO.: 44
Met Ala Lys Tyr Ser Glu Leu Glu Glu Gly Gly Val Ile Met Gln Ala
Phe Tyr Trp Asp Val Pro Gly Gly Gly Ile Trp Trp Asp Thr Ile Arg
Ser Lys Ile Pro Glu Trp Tyr Glu Ala Gly Ile Ser Ala Ile Trp Ile
Pro Pro Ala Ser Lys Gly Met Gly Gly Ala Tyr Ser Met Gly Tyr Asp
Pro Tyr Asp Phe Phe Asp Leu Gly Glu Tyr Asp Gln Lys Gly Thr Val
Glu Thr Arg Phe Gly Ser Lys Gln Glu Leu Val Asn Met Ile Asn Thr
Ala His Ala Tyr Gly Ile Lys Val Ile Ala Asp Ile Val Ile Asn His
Arg Ala Gly Gly Asp Leu Glu Trp Asn Pro Phe Val Gly Asp Tyr Thr
Trp Thr Asp Phe Ser Lys Val Ala Ser Gly Lys Tyr Thr Ala Asn Tyr
Leu Asp Phe His Pro Asn Glu Val Lys Cys Cys Asp Glu Gly Thr Phe
Gly Gly Phe Pro Asp Ile Ala His Glu Lys Ser Trp Asp Gln His Trp
Leu Trp Ala Ser Asp Glu Ser Tyr Ala Ala Tyr Leu Arg Ser Ile Gly
Val Asp Ala Trp Arg Phe Asp Tyr Val Lys Gly Tyr Gly Ala Trp Val
Val Lys Asp Trp Leu Asp Trp Trp Gly Gly Trp Ala Val Gly Glu Tyr
Trp Asp Thr Asn Val Asp Ala Leu Leu Asn Trp Ala Tyr Ser Ser Asp
Ala Lys Val Phe Asp Phe Pro Leu Tyr Tyr Lys Met Asp Glu Ala Phe
Asp Asn Lys Asn Ile Pro Ala Leu Val Ser Ala Leu Gln Asn Gly Gln
Thr Val Val Ser Arg Asp Pro Phe Lys Ala Val Thr Phe Val Ala Asn
His Asp Thr Asp Ile Ile Trp Asn Lys Tyr Pro Ala Tyr Ala Phe Ile
Leu Thr Tyr Glu Gly Gln Pro Thr Ile Phe Tyr Arg Asp Tyr Glu Glu
Trp Leu Asn Lys Asp Lys Leu Lys Asn Leu Ile Trp Ile His Asp Asn
Leu Val Gly Gly Ser Thr Ser Ile Val Tyr Tyr Asp Ser Asp Glu Met
Ile Phe Val Arg Asn Gly Tyr Gly Ser Lys Pro Gly Leu Ile Thr Tyr
Ile Asn Leu Gly Ser Ser Lys Val Gly Arg Trp Val Tyr Val Pro Lys
Phe Ala Gly Ser Cys Ile His Glu Tyr Thr Gly Asn Leu Gly Gly Trp
Val Asp Lys Trp Val Asp Ser Ser Gly Trp Val Tyr Leu Glu Ala Pro
Ala His Asp Pro Ala Asn Gly Gln Tyr Gly Tyr Ser Val Trp Ser Tyr
Cys Gly Val Gly

FIGURE 16WW
SEQ ID NO.: 45
atggccaagtactccgacctggaagagggcggcgttataatgcaggccttctactgggacgtccc
aggtggaggaatctggtgggacaccatcaggagcaagataccggagtggtacgaggcgggaatat
ccgccatttggattccccggcgagcaagggcatgggcggcgcctattcgatgggctacgacccc
tacgacttctttgacctcggtgagtacgaccagaagggaacggtagagacgcgctttggctccaa
gcaggagctcgtgaacatgataaacacggcccatgcctacggcataaaggtcatagcggacatcg
tcataaaccacgcgcaggcggagacctcgagtggaacccgttcgttggggactacacctggacg
gacttctcaaaggtggcctcgggcaaatactgccaactacctcgacttccaccccaacgaggt
caagtgctgtgacgagggcacatttggaggcttcccagacatagcccacgagaagagctgggacc
agcactggctctgggcgagcgatgagagctacgccgcctacctaaggagcatcggcgttgatgcc
tggcgctttgactacgtgaagggctacggagcgtgggtcgtcaaggactggctcaactggtgggg
cggctgggccgttggcgagtactgggacaccaacgttgatgcactcctcaactgggcctactcga
gcggcgccaaggtcttcgacttcccgctctactacaagatggatgaggcctttgacaacaaaaac
attccagcgctcgtctctgcccttcagaacggccagactgttgtctcccgcgacccgttcaaggc
cgtaacctttgtagcaaaccacgacaccgatataatctggaacaagtatccagcctacgcgttca
tcctcacctacgagggccagccgacaatattctaccgcgactacgaggagtggctcaacaaggat
aagctcaagaacctcatctggatacatgacaacctcgccggaggaagcaccgacatagtctacta
cgataacgatgaactcatcttcgtcaggaacggctacggggacaagccggggcttataacctaca
tcaacctaggctcgagcaaggccggaaggtgggtttatgtgccgaagttcgcgggcgcgtgcatc
cacgagtatactggtaacctcggaggctgggtagacaagtacgtctactcaagcggctgggtcta
tctcgaagctccagcttacgaccctgccaacgggcagtatggctactccgtgtggagctattgcg
gtgttgggtga

FIGURE 16XX
SEQ ID NO.: 46
Met Ala Lys Tyr Ser Asp Leu Glu Glu Gly Gly Val Ile Met Gln Ala
Phe Tyr Trp Asp Val Pro Gly Gly Gly Ile Trp Trp Asp Thr Ile Arg
Ser Lys Ile Pro Glu Trp Tyr Glu Ala Gly Ile Ser Ala Ile Trp Ile
Pro Pro Ala Ser Lys Gly Met Gly Gly Ala Tyr Ser Met Gly Tyr Asp
Pro Tyr Asp Phe Phe Asp Leu Gly Glu Tyr Asp Gln Lys Gly Thr Val
Glu Thr Arg Phe Gly Ser Lys Gln Glu Leu Val Asn Met Ile Asn Thr
Ala His Ala Tyr Gly Ile Lys Val Ile Ala Asp Ile Val Ile Asn His
Arg Ala Gly Gly Asp Leu Glu Trp Asn Pro Phe Val Gly Asp Tyr Thr
Trp Thr Asp Phe Ser Lys Val Ala Ser Gly Lys Tyr Thr Ala Asn Tyr
Leu Asp Phe His Pro Asn Glu Val Lys Cys Cys Asp Glu Gly Thr Phe
Gly Gly Phe Pro Asp Ile Ala His Glu Lys Ser Trp Asp Gln His Trp
Leu Trp Ala Ser Asp Glu Ser Tyr Ala Ala Tyr Leu Arg Ser Ile Gly
Val Asp Ala Trp Arg Phe Asp Tyr Val Lys Gly Tyr Gly Ala Trp Val
Val Lys Asp Trp Leu Asn Trp Trp Gly Gly Trp Ala Val Gly Glu Tyr
Trp Asp Thr Asn Val Asp Ala Leu Leu Asn Trp Ala Tyr Ser Ser Gly
Ala Lys Val Phe Asp Phe Pro Leu Tyr Tyr Lys Met Asp Glu Ala Phe
Asp Asn Lys Asn Ile Pro Ala Leu Val Ser Ala Leu Gln Asn Gly Gln
Thr Val Val Ser Arg Asp Pro Phe Lys Ala Val Thr Phe Val Ala Asn
His Asp Thr Asp Ile Ile Trp Asn Lys Tyr Pro Ala Tyr Ala Phe Ile
Leu Thr Tyr Glu Gly Gln Pro Thr Ile Phe Tyr Arg Asp Tyr Glu Glu
Trp Leu Asn Lys Asp Lys Leu Lys Asn Leu Ile Trp Ile His Asp Asn
Leu Ala Gly Gly Ser Thr Asp Ile Val Tyr Tyr Asp Asn Asp Glu Leu
Ile Phe Val Arg Asn Gly Tyr Gly Asp Lys Pro Gly Leu Ile Thr Tyr
Ile Asn Leu Gly Ser Ser Lys Ala Gly Arg Trp Val Tyr Val Pro Lys
Phe Ala Gly Ala Cys Ile His Glu Tyr Thr Gly Asn Leu Gly Gly Trp
Val Asp Lys Tyr Val Tyr Ser Ser Gly Trp Val Tyr Leu Glu Ala Pro
Ala Tyr Asp Pro Ala Asn Gly Gln Tyr Gly Tyr Ser Val Trp Ser Tyr
Cys Gly Val Gly

FIGURE 16YY
SEQ ID NO.: 47
atggccaagtacaccgagctggaagagggcggcgttataatgcaggccttctactgggacgtccc
aggtggaggaatctggtgggacaccatcaggagcaagataccggagtggtacgaggcgggaatat
ccgccatttggattccccggcgagcaagggcatgggcggcgcctattcgatgggctacgacccc
tacgacttctttgacctcggtgagtacgaccagaagggaacggtagagacgcgctttggctccaa
gcaggagctcgtgaacatgataaacaccgcccacgcctatggcatgaaggtaatagccgatatag
tcatcaaccaccgcgccggcggtgacctggagtggaacccttcgtgaacgactatacctggacc
gacttctcaaaggtcgcgtcgggtaaatacacggccaactacctcgacttccaccccaacgaggt
caagtgctgtgacgagggcacatttggaggcttcccagacatagcccacgagaagagctgggacc
agcactggctctgggcgagcgatgagagctacgccgcctacctaaggagcatcggcgttgatgcc
tggcgctttgactacgtgaagggctacggagcgtgggtcgtcaaggactggctcaactggtgggg
cggttgggccgttggcgagtactgggacaccaacgttgatgcactcctcaactgggcctactcga
gcggcgccaaggtcttcgacttcccgctctactacaagatggatgaggcctttgacaacaaaaac
attccagcgctcgtctctgcccttcagaacggccagactgttgtctcccgcgacccgttcaaggc
cgtaacctttgtagcaaaccacgacaccgatataatctggaacaagtaccttgcttatgctttca
tcctcacctacgaaggccagcccgtcatattctaccgcgactacgaggagtggctcaacaaggac
aggttgaacaacctcatatggatacacgaccacctcgcaggtggaagcacgagcatagtttacta
cgacagcgacgagatgatcttcgtgaggaacggctatggaagcaagcctggccttataacttaca
tcaacctcggctcgagcaaggttggaaggtgggtttacgttccgaagttcgcaggcccgtgcata
cacgagtacaccggcaatctcggcggctgggtggacaagtgggtggactcaagcggctgggtcta
cctcgaggctcctgcccacgaccggccaacggccagtacggctactccgtctggagctactgcg
gtgttgggtag

FIGURE 16ZZ
SEQ ID NO.: 48
Met Ala Lys Tyr Thr Glu Leu Glu Glu Gly Gly Val Ile Met Gln Ala
Phe Tyr Trp Asp Val Pro Gly Gly Gly Ile Trp Trp Asp Thr Ile Arg
Ser Lys Ile Pro Glu Trp Tyr Glu Ala Gly Ile Ser Ala Ile Trp Ile
Pro Pro Ala Ser Lys Gly Met Gly Gly Ala Tyr Ser Met Gly Tyr Asp
Pro Tyr Asp Phe Phe Asp Leu Gly Glu Tyr Asp Gln Lys Gly Thr Val
Glu Thr Arg Phe Gly Ser Lys Gln Glu Leu Val Asn Met Ile Asn Thr
Ala His Ala Tyr Gly Met Lys Val Ile Ala Asp Ile Val Ile Asn His
Arg Ala Gly Gly Asp Leu Glu Trp Asn Pro Phe Val Asn Asp Tyr Thr
Trp Thr Asp Phe Ser Lys Val Ala Ser Gly Lys Tyr Thr Ala Asn Tyr
Leu Asp Phe His Pro Asn Glu Val Lys Cys Cys Asp Glu Gly Thr Phe
Gly Gly Phe Pro Asp Ile Ala His Glu Lys Ser Trp Asp Gln His Trp
Leu Trp Ala Ser Asp Glu Ser Tyr Ala Ala Tyr Leu Arg Ser Ile Gly
Val Asp Ala Trp Arg Phe Asp Tyr Val Lys Gly Tyr Gly Ala Trp Val
Val Lys Asp Trp Leu Asn Trp Trp Gly Gly Trp Ala Val Gly Glu Tyr
Trp Asp Thr Asn Val Asp Ala Leu Leu Asn Trp Ala Tyr Ser Ser Gly
Ala Lys Val Phe Asp Phe Pro Leu Tyr Tyr Lys Met Asp Glu Ala Phe
Asp Asn Lys Asn Ile Pro Ala Leu Val Ser Ala Leu Gln Asn Gly Gln
Thr Val Val Ser Arg Asp Pro Phe Lys Ala Val Thr Phe Val Ala Asn
His Asp Thr Asp Ile Ile Trp Asn Lys Tyr Leu Ala Tyr Ala Phe Ile
Leu Thr Tyr Glu Gly Gln Pro Val Ile Phe Tyr Arg Asp Tyr Glu Glu
Trp Leu Asn Lys Asp Arg Leu Asn Asn Leu Ile Trp Ile His Asp His
Leu Ala Gly Gly Ser Thr Ser Ile Val Tyr Tyr Asp Ser Asp Glu Met
Ile Phe Val Arg Asn Gly Tyr Gly Ser Lys Pro Gly Leu Ile Thr Tyr
Ile Asn Leu Gly Ser Ser Lys Val Gly Arg Trp Val Tyr Val Pro Lys
Phe Ala Gly Pro Cys Ile His Glu Tyr Thr Gly Asn Leu Gly Gly Trp
Val Asp Lys Trp Val Asp Ser Ser Gly Trp Val Tyr Leu Glu Ala Pro
Ala His Asp Pro Ala Asn Gly Gln Tyr Gly Tyr Ser Val Trp Ser Tyr
Cys Gly Val Gly

FIGURE 16AAA
SEQ ID NO.: 53
ATGGCCAAGTACTCCGAGCTGGAAGAGGGCGGCGTTATAATGCAGGCCTTCTACTGGGACGTCCC
AGGTGGAGGAATCTGGTGGGACACCATCAGGAGCAAGATACCGGAGTGGTACGAGGCGGGAATAT
CCGCCATTTGGATTCCCCGGCGAGCAAGGGCATGGGCGGCGCCTATTCGATGGGCTACGACCCC
TACGACTTCTTTGACCTCGGTGAGTACGACCAGAAGGGAACGGTAGAGACGCGCTTTGGCTCCAA
GCAGGAGCTCGTGAACATGATAAACACGGCCCATGCCTACGGCATAAAGGTCATAGCGGACATCG
TCATAAACCACCGCACAGGCGGAGACCTCGAGTGGAACCCGTTCGTTGGGGACTACACCTGGACG
GACTTCTCAAAGGTGGCCTCGGGCAAATATACTGCCAACTACCTCGACTTCCACCCCAACGAGGT
CAAGTGCTGTGACGAGGGCACATTTGGAGGCTTCCCAGACATAGCCCACGAGAAGAGCTGGGACC
AGCACTGGCTCTGGGCGAGCGATGAGAGCTACGCCGCCTACCTAAGGAGCATCGGCGTTGATGCC
TGGCGCTTCGACTACGTCAAGGGCTACGGAGCGTGGGTCGTCAAGGACTGGCTGGACTGGTGGGG
AGGCTGGGCCGTCGGGGAGTACTGGGACACAAACGTTGATGCACTGCTCAACTGGGCCTACTCGA
GCGATGCAAAAGTCTTCGACTTCCCGCTCTACTACAAGATGGATGAGGCCTTTGACAACAAAAAC
ATTCCAGCGCTCGTCTCTGCCCTTCAGAACGGCCAGACTGTTGTCTCCCGCGACCCGTTCAAGGC
CGTAACCTTTGTAGCAAACCACGACACCGATATAATCTGGAACAAGTATCCAGCCTACGCGTTCA
TCCTCACCTACGAGGGCCAGCCGACAATATTCTACCGCGACTACGAGGAGTGGCTCAACAAGGAT
AAGCTCAAGAACCTCATCTGGATACATGACAACCTCGCCGGAGGAAGCACTGACATCGTTTACTA
CGACAACGACGAGCTGATATTCGTGAGAAACGGCTACGGAAGCAAGCCGGGACTGATAACATACA
TCAACCTCGCCTCAAGCAAAGCCGGAAGGTGGGTCTACGTTCCGAAGTTCGCGGGAGCGTGCATC
CACGAGTACACCGGCAACCTCGGCGGCTGGGTGGACAAGTGGGTGGACTCAAGCGGGTGGGTGTA
CCTCGAGGCCCCTGCCCACGACCCGGCCAACGGCTATTACGGCTACTCCGTCTGGAGCTACTGCG
GTGTTGGCTGA
FIGURE 16BBB
SEQ ID NO.: 54
MAKYSELEEGGVIMQAFYWDVPGGGIWWDTIRSKIPEWYEAGISAIWIPPASKGMGGAYSMGYDP
YDFFDLGEYDQKGTVETRFGSKQELVNMINTAHAYGIKVIADIVINHRTGGDLEWNPFVGDYTWT
DFSKVASGKYTANYLDFHPNEVKCCDEGTFGGFPDIAHEKSWDQHWLWASDESYAAYLRSIGVDA
WRFDYVKGYGAWVVKDWLDWWGGWAVGEYWDTNVDALLNWAYSSDAKVFDFPLYYKMDEAFDNKN
IPALVSALQNGQTVVSRDPFKAVTFVANHDTDIIWNKYPAYAFILTYEGQPTIFYRDYEEWLNKD
KLKNLIWIHDNLAGGSTDIVYYDNDELIFVRNGYGSKPGLITYINLASSKAGRWVYVPKFAGACI
HEYTGNLGGWVDKWVDSSGWVYLEAPAHDPANGYYGYSVWSYCGVG
FIGURE 16CCC
SEQ ID NO.: 55
ATGGCCAAGTACCTGGAGCTCGAGGAGGGCGGGGTCATAATGCAGGCGTTCTACTGGGACGTGCC
TTCAGGAGGAATATGGTGGGACACAATACGGCAGAAGATACCGGAGTGGTACGATGCCGGAATCT
CCGCAATATGGATTCCCCGGCGAGCAAGGGCATGGGCGGCGCCTATTCGATGGGCTACGACCCC
TACGACTTCTTTGACCTCGGTGAGTACGACCAGAAGGGAACGGTAGAGACGCGCTTTGGCTCCAA
GCAGGAGCTCGTGAACATGATAAACACGGCCCACGCCTATGGCATGAAGGTAATAGCCGATATAG
TCATCAACCACCGCGCCGGCGGTGACCTGGAGTGGAACCCCTTCGTGAACGACTATACCTGGACC
GACTTCTCAAAGGTCGCGTCGGGTAAATACACGGCCAACTACCTCGACTTCCACCCGAACGAGCT
CCATGCGGGCGATTCCGGAACATTTGGAGGCTATCCCGACATATGCCACGACAAGAGCTGGGACC
AGTACTGGCTCTGGGCCAGCCAGGAGAGCTACGCGGCATATCTCAGGAGCATCGGCATCGATGCC
TGGCGCTTTGACTACGTGAAGGGCTACGGAGCGTGGGTCGTCAAGGACTGGCTCAACTGGTGGGG
CGGCTGGGCCGTTGGCGAGTACTGGGACACCAACGTTGATGCACTCCTCAACTGGGCCTACTCGA
GCGGCGCCAAGGTCTTCGACTTCCCGCTCTACTACAAGATGGATGAGGCCTTTGACAACAAAAAC
ATTCCAGCGCTCGTCTCTGCCCTTCAGAACGGCCAGACTGTTGTCTCCCGCGACCCGTTCAAGGC
CGTAACCTTTGTAGCAAACCACGACACCGATATAATCTGGAACAAGTACCTTGCTTATGCTTTCA
TCCTCACCTACGAAGGCCAGCCCGTCATATTCTACCGCGACTACGAGGAGTGGCTCAACAAGGAC
AGGTTGAACAACCTCATATGGATACACGACCACCTCGCAGGTGGAAGCACGAGCATAGTTTACTA
CGACAGCGACGAGATGATCTTCGTGAGGAACGGCTATGGAAGCAAGCCTGGCCTTATAACTTACA
TCAACCTCGGCTCGAGCAAGGTTGGAAGGTGGGTTTACGTTCCGAAGTTCGCAGGCTCGTGCATA
CACGAGTACACCGGCAATCTCGGCGGCTGGGTGGACAAGTGGGTGGACTCAAGCGGCTGGGTCTA

FIGURE 16CCC cont,
CCTCGAGGCTCCTGCCCACGACCCGGCCAACGGCCAGTACGGCTACTCCGTCTGGAGCTATTGCG
GTGTTGGCTGA

FIGURE 16DDD
SEQ ID NO.: 56
MAKYLELEEGGVIMQAFYWDVPSGGIWWDTIRQKIPEWYDAGISAIWIPPASKGMGGAYSMGYDP
YDFFDLGEYDQKGTVETRFGSKQELVNMINTAHAYGMKVIADIVINHRAGGDLEWNPFVNDYTWT
DFSKVASGKYTANYLDFHPNELHAGDSGTFGGYPDICHDKSWDQYWLWASQESYAAYLRSIGIDA
WRFDYVKGYGAWVVKDWLNWWGGWAVGEYWDTNVDALLNWAYSSGAKVFDFPLYYKMDEAFDNKN
IPALVSALQNGQTVVSRDPFKAVTFVANHDTDIIWNKYLAYAFILTYEGQPVIFYRDYEEWLNKD
RLNNLIWIHDHLAGGSTSIVYYDSDEMIFVRNGYGSKPGLITYINLGSSKVGRWVYVPKFAGSCI
HEYTGNLGGWVDKWVDSSGWVYLEAPAHDPANGQYGYSVWSYCGVG

FIGURE 16EEE
SEQ ID NO.: 57
ATGGCCAAGTACCTGGAGCTCGAAGAGAGCGGGGTCATAATGCAGGCGTTCTACTGGGACGTGCC
TTCAGGAGGAATATGGTGGGACACAATACGGCAGAAGATACCGGAGTGGTACGATGCCGGAATCT
CCGCAATATGGATTCCTCCCGCGAGCAAGGGTATGAGCGGCGGCTATTCGATGGGCTACGACCCC
TACGATTATTTTGACCTCGGTGAGTACTACCAGAAGGGAACGGTGGAAACGAGGTTCGGCTCAAA
GCAGGAGCTCATAAACATGATAAACACCGCCCACGCCTACGGCATCAAGGTCATCGCAGACATAG
TAATCAACCACCGCGCCGGAGGAGACCTTGAGTGGAACCCCTTCGTCAATGACTACACCTGGACG
GACTTCTCGAAGGTCGCTTCCGGCAAGTACACGGCCAACTACCTCGACTTCCACCCCAACGAGGT
CAAGTGCTGTGACGAGGGCACATTTGGAGGCTTCCCAGACATAGCCCACGAGAAGAGCTGGGACC
AGCACTGGCTCTGGGCGAGCGATGAGAGCTACGCCGCCTACCTAAGGAGCATCGGCGTTGATGCC
TGGCGCTTTGACTACGTGAAGGGCTACGGAGCGTGGGTCGTCAAGGACTGGCTCAACTGGTGGGG
TGGCTGGGCCGTCGGGGAGTACTGGGACACAAACGTTGATGCACTGCTCAACTGGGCCTACTCGA
GCGATGCAAAAGTCTTCGACTTCCCGCTCTACTACAAGATGGACGAGGCCTTCGATAACAACAAC
ATTCCCGCCCTGGTGGACGCCCTCAGATACGGTCAGACAGTGGTCAGCCGCGACCCGTTCAAGGC
TGTGACGTTTGTAGCCAACCACGATACCGATATAATCTGGAACAAGTACCTTGCTTATGCTTTCA
TCCTCACCTACGAAGGCCAGCCCGTCATATTCTACCGCGACTACGAGGAGTGGCTCAACAAGGAC
AGGTTGAACAACCTCATATGGATACACGACCACCTCGCAGGTGGAAGCACTGACATCGTTTACTA
CGACAACGACGAGCTGATATTCGTGAGAAACGGCTACGGAAGCAAGCCGGGACTGATAACATACA
TCAACCTCGCCTCAAGCAAAGCCGGAAGGTGGGTCTACGTTCCGAAGTTCGCGGGAGCGTGCATC
CACGAGTACACCGGCAACCTCGGCGGCTGGGTGGACAAGTGGGTGGACTCAAGCGGGTGGGTGTA
CCTCGAGGCCCCTGCCCACGACCCGGCCAACGGCTATTACGGCTACTCCGTCTGGAGCTATTGCG
GTGTTGGCTGA

FIGURE 16FFF
SEQ ID NO.: 58
MAKYLELEESGVIMQAFYWDVPSGGIWWDTIRQKIPEWYDAGISAIWIPPASKGMSGGYSMGYDP
YDYFDLGEYYQKGTVETRFGSKQELINMINTAHAYGIKVIADIVINHRAGGDLEWNPFVNDYTWT
DFSKVASGKYTANYLDFHPNEVKCCDEGTFGGFPDIAHEKSWDQHWLWASDESYAAYLRSIGVDA
WRFDYVKGYGAWVVKDWLNWWGGWAVGEYWDTNVDALLNWAYSSDAKVFDFPLYYKMDEAFDNNN
IPALVDALRYGQTVVSRDPFKAVTFVANHDTDIIWNKYLAYAFILTYEGQPVIFYRDYEEWLNKD
RLNNLIWIHDHLAGGSTDIVYYDNDELIFVRNGYGSKPGLITYINLASSKAGRWVYVPKFAGACI
HEYTGNLGGWVDKWVDSSGWVYLEAPAHDPANGYYGYSVWSYCGVG

FIGURE 16GGG
SEQ ID NO.: 59
atggccaagtacctggagctcgaagagggcggggtcataatgcaggcgttctactgggacgtgcc
ttcaggaggaatatggtgggacacaatacggcagaagataccggagtggtacgatgccggaatct
ccgcaatatggattcctccgcgagcaagggtatgagcggcggctattcgatgggctacgacccc
tacgattattttgacctcggtgagtactaccagaagggaacggtggaaacgaggttcggctcaaa
gcaggagctcataaacatgataaacaccgcccacgcctacggcatcaaggtcatcgcagacatag
taatcaaccaccgcgccggaggagaccttgagtggaacccttcgtcaatgactacacctggacg
gacttctcgaaggtcgcttccggcaagtacacggccaactacctcgacttccacccgaacgagct
ccatgcgggcgattccggaacatttggaggctatcccgacatatgccacgacaagagctgggacc
agtactggctctgggccagccaggagagctacgcggcatatctcaggagcatcggcatcgatgcc
tggcgcttcgactacgtcaagggctatgctccctgggtcgtcaaggactggctgaactggtgggg
aggctgggcggttggagagtactgggacaccaacgtcgacgctgttctcaactgggcatactcga
gcggtgccaaggtctttgacttcgccctctactacaagatggacgaggccttcgataacaacaac
attcccgccctggtggacgccctcagatacggtcagacagtggtcagccgcgacccgttcaaggc
tgtgacgtttgtagccaaccacgataccgatataatttggaacaagtacccggcctacgccttca
tcctcacctacgagggccagccgacgatattctaccgcgactacgaggagtggctcaacaaggac
aggctcaagaacctcatctggatacacgaccacctcgccggtggaagcactgacatcgtttacta
cgacaacgacgagctgatattcgtgagaaacggctacggaagcaagccgggactgataacataca
tcaacctcgcgtcaagcaaagccggaaggtgggtttatgtgccgaagttcgcgggcgcgtgcatc
cacgagtatactggtaacctcggaggctgggtagacaagtacgtctactcaagcggctgggtcta
tctcgaagctccagcttacgaccctgccaacgggcagtatggctactccgtgtggagctattgcg
gtgttgggtga

FIGURE 16HHH
SEQ ID NO.: 60
Met Ala Lys Tyr Leu Glu Leu Glu Glu Gly Gly Val Ile Met Gln Ala
Phe Tyr Trp Asp Val Pro Ser Gly Gly Ile Trp Trp Asp Thr Ile Arg
Gln Lys Ile Pro Glu Trp Tyr Asp Ala Gly Ile Ser Ala Ile Trp Ile
Pro Pro Ala Ser Lys Gly Met Ser Gly Gly Tyr Ser Met Gly Tyr Asp
Pro Tyr Asp Tyr Phe Asp Leu Gly Glu Tyr Tyr Gln Lys Gly Thr Val
Glu Thr Arg Phe Gly Ser Lys Gln Glu Leu Ile Asn Met Ile Asn Thr
Ala His Ala Tyr Gly Ile Lys Val Ile Ala Asp Ile Val Ile Asn His
Arg Ala Gly Gly Asp Leu Glu Trp Asn Pro Phe Val Asn Asp Tyr Thr
Trp Thr Asp Phe Ser Lys Val Ala Ser Gly Lys Tyr Thr Ala Asn Tyr
Leu Asp Phe His Pro Asn Glu Leu His Ala Gly Asp Ser Gly Thr Phe
Gly Gly Tyr Pro Asp Ile Cys His Asp Lys Ser Trp Asp Gln Tyr Trp
Leu Trp Ala Ser Gln Glu Ser Tyr Ala Ala Tyr Leu Arg Ser Ile Gly
Ile Asp Ala Trp Arg Phe Asp Tyr Val Lys Gly Tyr Ala Pro Trp Val
Val Lys Asp Trp Leu Asn Trp Trp Gly Gly Trp Ala Val Gly Glu Tyr
Trp Asp Thr Asn Val Asp Ala Val Leu Asn Trp Ala Tyr Ser Ser Gly
Ala Lys Val Phe Asp Phe Ala Leu Tyr Tyr Lys Met Asp Glu Ala Phe
Asp Asn Asn Asn Ile Pro Ala Leu Val Asp Ala Leu Arg Tyr Gly Gln
Thr Val Val Ser Arg Asp Pro Phe Lys Ala Val Thr Phe Val Ala Asn
His Asp Thr Asp Ile Ile Trp Asn Lys Tyr Pro Ala Tyr Ala Phe Ile
Leu Thr Tyr Glu Gly Gln Pro Thr Ile Phe Tyr Arg Asp Tyr Glu Glu
Trp Leu Asn Lys Asp Arg Leu Lys Asn Leu Ile Trp Ile His Asp His
Leu Ala Gly Gly Ser Thr Asp Ile Val Tyr Tyr Asp Asn Asp Glu Leu
Ile Phe Val Arg Asn Gly Tyr Gly Ser Lys Pro Gly Leu Ile Thr Tyr
Ile Asn Leu Ala Ser Ser Lys Ala Gly Arg Trp Val Tyr Val Pro Lys
Phe Ala Gly Ala Cys Ile His Glu Tyr Thr Gly Asn Leu Gly Gly Trp
Val Asp Lys Tyr Val Tyr Ser Ser Gly Trp Val Tyr Leu Glu Ala Pro
Ala Tyr Asp Pro Ala Asn Gly Gln Tyr Gly Tyr Ser Val Trp Ser Tyr
Cys Gly Val Gly

FIGURE 16III
SEQ ID NO.: 61
atggccaagtactccgagctgaaaaagggcggggtcataatgcaggcgttctactgggacgtgcc
ttcaggaggaatatggtgggacacaatacggcagaagataccggagtggtacgaggcgggaatat
ccgccatttggattcctcccgcgagcaagggtatgagcggcggctattcgatgggctacgacccc
tacgattattttgacctcggtgagtactaccagaagggaacggtggaaacgaggttcggctcaaa
gcaggagctcataaacatgataaacaccgcccacgcctacggcatcaaggtcatcgcagacatag
taatcaaccaccgcgccggaggagaccttgagtggaacccttcgtcaatgactacacctggacg
gacttctcgaaggtcgcttccggcaagtacacggccaactacctcaacttccacccgaacgagct
ccatgcgggcgattccggaacatttggaggctatcccgacatatgccacgacaagagctgggacc
agtactggctctgggccagccaggagagctacgcggcatatctcaggagcatcggcatcgatgcc
tggcgcttcgactacgtcaagggctacggagcgtgggtcgtcaaggactggctggactggtgggg
aggctgggccgtcggggagtactggacacaaacgttgatgcactgctcaactgggcctactcga
gcgatgcaaaagtcttcgacttcccgctctactacaagatggatgaggcctttgacaacaaaaac
attccagcgctcgtctctgcccttcagaacggccagactgttgtctcccgcgacccgttcaaggc
cgtaacctttgtagcaaaccatgacaccgatataatctggaacaagtatccagcctacgcgttca
tcctcacctacgagggccagccgacaatattctaccgcgactacgaggagtggctcaacaaggat
aagctcaagaacctcatctggatacatgacaacctcgccggaggaagcaccgacatagtctacta
cgataacgatgaactcatcttcgtcaggaacggctacggggacaagccggggcttataacctaca
tcaacctaggctcgagcaaggccggaaggtgggtctacgttccgaagttcgcgggagcgtgcatc
cacgagtacaccggcaacctcggcggctgggtggacaagtgggtggactcaagcgggtgggtgta
cctcgaggccctgcccacgacccggccaacggctattacggctactccgtctggagctactgcg
gggtgggctga

FIGURE 16JJJ
SEQ ID NO.: 62
Met Ala Lys Tyr Ser Glu Leu Lys Lys Gly Gly Val Ile Met Gln Ala
Phe Tyr Trp Asp Val Pro Ser Gly Gly Ile Trp Trp Asp Thr Ile Arg
Gln Lys Ile Pro Glu Trp Tyr Glu Ala Gly Ile Ser Ala Ile Trp Ile
Pro Pro Ala Ser Lys Gly Met Ser Gly Gly Tyr Ser Met Gly Tyr Asp
Pro Tyr Asp Tyr Phe Asp Leu Gly Glu Tyr Tyr Gln Lys Gly Thr Val
Glu Thr Arg Phe Gly Ser Lys Gln Glu Leu Ile Asn Met Ile Asn Thr
Ala His Ala Tyr Gly Ile Lys Val Ile Ala Asp Ile Val Ile Asn His
Arg Ala Gly Gly Asp Leu Glu Trp Asn Pro Phe Val Asn Asp Tyr Thr
Trp Thr Asp Phe Ser Lys Val Ala Ser Gly Lys Tyr Thr Ala Asn Tyr
Leu Asn Phe His Pro Asn Glu Leu His Ala Gly Asp Ser Gly Thr Phe
Gly Gly Tyr Pro Asp Ile Cys His Asp Lys Ser Trp Asp Gln Tyr Trp
Leu Trp Ala Ser Gln Glu Ser Tyr Ala Ala Tyr Leu Arg Ser Ile Gly
Ile Asp Ala Trp Arg Phe Asp Tyr Val Lys Gly Tyr Gly Ala Trp Val
Val Lys Asp Trp Leu Asp Trp Trp Gly Gly Trp Ala Val Gly Glu Tyr
Trp Asp Thr Asn Val Asp Ala Leu Leu Asn Trp Ala Tyr Ser Ser Asp
Ala Lys Val Phe Asp Phe Pro Leu Tyr Tyr Lys Met Asp Glu Ala Phe
Asp Asn Lys Asn Ile Pro Ala Leu Val Ser Ala Leu Gln Asn Gly Gln
Thr Val Val Ser Arg Asp Pro Phe Lys Ala Val Thr Phe Val Ala Asn
His Asp Thr Asp Ile Ile Trp Asn Lys Tyr Pro Ala Tyr Ala Phe Ile
Leu Thr Tyr Glu Gly Gln Pro Thr Ile Phe Tyr Arg Asp Tyr Glu Glu
Trp Leu Asn Lys Asp Lys Leu Lys Asn Leu Ile Trp Ile His Asp Asn
Leu Ala Gly Gly Ser Thr Asp Ile Val Tyr Tyr Asp Asn Asp Glu Leu
Ile Phe Val Arg Asn Gly Tyr Gly Asp Lys Pro Gly Leu Ile Thr Tyr
Ile Asn Leu Gly Ser Ser Lys Ala Gly Arg Trp Val Tyr Val Pro Lys
Phe Ala Gly Ala Cys Ile His Glu Tyr Thr Gly Asn Leu Gly Gly Trp
Val Asp Lys Trp Val Asp Ser Ser Gly Trp Val Tyr Leu Glu Ala Pro
Ala His Asp Pro Ala Asn Gly Tyr Tyr Gly Tyr Ser Val Trp Ser Tyr
Cys Gly Val Gly

FIGURE 16KKK

SEQ ID NO.: 63
atggccaagtacctggagctcgaagagggcggggtcataatgcaggcgttctactgggacgtgcc
ttcaggaggaatatggtgggacacaatacggcagaagataccggagtggtacgatgccggaatct
ccgcaatatggattcccccggcgagcaagggcatgggcggcgcctattcgatgggctacgacccc
tacgacttctttgacctcggtgagtacgaccagaagggaacggtagagacgcgctttggctccaa
gcaggagctcgtgaacatgataaacacggcccatgcctacggcataaaggccatagcggacatcg
tcataaaccaccgcgcaggcggagacctcgagtggaacccgttcgttggggactacacctggacg
gacttctcaaaggtggcctcgggcaaatatactgccaactacctcgacttccaccccaacgaggt
caagtgctgtgacgagggcacatttggaggcttcccagacatagcccacgagaagagctgggacc
agcactggctctgggcgagcgatgagagctacgccgcctacctaaggagcatcggcgttgatgcc
tggcgctttgactacgtgaaggctacggagcgtgggtcgtcaaggactggctcaactggtgggg
cggctgggccgttggcgagtactgggacaccaacgttgatgcactcctcaactgggcctactcga
gcggcgccaaggtcttcgacttcccgctctactacaagatggacgcggcctttgacaacaagaac
attcccgcactcgtcgaggccctcaagaacgggggcacagtcgtcagccgcgacccgtttaaggc
cgtaaccttcgttgcaaaccacgacaccgatataatctggaacaagtatccagcctacgcgttca
tcctcacctacgagggccagccgacaatattctaccgcgactacgaggagtggctcaacaaggat
aagctcaagaacctcatctggatacatgacaacctcgccggaggaagcaccgacatagtctacta
cgataacgatgaactcatcttcgtcaggaacggctacggggacaagccggggcttataacctaca
tcaacctaggctggagcaaggccggaaggtgggtttatgtgccgaagttcgcgggcgcgtgcatc
cacgagtatactggtaacctcggaggctgggtagacaagtacgtctactcaagcggctggtcta
tctcgaagctccagcttacgaccctgccaacgggcagtatggctactccgtgtggagctactgcg
gggtggggtga

FIGURE 16LLL

SEQ ID NO.: 64
Met Ala Lys Tyr Leu Glu Leu Glu Glu Gly Gly Val Ile Met Gln Ala
Phe Tyr Trp Asp Val Pro Ser Gly Gly Ile Trp Trp Asp Thr Ile Arg
Gln Lys Ile Pro Glu Trp Tyr Asp Ala Gly Ile Ser Ala Ile Trp Ile
Pro Pro Ala Ser Lys Gly Met Gly Gly Ala Tyr Ser Met Gly Tyr Asp
Pro Tyr Asp Phe Phe Asp Leu Gly Glu Tyr Asp Gln Lys Gly Thr Val
Glu Thr Arg Phe Gly Ser Lys Gln Glu Leu Val Asn Met Ile Asn Thr
Ala His Ala Tyr Gly Ile Lys Ala Ile Ala Asp Ile Val Ile Asn His
Arg Ala Gly Gly Asp Leu Glu Trp Asn Pro Phe Val Gly Asp Tyr Thr
Trp Thr Asp Phe Ser Lys Val Ala Ser Gly Lys Tyr Thr Ala Asn Tyr
Leu Asp Phe His Pro Asn Glu Val Lys Cys Cys Asp Glu Gly Thr Phe
Gly Gly Phe Pro Asp Ile Ala His Glu Lys Ser Trp Asp Gln His Trp
Leu Trp Ala Ser Asp Glu Ser Tyr Ala Ala Tyr Leu Arg Ser Ile Gly
Val Asp Ala Trp Arg Phe Asp Tyr Val Lys Gly Tyr Gly Ala Trp Val
Val Lys Asp Trp Leu Asn Trp Trp Gly Gly Trp Ala Val Gly Glu Tyr
Trp Asp Thr Asn Val Asp Ala Leu Leu Asn Trp Ala Tyr Ser Ser Gly
Ala Lys Val Phe Asp Phe Pro Leu Tyr Tyr Lys Met Asp Ala Ala Phe
Asp Asn Lys Asn Ile Pro Ala Leu Val Glu Ala Leu Lys Asn Gly Gly
Thr Val Val Ser Arg Asp Pro Phe Lys Ala Val Thr Phe Val Ala Asn
His Asp Thr Asp Ile Ile Trp Asn Lys Tyr Pro Ala Tyr Ala Phe Ile
Leu Thr Tyr Glu Gly Gln Pro Thr Ile Phe Tyr Arg Asp Tyr Glu Glu
Trp Leu Asn Lys Asp Lys Leu Lys Asn Leu Ile Trp Ile His Asp Asn
Leu Ala Gly Gly Ser Thr Asp Ile Val Tyr Tyr Asp Asn Asp Glu Leu
Ile Phe Val Arg Asn Gly Tyr Gly Asp Lys Pro Gly Leu Ile Thr Tyr
Ile Asn Leu Gly Trp Ser Lys Ala Gly Arg Trp Val Tyr Val Pro Lys
Phe Ala Gly Ala Cys Ile His Glu Tyr Thr Gly Asn Leu Gly Gly Trp
Val Asp Lys Tyr Val Tyr Ser Ser Gly Trp Val Tyr Leu Glu Ala Pro
Ala Tyr Asp Pro Ala Asn Gly Gln Tyr Gly Tyr Ser Val Trp Ser Tyr
Cys Gly Val Gly

FIGURE 16MMM
SEQ ID NO.: 65
atggccaagtactccgagctggaagaaggcggcgttataatgcaggccttctactgggacgtccc
aggtggaggaatctggtggggcaccatcaggagcaagataccggagtggtacgaggcgggaatat
ccgccatttggattcctcccgcgagcaagggtatgagcggcggctattcgatgggctacgacccc
tacgattattttgacctcggtgagtactaccagaagggaacggtggaaacgaggttcggctcaaa
gcaggagctcataaacatgataaacaccgcccacgcctatggcatgaaggtaatagccgatatag
tcatcaaccaccgccggcggtgacctggagtggaaccccttcgtgaacgactatacctggacc
gacttctcaaaggtcgcgtcgggtaaatacacggccaactacctcgacttccacccgaacgagct
ccatgcgggcgattccggaacatttggaggctatcccgacatatgccacgacaagagctgggacc
agtactggctctgggccagccaggagagctacgcggcatatctcaggagcatcggcatcgatgcc
tggcgcttcgactacgtcaaggctatgctccctgggtcgtcaaggactggctgaactggtgggg
aggctgggcggttggagagtactgggacaccaacgtcgacgctgttctcaactgggcatactcga
gcggtgccaaggtctttgacttcgccctctactacaagatggacgaggccttcgataacaacaac
attcccgccctggtggacgccctcagatacggtcagacagtggtcagccgcgacccgttcaaggc
tgtgacgtttgtagccaaccacgataccgatataatttggaacaagtacccggcctacgccttca
tcctcacctacgagggccagccgacgatattctaccgcgactacgaggagtggctcaacaaggac
aggctcaagaacctcatctggatacacgaccacctcgccggtggaagcacgagcatagtttacta
cgacagcgacgagatgatcttcgtgaggaacggctatggaagcaagcctggccttataacttaca
tcaacctcggctcgagcaaggttggaaggtgggtttacgttccgaagttcgcaggctcgtgcata
cacgagtacaccggcaatctcggcggctgggtggacaagtgggtggactcaagcggctgggtcta
cctcgaggctcctgcccacgacccggccaacggccagtacggctactccgtctggagctattgcg
gtgttggctga
FIGURE 16NNN
SEQ ID NO.: 66
Met Ala Lys Tyr Ser Glu Leu Glu Glu Gly Gly Val Ile Met Gln Ala
Phe Tyr Trp Asp Val Pro Gly Gly Gly Ile Trp Trp Gly Thr Ile Arg
Ser Lys Ile Pro Glu Trp Tyr Glu Ala Gly Ile Ser Ala Ile Trp Ile
Pro Pro Ala Ser Lys Gly Met Ser Gly Gly Tyr Ser Met Gly Tyr Asp
Pro Tyr Asp Tyr Phe Asp Leu Gly Glu Tyr Tyr Gln Lys Gly Thr Val
Glu Thr Arg Phe Gly Ser Lys Gln Glu Leu Ile Asn Met Ile Asn Thr
Ala His Ala Tyr Gly Met Lys Val Ile Ala Asp Ile Val Ile Asn His
Arg Ala Gly Gly Asp Leu Glu Trp Asn Pro Phe Val Asn Asp Tyr Thr
Trp Thr Asp Phe Ser Lys Val Ala Ser Gly Lys Tyr Thr Ala Asn Tyr
Leu Asp Phe His Pro Asn Glu Leu His Ala Gly Asp Ser Gly Thr Phe
Gly Gly Tyr Pro Asp Ile Cys His Asp Lys Ser Trp Asp Gln Tyr Trp
Leu Trp Ala Ser Gln Glu Ser Tyr Ala Ala Tyr Leu Arg Ser Ile Gly
Ile Asp Ala Trp Arg Phe Asp Tyr Val Lys Gly Tyr Ala Pro Trp Val
Val Lys Asp Trp Leu Asn Trp Trp Gly Gly Trp Ala Val Gly Glu Tyr
Trp Asp Thr Asn Val Asp Ala Val Leu Asn Trp Ala Tyr Ser Ser Gly
Ala Lys Val Phe Asp Phe Ala Leu Tyr Tyr Lys Met Asp Glu Ala Phe
Asp Asn Asn Asn Ile Pro Ala Leu Val Asp Ala Leu Arg Tyr Gly Gln
Thr Val Val Ser Arg Asp Pro Phe Lys Ala Val Thr Phe Val Ala Asn
His Asp Thr Asp Ile Ile Trp Asn Lys Tyr Pro Ala Tyr Ala Phe Ile
Leu Thr Tyr Glu Gly Gln Pro Thr Ile Phe Tyr Arg Asp Tyr Glu Glu
Trp Leu Asn Lys Asp Arg Leu Lys Asn Leu Ile Trp Ile His Asp His
Leu Ala Gly Gly Ser Thr Ser Ile Val Tyr Tyr Asp Ser Asp Glu Met
Ile Phe Val Arg Asn Gly Tyr Gly Ser Lys Pro Gly Leu Ile Thr Tyr
Ile Asn Leu Gly Ser Ser Lys Val Gly Arg Trp Val Tyr Val Pro Lys
Phe Ala Gly Ser Cys Ile His Glu Tyr Thr Gly Asn Leu Gly Gly Trp
Val Asp Lys Trp Val Asp Ser Ser Gly Trp Val Tyr Leu Glu Ala Pro
Ala His Asp Pro Ala Asn Gly Gln Tyr Gly Tyr Ser Val Trp Ser Tyr
Cys Gly Val Gly

FIGURE 16OOO
SEQ ID NO.: 67
atggccaagtacctggagctcgaagagggcggggtcataatgcaggcgttctactgggacgtgcc
ttcgggaggaatatggtgggacacaatacggcagaagataccggagtggtacgatgccggaatct
ccgcaatatggattcctcccgcgagcaagggtatgagcggcggctattcgatgggctacgacccc
tacgattattttgacctcggtgagtactaccagaagggaacggtggaaacgaggttcggctcaaa
gcaggagctcataaacatgataaacacggcccatgcctacggcataaaggtcatagcggacatcg
tcataaaccaccgcgcaggcggagacctcgagtggaacccgttcgttggggactacacctggacg
gacttctcaaaggtggcctcgggcaaatatactgccaactacctcgacttccaccccaacgaggt
caagtgctgtgacgagggcacatttggaggcttcccagacatagcccacgagaagagctggacc
agcactggctctggccgagcgatgagagctacgccgcctacctaaggagcatcggcgttgatgcc
tggcgcttcgactacgtcaagggctacggagcgtgggtcgtcaaggactggctggactggtgggg
aggctgggccgtcgggagtactgggacacaaacgttgatgcactgctcaactgggcctactcga
gcgatgcaaaagtcttcgacttcccgctctactacaagatggacgaggccttcgataacaacaac
attcccgccctggtggacgccctcagatacggtcagacagtggtcagccgcgacccgttcaaggc
tgtgacgtttgtagccaaccacgataccgatataatctggaacaagtatccagcctacgcgttca
tcctcacctacgagggccagccgacaatattctaccgcgactacgaggagtggctcaacaaggat
aagctcaagaacctcatctggatacatgacaacctcgccggaggaagcacgagcatagtttacta
cgacagcgacgagatgatcttcgtgaggaacggctatggaagcaagcctggccttataacttaca
tcaacctcggctcgagcaaggttggaaggtgggtctacgttccgaagttcgcgggagcgtgcatc
cacgagtacaccggcaacctcggcggctgggtggacaagtgggtggactcaagcgggtgggtgta
cctcgaggccctgcccacgaccggccaacggctattacggctactccgtctggagctactgcg
tggtgggctga
FIGURE 16PPP
SEQ ID NO.: 68
Met Ala Lys Tyr Leu Glu Leu Glu Glu Gly Gly Val Ile Met Gln Ala
Phe Tyr Trp Asp Val Pro Ser Gly Gly Ile Trp Trp Asp Thr Ile Arg
Gln Lys Ile Pro Glu Trp Tyr Asp Ala Gly Ile Ser Ala Ile Trp Ile
Pro Pro Ala Ser Lys Gly Met Ser Gly Gly Tyr Ser Met Gly Tyr Asp
Pro Tyr Asp Tyr Phe Asp Leu Gly Glu Tyr Tyr Gln Lys Gly Thr Val
Glu Thr Arg Phe Gly Ser Lys Gln Glu Leu Ile Asn Met Ile Asn Thr
Ala His Ala Tyr Gly Ile Lys Val Ile Ala Asp Ile Val Ile Asn His
Arg Ala Gly Gly Asp Leu Glu Trp Asn Pro Phe Val Gly Asp Tyr Thr
Trp Thr Asp Phe Ser Lys Val Ala Ser Gly Lys Tyr Thr Ala Asn Tyr
Leu Asp Phe His Pro Asn Glu Val Lys Cys Cys Asp Glu Gly Thr Phe
Gly Gly Phe Pro Asp Ile Ala His Glu Lys Ser Trp Asp Gln His Trp
Leu Trp Ala Ser Asp Glu Ser Tyr Ala Ala Tyr Leu Arg Ser Ile Gly
Val Asp Ala Trp Arg Phe Asp Tyr Val Lys Gly Tyr Gly Ala Trp Val
Val Lys Asp Trp Leu Asp Trp Trp Gly Gly Trp Ala Val Gly Glu Tyr
Trp Asp Thr Asn Val Asp Ala Leu Leu Asn Trp Ala Tyr Ser Ser Asp
Ala Lys Val Phe Asp Phe Pro Leu Tyr Tyr Lys Met Asp Glu Ala Phe
Asp Asn Asn Asn Ile Pro Ala Leu Val Asp Ala Leu Arg Tyr Gly Gln
Thr Val Val Ser Arg Asp Pro Phe Lys Ala Val Thr Phe Val Ala Asn
His Asp Thr Asp Ile Ile Trp Asn Lys Tyr Pro Ala Tyr Ala Phe Ile
Leu Thr Tyr Glu Gly Gln Pro Thr Ile Phe Tyr Arg Asp Tyr Glu Glu
Trp Leu Asn Lys Asp Lys Leu Lys Asn Leu Ile Trp Ile His Asp Asn
Leu Ala Gly Gly Ser Thr Ser Ile Val Tyr Tyr Asp Ser Asp Glu Met
Ile Phe Val Arg Asn Gly Tyr Gly Ser Lys Pro Gly Leu Ile Thr Tyr
Ile Asn Leu Gly Ser Ser Lys Val Gly Arg Trp Val Tyr Val Pro Lys
Phe Ala Gly Ala Cys Ile His Glu Tyr Thr Gly Asn Leu Gly Gly Trp
Val Asp Lys Trp Val Asp Ser Ser Gly Trp Val Tyr Leu Glu Ala Pro
Ala His Asp Pro Ala Asn Gly Tyr Tyr Gly Tyr Ser Val Trp Ser Tyr
Cys Val Val Gly

FIGURE 16QQQ
SEQ ID NO.: 73
atggctctggaagagggcgggcttataatgcaggccttctactgggacgtcccaggtggaggaat
ctggtgggacaccatagcccagaagatacccgactgggcgagcgccgggatttcggcaatatgga
ttcctcccgcgagtaagggcatgagcggcggctattcgatgggctacgaccCctacgatttcttc
gacctcggtgagtactaccagaagggaagcgttgagacccgcttcggatcaaaagaggagcttgt
gaacatgataaacaccgcccatgctcacaacatgaaggtcatagcggacatagtcatcaaccacc
gcgccggcggcgacctggagtggaatcctttcaccaacagctacacctggaccgatttctcgaag
gtcgcgtcgggcaagtacacggccaactacctcgacttccacccgaacgagcttcacgcgggcga
ttccggaacatttggaggctatcccgacatatgccacgacaagagctgggaccagcactggctct
gggccagcaacgaaagctacgccgcctacctccggagcatcggcatcgacgcctggcgcttcgac
tacgtcaagggctacgctccctgggtcgttaagaactggctgaaccggtggggcggctgggcggt
tggagagtactgggacaccaacgtcgatgcactcctgagctgggcctacgacagcggtgctaaag
tcttcgacttcccgctctactacaagatggacgaggccttcgataacaacaacatccccgccctc
gtggacgccctcaagaacggaggcacggtcgtcagccgcgacccgttcaaagccgtgaccttcgt
tgccaaccacgataccaacataatctggaacaagtatccggcctacgccttcatcctcacctatg
agggacagccggcaatattctaccgcgactacgaggagtggctcaacaaggacaggctcaggaac
ctcatctggatacacgaccacctcgcgggaggaagcacagacatcatctactacgacagcgacga
gcttatcttcgtgagaaacggctacggggacaagccgggactgataacctacatcaacctcggct
caagcaaggccggaaggtgggtctacgttccgaagttcgcaggctcgtgcatacacgagtacacc
ggcaacctcggcggctggattgacaagtgggttgactcaagcggtcgggtctaccttgaggcccc
cgcccacgaccggccaacggccagtacggctactccgtatggagctactgcggtgttgggtga

FIGURE 16RRR
SEQ ID NO.: 74
Met Ala Leu Glu Glu Gly Gly Leu Ile Met Gln Ala Phe Tyr Trp Asp
Val Pro Gly Gly Gly Ile Trp Trp Asp Thr Ile Ala Gln Lys Ile Pro
Asp Trp Ala Ser Ala Gly Ile Ser Ala Ile Trp Ile Pro Pro Ala Ser
Lys Gly Met Ser Gly Gly Tyr Ser Met Gly Tyr Asp Pro Tyr Asp Phe
Phe Asp Leu Gly Glu Tyr Tyr Gln Lys Gly Ser Val Glu Thr Arg Phe
Gly Ser Lys Glu Glu Leu Val Asn Met Ile Asn Thr Ala His Ala His
Asn Met Lys Val Ile Ala Asp Ile Val Ile Asn His Arg Ala Gly Gly
Asp Leu Glu Trp Asn Pro Phe Thr Asn Ser Tyr Thr Trp Thr Asp Phe
Ser Lys Val Ala Ser Gly Lys Tyr Thr Ala Asn Tyr Leu Asp Phe His
Pro Asn Glu Leu His Ala Gly Asp Ser Gly Thr Phe Gly Gly Tyr Pro
Asp Ile Cys His Asp Lys Ser Trp Asp Gln His Trp Leu Trp Ala Ser
Asn Glu Ser Tyr Ala Ala Tyr Leu Arg Ser Ile Gly Ile Asp Ala Trp
Arg Phe Asp Tyr Val Lys Gly Tyr Ala Pro Trp Val Val Lys Asn Trp
Leu Asn Arg Trp Gly Gly Trp Ala Val Gly Glu Tyr Trp Asp Thr Asn
Val Asp Ala Leu Leu Ser Trp Ala Tyr Asp Ser Gly Ala Lys Val Phe
Asp Phe Pro Leu Tyr Tyr Lys Met Asp Glu Ala Phe Asp Asn Asn Asn
Ile Pro Ala Leu Val Asp Ala Leu Lys Asn Gly Gly Thr Val Val Ser
Arg Asp Pro Phe Lys Ala Val Thr Phe Val Ala Asn His Asp Thr Asn
Ile Ile Trp Asn Lys Tyr Pro Ala Tyr Ala Phe Ile Leu Thr Tyr Glu
Gly Gln Pro Ala Ile Phe Tyr Arg Asp Tyr Glu Glu Trp Leu Asn Lys
Asp Arg Leu Arg Asn Leu Ile Trp Ile His Asp His Leu Ala Gly Gly
Ser Thr Asp Ile Ile Tyr Tyr Asp Ser Asp Glu Leu Ile Phe Val Arg
Asn Gly Tyr Gly Asp Lys Pro Gly Leu Ile Thr Tyr Ile Asn Leu Gly
Ser Ser Lys Ala Gly Arg Trp Val Tyr Val Pro Lys Phe Ala Gly Ser
Cys Ile His Glu Tyr Thr Gly Asn Leu Gly Gly Trp Ile Asp Lys Trp
Val Asp Ser Ser Gly Arg Val Tyr Leu Glu Ala Pro Ala His Asp Pro
Ala Asn Gly Gln Tyr Gly Tyr Ser Val Trp Ser Tyr Cys Gly Val Gly

FIGURE 16SSS
SEQ ID NO.: 75 atggctctggaagagggcgggcttataatgcaggcattctactgggacgtccccatgggaggaat
ctggtgggacacgatagcccagaagatacccgactgggcaagcgcgggatttcggcgatatgga
ttcccccgcgagcaagggtatgagcggcggctattcgatgggctacgaccctacgattatttt
gacctcggtgagtactaccagaagggaacggtggaaacaagattcggctcaaagcaggagctcat
aaacatgataaacaccgcccacgcctatggcatgaaggtaatagccgatatagtcatcaaccacc
gcgccggcggcgatctggagtggaaccccttcgtgaacgactatacctggaccgacttctcgaag
gtcgcgtcgggtaaatacacggccaactacctcgacttccacccgaacgagctccacgcgggcga
ttccggaacatttggaggctatcccgacatatgccacgacaagagctgggaccagtactggctct
gggccagccaggagagctacgcggcctatctcaggagcatcggcatcgacgcctggcgcttcgac
tacgtcaagggctatgctccctgggtcgtcagggactggctgaactggtggggaggctgggcagt
tggagagtactgggacaccaacgtcgacgctgttctcaactgggcatactcgagcggtgccaagg
tctttgacttcgccctctactacaagatggacgaggccttcgataacaacaacattcccgccctg
gtggacgccctcagatacggccagacagtggtcagccgcgacccgttcaaggctgtgacgtttgt
agccaaccacgataccgacataatctggaacaagtatccagcctacgcgttcatcctcacctacg
agggccagccgacaatattctaccgcgactacgaggagtggctcaacaaggacaagctcaagaac
ctcatctggatacatgacaacctcgccggagggagcactgacatcgtttactacgacaacgacga
gctgatattcgtgagaaacggctacggaagcaagccgggactgataacatacatcaacctcggct
caagcaaagccggaaggtgggtttacgttccgaagttcgcaggctcgtgcatacacgagtacacc
ggcaacctcggcggctgggtggacaagtgggtggactcaagcggctgggtttacctcgaggctcc
tgcccacgacccggccaacggccagtacggctactccgtttggagctattgcggtgttgggtga

FIGURE 16TTT
SEQ ID NO.: 76

Met Ala Leu Glu Glu Gly Gly Leu Ile Met Gln Ala Phe Tyr Trp Asp
Val Pro Met Gly Gly Ile Trp Trp Asp Thr Ile Ala Gln Lys Ile Pro
Asp Trp Ala Ser Ala Gly Ile Ser Ala Ile Trp Ile Pro Pro Ala Ser
Lys Gly Met Ser Gly Gly Tyr Ser Met Gly Tyr Asp Pro Tyr Asp Tyr
Phe Asp Leu Gly Glu Tyr Tyr Gln Lys Gly Thr Val Glu Thr Arg Phe
Gly Ser Lys Gln Glu Leu Ile Asn Met Ile Asn Thr Ala His Ala Tyr
Gly Met Lys Val Ile Ala Asp Ile Val Ile Asn His Arg Ala Gly Gly
Asp Leu Glu Trp Asn Pro Phe Val Asn Asp Tyr Thr Trp Thr Asp Phe
Ser Lys Val Ala Ser Gly Lys Tyr Thr Ala Asn Tyr Leu Asp Phe His
Pro Asn Glu Leu His Ala Gly Asp Ser Gly Thr Phe Gly Gly Tyr Pro
Asp Ile Cys His Asp Lys Ser Trp Asp Gln Tyr Trp Leu Trp Ala Ser
Gln Glu Ser Tyr Ala Ala Tyr Leu Arg Ser Ile Gly Ile Asp Ala Trp
Arg Phe Asp Tyr Val Lys Gly Tyr Ala Pro Trp Val Val Arg Asp Trp
Leu Asn Trp Trp Gly Gly Trp Ala Val Gly Glu Tyr Trp Asp Thr Asn
Val Asp Ala Val Leu Asn Trp Ala Tyr Ser Ser Gly Ala Lys Val Phe
Asp Phe Ala Leu Tyr Tyr Lys Met Asp Glu Ala Phe Asp Asn Asn Asn
Ile Pro Ala Leu Val Asp Ala Leu Arg Tyr Gly Gln Thr Val Val Ser
Arg Asp Pro Phe Lys Ala Val Thr Phe Val Ala Asn His Asp Thr Asp
Ile Ile Trp Asn Lys Tyr Pro Ala Tyr Ala Phe Ile Leu Thr Tyr Glu
Gly Gln Pro Thr Ile Phe Tyr Arg Asp Tyr Glu Glu Trp Leu Asn Lys
Asp Lys Leu Lys Asn Leu Ile Trp Ile His Asp Asn Leu Ala Gly Gly
Ser Thr Asp Ile Val Tyr Tyr Asp Asn Asp Glu Leu Ile Phe Val Arg
Asn Gly Tyr Gly Ser Lys Pro Gly Leu Ile Thr Tyr Ile Asn Leu Gly
Ser Ser Lys Ala Gly Arg Trp Val Tyr Val Pro Lys Phe Ala Gly Ser
Cys Ile His Glu Tyr Thr Gly Asn Leu Gly Gly Trp Val Asp Lys Trp
Val Asp Ser Ser Gly Trp Val Tyr Leu Glu Ala Pro Ala His Asp Pro
Ala Asn Gly Gln Tyr Gly Tyr Ser Val Trp Ser Tyr Cys Gly Val Gly

FIGURE 16UUU
SEQ ID NO.: 77
atggctctggaagagggcgggctcataatgcaggccttctactgggacgtccccatgggaggaat
ctggtgggacacgatagcccagaagataccogactgggcaagcgccgggatttcggcgatatgga
tccctcccgcgagcaagggtatgagcggcggctattcgatgggctacgaccoctacgattatttt
gacctcggtgagtactaccagaagggaacggtggaaacgaggttcggctcaaagcaggagctcat
aaacatgataaacaccgcccacgcctatggcatgaaggtaatagccgatatagtcatcaaccacc
gcgccggcggtgacctggagtggaacccottcgtgaacgactatacctggaccgacttctcaaag
gtcgcgtcgggtaaatacacggccaactacctcgacttccacccgaacgagctccatgcgggcga
ttccggaacatttggaggctatcccgacatatgccacgacaagagctgggaccagtactggctct
gggccagccaggagagctacgcggcatatctcaggagcatcggcatcgatgcctggcgcttcgac
tacgtcaagggctatgctccctgggtcgtcaaggactggctgaactggtggggaggctggcggt
tggagagtactgggacaccaacgtcgacgctgttctcaactgggcatactcgagcggtgccaagg
tctttgacttcgccctctactacaagatggacgaggccttcgataacaacaacattcccgccctg
gtggacgccctcagatacggtcagacagtggtcagccgcgacccgttcaaggctgtgacgtttgt
agccaaccacgataccgacataatctggaacaagtatccagcctacgcgttcatcctcacctacg
agggccagccgacaatattctaccgcgactacgaggagtggctcaacaaggataagctcaagaac
ctcatctggatacatgacaacctcgccggagggagcactgacatcgtttactacgacaacgacga
gctgatattcgtgagaaacggctacggaagcaagccgggactgataacatacatcaacctcgcct
caagcaaagccggaaggtgggtttacgttccgaagttcgcaggctcgtgcatacacgagtacacc
ggcaatctcggcggctgggtggacaagtgggtggactcaagcggctgggtctacctcgaggctcc
tgcccacgaccoggccaacggccagtacggctactccgtctggagctactgcggtgttgggtga
FIGURE 16VVV
SEQ ID NO.: 78
Met Ala Leu Glu Glu Gly Gly Leu Ile Met Gln Ala Phe Tyr Trp Asp
Val Pro Met Gly Gly Ile Trp Trp Asp Thr Ile Ala Gln Lys Ile Pro
Asp Trp Ala Ser Ala Gly Ile Ser Ala Ile Trp Ile Pro Pro Ala Ser
Lys Gly Met Ser Gly Gly Tyr Ser Met Gly Tyr Asp Pro Tyr Asp Tyr
Phe Asp Leu Gly Glu Tyr Tyr Gln Lys Gly Thr Val Glu Thr Arg Phe
Gly Ser Lys Gln Glu Leu Ile Asn Met Ile Asn Thr Ala His Ala Tyr
Gly Met Lys Val Ile Ala Asp Ile Val Ile Asn His Arg Ala Gly Gly
Asp Leu Glu Trp Asn Pro Phe Val Asn Asp Tyr Thr Trp Thr Asp Phe
Ser Lys Val Ala Ser Gly Lys Tyr Thr Ala Asn Tyr Leu Asp Phe His
Pro Asn Glu Leu His Ala Gly Asp Ser Gly Thr Phe Gly Gly Tyr Pro
Asp Ile Cys His Asp Lys Ser Trp Asp Gln Tyr Trp Leu Trp Ala Ser
Gln Glu Ser Tyr Ala Ala Tyr Leu Arg Ser Ile Gly Ile Asp Ala Trp
Arg Phe Asp Tyr Val Lys Gly Tyr Ala Pro Trp Val Val Lys Asp Trp
Leu Asn Trp Trp Gly Gly Trp Ala Val Gly Glu Tyr Trp Asp Thr Asn
Val Asp Ala Val Leu Asn Trp Ala Tyr Ser Ser Gly Ala Lys Val Phe
Asp Phe Ala Leu Tyr Tyr Lys Met Asp Glu Ala Phe Asp Asn Asn Asn
Ile Pro Ala Leu Val Asp Ala Leu Arg Tyr Gly Gln Thr Val Val Ser
Arg Asp Pro Phe Lys Ala Val Thr Phe Val Ala Asn His Asp Thr Asp
Ile Ile Trp Asn Lys Tyr Pro Ala Tyr Ala Phe Ile Leu Thr Tyr Glu
Gly Gln Pro Thr Ile Phe Tyr Arg Asp Tyr Glu Glu Trp Leu Asn Lys
Asp Lys Leu Lys Asn Leu Ile Trp Ile His Asp Asn Leu Ala Gly Gly
Ser Thr Asp Ile Val Tyr Tyr Asp Asn Asp Glu Leu Ile Phe Val Arg
Asn Gly Tyr Gly Ser Lys Pro Gly Leu Ile Thr Tyr Ile Asn Leu Ala
Ser Ser Lys Ala Gly Arg Trp Val Tyr Val Pro Lys Phe Ala Gly Ser
Cys Ile His Glu Tyr Thr Gly Asn Leu Gly Gly Trp Val Asp Lys Trp
Val Asp Ser Ser Gly Trp Val Tyr Leu Glu Ala Pro Ala His Asp Pro
Ala Asn Gly Gln Tyr Gly Tyr Ser Val Trp Ser Tyr Cys Gly Val Gly

FIGURE 16WWW
SEQ ID NO.: 79
atgaagcctgcgaaactcctcgtctttgtgctcgtagtctctatcctcgcggggctctacgccca
gcccgcggggcggccaagtacctggagctcgaagagggcggcgtcataatgcaggcgttctact
gggacgtgccttcaggaggaatatggtgggacacaatacggcagaagataccggagtggtacgat
gccggaatctccgcaatatggattccccggcgagcaagggcatgggcggcgcctattcgatggg
ctacgaccctacgacttctttgacctcggtgagtacgaccagaagggaacggtagagacgcgct
ttggctccaagcaggagctcgtgaacatgataaacaccgcccacgcctacggcatcaaggtcatc
gcagacatagtaatcaaccaccgcgccggaggagaccttgagtggaaccccttcgtcaatgacta
cacctggacggacttctcgaaggtcgcttccggcaagtacacggccaactacctcgacttccacc
ccaacgaggtcaagtgctgcgacgagggcacctttggagggttcccggacatagcccacgagaag
agctgggaccagtactggctctgggcgagcaacgagagctacgccgcctacctcaggagcatcgg
cgttgacgcatggcgcttcgactacgtcaagggctacggagcgtgggtcgtcaaggactggctgg
actggtggggaggctgggccgtcggggagtactgggacacaaacgttgatgcactgctcaactgg
gcctactcgagcgatgcaaaagtcttcgacttcccgctctactacaagatggacgcggcctttga
caacaagaacattcccgcactcgtcgaggccctcaagaacgggggcacagtcgtcagccgcgacc
cgtttaaggccgtaaccttcgttgcaaaccacgacacggacataatttggaacaagtacccggcc
tacgccttcatcctcacctacgagggccagccgacgatattctaccgcgactacgaggagtggct
caacaaggacaggctcaagaacctcatctggatacacgaccacctcgccggtggaagcaccgaca
tagtctactacgataacgatgaactcatcttcgtcaggaacggctacggggacaagccggggctt
ataacctacatcaacctaggctcgagcaaggccgggaggtgggtctacgttccgaagttcgcggg
agcgtgcatccacgagtacaccggcaacctcggcggctgggtggacaagtgggtggactcaagcg
ggtgggtgtacctcgaggccctgcccacgacccggccaacggctattacggctactccgtctgg
agctactgcggggtgggctga

FIGURE 16XXX

SEQ ID NO.: 80

Met Lys Pro Ala Lys Leu Leu Val Phe Val Leu Val Val Ser Ile Leu
Ala Gly Leu Tyr Ala Gln Pro Ala Gly Ala Ala Lys Tyr Leu Glu Leu
Glu Glu Gly Gly Val Ile Met Gln Ala Phe Tyr Trp Asp Val Pro Ser
Gly Gly Ile Trp Trp Asp Thr Ile Arg Gln Lys Ile Pro Glu Trp Tyr
Asp Ala Gly Ile Ser Ala Ile Trp Ile Pro Pro Ala Ser Lys Gly Met
Gly Gly Ala Tyr Ser Met Gly Tyr Asp Pro Tyr Asp Phe Phe Asp Leu
Gly Glu Tyr Asp Gln Lys Gly Thr Val Glu Thr Arg Phe Gly Ser Lys
Gln Glu Leu Val Asn Met Ile Asn Thr Ala His Ala Tyr Gly Ile Lys
Val Ile Ala Asp Ile Val Ile Asn His Arg Ala Gly Gly Asp Leu Glu
Trp Asn Pro Phe Val Asn Asp Tyr Thr Trp Thr Asp Phe Ser Lys Val
Ala Ser Gly Lys Tyr Thr Ala Asn Tyr Leu Asp Phe His Pro Asn Glu
Val Lys Cys Cys Asp Glu Gly Thr Phe Gly Gly Phe Pro Asp Ile Ala
His Glu Lys Ser Trp Asp Gln Tyr Trp Leu Trp Ala Ser Asn Glu Ser
Tyr Ala Ala Tyr Leu Arg Ser Ile Gly Val Asp Ala Trp Arg Phe Asp
Tyr Val Lys Gly Tyr Gly Ala Trp Val Val Lys Asp Trp Leu Asp Trp
Trp Gly Gly Trp Ala Val Gly Glu Tyr Trp Asp Thr Asn Val Asp Ala
Leu Leu Asn Trp Ala Tyr Ser Ser Asp Ala Lys Val Phe Asp Phe Pro
Leu Tyr Tyr Lys Met Asp Ala Ala Phe Asp Asn Lys Asn Ile Pro Ala
Leu Val Glu Ala Leu Lys Asn Gly Gly Thr Val Val Ser Arg Asp Pro
Phe Lys Ala Val Thr Phe Val Ala Asn His Asp Thr Asp Ile Ile Trp
Asn Lys Tyr Pro Ala Tyr Ala Phe Ile Leu Thr Tyr Glu Gly Gln Pro
Thr Ile Phe Tyr Arg Asp Tyr Glu Glu Trp Leu Asn Lys Asp Arg Leu
Lys Asn Leu Ile Trp Ile His Asp His Leu Ala Gly Gly Ser Thr Asp
Ile Val Tyr Tyr Asp Asn Asp Glu Leu Ile Phe Val Arg Asn Gly Tyr
Gly Asp Lys Pro Gly Leu Ile Thr Tyr Ile Asn Leu Gly Ser Ser Lys
Ala Gly Arg Trp Val Tyr Val Pro Lys Phe Ala Gly Ala Cys Ile His
Glu Tyr Thr Gly Asn Leu Gly Gly Trp Val Asp Lys Trp Val Asp Ser
Ser Gly Trp Val Tyr Leu Glu Ala Pro Ala His Asp Pro Ala Asn Gly
Tyr Tyr Gly Tyr Ser Val Trp Ser Tyr Cys Gly Val Gly

FIGURE 16YYY

SEQ ID NO.: 81
atgaagaagtttgtcgccctgttcataaccatgttttttcgtagtgagcatggcagtcgttgcaca
gccagctagcgccgcaaagtattccgagctcgaagaaggcggcgttataatgcaggccttctact
gggacgtcccaggtggaggaatctggtgggacaccatcaggagcaagataccggagtggtacgag
gcgggaatatccgccatttggattccgccagccagcaaggggatgagcggcggttactcgatggg
ctacgatccctacgatttctttgacctcggcgagtacaaccagaagggaaccatcgaaacgcgct
ttggctctaaacaggagctcatcaatatgataaacacggcccatgcctacggcataaaggtcata
gcggacatcgtcataaaccaccgcgcaggcggagacctcgagtggaacccgttcgttggggacta
cacctggacggacttctcaaaggtggcctcgggcaaatatactgccaactacctcgacttccacc
ccaacgaggtcaagtgctgtgacgagggcacatttggaggcttcccagacatagcccacgagaag
agctgggaccagcactggctctgggcgagcgatgagagctacgccgcctacctaaggagcatcgg
cgttgatgcctggcgctttgactacgtgaagggctacggagcgtgggtcgtcaaggactggctca
actggtggggcggctggccgttggcgagtactgggacaccaacgttgatgcactcctcaactgg
gcctactcgagcggcgccaaggtcttcgacttcccgctctactacaagatggatgaggcctttga
caacaaaaacattccagcgctcgtctctgcccttcagaacggccagactgttgtctcccgcgacc
cgttcaaggccgtaacctttgtagcaaaccacgacaccgatataatctggaacaagtaccttgct
tatgctttcatcctcacctacgaaggccagcccgtcatattctaccgcgactacgaggagtggct
caacaaggacaggttgaacaacctcatatggatacacgaccacctcgcaggtggaagcacgagca
tagtctactacgacagcgacgagatgatcttcgtgaggaacggctatggaagcaagcctggcctt
ataacttacatcaacctcggctcgagcaaggttggaaggtgggtttatgtgccgaagttcgcggg
cgcgtgcatccacgagtatactggtaacctcggaggctgggtagacaagtacgtctactcaagcg
gctgggtctatctcgaagctccagcttacgaccctgccaacgggcagtatggctactccgtgtgg
agctattgcggtgttgggtga

FIGURE 16ZZZ
SEQ ID NO.: 82

Met Lys Lys Phe Val Ala Leu Phe Ile Thr Met Phe Phe Val Val Ser
Met Ala Val Val Ala Gln Pro Ala Ser Ala Ala Lys Tyr Ser Glu Leu
Glu Glu Gly Gly Val Ile Met Gln Ala Phe Tyr Trp Asp Val Pro Gly
Gly Gly Ile Trp Trp Asp Thr Ile Arg Ser Lys Ile Pro Glu Trp Tyr
Glu Ala Gly Ile Ser Ala Ile Trp Ile Pro Pro Ala Ser Lys Gly Met
Ser Gly Gly Tyr Ser Met Gly Tyr Asp Pro Tyr Asp Phe Phe Asp Leu
Gly Glu Tyr Asn Gln Lys Gly Thr Ile Glu Thr Arg Phe Gly Ser Lys
Gln Glu Leu Ile Asn Met Ile Asn Thr Ala His Ala Tyr Gly Ile Lys
Val Ile Ala Asp Ile Val Ile Asn His Arg Ala Gly Gly Asp Leu Glu
Trp Asn Pro Phe Val Gly Asp Tyr Thr Trp Thr Asp Phe Ser Lys Val
Ala Ser Gly Lys Tyr Thr Ala Asn Tyr Leu Asp Phe His Pro Asn Glu
Val Lys Cys Cys Asp Glu Gly Thr Phe Gly Gly Phe Pro Asp Ile Ala
His Glu Lys Ser Trp Asp Gln His Trp Leu Trp Ala Ser Asp Glu Ser
Tyr Ala Ala Tyr Leu Arg Ser Ile Gly Val Asp Ala Trp Arg Phe Asp
Tyr Val Lys Gly Tyr Gly Ala Trp Val Val Lys Asp Trp Leu Asn Trp
Trp Gly Gly Trp Ala Val Gly Glu Tyr Trp Asp Thr Asn Val Asp Ala
Leu Leu Asn Trp Ala Tyr Ser Ser Gly Ala Lys Val Phe Asp Phe Pro
Leu Tyr Tyr Lys Met Asp Glu Ala Phe Asp Asn Lys Asn Ile Pro Ala
Leu Val Ser Ala Leu Gln Asn Gly Gln Thr Val Val Ser Arg Asp Pro
Phe Lys Ala Val Thr Phe Val Ala Asn His Asp Thr Asp Ile Ile Trp
Asn Lys Tyr Leu Ala Tyr Ala Phe Ile Leu Thr Tyr Glu Gly Gln Pro
Val Ile Phe Tyr Arg Asp Tyr Glu Glu Trp Leu Asn Lys Asp Arg Leu
Asn Asn Leu Ile Trp Ile His Asp His Leu Ala Gly Gly Ser Thr Ser
Ile Val Tyr Tyr Asp Ser Asp Glu Met Ile Phe Val Arg Asn Gly Tyr
Gly Ser Lys Pro Gly Leu Ile Thr Tyr Ile Asn Leu Gly Ser Ser Lys
Val Gly Arg Trp Val Tyr Val Pro Lys Phe Ala Gly Ala Cys Ile His
Glu Tyr Thr Gly Asn Leu Gly Gly Trp Val Asp Lys Tyr Val Tyr Ser
Ser Gly Trp Val Tyr Leu Glu Ala Pro Ala Tyr Asp Pro Ala Asn Gly
Gln Tyr Gly Tyr Ser Val Trp Ser Tyr Cys Gly Val Gly

FIGURE 16AAAA
SEQ ID NO.: 83 atggctctggaagacggcgggctcataatgcaggccttctactgggatgttcctggaggaggaat
ctggtgggacacaatagctcaaaagatacccgaatgggcaagtgcaggaatctcagcgatatgga
ttccaccagcgagtaagggcatgagcggtggttattccatgggctacgatccctacgatttcttt
gacctcggcgagtactatcagaaggggacagttgagacgcgcttcggctcaaaggaagaactggt
gaacatgataaacaccgcacactcctacggcataaaggtgatagcagacatagtcataaaccacc
gcgccggtggagaccttgagtggaacccttcgtgaacgactatacctggacagacttctcaaaa
gtcgcctccggtaaatatacggccaactaccttgacttccacccaaacgagcttcactgttgtga
tgaaggtacctttggaggatacccctgatatatgtcacgacaaaagctgggaccagtactggctct
ggcgagcagcgaaagctacgctgcctacctcaggagcataggggttgacgcctggcgtttcgac
tacgtcaagggctacggagcatggttgttaacgactggctcagctggtggggaggctgggccgt
tggagagtactgggacacgaacgttgatgcactcctcaactgggcatacagcagcggcgccaagg
tctttgacttccgctctactacaagatggacgaagccttcgacaacaccaacatcccggcatta
gtggatgcactcagatacggccagacagtggtcagccgcgatcccttcaaggcggtaactttcgt
tgccaaccacgatacagatataatctggaacaagtatccggcttatgcattcatccttacctatg
agggacagcctgttatattctaccgcgactacgaggagtggctcaacaaggataagcttaacaac
ctcatctggatacacgatcaccttgctggagggagtactgacattgtttactacgacagcgacga
gcttatctttgtgagaaacggctatggcaccaaaccaggactgataacctatatcaacctcggct
caagcaaagttggaaggtgggtctacgttccaaagttcgccggttcatgcatccacgagtacacc
ggcaacctcggcggttggatagacaagtacgtctcctccagcggctgggtctatcttgaggcccc
agcccacgacccggcgaacggctactacggctactccgtatggagctactgcggggttgggtga

FIGURE 16BBBB
SEQ ID NO.: 84
Met Ala Leu Glu Asp Gly Gly Leu Ile Met Gln Ala Phe Tyr Trp Asp
Val Pro Gly Gly Gly Ile Trp Trp Asp Thr Ile Ala Gln Lys Ile Pro
Glu Trp Ala Ser Ala Gly Ile Ser Ala Ile Trp Ile Pro Pro Ala Ser
Lys Gly Met Ser Gly Gly Tyr Ser Met Gly Tyr Asp Pro Tyr Asp Phe
Phe Asp Leu Gly Glu Tyr Tyr Gln Lys Gly Thr Val Glu Thr Arg Phe
Gly Ser Lys Glu Glu Leu Val Asn Met Ile Asn Thr Ala His Ser Tyr
Gly Ile Lys Val Ile Ala Asp Ile Val Ile Asn His Arg Ala Gly Gly
Asp Leu Glu Trp Asn Pro Phe Val Asn Asp Tyr Thr Trp Thr Asp Phe
Ser Lys Val Ala Ser Gly Lys Tyr Thr Ala Asn Tyr Leu Asp Phe His
Pro Asn Glu Leu His Cys Cys Asp Glu Gly Thr Phe Gly Gly Tyr Pro
Asp Ile Cys His Asp Lys Ser Trp Asp Gln Tyr Trp Leu Trp Ala Ser
Ser Glu Ser Tyr Ala Ala Tyr Leu Arg Ser Ile Gly Val Asp Ala Trp
Arg Phe Asp Tyr Val Lys Gly Tyr Gly Ala Trp Val Val Asn Asp Trp
Leu Ser Trp Trp Gly Gly Trp Ala Val Gly Glu Tyr Trp Asp Thr Asn
Val Asp Ala Leu Leu Asn Trp Ala Tyr Ser Ser Gly Ala Lys Val Phe
Asp Phe Pro Leu Tyr Tyr Lys Met Asp Glu Ala Phe Asp Asn Thr Asn
Ile Pro Ala Leu Val Asp Ala Leu Arg Tyr Gly Gln Thr Val Val Ser
Arg Asp Pro Phe Lys Ala Val Thr Phe Val Ala Asn His Asp Thr Asp
Ile Ile Trp Asn Lys Tyr Pro Ala Tyr Ala Phe Ile Leu Thr Tyr Glu
Gly Gln Pro Val Ile Phe Tyr Arg Asp Tyr Glu Glu Trp Leu Asn Lys
Asp Lys Leu Asn Asn Leu Ile Trp Ile His Asp His Leu Ala Gly Gly
Ser Thr Asp Ile Val Tyr Tyr Asp Ser Asp Glu Leu Ile Phe Val Arg
Asn Gly Tyr Gly Thr Lys Pro Gly Leu Ile Thr Tyr Ile Asn Leu Gly
Ser Ser Lys Val Gly Arg Trp Val Tyr Val Pro Lys Phe Ala Gly Ser
Cys Ile His Glu Tyr Thr Gly Asn Leu Gly Gly Trp Ile Asp Lys Tyr
Val Ser Ser Ser Gly Trp Val Tyr Leu Glu Ala Pro Ala His Asp Pro
Ala Asn Gly Tyr Tyr Gly Tyr Ser Val Trp Ser Tyr Cys Gly Val Gly

FIGURE 16CCCC
SEQ ID NO.: 85
atggctctggaagagggcgggcttataatgcaggcattctattgggacgtcccaggtggaggaat
ctggtgggacaccatagcccagaagatacccgaatgggcaagtgcaggaatctcagcgatatgga
ttccaccagcgagtaagggaatgagcggtggttattccatgggctacgatccctacgatttcttt
gacctcggcgagtactatcagaaggggacagttgagacgcgcttcggctcaaaggaagaactggt
gaacatgataaacaccgcacactcctacggcataaaggtgatagcggacatagtcataaaccacc
gcgccggtggaggcctcgagtggaacccettcgtgaacgactatacctggacagacttctcaaaa
gtcgcctccggtaaatatacagccaactaccttgacttccacccaaacgagcttcactgttgtga
tgaaggtaccttttggaggatacccttgatatatgtcacgacaaaagctgggaccagtactggctct
gggcgagcagcgaaagctacgctgcctacctcaggagcatagggggttgacgcctggtgtttcgac
tacgtcaagggctacggagcctgggttgttaacgactggctcagctggtggggaggctgggccgt
tggagagtactgggacactaacgttgatgcactcctcaactgggcatacaacagcggcgccaagg
tcttcgacttcccgctctactacaagatggacgaagccttcgacaataccaacatcccgctttg
gtttacgccctcaagaatggcgggacagtggtcagccgcgacccattcaaggcggtaactttcgt
tgccaaccacgatacagatataatctggaacaagtatccggcttatgcattcatccttacctatg
agggacagcctgttatattctaccgcgactacgaggagtggctcaacaaggataagcttaacaac
ctcatctggatacacgatcaccttgctggagggagtactgacattgtttactacgacagcgacga
gcttatctttgtgagaaacggctatggcaccaaaccaggactgataacctatatcaacctcggct
caagcaaagctggaaggtgggtctacgttccaaagttcgccggttcatgcatccacgagtacacc
ggcagcctcggcggttggatagacaagtacgtctcctccagcggctgggtctaccttgaggcccc
ggcccacgacccggccaatggccagtatggctactccgtctggagctattgcggggttgggtga

FIGURE 16DDDD
SEQ ID NO.: 86

Met Ala Leu Glu Glu Gly Gly Leu Ile Met Gln Ala Phe Tyr Trp Asp
Val Pro Gly Gly Gly Ile Trp Trp Asp Thr Ile Ala Gln Lys Ile Pro
Glu Trp Ala Ser Ala Gly Ile Ser Ala Ile Trp Ile Pro Pro Ala Ser
Lys Gly Met Ser Gly Gly Tyr Ser Met Gly Tyr Asp Pro Tyr Asp Phe
Phe Asp Leu Gly Glu Tyr Tyr Gln Lys Gly Thr Val Glu Thr Arg Phe
Gly Ser Lys Glu Glu Leu Val Asn Met Ile Asn Thr Ala His Ser Tyr
Gly Ile Lys Val Ile Ala Asp Ile Val Ile Asn His Arg Ala Gly Gly
Gly Leu Glu Trp Asn Pro Phe Val Asn Asp Tyr Thr Trp Thr Asp Phe
Ser Lys Val Ala Ser Gly Lys Tyr Thr Ala Asn Tyr Leu Asp Phe His
Pro Asn Glu Leu His Cys Cys Asp Glu Gly Thr Phe Gly Gly Tyr Pro
Asp Ile Cys His Asp Lys Ser Trp Asp Gln Tyr Trp Leu Trp Ala Ser
Ser Glu Ser Tyr Ala Ala Tyr Leu Arg Ser Ile Gly Val Asp Ala Trp
Cys Phe Asp Tyr Val Lys Gly Tyr Gly Ala Trp Val Val Asn Asp Trp
Leu Ser Trp Trp Gly Gly Trp Ala Val Gly Glu Tyr Trp Asp Thr Asn
Val Asp Ala Leu Leu Asn Trp Ala Tyr Asn Ser Gly Ala Lys Val Phe
Asp Phe Pro Leu Tyr Tyr Lys Met Asp Glu Ala Phe Asp Asn Thr Asn
Ile Pro Ala Leu Val Tyr Ala Leu Lys Asn Gly Gly Thr Val Val Ser
Arg Asp Pro Phe Lys Ala Val Thr Phe Val Ala Asn His Asp Thr Asp
Ile Ile Trp Asn Lys Tyr Pro Ala Tyr Ala Phe Ile Leu Thr Tyr Glu
Gly Gln Pro Val Ile Phe Tyr Arg Asp Tyr Glu Glu Trp Leu Asn Lys
Asp Lys Leu Asn Asn Leu Ile Trp Ile His Asp His Leu Ala Gly Gly
Ser Thr Asp Ile Val Tyr Tyr Asp Ser Asp Glu Leu Ile Phe Val Arg
Asn Gly Tyr Gly Thr Lys Pro Gly Leu Ile Thr Tyr Ile Asn Leu Gly
Ser Ser Lys Ala Gly Arg Trp Val Tyr Val Pro Lys Phe Ala Gly Ser
Cys Ile His Glu Tyr Thr Gly Ser Leu Gly Gly Trp Ile Asp Lys Tyr
Val Ser Ser Ser Gly Trp Val Tyr Leu Glu Ala Pro Ala His Asp Pro
Ala Asn Gly Gln Tyr Gly Tyr Ser Val Trp Ser Tyr Cys Gly Val Gly

FIGURE 16EEEE
SEQ ID NO: 87

```
atgttcctgctcgcgttttgctcactgcctcgctgttctgcccaacaggacagcccgccaaggc
tgccgcaccgtttaacggcaccatgatgcagtattttgaatggtacttgccggatgatggcacgt
tatggaccaaagtggccaatgaagccaacaacttatccagccttggcatcaccgctctttggctg
ccgcccgcttacaaaggaacaagccgcagcgacgtagggtacggagtatacgacttgtatgacct
cggcgaattcaatcaaaagggaccgtccgcacaaaatacggaacaaaagctcaatatcttcaag
ccattcaagccgcccacgccgctggaatgcaagtgtacgccgatgtcgtgttcgaccataaggc
ggcgctgacggcacggaatggtggacgccgtcgaagtcaatccgtccgaccgcaaccaagaaat
ctcgggcacctatcaaatccaagcatggacgaaatttgatttcccgggcggggcaacacctact
ccagctttaagtggcgctggtaccattttgacggcgttgattgggacgaaagccgaaaattgagc
cgcatttacaaattccgcggcatcggcaaagcgtgggattgggaagtagacacggaaaacggaaa
ctatgactacttaatgtatgccgaccttgatatggatcatcccgaagtcgtgaccgagctgaaaa
actgggggaaatggtatgtcaacacaacgaacattgatgggttccggcttgatgccgtcaagcat
attaagttcagttttttttcctgattggttgtcgtatgtgcgttctcagactggcaagccgctatt
taccgtcggggaatattggagctatgacatcaacaagttgcacaattacattacgaaaacagacg
gaacgatgtctttgtttgatgccccgttacacaacaaattttataccgcttccaaatcaggggc
gcatttgatatgcgcacgttaatgaccaatactctcatgaaagatcaaccgacattggccgtcac
cttcgttgataatcatgacaccgaacccggccaagcgctgcagtcatgggtcgacccatggttca
aaccgttggcttacgcctttattctaactcggcaggaaggataccccgtgcgtctttatggtgac
tattatggcattccacaatataacattccttcgctgaaaagcaaaatcgatccgctcctcatcgc
gcgcagggattatgcttacggaacgcaacatgattatcttgatcactccgacatcatcgggtgga
caagggaaggggtcactgaaaaaccaggatccgggctggccgcactgatcaccgatgggccggga
ggaagcaaatggatgtactgttggcaaacaacacgctggaaaagtgttctatga
```

FIGURE 16FFFF
SEQ ID NO: 88
Met Phe Leu Leu Ala Phe Leu Leu Thr Ala Ser Leu Phe Cys Pro Thr
Gly Gln Pro Ala Lys Ala Ala Ala Pro Phe Asn Gly Thr Met Met Gln
Tyr Phe Glu Trp Tyr Leu Pro Asp Asp Gly Thr Leu Trp Thr Lys Val
Ala Asn Glu Ala Asn Asn Leu Ser Ser Leu Gly Ile Thr Ala Leu Trp
Leu Pro Pro Ala Tyr Lys Gly Thr Ser Arg Ser Asp Val Gly Tyr Gly
Val Tyr Asp Leu Tyr Asp Leu Gly Glu Phe Asn Gln Lys Gly Thr Val
Arg Thr Lys Tyr Gly Thr Lys Ala Gln Tyr Leu Gln Ala Ile Gln Ala
Ala His Ala Ala Gly Met Gln Val Tyr Ala Asp Val Val Phe Asp His
Lys Gly Gly Ala Asp Gly Thr Glu Trp Val Asp Ala Val Glu Val Asn
Pro Ser Asp Arg Asn Gln Glu Ile Ser Gly Thr Tyr Gln Ile Gln Ala
Trp Thr Lys Phe Asp Phe Pro Gly Arg Gly Asn Thr Tyr Ser Ser Phe
Lys Trp Arg Trp Tyr His Phe Asp Gly Val Asp Trp Asp Glu Ser Arg
Lys Leu Ser Arg Ile Tyr Lys Phe Arg Gly Ile Gly Lys Ala Trp Asp
Trp Glu Val Asp Thr Glu Asn Gly Asn Tyr Asp Tyr Leu Met Tyr Ala
Asp Leu Asp Met Asp His Pro Glu Val Val Thr Glu Leu Lys Asn Trp
Gly Lys Trp Tyr Val Asn Thr Thr Asn Ile Asp Gly Phe Arg Leu Asp
Ala Val Lys His Ile Lys Phe Ser Phe Phe Pro Asp Trp Leu Ser Tyr
Val Arg Ser Gln Thr Gly Lys Pro Leu Phe Thr Val Gly Glu Tyr Trp
Ser Tyr Asp Ile Asn Lys Leu His Asn Tyr Ile Thr Lys Thr Asp Gly
Thr Met Ser Leu Phe Asp Ala Pro Leu His Asn Lys Phe Tyr Thr Ala
Ser Lys Ser Gly Gly Ala Phe Asp Met Arg Thr Leu Met Thr Asn Thr
Leu Met Lys Asp Gln Pro Thr Leu Ala Val Thr Phe Val Asp Asn His
Asp Thr Glu Pro Gly Gln Ala Leu Gln Ser Trp Val Asp Pro Trp Phe
Lys Pro Leu Ala Tyr Ala Phe Ile Leu Thr Arg Gln Glu Gly Tyr Pro
Cys Val Phe Tyr Gly Asp Tyr Tyr Gly Ile Pro Gln Tyr Asn Ile Pro
Ser Leu Lys Ser Lys Ile Asp Pro Leu Leu Ile Ala Arg Arg Asp Tyr
Ala Tyr Gly Thr Gln His Asp Tyr Leu Asp His Ser Asp Ile Ile Gly
Trp Thr Arg Glu Gly Val Thr Glu Lys Pro Gly Ser Gly Leu Ala Ala
Leu Ile Thr Asp Gly Pro Gly Gly Ser Lys Trp Met Tyr Cys Trp Gln
Thr Thr Arg Trp Lys Ser Val Leu

FIGURE 16GGGG

SEQ ID NO: 89
```
atgaaagaagcggttgtgtatcaaattttcccggatcggttctttaatggcaaccttcaaatga
taacagcaagcagcaggcacgcggggcgcagccgattgagcatcgcgattggtcggatttgcccg
ataatccgcgcctgaaagggacgagcggctacgatggcgacggtgaatggtcgaatgactttttc
ggcggagacatcgccggaattgaacaaaagttggattatttgcagtcgcttggagtgaacacgat
ttacttaaatccgatcgccaatgcgccatcgaaccataaatatgatgcgagcaattacaaagaat
tggatccgatgttcggttccccggaagaattccaatcgtttgtgcaggcgcttgcgaaccggggg
atgcatctcatcttagacggggtgttcaaccacgtatccgacgattcgatttactttgaccgcta
ccaccgctatccgaccgtcggtgcgtatgaatattgggaagcggtttacgatttgatgaatgaaa
aaggattgagcgaggaagaagcgcggaaacaagtggaagagaagttcaaacaagagggacagacg
ttcagcccgtatgggtttcatctttggttcaatattgaaaacaaaaaagtcaatggccattatca
ataccaatcatggtggggctatgacagtctgccggagtttaagtcggtgacggggggaaaaagtgc
cgcatccgagtgaattgaacaacgatgcgctcgcgaattacattttccgtgaatcggattcggtg
gcgaaaagctggattgccctcggcgcctccggctggcggttggatgtggccaatgaggtggatcc
ggcgttttggcgcgagtttcgccaagaattgcttcaagggtcgtacggcgcggtccgacgttaa
aagagggggagcagccgctcattttaggggaaatttgggatgacgcatcgaaatattttctaggc
gaccagtacgattccgtgatgaactaccggttccgcggggcggtgcttgacttttttgaaaaacgg
aaatgcagaagaggcggacaagcggctgacggccataagggaagactacccaagtgaagcgtttt
atgcgctgatgaacttaatcggttcgcatgacacggcgcgggcggtctttctgcttgggaacgga
acggattcatccgagcgggcggagcttgatccgaattataatgaggaacttgggaaaaagcggct
caagctggcggtgattttgcagatgggatacccgggagcgccgacgatttattacggcgatgaag
cgggagtaacaggctcaaaagacccagacaaccgccgcacgtatccgtggggcaaagaagatcaa
aatctgttgtcccattatcagaaagtggggcacattcgccagcaccatcaatcgttgttggccca
tggcgacatcaagacggtgtatgcgcaaggggatgtatacgtatttgcccgccaatacggcgtg
aagcggcgctcattgccatcaaccgcggcaatgaggacaagacggtggcgcttgacgtcgcttcg
ttgcttccgaacggcaccgtgcttacggatgagttgcatgatggcggggaagctacggtcgctgg
cggaacgttgacggtcacgattccggccctggatggacggatgatgtttgggacggtgacggcgg
aaatgccggcagcagtcagcaatttgcaggcgagcgcttcggatggctgcgtgacgttaacgtgg
gaaggaaatgcatcgagataccgaatttacgagtccacgttaaaaggtgccggttatacgatggt
gcaagagacggaaacaacttcggccacgatcggttcgttgacgaacggaacagcctattactttg
ccgttgcggcggtcgatgaaaacgggaatgaatcaccgaaggtcgaaacgaatcgcgtcgttcct
cattacccgctgacgagcgacaatgtccagttcgtgacaacgttaagcgatgccacactggattt
gtcaaagccgcagcaagtggatgtccatgtcaacatcgacaatgtgacaagcaaaggagcagctg
atggttgcaagcggtgttgcaagtgaaaggcccgcatgacgaaacatggaaagaatacagagcg
gcttaccaaggacaagacggcgacgccaacgtgttccgagctgccttcactccgctcgccgcagg
gacgtatacgtatcgttatgcgctgacgaccaaccttggcgaggagtggatgtatacagaagaga
agcaagtgacgtttgcggcagacaacagcgaccaaatagcgccagcagacgccatcgagctgcgg
cagcctgcggttgaatcgggacaagtgaatttatcatggacgtttgtttgggaaaaaagatgggga
tgcttatttgttagccatcgagcgcaacggtgatatcgtgcatacaaccacttcgatcggcgatt
catttacagactacgatgtcgaaaacggcaccgagtacacgtatgttgtcaagttgtatgaccgc
gccggcaatgttgtggcgtcaaacacggtcaaggtgacgccggacattgtgatggtgaaagtgat
ttttaaagtgagagcgccggattacacaccgttggatgcccgaattacgattccgaacagcttga
acggctggaacacaggggcctggagatgtcgcgcaacggtgcggtgacgcccgattggcaattt
accgtcgaggtgcaggaaggggaaacgatcacctataagtatgtgaaaggcggatcgtgggatca
agagggggttggccgaccatacgcgtgaggacgacaacgatgatgacgtgagctactacggctatg
ggacgattggcaccgacttgaaagtgacggtccacaatgaaggaaacaatacgatgattgtgcaa
gaccgcattttcgcgctggatcgatatgccggtcgtcatcgaagaggtgcaaaaacaaggaagtca
agtgacgatcaagggcaatgccattaaaaacggtgttttgacgatcaatggcgagcgggtgccga
ttgatggccggatggcattctcgtacacgtttgcgccggccagccatcaaaaagaagtgttgatc
catatcgaaccatcggccgaaagcaaaacagccattttcaacaacgacggcggagcgattgcgaa
aaacacaaaagattacgtgctgaatttagaaacgaagcaattcaaaaagcttctcgagagtactt
ctagagcggccgcgggcccatcgattttccacccgggtggggtaccaggta
```

FIGURE 16HHHH
SEQ ID NO: 90

```
Met Lys Glu Ala Val Val Tyr Gln Ile Phe Pro Asp Arg Phe Phe Asn
Gly Asn Pro Ser Asn Asp Asn Ser Lys Gln Gln Ala Arg Gly Ala Gln
Pro Ile Glu His Arg Asp Trp Ser Asp Leu Pro Asp Asn Pro Arg Leu
Lys Gly Thr Ser Gly Tyr Asp Gly Asp Gly Glu Trp Ser Asn Asp Phe
Phe Gly Gly Asp Ile Ala Gly Ile Glu Gln Lys Leu Asp Tyr Leu Gln
Ser Leu Gly Val Asn Thr Ile Tyr Leu Asn Pro Ile Ala Asn Ala Pro
Ser Asn His Lys Tyr Asp Ala Ser Asn Tyr Lys Glu Leu Asp Pro Met
Phe Gly Ser Pro Glu Glu Phe Gln Ser Phe Val Gln Ala Leu Ala Asn
Arg Gly Met His Leu Ile Leu Asp Gly Val Phe Asn His Val Ser Asp
Asp Ser Ile Tyr Phe Asp Arg Tyr His Arg Tyr Pro Thr Val Gly Ala
Tyr Glu Tyr Trp Glu Ala Val Tyr Asp Leu Met Asn Glu Lys Gly Leu
Ser Glu Glu Glu Ala Arg Lys Gln Val Glu Glu Lys Phe Lys Gln Glu
Gly Gln Thr Phe Ser Pro Tyr Gly Phe His Leu Trp Phe Asn Ile Glu
Asn Lys Lys Val Asn Gly His Tyr Gln Tyr Gln Ser Trp Trp Gly Tyr
Asp Ser Leu Pro Glu Phe Lys Ser Val Thr Gly Glu Lys Val Pro His
Pro Ser Glu Leu Asn Asn Asp Ala Leu Ala Asn Tyr Ile Phe Arg Glu
Ser Asp Ser Val Ala Lys Ser Trp Ile Ala Leu Gly Ala Ser Gly Trp
Arg Leu Asp Val Ala Asn Glu Val Asp Pro Ala Phe Trp Arg Glu Phe
Arg Gln Glu Leu Leu Gln Gly Ser Tyr Gly Arg Gly Pro Thr Leu Lys
Glu Gly Glu Gln Pro Leu Ile Leu Gly Glu Ile Trp Asp Asp Ala Ser
Lys Tyr Phe Leu Gly Asp Gln Tyr Asp Ser Val Met Asn Tyr Arg Phe
Arg Gly Ala Val Leu Asp Phe Leu Lys Asn Gly Asn Ala Glu Glu Ala
Asp Lys Arg Leu Thr Ala Ile Arg Glu Asp Tyr Pro Ser Glu Ala Phe
Tyr Ala Leu Met Asn Leu Ile Gly Ser His Asp Thr Ala Arg Ala Val
Phe Leu Leu Gly Asn Gly Thr Asp Ser Ser Glu Arg Ala Glu Leu Asp
Pro Asn Tyr Asn Glu Glu Leu Gly Lys Lys Arg Leu Lys Leu Ala Val
Ile Leu Gln Met Gly Tyr Pro Gly Ala Pro Thr Ile Tyr Tyr Gly Asp
Glu Ala Gly Val Thr Gly Ser Lys Asp Pro Asp Asn Arg Arg Thr Tyr
Pro Trp Gly Lys Glu Asp Gln Asn Leu Leu Ser His Tyr Gln Lys Val
Gly His Ile Arg Gln His His Gln Ser Leu Leu Ala His Gly Asp Ile
Lys Thr Val Tyr Ala Gln Gly Asp Val Tyr Val Phe Ala Arg Gln Tyr
Gly Arg Glu Ala Ala Leu Ile Ala Ile Asn Arg Gly Asn Glu Asp Lys
Thr Val Ala Leu Asp Val Ala Ser Leu Leu Pro Asn Gly Thr Val Leu
Thr Asp Glu Leu His Asp Gly Gly Glu Ala Thr Val Ala Gly Gly Thr
Leu Thr Val Thr Ile Pro Ala Leu Asp Gly Arg Met Met Phe Gly Thr
Val Thr Ala Glu Met Pro Ala Ala Val Ser Asn Leu Gln Ala Ser Ala
Ser Asp Gly Cys Val Thr Leu Thr Trp Glu Gly Asn Ala Ser Arg Tyr
Arg Ile Tyr Glu Ser Thr Leu Lys Gly Ala Gly Tyr Thr Met Val Gln
Glu Thr Glu Thr Thr Ser Ala Thr Ile Gly Ser Leu Thr Asn Gly Thr
Ala Tyr Tyr Phe Ala Val Ala Ala Val Asp Glu Asn Gly Asn Glu Ser
Pro Lys Val Glu Thr Asn Arg Val Val Pro His Tyr Pro Leu Thr Ser
Asp Asn Val Gln Phe Val Thr Thr Leu Ser Asp Ala Thr Leu Asp Leu
Ser Lys Pro Gln Gln Val Asp Val His Val Asn Ile Asp Asn Val Thr
Ser Lys Gly Ala Ala Asp Gly Leu Gln Ala Val Leu Gln Val Lys Gly
Pro His Asp Glu Thr Trp Lys Glu Tyr Arg Ala Ala Tyr Gln Gly Gln
Asp Gly Asp Ala Asn Val Phe Arg Ala Ala Phe Thr Pro Leu Ala Ala
Gly Thr Tyr Thr Tyr Arg Tyr Ala Leu Thr Thr Asn Leu Gly Glu Glu
Trp Met Tyr Thr Glu Glu Lys Gln Val Thr Phe Ala Ala Asp Asn Ser
Asp Gln Ile Ala Pro Ala Asp Ala Ile Glu Leu Arg Gln Pro Ala Val
Glu Ser Gly Gln Val Asn Leu Ser Trp Thr Phe Val Gly Lys Lys Asp
Gly Asp Ala Tyr Leu Leu Ala Ile Glu Arg Asn Gly Asp Ile Val His
```

FIGURE 16HHHH cont.

Thr Thr Thr Ser Ile Gly Asp Ser Phe Thr Asp Tyr Asp Val Glu Asn
Gly Thr Glu Tyr Thr Tyr Val Val Lys Leu Tyr Asp Arg Ala Gly Asn
Val Val Ala Ser Asn Thr Val Lys Val Thr Pro Asp Ile Val Met Val
Lys Val Ile Phe Lys Val Arg Ala Pro Asp Tyr Thr Pro Leu Asp Ala
Arg Ile Thr Ile Pro Asn Ser Leu Asn Gly Trp Asn Thr Gly Ala Trp
Glu Met Ser Arg Asn Gly Ala Val Thr Pro Asp Trp Gln Phe Thr Val
Glu Val Gln Glu Gly Glu Thr Ile Thr Tyr Lys Tyr Val Lys Gly Gly
Ser Trp Asp Gln Glu Gly Leu Ala Asp His Thr Arg Glu Asp Asp Asn
Asp Asp Asp Val Ser Tyr Tyr Gly Tyr Gly Thr Ile Gly Thr Asp Leu
Lys Val Thr Val His Asn Glu Gly Asn Asn Thr Met Ile Val Gln Asp
Arg Ile Leu Arg Trp Ile Asp Met Pro Val Val Ile Glu Glu Val Gln
Lys Gln Gly Ser Gln Val Thr Ile Lys Gly Asn Ala Ile Lys Asn Gly
Val Leu Thr Ile Asn Gly Glu Arg Val Pro Ile Asp Gly Arg Met Ala
Phe Ser Tyr Thr Phe Ala Pro Ala Ser His Gln Lys Glu Val Leu Ile
His Ile Glu Pro Ser Ala Glu Ser Lys Thr Ala Ile Phe Asn Asn Asp
Gly Gly Ala Ile Ala Lys Asn Thr Lys Asp Tyr Val Leu Asn Leu Glu
Thr Lys Gln Phe Lys Lys Leu Leu Glu Ser Thr Ser Arg Ala Ala Ala
Gly Pro Ser Ile Phe His Pro Gly Gly Val Pro Gly

FIGURE 16IIII

SEQ ID NO: 91 gtgctaacgtttcaccgcatcattcgaaaaggatggatgttcctgctcgcgttttgctcactgc
ctcgctgttctgcccaacaggacagcccgccaaggctgccgcaccgtttaacggcaccatgatgc
agtatttgaatggtacttgccggatgatggcacgttatggaccaaagtggccaatgaagccaac
aacttatccagccttggcatcaccgctctttggctgccgcccgcttataaaggaacaagccgcag
cgacgtagggtacggagtatacgacttgtatgacctcggcgaattcaatcaaaaagggaccgtcc
gcacaaaatacggaacaaaagctcaatatcttcaagccattcaagccgccacgccgctggaatg
caagtgtacgccgatgtcgtgttcgaccataaaggcggcgccgacggcacggaatgggtggacgc
cgtcgaagtcaatccgtccgacgcaaccaagaaatctcgggcacctatcaaatccaagcatgga
cgaaatttgattttcccgggcggggcaacacctactccagctttaagtggcgctggtaccatttt
gacggcgttgattgggacgaaagccgaaaattgagccgcatttacaaattccgcggcatcggcaa
agcgtgggattgggaagtagacacggaaaacggaaactatgactacttaatgtatgccgacttgg
acatggaccatcctgaagtggttacggaactgaaaaactggggcaaatggtatgtcaacacaacg
aacattgatgggttccggcttgatgccgtcaagcatattaagttcagttttttcctgattggtt
gtcgtatgtgcgttctcagactggcaagccgctatttaccgtcggggaatattggagctatgaca
tcaacaagttgcacaattacattacgaaaacaaacggaacgatgtctttgtttgatgccccgtta
cacaacaaattttataccgcttccaaatcagggggcgcatttgatatgcgcacgttaatgaccaa
tactctcatgaaagatcaaccgacattggccgtcaccttcgttgataatcatgacaccgaacccg
gccaagcgctgcagtcatgggtcgacccatggttcaaaccgttggcttacgcctttattctaact
cggcaggaaggatacccgtgcgtcttttatggtgactattatggcatcccacaatataacattcc
ttcgctgaaaagcaaatcgatccgctcctcatcgcgcgcagggattatgcttacggaacgcaac
atgattatcttgatcactccgacatcatcgggtggacaagggaaggcgtcactgaaaaaccagga
tccggactggccgcactgatcaccgatgggccgggaggaagcaaatggatgtacgttggcaaaca
acacgccggaaaagtgttctatgaccttaccggcaaccggagtgacaccgtcaccatcaacagtg
atggatggggagaattcaaagtcaatggcggttcggtttcggtttgggttcctagaaaaacgacc
gtctctaccatcgcttggccgatcacaacccgaccgtggactggtgaattcgtccgttggaccga
accacggttggtggcatggccttga

FIGURE 16JJJJ

SEQ ID NO: 92

Val Leu Thr Phe His Arg Ile Ile Arg Lys Gly Trp Met Phe Leu Leu
Ala Phe Leu Leu Thr Ala Ser Leu Phe Cys Pro Thr Gly Gln Pro Ala
Lys Ala Ala Ala Pro Phe Asn Gly Thr Met Met Gln Tyr Phe Glu Trp
Tyr Leu Pro Asp Asp Gly Thr Leu Trp Thr Lys Val Ala Asn Glu Ala
Asn Asn Leu Ser Ser Leu Gly Ile Thr Ala Leu Trp Leu Pro Pro Ala
Tyr Lys Gly Thr Ser Arg Ser Asp Val Gly Tyr Gly Val Tyr Asp Leu
Tyr Asp Leu Gly Glu Phe Asn Gln Lys Gly Thr Val Arg Thr Lys Tyr
Gly Thr Lys Ala Gln Tyr Leu Gln Ala Ile Gln Ala Ala His Ala Ala
Gly Met Gln Val Tyr Ala Asp Val Val Phe Asp His Lys Gly Gly Ala
Asp Gly Thr Glu Trp Val Asp Ala Val Glu Val Asn Pro Ser Asp Arg
Asn Gln Glu Ile Ser Gly Thr Tyr Gln Ile Gln Ala Trp Thr Lys Phe
Asp Phe Pro Gly Arg Gly Asn Thr Tyr Ser Ser Phe Lys Trp Arg Trp
Tyr His Phe Asp Gly Val Asp Trp Asp Glu Ser Arg Lys Leu Ser Arg
Ile Tyr Lys Phe Arg Gly Ile Gly Lys Ala Trp Asp Trp Glu Val Asp
Thr Glu Asn Gly Asn Tyr Asp Tyr Leu Met Tyr Ala Asp Leu Asp Met
Asp His Pro Glu Val Val Thr Glu Leu Lys Asn Trp Gly Lys Trp Tyr
Val Asn Thr Thr Asn Ile Asp Gly Phe Arg Leu Asp Ala Val Lys His
Ile Lys Phe Ser Phe Phe Pro Asp Trp Leu Ser Tyr Val Arg Ser Gln
Thr Gly Lys Pro Leu Phe Thr Val Gly Glu Tyr Trp Ser Tyr Asp Ile
Asn Lys Leu His Asn Tyr Ile Thr Lys Thr Asn Gly Thr Met Ser Leu
Phe Asp Ala Pro Leu His Asn Lys Phe Tyr Thr Ala Ser Lys Ser Gly
Gly Ala Phe Asp Met Arg Thr Leu Met Thr Asn Thr Leu Met Lys Asp
Gln Pro Thr Leu Ala Val Thr Phe Val Asp Asn His Asp Thr Glu Pro
Gly Gln Ala Leu Gln Ser Trp Val Asp Pro Trp Phe Lys Pro Leu Ala
Tyr Ala Phe Ile Leu Thr Arg Gln Glu Gly Tyr Pro Cys Val Phe Tyr
Gly Asp Tyr Tyr Gly Ile Pro Gln Tyr Asn Ile Pro Ser Leu Lys Ser
Lys Ile Asp Pro Leu Leu Ile Ala Arg Arg Asp Tyr Ala Tyr Gly Thr
Gln His Asp Tyr Leu Asp His Ser Asp Ile Ile Gly Trp Thr Arg Glu
Gly Val Thr Glu Lys Pro Gly Ser Gly Leu Ala Ala Leu Ile Thr Asp
Gly Pro Gly Gly Ser Lys Trp Met Tyr Val Gly Lys Gln His Ala Gly
Lys Val Phe Tyr Asp Leu Thr Gly Asn Arg Ser Asp Thr Val Thr Ile
Asn Ser Asp Gly Trp Gly Glu Phe Lys Val Asn Gly Gly Ser Val Ser
Val Trp Val Pro Arg Lys Thr Thr Val Ser Thr Ile Ala Trp Pro Ile
Thr Thr Arg Pro Trp Thr Gly Glu Phe Val Arg Trp Thr Glu Pro Arg
Leu Val Ala Trp Pro

FIGURE 16KKKK

SEQ ID NO: 93 atgaaatcgtttgcattcatgcctatcctttttatgcaaacgatttcatcagtgaaagggaagg
aggaggaaaaatggggaagaatatgagaagaagattcacgtattttcaatcttcttattgttcg
ttcagctgttttcatttagtgcaaccgctagcgccaatggaacggtgaacagtagtcctgtggtt
aatggaaacgaagtcacgtttctatatggaggaacaggaaacgagcagtctgtgttactggcagg
ctcctttaatgattggcagaaagatggtgacaagaagattgcactaacaaaaggcgacaataacg
tctggtctgtcacgcaaacacttcaagatgggacatatacgtataagtttgttgtagatggtcaa
tgggtggcggatccgcttaacccgaatcaagtagacgacggttacggcggccgtaatagtgtcgt
tgttgtcgggacaccggtgcaacaagaacggacagtgacgcttgttggtaacttacaagacgaat
taggtcatacgagcgaatgggatccgaaagcgacagctacagtgatgaaaaggaagggaacggg
ttatatacgtttacaggtacacttccagccggaacgtacgagtataaaattgcgattaatggcag
ctgggacgaaaactatggtgtcggcggccgcgatggcgggaatattaagctgctattaaatgaac
aaacaacggttacattttattacaacgacagaacgcatgcgattgcggattcgacttggtatgca
ccaattctaaaagaaaagcagccgcggctcgttggaacgatttaccagctattggttatgaaac

FIGURE 16KKKK cont
agacgtgaacggttggacgccgcaaacatcaacggcgttgttgtcagatgatgattttgattcca
tttatacgtttaaggcgcgtgtgccaaaagggacatatgaatataaagtagttcttgggaatgat
tggacatatgaaaattatccacaagataatgccaaattaaatgtgcttgaagaaacgacaattac
ctttttctttaacgcgaaaacgaaagtagtgtataccgattacaatccaagcggttcggatggta
tcgtccaaaaagaccgtttgaagcataatacgtgggattcgttgtatcgccaaccgtttggtgcg
gtgaaagctgggacagaagtgacccttcgtttatcagcgaaaaaggtgatttgacaaaagcgga
tgtatatgtaaaaaatacgacaaccggcacagcgaaactatattcgatgaaaaaagccggtgttc
ttggcgaagaagaatattgggaagcgacattcacaccggatgtgaaaggagtatacggttataaa
tttattgcggtagatgctggaacgaaagcagaatacggggaagatacacaagaagggcagtgggg
aaaagcagtagataaaaatgcagagctgttccaattaacggtgtacgacccatcctaccaaacac
cggattggatgaaagaagcagttgtatatcaaattttccctgatccaaag

FIGURE 16LLLL
SEQ ID NO: 94
Met Lys Ser Phe Ala Phe Met Pro Ile Leu Phe Tyr Ala Asn Asp Phe
Ile Ser Glu Arg Glu Gly Gly Lys Met Gly Lys Asn Met Arg Arg
Arg Phe Thr Tyr Phe Ser Ile Phe Leu Leu Phe Val Gln Leu Phe Ser
Phe Ser Ala Thr Ala Ser Ala Asn Gly Thr Val Asn Ser Ser Pro Val
Val Asn Gly Asn Glu Val Thr Phe Leu Tyr Gly Gly Thr Gly Asn Glu
Gln Ser Val Leu Leu Ala Gly Ser Phe Asn Asp Trp Gln Lys Asp Gly
Asp Lys Lys Ile Ala Leu Thr Lys Gly Asp Asn Asn Val Trp Ser Val
Thr Gln Thr Leu Gln Asp Gly Thr Tyr Thr Tyr Lys Phe Val Val Asp
Gly Gln Trp Val Ala Asp Pro Leu Asn Pro Asn Gln Val Asp Asp Gly
Tyr Gly Gly Arg Asn Ser Val Val Val Val Gly Thr Pro Val Gln Gln
Glu Arg Thr Val Thr Leu Val Gly Asn Leu Gln Asp Glu Leu Gly His
Thr Ser Glu Trp Asp Pro Lys Ala Thr Ala Thr Val Met Lys Lys Glu
Gly Asn Gly Leu Tyr Thr Phe Thr Gly Thr Leu Pro Ala Gly Thr Tyr
Glu Tyr Lys Ile Ala Ile Asn Gly Ser Trp Asp Glu Asn Tyr Gly Val
Gly Gly Arg Asp Gly Gly Asn Ile Lys Leu Leu Leu Asn Glu Gln Thr
Thr Val Thr Phe Tyr Tyr Asn Asp Arg Thr His Ala Ile Ala Asp Ser
Thr Trp Tyr Ala Pro Ile Leu Lys Glu Lys Gln Pro Arg Leu Val Gly
Thr Ile Leu Pro Ala Ile Gly Tyr Glu Thr Asp Val Asn Gly Trp Thr
Pro Gln Thr Ser Thr Ala Leu Leu Ser Asp Asp Asp Phe Asp Ser Ile
Tyr Thr Phe Lys Ala Arg Val Pro Lys Gly Thr Tyr Glu Tyr Lys Val
Val Leu Gly Asn Asp Trp Thr Tyr Glu Asn Tyr Pro Gln Asp Asn Ala
Lys Leu Asn Val Leu Glu Glu Thr Thr Ile Thr Phe Phe Phe Asn Ala
Lys Thr Lys Val Val Tyr Thr Asp Tyr Asn Pro Ser Gly Ser Asp Gly
Ile Val Gln Lys Asp Arg Leu Lys His Asn Thr Trp Asp Ser Leu Tyr
Arg Gln Pro Phe Gly Ala Val Lys Ala Gly Thr Glu Val Thr Leu Arg
Leu Ser Ala Lys Lys Gly Asp Leu Thr Lys Ala Asp Val Tyr Val Lys
Asn Thr Thr Thr Gly Thr Ala Lys Leu Tyr Ser Met Lys Lys Ala Gly
Val Leu Gly Glu Glu Glu Tyr Trp Glu Ala Thr Phe Thr Pro Asp Val
Lys Gly Val Tyr Gly Tyr Lys Phe Ile Ala Val Asp Ala Gly Thr Lys
Ala Glu Tyr Gly Glu Asp Thr Gln Glu Gly Gln Trp Gly Lys Ala Val
Asp Lys Asn Ala Glu Leu Phe Gln Leu Thr Val Tyr Asp Pro Ser Tyr
Gln Thr Pro Asp Trp Met Lys Glu Ala Val Val Tyr Gln Ile Phe Pro
Asp Pro Lys

FIGURE 16MMMM
SEQ ID NO: 95
atgtatacactattcatccgttcatattttgatactgatggtgatggtgtaggagactttagtgg
agttgctgaaaaggtagattatctaaaatctcttggagtagatacagtctggtttttaccattta
ataaaagtaaatcttatcatggatatgatgttgaagattactatgatgtagaaccagattatgga
acactacaagatcttgataatatgataaaagttctaaatgaaatggaataaaggtagtaatgga
tcttgttgttaatcatacgtcggatacacatccatggtttcttgatgcagttgaaaatactacta
attctccatattggaactattacattatgagcttggatgagcctcaaaataagaatcattggcat
tataaggttaattcaaaaggacaaactgtgtggtattttggattgtttgattcatcaatgccgga
ccttaattacgacaaccctaaagtaatggatgaagtgaaaaaaataatagattttttgggcagata
tgggagtagatggatttagattagatgcagcaaaacattattatggatttgactggagcgatgga
attgaacagtcagcaagcgttgcaaaagagatagaagactatataaaagataaactaggggaaaa
tgcaatagttgtgagtgaggtttacgatggagattcaaatgttctttttaaaatttgctccaatgc
ctgtgtttaatttttagttttatgtacaatttgagaggaaattttgaagggagagataacttaatt
tcagactctattagttgggttgattcctcgttgtataatttaaatgtttttcattttccatttat
tgatagtcatgatcttgacagatttatttctgagcttgtagatagtaaatatcaggagatgtaa
tatctgccacaaaacaatatttgctagttaatgctttactactctcattaacaggcatgccaact
atttactatggtgatgaaataggacttaggggatggaagtggcattcagaaccatgggatatacc
tgtgcgtgagccaatgcaatggtataaggatcaaaaagggaacggtcaaacttattggacaaaag
agttttacgaaggtattactgaaggaagtgctaatgaagatggagcaatatacgatgatccagat
gatggagtatctgtagaagaacaagaaatggatattctattttaaactttttaaagaatttat
caacttacgaaaagattatccggcacttgcttttggaagtactacgattgagagagattggaaaa
acttgtatgttttgaaaaagtcgtataacttccaggatgttcttgtattaattaaccttgatcca
acgtattcaaatacatacgaagttccagaagggtataaatgggtgtggtatgcattttttgatgg
tgacaactatgaatttggagcaaaagatgaaatgattttacagaatacaagttggacgataaatc
caaggcaaatttatatatttgtaaagtaa
FIGURE 16NNNN
SEQ ID NO: 96
Met Tyr Thr Leu Phe Ile Arg Ser Tyr Phe Asp Thr Asp Gly Asp Gly
Val Gly Asp Phe Ser Gly Val Ala Glu Lys Val Asp Tyr Leu Lys Ser
Leu Gly Val Asp Thr Val Trp Phe Leu Pro Phe Asn Lys Ser Lys Ser
Tyr His Gly Tyr Asp Val Glu Asp Tyr Tyr Asp Val Glu Pro Asp Tyr
Gly Thr Leu Gln Asp Leu Asp Asn Met Ile Lys Val Leu Asn Glu Asn
Gly Ile Lys Val Val Met Asp Leu Val Val Asn His Thr Ser Asp Thr
His Pro Trp Phe Leu Asp Ala Val Glu Asn Thr Thr Asn Ser Pro Tyr
Trp Asn Tyr Tyr Ile Met Ser Leu Asp Glu Pro Gln Asn Lys Asn His
Trp His Tyr Lys Val Asn Ser Lys Gly Gln Thr Val Trp Tyr Phe Gly
Leu Phe Asp Ser Ser Met Pro Asp Leu Asn Tyr Asp Asn Pro Lys Val
Met Asp Glu Val Lys Lys Ile Ile Asp Phe Trp Ala Asp Met Gly Val
Asp Gly Phe Arg Leu Asp Ala Ala Lys His Tyr Tyr Gly Phe Asp Trp
Ser Asp Gly Ile Glu Gln Ser Ala Ser Val Ala Lys Glu Ile Glu Asp
Tyr Ile Lys Asp Lys Leu Gly Glu Asn Ala Ile Val Val Ser Glu Val
Tyr Asp Gly Asp Ser Asn Val Leu Leu Lys Phe Ala Pro Met Pro Val
Phe Asn Phe Ser Phe Met Tyr Asn Leu Arg Gly Asn Phe Glu Gly Arg
Asp Asn Leu Ile Ser Asp Ser Ile Ser Trp Val Asp Ser Ser Leu Tyr
Asn Leu Asn Val Phe His Phe Pro Phe Ile Asp Ser His Asp Leu Asp
Arg Phe Ile Ser Glu Leu Val Asp Ser Lys Tyr Gln Gly Asp Val Ile
Ser Ala Thr Lys Gln Tyr Leu Leu Val Asn Ala Leu Leu Leu Ser Leu
Thr Gly Met Pro Thr Ile Tyr Tyr Gly Asp Glu Ile Gly Leu Arg Gly
Trp Lys Trp His Ser Glu Pro Trp Asp Ile Pro Val Arg Glu Pro Met
Gln Trp Tyr Lys Asp Gln Lys Gly Asn Gly Gln Thr Tyr Trp Thr Lys
Glu Phe Tyr Glu Gly Ile Thr Glu Gly Ser Ala Asn Glu Asp Gly Ala
Ile Tyr Asp Asp Pro Asp Asp Gly Val Ser Val Glu Glu Gln Glu Asn

FIGURE 16NNNN cont.
```
Gly Tyr Ser Ile Leu Asn Phe Phe Lys Glu Phe Ile Asn Leu Arg Lys
Asp Tyr Pro Ala Leu Ala Phe Gly Ser Thr Thr Ile Glu Arg Asp Trp
Lys Asn Leu Tyr Val Leu Lys Lys Ser Tyr Asn Phe Gln Asp Val Leu
Val Leu Ile Asn Leu Asp Pro Thr Tyr Ser Asn Thr Tyr Glu Val Pro
Glu Gly Tyr Lys Trp Val Trp Tyr Ala Phe Phe Asp Gly Asp Asn Tyr
Glu Phe Gly Ala Lys Asp Glu Met Ile Leu Gln Asn Thr Ser Trp Thr
Ile Asn Pro Arg Gln Ile Tyr Ile Phe Val Lys
```

FIGURE 16OOOO

SEQ ID NO: 97
```
atgaggaagaagatgtcgcattcaagatttacttttcttttgatcttagcacttttattttctt
ctccggttgtatttcagaagttaaaagcgaaagccagctactaaattcaaagcaaaaggtccttg
taaaagtaaatgttaatacgccatttattgagaatgctactactaatacgtggagtgtttcaaaa
gaatctttattgattatcttagtaaagtgattattactgttaaggatgtaaatgatcagattgt
atttactaaggaaacaacgaacaaaacaaatatttattttgaaattgaacttcttcctggaactt
atacatttgaggtaaaaggatatgaggaagatttagttatattttcaggggaaaaagttaatcag
atcatagatgagaaaaataatattgttaatgtcgaaacttttttttgttaatggaatagttaggac
aataattgaagttgacgatattatttataaaaattatgatattcatcggcaacgttgatcttca
aaaaagatacagcacaagaagattatgaagaggtacctgtaacacttacaggtacttccactta
attaataaagaattatatcctggtatgtggactgtaaaatttgaagttgatcttaaatcaagga
tgcaagtatgttaccagaaaaagtcatcttgaaaatgaatttagcatagaagtgcttccagcaa
agacaaaaagtttaacatttaatgtagtctttgatacagaggttaatgaaccgaaattagtagtt
gtatttccgcaaattgagttgccttttgtggatcctgtaacaaatttaagtggagagataaatga
attagaagggaatctttcaatgaattgggactattcagatccaaatgcagaattttatgtgtata
aagaattagaggaacaaggagaatatttgtatgaatttgttggaaaaacacgcgagaaagttat
acaatagaaatttttaccaagcaagaattcgataaatttagtggaatcgctattaatgtttatgc
caacggtaaagagagtggattagttgttctaaaaaaagaaaatattaaacttatagatttagaaa
gtgttgacagtataagtgctacttataacgttgatacgaatgagcttaagttggattggaattat
accaattcaagtgttacttttgaagttttgaaaaaggtataaatagcaatgaatacgaataat
ttctcaactaacacaaaattcttttcaacagaattcacaggcaggcaattttgggatcttgaga
aaattgcgattagagtagttgctaatggatttgaaagtaagattaatgagatttcaagagatgat
ataactataacatcattgaatcttcctcttacatcgtctactatgtatacactattcatccgttc
atattttgatactgatggtgatggtgtaggagactttagtggagttgctgaaaaggtagattatc
taaaatctcttggagtagatacagtctggttttaccattaataaaagtaaatcttatcatgga
tatgatgttgaagattactatgatgtagaaccagattatggaacactacaagatcttgataatat
gataaaagttctaaatgaaaatggaataaaggtagtaatggatcttgttgttaatcatacgtcgg
atacacatccatggtttcttgatgcagttgaaaatactactaattctccatattggaactattac
attatgagcttggatgagcctcaaaataagaatcattggcattataaggttaattcaaaaggaca
aactgtgtggtattttggattgtttgattcatcaatgccggaccttaattacgacaaccctaaag
taatggatgaagtgaaaaaataatagattttttgggcagatatgggagtagatggatttagatta
gatgcagcaaaacattattatggatttgactggagcgatggaattgaacagtcagcaagcgttgc
aaaagagatagaagactatataaaagataaactaggggaaaatgcaatagttgtgagtgaggttt
acgatggagattcaaatgttcttttaaaatttgctccaatgcctgtgtttaattttagttttatg
tacaatttgagaggaaattttgaagggagagataacttaatttcagactctattagttgggttga
ttcctcgttgtataatttaaatgttttcattttccatttattgatagtcatgatcttgacagat
ttatttctgagcttgtagatagtaaatatcagggagatgtaatatctgccacaaaacaatatttg
ctagttaatgctttactactctcattaacaggcatgccaactatttactatggtgatgaaatagg
acttaggggatggaagtggcattcagaaccatgggatatacctgtgcgtgagccaatgcaatggt
ataaggatcaaaagggaacggtcaaacttattggacaaaagagttttacgaaggtattactgaa
ggaagtgctaatgaagatggagcaatatacgatgatccagatgatggagtatctgtagaagaaca
agaaaatggatattctatttaaactttttaagaatttatcaacttacgaaaagattatccgg
cacttgcttttggaagtactacgattgagagagattggaaaaacttgtatgttttgaaaagtcg
tataacttccaggatgttcttgtattaattaaccttgatccaacgtattcaaatacatacgaagt
```

FIGURE 16OOOO cont.
tccagaagggtataaatgggtgtggtatgcattttttgatggtgacaactatgaatttggagcaa
aagatgaaatgattttacagaatacaagttggacgataaatccaaggcaaatttatatatttgta
aagtaa

FIGURE 16PPPP
SEQ ID NO: 98
Met Arg Lys Lys Met Ser His Ser Arg Phe Thr Phe Leu Leu Ile Leu
Ala Leu Phe Ile Phe Phe Ser Gly Cys Ile Ser Glu Val Lys Ser Glu
Ser Gln Leu Leu Asn Ser Lys Gln Lys Val Leu Val Lys Val Asn Val
Asn Thr Pro Phe Ile Glu Asn Ala Thr Thr Asn Thr Trp Ser Val Ser
Lys Glu Ser Phe Ile Asp Tyr Leu Ser Lys Val Ile Ile Thr Val Lys
Asp Val Asn Asp Gln Ile Val Phe Thr Lys Glu Thr Thr Asn Lys Thr
Asn Ile Tyr Phe Glu Ile Glu Leu Leu Pro Gly Thr Tyr Thr Phe Glu
Val Lys Gly Tyr Glu Glu Asp Leu Val Ile Phe Ser Gly Glu Lys Val
Asn Gln Ile Ile Asp Glu Lys Asn Asn Ile Val Asn Val Glu Thr Phe
Phe Val Asn Gly Ile Val Arg Thr Ile Ile Glu Val Asp Asp Ile Ile
Tyr Lys Asn Tyr Asp Ile Thr Ser Ala Thr Leu Ile Phe Lys Lys Asp
Thr Ala Gln Glu Asp Tyr Glu Glu Val Pro Val Thr Leu Thr Gly Thr
Ser Thr Leu Ile Asn Lys Glu Leu Tyr Pro Gly Met Trp Thr Val Lys
Phe Glu Val Asp Leu Lys Ser Lys Asp Ala Ser Met Leu Pro Glu Lys
Val His Leu Glu Asn Glu Phe Ser Ile Glu Val Leu Pro Ala Lys Thr
Lys Ser Leu Thr Phe Asn Val Val Phe Asp Thr Glu Val Asn Glu Pro
Lys Leu Val Val Val Phe Pro Gln Ile Glu Leu Pro Phe Val Asp Pro
Val Thr Asn Leu Ser Gly Glu Ile Asn Glu Leu Glu Gly Asn Leu Ser
Met Asn Trp Asp Tyr Ser Asp Pro Asn Ala Glu Phe Tyr Val Tyr Lys
Glu Leu Glu Glu Gln Gly Glu Tyr Leu Tyr Glu Phe Val Gly Lys Thr
Arg Glu Lys Ser Tyr Thr Ile Glu Asn Phe Thr Lys Gln Glu Phe Asp
Lys Phe Ser Gly Ile Ala Ile Asn Val Tyr Ala Asn Gly Lys Glu Ser
Gly Leu Val Val Leu Lys Lys Glu Asn Ile Lys Leu Ile Asp Leu Glu
Ser Val Asp Ser Ile Ser Ala Thr Tyr Asn Val Asp Thr Asn Glu Leu
Lys Leu Asp Trp Asn Tyr Thr Asn Ser Ser Val Thr Phe Glu Val Leu
Lys Lys Gly Ile Asn Ser Asn Glu Tyr Glu Ile Ile Ser Gln Leu Thr
Gln Asn Ser Phe Ser Thr Glu Phe Thr Gly Arg Gln Phe Trp Asp Leu
Glu Lys Ile Ala Ile Arg Val Val Ala Asn Gly Phe Glu Ser Lys Ile
Asn Glu Ile Ser Arg Asp Asp Ile Thr Ile Thr Ser Leu Asn Leu Pro
Leu Thr Ser Ser Thr Met Tyr Thr Leu Phe Ile Arg Ser Tyr Phe Asp
Thr Asp Gly Asp Gly Val Gly Asp Phe Ser Gly Val Ala Glu Lys Val
Asp Tyr Leu Lys Ser Leu Gly Val Asp Thr Val Trp Phe Leu Pro Phe
Asn Lys Ser Lys Ser Tyr His Gly Tyr Asp Val Glu Asp Tyr Tyr Asp
Val Glu Pro Asp Tyr Gly Thr Leu Gln Asp Leu Asp Asn Met Ile Lys
Val Leu Asn Glu Asn Gly Ile Lys Val Val Met Asp Leu Val Val Asn
His Thr Ser Asp Thr His Pro Trp Phe Leu Asp Ala Val Glu Asn Thr
Thr Asn Ser Pro Tyr Trp Asn Tyr Tyr Ile Met Ser Leu Asp Glu Pro
Gln Asn Lys Asn His Trp His Tyr Lys Val Asn Ser Lys Gly Gln Thr
Val Trp Tyr Phe Gly Leu Phe Asp Ser Ser Met Pro Asp Leu Asn Tyr
Asp Asn Pro Lys Val Met Asp Glu Val Lys Lys Ile Ile Asp Phe Trp
Ala Asp Met Gly Val Asp Gly Phe Arg Leu Asp Ala Ala Lys His Tyr
Tyr Gly Phe Asp Trp Ser Asp Gly Ile Glu Gln Ser Ala Ser Val Ala
Lys Glu Ile Glu Asp Tyr Ile Lys Asp Lys Leu Gly Glu Asn Ala Ile
Val Val Ser Glu Val Tyr Asp Gly Asp Ser Asn Val Leu Leu Lys Phe
Ala Pro Met Pro Val Phe Asn Phe Ser Phe Met Tyr Asn Leu Arg Gly
Asn Phe Glu Gly Arg Asp Asn Leu Ile Ser Asp Ser Ile Ser Trp Val
Asp Ser Ser Leu Tyr Asn Leu Asn Val Phe His Phe Pro Phe Ile Asp

FIGURE 16PPPP cont.
Ser His Asp Leu Asp Arg Phe Ile Ser Glu Leu Val Asp Ser Lys Tyr
Gln Gly Asp Val Ile Ser Ala Thr Lys Gln Tyr Leu Leu Val Asn Ala
Leu Leu Leu Ser Leu Thr Gly Met Pro Thr Ile Tyr Tyr Gly Asp Glu
Ile Gly Leu Arg Gly Trp Lys Trp His Ser Glu Pro Trp Asp Ile Pro
Val Arg Glu Pro Met Gln Trp Tyr Lys Asp Gln Lys Gly Asn Gly Gln
Thr Tyr Trp Thr Lys Glu Phe Tyr Glu Gly Ile Thr Glu Gly Ser Ala
Asn Glu Asp Gly Ala Ile Tyr Asp Asp Pro Asp Asp Gly Val Ser Val
Glu Glu Gln Glu Asn Gly Tyr Ser Ile Leu Asn Phe Phe Lys Glu Phe
Ile Asn Leu Arg Lys Asp Tyr Pro Ala Leu Ala Phe Gly Ser Thr Thr
Ile Glu Arg Asp Trp Lys Asn Leu Tyr Val Leu Lys Lys Ser Tyr Asn
Phe Gln Asp Val Leu Val Leu Ile Asn Leu Asp Pro Thr Tyr Ser Asn
Thr Tyr Glu Val Pro Glu Gly Tyr Lys Trp Val Trp Tyr Ala Phe Phe
Asp Gly Asp Asn Tyr Glu Phe Gly Ala Lys Asp Glu Met Ile Leu Gln
Asn Thr Ser Trp Thr Ile Asn Pro Arg Gln Ile Tyr Ile Phe Val Lys

FIGURE 16QQQQ
SEQ ID NO: 99
atgtacacactcttcatccgctcttttttacgatacaaacaacgacggtgtaggtgactacaacgg
tgttgcccaaaaagtagactatctcaaaacgcttggagtggatacagtttggttcttgccgttca
acaaagcaaaatcgtaccacggttacgatgttgaagactactacgatgtagaacctgactatgga
acatacgcacaacttgaaaatatgataaagacactcaatcagaacggaattcgtgttgttatgga
cttggttgtgaaccacacttccgatacacactcgtggtttctggatgccgttgagaacacaacga
attcgaaatattggagctactacataatgacacttgaaaatagagacggttggaatcactggcat
tggaagataaactcaaaagggcaaaagtttactacttcggactgtttgactcatcaatgcccga
tttgaatttcgacaatccacaagtgatgaacgaaatcaagagaataatcgatttctggataacag
ttggtgtggatggtttcagacttgatgcaccaaagcactacaaaggctgggattgggacgacggc
atttcaggttcagcagcaatcgcgagggaaatagaaagttacatcaggagcaagttaggaaacga
tgcgatagttgtcggggaagtgtacgatggaaatccatcggttctttcacaatttgcaccgatgc
cggcgttcaacttcacattcatgtatggaataacaggcaaccatgaggggaaagataacctgctg
ggagaaacaatttcatggggttaatggagcgagttattatctcaacgtaaaacatttcccgttcat
agacaatcacgatttgaacagatggatatcgatacttatcgaccaaaagtatagtggaaacacac
aagttggtacgaagcagtatatttttaacaaatgcgctcttgctttccttaaacggtatgcctgtt
atttattatgggaatgaaataggcttgagaggatggaaatggggacaagaccgtgggatttgcc
ggtgagagagccgatgcagtggtacgcaagtcaaagtggagctgggcagacatggtggacaaagc
ctgtctaccagcaaaaaggaatcacatttggaaatgcaaacgtcgatggtgcgatgtacgatgat
ccaaatgatggggtttcagtagaagagcagatgaatggttacacgataaataacttctttaaaca
attcataaccctgaggaagacatatccggctctatcgaaaggttcgataacgatagaacgcgact
ggaagaacctgtacgttatcaaacgagtctacggaaatcaggaagtgcttgtattgataaactta
gacccaacttggccgaacaattacacgttaccaggtggatacaggtgggtctggtatgcgttctt
taatgggagtttgtttgaatttggcaataaaaacgaatcaccactgagccaagataccaactgga
cagtcaatccaaggcaagtgtatgtgtttgtgaaggactaa

FIGURE 16RRRR
SEQ ID NO: 100
Met Tyr Thr Leu Phe Ile Arg Ser Phe Tyr Asp Thr Asn Asn Asp Gly
Val Gly Asp Tyr Asn Gly Val Ala Gln Lys Val Asp Tyr Leu Lys Thr
Leu Gly Val Asp Thr Val Trp Phe Leu Pro Phe Asn Lys Ala Lys Ser
Tyr His Gly Tyr Asp Val Glu Asp Tyr Tyr Asp Val Glu Pro Asp Tyr
Gly Thr Tyr Ala Gln Leu Glu Asn Met Ile Lys Thr Leu Asn Gln Asn
Gly Ile Arg Val Val Met Asp Leu Val Val Asn His Thr Ser Asp Thr
His Ser Trp Phe Leu Asp Ala Val Glu Asn Thr Thr Asn Ser Lys Tyr
Trp Ser Tyr Tyr Ile Met Thr Leu Glu Asn Arg Asp Gly Trp Asn His
Trp His Trp Lys Ile Asn Ser Lys Gly Gln Lys Val Tyr Tyr Phe Gly
Leu Phe Asp Ser Ser Met Pro Asp Leu Asn Phe Asp Asn Pro Gln Val

FIGURE 16RRRR cont

Met Asn Glu Ile Lys Arg Ile Ile Asp Phe Trp Ile Thr Val Gly Val
Asp Gly Phe Arg Leu Asp Ala Pro Lys His Tyr Lys Gly Trp Asp Trp
Asp Asp Gly Ile Ser Gly Ser Ala Ala Ile Ala Arg Glu Ile Glu Ser
Tyr Ile Arg Ser Lys Leu Gly Asn Asp Ala Ile Val Val Gly Glu Val
Tyr Asp Gly Asn Pro Ser Val Leu Ser Gln Phe Ala Pro Met Pro Ala
Phe Asn Phe Thr Phe Met Tyr Gly Ile Thr Gly Asn His Glu Gly Lys
Asp Asn Leu Leu Gly Glu Thr Ile Ser Trp Val Asn Gly Ala Ser Tyr
Tyr Leu Asn Val Lys His Phe Pro Phe Ile Asp Asn His Asp Leu Asn
Arg Trp Ile Ser Ile Leu Ile Asp Gln Lys Tyr Ser Gly Asn Thr Gln
Val Gly Thr Lys Gln Tyr Ile Leu Thr Asn Ala Leu Leu Leu Ser Leu
Asn Gly Met Pro Val Ile Tyr Tyr Gly Asn Glu Ile Gly Leu Arg Gly
Trp Lys Trp Gly Gln Asp Pro Trp Asp Leu Pro Val Arg Glu Pro Met
Gln Trp Tyr Ala Ser Gln Ser Gly Ala Gly Gln Thr Trp Trp Thr Lys
Pro Val Tyr Gln Gln Lys Gly Ile Thr Phe Gly Asn Ala Asn Val Asp
Gly Ala Met Tyr Asp Asp Pro Asn Asp Gly Val Ser Val Glu Glu Gln
Met Asn Gly Tyr Thr Ile Asn Asn Phe Phe Lys Gln Phe Ile Thr Leu
Arg Lys Thr Tyr Pro Ala Leu Ser Lys Gly Ser Ile Thr Ile Glu Arg
Asp Trp Lys Asn Leu Tyr Val Ile Lys Arg Val Tyr Gly Asn Gln Glu
Val Leu Val Leu Ile Asn Leu Asp Pro Thr Trp Pro Asn Asn Tyr Thr
Leu Pro Gly Gly Tyr Arg Trp Val Trp Tyr Ala Phe Phe Asn Gly Ser
Leu Phe Glu Phe Gly Asn Lys Asn Glu Ser Pro Leu Ser Gln Asp Thr
Asn Trp Thr Val Asn Pro Arg Gln Val Tyr Val Phe Val Lys Asp

FIGURE 16SSSS

SEQ ID NO: 101 ttgcgattctttccaaagttaatatccccttttccgcaaaacaccagagagtggcagcgaagcgc
agtatcaagagacactgaacaattacaaaggaaagtaataatgatcaatttgaaaaaaaacacca
ttagcgccctggtcgcaggtatggtattaggctttgcatccaacgcaatggcggttcctagaacc
gcttttgtacacctctttgaatggaaatgggaagatgttgcacaggagtgtgaaacatttctcgg
acctaaaggctttgccgcagtgcaagtctctccgccaactaaatctcacaacacggatgcatggt
ggggccgttatcaacccgttagttatgcttttgaaggacgcagcggtaatcgcagccaatttaaa
aatatggtgcaacgttgtaaagctgtaggcgtcgatatatacgtagatgcagtgattaaccacat
ggcagcctacgacagaaatttccctgatgtacctatagcagtaatgactttaactcctgtacag
gagatattgactataataaccgttggcaaacacagcattgtgatttagtcggtcttaatgatcta
aaaacaggatctgactacgtccgccaaaaaatagcggattatatgaacgacgcaatcagtatggg
tgtagctggtttccgtattgatgcagccaaacatataccagcaggtgatatagctgccattaaag
gtaaattaaatggtaatccatacatcttccaagaggtaattggtgcatccggcgaacctgttcga
ccgactgaatacacctttatcggtggtgtcacggaatttcaatttgctcgaaaattgggtccagc
cttccgcaatagtaatattgcttggttaaaagacattggcagtcaaatggaattatccagtgctg
atgccgtaacatttgtaacgaatcatgatgaagagcgtcataacccgaatggtcctatttggcac
ggcgttcaaggtaatggttatgcattagcaaatattttcaccttagcttaccctttacggctatcc
aaaaatcatgtcaggatacttcttccacggtgactttaacgcagctccaccaagcagtggtatac
acacaggaaatgcgtgtggttttgatggcggagactgggtatgcgaacacaaatggcgcggtatt
gctaacatggttgccttccgcaactatacagcaagcgaatggcgtatcagtaattggtggcaaaa
cagtaacgaccaaattgcttttggtcgcggtggtttaggttttgttgttattaataaacgtgcta
atggtagcattaatcaaagttttgatacgggaatgcctgatggccaatactgtaacataatagaa
gctaactttgatgaaagcaccggccaatgtagtgcagctacagattccaacggtcaagccgttat
taccgtcagtggtgggcaagctaactttaatgtagcaggcgatcatgctgctgcaattcatgttg
gcgcaaaaattggtgatcaatgtagtggtgatgattgcccatgtacaggatccgattgtaataat
gatcctaaacctgattttgcagtaccagcaacatcaatttgtacatcagaaaatttacctacgct
atattactggggagcacagcctacagatagcttagcgaatgcagcttggccaggtgtcgcaatgc
aaacaaatggcgactttaagtgtcatgatttaggtgtcgaactaaccaaaattaacgccatcttt
agtgacaatggtgcaaataaaacagctgatctaactgttactggtgcaggttgttataaagacgg

FIGURE 16SSSS cont
gacttggagcaccttacaaaattgtggctttgaaattaccggtgcacaaaccaatccagtcggtg
gcgacgaagtctggtacttccgaggtactgctaatgactggggtaaagcacaattagattatgac
gcaactagcggttttgtattacacaatacaaagctttaatggtgaagaagcacctgcgcgttttaa
aattgataatggtagttggactgaagcttatccaacagctgattaccaagttacagataacaatt
cataccgcattaactttaatagcgatagcaaagcgattacagtaaacgcacaataa

FIGURE 16TTTT
SEQ ID NO: 102
Met Arg Phe Phe Pro Lys Leu Ile Ser Pro Phe Pro Gln Asn Thr Arg
Glu Trp Gln Arg Ser Ala Val Ser Arg Asp Thr Glu Gln Leu Gln Arg
Lys Val Ile Met Ile Asn Leu Lys Lys Asn Thr Ile Ser Ala Leu Val
Ala Gly Met Val Leu Gly Phe Ala Ser Asn Ala Met Ala Val Pro Arg
Thr Ala Phe Val His Leu Phe Glu Trp Lys Trp Glu Asp Val Ala Gln
Glu Cys Glu Thr Phe Leu Gly Pro Lys Gly Phe Ala Ala Val Gln Val
Ser Pro Pro Thr Lys Ser His Asn Thr Asp Ala Trp Trp Gly Arg Tyr
Gln Pro Val Ser Tyr Ala Phe Glu Gly Arg Ser Gly Asn Arg Ser Gln
Phe Lys Asn Met Val Gln Arg Cys Lys Ala Val Gly Val Asp Ile Tyr
Val Asp Ala Val Ile Asn His Met Ala Ala Tyr Asp Arg Asn Phe Pro
Asp Val Pro Tyr Ser Ser Asn Asp Phe Asn Ser Cys Thr Gly Asp Ile
Asp Tyr Asn Asn Arg Trp Gln Thr Gln His Cys Asp Leu Val Gly Leu
Asn Asp Leu Lys Thr Gly Ser Asp Tyr Val Arg Gln Lys Ile Ala Asp
Tyr Met Asn Asp Ala Ile Ser Met Gly Val Ala Gly Phe Arg Ile Asp
Ala Ala Lys His Ile Pro Ala Gly Asp Ile Ala Ala Ile Lys Gly Lys
Leu Asn Gly Asn Pro Tyr Ile Phe Gln Glu Val Ile Gly Ala Ser Gly
Glu Pro Val Arg Pro Thr Glu Tyr Thr Phe Ile Gly Gly Val Thr Glu
Phe Gln Phe Ala Arg Lys Leu Gly Pro Ala Phe Arg Asn Ser Asn Ile
Ala Trp Leu Lys Asp Ile Gly Ser Gln Met Glu Leu Ser Ser Ala Asp
Ala Val Thr Phe Val Thr Asn His Asp Glu Glu Arg His Asn Pro Asn
Gly Pro Ile Trp His Gly Val Gln Gly Asn Gly Tyr Ala Leu Ala Asn
Ile Phe Thr Leu Ala Tyr Pro Tyr Gly Tyr Pro Lys Ile Met Ser Gly
Tyr Phe Phe His Gly Asp Phe Asn Ala Ala Pro Pro Ser Ser Gly Ile
His Thr Gly Asn Ala Cys Gly Phe Asp Gly Gly Asp Trp Val Cys Glu
His Lys Trp Arg Gly Ile Ala Asn Met Val Ala Phe Arg Asn Tyr Thr
Ala Ser Glu Trp Arg Ile Ser Asn Trp Trp Gln Asn Ser Asn Asp Gln
Ile Ala Phe Gly Arg Gly Gly Leu Gly Phe Val Val Ile Asn Lys Arg
Ala Asn Gly Ser Ile Asn Gln Ser Phe Asp Thr Gly Met Pro Asp Gly
Gln Tyr Cys Asn Ile Ile Glu Ala Asn Phe Asp Glu Ser Thr Gly Gln
Cys Ser Ala Ala Thr Asp Ser Asn Gly Gln Ala Val Ile Thr Val Ser
Gly Gly Gln Ala Asn Phe Asn Val Ala Gly Asp His Ala Ala Ala Ile
His Val Gly Ala Lys Ile Gly Asp Gln Cys Ser Gly Asp Asp Cys Pro
Cys Thr Gly Ser Asp Cys Asn Asp Pro Lys Pro Asp Phe Ala Val
Pro Ala Thr Ser Ile Cys Thr Ser Glu Asn Leu Pro Thr Leu Tyr Tyr
Trp Gly Ala Gln Pro Thr Asp Ser Leu Ala Asn Ala Ala Trp Pro Gly
Val Ala Met Gln Thr Asn Gly Asp Phe Lys Cys His Asp Leu Gly Val
Glu Leu Thr Lys Ile Asn Ala Ile Phe Ser Asp Asn Gly Ala Asn Lys
Thr Ala Asp Leu Thr Val Thr Gly Ala Gly Cys Tyr Lys Asp Gly Thr
Trp Ser Thr Leu Gln Asn Cys Gly Phe Glu Ile Thr Gly Ala Gln Thr
Asn Pro Val Gly Gly Asp Glu Val Trp Tyr Phe Arg Gly Thr Ala Asn
Asp Trp Gly Lys Ala Gln Leu Asp Tyr Asp Ala Thr Ser Gly Leu Tyr
Tyr Thr Ile Gln Ser Phe Asn Gly Glu Glu Ala Pro Ala Arg Phe Lys
Ile Asp Asn Gly Ser Trp Thr Glu Ala Tyr Pro Thr Ala Asp Tyr Gln
Val Thr Asp Asn Asn Ser Tyr Arg Ile Asn Phe Asn Ser Asp Ser Lys
Ala Ile Thr Val Asn Ala Gln

FIGURE 16UUUU
SEQ ID NO: 103
gtgctaacgtttcaccgcatcattcgaaaaggatggatgttcctgctcgcgttttttgctcactgc
ctcgctgttctgcccaacaggacagcccgccaaggctgccgcaccgtttaacggcaccatgatgc
agtattttgaatggtacttgccggatgatggcacgttatggaccaaagtggccaatgaagccaac
aacttatccagccttggcatcaccgtctttggctgccgcccgcttacaaaggaacaagccgcag
cgacgtagggtacggagtatacgacttgtatgacctcggcgaattcaatcaaaagggaccgtcc
gcacaaaatacggaacaaaagctcaatatcttcaagccattcaagccgcccacgccgctggaatg
caagtgtacgccgatgtcgtgttcgaccataaaggcggcgccgacggcacggaatgggtggacgc
cgtcgaagtcaatccgtccgaccgcaaccaagaaatctcgggcacctatcaaatccaagcatgga
cgaaatttgattttcccgggcggggcaacacctactccagctttaagtggcgctggtaccatttt
gacggcgttgattgggacgaaagccgaaaattgagccgcatttacaaattccgcggcatcggcaa
agcgtgggattgggaagtagacacggaaaacggaaactatgactacttaatgtatgccgaccttg
atatggatcatcccgaagtcgtgaccgagctgaaaaactgggggggaatggtatgtcaacacaacg
aacattgatgggttccggcttgatgccgtcaagcatattaagttcagttttttttcctgattggtt
gtcgtatgtgcgttctcagactggcaagccgctatttacgtcggggaatattggagctatgaca
tcaacaagttgcacaattacattacgaaaacaaacggaacgatgtctttgtttgatgcccgtta
cacaacaaattttataccgcttccaaatcagggggcgcatttgatatgcgcacgttaatgaccaa
tactctcatgaaagatcaaccgacattggccgtcaccttcgttgataatcatgacaccgaacccg
gccaagcgctgcagtcatgggtcgacccatggttcaaaccgttggcttacgcctttattctaact
cggcaggaaggatacccgtgcgtctttatggtgactattatggcattccacaatataacattcc
ttcgctgaaaagcaaaatcgatccgctcctcatcgcgcgcagggattatgcttacggaacgcaac
atgattatcttgatcactccgacatcatcgggtggacaagggaaggggtcactgaaaaaccagga
tccgggctggccgcactgatcaccgatgggcgggaggagcaaatggatgtacgttggcaaaca
acacgctggaaaagtgttctatgaccttaccggcaaccggagtgacaccgtcaccatcaacagtg
atggatgggggaattcaaagtcaatggcggttcggtttcggtttgggttcctagaaaaacgacc
gtttctaccatcgctcggccgatcacaacccgacgtggactggtgaattcgtccgttggaccga
accacggttggtggcatggccttga
FIGURE 16VVVV
SEQ ID NO: 104
Val Leu Thr Phe His Arg Ile Ile Arg Lys Gly Trp Met Phe Leu Leu
Ala Phe Leu Leu Thr Ala Ser Leu Phe Cys Pro Thr Gly Gln Pro Ala
Lys Ala Ala Ala Pro Phe Asn Gly Thr Met Met Gln Tyr Phe Glu Trp
Tyr Leu Pro Asp Asp Gly Thr Leu Trp Thr Lys Val Ala Asn Glu Ala
Asn Asn Leu Ser Ser Leu Gly Ile Thr Ala Leu Trp Leu Pro Pro Ala
Tyr Lys Gly Thr Ser Arg Ser Asp Val Gly Tyr Gly Val Tyr Asp Leu
Tyr Asp Leu Gly Glu Phe Asn Gln Lys Gly Thr Val Arg Thr Lys Tyr
Gly Thr Lys Ala Gln Tyr Leu Gln Ala Ile Gln Ala Ala His Ala Ala
Gly Met Gln Val Tyr Ala Asp Val Val Phe Asp His Lys Gly Gly Ala
Asp Gly Thr Glu Trp Val Asp Ala Val Glu Val Asn Pro Ser Asp Arg
Asn Gln Glu Ile Ser Gly Thr Tyr Gln Ile Gln Ala Trp Thr Lys Phe
Asp Phe Pro Gly Arg Gly Asn Thr Tyr Ser Ser Phe Lys Trp Arg Trp
Tyr His Phe Asp Gly Val Asp Trp Asp Glu Ser Arg Lys Leu Ser Arg
Ile Tyr Lys Phe Arg Gly Ile Gly Lys Ala Trp Asp Trp Glu Val Asp
Thr Glu Asn Gly Asn Tyr Asp Tyr Leu Met Tyr Ala Asp Leu Asp Met
Asp His Pro Glu Val Val Thr Glu Leu Lys Asn Trp Gly Glu Trp Tyr
Val Asn Thr Thr Asn Ile Asp Gly Phe Arg Leu Asp Ala Val Lys His
Ile Lys Phe Ser Phe Phe Pro Asp Trp Leu Ser Tyr Val Arg Ser Gln
Thr Gly Lys Pro Leu Phe Thr Val Gly Glu Tyr Trp Ser Tyr Asp Ile
Asn Lys Leu His Asn Tyr Ile Thr Lys Thr Asn Gly Thr Met Ser Leu
Phe Asp Ala Pro Leu His Asn Lys Phe Tyr Thr Ala Ser Lys Ser Gly
Gly Ala Phe Asp Met Arg Thr Leu Met Thr Asn Thr Leu Met Lys Asp
Gln Pro Thr Leu Ala Val Thr Phe Val Asp Asn His Asp Thr Glu Pro

FIGURE 16VVVV cont
```
Gly Gln Ala Leu Gln Ser Trp Val Asp Pro Trp Phe Lys Pro Leu Ala
Tyr Ala Phe Ile Leu Thr Arg Gln Glu Gly Tyr Pro Cys Val Phe Tyr
Gly Asp Tyr Tyr Gly Ile Pro Gln Tyr Asn Ile Pro Ser Leu Lys Ser
Lys Ile Asp Pro Leu Leu Ile Ala Arg Arg Asp Tyr Ala Tyr Gly Thr
Gln His Asp Tyr Leu Asp His Ser Asp Ile Ile Gly Trp Thr Arg Glu
Gly Val Thr Glu Lys Pro Gly Ser Gly Leu Ala Ala Leu Ile Thr Asp
Gly Pro Gly Gly Ser Lys Trp Met Tyr Val Gly Lys Gln His Ala Gly
Lys Val Phe Tyr Asp Leu Thr Gly Asn Arg Ser Asp Thr Val Thr Ile
Asn Ser Asp Gly Trp Gly Glu Phe Lys Val Asn Gly Gly Ser Val Ser
Val Trp Val Pro Arg Lys Thr Thr Val Ser Thr Ile Ala Arg Pro Ile
Thr Thr Arg Pro Trp Thr Gly Glu Phe Val Arg Trp Thr Glu Pro Arg
Leu Val Ala Trp Pro
```
FIGURE 16WWWW
SEQ ID NO: 105
```
atgtccctattcaaaaaaatctttccgtggattgtatctctacttcttttgttttcgtttattgc
tccttttttccattcaaacagaaaaagtccgcgctggaagtgttccagtgaatggaacgatgatgc
aatatttcgaatggtaccttccagacgatggaacactatggacgaaagtagcaaataacgcccaa
tctttagcgaatcttggcattactgcccttggcttcccctgcctataaggaacaagcagcag
tgacgttggatatggcgtttatgatttatatgacctaggagagtttaatcaaaaaggaactgtcc
gaacaaaatacggaacaaaaacacaatatatccaagcaatccaagcggcgcatacagcaggaatg
caagtatatgcagatgtcgtctttaaccataaagccggtgcagatgggacagaactagtggatgc
agtagaagtaaacccttctgaccgcaatcaagaaatatcaggaacatatcaaatccaagcgtgga
caaaatttgattttcctggtcgtggaaacacctattctagttttaaatggcgttggtatcatttc
gatggaacggactgggatgagagtagaaaactaaatcgtatttacaaattccgcggcacgggaaa
agcatggattgggaagtagatacagaaaatgggaattatgactatctcatgtatgcagatttgg
atatggatcatccagaggttgtatctgaactaaaaaattggggaaagtggtatgtaaccacaacc
aatatcgacggattccgtctggatgcagtgaagcatattaaatatagcttttttcccagactggct
atcgtatgtacgaacccaaacacaaaagcctctttttgccgttggcgaattttggagctatgaca
ttaacaagctacacaactatattacaaagacgaacggctctatgtccctattcgatgccccgctg
cataacaatttttatatagcatcgaaatcaggtggctattttgatatgcgcacattactcaacaa
cacattgatgaaagatcaaccaacactatcggtcacattagtagacaatcacgatactgagccag
ggcaatctttgcagtcgtgggtcgagccgtggtttaaaccgttagcttacgcatttatcttgacc
cgccaagaaggttatccgtgcatcttttatggagattactatggtattccaaaatacaacattcc
tgcgctgaaaagcaaacttgatccgctgttaattgctcgaagagattatgcctacggaacacagc
acgactatattgacaatgcagatattatcggctggacgcgggaaggagtagctgaaaaagcaaat
tcgggacttgctgcactcattaccgacggacctggcggaagcaaatggatgtatgttggcaaaca
acacgctggcaaaacgttttatgatctaaccggcaatcgaagtgatacagtgacaatcaacgctg
atggatggggagaatttaaagtcaatggagggtctgtatccatatgggttccaaaaacatcaacc
acttcccaaatcacatttactgtaaataatgccacaaccgtttggggacaaaatgtatacgttgt
cgggaatatttcgcagctgggcaac
```

FIGURE 16XXXX
SEQ ID NO: 106

Met Ser Leu Phe Lys Lys Ile Phe Pro Trp Ile Val Ser Leu Leu Leu
Leu Phe Ser Phe Ile Ala Pro Phe Ser Ile Gln Thr Glu Lys Val Arg
Ala Gly Ser Val Pro Val Asn Gly Thr Met Met Gln Tyr Phe Glu Trp
Tyr Leu Pro Asp Asp Gly Thr Leu Trp Thr Lys Val Ala Asn Asn Ala
Gln Ser Leu Ala Asn Leu Gly Ile Thr Ala Leu Trp Leu Pro Pro Ala
Tyr Lys Gly Thr Ser Ser Ser Asp Val Gly Tyr Gly Val Tyr Asp Leu
Tyr Asp Leu Gly Glu Phe Asn Gln Lys Gly Thr Val Arg Thr Lys Tyr
Gly Thr Lys Thr Gln Tyr Ile Gln Ala Ile Gln Ala Ala His Thr Ala
Gly Met Gln Val Tyr Ala Asp Val Val Phe Asn His Lys Ala Gly Ala
Asp Gly Thr Glu Leu Val Asp Ala Val Glu Val Asn Pro Ser Asp Arg
Asn Gln Glu Ile Ser Gly Thr Tyr Gln Ile Gln Ala Trp Thr Lys Phe
Asp Phe Pro Gly Arg Gly Asn Thr Tyr Ser Ser Phe Lys Trp Arg Trp
Tyr His Phe Asp Gly Thr Asp Trp Asp Glu Ser Arg Lys Leu Asn Arg
Ile Tyr Lys Phe Arg Gly Thr Gly Lys Ala Trp Asp Trp Glu Val Asp
Thr Glu Asn Gly Asn Tyr Asp Tyr Leu Met Tyr Ala Asp Leu Asp Met
Asp His Pro Glu Val Val Ser Glu Leu Lys Asn Trp Gly Lys Trp Tyr
Val Thr Thr Thr Asn Ile Asp Gly Phe Arg Leu Asp Ala Val Lys His
Ile Lys Tyr Ser Phe Phe Pro Asp Trp Leu Ser Tyr Val Arg Thr Gln
Thr Gln Lys Pro Leu Phe Ala Val Gly Glu Phe Trp Ser Tyr Asp Ile
Asn Lys Leu His Asn Tyr Ile Thr Lys Thr Asn Gly Ser Met Ser Leu
Phe Asp Ala Pro Leu His Asn Asn Phe Tyr Ile Ala Ser Lys Ser Gly
Gly Tyr Phe Asp Met Arg Thr Leu Leu Asn Asn Thr Leu Met Lys Asp
Gln Pro Thr Leu Ser Val Thr Leu Val Asp Asn His Asp Thr Glu Pro
Gly Gln Ser Leu Gln Ser Trp Val Glu Pro Trp Phe Lys Pro Leu Ala
Tyr Ala Phe Ile Leu Thr Arg Gln Glu Gly Tyr Pro Cys Ile Phe Tyr
Gly Asp Tyr Tyr Gly Ile Pro Lys Tyr Asn Ile Pro Ala Leu Lys Ser
Lys Leu Asp Pro Leu Leu Ile Ala Arg Arg Asp Tyr Ala Tyr Gly Thr
Gln His Asp Tyr Ile Asp Asn Ala Asp Ile Ile Gly Trp Thr Arg Glu
Gly Val Ala Glu Lys Ala Asn Ser Gly Leu Ala Ala Leu Ile Thr Asp
Gly Pro Gly Gly Ser Lys Trp Met Tyr Val Gly Lys Gln His Ala Gly
Lys Thr Phe Tyr Asp Leu Thr Gly Asn Arg Ser Asp Thr Val Thr Ile
Asn Ala Asp Gly Trp Gly Glu Phe Lys Val Asn Gly Gly Ser Val Ser
Ile Trp Val Pro Lys Thr Ser Thr Thr Ser Gln Ile Thr Phe Thr Val
Asn Asn Ala Thr Thr Val Trp Gly Gln Asn Val Tyr Val Val Gly Asn
Ile Ser Gln Leu Gly Asn

FIGURE 16YYYY
SEQ ID NO: 107 atggacagcctcgacgcgccggagcagaagccctgggtgaaggatggcaggctctccgcgtacct
ggatacagggacagggaccgtggtcgctcccgaggcacctgcgccccgccgccccggccgagg
aagtccggcccgtggacaagtggaaaaacgatatcatctatttcgtcctcaccgaccgtttccag
gatggcgacaagaccaacaacatggacgtggtcccgacggacatgaaaaaatatcatggcggcga
catccaggggctcatcgacaagctcgactatatcaaggagaccggttcgacggccatctggctca
cgcccctatgaagggcagacccacttcttcgagaccgacaattaccatggttactggccatt
gacttctatgacacggaccccatgtgggcaccatgcagaaatttgaggagcttatcgagaaagc
ccatgagaaaggctgaagatcgtgctcgatattccctgaaccacacggcctgggagcatcct
tctacaaggacgacagcaagaaggactggttccaccatataggagatgtgaaggactgggaagat
ccctactgggctgaaaacggctccatattcggtcttcctgacctggcgcaggaaaaccctgccgt
ggaaaagtacctcatcgacgtggccaagttctgggtagacaagggtattgacggcttcaggcttg
acgccgtgaagaacgtgcccctcaacttctgggcgaagtttgaccgggcgattcacgattatgcg
ggcaaggacttcctcctcgtcggggaatactttgacggaaacccggcgaaagtcgcgaactacca
gagagaggacatgagctcactcttcgattacccgctctactggaccctgaaggacaccttcgcca

FIGURE 16YYYY cont
aggacgggagcatgcgcaacctggcggcgaagcttgatgagtgcgacaggaattatcccgacccg
ggcctcatgtcggttttccttgataaccacgacacgccgaggttcctcaccgaggccaacggcaa
caaggataagctcaaactggccctcgccttcgcgatgaccatcaaccgcatgcctaccatttatt
atggcaccgaggttgccatggaaggcaactgcgatatcatgggcgccgtagataaccggagggac
atgcagtgggacaaggatcctgacatgttcaaatacttcaagactctcaccactgcccgcaatga
gcatgaatccctcagggaaggaaagaagctcgagatgtggcaggatgacaaagtctacgcgtacg
ggaggcagaccccgaaggacgagtctatcgtggtgcttaacaacggctatgatacgcaggaacgg
gacataccgctccgccccgagagcggcatcaagaacggcacggtgctgaaggatgtcatcaccgg
cgaaaccgtgacggtacagaacggaaaaatccatgcgaaatgcggcggcaaacaggcgcggatct
acgtgcccgcgtag

FIGURE 16ZZZZ
SEQ ID NO: 108
Met Asp Ser Leu Asp Ala Pro Glu Gln Lys Pro Trp Val Lys Asp Gly
Arg Leu Ser Ala Tyr Leu Asp Thr Gly Thr Gly Thr Val Val Ala Pro
Glu Ala Pro Ala Pro Pro Pro Pro Ala Glu Glu Val Arg Pro Val
Asp Lys Trp Lys Asn Asp Ile Ile Tyr Phe Val Leu Thr Asp Arg Phe
Gln Asp Gly Asp Lys Thr Asn Asn Met Asp Val Val Pro Thr Asp Met
Lys Lys Tyr His Gly Gly Asp Ile Gln Gly Leu Ile Asp Lys Leu Asp
Tyr Ile Lys Glu Thr Gly Ser Thr Ala Ile Trp Leu Thr Pro Pro Met
Lys Gly Gln Thr His Phe Phe Glu Thr Asp Asn Tyr His Gly Tyr Trp
Pro Ile Asp Phe Tyr Asp Thr Asp Pro His Val Gly Thr Met Gln Lys
Phe Glu Glu Leu Ile Glu Lys Ala His Glu Lys Gly Leu Lys Ile Val
Leu Asp Ile Pro Leu Asn His Thr Ala Trp Glu His Pro Phe Tyr Lys
Asp Asp Ser Lys Lys Asp Trp Phe His His Ile Gly Asp Val Lys Asp
Trp Glu Asp Pro Tyr Trp Ala Glu Asn Gly Ser Ile Phe Gly Leu Pro
Asp Leu Ala Gln Glu Asn Pro Ala Val Glu Lys Tyr Leu Ile Asp Val
Ala Lys Phe Trp Val Asp Lys Gly Ile Asp Gly Phe Arg Leu Asp Ala
Val Lys Asn Val Pro Leu Asn Phe Trp Ala Lys Phe Asp Arg Ala Ile
His Asp Tyr Ala Gly Lys Asp Phe Leu Leu Val Gly Glu Tyr Phe Asp
Gly Asn Pro Ala Lys Val Ala Asn Tyr Gln Arg Glu Asp Met Ser Ser
Leu Phe Asp Tyr Pro Leu Tyr Trp Thr Leu Lys Asp Thr Phe Ala Lys
Asp Gly Ser Met Arg Asn Leu Ala Ala Lys Leu Asp Glu Cys Asp Arg
Asn Tyr Pro Asp Pro Gly Leu Met Ser Val Phe Leu Asp Asn His Asp
Thr Pro Arg Phe Leu Thr Glu Ala Asn Gly Asn Lys Asp Lys Leu Lys
Leu Ala Leu Ala Phe Ala Met Thr Ile Asn Arg Met Pro Thr Ile Tyr
Tyr Gly Thr Glu Val Ala Met Glu Gly Asn Cys Asp Ile Met Gly Ala
Val Asp Asn Arg Arg Asp Met Gln Trp Asp Lys Asp Pro Asp Met Phe
Lys Tyr Phe Lys Thr Leu Thr Thr Ala Arg Asn Glu His Glu Ser Leu
Arg Glu Gly Lys Lys Leu Glu Met Trp Gln Asp Asp Lys Val Tyr Ala
Tyr Gly Arg Gln Thr Pro Lys Asp Glu Ser Ile Val Val Leu Asn Asn
Gly Tyr Asp Thr Gln Glu Arg Asp Ile Pro Leu Arg Pro Glu Ser Gly
Ile Lys Asn Gly Thr Val Leu Lys Asp Val Ile Thr Gly Glu Thr Val
Thr Val Gln Asn Gly Lys Ile His Ala Lys Cys Gly Gly Lys Gln Ala
Arg Ile Tyr Val Pro Ala

FIGURE 16AAAAA
SEQ ID NO: 109
atggcaagaaaaacgctggccatattttttcgtacttctagtgcttcttagtctctcggcagttcc
ggcaaaggcagaaactctagagaatggtggagttataatgcaggctttctattgggatgttcctg
gaggaggaatctggtgggacacaatagctcaaaagatacccgaatgggcaagtgcaggaatctca
gcgatatggattccaccagcgagtaagggcatgagcggtggttattccatgggctacgatcccta
cgatttctttgacctcggcgagtactatcagaaggggacagttgagacgcgcttcggctcaaagg
aagaactggtgaacatgataaacaccgcacactcctacggcataaaggtgatagcggacatagtc
ataaaccaccgcgccggtggagaccttgagtggaacccttcgtgaacgactatacctggacaga
cttctcaaaagtcgcctccggtaaatatacggccaactaccttgacttccacccaaacgagcttc
actgttgtgatgaaggtacctttggaggatacctgatatatgtcacgacaaaagctgggaccag
tactggctctgggcgagcagcgaaagctacgctgcctacctcaggagcataggggttgacgcctg
gcgtttcgactacgtcaagggctacggagcatggttgttaacgactggctcagctggtggggag
gctggccgttggagagtactgggacacgaacgttgatgcactcctcaactgggcatacagcagc
ggcgccaaggtctttgacttcccgctctactacaagatggacgaagccttcgacaacaccaacat
cccggcattagtggatgcactcagatacggccagacagtggtcagccgcgatcccttcaaggcgg
taactttcgttgccaaccacgatacagatataatctggaacaagtatccggcttatgcattcatc
cttacctatgagggacagcctgttatattctaccgcgactacgaggagtggctcaacaaggataa
gcttaacaacctcatctggatacacgatcaccttgctggagggagtactgacattgtttactacg
acagcgacgagcttatctttgtgagaaacggctatggcaccaaaccaggactgataacctatatc
aacctcggctcaagcaaagttggaaggtgggtctacgttccaaagttcgccggttcatgcatcca
cgagtacaccggcaacctcggcggttggatagacaagtacgtctcctccagcggctgggtctatc
ttgaggccccagcccacgaccggcgaacggctactacggctactctgtctggagctactgcggt
gtgggttga

FIGURE 16BBBBB
SEQ ID NO: 110
Met Ala Arg Lys Thr Leu Ala Ile Phe Phe Val Leu Leu Val Leu Leu
Ser Leu Ser Ala Val Pro Ala Lys Ala Glu Thr Leu Glu Asn Gly Gly
Val Ile Met Gln Ala Phe Tyr Trp Asp Val Pro Gly Gly Gly Ile Trp
Trp Asp Thr Ile Ala Gln Lys Ile Pro Glu Trp Ala Ser Ala Gly Ile
Ser Ala Ile Trp Ile Pro Pro Ala Ser Lys Gly Met Ser Gly Gly Tyr
Ser Met Gly Tyr Asp Pro Tyr Asp Phe Phe Asp Leu Gly Glu Tyr Tyr
Gln Lys Gly Thr Val Glu Thr Arg Phe Gly Ser Lys Glu Glu Leu Val
Asn Met Ile Asn Thr Ala His Ser Tyr Gly Ile Lys Val Ile Ala Asp
Ile Val Ile Asn His Arg Ala Gly Gly Leu Glu Trp Asn Pro Phe
Val Asn Asp Tyr Thr Trp Thr Asp Phe Ser Lys Val Ala Ser Gly Lys
Tyr Thr Ala Asn Tyr Leu Asp Phe His Pro Asn Glu Leu His Cys Cys
Asp Glu Gly Thr Phe Gly Gly Tyr Pro Asp Ile Cys His Asp Lys Ser
Trp Asp Gln Tyr Trp Leu Trp Ala Ser Ser Glu Ser Tyr Ala Ala Tyr
Leu Arg Ser Ile Gly Val Asp Ala Trp Arg Phe Asp Tyr Val Lys Gly
Tyr Gly Ala Trp Val Val Asn Asp Trp Leu Ser Trp Trp Gly Gly Trp
Ala Val Gly Glu Tyr Trp Asp Thr Asn Val Asp Ala Leu Leu Asn Trp
Ala Tyr Ser Ser Gly Ala Lys Val Phe Asp Phe Pro Leu Tyr Tyr Lys
Met Asp Glu Ala Phe Asp Asn Thr Asn Ile Pro Ala Leu Val Asp Ala
Leu Arg Tyr Gly Gln Thr Val Val Ser Arg Asp Pro Phe Lys Ala Val
Thr Phe Val Ala Asn His Asp Thr Asp Ile Ile Trp Asn Lys Tyr Pro
Ala Tyr Ala Phe Ile Leu Thr Tyr Glu Gly Gln Pro Val Ile Phe Tyr
Arg Asp Tyr Glu Glu Trp Leu Asn Lys Asp Lys Leu Asn Asn Leu Ile
Trp Ile His Asp His Leu Ala Gly Gly Ser Thr Asp Ile Val Tyr Tyr
Asp Ser Asp Glu Leu Ile Phe Val Arg Asn Gly Tyr Gly Thr Lys Pro
Gly Leu Ile Thr Tyr Ile Asn Leu Gly Ser Ser Lys Val Gly Arg Trp
Val Tyr Val Pro Lys Phe Ala Gly Ser Cys Ile His Glu Tyr Thr Gly
Asn Leu Gly Gly Trp Ile Asp Lys Tyr Val Ser Ser Ser Gly Trp Val

FIGURE 16BBBBB cont
Tyr Leu Glu Ala Pro Ala His Asp Pro Ala Asn Gly Tyr Tyr Gly Tyr
Ser Val Trp Ser Tyr Cys Gly Val Gly

FIGURE 16CCCCC
SEQ ID NO: 111
atgcccgcgttcaaatctaaggtgatgcacatgaagttgaagtaccttgctttagttttgttggc
tgtggcttcgataggcctcctctcgactccagtgggtgctgccaagtactccgaactcgaagagg
gcggtgttataatgcaggccttctactgggacgtccctaccggtgggatctggtgggacaccata
agacagaaaatcccggagtggtacgacgctggaatctcggcgatatggattcctccagctagcaa
aggtatgggtggtgcatactccatgggttatgaccctacgatttctttgacctcggcgagtact
atcagaagggaacagttgagacgcgcttcggctcaaaggaggaactggtgaacatgataaacacc
gcacactcctatggcataaaggtgatagcggacatagtcataaaccaccgcgccggcggcgacct
ggagtggaacccctttgtaaacaactatacttggacagacttctccaaggtcgcctccggtaaat
acacggccaactaccttgacttccacccaaacgaggtcaagtgctgcgatgagggtacatttggt
gactttccggacatcgcccacgagaagagctggatcagtactggctctgggcaagcaatgagag
ctacgccgcctatctccggagcatagggatcgatgcatggcgtttcgactacgtcaaggttacg
gagcgtggttgttaacgactggctcagctggtggggaggttgggccgttggagagtactggac
accaacgttgatgcactccttaactgggcatacaacagcggtgccaaggtctttgacttcccgct
ctactacaagatggacgaagcctttgacaacaccaacatccccgctttggtttacgccctccaga
acggaggaacagtcgtttccgcgatcccttcaaggcagtaactttcgttgccaaccacgatacc
gatataatctggaacaagtatccggcttatgcgttcatccttacctatgagggacagcctgttat
attctaccgcgactacgaggagtggctcaacaaggataagcttaacaaccttatctggatacacg
agcaccttgccggaggaagtaccaagatcctctactacgataacgatgagctaatattcatgagg
gagggctacgggagcaagccgggcctcataacctacataaacctcggaaacgactgggccgagcg
ctgggtgaacgtcggctcaaagtttgccggctacacaatccatgaatacacaggcaatctcggtg
gctgggttgacaggtgggttcagtacgacggatggttaaactgacggcacctcctcacgatcca
gccaacggatattacggctactcagtctggagctacgcaggcgtcggatga

FIGURE 16DDDDD
SEQ ID NO: 112
Met Pro Ala Phe Lys Ser Lys Val Met His Met Lys Leu Lys Tyr Leu
Ala Leu Val Leu Leu Ala Val Ala Ser Ile Gly Leu Leu Ser Thr Pro
Val Gly Ala Ala Lys Tyr Ser Glu Leu Glu Glu Gly Gly Val Ile Met
Gln Ala Phe Tyr Trp Asp Val Pro Thr Gly Gly Ile Trp Trp Asp Thr
Ile Arg Gln Lys Ile Pro Glu Trp Tyr Asp Ala Gly Ile Ser Ala Ile
Trp Ile Pro Pro Ala Ser Lys Gly Met Gly Gly Ala Tyr Ser Met Gly
Tyr Asp Pro Tyr Asp Phe Phe Asp Leu Gly Glu Tyr Tyr Gln Lys Gly
Thr Val Glu Thr Arg Phe Gly Ser Lys Glu Glu Leu Val Asn Met Ile
Asn Thr Ala His Ser Tyr Gly Ile Lys Val Ile Ala Asp Ile Val Ile
Asn His Arg Ala Gly Gly Asp Leu Glu Trp Asn Pro Phe Val Asn Asn
Tyr Thr Trp Thr Asp Phe Ser Lys Val Ala Ser Gly Lys Tyr Thr Ala
Asn Tyr Leu Asp Phe His Pro Asn Glu Val Lys Cys Cys Asp Glu Gly
Thr Phe Gly Asp Phe Pro Asp Ile Ala His Glu Lys Ser Trp Asp Gln
Tyr Trp Leu Trp Ala Ser Asn Glu Ser Tyr Ala Ala Tyr Leu Arg Ser
Ile Gly Ile Asp Ala Trp Arg Phe Asp Tyr Val Lys Gly Tyr Gly Ala
Trp Val Val Asn Asp Trp Leu Ser Trp Trp Gly Gly Trp Ala Val Gly
Glu Tyr Trp Asp Thr Asn Val Asp Ala Leu Leu Asn Trp Ala Tyr Asn
Ser Gly Ala Lys Val Phe Asp Phe Pro Leu Tyr Tyr Lys Met Asp Glu
Ala Phe Asp Asn Thr Asn Ile Pro Ala Leu Val Tyr Ala Leu Gln Asn
Gly Gly Thr Val Val Ser Arg Asp Pro Phe Lys Ala Val Thr Phe Val
Ala Asn His Asp Thr Asp Ile Ile Trp Asn Lys Tyr Pro Ala Tyr Ala
Phe Ile Leu Thr Tyr Glu Gly Gln Pro Val Ile Phe Tyr Arg Asp Tyr
Glu Glu Trp Leu Asn Lys Asp Lys Leu Asn Asn Leu Ile Trp Ile His
Glu His Leu Ala Gly Gly Ser Thr Lys Ile Leu Tyr Tyr Asp Asn Asp

FIGURE 16DDDDD cont
Glu Leu Ile Phe Met Arg Glu Gly Tyr Gly Ser Lys Pro Gly Leu Ile
Thr Tyr Ile Asn Leu Gly Asn Asp Trp Ala Glu Arg Trp Val Asn Val
Gly Ser Lys Phe Ala Gly Tyr Thr Ile His Glu Tyr Thr Gly Asn Leu
Gly Gly Trp Val Asp Arg Trp Val Gln Tyr Asp Gly Trp Val Lys Leu
Thr Ala Pro Pro His Asp Pro Ala Asn Gly Tyr Tyr Gly Tyr Ser Val
Trp Ser Tyr Ala Gly Val Gly

FIGURE 16EEEEE
SEQ ID NO: 113
atgaaacaacaaaaacggcttttacgcccgattgctgacgctgttatttgcgctcatcttcttgct
gcctcattctgcagcagcggcggcaaatcttaatgggacgctgatgcagtattttgaatggtaca
tgcccaatgacggccaacattggaagcgcttgcaaaacgactcggcatatttggctgaacacggt
attactgccgtctggattccccggcatataagggaacgagccaagcggatgtgggctacggtgc
ttacgacctttatgatttaggggagtttcatcaaaagggacggttcggacaaagtacggcacaa
aaggagagctgcaatctgcgatcaaaagtcttcattcccgcgacattaacgtttacggggatgtg
gtcatcaaccacaaaggcggcgctgatgcgaccgaagatgtaaccgcggttgaagtcgatcccgc
tgaccgcaaccgcgtaatttcaggagaacaccgaattaaagcctggacacattttcattttccgg
ggcgcggcagcacatacagcgattttaaatggcattggtaccattttgacggaaccgattgggac
gagtcccgaaagctgaaccgcatctataagtttcaggaaaggcttgggattgggaagtttccaa
tgaaaacggcaactatgattatttgatgtatgccgacatcgattatgaccatcctgatgtcgcag
cagaaattaagagatggggcacttggtatgccaatgaactgcaattggacggtttccgtcttgat
gctgtcaaacacattaaattttcttttttgcgggattgggttaatcatgtcagggaaaaaacggg
gaaggaaatgtttacggtagctgaatattggcagaatgacttgggcgcgctggaaaactatttga
caaaacaaattttaatcattcagtgtttgacgtgccgcttcattatcagttccatgctgcatcg
acacaggaggcggctatgatatgaggaaattgctgaacggtacggtcgtttccaagcatccgtt
gaaagcggttacatttgtcgataaccatgatacacagccggggcaatcgcttgagtcgactgtcc
aaacatggtttaagccgcttgcttacgctttcattctcacaagggaatctggataccctcaggtt
ttctacggggatatgtacgggacgaaaggagactcccagcgcgaaattcctgccttgaaacacaa
aattgaaccgatcttaaaagcgagaaaacagtatgcgtacggagcacagcatgattatttcgacc
accatgacattgtcggctggacaagggaaggcgacagctcggttgcaaattcaggtttgcggca
ttaataacagacggacccgtggggcaaagcgaatgtatgtcggccggcaaaacgccggtgagac
atggcatgacattaccggaaaccgttcggagccggttgtcatcaattcggaaggctggggagagt
ttcacgtaaacggcggtcggtttcaatttatgttcaaagatag

FIGURE 16FFFFF
SEQ ID NO: 114
Met Lys Gln Gln Lys Arg Leu Tyr Ala Arg Leu Leu Thr Leu Leu Phe
Ala Leu Ile Phe Leu Leu Pro His Ser Ala Ala Ala Ala Ala Asn Leu
Asn Gly Thr Leu Met Gln Tyr Phe Glu Trp Tyr Met Pro Asn Asp Gly
Gln His Trp Lys Arg Leu Gln Asn Asp Ser Ala Tyr Leu Ala Glu His
Gly Ile Thr Ala Val Trp Ile Pro Pro Ala Tyr Lys Gly Thr Ser Gln
Ala Asp Val Gly Tyr Gly Ala Tyr Asp Leu Tyr Asp Leu Gly Glu Phe
His Gln Lys Gly Thr Val Arg Thr Lys Tyr Gly Thr Lys Gly Glu Leu
Gln Ser Ala Ile Lys Ser Leu His Ser Arg Asp Ile Asn Val Tyr Gly
Asp Val Val Ile Asn His Lys Gly Gly Ala Asp Ala Thr Glu Asp Val
Thr Ala Val Glu Val Asp Pro Ala Asp Arg Asn Arg Val Ile Ser Gly
Glu His Arg Ile Lys Ala Trp Thr His Phe His Phe Pro Gly Arg Gly
Ser Thr Tyr Ser Asp Phe Lys Trp His Trp Tyr His Phe Asp Gly Thr
Asp Trp Asp Glu Ser Arg Lys Leu Asn Arg Ile Tyr Lys Phe Gln Gly
Lys Ala Trp Asp Trp Glu Val Ser Asn Glu Asn Gly Asn Tyr Asp Tyr
Leu Met Tyr Ala Asp Ile Asp Tyr Asp His Pro Asp Val Ala Ala Glu
Ile Lys Arg Trp Gly Thr Trp Tyr Ala Asn Glu Leu Gln Leu Asp Gly
Phe Arg Leu Asp Ala Val Lys His Ile Lys Phe Ser Phe Leu Arg Asp
Trp Val Asn His Val Arg Glu Lys Thr Gly Lys Glu Met Phe Thr Val

FIGURE 16FFFFF cont
Ala Glu Tyr Trp Gln Asn Asp Leu Gly Ala Leu Glu Asn Tyr Leu Asn
Lys Thr Asn Phe Asn His Ser Val Phe Asp Val Pro Leu His Tyr Gln
Phe His Ala Ala Ser Thr Gln Gly Gly Gly Tyr Asp Met Arg Lys Leu
Leu Asn Gly Thr Val Val Ser Lys His Pro Leu Lys Ala Val Thr Phe
Val Asp Asn His Asp Thr Gln Pro Gly Gln Ser Leu Glu Ser Thr Val
Gln Thr Trp Phe Lys Pro Leu Ala Tyr Ala Phe Ile Leu Thr Arg Glu
Ser Gly Tyr Pro Gln Val Phe Tyr Gly Asp Met Tyr Gly Thr Lys Gly
Asp Ser Gln Arg Glu Ile Pro Ala Leu Lys His Lys Ile Glu Pro Ile
Leu Lys Ala Arg Lys Gln Tyr Ala Tyr Gly Ala Gln His Asp Tyr Phe
Asp His His Asp Ile Val Gly Trp Thr Arg Glu Gly Asp Ser Ser Val
Ala Asn Ser Gly Leu Ala Ala Leu Ile Thr Asp Gly Pro Gly Gly Ala
Lys Arg Met Tyr Val Gly Arg Gln Asn Ala Gly Glu Thr Trp His Asp
Ile Thr Gly Asn Arg Ser Glu Pro Val Val Ile Asn Ser Glu Gly Trp
Gly Glu Phe His Val Asn Gly Gly Ser Val Ser Ile Tyr Val Gln Arg

FIGURE 16GGGGG
SEQ ID NO: 115
atggcgaagtactccgagctggagcagggcggagtcataatgcaggccttctactgggacgttcc
ggagggaggaatctggtgggacacaatacggcagaagatccctgaatggtacgatgcaggcatat
ccgccatctggataccccggcgagcaagggcatgggcggggcctactcgatgggctacgacccc
tacgattacttcgatctgggcgagttttaccagaagggaaccgttgagcccgcttcggctccaa
ggaagagctcgtcaacatgatctccacggcccaccagtacggcatcaaggttatagcggacatag
tgataaaccaccgcgcaggtggagacctcgaatggaacccatacgtcggcgactatacctggacg
gactttctaaggtcgcctcgggaaatacaaggcccactacatggacttccatccaaacaacta
cagcacctcagacgagggaaccttcggtggcttcccagacattgatcacctcgtgccttcaacc
agtactggctgtgggcgagcaacgagagctacgccgcctacctcaggagcatagggatcgatgcg
tggcgctttgactacgttaagggctacggcgcgtgggtcgtcaaggactggctgagtcagtgggg
cggctgggccgtcggcagtactgggacaccaacgtcgatgcgctcctcaactgggcctacagca
gcggcgccaaggtcttcgacttcccgctctactacaagatggacgaggcctttgacaacaagaac
attcccgccctcgtttacgccatccagaacggtgaaaccgtcgtcagcagggatcccttcaaggc
cgttaccttcgtggctaaccacgatacgaacataatctggaacaagtaccctgcctatgccttca
tcctgacctacgaaggtcagcccgtcatcttctaccgcgactacgaggagtggctcaacaaggac
aaactcaacaacctcatatggattcacgagcacctggcaggggggaagcaccaagatcctctacta
cgacgacgatgagctcatcttcatgagggaaggctacggcgacaggcccgggcttataacctaca
tcaacctcggtagcgactgggcggagagatgggtgaacgttggctcaaagttcgcgggctataca
atccacgaatacaccggaaacctcggcggctgggtcgacaggtacgtccagtacgacggctggt
caagcttaccgctccgccacacgatccggcaaacggctattacggctactcggtctggagctacg
ccggagttggaagatctcatcaccatcaccatcactaa

FIGURE 16HHHHH
SEQ ID NO: 116

Met Ala Lys Tyr Ser Glu Leu Glu Gln Gly Gly Val Ile Met Gln Ala
Phe Tyr Trp Asp Val Pro Glu Gly Gly Ile Trp Trp Asp Thr Ile Arg
Gln Lys Ile Pro Glu Trp Tyr Asp Ala Gly Ile Ser Ala Ile Trp Ile
Pro Pro Ala Ser Lys Gly Met Gly Gly Ala Tyr Ser Met Gly Tyr Asp
Pro Tyr Asp Tyr Phe Asp Leu Gly Glu Phe Tyr Gln Lys Gly Thr Val
Glu Thr Arg Phe Gly Ser Lys Glu Glu Leu Val Asn Met Ile Ser Thr
Ala His Gln Tyr Gly Ile Lys Val Ile Ala Asp Ile Val Ile Asn His
Arg Ala Gly Gly Asp Leu Glu Trp Asn Pro Tyr Val Gly Asp Tyr Thr
Trp Thr Asp Phe Ser Lys Val Ala Ser Gly Lys Tyr Lys Ala His Tyr
Met Asp Phe His Pro Asn Asn Tyr Ser Thr Ser Asp Glu Gly Thr Phe
Gly Gly Phe Pro Asp Ile Asp His Leu Val Pro Phe Asn Gln Tyr Trp
Leu Trp Ala Ser Asn Glu Ser Tyr Ala Ala Tyr Leu Arg Ser Ile Gly
Ile Asp Ala Trp Arg Phe Asp Tyr Val Lys Gly Tyr Gly Ala Trp Val
Val Lys Asp Trp Leu Ser Gln Trp Gly Gly Trp Ala Val Gly Glu Tyr
Trp Asp Thr Asn Val Asp Ala Leu Leu Asn Trp Ala Tyr Ser Ser Gly
Ala Lys Val Phe Asp Phe Pro Leu Tyr Tyr Lys Met Asp Glu Ala Phe
Asp Asn Lys Asn Ile Pro Ala Leu Val Tyr Ala Ile Gln Asn Gly Glu
Thr Val Val Ser Arg Asp Pro Phe Lys Ala Val Thr Phe Val Ala Asn
His Asp Thr Asn Ile Ile Trp Asn Lys Tyr Pro Ala Tyr Ala Phe Ile
Leu Thr Tyr Glu Gly Gln Pro Val Ile Phe Tyr Arg Asp Tyr Glu Glu
Trp Leu Asn Lys Asp Lys Leu Asn Asn Leu Ile Trp Ile His Glu His
Leu Ala Gly Gly Ser Thr Lys Ile Leu Tyr Tyr Asp Asp Asp Glu Leu
Ile Phe Met Arg Glu Gly Tyr Gly Asp Arg Pro Gly Leu Ile Thr Tyr
Ile Asn Leu Gly Ser Asp Trp Ala Glu Arg Trp Val Asn Val Gly Ser
Lys Phe Ala Gly Tyr Thr Ile His Glu Tyr Thr Gly Asn Leu Gly Gly
Trp Val Asp Arg Tyr Val Gln Tyr Asp Gly Trp Val Lys Leu Thr Ala
Pro Pro His Asp Pro Ala Asn Gly Tyr Tyr Gly Tyr Ser Val Trp Ser
Tyr Ala Gly Val Gly Arg Ser His His His His His His

FIGURE 16IIIII
SEQ ID NO: 117 ttgcgagtgttcctggttgtgccaaagctgagccgcccatttcaggcagagtcacaacaacaaga
cagggacataacaatgaaacacacagcgggaatgctggcgatcgcaggtatgctgatcgccccct
tggcgcatgccgatgtcatactgcacgccttcaactggaaatacagtgaagtcaccgccaaggcc
gatctcatcaaggctgccggctacaagcaggtgctcatctcaccgcctctgaagtcctcgggcaa
cgagtggtgggctcgttaccagccccaggatctgcgcctggtcgacacccccttggcaacaagc
aggatctggagcagctgatcgccgcgatgcagacccggggcattgccgtctacgcggacgtggtg
ctcaaccacatggccaacgaaagctggaagcgcagcgacctcaactacccggcagcgagctgct
gcaaagctacgccggcaatccggcctactttgaacgccagaagctctttggcgatctggggcaga
acttcctcgccggccaggattttcatccggagggggtgcatcaccgactggaacaatccgggccat
gtccagtactggcgactgtgcggcggggcgggtgacaagggggctgccggatctggaccccaacaa
ctgggtggtgaaccagcaacaggcttacctgcaggcgctcaaggggatggggatcaagggttttc
gggtcgatgcggtcaagcacatgagcgattaccagatcaacgccgtgttcacccccgagatcaaa
cagggatgcacgtctttggcgaggtgatcaccacggggggcgccggcaacagcgactatgagaa
cttcctcaaaccctacctcgacagcagcggccaggggcctacgacttcccgctcttcgcctccc
tgcgtggagcgctgggctacggcggcagcatgaacctgctggccgatcccggtgcctatggtcag
gcgctgccgggtagccgcgccgtcaccttcgccatcacccacgacatcccaccaacgacggttt
ccgctaccagatcctcaaccagaccgacgagagactggcctatgcctacctgctcggtcgcgatg
gcggttcgcctctggtctactccgatcacggtgaaaccagggacaaggacggattgcgctggcag
gactactatctgcgcaccgatctcaaagggatgatccgcttccataacacagtgcagggtcaacc
gatgcagctcatcggcagtaacgactgcttcgtgctgttcaagcgtggcaagcagggcgtggtcg
gcatcaacaagtgcgactacgagcaggagtactggctcgataccgccagattcgagatgaactgg

FIGURE 16IIIII cont
tatcgcaactaccgggatgtgctcgaccagaatgccgtggtcaacgtgcagagccagtgggtaag
gctgaccatcccggcccgcggcgccagaatgtggctgcaggagtga

FIGURE 16JJJJJ
SEQ ID NO: 118
Met Arg Val Phe Leu Val Val Pro Lys Leu Ser Arg Pro Phe Gln Ala
Glu Ser Gln Gln Gln Asp Arg Asp Ile Thr Met Lys His Thr Ala Gly
Met Leu Ala Ile Ala Gly Met Leu Ile Ala Pro Leu Ala His Ala Asp
Val Ile Leu His Ala Phe Asn Trp Lys Tyr Ser Glu Val Thr Ala Lys
Ala Asp Leu Ile Lys Ala Ala Gly Tyr Lys Gln Val Leu Ile Ser Pro
Pro Leu Lys Ser Ser Gly Asn Glu Trp Trp Ala Arg Tyr Gln Pro Gln
Asp Leu Arg Leu Val Asp Thr Pro Leu Gly Asn Lys Gln Asp Leu Glu
Gln Leu Ile Ala Ala Met Gln Thr Arg Gly Ile Ala Val Tyr Ala Asp
Val Val Leu Asn His Met Ala Asn Glu Ser Trp Lys Arg Ser Asp Leu
Asn Tyr Pro Gly Ser Glu Leu Leu Gln Ser Tyr Ala Gly Asn Pro Ala
Tyr Phe Glu Arg Gln Lys Leu Phe Gly Asp Leu Gly Gln Asn Phe Leu
Ala Gly Gln Asp Phe His Pro Glu Gly Cys Ile Thr Asp Trp Asn Asn
Pro Gly His Val Gln Tyr Trp Arg Leu Cys Gly Gly Ala Gly Asp Lys
Gly Leu Pro Asp Leu Asp Pro Asn Asn Trp Val Val Asn Gln Gln Gln
Ala Tyr Leu Gln Ala Leu Lys Gly Met Gly Ile Lys Gly Phe Arg Val
Asp Ala Val Lys His Met Ser Asp Tyr Gln Ile Asn Ala Val Phe Thr
Pro Glu Ile Lys Gln Gly Met His Val Phe Gly Glu Val Ile Thr Thr
Gly Gly Ala Gly Asn Ser Asp Tyr Glu Asn Phe Leu Lys Pro Tyr Leu
Asp Ser Ser Gly Gln Gly Ala Tyr Asp Phe Pro Leu Phe Ala Ser Leu
Arg Gly Ala Leu Gly Tyr Gly Gly Ser Met Asn Leu Leu Ala Asp Pro
Gly Ala Tyr Gly Gln Ala Leu Pro Gly Ser Arg Ala Val Thr Phe Ala
Ile Thr His Asp Ile Pro Thr Asn Asp Gly Phe Arg Tyr Gln Ile Leu
Asn Gln Thr Asp Glu Arg Leu Ala Tyr Ala Tyr Leu Leu Gly Arg Asp
Gly Gly Ser Pro Leu Val Tyr Ser Asp His Gly Glu Thr Arg Asp Lys
Asp Gly Leu Arg Trp Gln Asp Tyr Tyr Leu Arg Thr Asp Leu Lys Gly
Met Ile Arg Phe His Asn Thr Val Gln Gly Gln Pro Met Gln Leu Ile
Gly Ser Asn Asp Cys Phe Val Leu Phe Lys Arg Gly Lys Gln Gly Val
Val Gly Ile Asn Lys Cys Asp Tyr Glu Gln Glu Tyr Trp Leu Asp Thr
Ala Arg Phe Glu Met Asn Trp Tyr Arg Asn Tyr Arg Asp Val Leu Asp
Gln Asn Ala Val Val Asn Val Gln Ser Gln Trp Val Arg Leu Thr Ile
Pro Ala Arg Gly Ala Arg Met Trp Leu Gln Glu

FIGURE 16KKKKK
SEQ ID NO: 119
atgcaaacgtttgcattcttatttactcaaagaaaggatgggtgtgcatgaattatttgaaaaa
agtgtggttgtattacgctatcgtcgctaccttaatcatttcctttcttacaccttttttcaacag
cacaagctaatactgcacctgttaacggaacaatgatgcaatatttcgaatgggacttacctaat
gatgggacgctttggacgaaagtaaaaaatgaagctaccaatctttcttcactaggtatcacagc
actatggctccctccagcatataaaggaacgagccaaagcgatgtcggatacggtgtttacgatt
tatatgaccttggggaatttaatcaaaaagggacgatccgaacgaaatacggaacaaaaacacaa
tatattcaagccattcaaactgcccaagccgcagggatgcaagtatatgcggatgttgtatttaa
tcataaggcaggggctgacagtacagaatttgtcgatgcagttgaggtaaaccttctaatcgaa
atcaagaaacatctggcacatatcaaattcaagcatggacaaaatttgattttcctggtcgtgga
aacacatactccagcttcaaatggcgctggtaccatttgatggtacggattgggacgaaagtcg
taaattaaatcgtatttacaaattccgcggtacaggaaaagcgtgggactgggaagtcgatacag
aaaacggaaactatgattatttaatgttcgctgatttagatatggatcaccctgaggttgtgaca
gaattaaaaaactggggaacgtggtacgtcaatactacaaatatcgatggattccgcttagatgc
cgtaaaacatattaaatacagcttttccctgactggctaacatatgtacgtaatcaaacaggaa
aaaatttatttgccgttggggaattttggagctatgacgtcaataagctgcataattacattaca
aaaacaaatgggtcgatgtcattatttgatgcaccttgcataacaactttataccgcttccaa
atcgagtggatattttgacatgcgttatttattgaataatacattaatgaaagatcaaccttcac
tcgctgtaacacttgtcgataaccacgacacgcaaccagggcaatctttacagtcatgggtcgaa
ccttggtttaaacagcttgcttacgcctttattttaacaagacaagaagggtatccttgcgtatt
ttacggtgattattatggaatccctaaatacaatatcccgggggttaaaaagtaaaatcgacccgc
ttttaattgctcgtcgtgattacgcttatggaacacaacgtgattacattgatcatcaagacatt
atcggatggacacgagaaggcattgatgcaaaaccgaactctggactggcggctttaattaccga
cggtcctggtggaagtaaatggatgtatgtcggtaaaaagcatgccgggaaagtatttatgatt
taactggaaatcgaagtgacacagtaacgattaatgcggatggttggggagaatttaaagtaaac
ggaggatccgtctcaatttgggtggctaaaacgtcaaacgtcacatttacagtcaataacgccac
aacaacaagcggacaaaacgtatatgttgtcggcaacattccagagctaggcaattgtcgcacgg
gttaa

FIGURE 16LLLLL
SEQ ID NO: 120
Met Gln Thr Phe Ala Phe Leu Phe Tyr Ser Lys Lys Gly Trp Val Cys
Met Asn Tyr Leu Lys Lys Val Trp Leu Tyr Tyr Ala Ile Val Ala Thr
Leu Ile Ile Ser Phe Leu Thr Pro Phe Ser Thr Ala Gln Ala Asn Thr
Ala Pro Val Asn Gly Thr Met Met Gln Tyr Phe Glu Trp Asp Leu Pro
Asn Asp Gly Thr Leu Trp Thr Lys Val Lys Asn Glu Ala Thr Asn Leu
Ser Ser Leu Gly Ile Thr Ala Leu Trp Leu Pro Pro Ala Tyr Lys Gly
Thr Ser Gln Ser Asp Val Gly Tyr Gly Val Tyr Asp Leu Tyr Asp Leu
Gly Glu Phe Asn Gln Lys Gly Thr Ile Arg Thr Lys Tyr Gly Thr Lys
Thr Gln Tyr Ile Gln Ala Ile Gln Thr Ala Gln Ala Ala Gly Met Gln
Val Tyr Ala Asp Val Val Phe Asn His Lys Ala Gly Ala Asp Ser Thr
Glu Phe Val Asp Ala Val Glu Val Asn Pro Ser Asn Arg Asn Gln Glu
Thr Ser Gly Thr Tyr Gln Ile Gln Ala Trp Thr Lys Phe Asp Phe Pro
Gly Arg Gly Asn Thr Tyr Ser Ser Phe Lys Trp Arg Trp Tyr His Phe
Asp Gly Thr Asp Trp Asp Glu Ser Arg Lys Leu Asn Arg Ile Tyr Lys
Phe Arg Gly Thr Gly Lys Ala Trp Asp Trp Glu Val Asp Thr Glu Asn
Gly Asn Tyr Asp Tyr Leu Met Phe Ala Asp Leu Asp Met Asp His Pro
Glu Val Val Thr Glu Leu Lys Asn Trp Gly Thr Trp Tyr Val Asn Thr
Thr Asn Ile Asp Gly Phe Arg Leu Asp Ala Val Lys His Ile Lys Tyr
Ser Phe Phe Pro Asp Trp Leu Thr Tyr Val Arg Asn Gln Thr Gly Lys
Asn Leu Phe Ala Val Gly Glu Phe Trp Ser Tyr Asp Val Asn Lys Leu
His Asn Tyr Ile Thr Lys Thr Asn Gly Ser Met Ser Leu Phe Asp Ala
Pro Leu His Asn Asn Phe Tyr Thr Ala Ser Lys Ser Ser Gly Tyr Phe

FIGURE 16LLLLL cont
Asp Met Arg Tyr Leu Leu Asn Asn Thr Leu Met Lys Asp Gln Pro Ser
Leu Ala Val Thr Leu Val Asp Asn His Asp Thr Gln Pro Gly Gln Ser
Leu Gln Ser Trp Val Glu Pro Trp Phe Lys Gln Leu Ala Tyr Ala Phe
Ile Leu Thr Arg Gln Glu Gly Tyr Pro Cys Val Phe Tyr Gly Asp Tyr
Tyr Gly Ile Pro Lys Tyr Asn Ile Pro Gly Leu Lys Ser Lys Ile Asp
Pro Leu Leu Ile Ala Arg Arg Asp Tyr Ala Tyr Gly Thr Gln Arg Asp
Tyr Ile Asp His Gln Asp Ile Ile Gly Trp Thr Arg Glu Gly Ile Asp
Ala Lys Pro Asn Ser Gly Leu Ala Ala Leu Ile Thr Asp Gly Pro Gly
Gly Ser Lys Trp Met Tyr Val Gly Lys Lys His Ala Gly Lys Val Phe
Tyr Asp Leu Thr Gly Asn Arg Ser Asp Thr Val Thr Ile Asn Ala Asp
Gly Trp Gly Glu Phe Lys Val Asn Gly Gly Ser Val Ser Ile Trp Val
Ala Lys Thr Ser Asn Val Thr Phe Thr Val Asn Asn Ala Thr Thr Thr
Ser Gly Gln Asn Val Tyr Val Val Gly Asn Ile Pro Glu Leu Gly Asn
Cys Arg Thr Gly

FIGURE 16MMMMM
SEQ ID NO: 121
atgctcgccctgtcgctcggcggctgcggcatcgacgcgggcccgacaggccctcgcgtcgtgga
gccgctgccgcagcgccccacgcttccgcaggagtaccgcgccagcggccacgcggccgccggcg
acgtgttcgtgcacctgttcgagtggaagtggccggacatcgcggaggaatgcgagaacgtgctg
gggccggcgggctacgaggcggtgcaggtgtcgccgccgcaggagcacctggtgcagcagggggc
gccgtggtggcagcggtaccagccggtgagctactcggtggcgctgagccgcagcggcacggggcg
tggagttcagcaacatgatcagccggtgcaaggccgccggcgtggacatctacgtggacgccgtc
atcaaccacatgacggccggtgcggggacggggagcaacggcaccgcctacaccaagtacaacta
ccccggcctgtacgcgcaggcggactttcacccgcagtgcgcggtgggcgactacaccagcgccg
ccaacgtgcaggactgcgaactgctggggctggctgacctgaacaccggcgcggccggcgtgcag
cagaagatcgcggactacctggtctcgctggcgcggctgggcgtggcgggttttcgcatcgacgc
cgccaagcacatccagccggtggaactggacgccatcgtggaccgcgtgaaccagacgctggcgg
cggaggggcgcccgcttccctactggttcgccgaggtgatcgacaacggcggcgagggggtgcgg
cgcgagcactactacggcctgggatacggcaccggcggcgccgcggacatcacggagttccgcta
caagggcgtgggcgacaagttcctgggcagcggcggccagcggctggtggacctgaagaacttct
cggcggtgacgtggaacctgatgccgtcggacaaggccgtcgtctttctggagaaccacgatacg
cagcgcggcggcggcatcggctaccgcgatggcacggcgttccggctggccaacgtgtggatgct
ggcgcagccgtacggctatccgtcggtgatgtccagctacgcctttgaccgcacctcccccttg
gccgcgacgccggcccgccctccgaggacggcgcgacgaaggacgtgacgtgcgcgccacgctg
gagacggcggtgctgggcacctgggtgtgcgagcaccgcgaccccgtcattcagcggatggtggg
ctttcgccgcgcgatggcgggcacggacctgaaccgctggtgggacaacggcggcaacgccattg
ccttttcgcgcggggaccggggcttcgtcgccatcagccgcgagccgaaggtgaccatggcggcc
gtgccagcggactgtccccggcacctactgcgacgtgctgaccggcggcaaggtgggcaacgc
ctgcgcgggaaccagcgtgacggtcgactctcagggcgtggtgcagctgagcatcgtcgagaact
cggctctggtgatccacctcggggccaagctgtaacggcgcgctggcggatgtgcggaggg

FIGURE 16NNNNN
SEQ ID NO: 122

Met Leu Ala Leu Ser Leu Gly Gly Cys Gly Ile Asp Ala Gly Pro Thr
Gly Pro Arg Val Val Glu Pro Leu Pro Gln Arg Pro Thr Leu Pro Gln
Glu Tyr Arg Ala Ser Gly His Ala Ala Ala Gly Asp Val Phe Val His
Leu Phe Glu Trp Lys Trp Pro Asp Ile Ala Glu Glu Cys Glu Asn Val
Leu Gly Pro Ala Gly Tyr Glu Ala Val Gln Val Ser Pro Pro Gln Glu
His Leu Val Gln Gln Gly Ala Pro Trp Trp Gln Arg Tyr Gln Pro Val
Ser Tyr Ser Val Ala Leu Ser Arg Ser Gly Thr Gly Val Glu Phe Ser
Asn Met Ile Ser Arg Cys Lys Ala Ala Gly Val Asp Ile Tyr Val Asp
Ala Val Ile Asn His Met Thr Ala Gly Ala Gly Thr Gly Ser Asn Gly
Thr Ala Tyr Thr Lys Tyr Asn Tyr Pro Gly Leu Tyr Ala Gln Ala Asp
Phe His Pro Gln Cys Ala Val Gly Asp Tyr Thr Ser Ala Ala Asn Val
Gln Asp Cys Glu Leu Leu Gly Leu Ala Asp Leu Asn Thr Gly Ala Ala
Gly Val Gln Gln Lys Ile Ala Asp Tyr Leu Val Ser Leu Ala Arg Leu
Gly Val Ala Gly Phe Arg Ile Asp Ala Ala Lys His Ile Gln Pro Val
Glu Leu Asp Ala Ile Val Asp Arg Val Asn Gln Thr Leu Ala Ala Glu
Gly Arg Pro Leu Pro Tyr Trp Phe Ala Glu Val Ile Asp Asn Gly Gly
Glu Gly Val Arg Arg Glu His Tyr Tyr Gly Leu Gly Tyr Gly Thr Gly
Gly Ala Ala Asp Ile Thr Glu Phe Arg Tyr Lys Gly Val Gly Asp Lys
Phe Leu Gly Ser Gly Gly Gln Arg Leu Val Asp Leu Lys Asn Phe Ser
Ala Val Thr Trp Asn Leu Met Pro Ser Asp Lys Ala Val Val Phe Leu
Glu Asn His Asp Thr Gln Arg Gly Gly Gly Ile Gly Tyr Arg Asp Gly
Thr Ala Phe Arg Leu Ala Asn Val Trp Met Leu Ala Gln Pro Tyr Gly
Tyr Pro Ser Val Met Ser Ser Tyr Ala Phe Asp Arg Thr Ser Pro Phe
Gly Arg Asp Ala Gly Pro Pro Ser Glu Asp Gly Ala Thr Lys Asp Val
Thr Cys Ala Pro Thr Leu Glu Thr Ala Val Leu Gly Thr Trp Val Cys
Glu His Arg Asp Pro Val Ile Gln Arg Met Val Gly Phe Arg Arg Ala
Met Ala Gly Thr Asp Leu Asn Arg Trp Trp Asp Asn Gly Gly Asn Ala
Ile Ala Phe Ser Arg Gly Asp Arg Gly Phe Val Ala Ile Ser Arg Glu
Pro Lys Val Thr Met Ala Ala Val Pro Ser Gly Leu Ser Pro Gly Thr
Tyr Cys Asp Val Leu Thr Gly Gly Lys Val Gly Asn Ala Cys Ala Gly
Thr Ser Val Thr Val Asp Ser Gln Gly Val Val Gln Leu Ser Ile Val
Glu Asn Ser Ala Leu Val Ile His Leu Gly Ala Lys Leu Arg Arg Ala
Gly Gly Cys Ala Glu

FIGURE 16OOOOO
SEQ ID NO: 123 atgccccaggccattcgcacttttttcacgttggacgttgttcggcttaatcggcgttttttctgct
tggtctcgtcttttctgtcccaccccgggcaatccaggcccagacaacccgggcccgtaccgtta
tggttcacctcttcgagtggaaatggaccgacatcgctaaagaatgcgagaatttcctcggaccg
aaaggctttgccgcaatccaggtatcgccgccccaggagcatgtccagggtcgcaatggtggac
ccgctatcagccggtcagctacaagatcgagagccgctccggcaccgggccgagttcgccaata
tggtctcgcgctgcaaagccgtcggggtcgatatctatgtcgatgccgtgatcaaccatatgacg
actgtcggctccggcactggtatggctggatcgacctacaccagctacacctatccgggctgta
tcagacccaggacttccaccactgcgggcgcaatggcaacgatgatatcagcagctacggcgatc
gctgggaagtacaaaactgcgaactgctcaacctagccgacctcaacaccggcgctgagtatgtc
cggggtaaactcgccgcctatatgaacgatctgcgcggcctgggcgtcgccggatttcggatcga
tgccgccaagcacatggataccaacgacatcaacaatatcgttggccgcctgcccaacgcgcct
acatctaccaggaagtgatcgaccagggcggcgagccaattaccgccggcgaatacttccagaat
ggcgatgtgaccgagttcaagtacagccgcgagatctcgcgcatgttcaaaaccggccagctgac
ccatatgagccagttcggcactgcctggggcttcatgtccagcgacctggcagtagttttcaccg
ataaccacgacaaccagcgcggtcacggcggcgccggcgatgtcttgacctacaaagatggccag
ctgtacaccctgggcaatatcttcgagctagcctggccgtatggctacccacaggtcatgtcgag

FIGURE 16OOOOO cont
ctacacgttcagcaacggcgaccaggggccgccatcgaccaatgtgtacgcaaccacaacgcctg
attgtggcaacggccgctgggtctgtgagcaccgctggcgaggaatcgccaacatggtcgcgttc
cgcaactacaccgccccgaccttcagcaccagcaactggtggagcaacggcaacaaccagatcgc
tttcagccgcgggaccctgggctttgtggcgatcaatcgggaaggtggcagcctgaaccgcacct
tccaaaccggcctgcccgtcggcacctactgcgatgtcattcacggcgatttcaatgccagcgcc
ggcacctgttccggcccaactatcgctgtcaacggctccggacaggcaaccatcacggtcaacgc
gatggacgcggtggcgatctacggcggagccaggctcgccactccggccagtgtcaacgtgacat
tcaacgaaaacgccacgaccacctgggggcagaatgtgtatatcgtcggcaacgtcgccgccctg
ggcagctggaacgcaggcagcgcggtcttactctcctccgctaactacccaatctggagcaagac
catcgccctgccagccaacaccgccattgagtacaagtacatcaaaaaggatggcgcgggcaatg
tggtgtgggaaagcggcgccaaccgcgtctttaccaccccggcagcggcagtgccacgcgcaac
gatacctggaaatag

FIGURE 16PPPPP
SEQ ID NO: 124
Met Pro Gln Ala Ile Arg Thr Phe Ser Arg Trp Thr Leu Phe Gly Leu
Ile Gly Val Phe Leu Leu Gly Leu Val Phe Ser Val Pro Pro Arg Ala
Ile Gln Ala Gln Thr Thr Pro Ala Arg Thr Val Met Val His Leu Phe
Glu Trp Lys Trp Thr Asp Ile Ala Lys Glu Cys Glu Asn Phe Leu Gly
Pro Lys Gly Phe Ala Ala Ile Gln Val Ser Pro Pro Gln Glu His Val
Gln Gly Ser Gln Trp Trp Thr Arg Tyr Gln Pro Val Ser Tyr Lys Ile
Glu Ser Arg Ser Gly Thr Arg Ala Glu Phe Ala Asn Met Val Ser Arg
Cys Lys Ala Val Gly Val Asp Ile Tyr Val Asp Ala Val Ile Asn His
Met Thr Thr Val Gly Ser Gly Thr Gly Met Ala Gly Ser Thr Tyr Thr
Ser Tyr Thr Tyr Pro Gly Leu Tyr Gln Thr Gln Asp Phe His His Cys
Gly Arg Asn Gly Asn Asp Asp Ile Ser Ser Tyr Gly Asp Arg Trp Glu
Val Gln Asn Cys Glu Leu Leu Asn Leu Ala Asp Leu Asn Thr Gly Ala
Glu Tyr Val Arg Gly Lys Leu Ala Ala Tyr Met Asn Asp Leu Arg Gly
Leu Gly Val Ala Gly Phe Arg Ile Asp Ala Ala Lys His Met Asp Thr
Asn Asp Ile Asn Asn Ile Val Gly Arg Leu Pro Asn Ala Pro Tyr Ile
Tyr Gln Glu Val Ile Asp Gln Gly Gly Glu Pro Ile Thr Ala Gly Glu
Tyr Phe Gln Asn Gly Asp Val Thr Glu Phe Lys Tyr Ser Arg Glu Ile
Ser Arg Met Phe Lys Thr Gly Gln Leu Thr His Met Ser Gln Phe Gly
Thr Ala Trp Gly Phe Met Ser Ser Asp Leu Ala Val Val Phe Thr Asp
Asn His Asp Asn Gln Arg Gly His Gly Gly Ala Gly Asp Val Leu Thr
Tyr Lys Asp Gly Gln Leu Tyr Thr Leu Gly Asn Ile Phe Glu Leu Ala
Trp Pro Tyr Gly Tyr Pro Gln Val Met Ser Ser Tyr Thr Phe Ser Asn
Gly Asp Gln Gly Pro Pro Ser Thr Asn Val Tyr Ala Thr Thr Thr Pro
Asp Cys Gly Asn Gly Arg Trp Val Cys Glu His Arg Trp Arg Gly Ile
Ala Asn Met Val Ala Phe Arg Asn Tyr Thr Ala Pro Thr Phe Ser Thr
Ser Asn Trp Trp Ser Asn Gly Asn Asn Gln Ile Ala Phe Ser Arg Gly
Thr Leu Gly Phe Val Ala Ile Asn Arg Glu Gly Gly Ser Leu Asn Arg
Thr Phe Gln Thr Gly Leu Pro Val Gly Thr Tyr Cys Asp Val Ile His
Gly Asp Phe Asn Ala Ser Ala Gly Thr Cys Ser Gly Pro Thr Ile Ala
Val Asn Gly Ser Gly Gln Ala Thr Ile Thr Val Asn Ala Met Asp Ala
Val Ala Ile Tyr Gly Gly Ala Arg Leu Ala Thr Pro Ala Ser Val Asn
Val Thr Phe Asn Glu Asn Ala Thr Thr Thr Trp Gly Gln Asn Val Tyr
Ile Val Gly Asn Val Ala Ala Leu Gly Ser Trp Asn Ala Gly Ser Ala
Val Leu Leu Ser Ser Ala Asn Tyr Pro Ile Trp Ser Lys Thr Ile Ala
Leu Pro Ala Asn Thr Ala Ile Glu Tyr Lys Tyr Ile Lys Lys Asp Gly
Ala Gly Asn Val Val Trp Glu Ser Gly Ala Asn Arg Val Phe Thr Thr
Pro Gly Ser Gly Ser Ala Thr Arg Asn Asp Thr Trp Lys

FIGURE 16QQQQQ
SEQ ID NO: 125
gtggtgcacatgaagttgaagtaccttgccttagttttgttggctgtggcttcgataggcctact
ctcgactccagtgggtgctgccaagtactccgaactcgaagagggcggtgttataatgcaggcct
tctactgggatgttcccggaggggggaatctggtgggacaccataagacagaaaatcccggagtgg
tacgacgctggaatctcggcgatatggattcctccagctagcaaagggatgggcggtggttattc
catgggctacgatccctacgatttctttgacctcggcgagtactatcagaagggaacagttgaga
cgcgcttcggctcaaaggaggaactggtgaacatgataaacaccgcacactcctatggcataaag
gtgatagcggacatagtcataaaccaccgcgccggtggagaccttgagtggaaccccttgtaaa
caactatacttggacagacttctccaaggtcgcctccggtaaatacacggccaactaccttgact
tccacccaaacgaggtcaagtgctgcgatgagggtacatttggtgactttccggacatcgcccac
gagaagagctgggatcagtactggctctgggcaagcaatgagagctacgccgcatatctccggag
catagggatcgatgcatggcgtttcgactacgtcaaaggttacggagcgtgggttgttaatgact
ggctcagctggtggggaggctggccgttggagagtactgggacacgaacgttgatgcactcctt
aactgggcatacgacagcggtgccaaggtctttgacttcccgctctactacaagatggacgaagc
ctttgacaacaccaacatccccgctttggtttacgccctccagaacggaggaacagtcgtttccc
gcgatcccttcaaggcagtaactttcgttgccaaccacgatacagatataatctggaacaagtat
ccggcttatgcgttcatccttacctatgagggacagcctgttatattttaccgcgactacgagga
gtggctcaacaaggataagcttaacaaccttatctggatacacgagcaccttgccggaggaagta
ccaagatcctctactacgataacgatgagctaatattcatgagggagggctacgggagcaagccg
ggcctcataacctacataaacctcggaaacgactgggccgagcgctgggtgaacgtcggctcaaa
gtttgccggctacacaatccatgaatacacaggcaatctcggtggctgggttgacaggtgggttc
agtacgatggatgggttaaactgacggcacctcctcatgatccagccaacggatattacggctac
tcagtctggagctacgcaggcgtcggatga
FIGURE 16RRRRR
SEQ ID NO: 126
Val Val His Met Lys Leu Lys Tyr Leu Ala Leu Val Leu Leu Ala Val
Ala Ser Ile Gly Leu Leu Ser Thr Pro Val Gly Ala Ala Lys Tyr Ser
Glu Leu Glu Glu Gly Gly Val Ile Met Gln Ala Phe Tyr Trp Asp Val
Pro Gly Gly Gly Ile Trp Trp Asp Thr Ile Arg Gln Lys Ile Pro Glu
Trp Tyr Asp Ala Gly Ile Ser Ala Ile Trp Ile Pro Pro Ala Ser Lys
Gly Met Gly Gly Gly Tyr Ser Met Gly Tyr Asp Pro Tyr Asp Phe Phe
Asp Leu Gly Glu Tyr Tyr Gln Lys Gly Thr Val Glu Thr Arg Phe Gly
Ser Lys Glu Glu Leu Val Asn Met Ile Asn Thr Ala His Ser Tyr Gly
Ile Lys Val Ile Ala Asp Ile Val Ile Asn His Arg Ala Gly Gly Asp
Leu Glu Trp Asn Pro Phe Val Asn Asn Tyr Thr Trp Thr Asp Phe Ser
Lys Val Ala Ser Gly Lys Tyr Thr Ala Asn Tyr Leu Asp Phe His Pro
Asn Glu Val Lys Cys Cys Asp Glu Gly Thr Phe Gly Asp Phe Pro Asp
Ile Ala His Glu Lys Ser Trp Asp Gln Tyr Trp Leu Trp Ala Ser Asn
Glu Ser Tyr Ala Ala Tyr Leu Arg Ser Ile Gly Ile Asp Ala Trp Arg
Phe Asp Tyr Val Lys Gly Tyr Gly Ala Trp Val Val Asn Asp Trp Leu
Ser Trp Trp Gly Gly Trp Ala Val Gly Glu Tyr Trp Asp Thr Asn Val
Asp Ala Leu Leu Asn Trp Ala Tyr Asp Ser Gly Ala Lys Val Phe Asp
Phe Pro Leu Tyr Tyr Lys Met Asp Glu Ala Phe Asp Asn Thr Asn Ile
Pro Ala Leu Val Tyr Ala Leu Gln Asn Gly Gly Thr Val Val Ser Arg
Asp Pro Phe Lys Ala Val Thr Phe Val Ala Asn His Asp Thr Asp Ile
Ile Trp Asn Lys Tyr Pro Ala Tyr Ala Phe Ile Leu Thr Tyr Glu Gly
Gln Pro Val Ile Phe Tyr Arg Asp Tyr Glu Glu Trp Leu Asn Lys Asp
Lys Leu Asn Asn Leu Ile Trp Ile His Glu His Leu Ala Gly Gly Ser
Thr Lys Ile Leu Tyr Tyr Asp Asn Asp Glu Leu Ile Phe Met Arg Glu
Gly Tyr Gly Ser Lys Pro Gly Leu Ile Thr Tyr Ile Asn Leu Gly Asn
Asp Trp Ala Glu Arg Trp Val Asn Val Gly Ser Lys Phe Ala Gly Tyr
Thr Ile His Glu Tyr Thr Gly Asn Leu Gly Gly Trp Val Asp Arg Trp

FIGURE 16RRRRR cont
Val Gln Tyr Asp Gly Trp Val Lys Leu Thr Ala Pro Pro His Asp Pro
Ala Asn Gly Tyr Tyr Gly Tyr Ser Val Trp Ser Tyr Ala Gly Val Gly

FIGURE 16SSSSS
SEQ ID NO: 127
gtgtgcatgaattatttgaaaaaagtgtggttgtattacgctatcgtcgctaccttaatcattta
ctttcttacgcccttttcaactgcacaagccaacactgcaccagtcaacggaacgatgatgcaat
atttcgaatgggatttaccgaatgatggcacactttggacgaaagtaaaaaacgaagcaagcagt
ctttcttctttaggtattactgcgttatggttaccacctgcatacaaaggaacgagccaaggga
tgtcgggtatggcgtgtacgatttgtatgacttaggagaatttaatcaaaaagggacgattcgaa
cgaaatacggaacaaaaacgcaatatttacaagccattcaagcggcaaaaagcgctggcatgcaa
gtatacgctgatgtcgtatttaatcacaagcgggggcagatagtacagaatggttgacgcagt
cgaagtgaatccttctaatcgaaaccaagaaacatctggcacatatcaaattcaagcatggacaa
aatttgatttccctggccgtggggaacacatactcaagctttaaatggcgatggtatcattttgac
ggtacggattgggatgaaagccgaaaactaaatcgtatttacaaatttcgtggcacaggaaaagc
atgggattgggaagtagacacagagaacggaaactatgactacttaatgtttgctgatttagata
tggatcaccctgaagtcgtgacagagctaaaaaactggggaacatggtacgtcaatacgacaaat
gtcgatgggtttcgcttagatgcagtaaagcatattaaatatagcttcttcccagattggttaac
acatgtgcgttcacaaacacgaaaaaatcttttgcagtaggagaatttggagctacgatgtca
ataaactgcataactacattacaaaaacaagtggaaccatgtcgttatttgatgcgccacttcat
aacaacttttacactgcttcaaaatctagcgggtattttgacatgcgctatttgttaaataatac
gttgatgaaagaccagccttctcttgcggtcacactcgttgataatcatgacacgcaaccgggac
aatctttacaatcatgggtagagccttggtttaagccgcttgcttatgcctttattttgacaaga
caagaaggatatccttgcgtatttttacggcgactattacggcatccctaaatacaacattccggg
attgaaaagtaaaatcgatccgcttctcattgcccgtagagactacgcatacggaacacaacgtg
attatattgaccatcaagacattattggatggacacgggaaggaattgactcaaaaccgaactct
ggacttgcggctttaattactgacggccctggtggaagtaaatggatgtatgtaggtaaaaagca
tgctggaaaagtgtttacgatctcactggaaatcgaagcgatacggtaacgattaatgcagacg
gctggggagagtttaaagtaaacggtggctccgtttccatttgggttgccaaaacatcacaagtc
acgtttaccgtcaacaatgcgacaacgataagcggacaaaatgtgtatgtcgttggtaacattcc
agagctcggaaattggaacacagcaaacgcaatcaaaatgaccccatcttcttatccaacgtgga
aagcaaccattgctcttccacaaggaaaagccattgaatttaaatttattaaaaaagaccaatcg
ggaaatgttgtttgggaaagcattccaaaccgaacatacaccgttccatttttatcaacaggctc
atatacagctagttggaatgtaccttaa

FIGURE 16TTTTT
SEQ ID NO: 128
Val Cys Met Asn Tyr Leu Lys Lys Val Trp Leu Tyr Tyr Ala Ile Val
Ala Thr Leu Ile Ile Tyr Phe Leu Thr Pro Phe Ser Thr Ala Gln Ala
Asn Thr Ala Pro Val Asn Gly Thr Met Met Gln Tyr Phe Glu Trp Asp
Leu Pro Asn Asp Gly Thr Leu Trp Thr Lys Val Lys Asn Glu Ala Ser
Ser Leu Ser Ser Leu Gly Ile Thr Ala Leu Trp Leu Pro Pro Ala Tyr
Lys Gly Thr Ser Gln Gly Asp Val Gly Tyr Gly Val Tyr Asp Leu Tyr
Asp Leu Gly Glu Phe Asn Gln Lys Gly Thr Ile Arg Thr Lys Tyr Gly
Thr Lys Thr Gln Tyr Leu Gln Ala Ile Gln Ala Ala Lys Ser Ala Gly
Met Gln Val Tyr Ala Asp Val Val Phe Asn His Lys Ala Gly Ala Asp
Ser Thr Glu Trp Val Asp Ala Val Glu Val Asn Pro Ser Asn Arg Asn
Gln Glu Thr Ser Gly Thr Tyr Gln Ile Gln Ala Trp Thr Lys Phe Asp
Phe Pro Gly Arg Gly Asn Thr Tyr Ser Ser Phe Lys Trp Arg Trp Tyr
His Phe Asp Gly Thr Asp Trp Asp Glu Ser Arg Lys Leu Asn Arg Ile
Tyr Lys Phe Arg Gly Thr Gly Lys Ala Trp Asp Trp Glu Val Asp Thr
Glu Asn Gly Asn Tyr Asp Tyr Leu Met Phe Ala Asp Leu Asp Met Asp
His Pro Glu Val Val Thr Glu Leu Lys Asn Trp Gly Thr Trp Tyr Val
Asn Thr Thr Asn Val Asp Gly Phe Arg Leu Asp Ala Val Lys His Ile

FIGURE 16TTTTT cont

Lys Tyr Ser Phe Phe Pro Asp Trp Leu Thr His Val Arg Ser Gln Thr
Arg Lys Asn Leu Phe Ala Val Gly Glu Phe Trp Ser Tyr Asp Val Asn
Lys Leu His Asn Tyr Ile Thr Lys Thr Ser Gly Thr Met Ser Leu Phe
Asp Ala Pro Leu His Asn Asn Phe Tyr Thr Ala Ser Lys Ser Ser Gly
Tyr Phe Asp Met Arg Tyr Leu Leu Asn Asn Thr Leu Met Lys Asp Gln
Pro Ser Leu Ala Val Thr Leu Val Asp Asn His Asp Thr Gln Pro Gly
Gln Ser Leu Gln Ser Trp Val Glu Pro Trp Phe Lys Pro Leu Ala Tyr
Ala Phe Ile Leu Thr Arg Gln Glu Gly Tyr Pro Cys Val Phe Tyr Gly
Asp Tyr Tyr Gly Ile Pro Lys Tyr Asn Ile Pro Gly Leu Lys Ser Lys
Ile Asp Pro Leu Leu Ile Ala Arg Arg Asp Tyr Ala Tyr Gly Thr Gln
Arg Asp Tyr Ile Asp His Gln Asp Ile Ile Gly Trp Thr Arg Glu Gly
Ile Asp Ser Lys Pro Asn Ser Gly Leu Ala Ala Leu Ile Thr Asp Gly
Pro Gly Gly Ser Lys Trp Met Tyr Val Gly Lys Lys His Ala Gly Lys
Val Phe Tyr Asp Leu Thr Gly Asn Arg Ser Asp Thr Val Thr Ile Asn
Ala Asp Gly Trp Gly Glu Phe Lys Val Asn Gly Gly Ser Val Ser Ile
Trp Val Ala Lys Thr Ser Gln Val Thr Phe Thr Val Asn Asn Ala Thr
Thr Ile Ser Gly Gln Asn Val Tyr Val Val Gly Asn Ile Pro Glu Leu
Gly Asn Trp Asn Thr Ala Asn Ala Ile Lys Met Thr Pro Ser Ser Tyr
Pro Thr Trp Lys Ala Thr Ile Ala Leu Pro Gln Gly Lys Ala Ile Glu
Phe Lys Phe Ile Lys Lys Asp Gln Ser Gly Asn Val Val Trp Glu Ser
Ile Pro Asn Arg Thr Tyr Thr Val Pro Phe Leu Ser Thr Gly Ser Tyr
Thr Ala Ser Trp Asn Val Pro

FIGURE 16UUUUU

SEQ ID NO: 129

```
ttgcgttgccgccgtggcagggacgggtgttggtgcgggcggcgtaatgcgctgccgcgacaccc
gcgtgaacaaaataatatgaattatttgaataggatgggggtgtcaagaatgacaaaatctcgag
agttgcggtgttcatgaaagtatttgttgttgggtgcctgttgtggatggcttggggatcttcc
gcgtccgccggcgtattgatgcaaggcttctactgggacgccagtaccgggaccagtgattcgtg
gtggacgcatttggccaagcaagccaacggtctaaaacggcgcggggttcaccgccgtatggattc
ctccggtgcttaaaggggcttcaggggctattccaacgggtacgatcccttgacgactatgat
atcggaagcaaggaccagaaaggtaccgtggcgacgcgatggggacgcgagaagaactgcaacg
tgccgtggccgtgatgcgcgcgaacggtctggatgtgtatgtggatctggtgctgaaccaccgca
acggggacgacgggaattggaattttcattacaaagatgcgtacggcaaagtgggttacgggcgg
tttcaaaagggggttttacgattttcaccccaactacaacattcaggatgccaatgttcccaacga
ggattccagcttcgggcgcgatttagcccatgacaatccgtatgtggccgatggactgaaggctg
caggcgattggctgaccaaagccctcgatgttcagggatatcgtctggattacgtgaaaggcatc
agctacaccttcctgaaaagttatctgtcctatggggccatgaacggaaaatttgccgtcggtga
gtactgggatgccaaccgggatacgttgaactggtgggcgaacacggcgatggaagggcgggccc
atgtgtttgattttgcgttgcgcgaggagctgaaaaacatgtgcaatgcggacgggtactacgac
atgcgtcgattggaccacgcgggtctggtcggaatcgaccgtggaaggcggtgacgtttgtcga
aaaccatgatacggatcggcacgacccatctacaataacaagcatttggcgtatgcctacatct
tgacgtcggaagggtatccgacggtgttctggaaggattactaccaatacggaatgaagccgatc
atcgacaacctcatttggatccacgaacacattgcgtacggaacgacccaagagcgttggaaaga
cgaagatgtctttgtgtatgagcggaccggaggcaagcggctattgtgggcttaacgacaatc
gcgccaccagcaaaacggtcaccgtacagaccggctttggtgccaacgtggccttgcacgactac
accggcaacggccccgatctccgtaccgacgcctacggtcgggtaaccttgaccattcctgcaaa
cgggtacgtggcctattccgttccgggcatctccggatcctttgtgccggtcgagaaaaccgtga
cgcaggagtttgccggggcgtccgacttggatattcgtccggccgataacacgcaatttgtgcag
gtcgggcggatatacgccaaggcaaacaagccggttacagcggaattgtattgggatgccaaaga
ctggacgacctccacgtcgattctcctagaagtgcgttcggcttcgggaacgctcatcacgacaa
agaccgtgacccaattgtcgtcccagggtacccgcgtttccttcacgccttcggctaccggatgg
```

FIGURE 16UUUUU cont
tacgtcttttccattcgaagctataacacgccttcgacgaacccaaagccggcctactggttaaa
ggtaacgtatacggcgccgcaattgcttcagtaa

FIGURE 16VVVVV
SEQ ID NO: 130
Met Arg Cys Arg Arg Gly Arg Asp Gly Cys Trp Cys Gly Arg Arg Asn
Ala Leu Pro Arg His Pro Arg Glu Gln Asn Asn Met Asn Tyr Leu Asn
Arg Met Gly Val Ser Arg Met Thr Lys Ser Arg Glu Leu Arg Cys Ser
Trp Lys Val Phe Val Val Gly Cys Leu Leu Trp Met Ala Trp Gly Ser
Ser Ala Ser Ala Gly Val Leu Met Gln Gly Phe Tyr Trp Asp Ala Ser
Thr Gly Thr Ser Asp Ser Trp Trp Thr His Leu Ala Lys Gln Ala Asn
Gly Leu Lys Arg Ala Gly Phe Thr Ala Val Trp Ile Pro Pro Val Leu
Lys Gly Ala Ser Gly Gly Tyr Ser Asn Gly Tyr Asp Pro Phe Asp Asp
Tyr Asp Ile Gly Ser Lys Asp Gln Lys Gly Thr Val Ala Thr Arg Trp
Gly Thr Arg Glu Glu Leu Gln Arg Ala Val Ala Val Met Arg Ala Asn
Gly Leu Asp Val Tyr Val Asp Leu Val Leu Asn His Arg Asn Gly Asp
Asp Gly Asn Trp Asn Phe His Tyr Lys Asp Ala Tyr Gly Lys Val Gly
Tyr Gly Arg Phe Gln Lys Gly Phe Tyr Asp Phe His Pro Asn Tyr Asn
Ile Gln Asp Ala Asn Val Pro Asn Glu Asp Ser Ser Phe Gly Arg Asp
Leu Ala His Asp Asn Pro Tyr Val Ala Asp Gly Leu Lys Ala Ala Gly
Asp Trp Leu Thr Lys Ala Leu Asp Val Gln Gly Tyr Arg Leu Asp Tyr
Val Lys Gly Ile Ser Tyr Thr Phe Leu Lys Ser Tyr Leu Ser Tyr Gly
Ala Met Asn Gly Lys Phe Ala Val Gly Glu Tyr Trp Asp Ala Asn Arg
Asp Thr Leu Asn Trp Trp Ala Asn Thr Ala Met Glu Gly Arg Ala His
Val Phe Asp Phe Ala Leu Arg Glu Glu Leu Lys Asn Met Cys Asn Ala
Asp Gly Tyr Tyr Asp Met Arg Arg Leu Asp His Ala Gly Leu Val Gly
Ile Asp Pro Trp Lys Ala Val Thr Phe Val Glu Asn His Asp Thr Asp
Arg His Asp Pro Ile Tyr Asn Asn Lys His Leu Ala Tyr Ala Tyr Ile
Leu Thr Ser Glu Gly Tyr Pro Thr Val Phe Trp Lys Asp Tyr Tyr Gln
Tyr Gly Met Lys Pro Ile Ile Asp Asn Leu Ile Trp Ile His Glu His
Ile Ala Tyr Gly Thr Thr Gln Glu Arg Trp Lys Asp Glu Asp Val Phe
Val Tyr Glu Arg Thr Gly Gly Lys Arg Leu Leu Val Gly Leu Asn Asp
Asn Arg Ala Thr Ser Lys Thr Val Thr Val Gln Thr Gly Phe Gly Ala
Asn Val Ala Leu His Asp Tyr Thr Gly Asn Gly Pro Asp Leu Arg Thr
Asp Ala Tyr Gly Arg Val Thr Leu Thr Ile Pro Ala Asn Gly Tyr Val
Ala Tyr Ser Val Pro Gly Ile Ser Gly Ser Phe Val Pro Val Glu Lys
Thr Val Thr Gln Glu Phe Ala Gly Ala Ser Asp Leu Asp Ile Arg Pro
Ala Asp Asn Thr Gln Phe Val Gln Val Gly Arg Ile Tyr Ala Lys Ala
Asn Lys Pro Val Thr Ala Glu Leu Tyr Trp Asp Ala Lys Asp Trp Thr
Thr Ser Thr Ser Ile Leu Leu Glu Val Arg Ser Ala Ser Gly Thr Leu
Ile Thr Thr Lys Thr Val Thr Gln Leu Ser Ser Gln Gly Thr Arg Val
Ser Phe Thr Pro Ser Ala Thr Gly Trp Tyr Val Phe Ser Ile Arg Ser
Tyr Asn Thr Pro Ser Thr Asn Pro Lys Pro Ala Tyr Trp Leu Lys Val
Thr Tyr Thr Ala Pro Gln Leu Leu Gln

FIGURE 16WWWWW
SEQ ID NO: 131
atgccgcagcttttacccattgccgccgcgctggcggcgcgcggcccggcagggcctggccgcctt
gacgctggccaccacggccctgggcatctcgacggcccaggcccagagtgcaccgcgcacggcct
tcgtgcatctgttcgaatggaagtggaccgacatcgcgcgcgagtgcgagaccttcctcgggccc
aagggcttcgcggcggtgcaggtgtcgccccgaacgagcacaactgggtgaccagcggtgatgg
tgcaccttatccgtggtggatgcgctaccagccggtgagctacagcctggaccgcagccgcagcg
gcacgcgcgccgagttccaggacatggtcaaccgatgcaatgccgtgggcgtgggcatctacgtg
gacgccgtgatcaatcacatgtccggcggcacgggcggcacctcgagcgctgggcgcagctggag
ctatcacaactaccctggctctatggccccaacgacttccaccagccggtgtgcagcatcacca
actacggggatgcgaacaatgtgcagcgttgcgagctctcgggcttgcaggacctggacactggg
agcgcttatgtgcgcggcaagatcgccgactatctggtggatctggtcaacatgggggtcaaggg
cttccgggtggatgcggccaagcacatcagcccgaccgacctgggcgccatcatcgatgcggtca
acagccgcaccggcgcgaaccgccctttctggtttctggaggtgattggcgcggccggcgaggca
gtgcagccgaaccagtacttctcgctcggcggcggccaggtcaccgtgaccgagttcaactatgg
gaagcaaatcttcggcaagttcgccggtggcggccgtctggccgagctgcgcagcttcggtgaaa
cctggggcctgatgccagcagcaaagcgattgctttcatcgacaaccacgacaagcagcgcggt
catggcggcggtggcaactatctgacctaccaccatggctcgacctacgatctggccaacatctt
catgctggcttggccttatggctaccggcgctgatgtccagctatgccttcaaccgcagcacgg
cctacgacacgagctttggcccgccacacgacagtggtggcgccacccgtggccctgggatggt
ggcggcagccagccggcctgcttcaaccagagcatcggtggctgggtgtgtgagcaccgctggcg
gggcatcgccaatatggtggccttccgcaacgccacgctgcccaactggaccgtgaccgactggt
gggacaacggcaacaaccagatcgctttcgggcggggtgacaagggcttcgtggtgatcaaccgc
gaagacgccgcgctgacgcgcaacttcaagaccagcctgccagccggccagtactgcgatgtcat
ctccggggacttcaacaatggtcagtgcacgggccatgtggtgacggtcgatgccggcggctacg
tgacgctgacggccgggcccaatggtgcggcggccatccacgtgggcgcccgtctggacggcgcc
tctcagccgccgacgaccgcctcggtgacgttcaacgcgtcggccgatacctttggggacagaa
cctgttcgtcgtgggcaaccacagcgcactgggcaactggtcgccggcggccgccaggccgatga
cttggatttccggttcgggcacgcgcgggaactggcgcgcggtgctcaatttgccggccaatacc
acctaccaatacaagttcatcaagaaggacggggctggaaacgtggtttgggagggcggtggcaa
tcgcgtcgtgaccacgccgtctggggcggatcggtgagcacgggcggcaattggcagtag

FIGURE 16XXXXX
SEQ ID NO: 132
Met Pro Gln Leu Tyr Pro Leu Pro Pro Arg Trp Arg Arg Ala Ala Arg
Gln Gly Leu Ala Ala Leu Thr Leu Ala Thr Thr Ala Leu Gly Ile Ser
Thr Ala Gln Ala Gln Ser Ala Pro Arg Thr Ala Phe Val His Leu Phe
Glu Trp Lys Trp Thr Asp Ile Ala Arg Glu Cys Glu Thr Phe Leu Gly
Pro Lys Gly Phe Ala Ala Val Gln Val Ser Pro Pro Asn Glu His Asn
Trp Val Thr Ser Gly Asp Gly Ala Pro Tyr Pro Trp Trp Met Arg Tyr
Gln Pro Val Ser Tyr Ser Leu Asp Arg Ser Arg Ser Gly Thr Arg Ala
Glu Phe Gln Asp Met Val Asn Arg Cys Asn Ala Val Gly Val Gly Ile
Tyr Val Asp Ala Val Ile Asn His Met Ser Gly Gly Thr Gly Gly Thr
Ser Ser Ala Gly Arg Ser Trp Ser Tyr His Asn Tyr Pro Gly Leu Tyr
Gly Pro Asn Asp Phe His Gln Pro Val Cys Ser Ile Thr Asn Tyr Gly
Asp Ala Asn Asn Val Gln Arg Cys Glu Leu Ser Gly Leu Gln Asp Leu
Asp Thr Gly Ser Ala Tyr Val Arg Gly Lys Ile Ala Asp Tyr Leu Val
Asp Leu Val Asn Met Gly Val Lys Gly Phe Arg Val Asp Ala Ala Lys
His Ile Ser Pro Thr Asp Leu Gly Ala Ile Ile Asp Ala Val Asn Ser
Arg Thr Gly Ala Asn Arg Pro Phe Trp Phe Leu Glu Val Ile Gly Ala
Ala Gly Glu Ala Val Gln Pro Asn Gln Tyr Phe Ser Leu Gly Gly Gly
Gln Val Thr Val Thr Glu Phe Asn Tyr Gly Lys Gln Ile Phe Gly Lys
Phe Ala Gly Gly Gly Arg Leu Ala Glu Leu Arg Ser Phe Gly Glu Thr
Trp Gly Leu Met Pro Ser Ser Lys Ala Ile Ala Phe Ile Asp Asn His

FIGURE 16XXXXX cont
Asp Lys Gln Arg Gly His Gly Gly Gly Asn Tyr Leu Thr Tyr His
His Gly Ser Thr Tyr Asp Leu Ala Asn Ile Phe Met Leu Ala Trp Pro
Tyr Gly Tyr Pro Ala Leu Met Ser Ser Tyr Ala Phe Asn Arg Ser Thr
Ala Tyr Asp Thr Ser Phe Gly Pro Pro His Asp Ser Gly Gly Ala Thr
Arg Gly Pro Trp Asp Gly Gly Gly Ser Gln Pro Ala Cys Phe Asn Gln
Ser Ile Gly Gly Trp Val Cys Glu His Arg Trp Arg Gly Ile Ala Asn
Met Val Ala Phe Arg Asn Ala Thr Leu Pro Asn Trp Thr Val Thr Asp
Trp Trp Asp Asn Gly Asn Asn Gln Ile Ala Phe Gly Arg Gly Asp Lys
Gly Phe Val Val Ile Asn Arg Glu Asp Ala Ala Leu Thr Arg Asn Phe
Lys Thr Ser Leu Pro Ala Gly Gln Tyr Cys Asp Val Ile Ser Gly Asp
Phe Asn Asn Gly Gln Cys Thr Gly His Val Val Thr Val Asp Ala Gly
Gly Tyr Val Thr Leu Thr Ala Gly Pro Asn Gly Ala Ala Ala Ile His
Val Gly Ala Arg Leu Asp Gly Ala Ser Gln Pro Pro Thr Thr Ala Ser
Val Thr Phe Asn Ala Ser Ala Asp Thr Phe Trp Gly Gln Asn Leu Phe
Val Val Gly Asn His Ser Ala Leu Gly Asn Trp Ser Pro Ala Ala Ala
Arg Pro Met Thr Trp Ile Ser Gly Ser Gly Thr Arg Gly Asn Trp Arg
Ala Val Leu Asn Leu Pro Ala Asn Thr Thr Tyr Gln Tyr Lys Phe Ile
Lys Lys Asp Gly Ala Gly Asn Val Val Trp Glu Gly Gly Gly Asn Arg
Val Val Thr Thr Pro Ser Gly Gly Gly Ser Val Ser Thr Gly Gly Asn
Trp Gln

FIGURE 16YYYYY
SEQ ID NO: 133
atgaataatgtgaaaaagtatggttgtattattctataattgctaccttagttatttccttttt
cacaccttttcaacagcacaagctaatactgcacctgtcaacggaacaatgatgcaatatttcg
aatgggatttaccgaatgatgggacgctttggacgaaagtaaaaaatgaagctaccatctttct
tcgctaggtattacagcgttatggctccctccagcatataaaggaacgagccaaagcgatgtcgg
atatggcgtgtacgatttatatgaccttggggaatttaatcaaaaagggacgatccgaacgaaat
acggaacaaaagcacaatatattcaagccatccaagctgccaaagccgcagggatgcaagtatat
gcagatgttgtatttaatcataaggcgggggctgacggcacagaatttgtcgatgcagttgaggt
aaacccttctaatcgaaatcaagaaacatctggcacatatcaaattcaagcatggacaaaatttg
atttcctggtcgtggaaacacatactccagcttcaaatggcgctggtatcattttgacggtacc
gattgggatgaaagtcgtaaattaaatcgtatttacaaattccgcggtacaggaaaagcgtggga
ctgggaagtcgatacagaaaacggaaactatgattatttaatgttcgctgatttagatatggatc
accctgaagttgtgacagagttaaaaaactggggaaaatggtatgtaaatacgacaaatgtagac
ggatttcgtttggatgccgtaaaacatattaaatacagctttttccctgactggctaacatatgt
acgtaatcaaacaggaaaaaatttatttgctgttggggaattttggagctatgacgtcaataagc
tgcataactacattacaaaaacaaatggatcgatgtcgttatttgatgcacctttgcataacaac
tttttatatcgcttccaaatcgagtggatattttgacatgcgttatttattgaataatacattaat
gaaagatcaaccttcactcgctgtaacacttgtcgataaccatgatacacaaccaggtcaatctt
tacaatcatgggtagaagcttggtttaaaccgcttgcttacgcctttattttaacaagacaagag
gggtatccttgcgtattttacggtgactattacggaatcccgaaatacaatattccgggattaaa
aagtaaaattgatccgcttttaattgctcgtcgtgattatgcttatggaacacaacgtgattaca
ttgatcatcaagacattatcggatggacacgagaaggcattgatgcaaaaccgaactctggactt
gcggctttaattaccgacggccctggcggaagtaaatggatgtatgtcggtaaaaaacatgctgg
gaaagtgttttatgatttaactggaaatcgaagtgacacagtaacgattaatgcggacggttggg
gagaatttaaagtaaacggcggctccgtttcgatttgggtggctaaaacatcaaacgtcacattt
acagtcaataacgccacaacaacaagtggacaaaacgtatatgttgttggcaacattccagagct
aggcaattctttg

FIGURE 16ZZZZZ
SEQ ID NO: 134
Met Asn Asn Val Lys Lys Val Trp Leu Tyr Tyr Ser Ile Ile Ala Thr
Leu Val Ile Ser Phe Phe Thr Pro Phe Ser Thr Ala Gln Ala Asn Thr
Ala Pro Val Asn Gly Thr Met Met Gln Tyr Phe Glu Trp Asp Leu Pro
Asn Asp Gly Thr Leu Trp Thr Lys Val Lys Asn Glu Ala Thr Asn Leu
Ser Ser Leu Gly Ile Thr Ala Leu Trp Leu Pro Pro Ala Tyr Lys Gly
Thr Ser Gln Ser Asp Val Gly Tyr Gly Val Tyr Asp Leu Tyr Asp Leu
Gly Glu Phe Asn Gln Lys Gly Thr Ile Arg Thr Lys Tyr Gly Thr Lys
Ala Gln Tyr Ile Gln Ala Ile Gln Ala Ala Lys Ala Ala Gly Met Gln
Val Tyr Ala Asp Val Val Phe Asn His Lys Ala Gly Ala Asp Gly Thr
Glu Phe Val Asp Ala Val Glu Val Asn Pro Ser Asn Arg Asn Gln Glu
Thr Ser Gly Thr Tyr Gln Ile Gln Ala Trp Thr Lys Phe Asp Phe Pro
Gly Arg Gly Asn Thr Tyr Ser Ser Phe Lys Trp Arg Trp Tyr His Phe
Asp Gly Thr Asp Trp Asp Glu Ser Arg Lys Leu Asn Arg Ile Tyr Lys
Phe Arg Gly Thr Gly Lys Ala Trp Asp Trp Glu Val Asp Thr Glu Asn
Gly Asn Tyr Asp Tyr Leu Met Phe Ala Asp Leu Asp Met Asp His Pro
Glu Val Val Thr Glu Leu Lys Asn Trp Gly Lys Trp Tyr Val Asn Thr
Thr Asn Val Asp Gly Phe Arg Leu Asp Ala Val Lys His Ile Lys Tyr
Ser Phe Phe Pro Asp Trp Leu Thr Tyr Val Arg Asn Gln Thr Gly Lys
Asn Leu Phe Ala Val Gly Glu Phe Trp Ser Tyr Asp Val Asn Lys Leu
His Asn Tyr Ile Thr Lys Thr Asn Gly Ser Met Ser Leu Phe Asp Ala
Pro Leu His Asn Asn Phe Tyr Ile Ala Ser Lys Ser Ser Gly Tyr Phe
Asp Met Arg Tyr Leu Leu Asn Asn Thr Leu Met Lys Asp Gln Pro Ser
Leu Ala Val Thr Leu Val Asp Asn His Asp Thr Gln Pro Gly Gln Ser
Leu Gln Ser Trp Val Glu Ala Trp Phe Lys Pro Leu Ala Tyr Ala Phe
Ile Leu Thr Arg Gln Glu Gly Tyr Pro Cys Val Phe Tyr Gly Asp Tyr
Tyr Gly Ile Pro Lys Tyr Asn Ile Pro Gly Leu Lys Ser Lys Ile Asp
Pro Leu Leu Ile Ala Arg Arg Asp Tyr Ala Tyr Gly Thr Gln Arg Asp
Tyr Ile Asp His Gln Asp Ile Ile Gly Trp Thr Arg Glu Gly Ile Asp
Ala Lys Pro Asn Ser Gly Leu Ala Ala Leu Ile Thr Asp Gly Pro Gly
Gly Ser Lys Trp Met Tyr Val Gly Lys Lys His Ala Gly Lys Val Phe
Tyr Asp Leu Thr Gly Asn Arg Ser Asp Thr Val Thr Ile Asn Ala Asp
Gly Trp Gly Glu Phe Lys Val Asn Gly Gly Ser Val Ser Ile Trp Val
Ala Lys Thr Ser Asn Val Thr Phe Thr Val Asn Asn Ala Thr Thr Thr
Ser Gly Gln Asn Val Tyr Val Val Gly Asn Ile Pro Glu Leu Gly Asn
Ser Leu

FIGURE 16AAAAAA
SEQ ID NO: 135
gtgacaggcaccccgtctttatacattcctccacataaaataaccatacagctttcaaatttgtt
gaaatgtataaaaataaaaaatagtattgtaagcgttaacatccgtcattataataacttcaaac
gcgtttatgttttaatgcaaacgtttgcatcctcattttatttaaagaaaggatgtgtgtgcatg
aattatttgaaaaaagtgtggttgtattacgctatcgtcgctaccttaatcatttcctttcttac
gcccttttcaactgcacaagccaacactgcaccagtcaacggaacgatgatgcaatatttcgaat
gggatttaccgaatgatggcacactttggacgaaagtaaaaaacgaagcaagcagcctttcttct
ttaggtattactgcgttatggttaccacctgcatacaaaggaacgagccaaggggatgtcgggta
tggcgtgtacgatttgtatgacttaggagaatttaatcaaaagggacgattcgaacgaaatacg
gaacaaaaacgcaatatttacaagccattcaagcggcaaaaagcgctggcatgcaagtatacgct
gatgtcgtatttaatcacaaggcgggggcagatagtacagaatggggttgacgcagtcgaagtgaa
tccttctaatcgaaaccaagaaacatctggcacatatcaaattcaagcatggacaaaatttgatt
tccctgaccgtgggaacacatactcaagctttaaatggcgctggtatcattttgacggtacggat
tgggatgaaagtcgaaaactaaatcgcatttacaaatttcgtggcacaggaaaagcatggattg
ggaagtagacacagagaacggaaactatgactacttaatgtttgctgatttagatatggatcacc

FIGURE 16AAAAAA cont
ctgaagtcgtgacagagctaaaaaactggggaacatggtacgtcaatacgacaaatgtcgatggg
tttcgcttagatgcagtaaagcatattaaatatagcttttcccagattggttaacatatgtgcg
ctcacaaacacaaaaaaatctgtttgcagtaggagaattttggagctacgatgtcaataaactgc
ataactacattacaaaaacaagtggaaccatgtcgttatttgatgcgccacttcataacaacttt
tacactgcttcaaaatctagcgggtattttgacatgcgctatttgttaaataatacgttgatgaa
agaccagccttctcttgcggtcacactcgttgataatcatgacacgcaaccgggacaatctttac
aatcatgggtagagccttggtttaagccgcttgcttatgcctttatttgacaagacaagaagga
tatccttgcgtattttacggcgactattacggcatccctaaatacaatattccgggattgaaaag
taaaatcgatccgcttctcattgcccgtagagactacgcatacggaacacaacgtgattatattg
accatcaagacattattggatggacacgggaaggaattgactcaaaaccgaactctggacttgcg
gctttaattactgacggtcctggtggaagtaaatggatgtatgtaggtaaaaagcatgctggaaa
agtgttttacgatctcactggaaatcgaagcgatacggtaacgattaatgcagacggctggggag
agtttaaagtaaacggtggctccgtttccatttggttgccaaaacatcacaagtcacgtttacc
gtcaacaatgcgacaacgacaagcggacaaaatgtgtatgtcgttggcaacattccagagctcgg
aaattggaacacagcaaacgcaatcaaaatgacccatcttcttatccaacgtggaaaacaacca
ttgctcttccacaaggaaaagcaattggcggcgtacgccatggcccttga

FIGURE 16BBBBBB
SEQ ID NO: 136
Val Thr Gly Thr Pro Ser Leu Tyr Ile Pro Pro His Lys Ile Thr Ile
Gln Leu Ser Asn Leu Leu Lys Cys Ile Lys Ile Lys Asn Ser Ile Val
Ser Val Asn Ile Arg His Tyr Asn Asn Phe Lys Arg Val Tyr Val Leu
Met Gln Thr Phe Ala Ser Ser Phe Tyr Leu Lys Lys Gly Cys Val Cys
Met Asn Tyr Leu Lys Lys Val Trp Leu Tyr Tyr Ala Ile Val Ala Thr
Leu Ile Ile Ser Phe Leu Thr Pro Phe Ser Thr Ala Gln Ala Asn Thr
Ala Pro Val Asn Gly Thr Met Met Gln Tyr Phe Glu Trp Asp Leu Pro
Asn Asp Gly Thr Leu Trp Thr Lys Val Lys Asn Glu Ala Ser Ser Leu
Ser Ser Leu Gly Ile Thr Ala Leu Trp Leu Pro Pro Ala Tyr Lys Gly
Thr Ser Gln Gly Asp Val Gly Tyr Gly Val Tyr Asp Leu Tyr Asp Leu
Gly Glu Phe Asn Gln Lys Gly Thr Ile Arg Thr Lys Tyr Gly Thr Lys
Thr Gln Tyr Leu Gln Ala Ile Gln Ala Ala Lys Ser Ala Gly Met Gln
Val Tyr Ala Asp Val Val Phe Asn His Lys Ala Gly Ala Asp Ser Thr
Glu Trp Val Asp Ala Val Glu Val Asn Pro Ser Asn Arg Asn Gln Glu
Thr Ser Gly Thr Tyr Gln Ile Gln Ala Trp Thr Lys Phe Asp Phe Pro
Asp Arg Gly Asn Thr Tyr Ser Ser Phe Lys Trp Arg Trp Tyr His Phe
Asp Gly Thr Asp Trp Asp Glu Ser Arg Lys Leu Asn Arg Ile Tyr Lys
Phe Arg Gly Thr Gly Lys Ala Trp Asp Trp Glu Val Asp Thr Glu Asn
Gly Asn Tyr Asp Tyr Leu Met Phe Ala Asp Leu Asp Met Asp His Pro
Glu Val Val Thr Glu Leu Lys Asn Trp Gly Thr Trp Tyr Val Asn Thr
Thr Asn Val Asp Gly Phe Arg Leu Asp Ala Val Lys His Ile Lys Tyr
Ser Phe Phe Pro Asp Trp Leu Thr Tyr Val Arg Ser Gln Thr Gln Lys
Asn Leu Phe Ala Val Gly Glu Phe Trp Ser Tyr Asp Val Asn Lys Leu
His Asn Tyr Ile Thr Lys Thr Ser Gly Thr Met Ser Leu Phe Asp Ala
Pro Leu His Asn Asn Phe Tyr Thr Ala Ser Lys Ser Ser Gly Tyr Phe
Asp Met Arg Tyr Leu Leu Asn Asn Thr Leu Met Lys Asp Gln Pro Ser
Leu Ala Val Thr Leu Val Asp Asn His Asp Thr Gln Pro Gly Gln Ser
Leu Gln Ser Trp Val Glu Pro Trp Phe Lys Pro Leu Ala Tyr Ala Phe
Ile Leu Thr Arg Gln Glu Gly Tyr Pro Cys Val Phe Tyr Gly Asp Tyr
Tyr Gly Ile Pro Lys Tyr Asn Ile Pro Gly Leu Lys Ser Lys Ile Asp
Pro Leu Leu Ile Ala Arg Arg Asp Tyr Ala Tyr Gly Thr Gln Arg Asp
Tyr Ile Asp His Gln Asp Ile Ile Gly Trp Thr Arg Glu Gly Ile Asp
Ser Lys Pro Asn Ser Gly Leu Ala Ala Leu Ile Thr Asp Gly Pro Gly
Gly Ser Lys Trp Met Tyr Val Gly Lys Lys His Ala Gly Lys Val Phe

FIGURE 16BBBBBB cont
Tyr Asp Leu Thr Gly Asn Arg Ser Asp Thr Val Thr Ile Asn Ala Asp
Gly Trp Gly Glu Phe Lys Val Asn Gly Gly Ser Val Ser Ile Trp Val
Ala Lys Thr Ser Gln Val Thr Phe Thr Val Asn Asn Ala Thr Thr Thr
Ser Gly Gln Asn Val Tyr Val Val Gly Asn Ile Pro Glu Leu Gly Asn
Trp Asn Thr Ala Asn Ala Ile Lys Met Thr Pro Ser Ser Tyr Pro Thr
Trp Lys Thr Thr Ile Ala Leu Pro Gln Gly Lys Ala Ile Gly Gly Val
Arg His Gly Pro

FIGURE 16CCCCCC
SEQ ID NO: 137
gtgggacgggcaggcttggcgcatcactcgaacacttccgccaaggggacatacgggtcacctct
cgaactgcgtccggatcgcccgccgtggccggggcggtcgagcttgaagatgtccagcggggag
ccgccgcgaggatcaccccggcggcgtactcgcccagggcggggctcagcttgaagccgtggcc
ggagccgcctcccaggagccagacgttggaggcccgcggatggcggtcgaggaggaggtggccgt
cggggctgttctcgtactggcagacgcgggtctcgaccagcggcgcgtccttcagggccgggaac
cggcgggccacctcggcccgggccgcttccagcagggccgggggtgatcgtccgctcgccgccgt
gggatcgatgggctcgccccgggtgtcgtccgccaccttgaagccgcggtgctcgttgccgggga
tgccgtagtagatccgctcgccgagatcgacccagaccggacagccgccctcctggaagcgcggg
tcgcccggcggcgtgccgaagaagaacacctcctggcgggtgttgcggaggaaccgctcaccgat
cacgtccgggaacagcccggccagccagggaccgcaggcgaagacgtagaggtcggccgcgagag
tggagccgtccgaaaggtgaagccgctccaagggccccgggaccatggcggcctgccggtactcc
ccgccctcgcctggaacagctccaccacggtccggcaggcgcgccgggcgaacagggcgccggc
ttcctcctcgtaccagatcgtgcggacgccgtcgaaatcgacctggggaagcggctccgggcct
cccctgagacagctcggcgaccggcagcccgcgtcctccagaaaaggaagggagtcgcggacg
tagctgtcgtcctcgccgcacatccagaggacccggtcctttgtacagccggtaaccggactg
gacttcggcgtcccgccagagctcgaaggagcgggcgacccactccacgtacagacggtcgggtc
cgtaggcgccgcggatgatccgcgtctcgccaccggagctggagcgggagtgccccggaccccag
gcgtccaggagggtcacccgggctccgcggcggaggagatgcaggcggtccagccgccgaaggc
gccggcgccgacgacggcgatatggggatggagggcatggcgggcgtaaggttatcgcagcccg
atccttcgctggcatcccatctccgaccggagtatcctggaaaattcgaagaaggagatcgacat
gcaatcgaacggaaacgtga

FIGURE 16DDDDDD
SEQ ID NO: 138
Val Gly Arg Ala Gly Leu Ala His His Ser Asn Thr Ser Ala Lys Gly
Thr Tyr Gly Ser Pro Leu Glu Leu Arg Pro Asp Arg Pro Ala Val Ala
Gly Ala Val Glu Leu Glu Asp Val Gln Arg Gly Ala Ala Ala Glu Asp
His Pro Gly Gly Val Leu Ala Gln Gly Gly Ala Gln Leu Glu Ala Val
Ala Gly Ala Ala Ser Gln Glu Pro Asp Val Gly Gly Pro Arg Met Ala
Val Glu Glu Val Ala Val Gly Ala Val Leu Val Leu Ala Asp Ala
Gly Leu Asp Gln Arg Arg Val Leu Gln Gly Arg Glu Pro Ala Gly His
Leu Gly Pro Gly Arg Phe Gln Gln Gly Arg Gly Asp Arg Pro Leu Ala
Arg Arg Gly Ile Asp Gly Leu Ala Pro Gly Val Val Arg His Leu Glu
Ala Ala Val Leu Val Ala Gly Asp Ala Val Val Asp Pro Leu Ala Glu
Ile Asp Pro Asp Arg Thr Ala Ala Leu Leu Glu Ala Arg Val Ala Arg
Arg Arg Ala Glu Glu Glu His Leu Leu Ala Gly Val Ala Glu Glu Pro
Leu Thr Asp His Val Arg Glu Gln Pro Gly Gln Pro Gly Thr Ala Gly
Glu Asp Val Glu Val Gly Arg Glu Ser Gly Ala Val Arg Lys Val Lys
Pro Leu Gln Gly Pro Arg Asp His Gly Gly Leu Pro Val Leu Pro Ala
Leu Ala Leu Glu Gln Leu His His Gly Pro Ala Gly Ala Pro Gly Glu
Gln Gly Ala Gly Phe Leu Leu Val Pro Asp Arg Ala Asp Ala Val Glu
Ile Asp Leu Gly Glu Ala Ala Pro Gly Leu Pro Leu Arg Gln Leu Gly
Asp Arg Gln Pro Arg Val Leu Gln Lys Arg Lys Gly Val Ala Asp Val
Ala Val Val Leu Ala Ala His Pro Glu Asp Pro Gly Pro Phe Val Gln

FIGURE 16DDDDDD cont
```
Pro Val Thr Gly Leu Asp Phe Gly Val Pro Pro Glu Leu Glu Gly Ala
Gly Asp Pro Leu His Val Gln Thr Val Gly Ser Val Gly Ala Ala Asp
Asp Pro Arg Leu Ala Thr Gly Ala Gly Ala Gly Val Pro Arg Thr Pro
Gly Val Gln Glu Gly His Pro Gly Ser Ala Ala Glu Glu Met Gln Gly
Gly Pro Ala Ala Glu Gly Ala Gly Ala Asp Asp Gly Asp Met Gly Met
Gly Gly His Gly Gly Arg Lys Val Ile Ala Ala Arg Ser Phe Ala Gly
Ile Pro Ser Pro Thr Gly Val Ser Trp Lys Ile Arg Arg Arg Arg Ser
Thr Cys Asn Arg Thr Glu Thr
```

FIGURE 16EEEEEE
SEQ ID NO: 139
```
atgaaaacattcaaccttaaacccacacttttacctttaactttgctgctgagttcgccggtatt
ggcggcacaaaatggaactatgatgcagtatttccattggtatgtgccaaatgacggcgcactct
ggacacaagttgaaaacaatgcgccagcactatccgacaacggttttacagcgctgtggttgcca
ccagcatataaaggcgcaggtggtagcaacgacgttggttacggtgtttacgatatgtatgactt
agggagtttgatcaaaaggatcggtacgaactaagtacggcaccaaagaccaatatctaaatg
ccatcaaagcagcacacaaaaacaatatccaaatttatggtgacgtagtgttcaaccatcgtggc
ggtgcagatggcaagtcgtgggtcgataccaagcgtgtggattggaataaccgcaatattgaact
tggcgataaatggattgaagcatgggttgaatttagcttcccaggacgtaacgataaatactcag
acttccattggacgtggtatcactttgatggcgtcgattgggatgacgcaggtaaagagaaagcg
atctttaaattcaaaggtgatggtaaagcatgggattgggaagtcagttctgaaaaaggcaacta
tgactacctcatgtacgcagacttagacatggatcacccagaagtgaagcaagagctgaaagatt
ggggtgaatggtacttaaacatgacgggtgttgatggcttccgaatggatgcagtgaaacacatc
aaatatcagtacctacaagagtggatcgattacttgcgtaagaaaacgggcaaagagctctttac
cgttggtgagtactggaactacgacgtgaacaatctgcacaactttatgactaagacttctggca
gcatgtcattgtttgatgcgcctttacatatgaacttctataacgcttcacgctctggtggcaac
tttgatatgcgccgaatcatggatggcaccttgatgaaagacaacccagtgaaagcagtaacact
ggttgagaaccatgatacgcaaccactacaggccttagagtctccggtggattggtggttcaaac
cacttgcgtacgcgttcattttgcttcgtgaggaaggttatccgtcagtcttctacgcagattac
tacggtgcgcaatacagcgataaagggcacgatatcaacatggtgaaagtgccttacattgagca
attggtgaaagcgcgtaaagattatgcttatggtaaacaacattcttaccttgaccactgggatg
tgattggttggacacgagaaggggatgcggaacatccgaactctatgcgggttatcatgagtgat
ggtcctggcggaacaaagtggatgtacacaggttcaccgagcacacgttatgtcgataaactagg
tattcgtaccgaagaagtatggactaacgctagtggatgggccgaattcccagtgaacggcggat
cggtttctgtttgggttggcgttaaataa
```

FIGURE 16FFFFFF
SEQ ID NO: 140
```
Met Lys Thr Phe Asn Leu Lys Pro Thr Leu Leu Pro Leu Thr Leu Leu
Leu Ser Ser Pro Val Leu Ala Ala Gln Asn Gly Thr Met Met Gln Tyr
Phe His Trp Tyr Val Pro Asn Asp Gly Ala Leu Trp Thr Gln Val Glu
Asn Asn Ala Pro Ala Leu Ser Asp Asn Gly Phe Thr Ala Leu Trp Leu
Pro Pro Ala Tyr Lys Gly Ala Gly Gly Ser Asn Asp Val Gly Tyr Gly
Val Tyr Asp Met Tyr Asp Leu Gly Glu Phe Asp Gln Lys Gly Ser Val
Arg Thr Lys Tyr Gly Thr Lys Asp Gln Tyr Leu Asn Ala Ile Lys Ala
Ala His Lys Asn Asn Ile Gln Ile Tyr Gly Asp Val Val Phe Asn His
Arg Gly Gly Ala Asp Gly Lys Ser Trp Val Asp Thr Lys Arg Val Asp
Trp Asn Asn Arg Asn Ile Glu Leu Gly Asp Lys Trp Ile Glu Ala Trp
Val Glu Phe Ser Phe Pro Gly Arg Asn Asp Lys Tyr Ser Asp Phe His
Trp Thr Trp Tyr His Phe Asp Gly Val Asp Trp Asp Asp Ala Gly Lys
Glu Lys Ala Ile Phe Lys Phe Lys Gly Asp Gly Lys Ala Trp Asp Trp
Glu Val Ser Ser Glu Lys Gly Asn Tyr Asp Tyr Leu Met Tyr Ala Asp
Leu Asp Met Asp His Pro Glu Val Lys Gln Glu Leu Lys Asp Trp Gly
Glu Trp Tyr Leu Asn Met Thr Gly Val Asp Gly Phe Arg Met Asp Ala
```

FIGURE 16FFFFFF cont

| | | | | | | | | | | | | | |
|---|---|---|---|---|---|---|---|---|---|---|---|---|---|
|Val|Lys|His|Ile|Lys|Tyr|Gln|Tyr|Leu|Gln|Glu|Trp|Ile|Asp|Tyr|Leu
|Arg|Lys|Lys|Thr|Gly|Lys|Glu|Leu|Phe|Thr|Val|Gly|Glu|Tyr|Trp|Asn
|Tyr|Asp|Val|Asn|Asn|Leu|His|Asn|Phe|Met|Thr|Lys|Thr|Ser|Gly|Ser
|Met|Ser|Leu|Phe|Asp|Ala|Pro|Leu|His|Met|Asn|Phe|Tyr|Asn|Ala|Ser
|Arg|Ser|Gly|Gly|Asn|Phe|Asp|Met|Arg|Arg|Ile|Met|Asp|Gly|Thr|Leu
|Met|Lys|Asp|Asn|Pro|Val|Lys|Ala|Val|Thr|Leu|Val|Glu|Asn|His|Asp
|Thr|Gln|Pro|Leu|Gln|Ala|Leu|Glu|Ser|Pro|Val|Asp|Trp|Trp|Phe|Lys
|Pro|Leu|Ala|Tyr|Ala|Phe|Ile|Leu|Leu|Arg|Glu|Glu|Gly|Tyr|Pro|Ser
|Val|Phe|Tyr|Ala|Asp|Tyr|Tyr|Gly|Ala|Gln|Tyr|Ser|Asp|Lys|Gly|His
|Asp|Ile|Asn|Met|Val|Lys|Val|Pro|Tyr|Ile|Glu|Gln|Leu|Val|Lys|Ala
|Arg|Lys|Asp|Tyr|Ala|Tyr|Gly|Lys|Gln|His|Ser|Tyr|Leu|Asp|His|Trp
|Asp|Val|Ile|Gly|Trp|Thr|Arg|Glu|Gly|Asp|Ala|Glu|His|Pro|Asn|Ser
|Met|Ala|Val|Ile|Met|Ser|Asp|Gly|Pro|Gly|Gly|Thr|Lys|Trp|Met|Tyr
|Thr|Gly|Ser|Pro|Ser|Thr|Arg|Tyr|Val|Asp|Lys|Leu|Gly|Ile|Arg|Thr
|Glu|Glu|Val|Trp|Thr|Asn|Ala|Ser|Gly|Trp|Ala|Glu|Phe|Pro|Val|Asn
|Gly|Gly|Ser|Val|Ser|Val|Trp|Val|Gly|Val|Lys| | | | |

FIGURE 16GGGGGG

SEQ ID NO: 141
atgaaaccaataaatacctactcatatccgcccttgctgtttgttctttcagttccgcgactta
cgccgatactattttgcacgcgttcaattggaagtattcagatgtgacggccaacgcgaatcaaa
ttgctcaagctggttataagaaagtgcttgttgcgcctgcaatgaaatcgagtggcagccaatgg
tgggctcgctatcaacctcaagatctacgcactatcgattctcctttgggcaataaacaagattt
agccgcaatgattgccgcactcaaaggtgtgggcgtcgatgtgtatgccgatgtggtactcaacc
atatggcgaatgaaagctggaagcgaagtgacttgaattaccctggcacagaagtgctaaacgat
tatgctagccgttcaagctactatgctgaccagactctgtttggcaacctagcacaaggttatgt
gtcagcgaacgactttcatccagcgggctgtatttcagattggaacgaccctggtcatgttcagt
attggcgtttgtgtggcgcagatggtgatgtaggtttacctgaccttgatccaaacaactgggtg
gtttcacaacagcgtttgtatctgaaagcgctaaaagatatgggcatcaaagggttccgaattga
tgcagtgaagcacatgagccaataccaaatcgatcaggtattcacgtctgaaattactgcgaaca
tgcatgtgtttggtgaagtgattactagcggtggagcagggaatagcggctatgaatcgttctta
gcgccttacctgaataatactaatcactctgcctacgatttcccgctgtttgcatcgattcgctc
ggcattttctatggggggcggtttaaatcaactgcatgatcctaaagcgtacggtcaggcacttg
atgataatcgctcgatcacctttgcgatcacacatgatattccaaccaatgacggcttccgctac
caaattatggacccacaagacgagcagcttgcttacgcgtatatccttggtaaagacggtggcac
gccgctgatctacagtgatgatcttcctgattctgaagacaaggataacggtcgttggggcaatg
tttggaacagttcgacaatgaaaaacatgttgagcttccataacgcgatgcaaggcaaaacaatg
acgatgatttctagcgaccattgcactttgttgtttaagcgtggcaaagaaggtgttgtgggtat
taacaagtgtggtgaaacgcgtggcgtgacggttgataccaccaacatgagtttaattggcatg
ttcaatacaaagacgtgttaagcagcgcaacagaaaccgtgacttctcgttaccatacgttcaat
ctaccaccacgcagtgcgcgtatgtttaagctgtag

FIGURE 16HHHHHH

SEQ ID NO: 142

| | | | | | | | | | | | | | | |
|---|---|---|---|---|---|---|---|---|---|---|---|---|---|---|
|Met|Lys|Pro|Ile|Asn|Thr|Leu|Leu|Ile|Ser|Ala|Leu|Ala|Val|Cys|Ser
|Phe|Ser|Ser|Ala|Thr|Tyr|Ala|Asp|Thr|Ile|Leu|His|Ala|Phe|Asn|Trp
|Lys|Tyr|Ser|Asp|Val|Thr|Ala|Asn|Ala|Asn|Gln|Ile|Ala|Gln|Ala|Gly
|Tyr|Lys|Lys|Val|Leu|Val|Ala|Pro|Ala|Met|Lys|Ser|Ser|Gly|Ser|Gln
|Trp|Trp|Ala|Arg|Tyr|Gln|Pro|Gln|Asp|Leu|Arg|Thr|Ile|Asp|Ser|Pro
|Leu|Gly|Asn|Lys|Gln|Asp|Leu|Ala|Ala|Met|Ile|Ala|Ala|Leu|Lys|Gly
|Val|Gly|Val|Asp|Val|Tyr|Ala|Asp|Val|Val|Leu|Asn|His|Met|Ala|Asn
|Glu|Ser|Trp|Lys|Arg|Ser|Asp|Leu|Asn|Tyr|Pro|Gly|Thr|Glu|Val|Leu
|Asn|Asp|Tyr|Ala|Ser|Arg|Ser|Ser|Tyr|Tyr|Ala|Asp|Gln|Thr|Leu|Phe
|Gly|Asn|Leu|Ala|Gln|Gly|Tyr|Val|Ser|Ala|Asn|Asp|Phe|His|Pro|Ala

FIGURE 16HHHHHH cont

Gly Cys Ile Ser Asp Trp Asn Asp Pro Gly His Val Gln Tyr Trp Arg
Leu Cys Gly Ala Asp Gly Asp Val Gly Leu Pro Asp Leu Asp Pro Asn
Asn Trp Val Val Ser Gln Gln Arg Leu Tyr Leu Lys Ala Leu Lys Asp
Met Gly Ile Lys Gly Phe Arg Ile Asp Ala Val Lys His Met Ser Gln
Tyr Gln Ile Asp Gln Val Phe Thr Ser Glu Ile Thr Ala Asn Met His
Val Phe Gly Glu Val Ile Thr Ser Gly Gly Ala Gly Asn Ser Gly Tyr
Glu Ser Phe Leu Ala Pro Tyr Leu Asn Asn Thr Asn His Ser Ala Tyr
Asp Phe Pro Leu Phe Ala Ser Ile Arg Ser Ala Phe Ser Met Gly Gly
Gly Leu Asn Gln Leu His Asp Pro Lys Ala Tyr Gly Gln Ala Leu Asp
Asp Asn Arg Ser Ile Thr Phe Ala Ile Thr His Asp Ile Pro Thr Asn
Asp Gly Phe Arg Tyr Gln Ile Met Asp Pro Gln Asp Glu Gln Leu Ala
Tyr Ala Tyr Ile Leu Gly Lys Asp Gly Gly Thr Pro Leu Ile Tyr Ser
Asp Asp Leu Pro Asp Ser Glu Asp Lys Asp Asn Gly Arg Trp Gly Asn
Val Trp Asn Ser Ser Thr Met Lys Asn Met Leu Ser Phe His Asn Ala
Met Gln Gly Lys Thr Met Thr Met Ile Ser Ser Asp His Cys Thr Leu
Leu Phe Lys Arg Gly Lys Glu Gly Val Val Gly Ile Asn Lys Cys Gly
Glu Thr Arg Gly Val Thr Val Asp Thr Tyr Gln His Glu Phe Asn Trp
His Val Gln Tyr Lys Asp Val Leu Ser Ser Ala Thr Glu Thr Val Thr
Ser Arg Tyr His Thr Phe Asn Leu Pro Pro Arg Ser Ala Arg Met Phe
Lys Leu

FIGURE 16IIIIII

SEQ ID NO: 143
atgccaaagagcacttttaccaaatccataacaaaatcacttcttgctacttccgttgttgtaag
cttattgcctgcctacgcacaggccgacactatcttgcatgcctttaactggaaatacagcgaca
ttacccgccaagcagagcaaattgcgcaagctggttataaaaagtactgatttcaccgccgctg
aagtccacaggcccacaatggtgggcacgttaccaaccacaggacattcgagtgattgactcccc
tgtcggcaacaagcaagatttacaagccctcattgcagccttaaaggcacaaggcgttgaagtat
acgcagacatcgtactcaaccacatggccaacgaaagctggaaacgagacgatctgaactaccccg
ggaagtgatttacttacccaatacagccaaaatatggcttacatgaaccagcaaaaattgtttgg
agatttagagcaaaatcagttctctgccaatgattttcacccggctggctgcattactgattgga
gtaacccggggcatgttcaatactggcgcttatgtggtggtaatggtgacactgggttacctgat
cttgatcctaactcgtgggtgatcgatcaacaaaaacgttatttacgtgctttgaaagacatggg
aataaagggcttccgagttgatgcggtaaaacacatgagcgattaccaaatcaaccaagtgttta
cgccagacatcatcgcaggcttacatgtatttggtgaagtgatcaccagtggtggcaagggcagc
aatgactaccactcttttctggaaccgtatttaaataacaccaatcacgccgcgtatgacttccc
gctatttgcctctatccgaaatgcatttagttatcatggcagcttgtctcaattacatgatccac
aagcttacgggcaagcacttcctaacgacagagccattactttcaccatcactcacgacattcca
accaatgatggtttccgttaccaaatcatggatccaaccagtgaaaaactcgcgtacgcgtacat
tctaggcaaagatgggggtagcccacttatctatagcgatgctttagacccaagtgaagataaag
ataagggccgctggcgtgatgtatggaaccaagaatacatggttaacatgatcagcttccacaac
aaggtgcaaggtaaaagcatggaggtcatgtacagcgatcaatgcttgctggtcttaaacgtga
aaaacaaggcttagtcggtattaataagtgcgctgaaagccgtacctacaccatagatacccatc
gttttgaatttaactggtaccaaccgtacaacgacacattaagccagcacagcgagacctttagc
agccgttatcatgctctgaccattccggcgcaaacagcacgaatgttggcgctataa

FIGURE 16JJJJJJ

SEQ ID NO: 144
Met Pro Lys Ser Thr Phe Thr Lys Ser Ile Thr Lys Ser Leu Leu Ala
Thr Ser Val Val Val Ser Leu Leu Pro Ala Tyr Ala Gln Ala Asp Thr
Ile Leu His Ala Phe Asn Trp Lys Tyr Ser Asp Ile Thr Arg Gln Ala
Glu Gln Ile Ala Gln Ala Gly Tyr Lys Lys Val Leu Ile Ser Pro Pro
Leu Lys Ser Thr Gly Pro Gln Trp Trp Ala Arg Tyr Gln Pro Gln Asp
Ile Arg Val Ile Asp Ser Pro Val Gly Asn Lys Gln Asp Leu Gln Ala

FIGURE 16JJJJJJ cont
```
Leu Ile Ala Ala Leu Lys Ala Gln Gly Val Glu Val Tyr Ala Asp Ile
Val Leu Asn His Met Ala Asn Glu Ser Trp Lys Arg Asp Asp Leu Asn
Tyr Pro Gly Ser Asp Leu Leu Thr Gln Tyr Ser Gln Asn Met Ala Tyr
Met Asn Gln Gln Lys Leu Phe Gly Asp Leu Glu Gln Asn Gln Phe Ser
Ala Asn Asp Phe His Pro Ala Gly Cys Ile Thr Asp Trp Ser Asn Pro
Gly His Val Gln Tyr Trp Arg Leu Cys Gly Gly Asn Gly Asp Thr Gly
Leu Pro Asp Leu Asp Pro Asn Ser Trp Val Ile Asp Gln Gln Lys Arg
Tyr Leu Arg Ala Leu Lys Asp Met Gly Ile Lys Gly Phe Arg Val Asp
Ala Val Lys His Met Ser Asp Tyr Gln Ile Asn Gln Val Phe Thr Pro
Asp Ile Ile Ala Gly Leu His Val Phe Gly Glu Val Ile Thr Ser Gly
Gly Lys Gly Ser Asn Asp Tyr His Ser Phe Leu Glu Pro Tyr Leu Asn
Asn Thr Asn His Ala Ala Tyr Asp Phe Pro Leu Phe Ala Ser Ile Arg
Asn Ala Phe Ser Tyr His Gly Ser Leu Ser Gln Leu His Asp Pro Gln
Ala Tyr Gly Gln Ala Leu Pro Asn Asp Arg Ala Ile Thr Phe Thr Ile
Thr His Asp Ile Pro Thr Asn Asp Gly Phe Arg Tyr Gln Ile Met Asp
Pro Thr Ser Glu Lys Leu Ala Tyr Ala Tyr Ile Leu Gly Lys Asp Gly
Gly Ser Pro Leu Ile Tyr Ser Asp Ala Leu Asp Pro Ser Glu Asp Lys
Asp Lys Gly Arg Trp Arg Asp Val Trp Asn Gln Glu Tyr Met Val Asn
Met Ile Ser Phe His Asn Lys Val Gln Gly Lys Ser Met Glu Val Met
Tyr Ser Asp Gln Cys Leu Leu Val Phe Lys Arg Glu Lys Gln Gly Leu
Val Gly Ile Asn Lys Cys Ala Glu Ser Arg Thr Tyr Thr Ile Asp Thr
His Arg Phe Glu Phe Asn Trp Tyr Gln Pro Tyr Asn Asp Thr Leu Ser
Gln His Ser Glu Thr Phe Ser Ser Arg Tyr His Ala Leu Thr Ile Pro
Ala Gln Thr Ala Arg Met Leu Ala Leu
```

FIGURE 16KKKKKK
SEQ ID NO: 145
```
atgttgaaaaggattacggtagtctgtttattatttattttgcttttcctaatatatatgggag
gaataaggcggaagcagcaacgataaataatggaacattaatgcagtattttgagtggtacgctc
cgaatgatgggaatcattggaatcgtttgcgttatgatgctgaaagtttagctcataagggaatc
acatctgtatggataccacctgcatataaagggacttcgcaaaatgatgtagggtatggggccta
tgatttatacgatttaggggagttcaatcaaaaaggaacggtgcggacgaaatatgggacaaagg
cacagttgaaatctgcaattgacgctttacataagcaaaacatcgacgtatacggtgatgtagtt
atgaatcataaggtggggctgattatactgaaaccgtaacagctgttgaggtagaccgtaacaa
tcgaaatattgaagtatcaggtgattatgaaattagtgcgtggacgggttttaactttccaggc
gcagagatgcttattctaatttcaaatggaaatggtatcattttgacggaacggattgggatgaa
ggaaggaaattaaaccgaatttataaatttagggggtataggtaaagcgtgggactgggaagtgtc
tagcgaaaatggaaattatgattatttgatgtatgcagatcttgattttgatcatccagatgttg
cgaatgaaatgaaaagttggggaacgtggtatgcgaatgaattaaatttagatggatttcgttta
gatgctgttaaacatattgatcatgaatatttacgcgattgggtaaatcatgtcagacagcaaac
ggggaaagaaatgtttacggtggctgaatattggcaaaatgatatccagactttaaacaattatt
tggcgaaagtcaattataatcaatctgtatttgatgcaccgcttcattacaattttcattatgct
tcaacaggaaatgggaattatgatatgagaaatattttaaatggaacagtaatgaaaaatcatcc
tgcactcgcagttactctcgttgagaatcatgattctcaacctgggcaatcattggaatctgtag
taagtccgtggtttaagccgctggcatatgcatttattttaactcgtgcagagggctatccttca
gttttttatggtgattactatgggacaagcggaaatagtagttatgaaattccagcgttaaaaga
taaaattgatccaattttgacggcacgaaaaaactttgcatatggtacgcagcgtgattatttag
accatccagatgtgattggctggacaagagaaggagatagtgtacatgctaagtctggtttagcg
gcattaatctccgatggaccaggaggatcaaagtggatggatgttggaaagaataacgctgggga
agtatggtacgatattacgggtaatcaaacaaatactgtaacaattaataaagatggatcggggc
aattccatgtaagtgcaggctctgtttctatatatgttcaacagtaa
```

FIGURE 16LLLLLL
SEQ ID NO: 146

Met Leu Lys Arg Ile Thr Val Val Cys Leu Leu Phe Ile Leu Leu Phe
Pro Asn Ile Tyr Gly Arg Asn Lys Ala Glu Ala Ala Thr Ile Asn Asn
Gly Thr Leu Met Gln Tyr Phe Glu Trp Tyr Ala Pro Asn Asp Gly Asn
His Trp Asn Arg Leu Arg Tyr Asp Ala Glu Ser Leu Ala His Lys Gly
Ile Thr Ser Val Trp Ile Pro Pro Ala Tyr Lys Gly Thr Ser Gln Asn
Asp Val Gly Tyr Gly Ala Tyr Asp Leu Tyr Asp Leu Gly Glu Phe Asn
Gln Lys Gly Thr Val Arg Thr Lys Tyr Gly Thr Lys Ala Gln Leu Lys
Ser Ala Ile Asp Ala Leu His Lys Gln Asn Ile Asp Val Tyr Gly Asp
Val Val Met Asn His Lys Gly Gly Ala Asp Tyr Thr Glu Thr Val Thr
Ala Val Glu Val Asp Arg Asn Asn Arg Asn Ile Glu Val Ser Gly Asp
Tyr Glu Ile Ser Ala Trp Thr Gly Phe Asn Phe Pro Gly Arg Arg Asp
Ala Tyr Ser Asn Phe Lys Trp Lys Trp Tyr His Phe Asp Gly Thr Asp
Trp Asp Glu Gly Arg Lys Leu Asn Arg Ile Tyr Lys Phe Arg Gly Ile
Gly Lys Ala Trp Asp Trp Glu Val Ser Ser Glu Asn Gly Asn Tyr Asp
Tyr Leu Met Tyr Ala Asp Leu Asp Phe Asp His Pro Asp Val Ala Asn
Glu Met Lys Ser Trp Gly Thr Trp Tyr Ala Asn Glu Leu Asn Leu Asp
Gly Phe Arg Leu Asp Ala Val Lys His Ile Asp His Glu Tyr Leu Arg
Asp Trp Val Asn His Val Arg Gln Gln Thr Gly Lys Glu Met Phe Thr
Val Ala Glu Tyr Trp Gln Asn Asp Ile Gln Thr Leu Asn Asn Tyr Leu
Ala Lys Val Asn Tyr Asn Gln Ser Val Phe Asp Ala Pro Leu His Tyr
Asn Phe His Tyr Ala Ser Thr Gly Asn Gly Asn Tyr Asp Met Arg Asn
Ile Leu Asn Gly Thr Val Met Lys Asn His Pro Ala Leu Ala Val Thr
Leu Val Glu Asn His Asp Ser Gln Pro Gly Gln Ser Leu Glu Ser Val
Val Ser Pro Trp Phe Lys Pro Leu Ala Tyr Ala Phe Ile Leu Thr Arg
Ala Glu Gly Tyr Pro Ser Val Phe Tyr Gly Asp Tyr Tyr Gly Thr Ser
Gly Asn Ser Ser Tyr Glu Ile Pro Ala Leu Lys Asp Lys Ile Asp Pro
Ile Leu Thr Ala Arg Lys Asn Phe Ala Tyr Gly Thr Gln Arg Asp Tyr
Leu Asp His Pro Asp Val Ile Gly Trp Thr Arg Glu Gly Asp Ser Val
His Ala Lys Ser Gly Leu Ala Ala Leu Ile Ser Asp Gly Pro Gly Gly
Ser Lys Trp Met Asp Val Gly Lys Asn Asn Ala Gly Glu Val Trp Tyr
Asp Ile Thr Gly Asn Gln Thr Asn Thr Val Thr Ile Asn Lys Asp Gly
Ser Gly Gln Phe His Val Ser Gly Gly Ser Val Ser Ile Tyr Val Gln
Gln

FIGURE 16MMMMMM
SEQ ID NO: 147
atgagcttaaataactttaaggtaaaactgcttagttttgctgtgtcttctgctgtattgtcact
ggctccaaatttagccaatgctgcaaattttgaaagtgagatggtgataatccatccgtttcagt
ggacatatgacaatatagcaaaagagtgtacagagtaccttggtccagccggatttgacggtgta
cagatttcccagccagcggaacataagcgggctgaaggagtatggtgggccgtatatcagccggt
taattataagaattttacaaccatgaccggtaacgaggagcagcttaaggcaatgatcaagacct
gtaatgatgcaggtgttaaggtgttcgctgacgctgttttcaaccaaaaggctacagacggtgta
ggctggggcggttcaacttggagttataagaactaccctgacggattctccggatcagatttcca
tggagactgttccattgacaaaagctatactgatgcaaataatgtcagaacctgtgcactctcag
gtatgccggacgttgccacagataactccgctactcaggaaaagattgcagattacctcgcttct
ttaatgaatatggggtctatggtttccgtattgacgctgcaaagcacatgggatacaacgatat
caactccattctttcaaaaactgcacagaagactggaagaagacctcctgcatatctggaagtaa
tcggagccggtaacgaagctgccgacattcagccggacaagtatacctttattgagaatgcggtt
gtaactgacttcggttatgtctgggatgcaaatgagagtttcggaaagggtaattacggtaaggc
actggaactcagtacctggctcggtgcaattcagaaacattcgtaaacaatcatgatgatgaat
ggggcagatgctcagccggtagctgctcaatgaaaactcagaattatgctgattataatctggct
cagtcctggcttgctgtatggcctgtaggtacagtaagacagatatattccggttattcattccc

FIGURE 16MMMMMM cont
tgtaaaagataatgatccttatcgcgtcagtgatgcaactcatgatcagggcgggcctcttggtg
ccgaccgctgtgaaggtggctggttgtgtcagcaccgtgtgtccttcgttctcaattccccaaga
tttgcgagagctaccagaggtactgctgtatcaaccaagggatttgacaatggtgctttgtggtt
taacagaggaagcaaaggttttttatgcacagaatactaccaacagtcctataacccagacattct
ctgttgaagtacctgacggaaattactgtgatatcttaggaacatcagatcctaagagcaatcca
tgcggagcagacgttgtcgtaagcggcggtaaggctacctttactattcctgcaaagacagctgt
ggctatctgtacagactcagactggtgcggcaaggggggttgatccttgtgaaagtgatccgaccg
gtgctgcctgtgtttgtaaggggggaaaccaccgttaatggtgtgtgcgtcagctggtgtaatgcg
cattcatcaaatgaggaatgcacctgtgtattgaatccgaatgatgccaactgtcaggctgatat
tgaacctaccaagggtaaactctgttacgccggtacttcaaacgggtggaaacaggatcctttaa
catataaccgtaaaacaggtttctggactattaatctgactcttgacggtgcaggtgataccagc
ggagctcagcgcttcaaggttacagacggatgttcatggaccggaacagtttacggttcttcagg
tactgccggaaagttggatgtaaatacatcatcaaccggcgatgaacctgtgtctcttgttggtg
attatgttctttccattaacgataagaccatggaatatacattcaccaaggcagatgaagtaact
aatcagccaccggttgcatcatttaccgcgacagttaacggtctgaccgtttcttttgccaataa
ttcatccgaccctgagaatgatgaattaacctacagctggaatttcggtaatggtaaaacatcat
ccgagaaagctcctagcataacctatgaagaatccggtaagtatactgttactttaaaggttact
gattcagctaataacactgatacatttactaaagatataactgtaacagcaccttctagtggcaa
gtacttaaaggttgcagtcagaggttcgcatgataattacggaactgatctgttaaccaagaacg
gttctgattggaccggcgtctttgaattctttggatccactagtgtcgacctgcaggcgcgcgag
ctc

FIGURE 16NNNNNN
SEQ ID NO: 148
```
Met Ser Leu Asn Asn Phe Lys Val Lys Leu Leu Ser Phe Ala Val Ser
Ser Ala Val Leu Ser Leu Ala Pro Asn Leu Ala Asn Ala Ala Asn Phe
Glu Ser Glu Met Val Ile Ile His Pro Phe Gln Trp Thr Tyr Asp Asn
Ile Ala Lys Glu Cys Thr Glu Tyr Leu Gly Pro Ala Gly Phe Asp Gly
Val Gln Ile Ser Gln Pro Ala Glu His Lys Arg Ala Glu Gly Val Trp
Trp Ala Val Tyr Gln Pro Val Asn Tyr Lys Asn Phe Thr Thr Met Thr
Gly Asn Glu Glu Gln Leu Lys Ala Met Ile Lys Thr Cys Asn Asp Ala
Gly Val Lys Val Phe Ala Asp Ala Val Phe Asn Gln Lys Ala Thr Asp
Gly Val Gly Trp Gly Gly Ser Thr Trp Ser Tyr Lys Asn Tyr Pro Asp
Gly Phe Ser Gly Ser Asp Phe His Gly Asp Cys Ser Ile Asp Lys Ser
Tyr Thr Asp Ala Asn Asn Val Arg Thr Cys Ala Leu Ser Gly Met Pro
Asp Val Ala Thr Asp Asn Ser Ala Thr Gln Glu Lys Ile Ala Asp Tyr
Leu Ala Ser Leu Met Asn Met Gly Val Tyr Gly Phe Arg Ile Asp Ala
Ala Lys His Met Gly Tyr Asn Asp Ile Asn Ser Ile Leu Ser Lys Thr
Ala Gln Lys Thr Gly Arg Arg Pro Pro Ala Tyr Leu Glu Val Ile Gly
Ala Gly Asn Glu Ala Ala Asp Ile Gln Pro Asp Lys Tyr Thr Phe Ile
Glu Asn Ala Val Val Thr Asp Phe Gly Tyr Val Trp Asp Ala Asn Glu
Ser Phe Gly Lys Gly Asn Tyr Gly Lys Ala Leu Glu Leu Ser Thr Trp
Leu Gly Ala Asn Ser Glu Thr Phe Val Asn Asn His Asp Asp Glu Trp
Gly Arg Cys Ser Ala Gly Ser Cys Ser Met Lys Thr Gln Asn Tyr Ala
Asp Tyr Asn Leu Ala Gln Ser Trp Leu Ala Val Trp Pro Val Gly Thr
Val Arg Gln Ile Tyr Ser Gly Tyr Ser Phe Pro Val Lys Asp Asn Asp
Pro Tyr Arg Val Ser Asp Ala Thr His Asp Gln Gly Gly Pro Leu Gly
Ala Asp Arg Cys Glu Gly Gly Trp Leu Cys Gln His Arg Val Ser Phe
Val Leu Asn Ser Pro Arg Phe Ala Arg Ala Thr Arg Gly Thr Ala Val
Ser Thr Lys Gly Phe Asp Asn Gly Ala Leu Trp Phe Asn Arg Gly Ser
Lys Gly Phe Tyr Ala Gln Asn Thr Thr Asn Ser Pro Ile Thr Gln Thr
Phe Ser Val Glu Val Pro Asp Gly Asn Tyr Cys Asp Ile Leu Gly Thr
Ser Asp Pro Lys Ser Asn Pro Cys Gly Ala Asp Val Val Val Ser Gly
```

FIGURE 16NNNNNN cont

Gly Lys Ala Thr Phe Thr Ile Pro Ala Lys Thr Ala Val Ala Ile Cys
Thr Asp Ser Asp Trp Cys Gly Lys Gly Val Asp Pro Cys Glu Ser Asp
Pro Thr Gly Ala Ala Cys Val Cys Lys Gly Glu Thr Thr Val Asn Gly
Val Cys Val Ser Trp Cys Asn Ala His Ser Ser Asn Glu Glu Cys Thr
Cys Val Leu Asn Pro Asn Asp Ala Asn Cys Gln Ala Asp Ile Glu Pro
Thr Lys Gly Lys Leu Cys Tyr Ala Gly Thr Ser Asn Gly Trp Lys Gln
Asp Pro Leu Thr Tyr Asn Arg Lys Thr Gly Phe Trp Thr Ile Asn Leu
Thr Leu Asp Gly Ala Gly Asp Thr Ser Gly Ala Gln Arg Phe Lys Val
Thr Asp Gly Cys Ser Trp Thr Gly Thr Val Tyr Gly Ser Ser Gly Thr
Ala Gly Lys Leu Asp Val Asn Thr Ser Ser Thr Gly Asp Glu Pro Val
Ser Leu Val Gly Asp Tyr Val Leu Ser Ile Asn Asp Lys Thr Met Glu
Tyr Thr Phe Thr Lys Ala Asp Glu Val Thr Asn Gln Pro Pro Val Ala
Ser Phe Thr Ala Thr Val Asn Gly Leu Thr Val Ser Phe Ala Asn Asn
Ser Ser Asp Pro Glu Asn Asp Glu Leu Thr Tyr Ser Trp Asn Phe Gly
Asn Gly Lys Thr Ser Ser Glu Lys Ala Pro Ser Ile Thr Tyr Glu Glu
Ser Gly Lys Tyr Thr Val Thr Leu Lys Val Thr Asp Ser Ala Asn Asn
Thr Asp Thr Phe Thr Lys Asp Ile Thr Val Thr Ala Pro Ser Ser Gly
Lys Tyr Leu Lys Val Ala Val Arg Gly Ser His Asp Asn Tyr Gly Thr
Asp Leu Leu Thr Lys Asn Gly Ser Asp Trp Thr Gly Val Phe Glu Phe
Phe Gly Ser Thr Ser Val Asp Leu Gln Ala Arg Glu Leu

FIGURE 16OOOOOO

SEQ ID NO: 149
atgatcttaagtaattttaaggtaaaacttcttagttttgctgtgtcttctgctgtactgacact
ggctgcaaatgtcgccaatgccaagaattatgaaagtgaaatggttattattcatccatttcagt
ggacatatgacaatatagcaaaagaatgtactgagtatctggacctgcgggatttgacggggtg
cagatttcccaggcggctgagcataaagatgccggtggtgcatggtggggtacctaccagcctgt
aaacttcaagagttttactaccatggttggtaatgaagaacagcttagagcaatgattaaaacct
gtaacgaggcaggtgttaaggtctttgccgatgccgtgattaatcagaaagccggcgacggtgta
ggtataggtggttcaactttcggaaattataattatcctgacggatttaccagtgatgattttca
tcataataactgcagtataggtaataattattcagatgcatgggtagtaagattctgtgacctca
gtggcatgccggatatagcaactgataacgacagtaccagaaataagattgctgattacttcgcc
agccttatgaatatgggggtatacggattccgtattgatgctgccaagcactttagctatgatga
tatagacgctattgtagagaaaacagcaaccaaagcaggcaggagacctcctgtctatatggagg
ttatcggtaatccgggtcaagaggcggatgatatccagccgaacaagtatacatggattgataat
gccgttgtaacagatttttacttatgctaatagcatgcataatatttttaacggaagcggttatgc
caaggctttgaacatgggggctagggcatgttgatgctgaaaatgccgaagtctttataagtaatc
atgataatgaatggggaagaaagtctgccggttcctgctcaataagaacccagaataatccggat
taccatctggctcagtcctggctcgcagtttggcctttaggcaaggttagacagatttattctgc
atatcagttcccggtctttgaagatagttgtgagcgggtcagtcagcaagcccatgatcagggcg
gtcctatcggggcagcccgctgtgaaggtggctggttgtgtcagcaccgtgtaccgtttgtgctc
aattctcctagatttgcaagagcaaccagagggacagtcgttactactaaaggttttgatgacgg
agctttgtggtttaacagaggaagcaagggcttctatgcccagaatactaccggcagttctataa
ctcatacattctcagttgaattacctgatggaaattactgtgatatccttggagcaaccgatccg
aagaataatccttgcggagcggatgtcactgtaagcggaggtaaagcaacctttaccattccggc
aaagaccgccgtagctatctgtactgatgaaaagtggtgtggcaaggggggttgacccttgtgaaa
gcgatcctaccggttccgcctgtgtatgtaagggtgaaaccacagttaacggcgtatgtgtaagc
tggtgtaatgctcactcatctaatgaagaatgtgcctgtgtgctaaatcctaatgacgctgagtg
tcaggccgacattgagccgaccaagggtaaactctgctatgtaggtacctccaacaagtggactc
aggaacctttaacctataatcgcaagaccggtttctggactctcaacgttgaacttgacggtaag
ggggataccagcggggcgcagcgctttaaagttaccgacggctgttcatggcagggtactgttta
cggttcatcaggagtagaaggcagacttgacgtaaatacttcagccaccggagatgaaccggttt
cactgacaggtaaatatgttctttccataaatgataagaccatggaatacacattcattcctgca

FIGURE 16OOOOOO cont
ggcagtggaaacaagcctccggttgcgtcatttactccgactgttaaagatctgactgtatctttt
tgtcaataattcatccgaccctgagaatgatgaattaacctacagctggaatttcggtaacggta
aaacctcatctgaaaagaatccgagtgttacatatgataaagccggtaaatatactgtttcactc
aaagtaaccgatactgcaaacaacactgataccaaaacactggaaatcgatttaacatctcctgt
taacggaaaatattccaaggttgcagtcagagttcacatgataactacggaacaaatctgttaa
ccaggaatggttcagaatggaccggtatctttgaattcagtaagacaaccaaattcaagcttgaa
gctctgcctcctgcagctgaccagtgtatcttcctcggcggtaatcgaggtgaggcattgactgc
ctccggtggatttatatctcttcctgccggaaggtatactataaagtttaatgaggaaagcaagg
ttcttactgcaggcgatgttgactgcaccggg

FIGURE 16PPPPPP
SEQ ID NO: 150

Met Ile Leu Ser Asn Phe Lys Val Lys Leu Leu Ser Phe Ala Val Ser
Ser Ala Val Leu Thr Leu Ala Ala Asn Val Ala Asn Ala Lys Asn Tyr
Glu Ser Glu Met Val Ile Ile His Pro Phe Gln Trp Thr Tyr Asp Asn
Ile Ala Lys Glu Cys Thr Glu Tyr Leu Gly Pro Ala Gly Phe Asp Gly
Val Gln Ile Ser Gln Ala Ala Glu His Lys Asp Ala Gly Gly Ala Trp
Trp Gly Thr Tyr Gln Pro Val Asn Phe Lys Ser Phe Thr Thr Met Val
Gly Asn Glu Glu Gln Leu Arg Ala Met Ile Lys Thr Cys Asn Glu Ala
Gly Val Lys Val Phe Ala Asp Ala Val Ile Asn Gln Lys Ala Gly Asp
Gly Val Gly Ile Gly Gly Ser Thr Phe Gly Asn Tyr Asn Tyr Pro Asp
Gly Phe Thr Ser Asp Asp Phe His His Asn Asn Cys Ser Ile Gly Asn
Asn Tyr Ser Asp Ala Trp Val Val Arg Phe Cys Asp Leu Ser Gly Met
Pro Asp Ile Ala Thr Asp Asn Asp Ser Thr Arg Asn Lys Ile Ala Asp
Tyr Phe Ala Ser Leu Met Asn Met Gly Val Tyr Gly Phe Arg Ile Asp
Ala Ala Lys His Phe Ser Tyr Asp Asp Ile Asp Ala Ile Val Glu Lys
Thr Ala Thr Lys Ala Gly Arg Arg Pro Pro Val Tyr Met Glu Val Ile
Gly Asn Pro Gly Gln Glu Ala Asp Asp Ile Gln Pro Asn Lys Tyr Thr
Trp Ile Asp Asn Ala Val Val Thr Asp Phe Thr Tyr Ala Asn Ser Met
His Asn Ile Phe Asn Gly Ser Gly Tyr Ala Lys Ala Leu Asn Met Gly
Leu Gly His Val Asp Ala Glu Asn Ala Glu Val Phe Ile Ser Asn His
Asp Asn Glu Trp Gly Arg Lys Ser Ala Gly Ser Cys Ser Ile Arg Thr
Gln Asn Asn Pro Asp Tyr His Leu Ala Gln Ser Trp Leu Ala Val Trp
Pro Leu Gly Lys Val Arg Gln Ile Tyr Ser Ala Tyr Gln Phe Pro Val
Phe Glu Asp Ser Cys Glu Arg Val Ser Gln Gln Ala His Asp Gln Gly
Gly Pro Ile Gly Ala Ala Arg Cys Glu Gly Gly Trp Leu Cys Gln His
Arg Val Pro Phe Val Leu Asn Ser Pro Arg Phe Ala Arg Ala Thr Arg
Gly Thr Val Val Thr Thr Lys Gly Phe Asp Asp Gly Ala Leu Trp Phe
Asn Arg Gly Ser Lys Gly Phe Tyr Ala Gln Asn Thr Thr Gly Ser Ser
Ile Thr His Thr Phe Ser Val Glu Leu Pro Asp Gly Asn Tyr Cys Asp
Ile Leu Gly Ala Thr Asp Pro Lys Asn Asn Pro Cys Gly Ala Asp Val
Thr Val Ser Gly Gly Lys Ala Thr Phe Thr Ile Pro Ala Lys Thr Ala
Val Ala Ile Cys Thr Asp Glu Lys Trp Cys Gly Lys Gly Val Asp Pro
Cys Glu Ser Asp Pro Thr Gly Ser Ala Cys Val Cys Lys Gly Glu Thr
Thr Val Asn Gly Val Cys Val Ser Trp Cys Asn Ala His Ser Ser Asn
Glu Glu Cys Ala Cys Val Leu Asn Pro Asn Asp Ala Glu Cys Gln Ala
Asp Ile Glu Pro Thr Lys Gly Lys Leu Cys Tyr Val Gly Thr Ser Asn
Lys Trp Thr Gln Glu Pro Leu Thr Tyr Asn Arg Lys Thr Gly Phe Trp
Thr Leu Asn Val Glu Leu Asp Gly Lys Gly Asp Thr Ser Gly Ala Gln
Arg Phe Lys Val Thr Asp Gly Cys Ser Trp Gln Gly Thr Val Tyr Gly
Ser Ser Gly Val Glu Gly Arg Leu Asp Val Asn Thr Ser Ala Thr Gly
Asp Glu Pro Val Ser Leu Thr Gly Lys Tyr Val Leu Ser Ile Asn Asp
Lys Thr Met Glu Tyr Thr Phe Ile Pro Ala Gly Ser Gly Asn Lys Pro

FIGURE 16PPPPPP cont
```
Pro Val Ala Ser Phe Thr Pro Thr Val Lys Asp Leu Thr Val Ser Phe
Val Asn Asn Ser Ser Asp Pro Glu Asn Asp Glu Leu Thr Tyr Ser Trp
Asn Phe Gly Asn Gly Lys Thr Ser Ser Glu Lys Asn Pro Ser Val Thr
Tyr Asp Lys Ala Gly Lys Tyr Thr Val Ser Leu Lys Val Thr Asp Thr
Ala Asn Asn Thr Asp Thr Lys Thr Leu Glu Ile Asp Leu Thr Ser Pro
Val Asn Gly Lys Tyr Ser Lys Val Ala Val Arg Gly Ser His Asp Asn
Tyr Gly Thr Asn Leu Leu Thr Arg Asn Gly Ser Glu Trp Thr Gly Ile
Phe Glu Phe Ser Lys Thr Thr Lys Phe Lys Leu Glu Ala Leu Pro Pro
Ala Ala Asp Gln Cys Ile Phe Leu Gly Gly Asn Arg Gly Glu Ala Leu
Thr Ala Ser Gly Gly Phe Ile Ser Leu Pro Ala Gly Arg Tyr Thr Ile
Lys Phe Asn Glu Glu Ser Lys Val Leu Thr Ala Gly Asp Val Asp Cys
Thr Gly
```
FIGURE 16QQQQQQ
SEQ ID NO: 151
```
atgaaaactattctttcaacaatcatggtgatggcggctgcggctgccaccaccgtagaggctca
aggctggccggaaaactacggcggcgtcatgttgcagggattctactgggattcctattcagcca
ccaagtggactaaactggaagcacaggctgacgagatctgcaactatttctcgctggtatgggta
ccacagtcggcctataccggcagcagtacctccatgggctacgacccgctgtattacttcgacca
gcattcatcgttcggcaccgaagagcagctacggtcgttcatcagtacctacaagcagaaggaa
ctggcatcatagccgatgtagttgtcaatcaccgaaagaatgtctcaaactgggtggatttcccg
gccgagacctacaacggtgtaacctatcagatggtaagcaccgacatcgtttcgaacgatgacgg
cggaaaaacagccacttgggcaaatcaaaacggctacagtctctcctccaatgccgacgaaggcg
aaggctgggacggcatgcgcgacctggaccacaagtcgcagaacgtgcagaaatcggttcttgcc
tacaccaaatatctggttgacgacttaggctataccggattccgctacgatatggtaaagggatt
tgacggatcgcatgtagccgactacaacaccaatgccggcgtgcagttctctgtcggcgaatatt
gggacggcactgcatcgaaagtttacagttggatcaacagcaccaaaaagagcgatgtgccgcag
tcggcagccttcgacttcgctttccgatacacctgccgcgatgccgtcaacaacaagaactgggc
gaacctgaagaacacttccggtatcagcgatgccgattacaggcgctattcggttacgtttgttg
aaaatcacgatacggaataccgttcagctacggcttccaggatcccatcaagggtgatacggtt
gccctcaatgcctggatgctggctatgccgggcacaccttgtgttttcctgaaacattggaccga
ctgcaaggaagagatcaagaatctcatcgaggcacgtcgcctggtcggtattcacaaccagagca
cctatgccgaatggatgagcggtgcagcctacatcggacgtaccgtaacaggtacgaacggcacc
ttacgtgttctgtgcggctcttatcagtataatgtagccgccaactacattcagattctctcagg
caaaaactataaatactacgtactcaacacgctcgaggctccctggatcgggaaaggttccggct
cgtacaccgaaggtgaaaccgtaacggttccgctcatcgccatatcggccgatgccaatgccaag
ctggtatataccaccgacggcacagaccccaccgcaacctcaacagccgtaaccagcggaacgga
actgaccatcacttcggacgccgtcctgaaggttggtctgctttccggcggcatcgtcaggaaca
tacagagccgtacattcaccttccaggctgcaaacacctccgagtattacacagccaccatgcac
gtatgcaaccagtccggagctctcaatccgctgtttgcctatgtttgggcaggaccggacaacga
gcagattaacggcaactggccgggcaccaagctcaccgctaccattaccgaaaacaaccttacct
ggtacacgcagtcgttccagattccgaagaacgtggactatgtcgtgaactttgttttcaccaca
accggcggcggtacgcagacagtggatgttaccggcatgaaggccgatgtctggtacattattaa
cagtaccaagagcggcaacaagtacacggtaaccgacgttacctcacagtattcttcgttagagg
ccatctttgatgaagaaaactccggctccttcctgtctatgacctgcagggacgccgcgtcagc
gaaattagaaacaggacaattatatcttcagaacggaaagaagatactcatcagataaacagagg
ttccgaaccattctcctattatgaaaatcagacacttagtaatctcagcactgctgggtttgggg
ggcttgtacaccatcagctgctcctcgtcggg
```

FIGURE 16RRRRRR
SEQ ID NO: 152

Met Lys Thr Ile Leu Ser Thr Ile Met Val Met Ala Ala Ala Ala Ala
Thr Thr Val Glu Ala Gln Gly Trp Pro Glu Asn Tyr Gly Gly Val Met
Leu Gln Gly Phe Tyr Trp Asp Ser Tyr Ser Ala Thr Lys Trp Thr Lys
Leu Glu Ala Gln Ala Asp Glu Ile Cys Asn Tyr Phe Ser Leu Val Trp
Val Pro Gln Ser Ala Tyr Thr Gly Ser Ser Thr Ser Met Gly Tyr Asp
Pro Leu Tyr Tyr Phe Asp Gln His Ser Ser Phe Gly Thr Glu Glu Gln
Leu Arg Ser Phe Ile Ser Thr Tyr Lys Gln Lys Gly Thr Gly Ile Ile
Ala Asp Val Val Val Asn His Arg Lys Asn Val Ser Asn Trp Val Asp
Phe Pro Ala Glu Thr Tyr Asn Gly Val Thr Tyr Gln Met Val Ser Thr
Asp Ile Val Ser Asn Asp Asp Gly Gly Lys Thr Ala Thr Trp Ala Asn
Gln Asn Gly Tyr Ser Leu Ser Ser Asn Ala Asp Glu Gly Glu Gly Trp
Asp Gly Met Arg Asp Leu Asp His Lys Ser Gln Asn Val Gln Lys Ser
Val Leu Ala Tyr Thr Lys Tyr Leu Val Asp Asp Leu Gly Tyr Thr Gly
Phe Arg Tyr Asp Met Val Lys Gly Phe Asp Gly Ser His Val Ala Asp
Tyr Asn Thr Asn Ala Gly Val Gln Phe Ser Val Gly Glu Tyr Trp Asp
Gly Thr Ala Ser Lys Val Tyr Ser Trp Ile Asn Ser Thr Lys Lys Ser
Asp Val Pro Gln Ser Ala Ala Phe Asp Phe Ala Phe Arg Tyr Thr Cys
Arg Asp Ala Val Asn Asn Lys Asn Trp Ala Asn Leu Lys Asn Thr Ser
Gly Ile Ser Asp Ala Asp Tyr Arg Arg Tyr Ser Val Thr Phe Val Glu
Asn His Asp Thr Glu Tyr Arg Ser Ala Thr Ala Ser Gln Asp Pro Ile
Lys Gly Asp Thr Val Ala Leu Asn Ala Trp Met Leu Ala Met Pro Gly
Thr Pro Cys Val Phe Leu Lys His Trp Thr Asp Cys Lys Glu Glu Ile
Lys Asn Leu Ile Glu Ala Arg Arg Leu Val Gly Ile His Asn Gln Ser
Thr Tyr Ala Glu Trp Met Ser Gly Ala Ala Tyr Ile Gly Arg Thr Val
Thr Gly Thr Asn Gly Thr Leu Arg Val Leu Cys Gly Ser Tyr Gln Tyr
Asn Val Ala Ala Asn Tyr Ile Gln Ile Leu Ser Gly Lys Asn Tyr Lys
Tyr Tyr Val Leu Asn Thr Leu Glu Ala Pro Trp Ile Gly Lys Gly Ser
Gly Ser Tyr Thr Glu Gly Glu Thr Val Thr Val Pro Leu Ile Ala Ile
Ser Ala Asp Ala Asn Ala Lys Leu Val Tyr Thr Thr Asp Gly Thr Asp
Pro Thr Ala Thr Ser Thr Ala Val Thr Ser Gly Thr Glu Leu Thr Ile
Thr Ser Asp Ala Val Leu Lys Val Gly Leu Leu Ser Gly Gly Ile Val
Arg Asn Ile Gln Ser Arg Thr Phe Thr Phe Gln Ala Ala Asn Thr Ser
Glu Tyr Tyr Thr Ala Thr Met His Val Cys Asn Gln Ser Gly Ala Leu
Asn Pro Leu Phe Ala Tyr Val Trp Ala Gly Pro Asp Asn Glu Gln Ile
Asn Gly Asn Trp Pro Gly Thr Lys Leu Thr Ala Thr Ile Thr Glu Asn
Asn Leu Thr Trp Tyr Thr Gln Ser Phe Gln Ile Pro Lys Asn Val Asp
Tyr Val Val Asn Phe Val Phe Thr Thr Thr Gly Gly Gly Thr Gln Thr
Val Asp Val Thr Gly Met Lys Ala Asp Val Trp Tyr Ile Ile Asn Ser
Thr Lys Ser Gly Asn Lys Tyr Thr Val Thr Asp Val Thr Ser Gln Tyr
Ser Ser Leu Glu Ala Ile Phe Asp Glu Glu Asn Ser Gly Ser Phe Pro
Val Tyr Asp Leu Gln Gly Arg Arg Val Ser Glu Ile Arg Asn Arg Thr
Ile Ile Ser Ser Glu Arg Lys Glu Asp Thr His Gln Ile Asn Arg Gly
Ser Glu Pro Phe Ser Tyr Tyr Glu Asn Gln Thr Leu Ser Asn Leu Ser
Thr Ala Gly Phe Gly Gly Leu Val His His Gln Leu Leu Leu Val Gly

FIGURE 16SSSSSS
SEQ ID NO: 69
atgttgaaaaggattacggtagtctgtttattgtttattttgcttttcctaatatatatgaggg
aaataaggcagaagcagcaacagtgaacaatggaacattaatgcagtattttgagtggtacgctc
cgaatgatgggaatcattggaatcgtttgcgttccgatgctgaaagtttagctcataaaggaatc
acatctgtatggataccacctgcatataaagggacttcgcaaaatgatgtagggtatgggccta
tgatttatatgatttaggggagttcaatcaaaaaggaacggtgcggacgaaatatgggacaaaag
cacagttgaaatctgcaattgacgctttacataagcaaaacatcgacgtatacggtgatgtagtt
atgaatcataaggtggggctgattatactgaaaccgtaacagctgttgaggtagaccgtaacaa
tcgaaatattgaagtatcaggtgattatcaaattagtgcatggacggggtttaattttccagggc
gcggagatgcttattctaatttcaaatggaaatggtatcattttgacggaacggattgggatgaa
ggaaggaaattaaatcgaatttataaatttagggggtgtagataaagcgtgggattgggaagtgtc
tagcgaaaatggaaattatgattatttgatgtatgcagatcttgatttgatcatcctgatgttg
cgaatgagatgaaaaattggggaacatggtatgcgaatgaattaaatttagatggctttcgtttg
gacgctgttaaacatattgatcatgaatatttacgcgattggtaaatcatgccagacagcaaac
ggggaaagaaatgtttacagtagctgaatattggcaaaatgatgttcaggctttaaacaattat
tagcgaaagtcaattataatcaatctgtgtttgatgcaccgcttcattacaattttcattatgct
tcaacaggaaatggaattatgatatgagaaatattttaaatggaacagtaatgaaaaatcaccc
tgcactcgcagttactctcgttgagaatcatgattctcagcctgggcagtcattggaatctgtag
taagtccgtggtttaagccgctggcatatgcatttatttaactcgtgcagagggctatccttca
gttttctatggtgattactatgggacaagcggaaatagtagttatgaaattccagcgttaaaaga
taaaattgatccaattttgacggcacgaaaaaactttgcatatggtacgcagcgtgattatttag
accatccagatgtgattggctggacaagagaaggcgatggtgtacatgctaattctggtttagcg
acattactctcggacggaccaggaggatcaaagtggatggatgttggaagaataacgctgggga
agtatggtacgatattacgggtaatcaaacaaatactgtaacaattaataaggacggatggggc
agttctatgtaagtggcggctcagtttccatatatgttcagcggtaa

FIGURE 16TTTTTT
SEQ ID NO: 70
Met Leu Lys Arg Ile Thr Val Val Cys Leu Leu Phe Ile Leu Leu Phe
Pro Asn Ile Tyr Glu Gly Asn Lys Ala Glu Ala Ala Thr Val Asn Asn
Gly Thr Leu Met Gln Tyr Phe Glu Trp Tyr Ala Pro Asn Asp Gly Asn
His Trp Asn Arg Leu Arg Ser Asp Ala Glu Ser Leu Ala His Lys Gly
Ile Thr Ser Val Trp Ile Pro Pro Ala Tyr Lys Gly Thr Ser Gln Asn
Asp Val Gly Tyr Gly Ala Tyr Asp Leu Tyr Asp Leu Gly Glu Phe Asn
Gln Lys Gly Thr Val Arg Thr Lys Tyr Gly Thr Lys Ala Gln Leu Lys
Ser Ala Ile Asp Ala Leu His Lys Gln Asn Ile Asp Val Tyr Gly Asp
Val Val Met Asn His Lys Gly Gly Ala Asp Tyr Thr Glu Thr Val Thr
Ala Val Glu Val Asp Arg Asn Asn Arg Asn Ile Glu Val Ser Gly Asp
Tyr Gln Ile Ser Ala Trp Thr Gly Phe Asn Phe Pro Gly Arg Gly Asp
Ala Tyr Ser Asn Phe Lys Trp Lys Trp Tyr His Phe Asp Gly Thr Asp
Trp Asp Glu Gly Arg Lys Leu Asn Arg Ile Tyr Lys Phe Arg Gly Val
Asp Lys Ala Trp Asp Trp Glu Val Ser Ser Glu Asn Gly Asn Tyr Asp
Tyr Leu Met Tyr Ala Asp Leu Asp Phe Asp His Pro Asp Val Ala Asn
Glu Met Lys Asn Trp Gly Thr Trp Tyr Ala Asn Glu Leu Asn Leu Asp
Gly Phe Arg Leu Asp Ala Val Lys His Ile Asp His Glu Tyr Leu Arg
Asp Trp Val Asn His Ala Arg Gln Gln Thr Gly Lys Glu Met Phe Thr
Val Ala Glu Tyr Trp Gln Asn Asp Val Gln Ala Leu Asn Asn Tyr Leu
Ala Lys Val Asn Tyr Asn Gln Ser Val Phe Asp Ala Pro Leu His Tyr
Asn Phe His Tyr Ala Ser Thr Gly Asn Gly Asn Tyr Asp Met Arg Asn
Ile Leu Asn Gly Thr Val Met Lys Asn His Pro Ala Leu Ala Val Thr
Leu Val Glu Asn His Asp Ser Gln Pro Gly Gln Ser Leu Glu Ser Val
Val Ser Pro Trp Phe Lys Pro Leu Ala Tyr Ala Phe Ile Leu Thr Arg
Ala Glu Gly Tyr Pro Ser Val Phe Tyr Gly Asp Tyr Tyr Gly Thr Ser

FIGURE 16TTTTTT cont
```
Gly Asn Ser Ser Tyr Glu Ile Pro Ala Leu Lys Asp Lys Ile Asp Pro
Ile Leu Thr Ala Arg Lys Asn Phe Ala Tyr Gly Thr Gln Arg Asp Tyr
Leu Asp His Pro Asp Val Ile Gly Trp Thr Arg Glu Gly Asp Gly Val
His Ala Asn Ser Gly Leu Ala Thr Leu Leu Ser Asp Gly Pro Gly Gly
Ser Lys Trp Met Asp Val Gly Lys Asn Asn Ala Gly Glu Val Trp Tyr
Asp Ile Thr Gly Asn Gln Thr Asn Thr Val Thr Ile Asn Lys Asp Gly
Trp Gly Gln Phe Tyr Val Ser Gly Gly Ser Val Ser Ile Tyr Val Gln
Arg
```
FIGURE 16UUUUUU
SEQ ID NO: 153
```
ttgccttcaattaatgcaagcgattgcaaaaaaagggagataggagtatgaagaggaaaaatg
gactgcgttagcactatctttaccactagttatgagcttatcaacaaacatacaagcagaaacat
tacataataataagggtcaaaaggcgcaaacaggaaataaagacggaattttttatgaactgtat
gttaattcttttatgatactgatagcaatggacatggtgatttaaaaggcgtcacaaagaaact
tgattatttaaatgatggaaatccaagaacaaataatgatcttcaaataaacggtatctggatga
tgcctattaacacctctcctagttatcacaaatatgatgtaacagattactataatatcgatcct
cagtatggaagtttacaagatttccgtgaactaacaacagaagcgcataaacgcaacgtaaaggt
agtaatagatcttgttattaatcatacaagcagtgagcatccttggtttgtcgatgcattaaaaa
ataaaaacagtaagtatcgagattactatatttgggctgataaaaatacagacttaaatgaaaaa
ggcccatggggtcaacaagtatggcacaaagcgtcgaacggagagtatttctacgcaacgttctg
ggaagggatgccggacttaaactatgacaaccctaaagtaagagaagaaatgattaaaatcggga
aattttggctcaaacaaggagctgatggctttcgtctagatgcagccatgcacatctttaaaggg
caaacacctgaaggagcaaagaaaaatattgaatggtggaatgaattccgcgacgcgatgagaga
aacgaatccaaatacgtatctagttggtgaaatatgggatcaaccagaagtagttgctccgtatt
atcaatcgttagattctacatttaacttcgacttagcatataaaatcgttaattccgttaaaaat
ggtactgatcaaggggtagccgcggcagctgttgcaacggatgagttatataaaacatataatcc
aaataaaattgatggaacgttttaacgaatcatgaccaaaatcgtgtaatgagtgagttaaatg
gtgatgtaaacaaagcaaaatcagcagcctctattctgttgacactccctggtaatccgttcatt
tattatggcgaagaaatcggcatgacaggccaaaaaccagatgagttgattcgtgagcctttccg
ttggtatgaagatgataaagaaggtcaaacgagctgggagactccagtatataacattgatcata
atggtgtttcagttgaagcacaagataaacaaaaagcttctcttctaagccattatcgtaaaatg
attcgtgttcgtcagcaacacgatgaacttgtcaaaggtaatttagaacctatttctgtcaataa
ttcacaggttgttgcctataatcgtacgtataaaaataaatcaattcaagtgtaccataatattt
cagacaagccggttacattaactgtttcaaacaaaggaaaactgatttttctagtgaattagga
gcaaaaaaggaaaaatcaacattagtaattccagcgaatacgacagtgctagtaaagtaa
```
FIGURE 16VVVVVV
SEQ ID NO: 154
```
Met Pro Ser Ile Asn Ala Ser Asp Cys Lys Lys Lys Gly Asp Arg Ser
Met Lys Arg Lys Lys Trp Thr Ala Leu Ala Leu Ser Leu Pro Leu Val
Met Ser Leu Ser Thr Asn Ile Gln Ala Glu Thr Leu His Asn Asn Lys
Gly Gln Lys Ala Gln Thr Gly Asn Lys Asp Gly Ile Phe Tyr Glu Leu
Tyr Val Asn Ser Phe Tyr Asp Thr Asp Ser Asn Gly His Gly Asp Leu
Lys Gly Val Thr Lys Lys Leu Asp Tyr Leu Asn Asp Gly Asn Pro Arg
Thr Asn Asn Asp Leu Gln Ile Asn Gly Ile Trp Met Met Pro Ile Asn
Thr Ser Pro Ser Tyr His Lys Tyr Asp Val Thr Asp Tyr Tyr Asn Ile
Asp Pro Gln Tyr Gly Ser Leu Gln Asp Phe Arg Glu Leu Thr Thr Glu
Ala His Lys Arg Asn Val Lys Val Val Ile Asp Leu Val Ile Asn His
Thr Ser Ser Glu His Pro Trp Phe Val Asp Ala Leu Lys Asn Lys Asn
Ser Lys Tyr Arg Asp Tyr Tyr Ile Trp Ala Asp Lys Asn Thr Asp Leu
Asn Glu Lys Gly Pro Trp Gly Gln Gln Val Trp His Lys Ala Ser Asn
Gly Glu Tyr Phe Tyr Ala Thr Phe Trp Glu Gly Met Pro Asp Leu Asn
Tyr Asp Asn Pro Lys Val Arg Glu Glu Met Ile Lys Ile Gly Lys Phe
```

FIGURE 16VVVVVV cont

```
Trp Leu Lys Gln Gly Ala Asp Gly Phe Arg Leu Asp Ala Ala Met His
Ile Phe Lys Gly Gln Thr Pro Glu Gly Ala Lys Lys Asn Ile Glu Trp
Trp Asn Glu Phe Arg Asp Ala Met Arg Glu Thr Asn Pro Asn Thr Tyr
Leu Val Gly Glu Ile Trp Asp Gln Pro Glu Val Val Ala Pro Tyr Tyr
Gln Ser Leu Asp Ser Thr Phe Asn Phe Asp Leu Ala Tyr Lys Ile Val
Asn Ser Val Lys Asn Gly Thr Asp Gln Gly Val Ala Ala Ala Ala Val
Ala Thr Asp Glu Leu Tyr Lys Thr Tyr Asn Pro Asn Lys Ile Asp Gly
Thr Phe Leu Thr Asn His Asp Gln Asn Arg Val Met Ser Glu Leu Asn
Gly Asp Val Asn Lys Ala Lys Ser Ala Ala Ser Ile Leu Leu Thr Leu
Pro Gly Asn Pro Phe Ile Tyr Tyr Gly Glu Glu Ile Gly Met Thr Gly
Gln Lys Pro Asp Glu Leu Ile Arg Glu Pro Phe Arg Trp Tyr Glu Asp
Asp Lys Glu Gly Gln Thr Ser Trp Glu Thr Pro Val Tyr Asn Ile Asp
His Asn Gly Val Ser Val Glu Ala Gln Asp Lys Gln Lys Ala Ser Leu
Leu Ser His Tyr Arg Lys Met Ile Arg Val Arg Gln Gln His Asp Glu
Leu Val Lys Gly Asn Leu Glu Pro Ile Ser Val Asn Asn Ser Gln Val
Val Ala Tyr Asn Arg Thr Tyr Lys Asn Lys Ser Ile Gln Val Tyr His
Asn Ile Ser Asp Lys Pro Val Thr Leu Thr Val Ser Asn Lys Gly Lys
Leu Ile Phe Ser Ser Glu Leu Gly Ala Lys Lys Glu Lys Ser Thr Leu
Val Ile Pro Ala Asn Thr Thr Val Leu Val Lys
```

FIGURE 16WWWWWW

SEQ ID NO: 155

```
gtgtcaagaatgtttgcaaaacgattcaaaacctctttactgccgttattcgctggatttttatt
gctgtttcatttggttctggcaggaccaacggctgcgaatgctgaaacggctaacaaatcaaatg
agcttacagcaccgtcgatcaaaagcggaaccattcttcatgcttggaattggtcgttcaatacg
ttaaaacacaatatgaaggatattcatgatgcaggatatacagcgattcagacgtctccgattaa
ccaagtcaaggaagggaaccaaggaaataaaaacatgtcgaactggtactggctctatcagccga
catcgtaccaaattggcaaccgttacttaggtactgaacaagaatttaaagaaatgtgtgcagcc
gctgaagaatatggcataaaggttattgttgacgcggtcatcaatcataccaccagtgactatgc
cgcgatttccaatgagattaagagtattccaaactggacacatggaaacacacaaattaaaaact
ggtctgatcgatggatgtcacgcagaatgcattgctcgggctgtatgactggaatacacaaaat
acacaagtacagtcctatttgaaacggttcttagaaagagcattgaatgacggggcagacggttt
tcgatttgatgccgccaaacatatagagcttccggatgatggcagttacggcagtcaattttggc
cgaatatcacaaatacatctgcagagttccaatacgagaaatcctgcaggatagtgcttcaaga
gatgcttcatatgcgaattatatgaatgtgacagcgtctaactatgggcattccataaggtccgc
tttaagaatcgtaatctgggcgtgtcgaatatctcccactatgcatcagatgtgtctgcggaca
agctagtgacatgggtagaatcgcatgatacgtatgccaatgatgatgaagagtcgacatggatg
agcgatgatgatatccgtttaggctgggcggtgatagcttctcgttcaggcagtacgcctcttt
cttttccagacctgagggaggcggaaatggtgtgagattcccggggaaaagccaataggcgatc
gcgggagtgctttatttgaagatcaggctatcactgcggtcaatagatttcacaatgtgatggct
ggacagcctgaggaactctcgacccaaatggaaacaaccagatatttatgaatcagcgcggctc
acatggcgttgtgctggcaaatgcaggttcatcctctgtttctatcaatacgccaacaaaattgc
ctgatggcaggtatgataataaagctggggcaggttcatttcaagtaaatgacggtaaactgaca
ggcacgatcaatgccaggtctgtggctgtgctttatcctgatgatattgcaaaagcgcctcatgt
tttccttgagaattacaaaacaggtgtaacacattctttcaatgatcaactgacgattacactgc
gtgcagatgcgaatacaacaaaagccgtttatcaaatcaataatggaccagagacggcgtttaag
gatggagatcaattcacaatcggaaaggagatccatttggcaaaacataccatcatgttaaa
aggaacgaacagtgatggtgtaacgaggaccgaggaatacagttttgttaaaagagatccagctt
cggccaaaaccatcggctatcaaaatccgaatcattggagccaggtaaatgcttatatctataaa
catgatgggggccgggca
```

FIGURE 16XXXXXX
SEQ ID NO: 156
Val Ser Arg Met Phe Ala Lys Arg Phe Lys Thr Ser Leu Leu Pro Leu
Phe Ala Gly Phe Leu Leu Leu Phe His Leu Val Leu Ala Gly Pro Thr
Ala Ala Asn Ala Glu Thr Ala Asn Lys Ser Asn Glu Leu Thr Ala Pro
Ser Ile Lys Ser Gly Thr Ile Leu His Ala Trp Asn Trp Ser Phe Asn
Thr Leu Lys His Asn Met Lys Asp Ile His Asp Ala Gly Tyr Thr Ala
Ile Gln Thr Ser Pro Ile Asn Gln Val Lys Glu Gly Asn Gln Gly Asn
Lys Asn Met Ser Asn Trp Tyr Trp Leu Tyr Gln Pro Thr Ser Tyr Gln
Ile Gly Asn Arg Tyr Leu Gly Thr Glu Gln Glu Phe Lys Glu Met Cys
Ala Ala Ala Glu Glu Tyr Gly Ile Lys Val Ile Val Asp Ala Val Ile
Asn His Thr Thr Ser Asp Tyr Ala Ala Ile Ser Asn Glu Ile Lys Ser
Ile Pro Asn Trp Thr His Gly Asn Thr Gln Ile Lys Asn Trp Ser Asp
Arg Trp Asp Val Thr Gln Asn Ala Leu Leu Gly Leu Tyr Asp Trp Asn
Thr Gln Asn Thr Gln Val Gln Ser Tyr Leu Lys Arg Phe Leu Glu Arg
Ala Leu Asn Asp Gly Ala Asp Gly Phe Arg Phe Asp Ala Ala Lys His
Ile Glu Leu Pro Asp Asp Gly Ser Tyr Gly Ser Gln Phe Trp Pro Asn
Ile Thr Asn Thr Ser Ala Glu Phe Gln Tyr Gly Glu Ile Leu Gln Asp
Ser Ala Ser Arg Asp Ala Ser Tyr Ala Asn Tyr Met Asn Val Thr Ala
Ser Asn Tyr Gly His Ser Ile Arg Ser Ala Leu Lys Asn Arg Asn Leu
Gly Val Ser Asn Ile Ser His Tyr Ala Ser Asp Val Ser Ala Asp Lys
Leu Val Thr Trp Val Glu Ser His Asp Thr Tyr Ala Asn Asp Asp Glu
Glu Ser Thr Trp Met Ser Asp Asp Ile Arg Leu Gly Trp Ala Val
Ile Ala Ser Arg Ser Gly Ser Thr Pro Leu Phe Phe Ser Arg Pro Glu
Gly Gly Gly Asn Gly Val Arg Phe Pro Gly Lys Ser Gln Ile Gly Asp
Arg Gly Ser Ala Leu Phe Glu Asp Gln Ala Ile Thr Ala Val Asn Arg
Phe His Asn Val Met Ala Gly Gln Pro Glu Glu Leu Ser Asn Pro Asn
Gly Asn Asn Gln Ile Phe Met Asn Gln Arg Gly Ser His Gly Val Val
Leu Ala Asn Ala Gly Ser Ser Ser Val Ser Ile Asn Thr Pro Thr Lys
Leu Pro Asp Gly Arg Tyr Asp Asn Lys Ala Gly Ala Gly Ser Phe Gln
Val Asn Asp Gly Lys Leu Thr Gly Thr Ile Asn Ala Arg Ser Val Ala
Val Leu Tyr Pro Asp Asp Ile Ala Lys Ala Pro His Val Phe Leu Glu
Asn Tyr Lys Thr Gly Val Thr His Ser Phe Asn Asp Gln Leu Thr Ile
Thr Leu Arg Ala Asp Ala Asn Thr Thr Lys Ala Val Tyr Gln Ile Asn
Asn Gly Pro Glu Thr Ala Phe Lys Asp Gly Asp Gln Phe Thr Ile Gly
Lys Gly Asp Pro Phe Gly Lys Thr Tyr Thr Ile Met Leu Lys Gly Thr
Asn Ser Asp Gly Val Thr Arg Thr Glu Glu Tyr Ser Phe Val Lys Arg
Asp Pro Ala Ser Ala Lys Thr Ile Gly Tyr Gln Asn Pro Asn His Trp
Ser Gln Val Asn Ala Tyr Ile Tyr Lys His Asp Gly Gly Arg Ala

FIGURE 16YYYYYY
SEQ ID NO: 157
atgcaaacgattgcaaaaaaggggatgaaacgatgaaagggaaaaaatggacagcattagctct
aacactgccgctggctgctagcttatcaacaggcgttcacgccgaaaccgtacataaaggtaaag
ctccaacagcagataaaaacggtgtctttttatgaggtgtatgtaaactcttttttacgatgcaaat
aaagatggacatggtgatttaaaaggtcttacacaaaagctggattatttgaatgacggcaattc
tcataccaaaaatgatcttcaagtaaacggaatttggatgatgccggtaaacccttctcctagct
atcataaatatgatgtaacggactattataacattgatccgcagtacggaaatctgcaagatttt
cgcaagctgatgaaagaagcagataaacgagacgtaaaggttattatggacctcgttgtgaatca
tacaagcagtgaacatccttggtttcaagctgcattaaagataaaaacagcaagtacagagatt
actatatttgggccgataaaaatactgatttaaatgaaaaaggatcttgggggcagcaagtatgg
cataaagctccaaacggagagtattttatggtacgttttgggaaggaatgcctgacttaaatta
cgataatcccgaagtaagaaaagaaatgattaacgtcgggaaattttggctaaagcaaggcgttg
acgggttccgcttagatgctgcgcttcatattttaaaggtcaaacacctgaaggcgctaagaaa

FIGURE 16YYYYYY cont
aatatcgtgtggtggaatgagtttagagatgcaatgaaaaaagaaaaccctaacgtatatctaac
gggtgaagtatgggatcaaccggaagtagtagctccttactatcaatcgcttgattctttattta
actttgatttagcaggaaagattgtaaactctgtaaaatcaggaaatgatcaaggaatcgcgact
gcagcagccgcaactgatgagctgttcaaatcatacaatccaaataaaattgacggcattttctt
aaccaaccatgaccaaaatcgcgtcatgagtgagctaagcggcgatgtgaataaagcaaagtcag
ctgcctctatcttacttacgcttcctggcaaccgtatatttattacggtgaagaaattggaatg
accggtgaaaagcctgatgagttaatccgtgaaccgttccgctggtacgaaggcaatggacttgg
acaaaccagctgggaaacatccgtatacaacaaaggcggcaatggtgtgtcagtagagacacaaa
caaaacaaaaggattctttgttaaatcattaccgtgaaatgattcgcgtgcgtcagcagcatgaa
gagttagtaaaaggaacccttcaatctatttcagtagacagtaaagaagtcgttgcctatagccg
cacgtataaaggcaaatcgattagcgtgtatcataatatttcaaatcaaccggtaaaagtatctg
taacagcgaaaggtaaattgattttttgctagtgaaaaaggtgcaaaaaaagtcaaaaatcagctt
gtggttccagctaatacaacggttttaataaaataa

FIGURE 16ZZZZZZ
SEQ ID NO: 158
Met Gln Thr Ile Ala Lys Lys Gly Asp Glu Thr Met Lys Gly Lys Lys
Trp Thr Ala Leu Ala Leu Thr Leu Pro Leu Ala Ala Ser Leu Ser Thr
Gly Val His Ala Glu Thr Val His Lys Gly Lys Ala Pro Thr Ala Asp
Lys Asn Gly Val Phe Tyr Glu Val Tyr Val Asn Ser Phe Tyr Asp Ala
Asn Lys Asp Gly His Gly Asp Leu Lys Gly Leu Thr Gln Lys Leu Asp
Tyr Leu Asn Asp Gly Asn Ser His Thr Lys Asn Asp Leu Gln Val Asn
Gly Ile Trp Met Met Pro Val Asn Pro Ser Pro Ser Tyr His Lys Tyr
Asp Val Thr Asp Tyr Tyr Asn Ile Asp Pro Gln Tyr Gly Asn Leu Gln
Asp Phe Arg Lys Leu Met Lys Glu Ala Asp Lys Arg Asp Val Lys Val
Ile Met Asp Leu Val Val Asn His Thr Ser Ser Glu His Pro Trp Phe
Gln Ala Ala Leu Lys Asp Lys Asn Ser Lys Tyr Arg Asp Tyr Tyr Ile
Trp Ala Asp Lys Asn Thr Asp Leu Asn Glu Lys Gly Ser Trp Gly Gln
Gln Val Trp His Lys Ala Pro Asn Gly Glu Tyr Phe Tyr Gly Thr Phe
Trp Glu Gly Met Pro Asp Leu Asn Tyr Asp Asn Pro Glu Val Arg Lys
Glu Met Ile Asn Val Gly Lys Phe Trp Leu Lys Gln Gly Val Asp Gly
Phe Arg Leu Asp Ala Ala Leu His Ile Phe Lys Gly Gln Thr Pro Glu
Gly Ala Lys Lys Asn Ile Val Trp Trp Asn Glu Phe Arg Asp Ala Met
Lys Lys Glu Asn Pro Asn Val Tyr Leu Thr Gly Glu Val Trp Asp Gln
Pro Glu Val Val Ala Pro Tyr Tyr Gln Ser Leu Asp Ser Leu Phe Asn
Phe Asp Leu Ala Gly Lys Ile Val Asn Ser Val Lys Ser Gly Asn Asp
Gln Gly Ile Ala Thr Ala Ala Ala Thr Asp Glu Leu Phe Lys Ser
Tyr Asn Pro Asn Lys Ile Asp Gly Ile Phe Leu Thr Asn His Asp Gln
Asn Arg Val Met Ser Glu Leu Ser Gly Asp Val Asn Lys Ala Lys Ser
Ala Ala Ser Ile Leu Leu Thr Leu Pro Gly Asn Pro Tyr Ile Tyr Tyr
Gly Glu Glu Ile Gly Met Thr Gly Glu Lys Pro Asp Glu Leu Ile Arg
Glu Pro Phe Arg Trp Tyr Glu Gly Asn Gly Leu Gly Gln Thr Ser Trp
Glu Thr Ser Val Tyr Asn Lys Gly Gly Asn Gly Val Ser Val Glu Thr
Gln Thr Lys Gln Lys Asp Ser Leu Leu Asn His Tyr Arg Glu Met Ile
Arg Val Arg Gln Gln His Glu Glu Leu Val Lys Gly Thr Leu Gln Ser
Ile Ser Val Asp Ser Lys Glu Val Val Ala Tyr Ser Arg Thr Tyr Lys
Gly Lys Ser Ile Ser Val Tyr His Asn Ile Ser Asn Gln Pro Val Lys
Val Ser Val Thr Ala Lys Gly Lys Leu Ile Phe Ala Ser Glu Lys Gly
Ala Lys Lys Val Lys Asn Gln Leu Val Val Pro Ala Asn Thr Thr Val
Leu Ile Lys

FIGURE 16AAAAAAA
SEQ ID NO: 159
ttgcaaaaaaaggggatgaaacgatgaaagggaaaaaatggacagctttagctctaacactgcc
gctggctgctagcttatcaacaggcgttcacgccgaaaccgtacataaaggtaaatctccaacag
cagataaaaacggtgtattttatgaggtgtatgtaaactcttttttacgatgcaaataaagatgga
catggtgatttaaaaggtcttacacaaaagttggattatttaaatgatggcaattctcatacaaa
gaatgatcttcaagtaaacgggatttggatgatgccggtcaaccttctcccagctatcataaat
atgatgtaacggactattataatattgatccgcagtatggaaatctgcaagattttcgcaaactg
atgaaagaagcagataaacgagatgtaaagtcattatggacctcgttgtgaatcatacgagcag
tgaacaccttggtttcaagctgcattaaaagataaaaacagcaagtacagagattactatatct
gggctgataaaaataccgacttgaatgaaaaggatcttggggacagcaagtatggcataaagct
ccaaacggagagtattttttacggaacgttttgggaaggaatgccggacttaaattacgataatcc
tgaagtaagaaaagaaatgattaacgtaggaaagttttggctaaagcaaggagttgatggttcc
gtctagatgctgcgcttcatatttttaaaggccaaacacctgaaggcgctaagaaaaatctcctg
tggtggaatgaatttagagatgcaatgaaaaaggaaaaccctaacgtatatctaacgggtgaagt
atgggatcaaccggaagtagtagctccttactatcaatcgcttgattctttatttaactttgatt
tagcaggaaagattgtaaactctgtaaaatcaggaaatgatcaaggaatcgcgactgcagcagcg
gcaacggatgaactgttcaaatcatacaatccaaataaaattgacggtattttcttaaccaacca
tgaccaaaatcgcgtcatgagtgagctaaacggcgatgtgaataaagcaaagtcagctgcctcta
tcttacttacgcttcctggcaacccgtatatttattacggtgaagaaatcggcatgaccggtgaa
aagcctgatgagttaatccgtgaaccgttccctggtacgaaggaaacggacttggacaaaccag
ctgggaaacacctgtatataacaaaggcggcaacggcgtgtctgtagaagcacaaacaaaacaaa
aggactctttgttaaatcattaccgtgaaatgattcgcgtgcgtcagcagcacgaagagttagta
aaaggaacgcttcaatctatttcagtagacagtaaagaagtcgttgcctatagccgtacgtataa
aggcaaatcgattagcgtgtatcataatatttcaaatcaaccggtaaaagtatctgtagcagcaa
aaggtaaattgattttgctagtgaaaaaggtgctaagaaagtcaaaaatcagcttgtgattccg
gcgaatacaacggttttaataaaataa

FIGURE 16BBBBBBB
SEQ ID NO: 160

| Met | Gln | Lys | Lys | Gly | Asp | Glu | Thr | Met | Lys | Gly | Lys | Lys | Trp | Thr | Ala |
|---|---|---|---|---|---|---|---|---|---|---|---|---|---|---|---|
| Leu | Ala | Leu | Thr | Leu | Pro | Leu | Ala | Ala | Ser | Leu | Ser | Thr | Gly | Val | His |
| Ala | Glu | Thr | Val | His | Lys | Gly | Lys | Ser | Pro | Thr | Ala | Asp | Lys | Asn | Gly |
| Val | Phe | Tyr | Glu | Val | Tyr | Val | Asn | Ser | Phe | Tyr | Asp | Ala | Asn | Lys | Asp |
| Gly | His | Gly | Asp | Leu | Lys | Gly | Leu | Thr | Gln | Lys | Leu | Asp | Tyr | Leu | Asn |
| Asp | Gly | Asn | Ser | His | Thr | Lys | Asn | Asp | Leu | Gln | Val | Asn | Gly | Ile | Trp |
| Met | Met | Pro | Val | Asn | Pro | Ser | Pro | Ser | Tyr | His | Lys | Tyr | Asp | Val | Thr |
| Asp | Tyr | Tyr | Asn | Ile | Asp | Pro | Gln | Tyr | Gly | Asn | Leu | Gln | Asp | Phe | Arg |
| Lys | Leu | Met | Lys | Glu | Ala | Asp | Lys | Arg | Asp | Val | Lys | Val | Ile | Met | Asp |
| Leu | Val | Val | Asn | His | Thr | Ser | Ser | Glu | His | Pro | Trp | Phe | Gln | Ala | Ala |
| Leu | Lys | Asp | Lys | Asn | Ser | Lys | Tyr | Arg | Asp | Tyr | Tyr | Ile | Trp | Ala | Asp |
| Lys | Asn | Thr | Asp | Leu | Asn | Glu | Lys | Gly | Ser | Trp | Gly | Gln | Gln | Val | Trp |
| His | Lys | Ala | Pro | Asn | Gly | Glu | Tyr | Phe | Tyr | Gly | Thr | Phe | Trp | Glu | Gly |
| Met | Pro | Asp | Leu | Asn | Tyr | Asp | Asn | Pro | Glu | Val | Arg | Lys | Glu | Met | Ile |
| Asn | Val | Gly | Lys | Phe | Trp | Leu | Lys | Gln | Gly | Val | Asp | Gly | Phe | Arg | Leu |
| Asp | Ala | Ala | Leu | His | Ile | Phe | Lys | Gly | Gln | Thr | Pro | Glu | Gly | Ala | Lys |
| Lys | Asn | Leu | Leu | Trp | Trp | Asn | Glu | Phe | Arg | Asp | Ala | Met | Lys | Lys | Glu |
| Asn | Pro | Asn | Val | Tyr | Leu | Thr | Gly | Glu | Val | Trp | Asp | Gln | Pro | Glu | Val |
| Val | Ala | Pro | Tyr | Tyr | Gln | Ser | Leu | Asp | Ser | Leu | Phe | Asn | Phe | Asp | Leu |
| Ala | Gly | Lys | Ile | Val | Asn | Ser | Val | Lys | Ser | Gly | Asn | Asp | Gln | Gly | Ile |
| Ala | Thr | Ala | Ala | Ala | Thr | Asp | Glu | Leu | Phe | Lys | Ser | Tyr | Asn | Pro |
| Asn | Lys | Ile | Asp | Gly | Ile | Phe | Leu | Thr | Asn | His | Asp | Gln | Asn | Arg | Val |
| Met | Ser | Glu | Leu | Asn | Gly | Asp | Val | Asn | Lys | Ala | Lys | Ser | Ala | Ala | Ser |
| Ile | Leu | Leu | Thr | Leu | Pro | Gly | Asn | Pro | Tyr | Ile | Tyr | Tyr | Gly | Glu | Glu |

FIGURE 16BBBBBBB cont
Ile Gly Met Thr Gly Glu Lys Pro Asp Glu Leu Ile Arg Glu Pro Phe
Pro Trp Tyr Glu Gly Asn Gly Leu Gly Gln Thr Ser Trp Glu Thr Pro
Val Tyr Asn Lys Gly Gly Asn Gly Val Ser Val Glu Ala Gln Thr Lys
Gln Lys Asp Ser Leu Leu Asn His Tyr Arg Glu Met Ile Arg Val Arg
Gln Gln His Glu Glu Leu Val Lys Gly Thr Leu Gln Ser Ile Ser Val
Asp Ser Lys Glu Val Val Ala Tyr Ser Arg Thr Tyr Lys Gly Lys Ser
Ile Ser Val Tyr His Asn Ile Ser Asn Gln Pro Val Lys Val Ser Val
Ala Ala Lys Gly Lys Leu Ile Phe Ala Ser Glu Lys Gly Ala Lys Lys
Val Lys Asn Gln Leu Val Ile Pro Ala Asn Thr Thr Val Leu Ile Lys

FIGURE 16CCCCCCC
SEQ ID NO: 161
gtggatccaaagaattgtagtcaatttatgcaaacgattgcaaaaaaggggatgaaacgatgaa
agggaaaaaatggacagctttagctctaacactgccgctggctgctagcttatcaacaggtgttc
acgccgaaaccgtacataaaggtaaagctccaacagcagataaaaacggtgtcttttatgaggta
tatgtaaactcttttacgatgcaaataaagatggacatggtgatttaaaaggccttacacaaaa
gttggactatttaaatgacggaaattctcatacaaagaatgatcttcaagtaaacgggatttgga
tgatgccggtcaacccttctcctagctatcataaatatgatgtaacggactattataatattgat
ccgcagtatggaaatctgcaagattttcgcaaacttatgaaagaagcagataaacgagacgtaaa
agtcattatggaccttgttgtgaatcatacgagcagtgaacacccttggtttcaagctgcgttga
aagataaaaacagcaagtacagagattactatatttgggctgataaaaatactgacttgaatgaa
aaaggatcttggggacaacaagtatggcataaagctccaaacggagagtattttacggaacgtt
ctgggaaggaatgcctgacttaaattacgataaccctgaagtaagaaaagaaatgattaacgtcg
gaaagttttggctaaaacaaggcgttgacggcttccgcttagatgctgcccttcatattttaaa
ggtcaaacgcctgaaggcgctaagaaaaacattctatggtggaatgagtttagagatgcgatgaa
aaaagaaaacccgaacgtatatctaacgggtgaagtgtgggaccagccagaagtagtagcccctt
actatcaatcacttgattctctatttaattttgatttagcaggaaaaattgtcagctctgtaaaa
gcaggaaatgatcaaggaatcgccactgcagcagcggcaactgatgagctgttcaaatcatacaa
tccaaataaaattgacggcatttcttaaccaaccatgaccaaaatcgcgtcatgagtgagttaa
gcggcgatgtgaataaagcaaaatcagccgcctctatcttacttacgcttcctggaaatccgtat
atttattacggtgaagaaattggcatgacaggtgaaaagcctgatgaattaatccgtgaaccgtt
ccgctggtacgaaggcaacggaattggacaaactagctgggaaacacctgtatataacaaaggcg
gtaacggcgtgtctgtagaagcacaaacaaaacaaaaggattccttgttaaatcattaccgtgaa
atgattcgtgtgcgccagcagcacgaagagttagtaaaaggaacgcttcaatccatttcagtaga
cagtaaagaagtcgttgcctatagccgcacgtacaaaggcaaatcgattagcgtgtatcataata
tttcaaatcaacctgtaaaagtatctgtagcagcgaaaggtaacttgattttgctagtgaaaaa
ggtgctaagaaagtcaaaaatcagcttgtgattccggcgaatgcgacggttttaataaaataa

FIGURE 16DDDDDDD
SEQ ID NO: 162
Val Asp Pro Lys Asn Cys Ser Gln Phe Met Gln Thr Ile Ala Lys Lys
Gly Asp Glu Thr Met Lys Gly Lys Lys Trp Thr Ala Leu Ala Leu Thr
Leu Pro Leu Ala Ala Ser Leu Ser Thr Gly Val His Ala Glu Thr Val
His Lys Gly Lys Ala Pro Thr Ala Asp Lys Asn Gly Val Phe Tyr Glu
Val Tyr Val Asn Ser Phe Tyr Asp Ala Asn Lys Asp Gly His Gly Asp
Leu Lys Gly Leu Thr Gln Lys Leu Asp Tyr Leu Asn Asp Gly Asn Ser
His Thr Lys Asn Asp Leu Gln Val Asn Gly Ile Trp Met Met Pro Val
Asn Pro Ser Pro Ser Tyr His Lys Tyr Asp Val Thr Asp Tyr Tyr Asn
Ile Asp Pro Gln Tyr Gly Asn Leu Gln Asp Phe Arg Lys Leu Met Lys
Glu Ala Asp Lys Arg Asp Val Lys Val Ile Met Asp Leu Val Val Asn
His Thr Ser Ser Glu His Pro Trp Phe Gln Ala Ala Leu Lys Asp Lys
Asn Ser Lys Tyr Arg Asp Tyr Tyr Ile Trp Ala Asp Lys Asn Thr Asp
Leu Asn Glu Lys Gly Ser Trp Gly Gln Gln Val Trp His Lys Ala Pro
Asn Gly Glu Tyr Phe Tyr Gly Thr Phe Trp Glu Gly Met Pro Asp Leu

FIGURE 16DDDDDDD cont
```
Asn Tyr Asp Asn Pro Glu Val Arg Lys Glu Met Ile Asn Val Gly Lys
Phe Trp Leu Lys Gln Gly Val Asp Gly Phe Arg Leu Asp Ala Ala Leu
His Ile Phe Lys Gly Gln Thr Pro Glu Gly Ala Lys Lys Asn Ile Leu
Trp Trp Asn Glu Phe Arg Asp Ala Met Lys Lys Glu Asn Pro Asn Val
Tyr Leu Thr Gly Glu Val Trp Asp Gln Pro Glu Val Val Ala Pro Tyr
Tyr Gln Ser Leu Asp Ser Leu Phe Asn Phe Asp Leu Ala Gly Lys Ile
Val Ser Ser Val Lys Ala Gly Asn Asp Gln Gly Ile Ala Thr Ala Ala
Ala Ala Thr Asp Glu Leu Phe Lys Ser Tyr Asn Pro Asn Lys Ile Asp
Gly Ile Phe Leu Thr Asn His Asp Gln Asn Arg Val Met Ser Glu Leu
Ser Gly Asp Val Asn Lys Ala Lys Ser Ala Ala Ser Ile Leu Leu Thr
Leu Pro Gly Asn Pro Tyr Ile Tyr Tyr Gly Glu Glu Ile Gly Met Thr
Gly Glu Lys Pro Asp Glu Leu Ile Arg Glu Pro Phe Arg Trp Tyr Glu
Gly Asn Gly Ile Gly Gln Thr Ser Trp Glu Thr Pro Val Tyr Asn Lys
Gly Gly Asn Gly Val Ser Val Glu Ala Gln Thr Lys Gln Lys Asp Ser
Leu Leu Asn His Tyr Arg Glu Met Ile Arg Val Arg Gln Gln His Glu
Glu Leu Val Lys Gly Thr Leu Gln Ser Ile Ser Val Asp Ser Lys Glu
Val Val Ala Tyr Ser Arg Thr Tyr Lys Gly Lys Ser Ile Ser Val Tyr
His Asn Ile Ser Asn Gln Pro Val Lys Val Ser Val Ala Ala Lys Gly
Asn Leu Ile Phe Ala Ser Glu Lys Gly Ala Lys Lys Val Lys Asn Gln
Leu Val Ile Pro Ala Asn Ala Thr Val Leu Ile Lys
```
FIGURE 16EEEEEEE
SEQ ID NO: 163
```
atggtacgtcccgaacgacgggctgcattggaaccgactatcgaacgactcgcagcacttgaaag
acattgggtgacgacggtgtggattccgccggcgtacaaaggcacgtcacagaacgatgtcgggt
atggggcgtacgatttatacgatctcggcgaattcaaccaaaaagggacgacccggacgaagtac
gggacgaaagcgcagctccagacgccatctcgaacttgcgcggtaaagggatcggtgtgtacgg
cgacgtcgtcatgaatcacaaggcgggccgattataccgaatccgttcaggcgatcgaggtca
atccgtcgaaccggaaccaagaaacgtccggtgagtatggcatctcggcctggactggttcaac
ttcgcggggcgcaacaatacatactcgccgttcaaatggcgctggtaccattttgacggtaccga
ttgggatcagtcacgcagcttgagccgcatctataagttcaagagcacaggcaaggcgtgggaca
cggacgtgtcgaacgagaacggcaactatgattatcttatgtatgccgacgtcgatttcgagcat
cccgaggtccgccaagagatgaagaactggggcaaatggtacgccgactcgctcgggctcgacgg
tttccggttggatgcggtcaaacatatcagccactcgtacttgaaggagtgggtgacgagcgtgc
gccagacgaccgggaaagagatgttcacggtcgccgagtattggaagaacgatctcggtgccatc
aacgactatctgtataagacgggctacacgcactccgtcttcgatgtgccgctccattataactt
ccaagcggccggtaacggcggcgggtattacgatatgcgcaacatcttgaaaggcaccgtcaccg
aacagcatccgtcgctgtccgtgacgattgtcgataaccacgactcacagccgggccagtcgctc
gagtcgacggtcgccaactggttcaaaccgctcgcctacgcgacgatcatgacgcgcggtcaggg
ttatccggccctcttctatggagactattatggcacgaaagggacgacgaaccgcgaaatcccga
acatgtcgggcacgctccaaccgattttgaaggcacgaaaagacttcgcctacgggacgcagcat
gactacctcgatcatcaggacgtcatcggctggacacgtgaaggtgtgaccgaccgtgccaaatc
gggtctcgcgacgattctatcggacggtccggcggctcgaagtggatgtacgtcggcaaacaga
acgccggcgaggtatggaaagacatgacgaacaacaacgcccgtctcgtcacgatcaatgctgac
ggctggggtcagttcttcgtcaacggaggctcggtctcgatttatacgcaacaataa
```

FIGURE 16FFFFFFF
SEQ ID NO: 164

Met Val Arg Pro Glu Arg Arg Ala Ala Leu Glu Pro Thr Ile Glu Arg
Leu Ala Ala Leu Glu Arg His Trp Val Thr Thr Val Trp Ile Pro Pro
Ala Tyr Lys Gly Thr Ser Gln Asn Asp Val Gly Tyr Gly Ala Tyr Asp
Leu Tyr Asp Leu Gly Glu Phe Asn Gln Lys Gly Thr Thr Arg Thr Lys
Tyr Gly Thr Lys Ala Gln Leu Gln Thr Ala Ile Ser Asn Leu Arg Gly
Lys Gly Ile Gly Val Tyr Gly Asp Val Val Met Asn His Lys Gly Gly
Ala Asp Tyr Thr Glu Ser Val Gln Ala Ile Glu Val Asn Pro Ser Asn
Arg Asn Gln Glu Thr Ser Gly Glu Tyr Gly Ile Ser Ala Trp Thr Gly
Phe Asn Phe Ala Gly Arg Asn Asn Thr Tyr Ser Pro Phe Lys Trp Arg
Trp Tyr His Phe Asp Gly Thr Asp Trp Asp Gln Ser Arg Ser Leu Ser
Arg Ile Tyr Lys Phe Lys Ser Thr Gly Lys Ala Trp Asp Thr Asp Val
Ser Asn Glu Asn Gly Asn Tyr Asp Tyr Leu Met Tyr Ala Asp Val Asp
Phe Glu His Pro Glu Val Arg Gln Glu Met Lys Asn Trp Gly Lys Trp
Tyr Ala Asp Ser Leu Gly Leu Asp Gly Phe Arg Leu Asp Ala Val Lys
His Ile Ser His Ser Tyr Leu Lys Glu Trp Val Thr Ser Val Arg Gln
Thr Thr Gly Lys Glu Met Phe Thr Val Ala Glu Tyr Trp Lys Asn Asp
Leu Gly Ala Ile Asn Asp Tyr Leu Tyr Lys Thr Gly Tyr Thr His Ser
Val Phe Asp Val Pro Leu His Tyr Asn Phe Gln Ala Ala Gly Asn Gly
Gly Gly Tyr Tyr Asp Met Arg Asn Ile Leu Lys Gly Thr Val Thr Glu
Gln His Pro Ser Leu Ser Val Thr Ile Val Asp Asn His Asp Ser Gln
Pro Gly Gln Ser Leu Glu Ser Thr Val Ala Asn Trp Phe Lys Pro Leu
Ala Tyr Ala Thr Ile Met Thr Arg Gly Gln Gly Tyr Pro Ala Leu Phe
Tyr Gly Asp Tyr Tyr Gly Thr Lys Gly Thr Thr Asn Arg Glu Ile Pro
Asn Met Ser Gly Thr Leu Gln Pro Ile Leu Lys Ala Arg Lys Asp Phe
Ala Tyr Gly Thr Gln His Asp Tyr Leu Asp His Gln Asp Val Ile Gly
Trp Thr Arg Glu Gly Val Thr Asp Arg Ala Lys Ser Gly Leu Ala Thr
Ile Leu Ser Asp Gly Pro Gly Gly Ser Lys Trp Met Tyr Val Gly Lys
Gln Asn Ala Gly Glu Val Trp Lys Asp Met Thr Asn Asn Asn Ala Arg
Leu Val Thr Ile Asn Ala Asp Gly Trp Gly Gln Phe Phe Val Asn Gly
Gly Ser Val Ser Ile Tyr Thr Gln Gln

FIGURE 16GGGGGGG
SEQ ID NO: 165

```
atgcagtatttcgagtggtacgtgccaaatgatggggaacattggaatcgtttgcgtaatgatgc
tgaaaatttagctcataaaggaattacatctgtatggataccaccgtatataaaggaacttcac
aaaatgatgtagggtatggagtgtatgatgtatatgatttgggagaattcaatcaaaaggaacg
atacggacaaaatatgggacaaaagcacaattaaaatctgcaattgaggctttacataatcaaaa
tatcgatgtatacggtgatgttgttatgaaccataaaggtggggcagattatactgaggttgtaa
cagccgttgaggtagaccgtaacaatcgaaatattgaaacatcgagtgattatcaaatagatgcg
tggacgggatttgattttccaggacgcagggactcctattctaatttaaatggagatggtttca
ttttgatggaacagattgggatgagggaaggaaattaaatagaatttataaatttaaaggcgtag
gtaaagcttgggactgggaagtgtctagtgagaatggtaactatgattatttaatgtatgcagat
cttgatttcgatcatcctgaagttgcaaatgaaatgaaaaactggggaacctggtatgcggacga
attaaatttagatggctttcgtttagacgcagttaaacatattgaccatgagtatcttcgtgatt
gggtaaatcatgttagaaagcaaacggggaaggaaatgtttacagtagctgaatattggcaaaat
gatattcgtactttaaacaattatttagggaaagtaaattataatcaatctgtgttcgatgcacc
tcttcattataattttcattatgcttcaacagggaatggaaattatgatatgaggaatatttaa
agggtacggtagtagaaagtcatcctacacttgctgttactcttgttgagaatcatgattctcag
cctggacagtcattagaatctgttgtgagtccttggtttaagccgttggcctatgcatttatttt
aacgcgtgcagaagggtatccttctgttttttatggagattactatggcacaaatggaaatagta
gttatgaaattccaacgttaaaggataaaattgatccaattctgacggcacgaaaaaactttgca
tatggtacgcaacatgattatttagaccatccagatgtgattggctggacaagagaagggatag
```

FIGURE 16GGGGGGG cont
tatacatgctaattctggtttagcaacattaatctctgatggaccaggaggatcaaaatggatga
atgttggaaagaacaacgcagggaaatatggtacgatattacgggcaatcaaacaaatactgta
acgattaataaagatggatgggggcagttccatgtaaatgggggctctgtttcaatatatgttca
gaagtaa

FIGURE 16HHHHHHH
SEQ ID NO: 166

| | | | | | | | | | | | | | |
|---|---|---|---|---|---|---|---|---|---|---|---|---|---|
| Met | Gln | Tyr | Phe | Glu | Trp | Tyr | Val | Pro | Asn | Asp | Gly | Glu | His | Trp | Asn |
| Arg | Leu | Arg | Asn | Asp | Ala | Glu | Asn | Leu | Ala | His | Lys | Gly | Ile | Thr | Ser |
| Val | Trp | Ile | Pro | Pro | Val | Tyr | Lys | Gly | Thr | Ser | Gln | Asn | Asp | Val | Gly |
| Tyr | Gly | Val | Tyr | Asp | Val | Tyr | Asp | Leu | Gly | Glu | Phe | Asn | Gln | Lys | Gly |
| Thr | Ile | Arg | Thr | Lys | Tyr | Gly | Thr | Lys | Ala | Gln | Leu | Lys | Ser | Ala | Ile |
| Glu | Ala | Leu | His | Asn | Gln | Asn | Ile | Asp | Val | Tyr | Gly | Asp | Val | Val | Met |
| Asn | His | Lys | Gly | Gly | Ala | Asp | Tyr | Thr | Glu | Val | Val | Thr | Ala | Val | Glu |
| Val | Asp | Arg | Asn | Asn | Arg | Asn | Ile | Glu | Thr | Ser | Ser | Asp | Tyr | Gln | Ile |
| Asp | Ala | Trp | Thr | Gly | Phe | Asp | Phe | Pro | Gly | Arg | Arg | Asp | Ser | Tyr | Ser |
| Asn | Phe | Lys | Trp | Arg | Trp | Phe | His | Phe | Asp | Gly | Thr | Asp | Trp | Asp | Glu |
| Gly | Arg | Lys | Leu | Asn | Arg | Ile | Tyr | Lys | Phe | Lys | Gly | Val | Gly | Lys | Ala |
| Trp | Asp | Trp | Glu | Val | Ser | Ser | Glu | Asn | Gly | Asn | Tyr | Asp | Tyr | Leu | Met |
| Tyr | Ala | Asp | Leu | Asp | Phe | Asp | His | Pro | Glu | Val | Ala | Asn | Glu | Met | Lys |
| Asn | Trp | Gly | Thr | Trp | Tyr | Ala | Asp | Glu | Leu | Asn | Leu | Asp | Gly | Phe | Arg |
| Leu | Asp | Ala | Val | Lys | His | Ile | Asp | His | Glu | Tyr | Leu | Arg | Asp | Trp | Val |
| Asn | His | Val | Arg | Lys | Gln | Thr | Gly | Lys | Glu | Met | Phe | Thr | Val | Ala | Glu |
| Tyr | Trp | Gln | Asn | Asp | Ile | Arg | Thr | Leu | Asn | Asn | Tyr | Leu | Gly | Lys | Val |
| Asn | Tyr | Asn | Gln | Ser | Val | Phe | Asp | Ala | Pro | Leu | His | Tyr | Asn | Phe | His |
| Tyr | Ala | Ser | Thr | Gly | Asn | Gly | Asn | Tyr | Asp | Met | Arg | Asn | Ile | Leu | Lys |
| Gly | Thr | Val | Val | Glu | Ser | His | Pro | Thr | Leu | Ala | Val | Thr | Leu | Val | Glu |
| Asn | His | Asp | Ser | Gln | Pro | Gly | Gln | Ser | Leu | Glu | Ser | Val | Val | Ser | Pro |
| Trp | Phe | Lys | Pro | Leu | Ala | Tyr | Ala | Phe | Ile | Leu | Thr | Arg | Ala | Glu | Gly |
| Tyr | Pro | Ser | Val | Phe | Tyr | Gly | Asp | Tyr | Tyr | Gly | Thr | Asn | Gly | Asn | Ser |
| Ser | Tyr | Glu | Ile | Pro | Thr | Leu | Lys | Asp | Lys | Ile | Asp | Pro | Ile | Leu | Thr |
| Ala | Arg | Lys | Asn | Phe | Ala | Tyr | Gly | Thr | Gln | His | Asp | Tyr | Leu | Asp | His |
| Pro | Asp | Val | Ile | Gly | Trp | Thr | Arg | Glu | Gly | Asp | Ser | Ile | His | Ala | Asn |
| Ser | Gly | Leu | Ala | Thr | Leu | Ile | Ser | Asp | Gly | Pro | Gly | Gly | Ser | Lys | Trp |
| Met | Asn | Val | Gly | Lys | Asn | Ala | Gly | Glu | Ile | Trp | Tyr | Asp | Ile | Thr |
| Gly | Asn | Gln | Thr | Asn | Thr | Val | Thr | Ile | Asn | Lys | Asp | Gly | Trp | Gly | Gln |
| Phe | His | Val | Asn | Gly | Gly | Ser | Val | Ser | Ile | Tyr | Val | Gln | Lys |

FIGURE 16IIIIII
SEQ ID NO: 167
atgcaaacgattgcaaaaaaggggatgaaacgatgaaagggaaaaaatggacagctttagctct
aacactgccgctggctgctagcttatcaacaggcgttcacgccgaaaccgtacataaaggtaaat
ctccaacagcagataaaaacggtgtattttatgaggtgtatgtaaactctttttacgatgcaaat
aaagatggacatggtgatttaaaaggtcttacacaaaagttggattatttaaatgatggcaattc
tcatacaaagaatgatcttcaagtaaacgggatttggatgatgccggtcaacccttctcccagct
atcataaatatgatgtaacggactattataatattgatccgcagtatggaaatctgcaagatttt
cgcaaactgatgaagaagcagataaacgagatgtaaaagtcattatggacctcgttgtgaatca
tacgagcagtgaacacccttggtttcaagctgcattaaagataaaaacagcaagtacagagatt
actatatctgggctgataaaaataccgacttgaatgaaaaggatcttggggacagcaagtatgg
cataaagccccaaacggagagtattttacggaacgttttgggaaggaatgccggacttaaatta
cgataatcctgaagtaagaaagaaatgattaacgtaggaaagttttggctaaagcaaggagttg
acgggttccgtctagatgctgcgcttcatatttttaaaggccaaacacctgaaggcgctaagaaa
aatctcctgtggtggaatgaatttagagatgcaatgaaaaaggaaaaccctaacgtatatctaac
gggtgaagtatgggatcaaccggaagtagtagctccttactatcaatcgcttgattctttattta

FIGURE 16IIIIIII cont
actttgatttagcaggaaagattgtaaactctgtaaaatcaggaaatgatcaaggaatcgcgact
gcagcagcggcaacggatgaactgttcaaatcatacaatccaaataaaattgacggtattttctt
aaccaaccatgaccaaaatcgcgtcatgagtgagctaagcggcgatgtgaataaagcaaagtcag
ctgcctctatcttacttacgcttcctggcaacccgtatatttattacggtgaagaaatcggcatg
accggtgaaaagcctgatgagttaatccgtgaaccgttccgctggtacgaaggaaacggacttgg
acaaaccagctgggaaacacctgtatacaacaaaggcggcaacggcgtgtctgtagaagcacaaa
caaaacaaaaggactctttgttaaatcattaccgtgaaatgattcgcgtgcgtcagcagcacgaa
gagttagtaaaaggaacgcttcaatctatttcagtagacagtaaagaagtcgttgcctatagccg
cacgtataaaggcaaatcgattagcgtgtatcataatatttcaaatcaaccggtaaaagtatctg
tagcagcaaaaggtaaattgattttggtagtgaaaaaggtgctaagaaagtcaaaaatcagctt
gtgattccggcgaatacaacggttttaataaaataa

FIGURE 16JJJJJJJ
SEQ ID NO: 168
Met Gln Thr Ile Ala Lys Lys Gly Asp Glu Thr Met Lys Gly Lys Lys
Trp Thr Ala Leu Ala Leu Thr Leu Pro Leu Ala Ala Ser Leu Ser Thr
Gly Val His Ala Glu Thr Val His Lys Gly Lys Ser Pro Thr Ala Asp
Lys Asn Gly Val Phe Tyr Glu Val Tyr Val Asn Ser Phe Tyr Asp Ala
Asn Lys Asp Gly His Gly Asp Leu Lys Gly Leu Thr Gln Lys Leu Asp
Tyr Leu Asn Asp Gly Asn Ser His Thr Lys Asn Asp Leu Gln Val Asn
Gly Ile Trp Met Met Pro Val Asn Pro Ser Pro Ser Tyr His Lys Tyr
Asp Val Thr Asp Tyr Tyr Asn Ile Asp Pro Gln Tyr Gly Asn Leu Gln
Asp Phe Arg Lys Leu Met Lys Glu Ala Asp Lys Arg Asp Val Lys Val
Ile Met Asp Leu Val Val Asn His Thr Ser Ser Glu His Pro Trp Phe
Gln Ala Ala Leu Lys Asp Lys Asn Ser Lys Tyr Arg Asp Tyr Tyr Ile
Trp Ala Asp Lys Asn Thr Asp Leu Asn Glu Lys Gly Ser Trp Gly Gln
Gln Val Trp His Lys Ala Pro Asn Gly Glu Tyr Phe Tyr Gly Thr Phe
Trp Glu Gly Met Pro Asp Leu Asn Tyr Asp Asn Pro Glu Val Arg Lys
Glu Met Ile Asn Val Gly Lys Phe Trp Leu Lys Gln Gly Val Asp Gly
Phe Arg Leu Asp Ala Ala Leu His Ile Phe Lys Gly Gln Thr Pro Glu
Gly Ala Lys Lys Asn Leu Leu Trp Trp Asn Glu Phe Arg Asp Ala Met
Lys Lys Glu Asn Pro Asn Val Tyr Leu Thr Gly Glu Val Trp Asp Gln
Pro Glu Val Val Ala Pro Tyr Tyr Gln Ser Leu Asp Ser Leu Phe Asn
Phe Asp Leu Ala Gly Lys Ile Val Asn Ser Val Lys Ser Gly Asn Asp
Gln Gly Ile Ala Thr Ala Ala Ala Thr Asp Glu Leu Phe Lys Ser
Tyr Asn Pro Asn Lys Ile Asp Gly Ile Phe Leu Thr Asn His Asp Gln
Asn Arg Val Met Ser Glu Leu Ser Gly Asp Val Asn Lys Ala Lys Ser
Ala Ala Ser Ile Leu Leu Thr Leu Pro Gly Asn Pro Tyr Ile Tyr Tyr
Gly Glu Glu Ile Gly Met Thr Gly Glu Lys Pro Asp Glu Leu Ile Arg
Glu Pro Phe Arg Trp Tyr Glu Gly Asn Gly Leu Gly Gln Thr Ser Trp
Glu Thr Pro Val Tyr Asn Lys Gly Gly Asn Gly Val Ser Val Glu Ala
Gln Thr Lys Gln Lys Asp Ser Leu Leu Asn His Tyr Arg Glu Met Ile
Arg Val Arg Gln Gln His Glu Glu Leu Val Lys Gly Thr Leu Gln Ser
Ile Ser Val Asp Ser Lys Glu Val Val Ala Tyr Ser Arg Thr Tyr Lys
Gly Lys Ser Ile Ser Val Tyr His Asn Ile Ser Asn Gln Pro Val Lys
Val Ser Val Ala Ala Lys Gly Lys Leu Ile Phe Gly Ser Glu Lys Gly
Ala Lys Lys Val Lys Asn Gln Leu Val Ile Pro Ala Asn Thr Thr Val
Leu Ile Lys

FIGURE 16KKKKKKK
SEQ ID NO: 169
atgaaaacattcaaattaaaacgcactttttaccgctaaccttgctgctcagtgctcctgcctt
tgctgggcaaaatggcaccatgatgcagtattttcattggtatgtacctaatgatggcgcattat
ggacgcaggttgaaagcaatgctccagcactcgctgaaaacggttttacagcgctctggctaccg
ccagcttacaaaggcgcgggcggcagtaatgacgtcggttatggcgtctatgatatgtacgattt
aggtgagtttgatcaaaaaggctcagtacgaaccaaatacggcaccaaggctcagtacatctctg
caatcaatgccgcgcacaacaacaatatccaaatctacggcgatgttgtgtttaaccaccgaggt
ggtgctgatgggaagtcgtgggtcgataccaagcgcgttgattgggacaaccgtaacattgaact
gggcgacaaatggattgaagcttgggttgagtttaattttcctggccgcaacgacaaatactcaa
acttccattggacttggtatcactttgacggtgttgactggatgatgccggcaaagaaaaagcg
atctttaaattcaaaggcgaaggaaaagcatgggattgggaagtcagctctgaaaaaggcaatta
cgactacctaatgtacgccgatttagacatggatcaccaagaagttaaacaagagctgaaagatt
ggggtgagtggtacatcaacatgaccggcgttgatggctttagaatggatgccgtgaagcacatt
aaatatcagtatctacaagagtggattgatcatttacgttggaaaacaggcaaagagcttttcac
cgttggtgagtattggaattacgacgtaaatcaactgcataactttattactaagacctctggca
gtatgtcgttgttcgatgcgccgcttcacatgaacttctacaacgcgtcaaaatctggcggcaat
tacgatatgcgccaaatcatgaatggcacgttgatgaaggacaacccagtcaaagctgtgactct
cgtagaaaaccacgatacacagccattgcaggcgttagagtcgacagtggattggtggttcaagc
ctcttgcttacgcattcatttattgcgtgaagaaggttatccatcagtgttctacgcagattac
tacggcgcgcagtacagcgacaaaggctacaacatcaatatggccaaagttccttacattgaaga
acttgtaacactgcgtaaagagtatgcgtatggcaaacagaattcttatctcgaccactgggatg
tgattggctggacccgagagggcgatgctgaacatccaaactcaatggcggtgatcatgagtgat
ggaccaggtggcaaaaaatggatgtataccggtaagccaagcacgcgctatgtcgacaagctggg
tatccgaactgaagaagtttggaccgataccaatggctgggcagaatttcctgtcaatggtggtt
cagtctcggtttgggtgggcgttaagtaa

FIGURE 16LLLLLLL
SEQ ID NO: 170

Met Lys Thr Phe Lys Leu Lys Arg Thr Phe Leu Pro Leu Thr Leu Leu
Leu Ser Ala Pro Ala Phe Ala Gly Gln Asn Gly Thr Met Met Gln Tyr
Phe His Trp Tyr Val Pro Asn Asp Gly Ala Leu Trp Thr Gln Val Glu
Ser Asn Ala Pro Ala Leu Ala Glu Asn Gly Phe Thr Ala Leu Trp Leu
Pro Pro Ala Tyr Lys Gly Ala Gly Gly Ser Asn Asp Val Gly Tyr Gly
Val Tyr Asp Met Tyr Asp Leu Gly Glu Phe Asp Gln Lys Gly Ser Val
Arg Thr Lys Tyr Gly Thr Lys Ala Gln Tyr Ile Ser Ala Ile Asn Ala
Ala His Asn Asn Asn Ile Gln Ile Tyr Gly Asp Val Val Phe Asn His
Arg Gly Gly Ala Asp Gly Lys Ser Trp Val Asp Thr Lys Arg Val Asp
Trp Asp Asn Arg Asn Ile Glu Leu Gly Asp Lys Trp Ile Glu Ala Trp
Val Glu Phe Asn Phe Pro Gly Arg Asn Asp Lys Tyr Ser Asn Phe His
Trp Thr Trp Tyr His Phe Asp Gly Val Asp Trp Asp Asp Ala Gly Lys
Glu Lys Ala Ile Phe Lys Phe Lys Gly Glu Gly Lys Ala Trp Asp Trp
Glu Val Ser Ser Glu Lys Gly Asn Tyr Asp Tyr Leu Met Tyr Ala Asp
Leu Asp Met Asp His Gln Glu Val Lys Gln Glu Leu Lys Asp Trp Gly
Glu Trp Tyr Ile Asn Met Thr Gly Val Asp Gly Phe Arg Met Asp Ala
Val Lys His Ile Lys Tyr Gln Tyr Leu Gln Glu Trp Ile Asp His Leu
Arg Trp Lys Thr Gly Lys Glu Leu Phe Thr Val Gly Glu Tyr Trp Asn
Tyr Asp Val Asn Gln Leu His Asn Phe Ile Thr Lys Thr Ser Gly Ser
Met Ser Leu Phe Asp Ala Pro Leu His Met Asn Phe Tyr Asn Ala Ser
Lys Ser Gly Gly Asn Tyr Asp Met Arg Gln Ile Met Asn Gly Thr Leu
Met Lys Asp Asn Pro Val Lys Ala Val Thr Leu Val Glu Asn His Asp
Thr Gln Pro Leu Gln Ala Leu Glu Ser Thr Val Asp Trp Trp Phe Lys
Pro Leu Ala Tyr Ala Phe Ile Leu Leu Arg Glu Glu Gly Tyr Pro Ser
Val Phe Tyr Ala Asp Tyr Tyr Gly Ala Gln Tyr Ser Asp Lys Gly Tyr

FIGURE 16LLLLLLL cont
```
Asn Ile Asn Met Ala Lys Val Pro Tyr Ile Glu Glu Leu Val Thr Leu
Arg Lys Glu Tyr Ala Tyr Gly Lys Gln Asn Ser Tyr Leu Asp His Trp
Asp Val Ile Gly Trp Thr Arg Glu Gly Asp Ala Glu His Pro Asn Ser
Met Ala Val Ile Met Ser Asp Gly Pro Gly Gly Lys Lys Trp Met Tyr
Thr Gly Lys Pro Ser Thr Arg Tyr Val Asp Lys Leu Gly Ile Arg Thr
Glu Glu Val Trp Thr Asp Thr Asn Gly Trp Ala Glu Phe Pro Val Asn
Gly Gly Ser Val Ser Val Trp Val Gly Val Lys
```

FIGURE 16MMMMMMM
SEQ ID NO: 171
```
gtgtatgtaaactcttttacgatgcaaataaagatggacatggtgatttaaaaggtcttacaca
aaagttggattatttaaatgatggcaattctcatacaaagaatgatcttcaagtaaacggattt
ggatgatgccggtcaacccttctcccagctatcataaatatgatgtaacggactattataatatt
gatccgcagtatggaaatctgcaagattttcgcaaactgatgaaagaagcagataaacgagatgt
aaaagtcattatggacctcgttgtgaatcatacgagcagtgaacacccttggtttcaagctgcat
taaaagataaaaacagcaagtacagagattactatatctgggctgataaaaataccgacttgaat
gaaaaaggatcttggggacagcaagtatggcataaagccccaaacggagagtattttttacggaac
gttttgggaaggaatgccggacttaaattacgataatcctgaagtaagaaaagaaatgattaacg
taggaaagttttggctaaagcaaggagttgacgggttccgtctagatgctgcgcttcatattttt
aaaggccaaacacctgaaggcgctaagaaaaatctcctgtggtggaatgaatttagagatgcaat
gaaaaaggaaaaccctaacgtatatctaacgggtgaagtatgggatcaaccggaagtagtagctc
cttactatcaatcgcttgattctttatttaactttgatttagcaggaaagattgtaaactctgta
aaatcaggaaatgatcaaggaatcgcgactgcagcagcggcaacggatgaactgttcaaatcata
caatccaaataaaattgacggtatttcttaaccaaccatgaccaaaatcgcgtcatgagtgagc
taagcggcgatgtgaataaagcaaagtcagctgcctctatcttacttacgcttcctggcaacccg
tatatttattacggtgaagaaatcggcatgaccggtgaaaagcctgatgagttaatccgtgaacc
gttccgctggtacgaaggaaacggacttggacaaaccagctgggaaacacctgtatacaacaaag
gcggcaacggcgtgtctgtagaagcacaaacaaaacaaaaggactctttgttaaatcattaccgt
gaaatgattcgcgtgcgtcagcagcacgaagagttagtaaaaggaacgcttcaatctatttcagt
agacagtaaagaagtcgttgcctatagccgcacgtataaaggcaaatcgattagcgtgtatcata
atatttcaaatcaaccggtaaaagtatctgtagcagcaaaaggtaaattgattttttggtagtgaa
aaaggtgctaagaaagtcaaaaatcagcttgtgattccggcgaatacaacggttttaataaaata
a
```

FIGURE 16NNNNNNN
SEQ ID NO: 172
```
Val Tyr Val Asn Ser Phe Tyr Asp Ala Asn Lys Asp Gly His Gly Asp
Leu Lys Gly Leu Thr Gln Lys Leu Asp Tyr Leu Asn Asp Gly Asn Ser
His Thr Lys Asn Asp Leu Gln Val Asn Gly Ile Trp Met Met Pro Val
Asn Pro Ser Pro Ser Tyr His Lys Tyr Asp Val Thr Asp Tyr Tyr Asn
Ile Asp Pro Gln Tyr Gly Asn Leu Gln Asp Phe Arg Lys Leu Met Lys
Glu Ala Asp Lys Arg Asp Val Lys Val Ile Met Asp Leu Val Val Asn
His Thr Ser Ser Glu His Pro Trp Phe Gln Ala Ala Leu Lys Asp Lys
Asn Ser Lys Tyr Arg Asp Tyr Tyr Ile Trp Ala Asp Lys Asn Thr Asp
Leu Asn Glu Lys Gly Ser Trp Gly Gln Gln Val Trp His Lys Ala Pro
Asn Gly Glu Tyr Phe Tyr Gly Thr Phe Trp Glu Gly Met Pro Asp Leu
Asn Tyr Asp Asn Pro Glu Val Arg Lys Glu Met Ile Asn Val Gly Lys
Phe Trp Leu Lys Gln Gly Val Asp Gly Phe Arg Leu Asp Ala Ala Leu
His Ile Phe Lys Gly Gln Thr Pro Glu Gly Ala Lys Lys Asn Leu Leu
Trp Trp Asn Glu Phe Arg Asp Ala Met Lys Lys Glu Asn Pro Asn Val
Tyr Leu Thr Gly Glu Val Trp Asp Gln Pro Glu Val Val Ala Pro Tyr
Tyr Gln Ser Leu Asp Ser Leu Phe Asn Phe Asp Leu Ala Gly Lys Ile
Val Asn Ser Val Lys Ser Gly Asn Asp Gln Gly Ile Ala Thr Ala Ala
Ala Ala Thr Asp Glu Leu Phe Lys Ser Tyr Asn Pro Asn Lys Ile Asp
```

FIGURE 16NNNNNNN cont
Gly Ile Phe Leu Thr Asn His Asp Gln Asn Arg Val Met Ser Glu Leu
Ser Gly Asp Val Asn Lys Ala Lys Ser Ala Ala Ser Ile Leu Leu Thr
Leu Pro Gly Asn Pro Tyr Ile Tyr Tyr Gly Glu Glu Ile Gly Met Thr
Gly Glu Lys Pro Asp Glu Leu Ile Arg Glu Pro Phe Arg Trp Tyr Glu
Gly Asn Gly Leu Gly Gln Thr Ser Trp Glu Thr Pro Val Tyr Asn Lys
Gly Gly Asn Gly Val Ser Val Glu Ala Gln Thr Lys Gln Lys Asp Ser
Leu Leu Asn His Tyr Arg Glu Met Ile Arg Val Arg Gln Gln His Glu
Glu Leu Val Lys Gly Thr Leu Gln Ser Ile Ser Val Asp Ser Lys Glu
Val Val Ala Tyr Ser Arg Thr Tyr Lys Gly Lys Ser Ile Ser Val Tyr
His Asn Ile Ser Asn Gln Pro Val Lys Val Ser Val Ala Ala Lys Gly
Lys Leu Ile Phe Gly Ser Glu Lys Gly Ala Lys Lys Val Lys Asn Gln
Leu Val Ile Pro Ala Asn Thr Thr Val Leu Ile Lys

FIGURE 16OOOOOOO
SEQ ID NO: 173
atgcaaacgattgcaaaaaaggggatgaaacgatgaaagggaaaaaatggacagctttagctct
aacactgccgctggctgctagcttatcacaggcgttcacgcagaaactgtacataaaggtaaag
ctccaacagcagataaaaacggtgttttttatgaggtgtatgtaaactcttttacgatgcaaat
aaagatggacatggtgatttaaaaggtctgacacaaaagttggattatttaaatgacggcaattc
tcatacaaagaatgatcttcaagtaaacgggatttggatgatgccggtaaaccttctcctagct
atcataaatatgatgtaacggactattataacattgatcctcagtacggaagtctgcaagatttc
cgcaaactgatgaaagaagcagataaacgagacgtaaaagttattatggaccttgttgtgaatca
tacgagcagtgaacacccttggtttcaagctgcactaaaagataaaaacagcaagtacagagatt
actatatttgggctgataaaaataccgatttgaatgaaaaggatcttggggacagcaagtatgg
cataaagctccaaacggagagtattttacggaacgttctgggaaggaatgcctgacttaaatta
cgataaccctgaagtaagaaaagaaatgattaacgtcggaaagttttggctaaagcaaggcgttg
atggcttccgcttagatgctgcccttcatatctttaaaggtcaaactcctgaaggcgctaagaaa
aatctcctgtggtggaatgagtttagagatgcaatgaaaaaagaaaaccctaacgtatatctaac
gggtgaagtatgggatcagccggaagtagtagctccttattatcaatcgcttgattccctattta
actttgatttagcaggaaaaattgtcagctctgtaaaagcaggaaatgatcaaggaatcgccact
gcagcagcggcaacggatgagctgttcaaatcatacaatccaaataaaattgacggcatttctt
aaccaaccatgaccaaaaccgcgtcatgagtgagctaagcggagatgtgaataaagcaaaatcag
ctgcttctatcttacttacgcttcctggaaatccgtatatttattacggtgaagaaattggcatg
accggtgaaaagcctgatgaattaatccgtgaaccgttccgctggtacgaaggcaacggaattgg
acaaactagctgggaaacacctgtatataacaaaggcggcaatggtgtgtctgtagaagcacaaa
ccaaacaaaaggattctttgttaaatcattaccgtgaaatgattcgcgtgcgtcagcagcacgaa
gagttagtaaaaggaacgcttcagtctatttcagtagacagtaaagaagttgtcgcttatagccg
tacgtataaaggcaactccattagtgtgtatcataatatttcaaatcaacctgtaaaagtatctg
tagcggcgaaaggtaaattgattttgctagtgaaaaaggtgctaaaaaaggcaaaaatcagctt
gtgattccggcgaatgcgacggttttaataaaataa

FIGURE 16PPPPPPP
SEQ ID NO: 174
Met Gln Thr Ile Ala Lys Lys Gly Asp Glu Thr Met Lys Gly Lys Lys
Trp Thr Ala Leu Ala Leu Thr Leu Pro Leu Ala Ala Ser Leu Ser Thr
Gly Val His Ala Glu Thr Val His Lys Gly Lys Ala Pro Thr Ala Asp
Lys Asn Gly Val Phe Tyr Glu Val Tyr Val Asn Ser Phe Tyr Asp Ala
Asn Lys Asp Gly His Gly Asp Leu Lys Gly Leu Thr Gln Lys Leu Asp
Tyr Leu Asn Asp Gly Asn Ser His Thr Lys Asn Asp Leu Gln Val Asn
Gly Ile Trp Met Met Pro Val Asn Pro Ser Pro Ser Tyr His Lys Tyr
Asp Val Thr Asp Tyr Tyr Asn Ile Asp Pro Gln Tyr Gly Ser Leu Gln
Asp Phe Arg Lys Leu Met Lys Glu Ala Asp Lys Arg Asp Val Lys Val
Ile Met Asp Leu Val Val Asn His Thr Ser Ser Glu His Pro Trp Phe
Gln Ala Ala Leu Lys Asp Lys Asn Ser Lys Tyr Arg Asp Tyr Tyr Ile

FIGURE 16PPPPPPP cont
Trp Ala Asp Lys Asn Thr Asp Leu Asn Glu Lys Gly Ser Trp Gly Gln
Gln Val Trp His Lys Ala Pro Asn Gly Glu Tyr Phe Tyr Gly Thr Phe
Trp Glu Gly Met Pro Asp Leu Asn Tyr Asp Asn Pro Glu Val Arg Lys
Glu Met Ile Asn Val Gly Lys Phe Trp Leu Lys Gln Gly Val Asp Gly
Phe Arg Leu Asp Ala Ala Leu His Ile Phe Lys Gly Gln Thr Pro Glu
Gly Ala Lys Lys Asn Leu Leu Trp Trp Asn Glu Phe Arg Asp Ala Met
Lys Lys Glu Asn Pro Asn Val Tyr Leu Thr Gly Glu Val Trp Asp Gln
Pro Glu Val Val Ala Pro Tyr Tyr Gln Ser Leu Asp Ser Leu Phe Asn
Phe Asp Leu Ala Gly Lys Ile Val Ser Ser Val Lys Ala Gly Asn Asp
Gln Gly Ile Ala Thr Ala Ala Ala Ala Thr Asp Glu Leu Phe Lys Ser
Tyr Asn Pro Asn Lys Ile Asp Gly Ile Phe Leu Thr Asn His Asp Gln
Asn Arg Val Met Ser Glu Leu Ser Gly Asp Val Asn Lys Ala Lys Ser
Ala Ala Ser Ile Leu Leu Thr Leu Pro Gly Asn Pro Tyr Ile Tyr Tyr
Gly Glu Glu Ile Gly Met Thr Gly Glu Lys Pro Asp Glu Leu Ile Arg
Glu Pro Phe Arg Trp Tyr Glu Gly Asn Gly Ile Gly Gln Thr Ser Trp
Glu Thr Pro Val Tyr Asn Lys Gly Gly Asn Gly Val Ser Val Glu Ala
Gln Thr Lys Gln Lys Asp Ser Leu Leu Asn His Tyr Arg Glu Met Ile
Arg Val Arg Gln Gln His Glu Glu Leu Val Lys Gly Thr Leu Gln Ser
Ile Ser Val Asp Ser Lys Glu Val Val Ala Tyr Ser Arg Thr Tyr Lys
Gly Asn Ser Ile Ser Val Tyr His Asn Ile Ser Asn Gln Pro Val Lys
Val Ser Val Ala Ala Lys Gly Lys Leu Ile Phe Ala Ser Glu Lys Gly
Ala Lys Lys Gly Lys Asn Gln Leu Val Ile Pro Ala Asn Ala Thr Val
Leu Ile Lys

FIGURE 16QQQQQQQ
SEQ ID NO: 175
atgaaaaatataatacgactttgtgctgccagcgctatcctcacggtgtcccacgccagttacgc
cgacgcaattttacacgcgtttaactggcaatataccgatgtaaccgccaatgcaaatcaaattg
ccgcaaatggctttaaaaaagtcctcatttcacccgcaatgaaatccagcggcagtcaatggtgg
gcccgctatcaaccgcaagacttgcgtgtcattgattctccgctgggcaacaaacaagatttagt
cgcgatgatcaatgcgctcaacagcgttggggtcgacgtgtatgctgacgtggtgcttaaccata
tggctaacgagtcatggaagcgcagtgacctgaactacccggggagtgaggtgctcaacgactat
caatcccgcagtgcttactatcaaaggcaaacacttttcggcaatttacaggagaaccttttttc
cgagaatgatttccatccggcaggctgtattaccaattggaatgatcctggccacgtccagtatt
ggcgcttgtcggcggacagggcgatactgggctaccggatctcgatcctaatcaatgggttgtg
agtcagcagaagagttacttgaacgcactcaaatcaatgggaatcaaagggttccgtatcgatgc
ggtcaaacatgagtcaatatcaaatagaccaagtgtttaccccagacattaccgctggtatgc
atatattcggagaagtcattaccagtggtgggcaaggtgatagcggctatgaggcttttcttgcc
ccttaccttaataataccgatcacgccgcttatgacttcccgctatttgcatcgattcgagccgc
gttttcattctctggtgggttaaatcagctacacaatccacaagcctatggccaagcgttacagg
actcacgtgcgatcacctttacgattacccacgacattccaaccaatgacggtttccgctaccag
atcatggatccaaccgatgaacagctcgcctatgcctacatcttgggcaaagatggaggaacgcc
acttgtctatagtgatgacctacctgacagcgaagacaaagacagtggtcgttgggccgatgtgt
ggcaagatccgaacatgattaacatgcttgccttccacaacgcgatgcaaggacaaagcatgact
gtagtggctagcgatcaatgtaccttgctatttaagcgcggcaagcaaggcgtggtaggaatcaa
taaatgtggcgagagtaagtcggtgactgtcgatacttaccagcatgagtttaactggtacaccc
cgtaccaagacgtattgagcggcgacatcaccacagtgagttctcgttatcaccaatttgttttg
ccagcgcgcagtgcaaggatgtggaaactataa

FIGURE 16RRRRRRR
SEQ ID NO: 176

Met Lys Asn Ile Ile Arg Leu Cys Ala Ala Ser Ala Ile Leu Thr Val
Ser His Ala Ser Tyr Ala Asp Ala Ile Leu His Ala Phe Asn Trp Gln
Tyr Thr Asp Val Thr Ala Asn Ala Asn Gln Ile Ala Ala Asn Gly Phe
Lys Lys Val Leu Ile Ser Pro Ala Met Lys Ser Ser Gly Ser Gln Trp
Trp Ala Arg Tyr Gln Pro Gln Asp Leu Arg Val Ile Asp Ser Pro Leu
Gly Asn Lys Gln Asp Leu Val Ala Met Ile Asn Ala Leu Asn Ser Val
Gly Val Asp Val Tyr Ala Asp Val Val Leu Asn His Met Ala Asn Glu
Ser Trp Lys Arg Ser Asp Leu Asn Tyr Pro Gly Ser Glu Val Leu Asn
Asp Tyr Gln Ser Arg Ser Ala Tyr Tyr Gln Arg Gln Thr Leu Phe Gly
Asn Leu Gln Glu Asn Leu Phe Ser Glu Asn Asp Phe His Pro Ala Gly
Cys Ile Thr Asn Trp Asn Asp Pro Gly His Val Gln Tyr Trp Arg Leu
Cys Gly Gly Gln Gly Asp Thr Gly Leu Pro Asp Leu Asp Pro Asn Gln
Trp Val Val Ser Gln Gln Lys Ser Tyr Leu Asn Ala Leu Lys Ser Met
Gly Ile Lys Gly Phe Arg Ile Asp Ala Val Lys His Met Ser Gln Tyr
Gln Ile Asp Gln Val Phe Thr Pro Asp Ile Thr Ala Gly Met His Ile
Phe Gly Glu Val Ile Thr Ser Gly Gly Gln Gly Asp Ser Gly Tyr Glu
Ala Phe Leu Ala Pro Tyr Leu Asn Asn Thr Asp His Ala Ala Tyr Asp
Phe Pro Leu Phe Ala Ser Ile Arg Ala Ala Phe Ser Phe Ser Gly Gly
Leu Asn Gln Leu His Asn Pro Gln Ala Tyr Gly Gln Ala Leu Gln Asp
Ser Arg Ala Ile Thr Phe Thr Ile Thr His Asp Ile Pro Thr Asn Asp
Gly Phe Arg Tyr Gln Ile Met Asp Pro Thr Asp Glu Gln Leu Ala Tyr
Ala Tyr Ile Leu Gly Lys Asp Gly Gly Thr Pro Leu Val Tyr Ser Asp
Asp Leu Pro Asp Ser Glu Asp Lys Asp Ser Gly Arg Trp Ala Asp Val
Trp Gln Asp Pro Asn Met Ile Asn Met Leu Ala Phe His Asn Ala Met
Gln Gly Gln Ser Met Thr Val Val Ala Ser Asp Gln Cys Thr Leu Leu
Phe Lys Arg Gly Lys Gln Gly Val Val Gly Ile Asn Lys Cys Gly Glu
Ser Lys Ser Val Thr Val Asp Thr Tyr Gln His Glu Phe Asn Trp Tyr
Thr Pro Tyr Gln Asp Val Leu Ser Gly Asp Ile Thr Thr Val Ser Ser
Arg Tyr His Gln Phe Val Leu Pro Ala Arg Ser Ala Arg Met Trp Lys
Leu

FIGURE 16SSSSSSS
SEQ ID NO: 177 atgaaaacattcaaattaaaacgcacttttttaccgctgaccttgctgctcagtgctcctgcctt
tgctgggcaaaatggcaccatgatgcagtattttcattggtacgtacctaatgatggcgcattat
ggacgcaggttgaaagcaatgctccagtactcgctgaaaacggttttacagcgctctggctaccg
cccgcatacaaaggcgcgggcggcagtaatgacgtcggttatggcgtctatgatatgtacgattt
aggtgagtttgaccaaaaaggctcagtacgaaccaaatacggcaccaaggctcagtacatctctg
caatcaatgccgcgcacaacaacaatatccaaatttacggcgacgttgtgtttaaccaccgaggt
ggcgctgatgggaagtcgtgggtcgataccaagcgcgttgattgggacaaccgcaatattgaact
gggcgacaaatggattgaagcttgggttgagtttaattttcctggccgcaacgacaaatactcga
acttccattggacttggtatcactttgacggtgttgactgggatgatgccggcaaagaaaaagcg
atctttaaattcaaaggcgaaggaaaagcatggattgggaagtcagctctgaaaaaggcaatta
cgactacctaatgtacgccgatttagacatggatcacccagaagttaaacaagagctgaaagatt
ggggtgagtggtacatcaacatgaccggcgttgatggctttagaatggatgccgtgaagcacatt
aaatatcagtatctacaagagtggattgatcatttacgttggaaaacaggcaaagagctttttcac
cgttggtgagtattggaattacgacgtaaatcaactgcacaacttttattactaagacctctggca
gtatgtcgttgttcgatgcgccgcttcacatgaatttctacaacgcgtcaaaatctggcggcact
tacgatatgcgccaaatcatgaatggcacgttgatgaaggacaacccagtcaaagcagtgactct
cgtagaaaccacgatacgcagccattgcaggcgttagagtcgacagtagattggtggttcaagc
ctcttgcttacgcattcattttattgcgtgaagaaggttatccatcggtgttctacgcagattac
tacggcgcgcagtacagcgacaaaggttacaacattaatatggccaaagtgccttacattgaaga

FIGURE 16SSSSSSS cont
acttgtaacactgcgtaaagagtatgcgtatggcaaacagaattcttatctcgaccattgggatg
tgattggctggacccgagagggcgatgctgaacatccaaactcaatggcggtgatcatgagtgat
ggaccgggcggcacaaaatggatgtataccggtaagccaagtacgcgctatgtcgacaagctggg
tatccgaactgaagatgtttggaccgatgccaatggctgggcagaatttcctgtcaatggtggtt
cagtctcggtttgggtgggcgttaagtaa

FIGURE 16TTTTTTT
SEQ ID NO: 178
Met Lys Thr Phe Lys Leu Lys Arg Thr Phe Leu Pro Leu Thr Leu Leu
Leu Ser Ala Pro Ala Phe Ala Gly Gln Asn Gly Thr Met Met Gln Tyr
Phe His Trp Tyr Val Pro Asn Asp Gly Ala Leu Trp Thr Gln Val Glu
Ser Asn Ala Pro Val Leu Ala Glu Asn Gly Phe Thr Ala Leu Trp Leu
Pro Pro Ala Tyr Lys Gly Ala Gly Gly Ser Asn Asp Val Gly Tyr Gly
Val Tyr Asp Met Tyr Asp Leu Gly Glu Phe Asp Gln Lys Gly Ser Val
Arg Thr Lys Tyr Gly Thr Lys Ala Gln Tyr Ile Ser Ala Ile Asn Ala
Ala His Asn Asn Asn Ile Gln Ile Tyr Gly Asp Val Val Phe Asn His
Arg Gly Gly Ala Asp Gly Lys Ser Trp Val Asp Thr Lys Arg Val Asp
Trp Asp Asn Arg Asn Ile Glu Leu Gly Asp Lys Trp Ile Glu Ala Trp
Val Glu Phe Asn Phe Pro Gly Arg Asn Asp Lys Tyr Ser Asn Phe His
Trp Thr Trp Tyr His Phe Asp Gly Val Asp Trp Asp Asp Ala Gly Lys
Glu Lys Ala Ile Phe Lys Phe Lys Gly Glu Gly Lys Ala Trp Asp Trp
Glu Val Ser Ser Glu Lys Gly Asn Tyr Asp Tyr Leu Met Tyr Ala Asp
Leu Asp Met Asp His Pro Glu Val Lys Gln Glu Leu Lys Asp Trp Gly
Glu Trp Tyr Ile Asn Met Thr Gly Val Asp Gly Phe Arg Met Asp Ala
Val Lys His Ile Lys Tyr Gln Tyr Leu Gln Glu Trp Ile Asp His Leu
Arg Trp Lys Thr Gly Lys Glu Leu Phe Thr Val Gly Glu Tyr Trp Asn
Tyr Asp Val Asn Gln Leu His Asn Phe Ile Thr Lys Thr Ser Gly Ser
Met Ser Leu Phe Asp Ala Pro Leu His Met Asn Phe Tyr Asn Ala Ser
Lys Ser Gly Gly Thr Tyr Asp Met Arg Gln Ile Met Asn Gly Thr Leu
Met Lys Asp Asn Pro Val Lys Ala Val Thr Leu Val Glu Asn His Asp
Thr Gln Pro Leu Gln Ala Leu Glu Ser Thr Val Asp Trp Trp Phe Lys
Pro Leu Ala Tyr Ala Phe Ile Leu Leu Arg Glu Glu Gly Tyr Pro Ser
Val Phe Tyr Ala Asp Tyr Tyr Gly Ala Gln Tyr Ser Asp Lys Gly Tyr
Asn Ile Asn Met Ala Lys Val Pro Tyr Ile Glu Glu Leu Val Thr Leu
Arg Lys Glu Tyr Ala Tyr Gly Lys Gln Asn Ser Tyr Leu Asp His Trp
Asp Val Ile Gly Trp Thr Arg Glu Gly Asp Ala Glu His Pro Asn Ser
Met Ala Val Ile Met Ser Asp Gly Pro Gly Gly Thr Lys Trp Met Tyr
Thr Gly Lys Pro Ser Thr Arg Tyr Val Asp Lys Leu Gly Ile Arg Thr
Glu Asp Val Trp Thr Asp Ala Asn Gly Trp Ala Glu Phe Pro Val Asn
Gly Gly Ser Val Ser Val Trp Val Gly Val Lys

FIGURE 16UUUUUUU
SEQ ID NO: 179
atgaaaacattcaaattaaaacgcacttttttaccgctaaccttgctgctcagtgctcctgcctt
tgccggcaaaatggcaccatgatgcagtactttcattggtacgtacctaatgatggcgcattat
ggacgcaggttgaaagcaatgctccagcactcgctgaaaacggttttacagcgctctggctaccg
ccagcttacaaaggcgcgggcggcagtaatgatgtcggttatggcgtctacgatatgtacgattt
aggtgagtttgatcaaaaggctcagtacgaaccaaatacggtaccaaggctcagtacatctctg
caatcaatgctgcgcacaacaacaatatccaaatttacggcgacgttgtgtttaaccatcgtggt
ggcgctgatgggaagtcgtgggtcgataccaagcgcgttgattgggacaaccgtaacattgaact
gggcgacaaatggattgaagcttgggttgagtttaattttcctagccgcaacgacaaatactcga
acttccattggacttggtatcactttgacggtgttgactgggatgatgccggcaagaaaaagcg
atctttaaattcaaaggcgaaggaaaagcatgggattgggaagtcagctctgaaaaaggcaatta
cgactacctaatgtacgccgatttagacatggatcacccagaagttaaacaagagctgaaagatt

FIGURE 16UUUUUUU cont
```
ggggtgagtggtacatcaacatgaccggcgttgatggctttagaatggatgccgttaagcacatt
aaatatcagtatctacaagagtggattgatcatttacgttggaaaacaggcaaagagcttttcac
cgttggtgagtattggaattacgacgtaaatcaactgcataactttattactaagacctctggca
gtatgtcgttgttcgatgcgccgcttcacatgaacttctacaacgcgtcaaaatctggcggcaat
tacgatatgcgccaaatcatgaatggcacgttgatgaaggacaacccagtcaaagctgtgactct
cgtagaaaaccacgatacgcagccattgcaggcgttagagtcgacagtggattggtggttcaagc
ctcttgcttacgcattcatcttgttgcgtgaagaaggttatccatcggtgttctacgcagattac
tacggcgcgcagtacagcgacaaaggttacaacattaatatggccaaagtgccttacattgaaga
acttgtaacactgcgtaaagagtatgcgtatggcaaacagaattcttatctcgaccattgggatg
tgattggctggactcgagagggcgatgctgaacatccaaactcaatggcggtgatcatgagtgat
ggaccgggcggaacaaaatggatgtataccggtaatccaagcacgcgctatgtcgacaagctggg
tatccgaactgaagatgtttggaccgatgccaatggctgggcagaatttcctgtcaatggtggtt
cagtctcggtttgggtgggcgttaagtaa
```
FIGURE 16VVVVVVV
SEQ ID NO: 180
```
Met Lys Thr Phe Lys Leu Lys Arg Thr Phe Leu Pro Leu Thr Leu Leu
Leu Ser Ala Pro Ala Phe Ala Gly Gln Asn Gly Thr Met Met Gln Tyr
Phe His Trp Tyr Val Pro Asn Asp Gly Ala Leu Trp Thr Gln Val Glu
Ser Asn Ala Pro Ala Leu Ala Glu Asn Gly Phe Thr Ala Leu Trp Leu
Pro Pro Ala Tyr Lys Gly Ala Gly Gly Ser Asn Asp Val Gly Tyr Gly
Val Tyr Asp Met Tyr Asp Leu Gly Glu Phe Asp Gln Lys Gly Ser Val
Arg Thr Lys Tyr Gly Thr Lys Ala Gln Tyr Ile Ser Ala Ile Asn Ala
Ala His Asn Asn Asn Ile Gln Ile Tyr Gly Asp Val Val Phe Asn His
Arg Gly Gly Ala Asp Gly Lys Ser Trp Val Asp Thr Lys Arg Val Asp
Trp Asp Asn Arg Asn Ile Glu Leu Gly Asp Lys Trp Ile Glu Ala Trp
Val Glu Phe Asn Phe Pro Ser Arg Asn Asp Lys Tyr Ser Asn Phe His
Trp Thr Trp Tyr His Phe Asp Gly Val Asp Trp Asp Asp Ala Gly Lys
Glu Lys Ala Ile Phe Lys Phe Lys Gly Glu Gly Lys Ala Trp Asp Trp
Glu Val Ser Ser Glu Lys Gly Asn Tyr Asp Tyr Leu Met Tyr Ala Asp
Leu Asp Met Asp His Pro Glu Val Lys Gln Glu Leu Lys Asp Trp Gly
Glu Trp Tyr Ile Asn Met Thr Gly Val Asp Gly Phe Arg Met Asp Ala
Val Lys His Ile Lys Tyr Gln Tyr Leu Gln Glu Trp Ile Asp His Leu
Arg Trp Lys Thr Gly Lys Glu Leu Phe Thr Val Gly Glu Tyr Trp Asn
Tyr Asp Val Asn Gln Leu His Asn Phe Ile Thr Lys Thr Ser Gly Ser
Met Ser Leu Phe Asp Ala Pro Leu His Met Asn Phe Tyr Asn Ala Ser
Lys Ser Gly Gly Asn Tyr Asp Met Arg Gln Ile Met Asn Gly Thr Leu
Met Lys Asp Asn Pro Val Lys Ala Val Thr Leu Val Glu Asn His Asp
Thr Gln Pro Leu Gln Ala Leu Glu Ser Thr Val Asp Trp Trp Phe Lys
Pro Leu Ala Tyr Ala Phe Ile Leu Leu Arg Glu Glu Gly Tyr Pro Ser
Val Phe Tyr Ala Asp Tyr Tyr Gly Ala Gln Tyr Ser Asp Lys Gly Tyr
Asn Ile Asn Met Ala Lys Val Pro Tyr Ile Glu Glu Leu Val Thr Leu
Arg Lys Glu Tyr Ala Tyr Gly Lys Gln Asn Ser Tyr Leu Asp His Trp
Asp Val Ile Gly Trp Thr Arg Glu Gly Asp Ala Glu His Pro Asn Ser
Met Ala Val Ile Met Ser Asp Gly Pro Gly Gly Thr Lys Trp Met Tyr
Thr Gly Asn Pro Ser Thr Arg Tyr Val Asp Lys Leu Gly Ile Arg Thr
Glu Asp Val Trp Thr Asp Ala Asn Gly Trp Ala Glu Phe Pro Val Asn
Gly Gly Ser Val Ser Val Trp Val Gly Val Lys
```
FIGURE 16WWWWWWW
SEQ ID NO: 181
```
ttgccagaggccttcggcctggccattacgccgtcacatagccggcggggaggttggtgggcgt
gtcgcgcggggcagcctgccgatgccggtcctccactggccggcgttcatcctcgtccggcgct
tcgtcgccggtcatccgaacaagcacaagaaccggagtattgcgatgagccacaccctgcgtgcc
```

FIGURE 16WWWWWWW cont
gccgtattggcggcgatcctgctgccgttccccgccctcgctgaccaggccggcaagagcccggc
cggcgtgcgctaccacggcggcgacgaaatcatcctccagggcttccactggaacgtcgtccgcg
aagcgcccaacgactggtacaacatccttcgccagcaggcctcgacgatcgccgcggacggcttc
tcggcaatctggatgccggtgccctggcgtgacttctccagctggaccgacggcggcaagtcagg
cggcggcgaaggctacttctggcacgacttcaacaagaacggccgctacggcagcgacgcccagc
tgcgccaggccgccggcgcactcggtggcgccggggtgaaggtgctctacgatgtggtgcccaat
cacatgaaccgcggctatccggacaaggagatcaacctgccggccggccagggcttctggcgcaa
cgactgcaccgacccgggcaactaccccaacgactgcgatgacggtgaccgcttcatcggcggca
agtcggacctgaacaccggccatccgcagatctacggcatgttcgcgacgagcttgccaacctg
cgcagcgggtacggcgccggcggcttccgcttcgacttcgttcgcggctatgcgcccgaacgggt
cgacagctggatgagcgacagcgccgacagcagtttctgcgttggcgagctgtggaaaagcccgt
ccgagtacccgagctgggactggcgcaacacggcgagctggcagcagatcatcaaggactggtcc
gaccgggccaagtgcccggtgttcgacttcgcgctcaaggagcgcatgcagaacggctcggtcgc
cgactggaagcatgcctcaatggcaacccggacccgcgctggcgcgaggtggcggtgacctttg
tcgacaaccacgacaccggctattcgcccgggcagaacggcggccagcaccactgggcgctgcag
gacgggctgatccgccaggcctacgcctacatcctcaccagcccgggcacgccggtggtgtactg
gtcgcacatgtacgactggggctacggcgacttcattcgccagctgatccaggtgcggcgcaccg
ctggcgtgcgcgccgattcggcgatcagcttccacagcggctacagcggcctggtcgctaccgtc
agcggcagccatcagaccctggtggtggcgctcaactccgatctggccaaccccggccaggtcgc
cagcggcagcttcagcgaggcggtcaacgccagcaacggccaggtgcgcgtctggcgcagcggta
gcggcgatggcggcggcaatgacggcggcgagggcggtctggtcaatgtgaacttccgctgcgac
aacggcgtgacgcagatgggcgacagcgtctacgcggtgggcaacgtcagccagctcggcaactg
gagcccggcctccgcggtacggctgaccgacaccagcagctatccgacctggaagggcagcatcg
ccctgcctgacggtcagaacgtggaatggaagtgcctgatccgtaacgaggcggacgcgacgctg
gtgcgccagtggcaatcgggcggcaacaaccaggtccaggccgctgccggcgcgagcaccagcgg
ctcgttctga

FIGURE 16XXXXXXX
SEQ ID NO: 182
Met Pro Glu Ala Phe Gly Leu Ala Ile Thr Pro Ser His Ser Arg Arg
Gly Arg Leu Val Gly Val Ser Arg Gly Gly Ser Leu Pro Met Pro Val
Leu His Trp Pro Ala Phe Ile Leu Val Arg Arg Phe Val Ala Gly His
Pro Asn Lys His Lys Asn Arg Ser Ile Ala Met Ser His Thr Leu Arg
Ala Ala Val Leu Ala Ala Ile Leu Leu Pro Phe Pro Ala Leu Ala Asp
Gln Ala Gly Lys Ser Pro Ala Gly Val Arg Tyr His Gly Gly Asp Glu
Ile Ile Leu Gln Gly Phe His Trp Asn Val Val Arg Glu Ala Pro Asn
Asp Trp Tyr Asn Ile Leu Arg Gln Gln Ala Ser Thr Ile Ala Ala Asp
Gly Phe Ser Ala Ile Trp Met Pro Val Pro Trp Arg Asp Phe Ser Ser
Trp Thr Asp Gly Gly Lys Ser Gly Gly Gly Glu Gly Tyr Phe Trp His
Asp Phe Asn Lys Asn Gly Arg Tyr Gly Ser Asp Ala Gln Leu Arg Gln
Ala Ala Gly Ala Leu Gly Gly Ala Gly Val Lys Val Leu Tyr Asp Val
Val Pro Asn His Met Asn Arg Gly Tyr Pro Lys Glu Ile Asn Leu
Pro Ala Gly Gln Gly Phe Trp Arg Asn Asp Cys Thr Asp Pro Gly Asn
Tyr Pro Asn Asp Cys Asp Asp Gly Asp Arg Phe Ile Gly Gly Lys Ser
Asp Leu Asn Thr Gly His Pro Gln Ile Tyr Gly Met Phe Arg Asp Glu
Leu Ala Asn Leu Arg Ser Gly Tyr Gly Ala Gly Gly Phe Arg Phe Asp
Phe Val Arg Gly Tyr Ala Pro Glu Arg Val Asp Ser Trp Met Ser Asp
Ser Ala Asp Ser Ser Phe Cys Val Gly Glu Leu Trp Lys Ser Pro Ser
Glu Tyr Pro Ser Trp Asp Trp Arg Asn Thr Ala Ser Trp Gln Gln Ile
Ile Lys Asp Trp Ser Asp Arg Ala Lys Cys Pro Val Phe Asp Phe Ala
Leu Lys Glu Arg Met Gln Asn Gly Ser Val Ala Asp Trp Lys His Gly
Leu Asn Gly Asn Pro Asp Pro Arg Trp Arg Glu Val Ala Val Thr Phe
Val Asp Asn His Asp Thr Gly Tyr Ser Pro Gly Gln Asn Gly Gly Gln

FIGURE 16XXXXXXX cont
```
His His Trp Ala Leu Gln Asp Gly Leu Ile Arg Gln Ala Tyr Ala Tyr
Ile Leu Thr Ser Pro Gly Thr Pro Val Val Tyr Trp Ser His Met Tyr
Asp Trp Gly Tyr Gly Asp Phe Ile Arg Gln Leu Ile Gln Val Arg Arg
Thr Ala Gly Val Arg Ala Asp Ser Ala Ile Ser Phe His Ser Gly Tyr
Ser Gly Leu Val Ala Thr Val Ser Gly Ser His Gln Thr Leu Val Val
Ala Leu Asn Ser Asp Leu Ala Asn Pro Gly Gln Val Ala Ser Gly Ser
Phe Ser Glu Ala Val Asn Ala Ser Asn Gly Gln Val Arg Val Trp Arg
Ser Gly Ser Gly Asp Gly Gly Gly Asn Asp Gly Gly Glu Gly Gly Leu
Val Asn Val Asn Phe Arg Cys Asp Asn Gly Val Thr Gln Met Gly Asp
Ser Val Tyr Ala Val Gly Asn Val Ser Gln Leu Gly Asn Trp Ser Pro
Ala Ser Ala Val Arg Leu Thr Asp Thr Ser Ser Tyr Pro Thr Trp Lys
Gly Ser Ile Ala Leu Pro Asp Gly Gln Asn Val Glu Trp Lys Cys Leu
Ile Arg Asn Glu Ala Asp Ala Thr Leu Val Arg Gln Trp Gln Ser Gly
Gly Asn Asn Gln Val Gln Ala Ala Ala Gly Ala Ser Thr Ser Gly Ser
Phe
```
FIGURE 16YYYYYYY
SEQ ID NO: 183
```
atgcaaacgattgcaaaaaaggggatgaaacgatgaaagggaaaaaatggacagctttagctct
aacactgccgctggctgctagcttatcaacaggcgttcacgccgaaaccgtacataaaggtaagt
ctgaagcaacagataaaaacggtgtcttttatgaggtgtatgtaaactcttttacgatacaaat
aaagatggacatggtgatttaaaaggtctgacacaaaagttggattatttaaatgacggcaattc
tcatacaaagaatgatcttcaagtaaacgggatttggatgatgccagtcaacccttctcctagct
atcataaatatgatgtaacggactattataacattgatcctcagtacggaaatctgcaagatttt
cgcaagctgatgaaagaagcagacaaacgagacgtaaaagtcattatggaccttgttgtgaatca
tacgagcagcgaacaccttggtttcaagctgcattaaaagataaaaacagcaagtacagagatt
actatatttgggctgataaaaataccgatttgaatgaaaaaggatcttgggggcagcaagtatgg
cataaagctccaaacggagagtattttttacggaacgttttgggaaggaatgcctgacttaaatta
cgataaccctgaagtaagaaaagaaatgattaacgtcggaaagttttggctaaagcaaggcgtta
atggcttccgcttagatgctgcgcttcatattttaaaggtcaaacacctgaaggcgctaagaaa
aatatcctgtggtggaatgagtttagagatgcgatgaaaaaagaaaaccctaacgtatatctaac
gggtgaagtatgggatcagcctgaagtggtagctccttactatcaatcgcttgattctttattta
atttttgatttagcaggaaaaattgtcagctctgtaaaagcaggaaatgatcaaggaatcgccact
gcagcagcggcaacagatgaactgttcaaatcatacaatccaaataaaattgacggcatttctt
aaccaaccatgaccaaaatcgcgtcatgagtgagctgagcggcgatgtgaacaaagcaaaatcag
ctgcttctatcttacttacgcttcctggcaacccgtatatttattacggtgaagaaattggcatg
accggtgaaaagcctgatgagttaatccgtgaaccattccgctggtacgaaggaaacggacttgg
acaaactagctgggaaacacctgtatataacaaaggcggcaacggcgtgtctgtagaagtacaaa
ccaaacaaaaggattctttgttaaatcattatcgtgaaatgattcgcgtgcgtcagcagcatgaa
gagttagtaaaaggaacgcttcaatctatttcagtagacagtaaagaagtggttgcctatagtcg
cacgtataaaggcaactcgattagcgtgtatcataatatttcaaatcaacctgtaaaagtatctg
tagcagcgaaaggtaaattgattttttgctagtgaaaaaggtgctaaaaaagtcaaaaatcagctt
gtaattccggctaatacaacggttttaataaaataa
```
FIGURE 16ZZZZZZZ
SEQ ID NO: 184
```
Met Gln Thr Ile Ala Lys Lys Gly Asp Glu Thr Met Lys Gly Lys Lys
Trp Thr Ala Leu Ala Leu Thr Leu Pro Leu Ala Ala Ser Leu Ser Thr
Gly Val His Ala Glu Thr Val His Lys Gly Lys Ser Glu Ala Thr Asp
Lys Asn Gly Val Phe Tyr Glu Val Tyr Val Asn Ser Phe Tyr Asp Thr
Asn Lys Asp Gly His Gly Asp Leu Lys Gly Leu Thr Gln Lys Leu Asp
Tyr Leu Asn Asp Gly Asn Ser His Thr Lys Asn Asp Leu Gln Val Asn
Gly Ile Trp Met Met Pro Val Asn Pro Ser Pro Ser Tyr His Lys Tyr
Asp Val Thr Asp Tyr Tyr Asn Ile Asp Pro Gln Tyr Gly Asn Leu Gln
```

FIGURE 16ZZZZZZZ cont
Asp Phe Arg Lys Leu Met Lys Glu Ala Asp Lys Arg Asp Val Lys Val
Ile Met Asp Leu Val Val Asn His Thr Ser Ser Glu His Pro Trp Phe
Gln Ala Ala Leu Lys Asp Lys Asn Ser Lys Tyr Arg Asp Tyr Tyr Ile
Trp Ala Asp Lys Asn Thr Asp Leu Asn Glu Lys Gly Ser Trp Gly Gln
Gln Val Trp His Lys Ala Pro Asn Gly Glu Tyr Phe Tyr Gly Thr Phe
Trp Glu Gly Met Pro Asp Leu Asn Tyr Asp Asn Pro Glu Val Arg Lys
Glu Met Ile Asn Val Gly Lys Phe Trp Leu Lys Gln Gly Val Asn Gly
Phe Arg Leu Asp Ala Ala Leu His Ile Phe Lys Gly Gln Thr Pro Glu
Gly Ala Lys Lys Asn Ile Leu Trp Trp Asn Glu Phe Arg Asp Ala Met
Lys Lys Glu Asn Pro Asn Val Tyr Leu Thr Gly Glu Val Trp Asp Gln
Pro Glu Val Val Ala Pro Tyr Tyr Gln Ser Leu Asp Ser Leu Phe Asn
Phe Asp Leu Ala Gly Lys Ile Val Ser Ser Val Lys Ala Gly Asn Asp
Gln Gly Ile Ala Thr Ala Ala Ala Thr Asp Glu Leu Phe Lys Ser
Tyr Asn Pro Asn Lys Ile Asp Gly Ile Phe Leu Thr Asn His Asp Gln
Asn Arg Val Met Ser Glu Leu Ser Gly Asp Val Asn Lys Ala Lys Ser
Ala Ala Ser Ile Leu Leu Thr Leu Pro Gly Asn Pro Tyr Ile Tyr Tyr
Gly Glu Glu Ile Gly Met Thr Gly Glu Lys Pro Asp Glu Leu Ile Arg
Glu Pro Phe Arg Trp Tyr Glu Gly Asn Gly Leu Gly Gln Thr Ser Trp
Glu Thr Pro Val Tyr Asn Lys Gly Gly Asn Gly Val Ser Val Glu Val
Gln Thr Lys Gln Lys Asp Ser Leu Leu Asn His Tyr Arg Glu Met Ile
Arg Val Arg Gln Gln His Glu Glu Leu Val Lys Gly Thr Leu Gln Ser
Ile Ser Val Asp Ser Lys Glu Val Val Ala Tyr Ser Arg Thr Tyr Lys
Gly Asn Ser Ile Ser Val Tyr His Asn Ile Ser Asn Gln Pro Val Lys
Val Ser Val Ala Ala Lys Gly Lys Leu Ile Phe Ala Ser Glu Lys Gly
Ala Lys Lys Val Lys Asn Gln Leu Val Ile Pro Ala Asn Thr Thr Val
Leu Ile Lys

FIGURE 16AAAAAAAA
SEQ ID NO: 185
atgaaactgatgaaagggaaaaaatggacagctttagctctaacactgccgctggctgctagctt
atcaacaggcgttcacgccgaaactgtacataaaggtaaagctccaacagcagataaaaacggtg
tcttttatgaggtgtatgtaaactcttttacgatgcaaataaagatggacatggtgatttaaaa
ggtcttacacaaaagctggactatttaaatgacggaaattctcatacaaagaatgatcttcaagt
aaacgggatttggatgatgccagtcaacccttctcctagctatcataaatatgatgtaacggatt
attataacattgatccgcagtacggaaatctgcaagattttcgcaagctgatgaagaagcagac
aaacgagacgtaaaagtcattatggaccttgttgtgaatcatacgagcagcgaacacccttggtt
tcaagctgcgttaaaagataaaaacagcaagtacagagattactatatttgggctgataaaata
ccgacttgaatgaaaaggatcttggggacagcaagtatggcataaagctccaaacggagagtat
ttttacggaacgttttgggaaggaatgcctgacttaaattacgataaccctgaagtaagaaaaga
aatgattaacgtcggaaagttttggctaaagcaaggcgttgatggcttccgcttagatgctgcgc
ttcatatttttaaaggtcaaacgcctgaaggcgctaagaaaaatattctgtggtggaatgagttt
agagatgcgatgaaaaaagaaaaccctaacgtatatctaacgggtgaagtatgggatcagcctga
agtggtagctccttactatcaatcgcttgatcccctatttaactttgatttagcagggaaaattg
tcagttctgtaaaagcaggaaatgatcaaggaatcgccactgcagcagcggcaacggatgagctg
ttcaaatcatacaatccaaataaaattgacggcatttttcttaaccaaccatgaccaaaaccgcgt
catgagtgaactgatcggcgatgtgaacaaagcaaaatcagctgcttctatcttacttacgcttc
ctggcaacccgtatatttattacggtgaagaaattggcatgaccggtgaaaagcctgatgagtta
atccgtgaaccgttccgctggtacgaaggaaacggacttggacaaaccagctgggaaacacctgt
atataacaaaggcggcaacggcgtgtctgtagaagcacaaaccaaacaaaaggattctttgttaa
atcattaccgtgaaatgattcgcgtgcgtcagcagcatgaagagttagtaaaaggaacgcttcaa
tctatttagtagacagtaaagaagttgttgcctatagccgtacgtataaagacaactcgattag
cgtgtatcataatatttcaaatcaaccggtaaaagtatctgtagcagcaaaaggtaaattaattt

FIGURE 16AAAAAAAA cont
ttgctagtgaaaaaggtgctaaaaaagtcaagaatcagcttgtgattccggctaatacaacggtt
ttaataaaataa

FIGURE 16BBBBBBBB
SEQ ID NO: 186
Met Lys Leu Met Lys Gly Lys Lys Trp Thr Ala Leu Ala Leu Thr Leu
Pro Leu Ala Ala Ser Leu Ser Thr Gly Val His Ala Glu Thr Val His
Lys Gly Lys Ala Pro Thr Ala Asp Lys Asn Gly Val Phe Tyr Glu Val
Tyr Val Asn Ser Phe Tyr Asp Ala Asn Lys Asp Gly His Gly Asp Leu
Lys Gly Leu Thr Gln Lys Leu Asp Tyr Leu Asn Asp Gly Asn Ser His
Thr Lys Asn Asp Leu Gln Val Asn Gly Ile Trp Met Met Pro Val Asn
Pro Ser Pro Ser Tyr His Lys Tyr Asp Val Thr Asp Tyr Tyr Asn Ile
Asp Pro Gln Tyr Gly Asn Leu Gln Asp Phe Arg Lys Leu Met Lys Glu
Ala Asp Lys Arg Asp Val Lys Val Ile Met Asp Leu Val Val Asn His
Thr Ser Ser Glu His Pro Trp Phe Gln Ala Ala Leu Lys Asp Lys Asn
Ser Lys Tyr Arg Asp Tyr Tyr Ile Trp Ala Asp Lys Asn Thr Asp Leu
Asn Glu Lys Gly Ser Trp Gly Gln Gln Val Trp His Lys Ala Pro Asn
Gly Glu Tyr Phe Tyr Gly Thr Phe Trp Glu Gly Met Pro Asp Leu Asn
Tyr Asp Asn Pro Glu Val Arg Lys Glu Met Ile Asn Val Gly Lys Phe
Trp Leu Lys Gln Gly Val Asp Gly Phe Arg Leu Asp Ala Ala Leu His
Ile Phe Lys Gly Gln Thr Pro Glu Gly Ala Lys Lys Asn Ile Leu Trp
Trp Asn Glu Phe Arg Asp Ala Met Lys Lys Glu Asn Pro Asn Val Tyr
Leu Thr Gly Glu Val Trp Asp Gln Pro Glu Val Val Ala Pro Tyr Tyr
Gln Ser Leu Asp Ser Leu Phe Asn Phe Asp Leu Ala Gly Lys Ile Val
Ser Ser Val Lys Ala Gly Asn Asp Gln Gly Ile Ala Thr Ala Ala Ala
Ala Thr Asp Glu Leu Phe Lys Ser Tyr Asn Pro Asn Lys Ile Asp Gly
Ile Phe Leu Thr Asn His Asp Gln Asn Arg Val Met Ser Glu Leu Ile
Gly Asp Val Asn Lys Ala Lys Ser Ala Ala Ser Ile Leu Leu Thr Leu
Pro Gly Asn Pro Tyr Ile Tyr Tyr Gly Glu Glu Ile Gly Met Thr Gly
Glu Lys Pro Asp Glu Leu Ile Arg Glu Pro Phe Arg Trp Tyr Glu Gly
Asn Gly Leu Gly Gln Thr Ser Trp Glu Thr Pro Val Tyr Asn Lys Gly
Gly Asn Gly Val Ser Val Glu Ala Gln Thr Lys Gln Lys Asp Ser Leu
Leu Asn His Tyr Arg Glu Met Ile Arg Val Arg Gln His Glu Glu
Leu Val Lys Gly Thr Leu Gln Ser Ile Leu Val Asp Ser Lys Glu Val
Val Ala Tyr Ser Arg Thr Tyr Lys Asp Asn Ser Ile Ser Val Tyr His
Asn Ile Ser Asn Gln Pro Val Lys Val Ser Val Ala Ala Lys Gly Lys
Leu Ile Phe Ala Ser Glu Lys Gly Ala Lys Lys Val Lys Asn Gln Leu
Val Ile Pro Ala Asn Thr Thr Val Leu Ile Lys

FIGURE 16CCCCCCCC
SEQ ID NO: 187
ttgtatctcatccaggaggggcacatgcgttttccgccattattcaccgcttaccggcctggc
cgttccggttggagctctgcgtaccgcacagagctgcggcataggggagtttgccgacttgccgg
ttcttgccgaattctgcaaaaaagccggatttgatcttgtacagcttcttccggtcaatgacacc
ggcacagaaagttctccatacagcgcgctttctgcctttgccctgcaccgctgtatatcaggct
ttccgacctgcctgaagcagcgggtttcgaaaagcagattacagatctgaaagccggtttgagg
acttgctcgtttcagctatacggagctgcgccgtgccaaactggatatcctgcgtgcagtgttt
gataaaaacaaggcaaccatcatcggcagtgccgaactggaagcctggatttcagataacccctg
gatcatcgaatatgcggttttatgaaccagaaacaccgcaactttgaagccggctggaaacatt
gggaaaagctgcgcaacccccactcataacgaaatacaaaaaacctggcagggtaaaacctggcag
gctgaccatcaattctttgcatggctgcagatgcggctggaccagcagtttactgccgccgctac
agagtgcaacgccctgggtgtctatcttaaggcgatatacctataatgatgaacgaggattccg
cagatgcctgggcgaatccggaattcttccgtgacgatcttcgggccggaagtccccctgacggt
gaaaaccccccagggacaaaactggggcttccccatttataactgggaaaaccttgcaaatgacgg

FIGURE 16CCCCCCCC cont
gtacagctggtggaaaaaacgtctgaagcacagcgcacggtattaccatgcctaccgcattgacc
atattcttgggttttttccggatatgggctataccctatggcgaatactccggctacctgggatgg
cccttgccgcatgaaccggtaagtgcagcagaactggcagaacggggcttttccaaggaccgctt
gcgctggcttaccgaaccccacttgcctacacgggcagccgaggaagcgaataactgggactatc
tgggaacacacggctatctgaatcagatcatgaaccgtatcggtgaagaagaactatggctgttc
aagcccgagatcacctgcgaggcagatatacgaaacacaaacctgccggatgccctgaaagaggt
tctggtacggcagtggaaaaaccggctgctgcaggttaccggccgcgacgaaaaaggacggacaa
tctactatccgctgtggcgtttccgtgacagcactgcatggcagacgcttaccgatggcgagaaa
cactccctggaagagctgttcgcccaaaaagcggcgcacaatgaaaccctgtggcgagaacaggc
ggtggaacttctgggtgagctgacgcgatctacggatatgcttgcctgtgctgaagatctgggaa
gtattccccacagtgtaccggaagtgctttcaaacctttcaatttacagtctgcgggttaccgc
tgggcccgccaatgggatgccccggccagcccttcacagactggaggagtatccgctcatgtc
ggtagcgacccatcggttcatgattcctctaccctgcgcggatggtgggaaaccgaaggcggcg
accgggcctttatggacgcatggcctccggaacaggatgcatacgcaggagcaggccgccatgag
ttcgaaggcgcctggggaccccgccaggcatcctgggtactccgtaaactctgcgaagcccgttc
cgcgctctgtgttttccccatccaggatattttggccctgtcttcagacttttatgcaatgacag
cggacgaggaacgcatcaatattccgggcagtgtatccggatttaactggacataccggttgcct
gcggcaatcgaggatttatctaaaaacagccaacttataaccgcaatccagaccgcgttgcagga
ccgccgggcgaggaaggcacaaggagcacagcaatga

FIGURE 16DDDDDDDD
SEQ ID NO: 188
Met Tyr Leu Ile Gln Glu Gly His Met Arg Phe Pro Pro Ile Ile His
Pro Leu Thr Gly Leu Ala Val Pro Val Gly Ala Leu Arg Thr Ala Gln
Ser Cys Gly Ile Gly Glu Phe Ala Asp Leu Pro Val Leu Ala Glu Phe
Cys Lys Lys Ala Gly Phe Asp Leu Val Gln Leu Leu Pro Val Asn Asp
Thr Gly Thr Glu Ser Ser Pro Tyr Ser Ala Leu Ser Ala Phe Ala Leu
His Pro Leu Tyr Ile Arg Leu Ser Asp Leu Pro Glu Ala Ala Gly Phe
Glu Lys Gln Ile Thr Asp Leu Lys Ser Arg Phe Glu Asp Leu Pro Arg
Phe Ser Tyr Thr Glu Leu Arg Arg Ala Lys Leu Asp Ile Leu Arg Ala
Val Phe Asp Lys Asn Lys Ala Thr Ile Ile Gly Ser Ala Glu Leu Glu
Ala Trp Ile Ser Asp Asn Pro Trp Ile Ile Glu Tyr Ala Val Phe Met
Asn Gln Lys His Arg Asn Phe Glu Ala Gly Trp Lys His Trp Glu Lys
Leu Arg Asn Pro Thr His Asn Glu Ile Gln Lys Thr Trp Gln Gly Lys
Thr Trp Gln Ala Asp His Gln Phe Phe Ala Trp Leu Gln Met Arg Leu
Asp Gln Gln Phe Thr Ala Ala Ala Thr Glu Cys Asn Ala Leu Gly Val
Tyr Leu Lys Gly Asp Ile Pro Ile Met Met Asn Glu Asp Ser Ala Asp
Ala Trp Ala Asn Pro Glu Phe Phe Arg Asp Asp Leu Arg Ala Gly Ser
Pro Pro Asp Gly Glu Asn Pro Gln Gly Gln Asn Trp Gly Phe Pro Ile
Tyr Asn Trp Glu Asn Leu Ala Asn Asp Gly Tyr Ser Trp Trp Lys Lys
Arg Leu Lys His Ser Ala Arg Tyr Tyr His Ala Tyr Arg Ile Asp His
Ile Leu Gly Phe Phe Arg Ile Trp Ala Ile Pro Tyr Gly Glu Tyr Ser
Gly Tyr Leu Gly Trp Pro Leu Pro His Glu Pro Val Ser Ala Ala Glu
Leu Ala Glu Arg Gly Phe Ser Lys Asp Arg Leu Arg Trp Leu Thr Glu
Pro His Leu Pro Thr Arg Ala Ala Glu Glu Ala Asn Asn Trp Asp Tyr
Leu Gly Thr His Gly Tyr Leu Asn Gln Ile Met Asn Arg Ile Gly Glu
Glu Glu Leu Trp Leu Phe Lys Pro Gly Ile Thr Cys Glu Ala Asp Ile
Arg Asn Thr Asn Leu Pro Asp Ala Leu Lys Glu Val Leu Val Arg Gln
Trp Lys Asn Arg Leu Leu Gln Val Thr Gly Arg Asp Glu Lys Gly Arg
Thr Ile Tyr Tyr Pro Leu Trp Arg Phe Arg Asp Ser Thr Ala Trp Gln
Thr Leu Thr Asp Gly Glu Lys His Ser Leu Glu Glu Leu Phe Ala Gln
Lys Ala Ala His Asn Glu Thr Leu Trp Arg Glu Gln Ala Val Glu Leu
Leu Gly Glu Leu Thr Arg Ser Thr Asp Met Leu Ala Cys Ala Glu Asp

FIGURE 16DDDDDDDD cont
Leu Gly Ser Ile Pro His Ser Val Pro Glu Val Leu Ser Asn Leu Ser
Ile Tyr Ser Leu Arg Val Thr Arg Trp Ala Arg Gln Trp Asp Ala Pro
Gly Gln Pro Phe His Arg Leu Glu Glu Tyr Pro Leu Met Ser Val Ala
Thr Pro Ser Val His Asp Ser Ser Thr Leu Arg Gly Trp Trp Glu Thr
Glu Gly Gly Asp Arg Ala Phe Met Asp Ala Trp Pro Pro Glu Gln Asp
Ala Tyr Ala Gly Ala Gly Arg His Glu Phe Glu Gly Ala Trp Gly Pro
Arg Gln Ala Ser Trp Val Leu Arg Lys Leu Cys Glu Ala Arg Ser Ala
Leu Cys Val Phe Pro Ile Gln Asp Ile Leu Ala Leu Ser Ser Asp Phe
Tyr Ala Met Thr Ala Asp Glu Glu Arg Ile Asn Ile Pro Gly Ser Val
Ser Gly Phe Asn Trp Thr Tyr Arg Leu Pro Ala Ala Ile Glu Asp Leu
Ser Lys Asn Ser Gln Leu Ile Thr Ala Ile Gln Thr Ala Leu Gln Asp
Arg Arg Ala Arg Lys Ala Gln Gly Ala Gln Gln

FIGURE 16EEEEEEEE
SEQ ID NO: 189
atgcaaacgattgcaaaaaaggggatgaaacgatgaaagggaaaaaatggacagctttagctct
aacactgccgctggctgctagcttatcaacaggcgttcacgccgaaaccgtacataaaggtaaat
ctccagctgcagataaaaacggtgtctttatgaggtgtatgtaaactcttttttacgatgcaaat
aaagatggacatggtgatttaaaaggtcttacacaaaaactggactatttaaatgatggcaattc
tcatacaaagaatgatcttcaagtaaacgggatttggatgatgccgatcaacccttctcctagct
atcataaatatgatgtaacggactattataacattgattctcagtacggaaatctgcaagatttt
cgcaagctaatgaaagaagcagataaacgagatgtaaaagttattatggacctcgttgtgaatca
tacgagcagtgaacacccttggtttcaagctgcgttaaaagataaaaacagcaagtacagagatt
actatatttgggctgataaaaataccgatttgaatgaaaaggatcttggggacaacaagtatgg
cacaaagctccaaacggagagtatttttacggaacgttctgggaaggaatgcctgacttaaatta
cgataaccctgaagtaagaaaagaaatgattaacgtcggaaagttttggctaaagcaaggcgttg
acggcttccgcttagatgctgcccttcatatctttaaaggtcaaacacctgaaggcgctaagaaa
aatattgtgtggtggaatgaatttagagatgcgatgaaaaaagaaaacccgaacgtatatctaac
gggcgaagtatgggatcagccggaagtggtagctccttattatcagtcgcttgattccctattta
actttgatttagcaggaaaaattgtcagctctgtaaaagcaggaaatgatcaaggaatcgctact
gcagcagcggcaacagatgaactgttcaaatcatacaatccaaataaaattgacggcattttctt
aaccaatcatgaccaaaatcgcgtcatgagtgagttaagcggagatgtcaataaagcaaagtcag
ctgcctctatcttacttacgcttcctggaaatccgtatatttattacggtgaagaaatcggcatg
accggtgaaaagcctgatgaattaatccgtgaaccgttccgctggtacgaaggaaacggacttgg
acaaactagttgggaaacacctgtatacaataaaggcggcaacggcgtgtctgtagaagcacaaa
ccaaacaaaggactctttgttaaatcattaccgtgaaatgattcgcgtgcgtcagcagcacgaa
gagttagtaaaaggaacgcttcaatctatttcagtagacagtaaagaagttgttgcttatagccg
tacgtataaaggcaactccattagtgtgtatcataatatttcaaatcaacctgtaaaagtatctg
tagcagcgaaaggtaaattgattttgctagtgaaaaaggtgctaaaaaggtcaaaaatcagctt
gtgattccggcgaatacaacggttttagtaaaataa

FIGURE 16FFFFFFFF
SEQ ID NO: 190
Met Gln Thr Ile Ala Lys Lys Gly Asp Glu Thr Met Lys Gly Lys Lys
Trp Thr Ala Leu Ala Leu Thr Leu Pro Leu Ala Ala Ser Leu Ser Thr
Gly Val His Ala Glu Thr Val His Lys Gly Lys Ser Pro Ala Ala Asp
Lys Asn Gly Val Phe Tyr Glu Val Tyr Val Asn Ser Phe Tyr Asp Ala
Asn Lys Asp Gly His Gly Asp Leu Lys Gly Leu Thr Gln Lys Leu Asp
Tyr Leu Asn Asp Gly Asn Ser His Thr Lys Asn Asp Leu Gln Val Asn
Gly Ile Trp Met Met Pro Ile Asn Pro Ser Pro Ser Tyr His Lys Tyr
Asp Val Thr Asp Tyr Tyr Asn Ile Asp Ser Gln Tyr Gly Asn Leu Gln
Asp Phe Arg Lys Leu Met Lys Glu Ala Asp Lys Arg Asp Val Lys Val
Ile Met Asp Leu Val Val Asn His Thr Ser Ser Glu His Pro Trp Phe
Gln Ala Ala Leu Lys Asp Lys Asn Ser Lys Tyr Arg Asp Tyr Tyr Ile

FIGURE 16FFFFFFFF cont

Trp Ala Asp Lys Asn Thr Asp Leu Asn Glu Lys Gly Ser Trp Gly Gln
Gln Val Trp His Lys Ala Pro Asn Gly Glu Tyr Phe Tyr Gly Thr Phe
Trp Glu Gly Met Pro Asp Leu Asn Tyr Asp Asn Pro Glu Val Arg Lys
Glu Met Ile Asn Val Gly Lys Phe Trp Leu Lys Gln Gly Val Asp Gly
Phe Arg Leu Asp Ala Ala Leu His Ile Phe Lys Gly Gln Thr Pro Glu
Gly Ala Lys Lys Asn Ile Val Trp Trp Asn Glu Phe Arg Asp Ala Met
Lys Lys Glu Asn Pro Asn Val Tyr Leu Thr Gly Glu Val Trp Asp Gln
Pro Glu Val Val Ala Pro Tyr Tyr Gln Ser Leu Asp Ser Leu Phe Asn
Phe Asp Leu Ala Gly Lys Ile Val Ser Ser Val Lys Ala Gly Asn Asp
Gln Gly Ile Ala Thr Ala Ala Ala Thr Asp Glu Leu Phe Lys Ser
Tyr Asn Pro Asn Lys Ile Asp Gly Ile Phe Leu Thr Asn His Asp Gln
Asn Arg Val Met Ser Glu Leu Ser Gly Asp Val Asn Lys Ala Lys Ser
Ala Ala Ser Ile Leu Leu Thr Leu Pro Gly Asn Pro Tyr Ile Tyr Tyr
Gly Glu Glu Ile Gly Met Thr Gly Glu Lys Pro Asp Glu Leu Ile Arg
Glu Pro Phe Arg Trp Tyr Glu Gly Asn Gly Leu Gly Gln Thr Ser Trp
Glu Thr Pro Val Tyr Asn Lys Gly Gly Asn Gly Val Ser Val Glu Ala
Gln Thr Lys Gln Lys Asp Ser Leu Leu Asn His Tyr Arg Glu Met Ile
Arg Val Arg Gln Gln His Glu Glu Leu Val Lys Gly Thr Leu Gln Ser
Ile Ser Val Asp Ser Lys Glu Val Val Ala Tyr Ser Arg Thr Tyr Lys
Gly Asn Ser Ile Ser Val Tyr His Asn Ile Ser Asn Gln Pro Val Lys
Val Ser Val Ala Ala Lys Gly Lys Leu Ile Phe Ala Ser Glu Lys Gly
Ala Lys Lys Val Lys Asn Gln Leu Val Ile Pro Ala Asn Thr Thr Val
Leu Val Lys

FIGURE 16GGGGGGGG

SEQ ID NO: 191

```
atgcaaacgattgcaaaaaaggggatgaaacgatgaaagggaaaaaatggacagctttagctct
aacactgccgctggctgctagcttatcaacaggcgttcacgccgaaaccgtacataaaggtaaat
ctccaacagcagataaaaacggtgtcttttatgaagtgtatgtaaactcttttttacgatgcaaat
aaagatggacatggtgacttaaaaggtcttacacaaaagttggactatttaaatgacggcaattc
tcatacaaaaaatgatcttcaagtaaacgggatttggatgatgccagtcaaccttctcctagct
atcataaatatgatgtaacggactattataacattgatccgcagtacggaaatctgcaagatttt
cgcaagctgatgaaagaagcagacaaacgagacgtaaaagtcattatggaccttgttgtgaatca
tacgagcagtgaacacccttggtttcaagctgcgttaaaagataaaaacagcaagtacagagatt
actatatttgggctgataaaaataccgacttgaatgaaaaaggatcttggggacaacaagtatgg
cataaagctccaaacggagagtattttttacggaacgttctgggaaggaatgcctgacttaaatta
cgataaccctgaagtaagaaaagaaatgattaacgtcggaaagttttggctaaagcaaggcgttg
acgggttccgcttagatgctgcgcttcatattttttaaaggtcaaacagctgaaggcgctaagaaa
aatatcctgtggtggaatgagtttagagatgcgatgaaaaaagaaaatccgaatgtatatctaac
gggtgaagtatgggatcagctgaagtggtagctccttattatcaatcgcttgattctttatttta
attttgatttagcaggaaaaattgtcagctctgtaaaagcaggaaatgatcaaggaatcgccact
gcagcagcagcaacagatgaactgttcaaatcatacaatccaaacaaaattgatggcatattctt
aaccaaccatgaccaaaatcgcgtcatgagtgagctgagcggcgatgtgagcaaagcaaaatcag
ctgcttctatcttacttacgcttcctggcaacccgtatatttattacggtgaagaaatcggcatg
accggtgaaaagcctgatgaattaatccgtgaaccgttccgctggtacgaaggaaacggacttgg
acaaaccagttgggaaacacctgtatacaataaaggcggaaacggtgtgtctgtagaagcacaaa
ccaaacaaaggattctttgttaaatcattaccgtgaaatgattcgcgtgcgtcagcagcatgaa
gagttagtaaaaggaacgcttcaatctatttcagtagacagtaaagaagttgttgcttatagccg
tacgtataaaggcaactccattagtgtgtatcataatatttcaaatcaaccggtaaaagtatctg
tagcagcgaaaggtaaattgatttttgctagtgaaaaaggtgctaagaaagtcaaaaatcagctt
gtggttccggcgaatacaacggttttaatgaaataa
```

FIGURE 16HHHHHHHH
SEQ ID NO: 192
Met Gln Thr Ile Ala Lys Lys Gly Asp Glu Thr Met Lys Gly Lys Lys
Trp Thr Ala Leu Ala Leu Thr Leu Pro Leu Ala Ala Ser Leu Ser Thr
Gly Val His Ala Glu Thr Val His Lys Gly Lys Ser Pro Thr Ala Asp
Lys Asn Gly Val Phe Tyr Glu Val Tyr Val Asn Ser Phe Tyr Asp Ala
Asn Lys Asp Gly His Gly Asp Leu Lys Gly Leu Thr Gln Lys Leu Asp
Tyr Leu Asn Asp Gly Asn Ser His Thr Lys Asn Asp Leu Gln Val Asn
Gly Ile Trp Met Met Pro Val Asn Pro Ser Pro Ser Tyr His Lys Tyr
Asp Val Thr Asp Tyr Tyr Asn Ile Asp Pro Gln Tyr Gly Asn Leu Gln
Asp Phe Arg Lys Leu Met Lys Glu Ala Asp Lys Arg Asp Val Lys Val
Ile Met Asp Leu Val Val Asn His Thr Ser Ser Glu His Pro Trp Phe
Gln Ala Ala Leu Lys Asp Lys Asn Ser Lys Tyr Arg Asp Tyr Tyr Ile
Trp Ala Asp Lys Asn Thr Asp Leu Asn Glu Lys Gly Ser Trp Gly Gln
Gln Val Trp His Lys Ala Pro Asn Gly Glu Tyr Phe Tyr Gly Thr Phe
Trp Glu Gly Met Pro Asp Leu Asn Tyr Asp Asn Pro Glu Val Arg Lys
Glu Met Ile Asn Val Gly Lys Phe Trp Leu Lys Gln Gly Val Asp Gly
Phe Arg Leu Asp Ala Ala Leu His Ile Phe Lys Gly Gln Thr Ala Glu
Gly Ala Lys Lys Asn Ile Leu Trp Trp Asn Glu Phe Arg Asp Ala Met
Lys Lys Glu Asn Pro Asn Val Tyr Leu Thr Gly Glu Val Trp Asp Gln
Pro Glu Val Val Ala Pro Tyr Tyr Gln Ser Leu Asp Ser Leu Phe Asn
Phe Asp Leu Ala Gly Lys Ile Val Ser Ser Val Lys Ala Gly Asn Asp
Gln Gly Ile Ala Thr Ala Ala Ala Thr Asp Glu Leu Phe Lys Ser
Tyr Asn Pro Asn Lys Ile Asp Gly Ile Phe Leu Thr Asn His Asp Gln
Asn Arg Val Met Ser Glu Leu Ser Gly Asp Val Ser Lys Ala Lys Ser
Ala Ala Ser Ile Leu Leu Thr Leu Pro Gly Asn Pro Tyr Ile Tyr Tyr
Gly Glu Glu Ile Gly Met Thr Gly Glu Lys Pro Asp Glu Leu Ile Arg
Glu Pro Phe Arg Trp Tyr Glu Gly Asn Gly Leu Gly Gln Thr Ser Trp
Glu Thr Pro Val Tyr Asn Lys Gly Gly Asn Gly Val Ser Val Glu Ala
Gln Thr Lys Gln Lys Asp Ser Leu Leu Asn His Tyr Arg Glu Met Ile
Arg Val Arg Gln Gln His Glu Glu Leu Val Lys Gly Thr Leu Gln Ser
Ile Ser Val Asp Ser Lys Glu Val Val Ala Tyr Ser Arg Thr Tyr Lys
Gly Asn Ser Ile Ser Val Tyr His Asn Ile Ser Asn Gln Pro Val Lys
Val Ser Val Ala Ala Lys Gly Lys Leu Ile Phe Ala Ser Glu Lys Gly
Ala Lys Lys Val Lys Asn Gln Leu Val Val Pro Ala Asn Thr Thr Val
Leu Met Lys

FIGURE 16IIIIIIII
SEQ ID NO: 193
atgaaattcaaaaagagtttatctgccgggctccttttgttcggaggtctgagcggtgtgacacc
atccgtcgctgcggaggtgccacgaaccgcatttgtccatttattcgaatggagttggccggata
ttgccaccgaatgcgaaacctttcttggccctaaggggttctctgcggttcaggtgtctccgccg
caaaaaagcgtcagcaatgctgcctggtgggcgcgctaccaacctgttagttactcttttgaagg
gcgcagtggaacccggctcaatttgcggatatggtccagcgttgtaaagcggtgggggtcgata
tttatctggatgcggtgatcaaccatatggcagcacaagatcgctattttccagaagtaccttac
agcagtaatgattttcacagttgcacgggcgatatcgattattccaaccgctggtcgattcaaaa
ttgcgatctggttgggctgaacgatctcaaaaccgagtcagaatacgttcggcagaaaattgcag
actatatgaacgatgcgctcagtctgggcgtggcggggtttcggattgatgccgccaagcatatc
ccggccggcgacatcgcggcgatcaagagcaagctcaacggcagcccgtatatctatcaggaggt
tatcggggcggcaggggagccggtacaaaccagcgagtacacgtatattggagacgtgacggaat
taacttcgcccggaccatcgggcctaaatttaagcaaggtaatattaaagacctgcaggggatt
ggttcgtggagcggctggctgagcagcgacgatgcggtgacctttgtgaccaaccatgacgaaga
acgccataaccctggccaggttctcagccatcaggactttggcaatctgtatttcctcggtaacg
tgtttactctggcgtatccttacggctacccaaaagtgatgtcggggtactacttcagtaattt

FIGURE 16IIIIIIII cont
gatgccggccaccatcgacaggggtacattctggtaatgcgtgtggctttgatggcggtgattg
ggtctgcgaacacaaatggcgtggtgtagccaacatggtggcgtttcgcaaccacacagcagccc
agtggcaggtcactgactggtgggacgatggttacaatcaggtggcgtttggtcgtggcgggctg
ggctttgtggtgatcaatcgagatgacaataaaggcatcaatcagagtttccagacgggaatgcc
cgctggcgagtattgtgacatcattgccggtgatttcgacacccagagcggtcattgcagcgcta
cgacgatcaccgtcgacagtcaggggtatgcacattttactgtcggtagtcatcaggccgctgcg
attcacattggcgcgaaactcggctccgtgtgccaggactgtggcggcacggccgcagagacaaa
agtctgctttgacaatgcacaaaactttagccaaccgtatttgcattactggaatgtcaatgcgg
atcaggccgtagcgaatgcaacctggccgggcgtcgcgatgacggctgaaaatggcggttactgc
tacgattttggtgtcggtctcaattcacttcaggtaattttcagcgataacggcgccagccaaac
cgctgatctgaccgccagcagtccgacgttgtgttaccagaacggaacgtggcgtgacagtgact
tctgtcagagtagcaatgtgggcaacgagagttggtatttccgtggaacctcaaacggttgggc
gtgagcgcactcacttatgagctgcgacaggcctgtacactacggtgcagagctttaacgggga
ggagtcgcccgcacgctttaaaattgatgatggcaactggagtgagtcgtatccaagtgctgatt
atcaagtcggtgattatgccacctacacgatcacgtttgacagccagacgaaggccatcaccgtg
acttcgcagtaa

FIGURE 16JJJJJJJJ
SEQ ID NO: 194
Met Lys Phe Lys Lys Ser Leu Ser Ala Gly Leu Leu Leu Phe Gly Gly
Leu Ser Gly Val Thr Pro Ser Val Ala Ala Glu Val Pro Arg Thr Ala
Phe Val His Leu Phe Glu Trp Ser Trp Pro Asp Ile Ala Thr Glu Cys
Glu Thr Phe Leu Gly Pro Lys Gly Phe Ser Ala Val Gln Val Ser Pro
Pro Gln Lys Ser Val Ser Asn Ala Ala Trp Trp Ala Arg Tyr Gln Pro
Val Ser Tyr Ser Phe Glu Gly Arg Ser Gly Thr Arg Ala Gln Phe Ala
Asp Met Val Gln Arg Cys Lys Ala Val Gly Val Asp Ile Tyr Leu Asp
Ala Val Ile Asn His Met Ala Ala Gln Asp Arg Tyr Phe Pro Glu Val
Pro Tyr Ser Ser Asn Asp Phe His Ser Cys Thr Gly Asp Ile Asp Tyr
Ser Asn Arg Trp Ser Ile Gln Asn Cys Asp Leu Val Gly Leu Asn Asp
Leu Lys Thr Glu Ser Glu Tyr Val Arg Gln Lys Ile Ala Asp Tyr Met
Asn Asp Ala Leu Ser Leu Gly Val Ala Gly Phe Arg Ile Asp Ala Ala
Lys His Ile Pro Ala Gly Asp Ile Ala Ala Ile Lys Ser Lys Leu Asn
Gly Ser Pro Tyr Ile Tyr Gln Glu Val Ile Gly Ala Ala Gly Glu Pro
Val Gln Thr Ser Glu Tyr Thr Tyr Ile Gly Asp Val Thr Glu Phe Asn
Phe Ala Arg Thr Ile Gly Pro Lys Phe Lys Gln Gly Asn Ile Lys Asp
Leu Gln Gly Ile Gly Ser Trp Ser Gly Trp Leu Ser Ser Asp Asp Ala
Val Thr Phe Val Thr Asn His Asp Glu Glu Arg His Asn Pro Gly Gln
Val Leu Ser His Gln Asp Phe Gly Asn Leu Tyr Phe Leu Gly Asn Val
Phe Thr Leu Ala Tyr Pro Tyr Gly Tyr Pro Lys Val Met Ser Gly Tyr
Tyr Phe Ser Asn Phe Asp Ala Gly Pro Pro Ser Thr Gly Val His Ser
Gly Asn Ala Cys Gly Phe Asp Gly Gly Asp Trp Val Cys Glu His Lys
Trp Arg Gly Val Ala Asn Met Val Ala Phe Arg Asn His Thr Ala Ala
Gln Trp Gln Val Thr Asp Trp Trp Asp Asp Gly Tyr Asn Gln Val Ala
Phe Gly Arg Gly Gly Leu Gly Phe Val Val Ile Asn Arg Asp Asp Asn
Lys Gly Ile Asn Gln Ser Phe Gln Thr Gly Met Pro Ala Gly Glu Tyr
Cys Asp Ile Ile Ala Gly Asp Phe Asp Thr Gln Ser Gly His Cys Ser
Ala Thr Thr Ile Thr Val Asp Ser Gln Gly Tyr Ala His Phe Thr Val
Gly Ser His Gln Ala Ala Ile His Ile Gly Ala Lys Leu Gly Ser
Val Cys Gln Asp Cys Gly Gly Thr Ala Ala Glu Thr Lys Val Cys Phe
Asp Asn Ala Gln Asn Phe Ser Gln Pro Tyr Leu His Tyr Trp Asn Val
Asn Ala Asp Gln Ala Val Ala Asn Ala Thr Trp Pro Gly Val Ala Met
Thr Ala Glu Asn Gly Gly Tyr Cys Tyr Asp Phe Gly Val Gly Leu Asn
Ser Leu Gln Val Ile Phe Ser Asp Asn Gly Ala Ser Gln Thr Ala Asp

FIGURE 16JJJJJJJJ cont
```
Leu Thr Ala Ser Ser Pro Thr Leu Cys Tyr Gln Asn Gly Thr Trp Arg
Asp Ser Asp Phe Cys Gln Ser Ser Asn Val Gly Asn Glu Ser Trp Tyr
Phe Arg Gly Thr Ser Asn Gly Trp Gly Val Ser Ala Leu Thr Tyr Glu
Ala Ala Thr Gly Leu Tyr Thr Thr Val Gln Ser Phe Asn Gly Glu Glu
Ser Pro Ala Arg Phe Lys Ile Asp Asp Gly Asn Trp Ser Glu Ser Tyr
Pro Ser Ala Asp Tyr Gln Val Gly Asp Tyr Ala Thr Tyr Thr Ile Thr
Phe Asp Ser Gln Thr Lys Ala Ile Thr Val Thr Ser Gln
```
FIGURE 16KKKKKKKK
SEQ ID NO: 195
```
atgctgacagaccgtttctttgatggcgatacatcaaacaacgacccttacaaccagaactacga
tgctaaaaacgaccggggaacttatcagggcggcgattttaaaggaatcacgcaaaaattggatt
atctcgataagctaggcgtgaacacaatctggatcagcccgatcgtggaaaatatcaagcatgat
gtccgttatgacaactctgaagggcattcatactatgcttaccacggctactgggcaagcaactt
cggtgcgttaaacccacacttcggtacaatggaagatttccatacactgattgacgctgcccatg
aaaaaggcatcaagatcatggttgacgtagtattaaaccacactggttatggcttaaaagatatc
aacggagaagtttccaatcctccagccggttacccaactgacgcagaacgcagcacatatagcag
cctgcttcgccagggttcaaatgtcggctctgatgaggttgttggcgaattagctggcctacctg
acttaaaaacagaagaccccgcagtccgccagacaatcatcgactggcaaacagactggatcacg
aaagctactacagctaaaggaaacacaattgactacttccgtgtcgacactgtgaagcacgttga
agacgcaacatggatggcattcaaaaatgacctcactgaaaaaatgccgacacacaaaatgatcg
gggaagcttggggagcaagtgccaataaccaacttggataccttgaaacaggtatgatggactca
ctgcttgacttcgacttcaaaggcattgcgcacgatttcgtgaacggcaagcttaaggcagcaaa
cgatgccctgactgcccgcaacggtaaaattgacaacacagctactttaggttcattccttggaa
gccatgacgaagatggtttcctatttaaagaaggaaatgacaaaggcaagcttaaggttgctgct
tccctgcaagcaacatcaaaaggccagccggtcatctattatggtgaagagcttggtcaaagtgg
agcaaacaactatccgcaatacgataaccgttatgacctggcatgggacaaagttgaaaacaacg
acgtccttgagcactacactaaggtcctgaacttcagaagcgctcattcagaagtgttcgctaaa
ggtgaacgcgcaacaattggcggttctgacgctgataaattcttacttttgctcgtaaaaatgg
aaacgaagctgcttacgtcggcttgaacgttgctgacacagcaaaagacgtaacactgactgttt
ctgcaggtgcagtcgtaactgaccactatgcagataaaacttatactgcttcagaagctggagaa
atcacattgacgatcccggcaaaagctgatggcggtactgttttactaacggttgaaggcggaga
aatcacagctgctaaagcggcaagcgaaggcgacggcacagttgagccagtccctgcgaaccaca
tccgcattcactacaaccgtacagacaacaactatgaaaactacggtgcatggctgtggaacgat
gtagcctcccttctgccaactggccgactggcgctacaatgtttgaaaaaacagacagctacgg
tgcatacatcgacgtaccacttaaagagggcgctaagaacatcggcttcctcgttatggatgtaa
caaaaggtgatcagggtaaagacggcggcgacaaaggttttacgatctcatcacctgaaatgaac
gaaatttggatcaagcaaggttctgacaaggtgtacacttacgagccagttgatcttccggcgaa
cactgtccgcgtccactatgtacgtgacaacgcagactacgaaaacttcggtatctggaactggg
gcgatgtaacagcaccttccgaaaactggcctacaggcgcagcgaaattcgatggtacagaccgt
tacggtgcgtatgtcgacattacgctaaaagaaggcgcaaagaacattggaatgattgctcttaa
cactgcaaatggagagaaagacggcggagataaatccttcaaccttctggataaatataatcgca
tttggattaaacaaggtgatgacaatgtctacgtttctccatactgggagcaggcaacaggaatc
accaatgcagaggtaatctctgaagatacgattctattaggcttcacaatgactgacggcttaac
acctgaatctttaaaggaggtcttgtaattaaagattcaactggtgctgaagttgccatcgaaa
gtgctgaaatcacaagcgcaacctctgtaaaagtaaaagcaacattcgatttagaaaagcttcca
ttatccatcacatacgcaggcagaacagtttcagcttcaactggctggagaatgcttgatgaaat
gtacgcttatgatggaaacgaccttggtgcgacttacaaggacggagcagcgacgcttaaattat
gggctccgaaagcgagcaaggtaaccgctaacttctttgataaaaataatgccgctgaaaaaatc
ggcagcgtcgagttaacgaagggtgaaaaaggagtctggtcagctatggttgctcctggcgacct
gaacgtaaccgatcttgaaggttattttaccagtatgatgtaacaaatgacggtataactcgcc
aggtgttagatccttatgcaaaatcaatggcagcctttactgtgaatacagaaggcaatgctggt
cctgacggggacactgttggcaaggcggcaattcaaaaagcttctcgagagtacttctag
```

FIGURE 16LLLLLLLL
SEQ ID NO: 196

```
Met Leu Thr Asp Arg Phe Phe Asp Gly Asp Thr Ser Asn Asn Asp Pro
Tyr Asn Gln Asn Tyr Asp Ala Lys Asn Asp Arg Gly Thr Tyr Gln Gly
Gly Asp Phe Lys Gly Ile Thr Gln Lys Leu Asp Tyr Leu Asp Lys Leu
Gly Val Asn Thr Ile Trp Ile Ser Pro Ile Val Glu Asn Ile Lys His
Asp Val Arg Tyr Asp Asn Ser Glu Gly His Ser Tyr Tyr Ala Tyr His
Gly Tyr Trp Ala Ser Asn Phe Gly Ala Leu Asn Pro His Phe Gly Thr
Met Glu Asp Phe His Thr Leu Ile Asp Ala Ala His Glu Lys Gly Ile
Lys Ile Met Val Asp Val Val Leu Asn His Thr Gly Tyr Gly Leu Lys
Asp Ile Asn Gly Glu Val Ser Asn Pro Pro Ala Gly Tyr Pro Thr Asp
Ala Glu Arg Ser Thr Tyr Ser Ser Leu Leu Arg Gln Gly Ser Asn Val
Gly Ser Asp Glu Val Val Gly Glu Leu Ala Gly Leu Pro Asp Leu Lys
Thr Glu Asp Pro Ala Val Arg Gln Thr Ile Ile Asp Trp Gln Thr Asp
Trp Ile Thr Lys Ala Thr Thr Ala Lys Gly Asn Thr Ile Asp Tyr Phe
Arg Val Asp Thr Val Lys His Val Glu Asp Ala Thr Trp Met Ala Phe
Lys Asn Asp Leu Thr Glu Lys Met Pro Thr His Lys Met Ile Gly Glu
Ala Trp Gly Ala Ser Ala Asn Asn Gln Leu Gly Tyr Leu Glu Thr Gly
Met Met Asp Ser Leu Leu Asp Phe Asp Phe Lys Gly Ile Ala His Asp
Phe Val Asn Gly Lys Leu Lys Ala Ala Asn Asp Ala Leu Thr Ala Arg
Asn Gly Lys Ile Asp Asn Thr Ala Thr Leu Gly Ser Phe Leu Gly Ser
His Asp Glu Asp Gly Phe Leu Phe Lys Glu Gly Asn Asp Lys Gly Lys
Leu Lys Val Ala Ala Ser Leu Gln Ala Thr Ser Lys Gly Gln Pro Val
Ile Tyr Tyr Gly Glu Glu Leu Gly Gln Ser Gly Ala Asn Asn Tyr Pro
Gln Tyr Asp Asn Arg Tyr Asp Leu Ala Trp Asp Lys Val Glu Asn Asn
Asp Val Leu Glu His Tyr Thr Lys Val Leu Asn Phe Arg Ser Ala His
Ser Glu Val Phe Ala Lys Gly Glu Arg Ala Thr Ile Gly Gly Ser Asp
Ala Asp Lys Phe Leu Leu Phe Ala Arg Lys Asn Gly Asn Glu Ala Ala
Tyr Val Gly Leu Asn Val Ala Asp Thr Ala Lys Asp Val Thr Leu Thr
Val Ser Ala Gly Ala Val Val Thr Asp His Tyr Ala Asp Lys Thr Tyr
Thr Ala Ser Glu Ala Gly Glu Ile Thr Leu Thr Ile Pro Ala Lys Ala
Asp Gly Gly Thr Val Leu Leu Thr Val Glu Gly Gly Glu Ile Thr Ala
Ala Lys Ala Ala Ser Glu Gly Asp Gly Thr Val Glu Pro Val Pro Ala
Asn His Ile Arg Ile His Tyr Asn Arg Thr Asp Asn Asn Tyr Glu Asn
Tyr Gly Ala Trp Leu Trp Asn Asp Val Ala Ser Pro Ser Ala Asn Trp
Pro Thr Gly Ala Thr Met Phe Glu Lys Thr Asp Ser Tyr Gly Ala Tyr
Ile Asp Val Pro Leu Lys Glu Gly Ala Lys Asn Ile Gly Phe Leu Val
Met Asp Val Thr Lys Gly Asp Gln Gly Lys Asp Gly Gly Asp Lys Gly
Phe Thr Ile Ser Ser Pro Glu Met Asn Glu Ile Trp Ile Lys Gln Gly
Ser Asp Lys Val Tyr Thr Tyr Glu Pro Val Asp Leu Pro Ala Asn Thr
Val Arg Val His Tyr Val Arg Asp Asn Ala Asp Tyr Glu Asn Phe Gly
Ile Trp Asn Trp Gly Asp Val Thr Ala Pro Ser Glu Asn Trp Pro Thr
Gly Ala Ala Lys Phe Asp Gly Thr Asp Arg Tyr Gly Ala Tyr Val Asp
Ile Thr Leu Lys Glu Gly Ala Lys Asn Ile Gly Met Ile Ala Leu Asn
Thr Ala Asn Gly Glu Lys Asp Gly Gly Asp Lys Ser Phe Asn Leu Leu
Asp Lys Tyr Asn Arg Ile Trp Ile Lys Gln Gly Asp Asp Asn Val Tyr
Val Ser Pro Tyr Trp Glu Gln Ala Thr Gly Ile Thr Asn Ala Glu Val
Ile Ser Glu Asp Thr Ile Leu Leu Gly Phe Thr Met Thr Asp Gly Leu
Thr Pro Glu Ser Leu Lys Gly Gly Leu Val Ile Lys Asp Ser Thr Gly
Ala Glu Val Ala Ile Glu Ser Ala Glu Ile Thr Ser Ala Thr Ser Val
Lys Val Lys Ala Thr Phe Asp Leu Glu Lys Leu Pro Leu Ser Ile Thr
Tyr Ala Gly Arg Thr Val Ser Ala Ser Thr Gly Trp Arg Met Leu Asp
Glu Met Tyr Ala Tyr Asp Gly Asn Asp Leu Gly Ala Thr Tyr Lys Asp
```

FIGURE 16LLLLLLLL cont
Gly Ala Ala Thr Leu Lys Leu Trp Ala Pro Lys Ala Ser Lys Val Thr
Ala Asn Phe Phe Asp Lys Asn Asn Ala Ala Glu Lys Ile Gly Ser Val
Glu Leu Thr Lys Gly Glu Lys Gly Val Trp Ser Ala Met Val Ala Pro
Gly Asp Leu Asn Val Thr Asp Leu Glu Gly Tyr Phe Tyr Gln Tyr Asp
Val Thr Asn Asp Gly Ile Thr Arg Gln Val Leu Asp Pro Tyr Ala Lys
Ser Met Ala Ala Phe Thr Val Asn Thr Glu Gly Asn Ala Gly Pro Asp
Gly Asp Thr Val Gly Lys Ala Ala Ile Gln Lys Ala Ser Arg Glu Tyr
Phe

FIGURE 16MMMMMMMM
SEQ ID NO: 197
atgaaaccgtcaaaattcgttttctctctgctgccatcgcttgcagcctctccagtaccgccaa
tgctgacgccatttgcatgcatttaactggaagtactccgacgtcacgcaaaacgcctcgcaaa
tcgcggcggcgggttataaaaaagtgctgatttcgccagcactgaaatcgagtggcaatgaatgg
tgggcacgttatcaaccgcaagatctgcgcgtgatcgattccccacttggcaacaaaagtgactt
aaaatccatgattgatgctctgaaggcggtcggcgttgatgtgtatgccgatgtggtgcttaacc
atatggccaatgaaacatggaagcgtgaagacttaaattaccctggcagtgaagtgctgcaacaa
tacgcagctaacaccagttattatgcggaccaaacgctttttggcaatttaacggaaaacctatt
ctctggctttgacttccacccagaaggctgtattagcgattggaatgatgccggcaatgttcagt
actggcgtctttgtggcggtgctggtgaccgagggctgccagacttagatccgaacaactgggtg
gtgtcacagcaacgtttgtatttgaatgcgctaaaaggtttaggtgtgaaaggcttccgcattga
tgcggttaaacacatgagccaatatcaaatcgaccagattttcactgcagagattaccgccggaa
tgcacgtgtttggtgaagtgatcaccagtggtggcaaaggcgactccagctatgagaacttcta
gcgccttatctcaacgccaccaaccattcggcttacgatttcccactgtttgcctctattcgcaa
cgccttctcctacagcggtggcatgaacatgcttcatgatccacaagcctatggccaagggcttg
aaaacgcacgttcaattaccttaccatcacgcacgacatcccaacgaacgacggtttccgttat
caaatcatggatccgaaagatgaagagctggcttacgcttatatcctcggtaaagatggcggcac
acctctgatttacagcgacaacttacctgataacgaagatcgtgataatcgccgttgggaaggtg
tttggaaccgtgacctgatgaagaacatgttgcgcttccataaccaaatgcaagggcaagagatg
acgatgctgtacagcgaccaatgtctactgatgtttaagcgcggtaaacaaggggtggtcggcat
taataaatgcggtgaagagcgttctcataccgttgacacctatcagcatgagttcaactggtatc
agccttacacagatacactcactggcgtgactgaaaccgtgagttcgcgttaccacaccttccga
attccagctcgcagcgcgcgcatgtacatgctctaa

FIGURE 16NNNNNNNN
SEQ ID NO: 198
Met Lys Pro Ser Lys Phe Val Phe Leu Ser Ala Ala Ile Ala Cys Ser
Leu Ser Ser Thr Ala Asn Ala Asp Ala Ile Leu His Ala Phe Asn Trp
Lys Tyr Ser Asp Val Thr Gln Asn Ala Ser Gln Ile Ala Ala Ala Gly
Tyr Lys Lys Val Leu Ile Ser Pro Ala Leu Lys Ser Ser Gly Asn Glu
Trp Trp Ala Arg Tyr Gln Pro Gln Asp Leu Arg Val Ile Asp Ser Pro
Leu Gly Asn Lys Ser Asp Leu Lys Ser Met Ile Asp Ala Leu Lys Ala
Val Gly Val Asp Val Tyr Ala Asp Val Val Leu Asn His Met Ala Asn
Glu Thr Trp Lys Arg Glu Asp Leu Asn Tyr Pro Gly Ser Glu Val Leu
Gln Gln Tyr Ala Ala Asn Thr Ser Tyr Tyr Ala Asp Gln Thr Leu Phe
Gly Asn Leu Thr Glu Asn Leu Phe Ser Gly Phe Asp Phe His Pro Glu
Gly Cys Ile Ser Asp Trp Asn Asp Ala Gly Asn Val Gln Tyr Trp Arg
Leu Cys Gly Gly Ala Gly Asp Arg Gly Leu Pro Asp Leu Asp Pro Asn
Asn Trp Val Val Ser Gln Gln Arg Leu Tyr Leu Asn Ala Leu Lys Gly
Leu Gly Val Lys Gly Phe Arg Ile Asp Ala Val Lys His Met Ser Gln
Tyr Gln Ile Asp Gln Ile Phe Thr Ala Glu Ile Thr Ala Gly Met His
Val Phe Gly Glu Val Ile Thr Ser Gly Gly Lys Gly Asp Ser Ser Tyr
Glu Asn Phe Leu Ala Pro Tyr Leu Asn Ala Thr Asn His Ser Ala Tyr
Asp Phe Pro Leu Phe Ala Ser Ile Arg Asn Ala Phe Ser Tyr Ser Gly

FIGURE 16NNNNNNNN cont

Gly Met Asn Met Leu His Asp Pro Gln Ala Tyr Gly Gln Gly Leu Glu
Asn Ala Arg Ser Ile Thr Phe Thr Ile Thr His Asp Ile Pro Thr Asn
Asp Gly Phe Arg Tyr Gln Ile Met Asp Pro Lys Asp Glu Glu Leu Ala
Tyr Ala Tyr Ile Leu Gly Lys Asp Gly Gly Thr Pro Leu Ile Tyr Ser
Asp Asn Leu Pro Asp Asn Glu Asp Arg Asp Asn Arg Arg Trp Glu Gly
Val Trp Asn Arg Asp Leu Met Lys Asn Met Leu Arg Phe His Asn Gln
Met Gln Gly Gln Glu Met Thr Met Leu Tyr Ser Asp Gln Cys Leu Leu
Met Phe Lys Arg Gly Lys Gln Gly Val Val Gly Ile Asn Lys Cys Gly
Glu Glu Arg Ser His Thr Val Asp Thr Tyr Gln His Glu Phe Asn Trp
Tyr Gln Pro Tyr Thr Asp Thr Leu Thr Gly Val Thr Glu Thr Val Ser
Ser Arg Tyr His Thr Phe Arg Ile Pro Ala Arg Ser Ala Arg Met Tyr
Met Leu

FIGURE 16OOOOOOOO

SEQ ID NO: 199
gtgagtttgaccaaaaaggctcagtacgaaccaaatacggcaccaaggctcagtacatctctgca
atcaatgccgcgcacaacaacaatatccaaatttacggcgatgttgtgtttaaccaccgaggtgg
tgctgatgggaagtcgtgggtcgataccaagcgcgttgattgggacaaccgcaatattgaactgg
gcgacaaatggattgaagcttgggttgagtttaattttcctggccgcaacgacaaatactcgaac
ttccattggacttggtatcactttgacggtgttgactgggatgacgccggcaaagaaaaagcgat
ctttaaattcaaaggcgaaggaaaagcatgggattgggaagtcagctctgaaaaggcaattacg
actacctaa

FIGURE 16PPPPPPPP

SEQ ID NO: 200
Val Ser Leu Thr Lys Lys Ala Gln Tyr Glu Pro Asn Thr Ala Pro Arg
Leu Ser Thr Ser Leu Gln Ser Met Pro Arg Thr Thr Thr Ile Ser Lys
Phe Thr Ala Met Leu Cys Leu Thr Thr Glu Val Val Leu Met Gly Ser
Arg Gly Ser Ile Pro Ser Ala Leu Ile Gly Thr Thr Ala Ile Leu Asn
Trp Ala Thr Asn Gly Leu Lys Leu Gly Leu Ser Leu Ile Phe Leu Ala
Ala Thr Thr Asn Thr Arg Thr Ser Ile Gly Leu Gly Ile Thr Leu Thr
Val Leu Thr Gly Met Thr Pro Ala Lys Lys Lys Arg Ser Leu Asn Ser
Lys Ala Lys Glu Lys His Gly Ile Gly Lys Ser Ala Leu Lys Lys Ala
Ile Thr Thr Thr

FIGURE 16QQQQQQQQ

SEQ ID NO: 201
atgacagccaaggctgatgacttacgcatttaccagatcatggtggaaagctttgtggatggcga
taaacaggtcggccatggcaccggctacggtaccagccatcacaaaggcgatctgcaagggatca
ttgactcgctggattacattcatcgctgggcgtcaatgccatttggctaacgccgattttgaa
tctattccggtggagggacaagaccattgggcggacaggcttgatgctacaggctactttgccag
tgactatttcaagatagaccctcgctttggcacgttagaacaagcccgtgagctggtggaaaagg
cacacgcgaaaggcttgtatgtcttctttgatggagtatttggtcaccataaaggcaatgtggtg
ccatcaccacaaggtagactgcctgtcggtgaaaataacccggtcagctacccagagagcctggc
gttttacgaagaagtcgccagttactgggtgaaagagttaaagattgatggctggcgtctggatc
aagcctatcaagtgccgaccgatgcatggaaagcgatccgtcagagcgttgatgaagcgtcacag
tccgtaacttatgtgaataacaaaggggaaaccgtccatcctttgggttacatggtggctgaaat
ttggaataacgaacgttacatcacagaaaccggttacggcaaagaaggcgatccggcgttgtgct
cggcttttgattttccgatgcgtttccgagtggtcgaaaccctttgcggttaacgaaagtggtgtc
agccgaaaaggcggcgaatggttgaatgacggcatgtcactgcacagtcagtatccggatcatgc
caagcctaatttaatgttgggcaaccatgatgtggtgcgctttggggatctgctgcaacgtggcg
gtattgcgtcaccagaacaaccgcaatactggcagcgtcataaagcggcgatgtctttcttagca
gcgtataccggcccaattaccttgtattacggtgaagaaattggcgatcaggttgacggctttgc
taaaaaaatcaaagaagattgtgccgttattggtttgtgtgatgaccacgtggcgcgcaccagtg
cgaagattgatggcgtgacggcgtcactgaatgcacagcagtctgaactcaaagtatatgtctct

FIGURE 16QQQQQQQQ cont
tcattgatgacattacgtcagcaacatcctgcgttatcacaaggggaacgtactaatgtgatggc
gacagagacagtatacgtagaccataaacaggcagacaatgaagccctgttgtacatggtgagta
cgactgataacgcggagtcagtcaccttgaagggcaaagcgattggttcacaaggtgtgctgatt
gatttgttaacgaacgagcgttttatgcccaataatggggagtatgccattccattaacgggctt
tggcgcacgattcctcaagattgacactccgacagcggcgggtgtgatggcgcaatctgctgcct
cggtatcgctagtaggtgaagggatcatggcccaatgtgataccccaaccgttgaaggcaccggt
ccggtagcagaaaccttgtacgtggttggcgattttgccgatgctggttggaagcaaaagccgca
gcgcgcgtatcaatacaaaggcaagcacaatggcagcaacttgtatcaagtggttgtcgatgaaa
aagcgggcgcctacaagatgcaatacgccacgaaagattggagcccacagtttactgcagacggt
atggcattgaagccgggtaccgcaaagtcgctcatagcgggtggctacggtaaagacaccgccgt
gacgttgccggaatccggtaagtatgtgtggagcttaacattcagtgatcttggcgagccggagc
aaatcatggtgtctaagtgtcagtaa

FIGURE 16RRRRRRRR
SEQ ID NO: 202
Met Thr Ala Lys Ala Asp Asp Leu Arg Ile Tyr Gln Ile Met Val Glu
Ser Phe Val Asp Gly Asp Lys Gln Val Gly His Gly Thr Gly Tyr Gly
Thr Ser His His Lys Gly Asp Leu Gln Gly Ile Ile Asp Ser Leu Asp
Tyr Ile Gln Ser Leu Gly Val Asn Ala Ile Trp Leu Thr Pro Ile Phe
Glu Ser Ile Pro Val Glu Gly Gln Asp His Trp Ala Asp Arg Leu Asp
Ala Thr Gly Tyr Phe Ala Ser Asp Tyr Phe Lys Ile Asp Pro Arg Phe
Gly Thr Leu Glu Gln Ala Arg Glu Leu Val Glu Lys Ala His Ala Lys
Gly Leu Tyr Val Phe Phe Asp Gly Val Phe Gly His His Lys Gly Asn
Val Val Pro Ser Pro Gln Gly Arg Leu Pro Val Gly Glu Asn Asn Pro
Val Ser Tyr Pro Glu Ser Leu Ala Phe Tyr Glu Glu Val Ala Ser Tyr
Trp Val Lys Glu Leu Lys Ile Asp Gly Trp Arg Leu Asp Gln Ala Tyr
Gln Val Pro Thr Asp Ala Trp Lys Ala Ile Arg Gln Ser Val Asp Glu
Ala Ser Gln Ser Val Thr Tyr Val Asn Asn Lys Gly Glu Thr Val His
Pro Leu Gly Tyr Met Val Ala Glu Ile Trp Asn Asn Glu Arg Tyr Ile
Thr Glu Thr Gly Tyr Gly Lys Glu Gly Asp Pro Ala Leu Cys Ser Ala
Phe Asp Phe Pro Met Arg Phe Arg Val Val Glu Thr Phe Ala Val Asn
Glu Ser Gly Val Ser Arg Lys Gly Gly Glu Trp Leu Asn Asp Gly Met
Ser Leu His Ser Gln Tyr Pro Asp His Ala Lys Pro Asn Leu Met Leu
Gly Asn His Asp Val Val Arg Phe Gly Asp Leu Leu Gln Arg Gly Gly
Ile Ala Ser Pro Glu Gln Pro Gln Tyr Trp Gln Arg His Lys Ala Ala
Met Ser Phe Leu Ala Ala Tyr Thr Gly Pro Ile Thr Leu Tyr Tyr Gly
Glu Glu Ile Gly Asp Gln Val Asp Gly Phe Ala Lys Lys Ile Lys Glu
Asp Cys Ala Val Ile Gly Leu Cys Asp Asp His Val Ala Arg Thr Ser
Ala Lys Ile Asp Gly Val Thr Ala Ser Leu Asn Ala Gln Gln Ser Glu
Leu Lys Val Tyr Val Ser Ser Leu Met Thr Leu Arg Gln Gln His Pro
Ala Leu Ser Gln Gly Glu Arg Thr Asn Val Met Ala Thr Glu Thr Val
Tyr Val Asp His Lys Gln Ala Asp Asn Glu Ala Leu Leu Tyr Met Val
Ser Thr Thr Asp Asn Ala Glu Ser Val Thr Leu Lys Gly Lys Ala Ile
Gly Ser Gln Gly Val Leu Ile Asp Leu Leu Thr Asn Glu Arg Phe Met
Pro Asn Asn Gly Glu Tyr Ala Ile Pro Leu Thr Gly Phe Gly Ala Arg
Phe Leu Lys Ile Asp Thr Pro Thr Ala Ala Gly Val Met Ala Gln Ser
Ala Ala Ser Val Ser Leu Val Gly Glu Gly Ile Met Ala Gln Cys Asp
Thr Pro Thr Val Glu Gly Thr Gly Pro Val Ala Glu Thr Leu Tyr Val
Val Gly Asp Phe Ala Asp Ala Gly Trp Lys Gln Lys Pro Gln Arg Ala
Tyr Gln Tyr Lys Gly Lys His Asn Gly Ser Asn Leu Tyr Gln Val Val
Val Asp Glu Lys Ala Gly Ala Tyr Lys Met Gln Tyr Ala Thr Lys Asp
Trp Ser Pro Gln Phe Thr Ala Asp Gly Met Ala Leu Lys Pro Gly Thr
Ala Lys Ser Leu Ile Ala Gly Gly Tyr Gly Lys Asp Thr Ala Val Thr

FIGURE 16RRRRRRRR cont
Leu Pro Glu Ser Gly Lys Tyr Val Trp Ser Leu Thr Phe Ser Asp Leu
Gly Glu Pro Glu Gln Ile

FIGURE 16SSSSSSSS
SEQ ID NO: 203
atgaagatgaagtcccggggcgtggttgttaggtagtgcagtggccatggcgttggcctcttcggc
agccaatgccggtgtcatggttcacctgttccagtggaagtacaatgacatcgccaacgagtgcg
aaaaggtgctcggtcccaaagggtatgaagcagtgcagatcacgccgcctgctgaacacctgcaa
ggctcctcctggtgggtggtctatcagcccgtcagctacaagaacttcacttctctgggcggtaa
cgaggccgaactcaaaagcatgatcgcccgttgcaaggccgccggggtcaagatttacgccgatg
cggtattcaaccagctggctggtggatcaggcgtcggtacaggtggtagcagctacaatgccggc
agcttcagctatccccaatttggctacaacgatttccatcacgctgggagcctcaccaactatgc
cgaccgcaacaatgtgcaaaacggtgccctgctggggctgccggatctggataccggctctgcct
atgtgcaggatcagctggctacctatatgaagaccctgagtggctgggggtgtggcaggttttcgt
cttgatgcagcaaagcatatgagcgttgccgatctctcggccatcgtcagcaaggcgggcaatcc
tttTgtctactccgaggtgattggtgccacgggtgaaccaatccagccggggcgaatataccggca
ttggtgccgtgaccgaatttaaatacggcaccgatctggcctccaacttcaaggggcagatcaag
aatctcaagagcatgggcgagagctggggtctgcttgcgtcgaacaaggctgaagtctttgtggt
caaccatgaccgtgagcggggacatggcggtggcggtatgctgacctacaaggatggtgccctct
acaatctggccaacatcttcatgctggcctggccctatggcgcctatccccaggtgatgtccggc
tatgatttcggcaccaataccgatattggtgggccgagcgctacccccttgttcttccggctctag
ctggaactgcgaacaccgctggagcaacatcgccaacatggtctcgttccacaatgccgcccaag
gcacgtccatgaccaactggtgggataatggtaataaccagatcgcctttggtcgcggcgccaag
gcctttgtggtgatcaacaatgaatcttccactctgagcaagagcctgcagacgggtctgccagc
cggggagtactgcaacattctggccggtgatgccctgtgcagcggcagcaccatcaaggtggatg
ccagcggtatggccaccttcaacgtggcagggatgaaggcggcagcgatccatatcaatgccaag
cccgatagcaccagcagtggcagctcaggctcttcctctggctcttcttcctctgccaccagtaa
caagtttgccagcatgaatctgcggggcaccaacaatggctgggccagcaccgccatgacagtgg
atgccaacgtgtctggtcggcggatgtcacctttaccggggccgcggatgccaatggtgcccag
cgcttcaagtttgatgtctatggcaactggacagagagctatggcgatacacaagccgatggcat
tgccgacaaggggagcgccaaggacatctatttcaatggtgtgggcaagtatcgtgtctcgctca
aggagagcgacatgagctacaccctgacccagctctccagcaatcaggcaccggtggcggccatc
acccccaagacactctccgtcaagctgggtgactcagtggtgttcgatgcctccggctccaccga
tgatgtgggtgtcactggctacagctggtctaccggtggcagtgccaagaccgaaactgtgctgt
ttgatgctctgggtaccaagaccattaccgtgacagtggccgatgccgatggcttgacctccaag
gccagtgccaccgtcaccgtcaccgatggcagcgtggcttataacagcaactttgccagcctgaa
cttccgtggcactccaacagttggggcgcggcagccatgacgctggtggcagacaacacctggg
aggcaacggtcaacttcgatggtcaggccaatcagcgcttcaagttcgatatcaagggtgactgg
agccagaactatggtgatagcaacaaggatggggtggccgaacgtaccggtgccgatatttacac
cactgtgaccggtcaatataaggtgcaatttaacgactccactttgaagtacacccctgaccaagc
tggccgatagcagcgccaccagctatagcgcgaactttgccagcctctacctgcgtggcacccg
aacagctggggcaccaccgccatgaagctggtggccaataacagctggcaggccgaggtgacctt
caccggcaagggcgatgccactggtgcccaacgcttcaagttcgacgtcaagggtgactggagcc
agaactacggtgacagcaacatggacgggactgccgaacggactggtggcgatatcaccagtgcc
gtggtgggcacctatctggtgaccttaatgacagcacactgaaatacaccctgaccgccaaata
a

FIGURE 16TTTTTTTT
SEQ ID NO: 204
Met Lys Met Lys Ser Arg Ala Trp Leu Leu Gly Ser Ala Val Ala Met
Ala Leu Ala Ser Ser Ala Ala Asn Ala Gly Val Met Val His Leu Phe
Gln Trp Lys Tyr Asn Asp Ile Ala Asn Glu Cys Glu Lys Val Leu Gly
Pro Lys Gly Tyr Glu Ala Val Gln Ile Thr Pro Pro Ala Glu His Leu
Gln Gly Ser Ser Trp Trp Val Val Tyr Gln Pro Val Ser Tyr Lys Asn

FIGURE 16TTTTTTTT cont

```
Phe Thr Ser Leu Gly Gly Asn Glu Ala Glu Leu Lys Ser Met Ile Ala
Arg Cys Lys Ala Ala Gly Val Lys Ile Tyr Ala Asp Ala Val Phe Asn
Gln Leu Ala Gly Gly Ser Gly Val Gly Thr Gly Gly Ser Ser Tyr Asn
Ala Gly Ser Phe Ser Tyr Pro Gln Phe Gly Tyr Asn Asp Phe His His
Ala Gly Ser Leu Thr Asn Tyr Ala Asp Arg Asn Asn Val Gln Asn Gly
Ala Leu Leu Gly Leu Pro Asp Leu Asp Thr Gly Ser Ala Tyr Val Gln
Asp Gln Leu Ala Thr Tyr Met Lys Thr Leu Ser Gly Trp Gly Val Ala
Gly Phe Arg Leu Asp Ala Ala Lys His Met Ser Val Ala Asp Leu Ser
Ala Ile Val Ser Lys Ala Gly Asn Pro Phe Val Tyr Ser Glu Val Ile
Gly Ala Thr Gly Glu Pro Ile Gln Pro Gly Glu Tyr Thr Gly Ile Gly
Ala Val Thr Glu Phe Lys Tyr Gly Thr Asp Leu Ala Ser Asn Phe Lys
Gly Gln Ile Lys Asn Leu Lys Ser Met Gly Glu Ser Trp Gly Leu Leu
Ala Ser Asn Lys Ala Glu Val Phe Val Val Asn His Asp Arg Glu Arg
Gly His Gly Gly Gly Gly Met Leu Thr Tyr Lys Asp Gly Ala Leu Tyr
Asn Leu Ala Asn Ile Phe Met Leu Ala Trp Pro Tyr Gly Ala Tyr Pro
Gln Val Met Ser Gly Tyr Asp Phe Gly Thr Asn Thr Asp Ile Gly Gly
Pro Ser Ala Thr Pro Cys Ser Ser Gly Ser Ser Trp Asn Cys Glu His
Arg Trp Ser Asn Ile Ala Asn Met Val Ser Phe His Asn Ala Ala Gln
Gly Thr Ser Met Thr Asn Trp Trp Asp Asn Gly Asn Asn Gln Ile Ala
Phe Gly Arg Gly Ala Lys Ala Phe Val Val Ile Asn Asn Glu Ser Ser
Thr Leu Ser Lys Ser Leu Gln Thr Gly Leu Pro Ala Gly Glu Tyr Cys
Asn Ile Leu Ala Gly Asp Ala Leu Cys Ser Gly Ser Thr Ile Lys Val
Asp Ala Ser Gly Met Ala Thr Phe Asn Val Ala Gly Met Lys Ala Ala
Ala Ile His Ile Asn Ala Lys Pro Asp Ser Thr Ser Ser Gly Ser Ser
Gly Ser Ser Ser Gly Ser Ser Ser Ala Thr Ser Asn Lys Phe Ala
Ser Met Asn Leu Arg Gly Thr Asn Asn Gly Trp Ala Ser Thr Ala Met
Thr Val Asp Ala Asn Arg Val Trp Ser Ala Asp Val Thr Phe Thr Gly
Ala Ala Asp Ala Asn Gly Ala Gln Arg Phe Lys Phe Asp Val Tyr Gly
Asn Trp Thr Glu Ser Tyr Gly Asp Thr Gln Ala Asp Gly Ile Ala Asp
Lys Gly Ser Ala Lys Asp Ile Tyr Phe Asn Gly Val Gly Lys Tyr Arg
Val Ser Leu Lys Glu Ser Asp Met Ser Tyr Thr Leu Thr Gln Leu Ser
Ser Asn Gln Ala Pro Val Ala Ala Ile Thr Pro Lys Thr Leu Ser Val
Lys Leu Gly Asp Ser Val Val Phe Asp Ala Ser Gly Ser Thr Asp Asp
Val Gly Val Thr Gly Tyr Ser Trp Ser Thr Gly Gly Ser Ala Lys Thr
Glu Thr Val Leu Phe Asp Ala Leu Gly Thr Lys Thr Ile Thr Val Thr
Val Ala Asp Ala Asp Gly Leu Thr Ser Lys Ala Ser Ala Thr Val Thr
Val Thr Asp Gly Ser Val Ala Tyr Asn Ser Asn Phe Ala Ser Leu Asn
Phe Arg Gly Thr Pro Asn Ser Trp Gly Ala Ala Ala Met Thr Leu Val
Ala Asp Asn Thr Trp Glu Ala Thr Val Asn Phe Asp Gly Gln Ala Asn
Gln Arg Phe Lys Phe Asp Ile Lys Gly Asp Trp Ser Gln Asn Tyr Gly
Asp Ser Asn Lys Asp Gly Val Ala Glu Arg Thr Gly Ala Asp Ile Tyr
Thr Thr Val Thr Gly Gln Tyr Lys Val Gln Phe Asn Asp Ser Thr Leu
Lys Tyr Thr Leu Thr Lys Leu Ala Asp Ser Ser Ala Thr Ser Tyr Ser
Ala Asn Phe Ala Ser Leu Tyr Leu Arg Gly Thr Pro Asn Ser Trp Gly
Thr Thr Ala Met Lys Leu Val Ala Asn Asn Ser Trp Gln Ala Glu Val
Thr Phe Thr Gly Lys Gly Asp Ala Thr Gly Ala Gln Arg Phe Lys Phe
Asp Val Lys Gly Asp Trp Ser Gln Asn Tyr Gly Asp Ser Asn Met Asp
Gly Thr Ala Glu Arg Thr Gly Gly Asp Ile Thr Ser Ala Val Val Gly
Thr Tyr Leu Val Thr Phe Asn Asp Ser Thr Leu Lys Tyr Thr Leu Thr
Ala Lys
```

FIGURE 16UUUUUUUU
SEQ ID NO: 205
atgtaccgcgtaatacctattattttgattatgagtatgattgtagcttgtgagtctccaaagaa
aaaaacaaccgaaaccgctcaaccttcaacaaatgccgaaaaacccttgtttgggaggctgcca
atgtatattttttgttaactgaccgttttaacaacggtaacccaaacaatgacatcaattttaat
aggactaaagaatcaggaaaactccgcaattttatgggaggcgatatcaagggcatcacccaaa
aataaatgagggtatttagtaaactaggcgttaatgccatctggcttaccccggttgttgaac
aaatacatggcagtgttgatgaaggtaccggcaatacctatgcctttcatggctattgggccaaa
gattggacaaacttagacccaaattttggcacaaaagaagaccttgccgaactggtggcaactgc
ccatgcaaaaggcatcaggatacttttagatgtggtaataaaccacaccggcccggtaaccgacc
aagacccggtttggggagaagattgggtacgtacaggcccgcagtgtacctatgataattacacc
aataccaccagttgcacgctggtagccaatttacctgatatacttacagaaagtaatgaaaatgt
ggccttaccaaccttttttgttagataaatggaaagccgaaggcagattagagcaagaactaaaag
aacttgacgatttttttcccgcacaggccacccacgcgcacccgcttttacattattaaatgg
cttaccgattacatccgagaatttggggtagatgggtttagggttgataccgtaaaacataccga
agaaacggtttgggccgagttgtatgatgaagccgtaattgcttttgccgaatataaaaaagcca
acccagacaaggtattggacgataatgaattttatatggtaggcgaagtgtacaactacggtatt
tccggcggaaggttctatgatttcggcgataaaaaggtggactattttgaccacggatttaaaag
cctcatcaattttgaaatgaaatatgatgccaattttacctacgatacacttttaggaagtacg
atacccttttgcataccaaacttaaaggcagaagtgtgctcaactacctctcatctcacgacgat
ggaagtccatttgataaaatgcggcaaaaaccatacgagtcggctacaaaattactgctcactcc
gggcgcatcccaaattttattacggtgacgaaaccgccagaagccttaacatagaaggcgcacagg
gagatgctacgcttcgttcgtttatgaattgggaagagctcgcagaagaccctgccaagcaaaaa
atacttcagcattggcaaaaactgggcagtttcaggaacaaccaccccgcagttggtgccggaag
gcacaaaacccttggcaaaaagccgttttacacctttagcagggtttatcaaaaaatggtttta
ttgacaaagttgtggtagcattagatgcccctaaaggccaaaaacaaattaccgttaatggtgtt
tttgatgacggtacaaaacttgtagatgcctattcaggcaaagaaacctcagttaaaaatggtat
cgtttcactttcttctgaatttgatattgttttgttagaacaaaaataa

FIGURE 16VVVVVVVV
SEQ ID NO: 206

Met Tyr Arg Val Ile Pro Ile Ile Leu Ile Met Ser Met Ile Val Ala
Cys Glu Ser Pro Lys Lys Lys Thr Thr Glu Thr Ala Gln Pro Ser Thr
Asn Ala Glu Lys Pro Phe Val Trp Glu Ala Ala Asn Val Tyr Phe Leu
Leu Thr Asp Arg Phe Asn Asn Gly Asn Pro Asn Asn Asp Ile Asn Phe
Asn Arg Thr Lys Glu Ser Gly Lys Leu Arg Asn Phe Met Gly Gly Asp
Ile Lys Gly Ile Thr Gln Lys Ile Asn Glu Gly Tyr Phe Ser Lys Leu
Gly Val Asn Ala Ile Trp Leu Thr Pro Val Val Glu Gln Ile His Gly
Ser Val Asp Glu Gly Thr Gly Asn Thr Tyr Ala Phe His Gly Tyr Trp
Ala Lys Asp Trp Thr Asn Leu Asp Pro Asn Phe Gly Thr Lys Glu Asp
Leu Ala Glu Leu Val Ala Thr Ala His Ala Lys Gly Ile Arg Ile Leu
Leu Asp Val Val Ile Asn His Thr Gly Pro Val Thr Asp Gln Asp Pro
Val Trp Gly Glu Asp Trp Val Arg Thr Gly Pro Gln Cys Thr Tyr Asp
Asn Tyr Thr Asn Thr Thr Ser Cys Thr Leu Val Ala Asn Leu Pro Asp
Ile Leu Thr Glu Ser Asn Glu Asn Val Ala Leu Pro Thr Phe Leu Leu
Asp Lys Trp Lys Ala Glu Gly Arg Leu Glu Gln Glu Leu Lys Glu Leu
Asp Asp Phe Phe Ser Arg Thr Gly His Pro Arg Ala Pro Arg Phe Tyr
Ile Ile Lys Trp Leu Thr Asp Tyr Ile Arg Glu Phe Gly Val Asp Gly
Phe Arg Val Asp Thr Val Lys His Thr Glu Glu Thr Val Trp Ala Glu
Leu Tyr Asp Glu Ala Val Ile Ala Phe Ala Glu Tyr Lys Lys Ala Asn
Pro Asp Lys Val Leu Asp Asp Asn Glu Phe Tyr Met Val Gly Glu Val
Tyr Asn Tyr Gly Ile Ser Gly Gly Arg Phe Tyr Asp Phe Gly Asp Lys
Lys Val Asp Tyr Phe Asp His Gly Phe Lys Ser Leu Ile Asn Phe Glu
Met Lys Tyr Asp Ala Asn Phe Thr Tyr Asp Thr Leu Phe Arg Lys Tyr

FIGURE 16VVVVVVVV cont
```
Asp Thr Leu Leu His Thr Lys Leu Lys Gly Arg Ser Val Leu Asn Tyr
Leu Ser Ser His Asp Asp Gly Ser Pro Phe Asp Lys Met Arg Gln Lys
Pro Tyr Glu Ser Ala Thr Lys Leu Leu Leu Thr Pro Gly Ala Ser Gln
Ile Tyr Tyr Gly Asp Glu Thr Ala Arg Ser Leu Asn Ile Glu Gly Ala
Gln Gly Asp Ala Thr Leu Arg Ser Phe Met Asn Trp Glu Glu Leu Ala
Glu Asp Pro Ala Lys Gln Lys Ile Leu Gln His Trp Gln Lys Leu Gly
Ser Phe Arg Asn Asn His Pro Ala Val Gly Ala Gly Arg His Lys Thr
Leu Gly Lys Lys Pro Phe Tyr Thr Phe Ser Arg Val Tyr Gln Lys Asn
Gly Phe Ile Asp Lys Val Val Val Ala Leu Asp Ala Pro Lys Gly Gln
Lys Gln Ile Thr Val Asn Gly Val Phe Asp Asp Gly Thr Lys Leu Val
Asp Ala Tyr Ser Gly Lys Glu Thr Ser Val Lys Asn Gly Ile Val Ser
Leu Ser Ser Glu Phe Asp Ile Val Leu Leu Glu Gln Lys
```
FIGURE 16WWWWWWWW
SEQ ID NO: 207
```
ctgtcgactgagcctttcgttttgggctcgagactgactctcagcccacccgcagtagctccag
acggagtagccgtaatagccgttggccgggtcgtgggcaggggcctcgaggtacacccacccgct
tgagtccacccacttgtccacccagccgccgaggttgccggtgtactcgtggatgcacgctcccg
cgaacttcggaacgtagacccaccttccggctttgcttgaggcgaggttgatgtatgttatcagt
cccggcttgcttccgtagccgtttctcacgaatatcagctcgtcgttgtcgtagtaaacgacgtc
agtgcttcctccggccaggttgtcatgtatccagatgaggttcttgagcttatccttgttgagcc
actcctcgtagtcgcggtagaatattgtcggctggccctcgtaggtgaggatgaacgcgtaggct
ggatacttgttccagattatatcggtgtcgtggtttgcaacgaaggttacggccttaaacgggtc
gcggctgacgactgtgccccgttcttgagggcctcgacgagtgcgggaatgttcttgttgtcaa
aggccgcgtccatcttgtagtagagcgggaagtcgaagaccttggcgccgctcgagtaggcccag
ttgaggagtgcatcaacgttggtgtcccagtactcgccaacggcccagccgccccaccagttgag
ccagtccttgacgacccacgctccgtggcccttcacgtagtcaaagcgccaggcatcaacgccga
tgctccttaggtaggcggcgtagctctcatcgctcgcccagagccagtgctggtcccagctcttc
tcgtgggctatgtctgggaagcctccaaatgtgccctcgtcacagcacttgacctcgttggggtg
gaagtcgaggtagttggcagtatatttgcccgaggccacctttgagaagtccgtccaggtgtagt
ccccaacgaacgggttccactcgaggtctccgcctgcgcggtggtttatgacgatgtccgctatg
acctttatgccgtaggcatgggccgtgtttatcatgttcacgagctcctgcttggagccaaagcg
cgtctctaccgttcccttctggtcgtactcaccgaggtcaaagaagtcgtaggggtcgtagccca
tcgaataggcgccgccatgcccttgctcgccgggggaatccaaatggcggatattcccgcctcg
taccactccggtatcttgctcctgatggtgtcccaccagattcctccacctgggacgtcccagta
gaaggcctgcattataacgccgccctcttccagctcggagtacttggccataagttacctcctac
tagtagattaaaa
```
FIGURE 16XXXXXXXX
SEQ ID NO: 208
```
Leu Ser Thr Glu Pro Phe Val Leu Gly Ser Arg Leu Thr Leu Ser Pro
Pro Arg Ser Ser Arg Arg Ser Arg Asn Ser Arg Trp Pro Gly
Arg Gly Gln Gly Pro Arg Gly Thr Pro Thr Arg Leu Ser Pro Pro Thr
Cys Pro Pro Ser Arg Arg Gly Cys Arg Cys Thr Arg Gly Cys Thr Leu
Pro Arg Thr Ser Glu Arg Arg Pro Thr Phe Arg Leu Cys Leu Arg Arg
Gly Cys Met Leu Ser Val Pro Ala Cys Phe Arg Ser Arg Phe Ser Arg
Ile Ser Ala Arg Arg Cys Arg Ser Lys Arg Arg Gln Cys Phe Leu Arg
Pro Gly Cys His Val Ser Arg Gly Ser Ala Tyr Pro Cys Ala Thr Pro
Arg Ser Arg Gly Arg Ile Leu Ser Ala Gly Pro Arg Arg Gly Thr Arg
Arg Leu Asp Thr Cys Ser Arg Leu Tyr Arg Cys Arg Gly Leu Gln Arg
Arg Leu Arg Pro Thr Gly Arg Gly Arg Leu Cys Pro Arg Ser Gly Pro
Arg Arg Val Arg Glu Cys Ser Cys Cys Gln Arg Pro Arg Pro Ser Cys
Ser Arg Ala Gly Ser Arg Arg Pro Trp Arg Arg Ser Ser Arg Pro Ser
Gly Val His Gln Arg Trp Cys Pro Ser Thr Arg Gln Arg Pro Ser Arg
```

FIGURE 16XXXXXXXX cont

Pro Thr Ser Ala Ser Pro Arg Pro Thr Leu Arg Gly Pro Ser Arg Ser
Gln Ser Ala Arg His Gln Arg Arg Cys Ser Leu Gly Arg Arg Arg Ser
Ser His Arg Ser Pro Arg Ala Ser Ala Gly Pro Ser Ser Ser Arg Gly
Leu Cys Leu Gly Ser Leu Gln Met Cys Pro Arg His Ser Thr Pro Arg
Trp Gly Gly Ser Arg Gly Ser Trp Gln Tyr Ile Cys Pro Arg Pro Pro
Leu Arg Ser Pro Ser Arg Cys Ser Pro Gln Arg Thr Gly Ser Thr Arg
Gly Leu Arg Leu Arg Gly Gly Leu Arg Cys Pro Leu Pro Leu Cys Arg
Arg His Gly Pro Cys Leu Ser Cys Ser Arg Ala Pro Ala Trp Ser Gln
Ser Ala Ser Leu Pro Phe Pro Ser Gly Arg Thr His Arg Gly Gln Arg
Ser Arg Arg Gly Arg Ser Pro Ser Asn Arg Arg Arg Pro Cys Pro Cys
Ser Pro Gly Glu Ser Lys Trp Arg Ile Phe Pro Pro Arg Thr Thr Pro
Val Ser Cys Ser Trp Cys Pro Thr Arg Phe Leu His Leu Gly Arg Pro
Ser Arg Arg Pro Ala Leu Arg Arg Pro Leu Pro Ala Arg Ser Thr Trp
Pro Val Thr Ser Tyr Ile Lys

FIGURE 16YYYYYYYY

SEQ ID NO: 209
atgattcagcccatgcactctcgggaacaggcctgccgtctcattccggcactgatcatgacattt
gcactggcactgccgttgcaaattcgtgccgatgtcaccctgcatgctttcaactggagctatgcc
gatgtcgctgatcgggccgttgacatcgctgcagcagggtacagtgccgtgctggtggccccgcca
cttcgatccgaaggcacggcctggtgggcgcgataccagcccaggatctccgcctatcgaccat
ccgctgggcaatacacatgacttcgtcaacatgatcgatgctctcgatgatgtgggtgtgggcgtg
tacgccgacatcgtgctcaaccacatggccaatgaggctgcacaaaggcctgacctgaactaccct
ggtcaggcagtgcttgacgaatatgcttccgatcccggtcatttcgagggcttgaggctgttcggt
aatctgagcttcaatttcctgtcggaacatgatttcggacccgccagtgcattcaggattacagc
gatgtgtttcaggtccagaactggcggctgtgcggaccgccgccggacccgggcctgccgacctg
gtcgccaatgactggtgatctctcaacagcgccagtatctggaagccatcaaggcgctgggtgtg
gctggcatgcgcatcgacgcggtcaagcatatgcccatgagccatatcaatgccgttctcaccccc
gagatccggtcgggcttgcatgtgtttggcgaagtcatcacctccggtggcgctggtgatacatcc
tacgaccgttttctggcccttacctggcacaaagcgaccatggtgcctatgactttccattgttt
gaaaccattcgccgtgctttcggcttcggtggcagcatgagtgaactggtcgatcctgctgcctac
ggtcaggccctgccaccggaccgcgccatcaccttcgtcatcacgcacgatattccgaacaatgac
ggatttcgctaccagatactcgaccccgtcgatgaatcactggcctacgcctacattctgggccgc
gatggcggtgtcccgcttctgtattccgacaacaatgaaagcggcgatggccgctggatcgatgcc
tggcaacgtccggatctggttgcaatggtcggcttccacaatgcagtccacggtcaggacatggcc
gtgctttcacatgacgactgccacctgctgtttcggcgcggcagcctcgggattgtcggcatcaac
aagtgcggccatgcactcagctcctgggtcaacatgaaccagagcgtactgtggtggtacgcggac
tacacagacgtgctcgacagcaacagcgttgtcaacatccagtcatcctggcacgagttcatcctt
cccgccgccaggcacgcctgtggttgcga

FIGURE 16ZZZZZZZZ

SEQ ID NO: 210
MIQPMHSREQACRLIPALIMTFALALPLQIRADVTLHAFNWSYADVADRAVDIAAAGYSAVLVAP
PLRSEGTAWWARYQPQDLRLIDHPLGNTHDFVNMIDALDDVGVGVYADIVLNHMANEAAQRPDLN
YPGQAVLDEYASDPGHFEGLRLFGNLSFNFLSEHDFGPAQCIQDYSDVFQVQNWRLCGPPPDPGL
PDLVANDWVISQQRQYLEAIKALGVAGMRIDAVKHMPMSHINAVLTPEIRSGLHVFGEVITSGGA
GDTSYDRFLAPYLAQSDHGAYDFPLFETIRRAFGFGGSMSELVDPAAYGQALPPDRAITFVITHD
IPNNDGFRYQILDPVDESLAYAYILGRDGGVPLLYSDNNESGDGRWIDAWQRPDLVAMVGFHNAV
HGQDMAVLSHDDCHLLFRRGSLGIVGINKCGHALSSWVNMQSVLWWYADYTDVLDSNSVVNIQS
SWHEFILPARQARLWLR

FIGURE 16AAAAAAAAA
SEQ ID NO: 211
```
GTGTTTCGTTCTGACACAGTTTCGCGTACCTGCATGTATGGTGCGCTGCGTAATGCCTACCAACC
CGATCGGGTGTTTACTGGAGTCACGGTGCGGACATGCAACTTAAAAAAGCATGCTCATCGCCAGG
CGCTGTTGTTCATCGTGACGCGGTGCCTGTGCCTGAAATCCAGGCAGACCCATAAAAACAACAAC
AAACCGATAACAAACGACCCAAGCCTTCTAAGAGGAGAAAACGGGATGGCTTTTAAACTACGCAA
AAAGGCGCTCGTTGGCCTGTTCACGGCCGGCGCAATGGTATATGCCGGTGCAGCGGCGAGTGGTG
AAATCATTCTGCAGGGCTTCCACTGGCACTCCAAGTGGGGCGGCAACAATCAGGGTTGGTGGCAG
GTGATGGAAGGTCAGGCCAACACCATCGCCAACGCCGGCTTTACGCACGTGTGGTTCCCGCCGGT
CCATAACTCGGCCGATGCCGAGGGTTACCTACCCCGCGAGCTGAACAACCTCAACTCCAGCTATG
GCTCCGAAGCACAGCTGCGCAGCGCCATCCAGGCACTGAACAATCGCGGCGTGCATGCGATTGCC
GATGTGGTCATGAACCACCGGGTGGGCTGCTCTGGCTGGGCGGATTTCTGTAACCCGGACTGGCC
GACCTGGTACATCGTCGCCAATGATTCCTGGCCCGGTGGCCCGAAAAGCCAGAACTGGGACACGG
GTGAGACGTACCACGCCGCCGTGACCTCGATCACGCCAATCCGCAGGTGCGCAACGATATCTCG
CACTACCTGAACAGCCGCCTCAAGGACGTCGGCTTCTCCGGCTGGCGCTGGGACTATGCCAAGGG
TTTCTGGCCCGGCTATGTCGGCGAGTACAACTGGAACACCAACCCGAACTTCTGTGTGGGTGAGG
TGTGGGACGATCTCGACCCCAACAATCCCAACCCGCACCGCCAGCAACTGGTGGACTGGGTTGAT
GCTACCGGTGGCAGTTGTCACGTCTTCGACTTCACCACCAAGGGGCTGACGAACTATGCGCTGCA
GCATGGCCAGTACTGGCGCCTGCAGGGTGATAATGGTGGCCCGGCTGGCGGCATCGGCTGGTGGC
CGCAACGCATGGTGACCTTCGTCGACAACCATGACACGGGCCCGAGCAATCACTGTGGTGACGGC
CAGAACCTCTGGCCCGTGCCCTGTGACAAGGTCATGGAGGCGTATGCCTACATCCTGACCCATCC
GGGCGTGCCGTCGGTGTACTGGACGCACTTCTTCAACTGGAATCTTGGTAGCGAGATCAGCCAGT
TGATGCAGATCCGCAAGAACCAGGGCGTGCACTCCGGTTCCGACGTCTGGATCGCCGAGGCCCGT
CACGGCCTGTACGCCGCCTATATCAACGGTAATGTGGCGATGAAGATGGGCTGGGATAACTGGAG
CCCGGGCTGGGGCTGGTCGCTGGCGGCCTCCGGTAACAACTGGGCCGTCTGGACACGCTGA
```

FIGURE 16BBBBBBBBB
SEQ ID NO: 212
```
VFRSDTVSRTCMYGALRNAYQPDRVFTGVTVRTCNLKKHAHRQALLFIVTRCLCLKSRQTHKNNN
KPITNDPSLLRGENGMAFKLRKKALVGLFTAGAMVYAGAAASGEIILQGFHWHSKWGGNNQGWWQ
VMEGQANTIANAGFTHVWFPPVHNSADAEGYLPRELNNLNSSYGSEAQLRSAIQALNNRGVHAIA
DVVMNHRVGCSGWADFCNPDWPTWYIVANDSWPGGPKSQNWDTGETYHAARDLDHANPQVRNDIS
HYLNSRLKDVGFSGWRWDYAKGFWPGYVGEYNWNTNPNFCVGEVWDDLDPNNPNPHRQQLVDWVD
ATGGSCHVFDFTTKGLTNYALQHGQYWRLQGDNGGPAGGIGWWPQRMVTFVDNHDTGPSNHCGDG
QNLWPVPCDKVMEAYAYILTHPGVPSVYWTHFFNWNLGSEISQLMQIRKNQGVHSGSDVWIAEAR
HGLYAAYINGNVAMKMGWDNWSPGWGWSLAASG
```

15314293
042913

ENZYMES HAVING ALPHA AMYLASE ACTIVITY AND METHODS OF MAKING AND USING THEM

This application is a continuation of U.S. patent application Ser. No. 13/669,707, filed Nov. 6, 2012, now abandoned, which is a continuation of U.S. patent application Ser. No. 12/567,550, filed Sep. 25, 2009, now U.S. Pat. No. 8,334,118, which is a continuation of U.S. patent application Ser. No. 11/621,528, filed Jan. 9, 2007, now U.S. Pat. No. 7,785,855; which is a divisional of U.S. patent application Ser. No. 10/081,872, filed Feb. 21, 2002, now U.S. Pat. No. 7,407,677; which claims priority of U.S. Provisional Application No. 60/291,122, filed May 14, 2001; U.S. Provisional Application No. 60/270,496, filed Feb. 21, 2001; and U.S. Provisional Application No. 60/270,495, filed Feb. 21, 2001.

SEQUENCE LISTING

This application includes an amino acid sequence listing in computer readable form (CRF) and conforming to the requirements of 37 C.F.R. 1.821 through 1.825. The sequence listing of this application is being submitted to the USPTO via the EFS-WEB server as authorized and set forth in MPEP § 502.05. The sequence listing of this application is filed in an ASC II text (.txt) file as identified below and is hereby incorporated by reference into the specification of this application in its entirety and for all purposes.

| File Name | Date of Creation | Size |
|---|---|---|
| SEQLISTINGD15305C3 | Apr. 20, 2016 | 673 KB (689,171 bytes) |

FIELD OF THE INVENTION

This invention relates generally to enzymes, polynucleotides encoding the enzymes, the use of such polynucleotides and polypeptides, and more specifically to enzymes having alpha amylase activity.

BACKGROUND

Starch is a complex carbohydrate often found in the human diet. The structure of starch is glucose polymers linked by $\alpha$-1,4 and $\alpha$-1,6 glucosidic bonds. Amylase is an enzyme that catalyzes the hydrolysis of starches into sugars. Amylases hydrolyze internal $\alpha$-1,4-glucosidic linkages in starch, largely at random, to produce smaller molecular weight malto-dextrins. The breakdown of starch is important in the digestive system and commercially. Amylases are of considerable commercial value, being used in the initial stages (liquefaction) of starch processing; in wet corn milling; in alcohol production; as cleaning agents in detergent matrices; in the textile industry for starch desizing; in baking applications; in the beverage industry; in oilfields in drilling processes; in inking of recycled paper; and in animal feed.

Amylases are produced by a wide variety of microorganisms including *Bacillus* and *Aspergillus*, with most commercial amylases being produced from bacterial sources such as *Bacillus licheniformis, Bacillus amyloliquefaciens, Bacillus subtilis*, or *Bacillus stearothermophilus*. In recent years, the enzymes in commercial use have been those from *Bacillus licheniformis* because of their heat stability and performance, at least at neutral and mildly alkaline pHs.

In general, starch to fructose processing consists of four steps: liquefaction of granular starch, saccharification of the liquefied starch into dextrose, purification, and isomerization to fructose. The object of a starch liquefaction process is to convert a concentrated suspension of starch polymer granules into a solution of soluble shorter chain length dextrins of low viscosity. This step is essential for convenient handling with standard equipment and for efficient conversion to glucose or $10^3$ other sugars. To liquefy granular starch, it is necessary to gelatinize the granules by raising the temperature of the granular starch to over about 72° C. The heating process instantaneously disrupts the insoluble starch granules to produce a water soluble starch solution. The solubilized starch solution is then liquefied by amylase. A starch granule is composed of: 69-74% amylopectin, 26-31% amylose, 11-14% water, 0.2-0.4% protein, 0.5-0.9% lipid, 0.05-0.1% ash, 0.02-0.03% phosphorus, 0.1% pentosan. Approximately 70% of a granule is amorphous and 30% is crystalline.

A common enzymatic liquefaction process involves adjusting the pH of a granular starch slurry to between 6.0 and 6.5, the pH optimum of alpha-amylase derived from *Bacillus licheniformis*, with the addition of calcium hydroxide, sodium hydroxide or sodium carbonate. The addition of calcium hydroxide has the advantage of also providing calcium ions which are known to stabilize the alpha-amylase against inactivation. Upon addition of alpha-amylase, the suspension is pumped through a steam jet to instantaneously raise the temperature to between 80 degree-115 degrees C. The starch is immediately gelatinized and, due to the presence of alpha-amylase, depolymerized through random hydrolysis of a (1-4) glycosidic bonds by alpha-amylase to a fluid mass which is easily pumped.

In a second variation to the liquefaction process, alpha-amylase is added to the starch suspension, the suspension is held at a temperature of 80-100 degrees C. to partially hydrolyze the starch granules, and the partially hydrolyzed starch suspension is pumped through a jet at temperatures in excess of about 105 degrees C. to thoroughly gelatinize any remaining granular structure. After cooling the gelatinized starch, a second addition of alpha-amylase can be made to further hydrolyze the starch.

A third variation of this process is called the dry milling process. In dry milling, whole grain is ground and combined with water. The germ is optionally removed by flotation separation or equivalent techniques. The resulting mixture, which contains starch, fiber, protein and other components of the grain, is liquefied using .alpha.-amylase. The general practice in the art is to undertake enzymatic liquefaction at a lower temperature when using the dry milling process. Generally, low temperature liquefaction is believed to be less efficient than high temperature liquefaction in converting starch to soluble dextrins.

Typically, after gelatinization the starch solution is held at an elevated temperature in the presence of alpha-amylase until a DE of 10-20 is achieved, usually a period of 1-3 hours. Dextrose equivalent (DE) is the industry standard for measuring the concentration of total reducing sugars, calculated as D-glucose on a dry weight basis. Unhydrolyzed granular starch has a DE of virtually zero, whereas the DE of D-glucose is defined as 100.

Corn wet milling is a process which produces corn oil, gluten meal, gluten feed and starch. Alkaline-amylase is used in the liquefaction of starch and glucoamylase is used in saccharification, producing glucose. Corn, a kernel of which consists of a outer seed coat (fiber), starch, a combination of starch and glucose and the inner germ, is subjected to a four step process, which results in the production of starch. The corn is steeped, de-germed, de-fibered, and finally the gluten is separated. In the steeping process, the solubles are taken out. The product remaining after removal of the solubles is de-germed, resulting in production of corn oil and production of an oil cake, which is added to the solubles from the steeping step. The remaining product is de-fibered and the fiber solids are added to the oil cake/solubles mixture. This mixture of fiber solids, oil cake and solubles forms a gluten feed. After de-fibering, the remaining product is subjected to gluten separation. This separation results in a gluten meal and starch. The starch is then subjected to liquefaction and saccharification to produce glucose.

Staling of baked products (such as bread) has been recognized as a problem which becomes more serious as more time lies between the moment of preparation of the bread product and the moment of consumption. The term staling is used to describe changes undesirable to the consumer in the properties of the bread product after leaving the oven, such as an increase of the firmness of the crumb, a decrease of the elasticity of the crumb, and changes in the crust, which becomes tough and leathery. The firmness of the bread crumb increases further during storage up to a level, which is considered as negative. The increase in crumb firmness, which is considered as the most important aspect of staling, is recognized by the consumer a long time before the bread product has otherwise become unsuitable for consumption.

There is a need in the industry for the identification and optimization of amylases, useful for various uses, including commercial cornstarch liquefaction processes. These second generation acid amylases will offer improved manufacturing and/or performance characteristics over the industry standard enzymes from *Bacillus licheniformis*, for example.

There is also a need for the identification and optimization of amylases having utility in automatic dish wash (ADW) products and laundry detergent. In ADW products, the amylase will function at pH 10-11 and at 45-60° C. in the presence of calcium chelators and oxidative conditions. For laundry, activity at pH 9-10 and 40° C. in the appropriate detergent matrix will be required. Amylases are also useful in textile desizing, brewing processes, starch modification in the paper and pulp industry and other processes described in the art.

The publications discussed herein are provided solely for their disclosure prior to the filing date of the present application. Nothing herein is to be construed as an admission that the invention is not entitled to antedate such disclosure by virtue of prior invention.

SUMMARY OF THE INVENTION

The invention provides an isolated nucleic acid having a sequence as set forth in SEQ ID Nos.: 1, 3, 5, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299 and variants thereof having at least 50% sequence identity to SEQ ID Nos.: 1, 3, 5, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299 and encoding polypeptides having alpha amylase activity.

One aspect of the invention is an isolated nucleic acid having a sequence as set forth in SEQ ID Nos: 1, 3, 5, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299 (hereinafter referred to as "Group A nucleic acid sequences"), sequences substantially identical thereto, and sequences complementary thereto.

Another aspect of the invention is an isolated nucleic acid including at least 10 consecutive bases of a sequence as set forth in Group A nucleic acid sequences, sequences substantially identical thereto, and the sequences complementary thereto.

In yet another aspect, the invention provides an isolated nucleic acid encoding a polypeptide having a sequence as set forth in SEQ ID Nos.: 2, 4, 6, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298 and variants thereof encoding a polypeptide having alpha amylase activity and having at least 50% sequence identity to such sequences.

Another aspect of the invention is an isolated nucleic acid encoding a polypeptide or a functional fragment thereof having a sequence as set forth in SEQ ID No.s: 2, 4, 6, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298 (hereinafter referred to as "Group B amino acid sequences"), and sequences substantially identical thereto.

Another aspect of the invention is an isolated nucleic acid encoding a polypeptide having at least 10 consecutive amino acids of a sequence as set forth in Group B amino acid sequences, and sequences substantially identical thereto.

In yet another aspect, the invention provides a purified polypeptide having a sequence as set forth in Group B amino acid sequences, and sequences substantially identical thereto.

Another aspect of the invention is an isolated or purified antibody that specifically binds to a polypeptide having a sequence as set forth in Group B amino acid sequences, and sequences substantially identical thereto.

Another aspect of the invention is an isolated or purified antibody or binding fragment thereof, which specifically binds to a polypeptide having at least 10 consecutive amino acids of one of the polypeptides of Group B amino acid sequences, and sequences substantially identical thereto.

Another aspect of the invention is a method of making a polypeptide having a sequence as set forth in Group B amino acid sequences, and sequences substantially identical thereto. The method includes introducing a nucleic acid encoding the polypeptide into a host cell, wherein the nucleic acid is operably linked to a promoter, and culturing the host cell under conditions that allow expression of the nucleic acid.

Another aspect of the invention is a method of making a polypeptide having at least 10 amino acids of a sequence as set forth in Group B amino acid sequences, and sequences substantially identical thereto. The method includes introducing a nucleic acid encoding the polypeptide into a host cell, wherein the nucleic acid is operably linked to a promoter, and culturing the host cell under conditions that allow expression of the nucleic acid, thereby producing the polypeptide.

Another aspect of the invention is a method of generating a variant including obtaining a nucleic acid having a sequence as set forth in Group A nucleic acid sequences, sequences substantially identical thereto, sequences complementary to the sequences of Group A nucleic acid sequences, fragments comprising at least 30 consecutive nucleotides of the foregoing sequences, and changing one or more nucleotides in the sequence to another nucleotide, deleting one or more nucleotides in the sequence, or adding one or more nucleotides to the sequence.

Another aspect of the invention is a computer readable medium having stored thereon a sequence as set forth in Group A nucleic acid sequences, and sequences substantially identical thereto, or a polypeptide sequence as set forth in Group B amino acid sequences, and sequences substantially identical thereto.

Another aspect of the invention is a computer system including a processor and a data storage device wherein the data storage device has stored thereon a sequence as set forth in Group A nucleic acid sequences, and sequences substantially identical thereto, or a polypeptide having a sequence as set forth in Group B amino acid sequences, and sequences substantially identical thereto.

Another aspect of the invention is a method for comparing a first sequence to a reference sequence wherein the first sequence is a nucleic acid having a sequence as set forth in Group A nucleic acid sequences, and sequences substantially identical thereto, or a polypeptide code of Group B amino acid sequences, and sequences substantially identical thereto. The method includes reading the first sequence and the reference sequence through use of a computer program which compares sequences; and determining differences between the first sequence and the reference sequence with the computer program.

Another aspect of the invention is a method for identifying a feature in a sequence as set forth in Group A nucleic acid sequences, and sequences substantially identical thereto, or a polypeptide having a sequence as set forth in Group B amino acid sequences, and sequences substantially identical thereto, including reading the sequence through the use of a computer program which identifies features in sequences; and identifying features in the sequence with the computer program.

Another aspect of the invention is an assay for identifying fragments or variants of Group B amino acid sequences, and sequences substantially identical thereto, which retain the enzymatic function of the polypeptides of Group B amino acid sequences, and sequences substantially identical thereto. The assay includes contacting the polypeptide of Group B amino acid sequences, sequences substantially identical thereto, or polypeptide fragment or variant with a substrate molecule under conditions which allow the polypeptide fragment or variant to function, and detecting either a decrease in the level of substrate or an increase in the level of the specific reaction product of the reaction between the polypeptide and substrate thereby identifying a fragment or variant of such sequences.

The invention also provides a process for preparing a dough or a baked product prepared from the dough which comprises adding an amylase of the invention to the dough in an amount which is effective to retard the staling of the bread. The invention also provides a dough comprising said amylase and a premix comprising flour together with said amylase. Finally, the invention provides an enzymatic baking additive, which contains said amylase.

The use of the amylase in accordance with the present invention provides an improved anti-staling effect as measured by, e.g. less crumb firming, retained crumb elasticity, improved slice-ability (e.g. fewer crumbs, non-gummy crumb), improved palatability or flavor.

BRIEF DESCRIPTION OF THE DRAWINGS

The following drawings are illustrative of embodiments of the invention and are not meant to limit the scope of the invention as encompassed by the claims.

FIG. 9a is a graph showing the data at pH 8 and 40° C.

FIG. 10 sets forth the sequences to be used in reassembly experiments with the enzymes.

FIG. 11 illustrates a sample Standard Curve of the assay of Example 5.

FIG. 12 illustrates the pH rate profiles for SEQ ID NO.: 127, which has a neutral optimum pH and SEQ ID NO.: 211, which has an optimum around pH 10.

FIG. 13 shows the stability of Diversa amylases vs. a commercial enzyme, as discussed in Example 2.

FIGS. 14A-C show the sequence alignments of hypothermophilic α-amylases, as set forth in Example 8.

FIG. 14A shows an alignment of amylase sequences. SEQ ID NO.: 81=an environmental clone; pyro=*Pyrococcus* sp. (strain:KOD1), Tachibana, Y., Mendez, L., Takagi, M. and Imanaka, T., J Ferment. Bioeng. 82:224-232, 1996; pyro2=*Pyrococcus furiosus*, Appl. Environ. Microbiol. 63 (9):3569-3576, 1997; Thermo=*Thermococcus* sp.; Thermo2=*Thermococcus hydrothermalis*, Leveque, E. et al. Patent: France 98.05655 5 May 1998, unpublished.

FIG. 14B shows the amino acid sequence alignment of identified sequences: SEQ ID NO.: 81; pyro; SEQ ID NO.:75; SEQ ID NO.: 77; SEQ ID NO.: 83; SEQ ID NO.: 85; thermo2; SEQ ID NO.: 79; thermo; pyro2; clone A; thermo3.

FIG. 14C shows the nucleic acid sequence alignment corresponding to the polypeptide sequence of FIGS. 5 and 6. SEQ ID NO.: 81; SEQ ID NO.:75; SEQ ID NO.: 77; SEQ ID NO.: 83; SEQ ID NO.: 85; SEQ ID NO.: 79; clone A; and SEQ ID NO.: 73.

FIGS. 16A-16BBBBBBBBB show the sequences of the invention.

FIG. 16A shows a sequence of the invention.
FIG. 16B shows a sequence of the invention.
FIG. 16C shows a sequence of the invention.
FIG. 16D shows a sequence of the invention.
FIG. 16E shows a sequence of the invention.
FIG. 16F shows a sequence of the invention.
FIG. 16G shows a sequence of the invention.
FIG. 16H shows a sequence of the invention.
FIG. 16I shows a sequence of the invention.
FIG. 16J shows a sequence of the invention.
FIG. 16K shows a sequence of the invention.
FIG. 16L shows a sequence of the invention.
FIG. 16M shows a sequence of the invention.
FIG. 16N shows a sequence of the invention.
FIG. 16O shows a sequence of the invention.
FIG. 16P shows a sequence of the invention.
FIG. 16Q shows a sequence of the invention.
FIG. 16R shows a sequence of the invention.
FIG. 16S shows a sequence of the invention.
FIG. 16T shows a sequence of the invention.
FIG. 16U shows a sequence of the invention.
FIG. 16V shows a sequence of the invention.
FIG. 16W shows a sequence of the invention.
FIG. 16X shows a sequence of the invention.
FIG. 16Y shows a sequence of the invention.
FIG. 16Z shows a sequence of the invention.
FIG. 16AA shows a sequence of the invention.
FIG. 16BB shows a sequence of the invention.
FIG. 16CC shows a sequence of the invention.
FIG. 16DD shows a sequence of the invention.
FIG. 16EE shows a sequence of the invention.
FIG. 16FF shows a sequence of the invention.
FIG. 16GG shows a sequence of the invention.
FIG. 16HH shows a sequence of the invention.
FIG. 16II shows a sequence of the invention.
FIG. 16JJ shows a sequence of the invention.
FIG. 16KK shows a sequence of the invention.
FIG. 16LL shows a sequence of the invention.
FIG. 16MM shows a sequence of the invention.
FIG. 16NN shows a sequence of the invention.
FIG. 16OO shows a sequence of the invention.
FIG. 16PP shows a sequence of the invention.
FIG. 16QQ shows a sequence of the invention.
FIG. 16RR shows a sequence of the invention.
FIG. 16SS shows a sequence of the invention.
FIG. 16TT shows a sequence of the invention.
FIG. 16UU shows a sequence of the invention.
FIG. 16VV shows a sequence of the invention.
FIG. 16WW shows a sequence of the invention.
FIG. 16XX shows a sequence of the invention.
FIG. 16YY shows a sequence of the invention.
FIG. 16ZZ shows a sequence of the invention.
FIG. 16AAA shows a sequence of the invention.
FIG. 16BBB shows a sequence of the invention.
FIG. 16CCC shows a sequence of the invention.
FIG. 16DDD shows a sequence of the invention.
FIG. 16EEE shows a sequence of the invention.
FIG. 16FFF shows a sequence of the invention.
FIG. 16GGG shows a sequence of the invention.
FIG. 16HHH shows a sequence of the invention.
FIG. 16III shows a sequence of the invention.
FIG. 16JJJ shows a sequence of the invention.
FIG. 16KKK shows a sequence of the invention.
FIG. 16LLL shows a sequence of the invention.
FIG. 16MMM shows a sequence of the invention.
FIG. 16NNN shows a sequence of the invention.
FIG. 16OOO shows a sequence of the invention.
FIG. 16PPP shows a sequence of the invention.
FIG. 16QQQ shows a sequence of the invention.
FIG. 16RRR shows a sequence of the invention.
FIG. 16SSS shows a sequence of the invention.
FIG. 16TTT shows a sequence of the invention.
FIG. 16UUU shows a sequence of the invention.
FIG. 16VVV shows a sequence of the invention.
FIG. 16WWW shows a sequence of the invention.
FIG. 16XXX shows a sequence of the invention.
FIG. 16YYY shows a sequence of the invention.
FIG. 16ZZZ shows a sequence of the invention.
FIG. 16AAAA shows a sequence of the invention.
FIG. 16BBBB shows a sequence of the invention.
FIG. 16CCCC shows a sequence of the invention.
FIG. 16DDDD shows a sequence of the invention.
FIG. 16EEEE shows a sequence of the invention.
FIG. 16FFFF shows a sequence of the invention.
FIG. 16GGGG shows a sequence of the invention.
FIG. 16HHHH shows a sequence of the invention.
FIG. 16IIII shows a sequence of the invention.
FIG. 16JJJJ shows a sequence of the invention.
FIG. 16KKKK shows a sequence of the invention.
FIG. 16LLLL shows a sequence of the invention.
FIG. 16MMMM shows a sequence of the invention.
FIG. 16NNNN shows a sequence of the invention.
FIG. 16OOOO shows a sequence of the invention.
FIG. 16PPPP shows a sequence of the invention.
FIG. 16QQQQ shows a sequence of the invention.
FIG. 16RRRR shows a sequence of the invention.
FIG. 16SSSS shows a sequence of the invention.
FIG. 16TTTT shows a sequence of the invention.
FIG. 16UUUU shows a sequence of the invention.

FIG. 16VVVV shows a sequence of the invention.
FIG. 16WWWW shows a sequence of the invention.
FIG. 16XXXX shows a sequence of the invention.
FIG. 16YYYY shows a sequence of the invention.
FIG. 16ZZZZ shows a sequence of the invention.
FIG. 16AAAAA shows a sequence of the invention.
FIG. 16BBBBB shows a sequence of the invention.
FIG. 16CCCCC shows a sequence of the invention.
FIG. 16DDDDD shows a sequence of the invention.
FIG. 16EEEEE shows a sequence of the invention.
FIG. 16FFFFF shows a sequence of the invention.
FIG. 16GGGGG shows a sequence of the invention.
FIG. 16HHHHH shows a sequence of the invention.
FIG. 16IIIII shows a sequence of the invention.
FIG. 16JJJJJ shows a sequence of the invention.
FIG. 16KKKKK shows a sequence of the invention.
FIG. 16LLLLL shows a sequence of the invention.
FIG. 16MMMMM shows a sequence of the invention.
FIG. 16NNNNN shows a sequence of the invention.
FIG. 16OOOOO shows a sequence of the invention.
FIG. 16PPPPP shows a sequence of the invention.
FIG. 16QQQQQ shows a sequence of the invention.
FIG. 16RRRRR shows a sequence of the invention.
FIG. 16SSSSS shows a sequence of the invention.
FIG. 16TTTTT shows a sequence of the invention.
FIG. 16UUUUU shows a sequence of the invention.
FIG. 16VVVVV shows a sequence of the invention.
FIG. 16WWWWW shows a sequence of the invention.
FIG. 16XXXXX shows a sequence of the invention.
FIG. 16YYYYY shows a sequence of the invention.
FIG. 16ZZZZZ shows a sequence of the invention.
FIG. 16AAAAAA shows a sequence of the invention.
FIG. 16BBBBBB shows a sequence of the invention.
FIG. 16CCCCCC shows a sequence of the invention.
FIG. 16DDDDDD shows a sequence of the invention.
FIG. 16EEEEEE shows a sequence of the invention.
FIG. 16FFFFFF shows a sequence of the invention.
FIG. 16GGGGGG shows a sequence of the invention.
FIG. 16HHHHHH shows a sequence of the invention.
FIG. 16IIIIII shows a sequence of the invention.
FIG. 16JJJJJJ shows a sequence of the invention.
FIG. 16KKKKKK shows a sequence of the invention.
FIG. 16LLLLLL shows a sequence of the invention.
FIG. 16MMMMMM shows a sequence of the invention.
FIG. 16NNNNNN shows a sequence of the invention.
FIG. 16OOOOOO shows a sequence of the invention.
FIG. 16PPPPPP shows a sequence of the invention.
FIG. 16QQQQQQ shows a sequence of the invention.
FIG. 16RRRRRR shows a sequence of the invention.
FIG. 16SSSSSS shows a sequence of the invention.
FIG. 16TTTTTT shows a sequence of the invention.
FIG. 16UUUUUU shows a sequence of the invention.
FIG. 16VVVVVV shows a sequence of the invention.
FIG. 16WWWWWW shows a sequence of the invention.
FIG. 16XXXXXX shows a sequence of the invention.
FIG. 16YYYYYY shows a sequence of the invention.
FIG. 16ZZZZZZ shows a sequence of the invention.
FIG. 16AAAAAAA shows a sequence of the invention.
FIG. 16BBBBBBB shows a sequence of the invention.
FIG. 16CCCCCCC shows a sequence of the invention.
FIG. 16DDDDDDD shows a sequence of the invention.
FIG. 16EEEEEEE shows a sequence of the invention.
FIG. 16FFFFFFF shows a sequence of the invention.
FIG. 16GGGGGGG shows a sequence of the invention.
FIG. 16HHHHHHH shows a sequence of the invention.
FIG. 16IIIIIII shows a sequence of the invention.
FIG. 16JJJJJJJ shows a sequence of the invention.
FIG. 16KKKKKKK shows a sequence of the invention.
FIG. 16LLLLLLL shows a sequence of the invention.
FIG. 16MMMMMMM shows a sequence of the invention.
FIG. 16NNNNNNN shows a sequence of the invention.
FIG. 16OOOOOOO shows a sequence of the invention.
FIG. 16PPPPPPP shows a sequence of the invention.
FIG. 16QQQQQQQ shows a sequence of the invention.
FIG. 16RRRRRRR shows a sequence of the invention.
FIG. 16SSSSSSS shows a sequence of the invention.
FIG. 16TTTTTTT shows a sequence of the invention.
FIG. 16UUUUUUU shows a sequence of the invention.
FIG. 16VVVVVVV shows a sequence of the invention.
FIG. 16WWWWWWW shows a sequence of the invention.
FIG. 16XXXXXXX shows a sequence of the invention.
FIG. 16YYYYYYY shows a sequence of the invention.
FIG. 16ZZZZZZZ shows a sequence of the invention.
FIG. 16AAAAAAAA shows a sequence of the invention.
FIG. 16BBBBBBBB shows a sequence of the invention.
FIG. 16CCCCCCCC shows a sequence of the invention.
FIG. 16DDDDDDDD shows a sequence of the invention.
FIG. 16EEEEEEEE shows a sequence of the invention.
FIG. 16FFFFFFFF shows a sequence of the invention.
FIG. 16GGGGGGGG shows a sequence of the invention.
FIG. 16HHHHHHHH shows a sequence of the invention.
FIG. 16IIIIIIII shows a sequence of the invention.
FIG. 16JJJJJJJJ shows a sequence of the invention.
FIG. 16KKKKKKKK shows a sequence of the invention.
FIG. 16LLLLLLLL shows a sequence of the invention.
FIG. 16MMMMMMMM shows a sequence of the invention.
FIG. 16NNNNNNNN shows a sequence of the invention.
FIG. 16OOOOOOOO shows a sequence of the invention.
FIG. 16PPPPPPPP shows a sequence of the invention.
FIG. 16QQQQQQQQ shows a sequence of the invention.
FIG. 16RRRRRRRR shows a sequence of the invention.
FIG. 16SSSSSSSS shows a sequence of the invention.
FIG. 16TTTTTTTT shows a sequence of the invention.
FIG. 16UUUUUUUU shows a sequence of the invention.
FIG. 16VVVVVVVV shows a sequence of the invention.
FIG. 16WWWWWWWW shows a sequence of the invention.
FIG. 16XXXXXXXX shows a sequence of the invention.
FIG. 16YYYYYYYY shows a sequence of the invention.
FIG. 16ZZZZZZZZ shows a sequence of the invention.
FIG. 16AAAAAAAAA shows a sequence of the invention.
FIG. 16BBBBBBBBB shows a sequence of the invention.

DETAILED DESCRIPTION OF THE INVENTION

Figure 1:
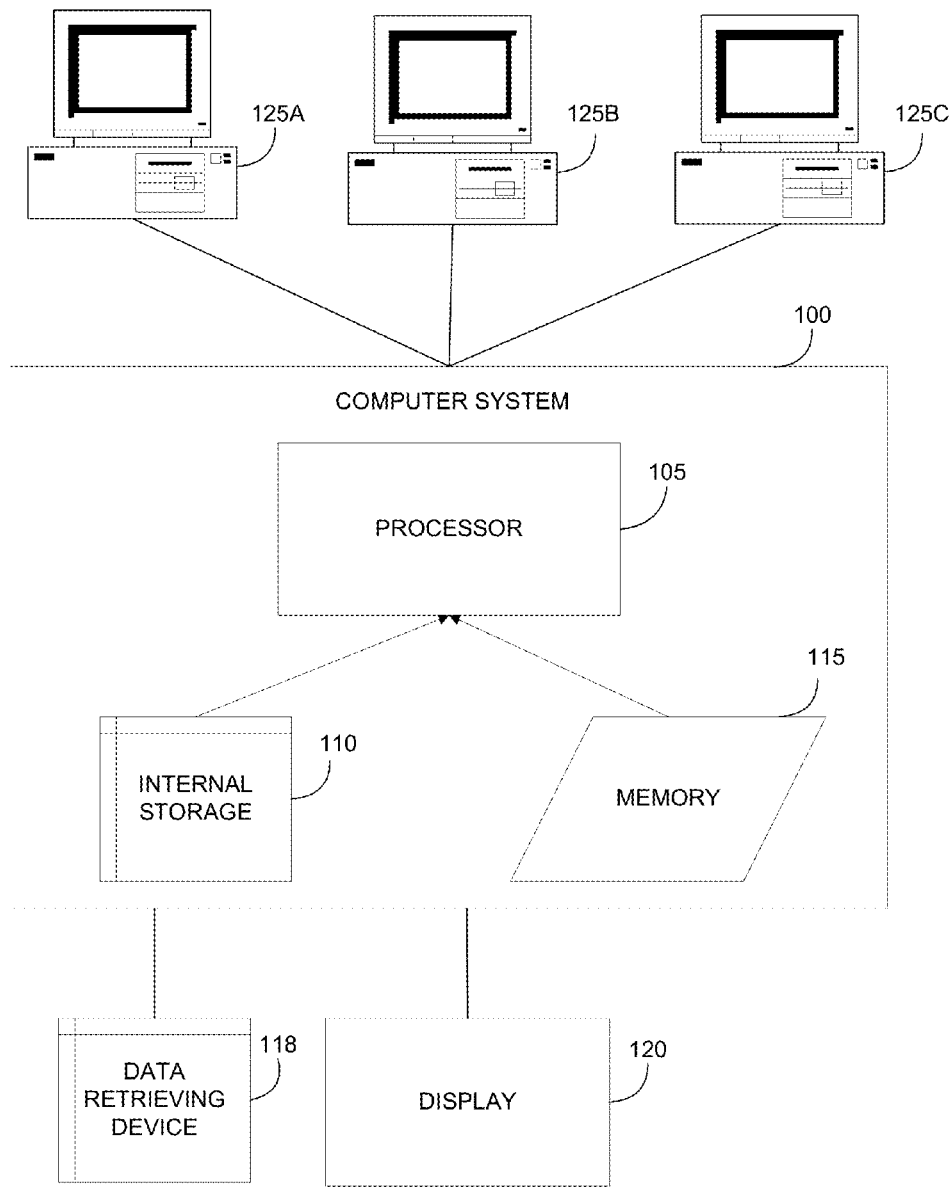
FIG. 1 is a block diagram of a computer system.

The present invention relates to amylases and polynucleotides encoding them. As used herein, the term "amylase" encompasses enzymes having alpha amylase activity, for example, alpha amylases capable of hydrolyzing internal α-1,4-glucan links in polysaccharides, including amylase enzymes capable of hydrolyzing starch to sugars at alkaline pHs or at acidic pHs. Amylases of the invention are particularly useful in corn-wet milling processes, detergents, baking processes, beverages and in oilfields (fuel ethanol). Amylases are also useful in textile desizing, brewing processes, starch modification in the paper and pulp industry and other processes described in the art.

The polynucleotides of the invention have been identified as encoding polypeptides having alpha amylase or alkaline amylase activity. Alkaline amylases of the invention may include, but are not limited to: SEQ ID NO.: 115, SEQ ID NO.:207, SEQ ID NO.: 139, SEQ ID NO.:127, SEQ ID NO.: 137, SEQ ID NO.:113, SEQ ID NO.:205, SEQ ID NO.: 179, SEQ ID NO.: 151, SEQ ID NO.: 187, SEQ ID NO.:97, SEQ ID NO.: 153, SEQ ID NO.: 69, SEQ ID NO.: 135, SEQ ID NO.: 189, SEQ ID NO.: 119, SEQ ID NO: 209 and SEQ ID NO: 211.

Alterations in properties which may be achieved in variants of the invention are alterations in, e.g., substrate specificity, substrate binding, substrate cleavage pattern, thermal stability, pH/activity profile, pH/stability profile [such as increased stability at low (e.g. pH<6, in particular pH<5) or high (e.g. pH>9) pH values], stability towards oxidation, $Ca^{2+}$ dependency, specific activity, and other properties of interest. For instance, the alteration may result in a variant which, as compared to the parent amylase, has a reduced $Ca^{2+}$ dependency and/or an altered pH/activity profile.

The present invention relates to alpha amylases and polynucleotides encoding them. As used herein, the term "alpha amylase" encompasses enzymes having alpha amylase activity, for example, enzymes capable of hydrolyzing starch to sugars. Unlike many known amylases, the amylases of the invention may not be calcium-dependent enzymes.

It is highly desirable to be able to decrease the Ca2+ dependency of an alpha amylase. Accordingly, one aspect of the invention provides an amylase enzyme that has a decreased Ca2+ dependency as compared to commercial or parent amylases. Decreased Ca2+ dependency will in general have the functional consequence that the variant exhibits a satisfactory amylolytic activity in the presence of a lower concentration of calcium ion in the extraneous medium than is necessary for a commercial or parent enzyme. It will further often have the consequence that the variant is less sensitive to calcium ion-depleting conditions such as those obtained in media containing calcium-complexing agents (such as certain detergent builders).

"Liquefaction" or "liquefy" means a process by which starch is converted to shorter chain and less viscous dextrins. Generally, this process involves gelatinization of starch simultaneously with or followed by the addition of alpha amylase. In commercial processes, it is preferred that the granular starch is derived from a source comprising corn, wheat, milo, sorghum, rye or bulgher. However, the present invention applies to any grain starch source which is useful in liquefaction, e.g., any other grain or vegetable source known to produce starch suitable for liquefaction.

"Granular starch" or "starch granules" means a water-insoluble component of edible grains which remains after removal of the hull, fiber, protein, fat, germ, and solubles through the steeping, mechanical cracking, separations, screening, countercurrent rinsing and centrifugation steps typical of the grain wet-milling process. Granular starch comprises intact starch granules containing, almost exclusively, packed starch molecules (i.e., amylopectin and amylose). In corn, the granular starch component comprises about 99% starch; the remaining 1% being comprised of protein, fat, ash, fiber and trace components tightly associated with the granules. The packing structure of granular starch severely retards the ability of .alpha.-amylase to hydrolyze starch. Gelatinization of the starch is utilized to disrupt the granules to form a soluble starch solution and facilitate enzymatic hydrolysis.

"Starch solution" means the water soluble gelatinized starch which results from heating granular starch. Upon heating of the granules to above about 72 degrees C., granular starch dissociates to form an aqueous mixture of loose starch molecules. This mixture comprising, for example, about 75% amylopectin and 25% amylose in yellow dent corn forms a viscous solution in water. In commercial processes to form glucose or fructose, it is the starch solution which is liquefied to form a soluble dextrin solution. "alpha amylase" means an enzymatic activity which cleaves or hydrolyzes the alpha (1-4) glycosidic bond, e.g., that in starch, amylopectin or amylose polymers. Suitable alpha amylases are the naturally occurring alpha amylases as well as recombinant or mutant amylases which are useful in liquefaction of starch. Techniques for producing variant amylases having activity at a pH or temperature, for example, that is different from the wild-type amylase, are included herein.

The temperature range of the liquefaction is generally any liquefaction temperature which is known to be effective in liquefying starch. Preferably, the temperature of the starch is between about 80 degrees C. to about 115 degrees C., more preferably from about 100 degrees C. to about 110 degrees C., and most preferably from about 105 degrees C. to about 108 degrees C.

In one embodiment, the signal sequences of the invention are identified following identification of novel amylase polypeptides. The pathways by which proteins are sorted and transported to their proper cellular location are often referred to as protein targeting pathways. One of the most important elements in all of these targeting systems is a short amino acid sequence at the amino terminus of a newly synthesized polypeptide called the signal sequence. This signal sequence directs a protein to its appropriate location in the cell and is removed during transport or when the protein reaches its final destination. Most lysosomal, membrane, or secreted proteins have an amino-terminal signal sequence that marks them for translocation into the lumen of the endoplasmic reticulum. More than 100 signal sequences for proteins in this group have been determined. The sequences vary in length from 13 to 36 amino acid residues. Various methods of recognition of signal sequences are known to those of skill in the art. In one embodiment, the peptides are identified by a method referred to as SignalP. SignalP uses a combined neural network which recognizes both signal peptides and their cleavage sites. (Nielsen, H., Engelbrecht, J., Brunalk, S., von Heijne, G., "Identification of prokaryotic and eukaryotic signal peptides and prediction of their cleavage sites." Protein Engineering, vol. 10, no. 1, p. 1-6 (1997), hereby incorporated by reference) It should be understood that some of the amylases of the invention may not have signal sequences. It may be desirable to include a nucleic acid sequence encoding a signal sequence from one amylase operably linked to a nucleic acid sequence of a different amylase or, optionally, a signal sequence from a non-amylase protein may be desired. Table 3 shows signal sequences of the invention.

The phrases "nucleic acid" or "nucleic acid sequence" as used herein refer to an oligonucleotide, nucleotide, polynucleotide, or to a fragment of any of these, to DNA or RNA of genomic or synthetic origin which may be single-stranded or double-stranded and may represent a sense or antisense strand, to peptide nucleic acid (PNA), or to any DNA-like or RNA-like material, natural or synthetic in origin.

A "coding sequence of" or a "nucleotide sequence encoding" a particular polypeptide or protein, is a nucleic acid sequence which is transcribed and translated into a polypeptide or protein when placed under the control of appropriate regulatory sequences.

The term "gene" means the segment of DNA involved in producing a polypeptide chain; it includes regions preceding and following the coding region (leader and trailer) as well as, where applicable, intervening sequences (introns) between individual coding segments (exons).

"Amino acid" or "amino acid sequence" as used herein refer to an oligopeptide, peptide, polypeptide, or protein sequence, or to a fragment, portion, or subunit of any of these, and to naturally occurring or synthetic molecules.

The term "polypeptide" as used herein, refers to amino acids joined to each other by peptide bonds or modified peptide bonds, i.e., peptide isosteres, and may contain modified amino acids other than the 20 gene-encoded amino acids. The polypeptides may be modified by either natural processes, such as post-translational processing, or by chemical modification techniques which are well known in the art. Modifications can occur anywhere in the polypeptide, including the peptide backbone, the amino acid sidechains and the amino or carboxyl termini. It will be appreciated that the same type of modification may be present in the same or varying degrees at several sites in a given polypeptide. Also a given polypeptide may have many types of modifications. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of a phosphytidylinositol, cross-linking cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristolyation, oxidation, pergylation, proteolytic processing, phosphorylation, prenylation, racemization, selenoylation, sulfation, and transfer-RNA mediated addition of amino acids to protein such as arginylation. (See Creighton, T. E., Proteins—Structure and Molecular Properties 2nd Ed., W.H. Freeman and Company, New York (1993); Posttranslational Covalent Modification of Proteins, B. C. Johnson, Ed., Academic Press, New York, pp. 1-12 (1983)).

As used herein, the term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

As used herein, the term "purified" does not require absolute purity; rather, it is intended as a relative definition. Individual nucleic acids obtained from a library have been conventionally purified to electrophoretic homogeneity. The sequences obtained from these clones could not be obtained directly either from the library or from total human DNA. The purified nucleic acids of the invention have been purified from the remainder of the genomic DNA in the organism by at least 104-106 fold. However, the term "purified" also includes nucleic acids which have been purified from the remainder of the genomic DNA or from other sequences in a library or other environment by at least one order of magnitude, typically two or three orders, and more typically four or five orders of magnitude.

As used herein, the term "recombinant" means that the nucleic acid is adjacent to a "backbone" nucleic acid to which it is not adjacent in its natural environment. Additionally, to be "enriched" the nucleic acids will represent 5% or more of the number of nucleic acid inserts in a population of nucleic acid backbone molecules. Backbone molecules according to the invention include nucleic acids such as expression vectors, self-replicating nucleic acids, viruses, integrating nucleic acids, and other vectors or nucleic acids used to maintain or manipulate a nucleic acid insert of interest. Typically, the enriched nucleic acids represent 15% or more of the number of nucleic acid inserts in the population of recombinant backbone molecules. More typically, the enriched nucleic acids represent 50% or more of the number of nucleic acid inserts in the population of recombinant backbone molecules. In a one embodiment, the enriched nucleic acids represent 90% or more of the number of nucleic acid inserts in the population of recombinant backbone molecules.

"Recombinant" polypeptides or proteins refer to polypeptides or proteins produced by recombinant DNA techniques; i.e., produced from cells transformed by an exogenous DNA construct encoding the desired polypeptide or protein. "Synthetic" polypeptides or protein are those prepared by chemical synthesis. Solid-phase chemical peptide synthesis methods can also be used to synthesize the polypeptide or fragments of the invention. Such method have been known in the art since the early 1960's (Merrifield, R. B., J. Am. Chem. Soc., 85:2149-2154, 1963) (See also Stewart, J. M. and Young, J. D., Solid Phase Peptide Synthesis, 2nd Ed., Pierce Chemical Co., Rockford, Ill., pp. 11-12)) and have recently been employed in commercially available laboratory peptide design and synthesis kits (Cambridge Research Biochemicals). Such commercially available laboratory kits have generally utilized the teachings of H. M. Geysen et al, Proc. Natl. Acad. Sci., USA, 81:3998 (1984) and provide for synthesizing peptides upon the tips of a multitude of "rods" or "pins" all of which are connected to a single plate. When such a system is utilized, a plate of rods or pins is inverted and inserted into a second plate of corresponding wells or reservoirs, which contain solutions for attaching or anchoring an appropriate amino acid to the pin's or rod's tips. By repeating such a process step, i.e., inverting and inserting the rod's and pin's tips into appropriate solutions, amino acids are built into desired peptides. In addition, a number of available FMOC peptide synthesis systems are available. For example, assembly of a polypeptide or fragment can be carried out on a solid support using an Applied Biosystems, Inc. Model 431A automated peptide synthesizer. Such equipment provides ready access to the peptides of the invention, either by direct synthesis or by synthesis of a series of fragments that can be coupled using other known techniques.

A promoter sequence is "operably linked to" a coding sequence when RNA polymerase which initiates transcription at the promoter will transcribe the coding sequence into mRNA.

"Plasmids" are designated by a lower case "p" preceded and/or followed by capital letters and/or numbers. The starting plasmids herein are either commercially available, publicly available on an unrestricted basis, or can be constructed from available plasmids in accord with published procedures. In addition, equivalent plasmids to those described herein are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 µs of plasmid or DNA fragment is used with about 2 units of enzyme in about 20 µl of buffer solution. For the purpose of isolating DNA fragments for plasmid construction, typically 5 to 50 µg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion, gel electrophoresis may be performed to isolate the desired fragment.

"Oligonucleotide" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

The phrase "substantially identical" in the context of two nucleic acids or polypeptides, refers to two or more sequences that have at least 50%, 60%, 70%, 80%, and in some aspects 90-95% nucleotide or amino acid residue identity, when compared and aligned for maximum correspondence, as measured using one of the known sequence comparison algorithms or by visual inspection. Typically, the substantial identity exists over a region of at least about 100 residues, and most commonly the sequences are substantially identical over at least about 150-200 residues. In some embodiments, the sequences are substantially identical over the entire length of the coding regions.

Additionally a "substantially identical" amino acid sequence is a sequence that differs from a reference sequence by one or more conservative or non-conservative amino acid substitutions, deletions, or insertions, particularly when such a substitution occurs at a site that is not the active site of the molecule, and provided that the polypeptide essentially retains its functional properties. A conservative amino acid substitution, for example, substitutes one amino acid for another of the same class (e.g., substitution of one hydrophobic amino acid, such as isoleucine, valine, leucine, or methionine, for another, or substitution of one polar amino acid for another, such as substitution of arginine for lysine, glutamic acid for aspartic acid or glutamine for asparagine). One or more amino acids can be deleted, for example, from an alpha amylase polypeptide, resulting in modification of the structure of the polypeptide, without significantly altering its biological activity. For example, amino- or carboxyl-terminal amino acids that are not required for alpha amylase biological activity can be removed. Modified polypeptide sequences of the invention can be assayed for alpha amylase biological activity by any number of methods, including contacting the modified polypeptide sequence with an alpha amylase substrate and determining whether the modified polypeptide decreases the amount of specific substrate in the assay or increases the bioproducts of the enzymatic reaction of a functional alpha amylase polypeptide with the substrate.

"Fragments" as used herein are a portion of a naturally occurring protein which can exist in at least two different conformations. Fragments can have the same or substantially the same amino acid sequence as the naturally occurring protein. "Substantially the same" means that an amino acid sequence is largely, but not entirely, the same, but retains at least one functional activity of the sequence to which it is related. In general two amino acid sequences are "substantially the same" or "substantially homologous" if they are at least about 85% identical. Fragments which have different three dimensional structures as the naturally occurring protein are also included. An example of this, is a "pro-form" molecule, such as a low activity proprotein that can be modified by cleavage to produce a mature enzyme with significantly higher activity.

"Hybridization" refers to the process by which a nucleic acid strand joins with a complementary strand through base pairing. Hybridization reactions can be sensitive and selective so that a particular sequence of interest can be identified even in samples in which it is present at low concentrations. Suitably stringent conditions can be defined by, for example, the concentrations of salt or formamide in the prehybridization and hybridization solutions, or by the hybridization temperature, and are well known in the art. In particular, stringency can be increased by reducing the concentration of salt, increasing the concentration of formamide, or raising the hybridization temperature.

For example, hybridization under high stringency conditions could occur in about 50% formamide at about 37° C. to 42° C. Hybridization could occur under reduced stringency conditions in about 35% to 25% formamide at about 30° C. to 35° C. In particular, hybridization could occur under high stringency conditions at 42° C. in 50% formamide, 5×SSPE, 0.3% SDS, and 200 n/ml sheared and denatured salmon sperm DNA. Hybridization could occur under reduced stringency conditions as described above, but in 35% formamide at a reduced temperature of 35° C. The temperature range corresponding to a particular level of stringency can be further narrowed by calculating the purine to pyrimidine ratio of the nucleic acid of interest and adjusting the temperature accordingly. Variations on the above ranges and conditions are well known in the art.

The term "variant" refers to polynucleotides or polypeptides of the invention modified at one or more base pairs, codons, introns, exons, or amino acid residues (respectively) yet still retain the biological activity of an alpha amylase of the invention. Variants can be produced by any number of means included methods such as, for example, error-prone PCR, shuffling, oligonucleotide-directed mutagenesis, assembly PCR, sexual PCR mutagenesis, in vivo mutagenesis, cassette mutagenesis, recursive ensemble mutagenesis, exponential ensemble mutagenesis, site-specific mutagenesis, gene reassembly, GSSM and any combination thereof. Techniques for producing variant amylases having activity at a pH or temperature, for example, that is different from the wild-type amylase, are included herein.

Enzymes are highly selective catalysts. Their hallmark is the ability to catalyze reactions with exquisite stereo-, regio-, and chemo-selectivities that are unparalleled in conventional synthetic chemistry. Moreover, enzymes are remarkably versatile. They can be tailored to function in organic solvents, operate at extreme pHs (for example, high pHs and low pHs) extreme temperatures (for example, high temperatures and low temperatures), extreme salinity levels (for example, high salinity and low salinity), and catalyze reactions with compounds that are structurally unrelated to their natural, physiological substrates.

Enzymes are reactive toward a wide range of natural and unnatural substrates, thus enabling the modification of virtually any organic lead compound. Moreover, unlike traditional chemical catalysts, enzymes are highly enantio- and regio-selective. The high degree of functional group specificity exhibited by enzymes enables one to keep track of each reaction in a synthetic sequence leading to a new active compound. Enzymes are also capable of catalyzing many diverse reactions unrelated to their physiological function in nature. For example, peroxidases catalyze the oxidation of phenols by hydrogen peroxide. Peroxidases can also catalyze hydroxylation reactions that are not related to the native function of the enzyme. Other examples are proteases which catalyze the breakdown of polypeptides. In organic solution some proteases can also acylate sugars, a function unrelated to the native function of these enzymes.

In one aspect, the invention includes a method for liquefying a starch containing composition comprising contacting the starch with a polypeptide of the invention (e.g., a purified polypeptide selected from polypeptides having an amino acid sequence selected from the group consisting of: Group B amino acid sequences; variants having at least about 50% homology to at least one of Group B amino acid sequences, over a region of at least about 100 residues, as determined by analysis with a sequence comparison algorithm or by visual inspection; sequences complementary to any one of Group B amino acid sequences; and sequences complementary to variants having at least about 50% homology to any one of Group B amino acid sequences over a region of at least about 100 residues, as determined by analysis with a sequence comparison algorithm or by visual inspection; and polypeptides having at least 10 consecutive amino acids of a polypeptide having a sequence selected from the group consisting of Group B amino acid sequences). In one preferred embodiment, the polypeptide is set forth in Group B amino acid sequences. The starch may be from a material selected from rice, germinated rice, corn, barley, wheat, legumes and sweet potato. A glucose syrup produced by the method of the invention is included herein. Such a syrup can be a maltose syrup, a glucose syrup, or a combination thereof. In particular, the syrups produced using the amylases of the invention there is a higher level of DP2 fraction and a higher level of DP3 (maltotriose and/or panose) and less of the greater than DP7 fragments as compared to the syrups produced by commercial enzymes. This is consistent with the liquefaction profile since less of the large fragments are in the invention liquefied syrups.

The invention also provides a method for removing starch containing stains from a material comprising contacting the material with a polypeptide of the invention. In one aspect, the invention provides a method for washing an object comprising contacting the object with a polypeptide of the invention under conditions sufficient for washing. A polypeptide of the invention may be included as a detergent additive for example. The invention also includes a method for textile desizing comprising contacting the textile with a polypeptide of the invention under conditions sufficient for desizing.

The invention also provides a method of reducing the staling of bakery products comprising addition of a polypeptide of the invention to the bakery product, prior to baking.

The invention also provides a method for the treatment of lignocellulosic fibers, wherein the fibers are treated with a polypeptide of the invention, in an amount which is efficient for improving the fiber properties. The invention includes a for enzymatic deinking of recycled paper pulp, wherein the polypeptide is applied in an amount which is efficient for effective deinking of the fiber surface.

Any of the methods described herein include the possibility of the addition of a second alpha amylase or a beta amylase or a combination thereof. Commercial amylases or other enzymes suitable for use in combination with an enzyme of the invention are known to those of skill in the art.

The invention also includes a method of increasing the flow of production fluids from a subterranean formation by removing a viscous, starch-containing, damaging fluid formed during production operations and found within the subterranean formation which surrounds a completed well bore comprising allowing production fluids to flow from the well bore; reducing the flow of production fluids from the formation below expected flow rates; formulating an enzyme treatment by blending together an aqueous fluid and a polypeptide of the invention; pumping the enzyme treatment to a desired location within the well bore; allowing the enzyme treatment to degrade the viscous, starch-containing, damaging fluid, whereby the fluid can be removed from the subterranean formation to the well surface; and wherein the enzyme treatment is effective to attack the alpha glucosidic linkages in the starch-containing fluid.

The present invention exploits the unique catalytic properties of enzymes. Whereas the use of biocatalysts (i.e., purified or crude enzymes, non-living or living cells) in chemical transformations normally requires the identification of a particular biocatalyst that reacts with a specific starting compound, the present invention uses selected biocatalysts and reaction conditions that are specific for functional groups that are present in many starting compounds.

Each biocatalyst is specific for one functional group, or several related functional groups, and can react with many starting compounds containing this functional group.

The biocatalytic reactions produce a population of derivatives from a single starting compound. These derivatives can be subjected to another round of biocatalytic reactions to produce a second population of derivative compounds. Thousands of variations of the original compound can be produced with each iteration of biocatalytic derivatization.

Enzymes react at specific sites of a starting compound without affecting the rest of the molecule, a process which is very difficult to achieve using traditional chemical methods. This high degree of biocatalytic specificity provides the means to identify a single active compound within the library. The library is characterized by the series of biocatalytic reactions used to produce it, a so-called "biosynthetic history". Screening the library for biological activities and tracing the biosynthetic history identifies the specific reaction sequence producing the active compound. The reaction sequence is repeated and the structure of the synthesized compound determined. This mode of identification, unlike other synthesis and screening approaches, does not require immobilization technologies, and compounds can be synthesized and tested free in solution using virtually any type of screening assay. It is important to note, that the high degree of specificity of enzyme reactions on functional groups allows for the "tracking" of specific enzymatic reactions that make up the biocatalytically produced library.

There are many advantages to screening lambda phage libraries for expression-based discovery of amylases. These include improved detection of toxic clones; improved access to substrate; reduced need for engineering a host; by-passing the potential for any bias resulting from mass excision of the library; and faster growth at low clone densities. Additionally, there are advantages to screening lambda phage libraries in liquid phase over solid phase. These include: greater flexibility in assay conditions; additional substrate flexibility; higher sensitivity for weak clones; and ease of automation.

Many of the procedural steps are performed using robotic automation enabling the execution of many thousands of biocatalytic reactions and screening assays per day as well as ensuring a high level of accuracy and reproducibility. As a result, a library of derivative compounds can be produced in a matter of weeks which would take years to produce using current chemical methods. (For further teachings on modification of molecules, including small molecules, see PCT/US94/09174, herein incorporated by reference in its entirety).

In one aspect, the present invention provides a non-stochastic method termed synthetic gene reassembly, that is somewhat related to stochastic shuffling, save that the nucleic acid building blocks are not shuffled or concatenated or chimerized randomly, but rather are assembled non-stochastically.

The synthetic gene reassembly method does not depend on the presence of a high level of homology between polynucleotides to be shuffled. The invention can be used to non-stochastically generate libraries (or sets) of progeny molecules comprised of over $10^{100}$ different chimeras. Conceivably, synthetic gene reassembly can even be used to generate libraries comprised of over $10^{1000}$ different progeny chimeras. Thus, in one aspect, the invention provides a non-stochastic method of producing a set of finalized chimeric nucleic acid molecules having an overall assembly order that is chosen by design, which method is comprised of the steps of generating by design a plurality of specific nucleic acid building blocks having serviceable mutually compatible ligatable ends, and assembling these nucleic acid building blocks, such that a designed overall assembly order is achieved.

The mutually compatible ligatable ends of the nucleic acid building blocks to be assembled are considered to be "serviceable" for this type of ordered assembly if they enable the building blocks to be coupled in predetermined orders. Thus, in one aspect, the overall assembly order in which the nucleic acid building blocks can be coupled is specified by the design of the ligatable ends and, if more than one assembly step is to be used, then the overall assembly order in which the nucleic acid building blocks can be coupled is also specified by the sequential order of the assembly step(s). In a one embodiment of the invention, the annealed building pieces are treated with an enzyme, such as a ligase (e.g., T4 DNA ligase) to achieve covalent bonding of the building pieces.

In a another embodiment, the design of nucleic acid building blocks is obtained upon analysis of the sequences of a set of progenitor nucleic acid templates that serve as a basis for producing a progeny set of finalized chimeric nucleic acid molecules. These progenitor nucleic acid templates thus serve as a source of sequence information that aids in the design of the nucleic acid building blocks that are to be mutagenized, e.g., chimerized or shuffled.

In one exemplification, the invention provides for the chimerization of a family of related genes and their encoded family of related products. In a particular exemplification, the encoded products are enzymes. The amylases of the present invention, for example, alpha amylases or alkaline amylases, can be mutagenized in accordance with the methods described herein.

Thus according to one aspect of the invention, the sequences of a plurality of progenitor nucleic acid templates (e.g., polynucleotides of Group A nucleic acid sequences) are aligned in order to select one or more demarcation points, which demarcation points can be located at an area of homology. The demarcation points can be used to delineate the boundaries of nucleic acid building blocks to be generated. Thus, the demarcation points identified and selected in the progenitor molecules serve as potential chimerization points in the assembly of the progeny molecules.

Typically a serviceable demarcation point is an area of homology (comprised of at least one homologous nucleotide base) shared by at least two progenitor templates, but the demarcation point can be an area of homology that is shared by at least half of the progenitor templates, at least two thirds of the progenitor templates, at least three fourths of the progenitor templates, and preferably at almost all of the progenitor templates. Even more preferably still a serviceable demarcation point is an area of homology that is shared by all of the progenitor templates.

In a one embodiment, the gene reassembly process is performed exhaustively in order to generate an exhaustive library. In other words, all possible ordered combinations of the nucleic acid building blocks are represented in the set of finalized chimeric nucleic acid molecules. At the same time, the assembly order (i.e. the order of assembly of each building block in the 5' to 3 sequence of each finalized chimeric nucleic acid) in each combination is by design (or non-stochastic). Because of the non-stochastic nature of the method, the possibility of unwanted side products is greatly reduced.

In another embodiment, the method provides that the gene reassembly process is performed systematically, for example to generate a systematically compartmentalized library, with compartments that can be screened systematically, e.g., one by one. In other words the invention provides that, through the selective and judicious use of specific nucleic acid building blocks, coupled with the selective and judicious use of sequentially stepped assembly reactions, an experimental design can be achieved where specific sets of progeny products are made in each of several reaction vessels. This allows a systematic examination and screening procedure to be performed. Thus, it allows a potentially very large number of progeny molecules to be examined systematically in smaller groups.

Because of its ability to perform chimerizations in a manner that is highly flexible yet exhaustive and systematic as well, particularly when there is a low level of homology among the progenitor molecules, the instant invention provides for the generation of a library (or set) comprised of a large number of progeny molecules. Because of the non-stochastic nature of the instant gene reassembly invention, the progeny molecules generated preferably comprise a library of finalized chimeric nucleic acid molecules having an overall assembly order that is chosen by design. In a particularly embodiment, such a generated library is comprised of greater than 103 to greater than 101000 different progeny molecular species.

In one aspect, a set of finalized chimeric nucleic acid molecules, produced as described is comprised of a polynucleotide encoding a polypeptide. According to one embodiment, this polynucleotide is a gene, which may be a man-made gene. According to another embodiment, this polynucleotide is a gene pathway, which may be a man-made gene pathway. The invention provides that one or more man-made genes generated by the invention may be incorporated into a man-made gene pathway, such as pathway operable in a eukaryotic organism (including a plant).

In another exemplification, the synthetic nature of the step in which the building blocks are generated allows the design and introduction of nucleotides (e.g., one or more nucleotides, which may be, for example, codons or introns or regulatory sequences) that can later be optionally removed in an in vitro process (e.g., by mutagenesis) or in an in vivo process (e.g., by utilizing the gene splicing ability of a host organism). It is appreciated that in many instances the introduction of these nucleotides may also be desirable for many other reasons in addition to the potential benefit of creating a serviceable demarcation point.

Thus, according to another embodiment, the invention provides that a nucleic acid building block can be used to introduce an intron. Thus, the invention provides that functional introns may be introduced into a man-made gene of the invention. The invention also provides that functional introns may be introduced into a man-made gene pathway of the invention. Accordingly, the invention provides for the generation of a chimeric polynucleotide that is a man-made gene containing one (or more) artificially introduced intron(s).

Accordingly, the invention also provides for the generation of a chimeric polynucleotide that is a man-made gene pathway containing one (or more) artificially introduced intron(s). Preferably, the artificially introduced intron(s) are functional in one or more host cells for gene splicing much in the way that naturally-occurring introns serve functionally in gene splicing. The invention provides a process of producing man-made intron-containing polynucleotides to be introduced into host organisms for recombination and/or splicing.

A man-made gene produced using the invention can also serve as a substrate for recombination with another nucleic acid. Likewise, a man-made gene pathway produced using the invention can also serve as a substrate for recombination with another nucleic acid. In a preferred instance, the recombination is facilitated by, or occurs at, areas of homology between the man-made, intron-containing gene and a nucleic acid, which serves as a recombination partner. In a particularly preferred instance, the recombination partner may also be a nucleic acid generated by the invention, including a man-made gene or a man-made gene pathway. Recombination may be facilitated by or may occur at areas of homology that exist at the one (or more) artificially introduced intron(s) in the man-made gene.

The synthetic gene reassembly method of the invention utilizes a plurality of nucleic acid building blocks, each of which preferably has two ligatable ends. The two ligatable ends on each nucleic acid building block may be two blunt ends (i.e. each having an overhang of zero nucleotides), or preferably one blunt end and one overhang, or more preferably still two overhangs.

A useful overhang for this purpose may be a 3' overhang or a 5' overhang. Thus, a nucleic acid building block may have a 3' overhang or alternatively a 5' overhang or alternatively two 3' overhangs or alternatively two 5' overhangs. The overall order in which the nucleic acid building blocks are assembled to form a finalized chimeric nucleic acid molecule is determined by purposeful experimental design and is not random.

According to one preferred embodiment, a nucleic acid building block is generated by chemical synthesis of two single-stranded nucleic acids (also referred to as single-stranded oligos) and contacting them so as to allow them to anneal to form a double-stranded nucleic acid building block.

A double-stranded nucleic acid building block can be of variable size. The sizes of these building blocks can be small or large. Preferred sizes for building block range from 1 base pair (not including any overhangs) to 100,000 base pairs (not including any overhangs). Other preferred size ranges are also provided, which have lower limits of from 1 bp to 10,000 bp (including every integer value in between), and upper limits of from 2 bp to 100,000 bp (including every integer value in between).

Many methods exist by which a double-stranded nucleic acid building block can be generated that is serviceable for the invention; and these are known in the art and can be readily performed by the skilled artisan.

According to one embodiment, a double-stranded nucleic acid building block is generated by first generating two single stranded nucleic acids and allowing them to anneal to form a double-stranded nucleic acid building block. The two strands of a double-stranded nucleic acid building block may be complementary at every nucleotide apart from any that form an overhang; thus containing no mismatches, apart from any overhang(s). According to another embodiment, the two strands of a double-stranded nucleic acid building block are complementary at fewer than every nucleotide apart from any that form an overhang. Thus, according to this embodiment, a double-stranded nucleic acid building block can be used to introduce codon degeneracy. Preferably the codon degeneracy is introduced using the site-saturation mutagenesis described herein, using one or more N,N,G/T cassettes or alternatively using one or more N,N,N cassettes.

The in vivo recombination method of the invention can be performed blindly on a pool of unknown hybrids or alleles of a specific polynucleotide or sequence. However, it is not necessary to know the actual DNA or RNA sequence of the specific polynucleotide.

The approach of using recombination within a mixed population of genes can be useful for the generation of any useful proteins, for example, interleukin I, antibodies, tPA and growth hormone. This approach may be used to generate proteins having altered specificity or activity. The approach may also be useful for the generation of hybrid nucleic acid sequences, for example, promoter regions, introns, exons, enhancer sequences, 31 untranslated regions or 51 untranslated regions of genes. Thus this approach may be used to generate genes having increased rates of expression. This approach may also be useful in the study of repetitive DNA sequences. Finally, this approach may be useful to mutate ribozymes or aptamers.

In one aspect the invention described herein is directed to the use of repeated cycles of reductive reassortment, recombination and selection which allow for the directed molecular evolution of highly complex linear sequences, such as DNA, RNA or proteins thorough recombination.

In vivo shuffling of molecules is useful in providing variants and can be performed utilizing the natural property of cells to recombine multimers. While recombination in vivo has provided the major natural route to molecular diversity, genetic recombination remains a relatively complex process that involves 1) the recognition of homologies; 2) strand cleavage, strand invasion, and metabolic steps leading to the production of recombinant chiasma; and finally 3) the resolution of chiasma into discrete recombined molecules. The formation of the chiasma requires the recognition of homologous sequences.

In another embodiment, the invention includes a method for producing a hybrid polynucleotide from at least a first polynucleotide and a second polynucleotide. The invention can be used to produce a hybrid polynucleotide by introducing at least a first polynucleotide and a second polynucleotide which share at least one region of partial sequence homology into a suitable host cell. The regions of partial sequence homology promote processes which result in sequence reorganization producing a hybrid polynucleotide. The term "hybrid polynucleotide", as used herein, is any nucleotide sequence which results from the method of the present invention and contains sequence from at least two original polynucleotide sequences. Such hybrid polynucleotides can result from intermolecular recombination events which promote sequence integration between DNA molecules. In addition, such hybrid polynucleotides can result from intramolecular reductive reassortment processes which utilize repeated sequences to alter a nucleotide sequence within a DNA molecule.

The invention provides a means for generating hybrid polynucleotides which may encode biologically active hybrid polypeptides (e.g., hybrid alpha amylases). In one aspect, the original polynucleotides encode biologically active polypeptides. The method of the invention produces new hybrid polypeptides by utilizing cellular processes which integrate the sequence of the original polynucleotides such that the resulting hybrid polynucleotide encodes a polypeptide demonstrating activities derived from the original biologically active polypeptides. For example, the original polynucleotides may encode a particular enzyme from different microorganisms. An enzyme encoded by a first polynucleotide from one organism or variant may, for example, function effectively under a particular environmental condition, e.g. high salinity. An enzyme encoded by a second polynucleotide from a different organism or variant may function effectively under a different environmental condition, such as extremely high temperatures. A hybrid polynucleotide containing sequences from the first and second original polynucleotides may encode an enzyme which exhibits characteristics of both enzymes encoded by the original polynucleotides. Thus, the enzyme encoded by the hybrid polynucleotide may function effectively under environmental conditions shared by each of the enzymes encoded by the first and second polynucleotides, e.g., high salinity and extreme temperatures.

Enzymes encoded by the polynucleotides of the invention include, but are not limited to, hydrolases, such as alpha amylases and alkaline amylases. A hybrid polypeptide resulting from the method of the invention may exhibit specialized enzyme activity not displayed in the original enzymes. For example, following recombination and/or reductive reassortment of polynucleotides encoding hydrolase activities, the resulting hybrid polypeptide encoded by a hybrid polynucleotide can be screened for specialized hydrolase activities obtained from each of the original enzymes, i.e. the type of bond on which the hydrolase acts and the temperature at which the hydrolase functions. Thus, for example, the hydrolase may be screened to ascertain those chemical functionalities which distinguish the hybrid hydrolase from the original hydrolases, such as: (a) amide (peptide bonds), i.e., proteases; (b) ester bonds, i.e., amylases and lipases; (c) acetals, i.e., glycosidases and, for example, the temperature, pH or salt concentration at which the hybrid polypeptide functions.

Sources of the original polynucleotides may be isolated from individual organisms ("isolates"), collections of organisms that have been grown in defined media ("enrichment cultures"), or, uncultivated organisms ("environmental samples"). The use of a culture-independent approach to derive polynucleotides encoding novel bioactivities from environmental samples is most preferable since it allows one to access untapped resources of biodiversity.

"Environmental libraries" are generated from environmental samples and represent the collective genomes of naturally occurring organisms archived in cloning vectors that can be propagated in suitable prokaryotic hosts. Because the cloned DNA is initially extracted directly from environmental samples, the libraries are not limited to the small fraction of prokaryotes that can be grown in pure culture. Additionally, a normalization of the environmental DNA present in these samples could allow more equal representation of the DNA from all of the species present in the original sample. This can dramatically increase the efficiency of finding interesting genes from minor constituents of the sample which may be under-represented by several orders of magnitude compared to the dominant species.

For example, gene libraries generated from one or more uncultivated microorganisms are screened for an activity of interest. Potential pathways encoding bioactive molecules of interest are first captured in prokaryotic cells in the form of gene expression libraries. Polynucleotides encoding activities of interest are isolated from such libraries and introduced into a host cell. The host cell is grown under conditions which promote recombination and/or reductive reassortment creating potentially active biomolecules with novel or enhanced activities.

The microorganisms from which the polynucleotide may be prepared include prokaryotic microorganisms, such as Eubacteria and Archaebacteria, and lower eukaryotic microorganisms such as fungi, some algae and protozoa. Polynucleotides may be isolated from environmental samples in which case the nucleic acid may be recovered without culturing of an organism or recovered from one or more cultured organisms. In one aspect, such microorganisms may be extremophiles, such as hyperthermophiles, psychrophiles, psychrotrophs, halophiles, barophiles and acidophiles. Polynucleotides encoding enzymes isolated from extremophilic microorganisms are particularly preferred. Such enzymes may function at temperatures above 100° C. in terrestrial hot springs and deep sea thermal vents, at temperatures below 0° C. in arctic waters, in the saturated salt environment of the Dead Sea, at pH values around 0 in coal deposits and geothermal sulfur-rich springs, or at pH values greater than 11 in sewage sludge. For example, several amylases and lipases cloned and expressed from extremophilic organisms show high activity throughout a wide range of temperatures and pHs.

Of the novel enzymes of the present invention, many have been purified and characterized at pH 8, at both 40° C. and 50° C., and pH 10 at both 40° C. and 50° C. Of the enzymes found to be purified and characterized at pH 8 and 40° C., was seen to have three times (682 U/mg) the specific activity of a *B. lichenoformis* enzyme (228 U/mg). Additionally, another enzyme was seen to have approximately equivalent activity (250 U/mg) to the *B. lichenoformis* enzyme. At a pH 10 and 50° C., one of the enzymes has a specific activity of 31 U/mg and another has a specific activity of 27.5 U/mg, while *B. lichenoformis* has a specific activity of 27 U/mg.

Polynucleotides selected and isolated as hereinabove described are introduced into a suitable host cell. A suitable host cell is any cell which is capable of promoting recombination and/or reductive reassortment. The selected polynucleotides are preferably already in a vector which includes appropriate control sequences. The host cell can be a higher eukaryotic cell, such as a mammalian cell, or a lower eukaryotic cell, such as a yeast cell, or preferably, the host cell can be a prokaryotic cell, such as a bacterial cell. Introduction of the construct into the host cell can be effected by calcium phosphate transfection, DEAE-Dextran mediated transfection, or electroporation (Davis et al., 1986).

As representative examples of appropriate hosts, there may be mentioned: bacterial cells, such as *E. coli, Streptomyces, Salmonella typhimurium*; fungal cells, such as yeast; insect cells such as *Drosophila* S2 and *Spodoptera* Sf9; animal cells such as CHO, COS or Bowes melanoma; adenoviruses; and plant cells. The selection of an appropriate host is deemed to be within the scope of those skilled in the art from the teachings herein.

With particular references to various mammalian cell culture systems that can be employed to express recombinant protein, examples of mammalian expression systems include the COS-7 lines of monkey kidney fibroblasts, described in "SV40-transformed simian cells support the replication of early SV40 mutants" (Gluzman, 1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

Host cells containing the polynucleotides of interest can be cultured in conventional nutrient media modified as appropriate for activating promoters, selecting transformants or amplifying genes. The culture conditions, such as temperature, pH and the like, are those previously used with the host cell selected for expression, and will be apparent to the ordinarily skilled artisan. The clones which are identified as having the specified enzyme activity may then be sequenced to identify the polynucleotide sequence encoding an enzyme having the enhanced activity.

In another aspect, it is envisioned the method of the present invention can be used to generate novel polynucleotides encoding biochemical pathways from one or more operons or gene clusters or portions thereof. For example, bacteria and many eukaryotes have a coordinated mechanism for regulating genes whose products are involved in related processes. The genes are clustered, in structures referred to as "gene clusters," on a single chromosome and are transcribed together under the control of a single regulatory sequence, including a single promoter which initiates transcription of the entire cluster. Thus, a gene cluster is a group of adjacent genes that are either identical or related, usually as to their function. An example of a biochemical pathway encoded by gene clusters are polyketides. Polyketides are molecules which are an extremely rich source of bioactivities, including antibiotics (such as tetracyclines and erythromycin), anti-cancer agents (daunomycin), immunosuppressants (FK506 and rapamycin), and veterinary products (monensin). Many polyketides (produced by polyketide synthases) are valuable as therapeutic agents. Polyketide synthases are multifunctional enzymes that catalyze the biosynthesis of an enormous variety of carbon chains differing in length and patterns of functionality and cyclization. Polyketide synthase genes fall into gene clusters and at least one type (designated type I) of polyketide synthases have large size genes and enzymes, complicating genetic manipulation and in vitro studies of these genes/proteins.

Gene cluster DNA can be isolated from different organisms and ligated into vectors, particularly vectors containing expression regulatory sequences which can control and regulate the production of a detectable protein or protein-related array activity from the ligated gene clusters. Use of vectors which have an exceptionally large capacity for exogenous DNA introduction are particularly appropriate for use with such gene clusters and are described by way of example herein to include the f-factor (or fertility factor) of *E. coli*. This f-factor of *E. coli* is a plasmid which affect high-frequency transfer of itself during conjugation and is ideal to achieve and stably propagate large DNA fragments, such as gene clusters from mixed microbial samples. A particularly preferred embodiment is to use cloning vectors, referred to as "fosmids" or bacterial artificial chromosome (BAC) vectors. These are derived from *E. coli* f-factor which is able to stably integrate large segments of genomic DNA. When integrated with DNA from a mixed uncultured environmental sample, this makes it possible to achieve large genomic fragments in the form of a stable "environmental DNA library." Another type of vector for use in the present invention is a cosmid vector. Cosmid vectors were originally designed to clone and propagate large segments of genomic DNA. Cloning into cosmid vectors is described in detail in Sambrook et al., Molecular Cloning: A Laboratory Manual, 2nd Ed., Cold Spring Harbor Laboratory Press (1989). Once ligated into an appropriate vector, two or more vectors containing different polyketide synthase gene clusters can be introduced into a suitable host cell. Regions of partial sequence homology shared by the gene clusters will promote processes which result in sequence reorganization resulting in a hybrid gene cluster. The novel hybrid gene cluster can then be screened for enhanced activities not found in the original gene clusters.

Therefore, in a one embodiment, the invention relates to a method for producing a biologically active hybrid polypeptide and screening such a polypeptide for enhanced activity by:

1) introducing at least a first polynucleotide in operable linkage and a second polynucleotide in operable linkage, said at least first polynucleotide and second polynucleotide sharing at least one region of partial sequence homology, into a suitable host cell;

2) growing the host cell under conditions which promote sequence reorganization resulting in a hybrid polynucleotide in operable linkage;

3) expressing a hybrid polypeptide encoded by the hybrid polynucleotide;

4) screening the hybrid polypeptide under conditions which promote identification of enhanced biological activity; and 5) isolating the a polynucleotide encoding the hybrid polypeptide.

Methods for screening for various enzyme activities are known to those of skill in the art and are discussed throughout the present specification. Such methods may be employed when isolating the polypeptides and polynucleotides of the invention.

As representative examples of expression vectors which may be used, there may be mentioned viral particles, baculovirus, phage, plasmids, phagemids, cosmids, fosmids, bacterial artificial chromosomes, viral DNA (e.g., vaccinia, adenovirus, foul pox virus, pseudorabies and derivatives of SV40), P1-based artificial chromosomes, yeast plasmids, yeast artificial chromosomes, and any other vectors specific for specific hosts of interest (such as bacillus, aspergillus and yeast). Thus, for example, the DNA may be included in any one of a variety of expression vectors for expressing a polypeptide. Such vectors include chromosomal, nonchromosomal and synthetic DNA sequences. Large numbers of suitable vectors are known to those of skill in the art, and are commercially available. The following vectors are provided by way of example; Bacterial: pQE vectors (Qiagen), pBluescript plasmids, pNH vectors, (lambda-ZAP vectors (Stratagene); ptrc99a, pKK223-3, pDR540, pRIT2T (Pharmacia); Eukaryotic: pXT1, pSG5 (Stratagene), pSVK3, pBPV, pMSG, pSVLSV40 (Pharmacia). However, any other plasmid or other vector may be used so long as they are replicable and viable in the host. Low copy number or high copy number vectors may be employed with the present invention.

The DNA sequence in the expression vector is operatively linked to an appropriate expression control sequence(s) (promoter) to direct RNA synthesis. Particular named bacterial promoters include lad, lacZ, T3, T7, gpt, lambda PR, PL and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art. The expression vector also contains a ribosome binding site for translation initiation and a transcription terminator. The vector may also include appropriate sequences for amplifying expression. Promoter regions can be selected from any desired gene using chloramphenicol transferase (CAT) vectors or other vectors with selectable markers. In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in *E. coli*.

In vivo reassortment is focused on "inter-molecular" processes collectively referred to as "recombination" which in bacteria, is generally viewed as a "RecA-dependent" phenomenon. The invention can rely on recombination processes of a host cell to recombine and re-assort sequences, or the cells' ability to mediate reductive processes to decrease the complexity of quasi-repeated sequences in the cell by deletion. This process of "reductive reassortment" occurs by an "intra-molecular", RecA-independent process.

Therefore, in another aspect of the invention, novel polynucleotides can be generated by the process of reductive reassortment. The method involves the generation of constructs containing consecutive sequences (original encoding sequences), their insertion into an appropriate vector, and their subsequent introduction into an appropriate host cell. The reassortment of the individual molecular identities occurs by combinatorial processes between the consecutive sequences in the construct possessing regions of homology, or between quasi-repeated units. The reassortment process recombines and/or reduces the complexity and extent of the repeated sequences, and results in the production of novel molecular species. Various treatments may be applied to enhance the rate of reassortment. These could include treatment with ultra-violet light, or DNA damaging chemicals, and/or the use of host cell lines displaying enhanced levels of "genetic instability". Thus the reassortment process may involve homologous recombination or the natural property of quasi-repeated sequences to direct their own evolution.

Repeated or "quasi-repeated" sequences play a role in genetic instability. In the present invention, "quasi-repeats" are repeats that are not restricted to their original unit structure. Quasi-repeated units can be presented as an array of sequences in a construct; consecutive units of similar sequences. Once ligated, the junctions between the consecutive sequences become essentially invisible and the quasi-repetitive nature of the resulting construct is now continuous at the molecular level. The deletion process the cell performs to reduce the complexity of the resulting construct operates between the quasi-repeated sequences. The quasi-repeated units provide a practically limitless repertoire of templates upon which slippage events can occur. The constructs containing the quasi-repeats thus effectively provide sufficient molecular elasticity that deletion (and potentially insertion) events can occur virtually anywhere within the quasi-repetitive units.

When the quasi-repeated sequences are all ligated in the same orientation, for instance head to tail or vice versa, the cell cannot distinguish individual units. Consequently, the reductive process can occur throughout the sequences. In contrast, when for example, the units are presented head to head, rather than head to tail, the inversion delineates the endpoints of the adjacent unit so that deletion formation will favor the loss of discrete units. Thus, it is preferable with the present method that the sequences are in the same orientation. Random orientation of quasi-repeated sequences will result in the loss of reassortment efficiency, while consistent orientation of the sequences will offer the highest efficiency. However, while having fewer of the contiguous sequences in the same orientation decreases the efficiency, it may still provide sufficient elasticity for the effective recovery of novel molecules. Constructs can be made with the quasi-repeated sequences in the same orientation to allow higher efficiency.

Sequences can be assembled in a head to tail orientation using any of a variety of methods, including the following:

a) Primers that include a poly-A head and poly-T tail which when made single-stranded would provide orientation can be utilized. This is accomplished by having the first few bases of the primers made from RNA and hence easily removed RNAseH.

b) Primers that include unique restriction cleavage sites can be utilized. Multiple sites, a battery of unique sequences, and repeated synthesis and ligation steps would be required.

c) The inner few bases of the primer could be thiolated and an exonuclease used to produce properly tailed molecules.

The recovery of the re-assorted sequences relies on the identification of cloning vectors with a reduced repetitive index (RI). The re-assorted encoding sequences can then be recovered by amplification. The products are re-cloned and expressed. The recovery of cloning vectors with reduced RI can be affected by:

1) The use of vectors only stably maintained when the construct is reduced in complexity.

2) The physical recovery of shortened vectors by physical procedures. In this case, the cloning vector would be recovered using standard plasmid isolation procedures and size fractionated on either an agarose gel, or column with a low molecular weight cut off utilizing standard procedures.

3) The recovery of vectors containing interrupted genes which can be selected when insert size decreases.

4) The use of direct selection techniques with an expression vector and the appropriate selection.

Encoding sequences (for example, genes) from related organisms may demonstrate a high degree of homology and encode quite diverse protein products. These types of sequences are particularly useful in the present invention as quasi-repeats. However, while the examples illustrated below demonstrate the reassortment of nearly identical original encoding sequences (quasi-repeats), this process is not limited to such nearly identical repeats.

The following example demonstrates a method of the invention. Encoding nucleic acid sequences (quasi-repeats) derived from three (3) unique species are described. Each sequence encodes a protein with a distinct set of properties. Each of the sequences differs by a single or a few base pairs at a unique position in the sequence. The quasi-repeated sequences are separately or collectively amplified and ligated into random assemblies such that all possible permutations and combinations are available in the population of ligated molecules. The number of quasi-repeat units can be controlled by the assembly conditions. The average number of quasi-repeated units in a construct is defined as the repetitive index (RI).

Once formed, the constructs may, or may not be size fractionated on an agarose gel according to published protocols, inserted into a cloning vector, and transfected into an appropriate host cell. The cells are then propagated and "reductive reassortment" is effected. The rate of the reductive reassortment process may be stimulated by the introduction of DNA damage if desired. Whether the reduction in RI is mediated by deletion formation between repeated sequences by an "intra-molecular" mechanism, or mediated by recombination-like events through "inter-molecular" mechanisms is immaterial. The end result is a reassortment of the molecules into all possible combinations.

Optionally, the method comprises the additional step of screening the library members of the shuffled pool to identify individual shuffled library members having the ability to bind or otherwise interact, or catalyze a particular reaction (e.g., such as catalytic domain of an enzyme) with a predetermined macromolecule, such as for example a proteinaceous receptor, an oligosaccharide, viron, or other predetermined compound or structure.

The polypeptides that are identified from such libraries can be used for therapeutic, diagnostic, research and related purposes (e.g., catalysts, solutes for increasing osmolarity of an aqueous solution, and the like), and/or can be subjected to one or more additional cycles of shuffling and/or selection.

In another aspect, it is envisioned that prior to or during recombination or reassortment, polynucleotides generated by the method of the invention can be subjected to agents or processes which promote the introduction of mutations into the original polynucleotides. The introduction of such mutations would increase the diversity of resulting hybrid polynucleotides and polypeptides encoded therefrom. The agents or processes which promote mutagenesis can include, but are not limited to: (+)-CC-1065, or a synthetic analog such as (+)-CC-1065-(N3-Adenine (See Sun and Hurley, (1992); an N-acelylated or deacetylated 4'-fluro-4-aminobiphenyl adduct capable of inhibiting DNA synthesis (See, for example, van de Poll et al. (1992)); or a N-acetylated or deacetylated 4-aminobiphenyl adduct capable of inhibiting DNA synthesis (See also, van de Poll et al. (1992), pp. 751-758); trivalent chromium, a trivalent chromium salt, a polycyclic aromatic hydrocarbon (PAH) DNA adduct capable of inhibiting DNA replication, such as 7-bromomethyl-benz[a]anthracene ("BMA"), tris(2,3-dibromopropyl) phosphate ("Tris-BP"), 1,2-dibromo-3-chloropropane ("DBCP"), 2-bromoacrolein (2BA), benzo[a]pyrene-7,8-dihydrodiol-9-10-epoxide ("BPDE"), a platinum(II) halogen salt, N-hydroxy-2-amino-3-methylimidazo[4,5-f]-quinoline ("N-hydroxy-IQ"), and N-hydroxy-2-amino-1-methyl-6-phenylimidazo[4,5-f]-pyridine ("N-hydroxy-PhIP"). Especially preferred means for slowing or halting PCR amplification consist of UV light (+)-CC-1065 and (+)-CC-1065-(N3-Adenine). Particularly encompassed means are DNA adducts or polynucleotides comprising the DNA adducts from the polynucleotides or polynucleotides pool, which can be released or removed by a process including heating the solution comprising the polynucleotides prior to further processing.

In another aspect the invention is directed to a method of producing recombinant proteins having biological activity by treating a sample comprising double-stranded template polynucleotides encoding a wild-type protein under conditions according to the invention which provide for the production of hybrid or re-assorted polynucleotides.

The invention also provides for the use of proprietary codon primers (containing a degenerate N,N,N sequence) to introduce point mutations into a polynucleotide, so as to generate a set of progeny polypeptides in which a full range of single amino acid substitutions is represented at each amino acid position (gene site saturated mutagenesis (GSSM)). The oligos used are comprised contiguously of a first homologous sequence, a degenerate N,N,N sequence, and preferably but not necessarily a second homologous sequence. The downstream progeny translational products from the use of such oligos include all possible amino acid changes at each amino acid site along the polypeptide, because the degeneracy of the N,N,N sequence includes codons for all 20 amino acids.

In one aspect, one such degenerate oligo (comprised of one degenerate N,N,N cassette) is used for subjecting each original codon in a parental polynucleotide template to a full range of codon substitutions. In another aspect, at least two degenerate N,N,N cassettes are used—either in the same oligo or not, for subjecting at least two original codons in a parental polynucleotide template to a full range of codon substitutions. Thus, more than one N,N,N sequence can be contained in one oligo to introduce amino acid mutations at more than one site. This plurality of N,N,N sequences can be directly contiguous, or separated by one or more additional nucleotide sequence(s). In another aspect, oligos serviceable for introducing additions and deletions can be used either alone or in combination with the codons containing an N,N,N sequence, to introduce any combination or permutation of amino acid additions, deletions, and/or substitutions.

In a particular exemplification, it is possible to simultaneously mutagenize two or more contiguous amino acid positions using an oligo that contains contiguous N,N,N triplets, i.e. a degenerate (N,N,N)n sequence.

In another aspect, the present invention provides for the use of degenerate cassettes having less degeneracy than the N,N,N sequence. For example, it may be desirable in some instances to use (e.g. in an oligo) a degenerate triplet sequence comprised of only one N, where said N can be in the first second or third position of the triplet. Any other bases including any combinations and permutations thereof can be used in the remaining two positions of the triplet. Alternatively, it may be desirable in some instances to use (e.g., in an oligo) a degenerate N,N,N triplet sequence, N,N,G/T, or an N,N, G/C triplet sequence.

It is appreciated, however, that the use of a degenerate triplet (such as N,N,G/T or an N,N, G/C triplet sequence) as disclosed in the instant invention is advantageous for several reasons. In one aspect, this invention provides a means to systematically and fairly easily generate the substitution of the full range of possible amino acids (for a total of 20 amino acids) into each and every amino acid position in a polypeptide. Thus, for a 100 amino acid polypeptide, the invention provides a way to systematically and fairly easily generate 2000 distinct species (i.e., 20 possible amino acids per position times 100 amino acid positions). It is appreciated that there is provided, through the use of an oligo containing a degenerate N,N,G/T or an N,N, G/C triplet sequence, 32 individual sequences that code for 20 possible amino acids. Thus, in a reaction vessel in which a parental polynucleotide sequence is subjected to saturation mutagenesis using one such oligo, there are generated 32 distinct progeny polynucleotides encoding 20 distinct polypeptides. In contrast, the use of a non-degenerate oligo in site-directed mutagenesis leads to only one progeny polypeptide product per reaction vessel.

This invention also provides for the use of nondegenerate oligos, which can optionally be used in combination with degenerate primers disclosed. It is appreciated that in some situations, it is advantageous to use nondegenerate oligos to generate specific point mutations in a working polynucleotide. This provides a means to generate specific silent point mutations, point mutations leading to corresponding amino acid changes, and point mutations that cause the generation of stop codons and the corresponding expression of polypeptide fragments.

Thus, in a preferred embodiment of this invention, each saturation mutagenesis reaction vessel contains polynucleotides encoding at least 20 progeny polypeptide molecules such that all 20 amino acids are represented at the one specific amino acid position corresponding to the codon position mutagenized in the parental polynucleotide. The 32-fold degenerate progeny polypeptides generated from each saturation mutagenesis reaction vessel can be subjected to clonal amplification (e.g., cloned into a suitable $E.$ $coli$ host using an expression vector) and subjected to expression screening. When an individual progeny polypeptide is identified by screening to display a favorable change in property (when compared to the parental polypeptide), it can be sequenced to identify the correspondingly favorable amino acid substitution contained therein.

It is appreciated that upon mutagenizing each and every amino acid position in a parental polypeptide using saturation mutagenesis as disclosed herein, favorable amino acid changes may be identified at more than one amino acid position. One or more new progeny molecules can be generated that contain a combination of all or part of these favorable amino acid substitutions. For example, if 2 specific favorable amino acid changes are identified in each of 3 amino acid positions in a polypeptide, the permutations include 3 possibilities at each position (no change from the original amino acid, and each of two favorable changes) and 3 positions. Thus, there are 3×3×3 or 27 total possibilities, including 7 that were previously examined—6 single point mutations (i.e., 2 at each of three positions) and no change at any position.

In yet another aspect, site-saturation mutagenesis can be used together with shuffling, chimerization, recombination and other mutagenizing processes, along with screening. This invention provides for the use of any mutagenizing process(es), including saturation mutagenesis, in an iterative manner. In one exemplification, the iterative use of any mutagenizing process(es) is used in combination with screening.

Thus, in a non-limiting exemplification, this invention provides for the use of saturation mutagenesis in combination with additional mutagenization processes, such as process where two or more related polynucleotides are introduced into a suitable host cell such that a hybrid polynucleotide is generated by recombination and reductive reassortment.

In addition to performing mutagenesis along the entire sequence of a gene, the instant invention provides that mutagenesis can be use to replace each of any number of bases in a polynucleotide sequence, wherein the number of bases to be mutagenized is preferably every integer from 15 to 100,000. Thus, instead of mutagenizing every position along a molecule, one can subject every or a discrete number of bases (preferably a subset totaling from 15 to 100,000) to mutagenesis. Preferably, a separate nucleotide is used for mutagenizing each position or group of positions along a polynucleotide sequence. A group of 3 positions to be mutagenized may be a codon. The mutations are preferably introduced using a mutagenic primer, containing a heterologous cassette, also referred to as a mutagenic cassette. Preferred cassettes can have from 1 to 500 bases. Each nucleotide position in such heterologous cassettes be N, A, C, G, T, A/C, A/G, A/T, C/G, C/T, G/T, C/G/T, A/G/T, A/C/T, A/C/G, or E, where E is any base that is not A, C, G, or T (E can be referred to as a designer oligo).

In a general sense, saturation mutagenesis is comprised of mutagenizing a complete set of mutagenic cassettes (wherein each cassette is preferably about 1-500 bases in length) in defined polynucleotide sequence to be mutagenized (wherein the sequence to be mutagenized is preferably from about 15 to 100,000 bases in length). Thus, a group of mutations (ranging from 1 to 100 mutations) is introduced into each cassette to be mutagenized. A grouping of mutations to be introduced into one cassette can be different or the same from a second grouping of mutations to be introduced into a second cassette during the application of one round of saturation mutagenesis. Such groupings are exemplified by deletions, additions, groupings of particular codons, and groupings of particular nucleotide cassettes.

Defined sequences to be mutagenized include a whole gene, pathway, cDNA, an entire open reading frame (ORF), and entire promoter, enhancer, repressor/transactivator, origin of replication, intron, operator, or any polynucleotide functional group. Generally, a "defined sequences" for this purpose may be any polynucleotide that a 15 base-polynucleotide sequence, and polynucleotide sequences of lengths between 15 bases and 15,000 bases (this invention specifically names every integer in between). Considerations in choosing groupings of codons include types of amino acids encoded by a degenerate mutagenic cassette.

In a particularly preferred exemplification a grouping of mutations that can be introduced into a mutagenic cassette, this invention specifically provides for degenerate codon substitutions (using degenerate oligos) that code for 2, 3, 4, 5, 6, 7, 8, 9, 10, 11, 12, 13, 14, 15, 16, 17, 18, 19, and 20 amino acids at each position, and a library of polypeptides encoded thereby.

One aspect of the invention is an isolated nucleic acid comprising one of the sequences of Group A nucleic acid sequences, and sequences substantially identical thereto, the sequences complementary thereto, or a fragment comprising at least 10, 15, 20, 25, 30, 35, 40, 50, 75, 100, 150, 200, 300, 400, or 500 consecutive bases of one of the sequences of a Group A nucleic acid sequence (or the sequences complementary thereto). The isolated, nucleic acids may comprise DNA, including cDNA, genomic DNA, and synthetic DNA. The DNA may be double-stranded or single-stranded, and if single stranded may be the coding strand or non-coding (anti-sense) strand. Alternatively, the isolated nucleic acids may comprise RNA.

As discussed in more detail below, the isolated nucleic acids of one of the Group A nucleic acid sequences, and sequences substantially identical thereto, may be used to prepare one of the polypeptides of a Group B amino acid sequence, and sequences substantially identical thereto, or fragments comprising at least 5, 10, 15, 20, 25, 30, 35, 40, 50, 75, 100, or 150 consecutive amino acids of one of the polypeptides of Group B amino acid sequences, and sequences substantially identical thereto.

Accordingly, another aspect of the invention is an isolated nucleic acid which encodes one of the polypeptides of Group B amino acid sequences, and sequences substantially identical thereto, or fragments comprising at least 5, 10, 15, 20, 25, 30, 35, 40, 50, 75, 100, or 150 consecutive amino acids of one of the polypeptides of the Group B amino acid sequences. The coding sequences of these nucleic acids may be identical to one of the coding sequences of one of the nucleic acids of Group A nucleic acid sequences, or a fragment thereof or may be different coding sequences which encode one of the polypeptides of Group B amino acid sequences, sequences substantially identical thereto, and fragments having at least 5, 10, 15, 20, 25, 30, 35, 40, 50, 75, 100, or 150 consecutive amino acids of one of the polypeptides of Group B amino acid sequences, as a result of the redundancy or degeneracy of the genetic code. The genetic code is well known to those of skill in the art and can be obtained, for example, on page 214 of B. Lewin, Genes VI, Oxford University Press, 1997, the disclosure of which is incorporated herein by reference.

The isolated nucleic acid which encodes one of the polypeptides of Group B amino acid sequences, and sequences substantially identical thereto, may include, but is not limited to: only the coding sequence of one of Group A nucleic acid sequences, and sequences substantially identical thereto, and additional coding sequences, such as leader sequences or proprotein sequences and non-coding sequences, such as introns or non-coding sequences 5' and/or 3' of the coding sequence. Thus, as used herein, the term "polynucleotide encoding a polypeptide" encompasses a polynucleotide which includes only the coding sequence for the polypeptide as well as a polynucleotide which includes additional coding and/or non-coding sequence.

Alternatively, the nucleic acid sequences of Group A nucleic acid sequences, and sequences substantially identical thereto, may be mutagenized using conventional techniques, such as site directed mutagenesis, or other techniques familiar to those skilled in the art, to introduce silent changes into the polynucleotides of Group A nucleic acid sequences, and sequences substantially identical thereto. As used herein, "silent changes" include, for example, changes which do not alter the amino acid sequence encoded by the polynucleotide. Such changes may be desirable in order to increase the level of the polypeptide produced by host cells containing a vector encoding the polypeptide by introducing codons or codon pairs which occur frequently in the host organism.

The invention also relates to polynucleotides which have nucleotide changes which result in amino acid substitutions, additions, deletions, fusions and truncations in the polypeptides of Group B amino acid sequences, and sequences substantially identical thereto. Such nucleotide changes may be introduced using techniques such as site directed mutagenesis, random chemical mutagenesis, exonuclease III deletion, and other recombinant DNA techniques. Alternatively, such nucleotide changes may be naturally occurring allelic variants which are isolated by identifying nucleic acids which specifically hybridize to probes comprising at least 10, 15, 20, 25, 30, 35, 40, 50, 75, 100, 150, 200, 300, 400, or 500 consecutive bases of one of the sequences of Group A nucleic acid sequences, and sequences substantially identical thereto (or the sequences complementary thereto) under conditions of high, moderate, or low stringency as provided herein.

The isolated nucleic acids of Group A nucleic acid sequences, and sequences substantially identical thereto, the sequences complementary thereto, or a fragment comprising at least 10, 15, 20, 25, 30, 35, 40, 50, 75, 100, 150, 200, 300, 400, or 500 consecutive bases of one of the sequences of Group A nucleic acid sequences, and sequences substantially identical thereto, or the sequences complementary thereto may also be used as probes to determine whether a biological sample, such as a soil sample, contains an organism having a nucleic acid sequence of the invention or an organism from which the nucleic acid was obtained. In such procedures, a biological sample potentially harboring the organism from which the nucleic acid was isolated is obtained and nucleic acids are obtained from the sample. The nucleic acids are contacted with the probe under conditions which permit the probe to specifically hybridize to any complementary sequences from which are present therein.

Where necessary, conditions which permit the probe to specifically hybridize to complementary sequences may be determined by placing the probe in contact with complementary sequences from samples known to contain the complementary sequence as well as control sequences which do not contain the complementary sequence. Hybridization conditions, such as the salt concentration of the hybridization buffer, the formamide concentration of the hybridization buffer, or the hybridization temperature, may be varied to identify conditions which allow the probe to hybridize specifically to complementary nucleic acids.

If the sample contains the organism from which the nucleic acid was isolated, specific hybridization of the probe is then detected. Hybridization may be detected by labeling the probe with a detectable agent such as a radioactive isotope, a fluorescent dye or an enzyme capable of catalyzing the formation of a detectable product.

Many methods for using the labeled probes to detect the presence of complementary nucleic acids in a sample are familiar to those skilled in the art. These include Southern Blots, Northern Blots, colony hybridization procedures, and dot blots. Protocols for each of these procedures are provided in Ausubel et al. Current Protocols in Molecular Biology, John Wiley 503 Sons, Inc. (1997) and Sambrook et al., Molecular Cloning: A Laboratory Manual 2nd Ed., Cold Spring Harbor Laboratory Press (1989), the entire disclosures of which are incorporated herein by reference.

Alternatively, more than one probe (at least one of which is capable of specifically hybridizing to any complementary sequences which are present in the nucleic acid sample), may be used in an amplification reaction to determine whether the sample contains an organism containing a nucleic acid sequence of the invention (e.g., an organism from which the nucleic acid was isolated). Typically, the probes comprise oligonucleotides. In one embodiment, the amplification reaction may comprise a PCR reaction. PCR protocols are described in Ausubel and Sambrook, supra. Alternatively, the amplification may comprise a ligase chain reaction, 3SR, or strand displacement reaction. (See Barany, F., "The Ligase Chain Reaction in a PCR World", PCR Methods and Applications 1:5-16, 1991; E. Fahy et al., "Self-sustained Sequence Replication (3SR): An Isothermal Transcription-based Amplification System Alternative to PCR", PCR Methods and Applications 1:25-33, 1991; and Walker G. T. et al., "Strand Displacement Amplification—an Isothermal in vitro DNA Amplification Technique", Nucleic Acid Research 20:1691-1696, 1992, the disclosures of which are incorporated herein by reference in their entireties). In such procedures, the nucleic acids in the sample are contacted with the probes, the amplification reaction is performed, and any resulting amplification product is detected. The amplification product may be detected by performing gel electrophoresis on the reaction products and staining the gel with an intercalator such as ethidium bromide. Alternatively, one or more of the probes may be labeled with a radioactive isotope and the presence of a radioactive amplification product may be detected by autoradiography after gel electrophoresis.

Probes derived from sequences near the ends of the sequences of Group A nucleic acid sequences, and sequences substantially identical thereto, may also be used in chromosome walking procedures to identify clones containing genomic sequences located adjacent to the sequences of Group A nucleic acid sequences, and sequences substantially identical thereto. Such methods allow the isolation of genes which encode additional proteins from the host organism.

The isolated nucleic acids of Group A nucleic acid sequences, and sequences substantially identical thereto, the sequences complementary thereto, or a fragment comprising at least 10, 15, 20, 25, 30, 35, 40, 50, 75, 100, 150, 200, 300, 400, or 500 consecutive bases of one of the sequences of Group A nucleic acid sequences, and sequences substantially identical thereto, or the sequences complementary thereto may be used as probes to identify and isolate related nucleic acids. In some embodiments, the related nucleic acids may be cDNAs or genomic DNAs from organisms other than the one from which the nucleic acid was isolated. For example, the other organisms may be related organisms. In such procedures, a nucleic acid sample is contacted with the probe under conditions which permit the probe to specifically hybridize to related sequences. Hybridization of the probe to nucleic acids from the related organism is then detected using any of the methods described above.

In nucleic acid hybridization reactions, the conditions used to achieve a particular level of stringency will vary, depending on the nature of the nucleic acids being hybridized. For example, the length, degree of complementarity, nucleotide sequence composition (e.g., GC v. AT content), and nucleic acid type (e.g., RNA v. DNA) of the hybridizing regions of the nucleic acids can be considered in selecting hybridization conditions. An additional consideration is whether one of the nucleic acids is immobilized, for example, on a filter.

Hybridization may be carried out under conditions of low stringency, moderate stringency or high stringency. As an example of nucleic acid hybridization, a polymer membrane containing immobilized denatured nucleic acids is first prehybridized for 30 minutes at 45° C. in a solution consisting of 0.9 M NaCl, 50 mM NaH2PO4, pH 7.0, 5.0 mM Na2EDTA, 0.5% SDS, 10×Denhardt's, and 0.5 mg/ml polyriboadenylic acid. Approximately 2×10$^7$ cpm (specific activity 4-9×10$^8$ cpm/ug) of $^{32}$P end-labeled oligonucleotide probe are then added to the solution. After 12-16 hours of incubation, the membrane is washed for 30 minutes at room temperature in 1×SET (150 mM NaCl, 20 mM Tris hydrochloride, pH 7.8, 1 mM Na2EDTA) containing 0.5% SDS, followed by a 30 minute wash in fresh 1×SET at Tm-10° C. for the oligonucleotide probe. The membrane is then exposed to auto-radiographic film for detection of hybridization signals.

By varying the stringency of the hybridization conditions used to identify nucleic acids, such as cDNAs or genomic DNAs, which hybridize to the detectable probe, nucleic acids having different levels of homology to the probe can be identified and isolated. Stringency may be varied by conducting the hybridization at varying temperatures below the melting temperatures of the probes. The melting temperature, Tm, is the temperature (under defined ionic strength and pH) at which 50% of the target sequence hybridizes to a perfectly complementary probe. Very stringent conditions are selected to be equal to or about 5° C. lower than the Tm for a particular probe. The melting temperature of the probe may be calculated using the following formulas:

For probes between 14 and 70 nucleotides in length the melting temperature (Tm) is calculated using the formula: Tm=81.5+16.6 (log [Na+])+0.41 (fraction G+C)−(600/N) where N is the length of the probe.

If the hybridization is carried out in a solution containing formamide, the melting temperature may be calculated using the equation: Tm=81.5+16.6 (log [Na+])+0.41 (fraction G+C)−(0.63% formamide)−(600/N) where N is the length of the probe.

Prehybridization may be carried out in 6×SSC, 5×Denhardt's reagent, 0.5% SDS, 100 µg denatured fragmented salmon sperm DNA or 6×SSC, 5×Denhardt's reagent, 0.5% SDS, 100 µg denatured fragmented salmon sperm DNA, 50% formamide. The formulas for SSC and Denhardt's solutions are listed in Sambrook et al., supra.

Hybridization is conducted by adding the detectable probe to the prehybridization solutions listed above. Where the probe comprises double stranded DNA, it is denatured before addition to the hybridization solution. The filter is contacted with the hybridization solution for a sufficient period of time to allow the probe to hybridize to cDNAs or genomic DNAs containing sequences complementary thereto or homologous thereto. For probes over 200 nucleotides in length, the hybridization may be carried out at 15-25° C. below the Tm. For shorter probes, such as oligonucleotide probes, the hybridization may be conducted at 5-10° C. below the Tm. Typically, for hybridizations in 6×SSC, the hybridization is conducted at approximately 68° C. Usually, for hybridizations in 50% formamide containing solutions, the hybridization is conducted at approximately 42° C.

All of the foregoing hybridizations would be considered to be under conditions of high stringency.

Following hybridization, the filter is washed to remove any non-specifically bound detectable probe. The stringency used to wash the filters can also be varied depending on the nature of the nucleic acids being hybridized, the length of the nucleic acids being hybridized, the degree of complementarity, the nucleotide sequence composition (e.g., GC v. AT content), and the nucleic acid type (e.g., RNA v. DNA). Examples of progressively higher stringency condition washes are as follows: 2×SSC, 0.1% SDS at room temperature for 15 minutes (low stringency); 0.1×SSC, 0.5% SDS at room temperature for 30 minutes to 1 hour (moderate stringency); 0.1×SSC, 0.5% SDS for 15 to 30 minutes at between the hybridization temperature and 68° C. (high stringency); and 0.15M NaCl for 15 minutes at 72° C. (very high stringency). A final low stringency wash can be conducted in 0.1×SSC at room temperature. The examples above are merely illustrative of one set of conditions that can be used to wash filters. One of skill in the art would know that there are numerous recipes for different stringency washes. Some other examples are given below.

Nucleic acids which have hybridized to the probe are identified by autoradiography or other conventional techniques.

The above procedure may be modified to identify nucleic acids having decreasing levels of homology to the probe sequence. For example, to obtain nucleic acids of decreasing homology to the detectable probe, less stringent conditions may be used. For example, the hybridization temperature may be decreased in increments of 5° C. from 68° C. to 42° C. in a hybridization buffer having a Na+ concentration of approximately 1M. Following hybridization, the filter may be washed with 2×SSC, 0.5% SDS at the temperature of hybridization. These conditions are considered to be "moderate" conditions above 50° C. and "low" conditions below 50° C. A specific example of "moderate" hybridization conditions is when the above hybridization is conducted at 55° C. A specific example of "low stringency" hybridization conditions is when the above hybridization is conducted at 45° C.

Alternatively, the hybridization may be carried out in buffers, such as 6×SSC, containing formamide at a temperature of 42° C. In this case, the concentration of formamide in the hybridization buffer may be reduced in 5% increments from 50% to 0% to identify clones having decreasing levels of homology to the probe. Following hybridization, the filter may be washed with 6×SSC, 0.5% SDS at 50° C. These conditions are considered to be "moderate" conditions above 25% formamide and "low" conditions below 25% formamide. A specific example of "moderate" hybridization conditions is when the above hybridization is conducted at 30% formamide. A specific example of "low stringency" hybridization conditions is when the above hybridization is conducted at 10% formamide.

For example, the preceding methods may be used to isolate nucleic acids having a sequence with at least about 97%, at least 95%, at least 90%, at least 85%, at least 80%, at least 70%, at least 65%, at least 60%, at least 55%, or at least 50% homology to a nucleic acid sequence selected from the group consisting of one of the sequences of Group A nucleic acid sequences, and sequences substantially identical thereto, or fragments comprising at least about 10, 15, 20, 25, 30, 35, 40, 50, 75, 100, 150, 200, 300, 400, or 500 consecutive bases thereof, and the sequences complementary thereto. Homology may be measured using the alignment algorithm. For example, the homologous polynucleotides may have a coding sequence which is a naturally occurring allelic variant of one of the coding sequences described herein. Such allelic variants may have a substitution, deletion or addition of one or more nucleotides when compared to the nucleic acids of Group A nucleic acid sequences or the sequences complementary thereto.

Additionally, the above procedures may be used to isolate nucleic acids which encode polypeptides having at least about 99%, 95%, at least 90%, at least 85%, at least 80%, at least 75%, at least 70%, at least 65%, at least 60%, at least 55%, or at least 50% homology to a polypeptide having the sequence of one of Group B amino acid sequences, and sequences substantially identical thereto, or fragments comprising at least 5, 10, 15, 20, 25, 30, 35, 40, 50, 75, 100, or 150 consecutive amino acids thereof as determined using a sequence alignment algorithm (e.g., such as the FASTA version 3.0t78 algorithm with the default parameters).

Another aspect of the invention is an isolated or purified polypeptide comprising the sequence of one of Group A nucleic acid sequences, and sequences substantially identical thereto, or fragments comprising at least about 5, 10, 15, 20, 25, 30, 35, 40, 50, 75, 100, or 150 consecutive amino acids thereof. As discussed above, such polypeptides may be obtained by inserting a nucleic acid encoding the polypeptide into a vector such that the coding sequence is operably linked to a sequence capable of driving the expression of the encoded polypeptide in a suitable host cell. For example, the expression vector may comprise a promoter, a ribosome binding site for translation initiation and a transcription terminator. The vector may also include appropriate sequences for amplifying expression.

Promoters suitable for expressing the polypeptide or fragment thereof in bacteria include the E. coli lac or trp promoters, the lacI promoter, the lacZ promoter, the T3 promoter, the T7 promoter, the gpt promoter, the lambda $P_R$ promoter, the lambda $P_L$ promoter, promoters from operons encoding glycolytic enzymes such as 3-phosphoglycerate kinase (PGK), and the acid phosphatase promoter. Fungal promoters include the V factor promoter. Eukaryotic promoters include the CMV immediate early promoter, the HSV thymidine kinase promoter, heat shock promoters, the early and late SV40 promoter, LTRs from retroviruses, and the mouse metallothionein-I promoter. Other promoters known to control expression of genes in prokaryotic or eukaryotic cells or their viruses may also be used.

Mammalian expression vectors may also comprise an origin of replication, any necessary ribosome binding sites, a polyadenylation site, splice donor and acceptor sites, transcriptional termination sequences, and 5' flanking non-transcribed sequences. In some embodiments, DNA sequences derived from the SV40 splice and polyadenylation sites may be used to provide the required nontranscribed genetic elements.

Vectors for expressing the polypeptide or fragment thereof in eukaryotic cells may also contain enhancers to increase expression levels. Enhancers are cis-acting elements of DNA, usually from about 10 to about 300 bp in length that act on a promoter to increase its transcription. Examples include the SV40 enhancer on the late side of the replication origin by 100 to 270, the cytomegalovirus early promoter enhancer, the polyoma enhancer on the late side of the replication origin, and the adenovirus enhancers.

In addition, the expression vectors typically contain one or more selectable marker genes to permit selection of host cells containing the vector. Such selectable markers include genes encoding dihydrofolate reductase or genes conferring neomycin resistance for eukaryotic cell culture, genes conferring tetracycline or ampicillin resistance in E. coli, and the S. cerevisiae TRP1 gene.

In some embodiments, the nucleic acid encoding one of the polypeptides of Group B amino acid sequences, and sequences substantially identical thereto, or fragments comprising at least about 5, 10, 15, 20, 25, 30, 35, 40, 50, 75, 100, or 150 consecutive amino acids thereof is assembled in appropriate phase with a leader sequence capable of directing secretion of the translated polypeptide or fragment thereof. Optionally, the nucleic acid can encode a fusion polypeptide in which one of the polypeptides of Group B amino acid sequences, and sequences substantially identical thereto, or fragments comprising at least 5, 10, 15, 20, 25, 30, 35, 40, 50, 75, 100, or 150 consecutive amino acids thereof is fused to heterologous peptides or polypeptides, such as N-terminal identification peptides which impart desired characteristics, such as increased stability or simplified purification.

The appropriate DNA sequence may be inserted into the vector by a variety of procedures. In general, the DNA sequence is ligated to the desired position in the vector following digestion of the insert and the vector with appropriate restriction endonucleases. Alternatively, blunt ends in both the insert and the vector may be ligated. A variety of cloning techniques are disclosed in Ausubel et al. Current Protocols in Molecular Biology, John Wiley 503 Sons, Inc. 1997 and Sambrook et al., Molecular Cloning: A Laboratory Manual 2nd Ed., Cold Spring Harbor Laboratory Press (1989), the entire disclosures of which are incorporated herein by reference. Such procedures and others are deemed to be within the scope of those skilled in the art.

The vector may be, for example, in the form of a plasmid, a viral particle, or a phage. Other vectors include chromosomal, nonchromosomal and synthetic DNA sequences, derivatives of SV40; bacterial plasmids, phage DNA, baculovirus, yeast plasmids, vectors derived from combinations of plasmids and phage DNA, viral DNA such as vaccinia, adenovirus, fowl pox virus, and pseudorabies. A variety of cloning and expression vectors for use with prokaryotic and eukaryotic hosts are described by Sambrook, et al., Molecular Cloning: A Laboratory Manual, 2nd Ed., Cold Spring Harbor, N.Y., (1989), the disclosure of which is hereby incorporated by reference.

Particular bacterial vectors which may be used include the commercially available plasmids comprising genetic elements of the well known cloning vector pBR322 (ATCC 37017), pKK223-3 (Pharmacia Fine Chemicals, Uppsala, Sweden), GEM1 (Promega Biotec, Madison, Wis., USA) pQE70, pQE60, pQE-9 (Qiagen), pD10, psiX174 pBluescript II KS, pNH8A, pNH16a, pNH18A, pNH46A (Stratagene), ptrc99a, pKK223-3, pKK233-3, pDR540, pRIT5 (Pharmacia), pKK232-8 and pCM7. Particular eukaryotic vectors include pSV2CAT, pOG44, pXT1, pSG (Stratagene) pSVK3, pBPV, pMSG, and pSVL (Pharmacia). However, any other vector may be used as long as it is replicable and viable in the host cell.

The host cell may be any of the host cells familiar to those skilled in the art, including prokaryotic cells, eukaryotic cells, mammalian cells, insect cells, or plant cells. As representative examples of appropriate hosts, there may be mentioned: bacterial cells, such as *E. coli, Streptomyces, Bacillus subtilis, Salmonella typhimurium* and various species within the genera *Pseudomonas, Streptomyces*, and *Staphylococcus*, fungal cells, such as yeast, insect cells such as *Drosophila* S2 and *Spodoptera* Sf9, animal cells such as CHO, COS or Bowes melanoma, and adenoviruses. The selection of an appropriate host is within the abilities of those skilled in the art.

The vector may be introduced into the host cells using any of a variety of techniques, including transformation, transfection, transduction, viral infection, gene guns, or Ti-mediated gene transfer. Particular methods include calcium phosphate transfection, DEAE-Dextran mediated transfection, lipofection, or electroporation (Davis, L., Dibner, M., Battey, I., Basic Methods in Molecular Biology, (1986)).

Where appropriate, the engineered host cells can be cultured in conventional nutrient media modified as appropriate for activating promoters, selecting transformants or amplifying the genes of the invention. Following transformation of a suitable host strain and growth of the host strain to an appropriate cell density, the selected promoter may be induced by appropriate means (e.g., temperature shift or chemical induction) and the cells may be cultured for an additional period to allow them to produce the desired polypeptide or fragment thereof.

Cells are typically harvested by centrifugation, disrupted by physical or chemical means, and the resulting crude extract is retained for further purification. Microbial cells employed for expression of proteins can be disrupted by any convenient method, including freeze-thaw cycling, sonication, mechanical disruption, or use of cell lysing agents. Such methods are well known to those skilled in the art. The expressed polypeptide or fragment thereof can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the polypeptide. If desired, high performance liquid chromatography (HPLC) can be employed for final purification steps.

Various mammalian cell culture systems can also be employed to express recombinant protein. Examples of mammalian expression systems include the COS-7 lines of monkey kidney fibroblasts (described by Gluzman, Cell, 23:175, 1981), and other cell lines capable of expressing proteins from a compatible vector, such as the C127, 3T3, CHO, HeLa and BHK cell lines.

The constructs in host cells can be used in a conventional manner to produce the gene product encoded by the recombinant sequence. Depending upon the host employed in a recombinant production procedure, the polypeptides produced by host cells containing the vector may be glycosylated or may be non-glycosylated. Polypeptides of the invention may or may not also include an initial methionine amino acid residue.

Alternatively, the polypeptides of Group B amino acid sequences, and sequences substantially identical thereto, or fragments comprising at least 5, 10, 15, 20, 25, 30, 35, 40, 50, 75, 100, or 150 consecutive amino acids thereof can be synthetically produced by conventional peptide synthesizers. In other embodiments, fragments or portions of the polypeptides may be employed for producing the corresponding full-length polypeptide by peptide synthesis; therefore, the fragments may be employed as intermediates for producing the full-length polypeptides.

Cell-free translation systems can also be employed to produce one of the polypeptides of Group B amino acid sequences, and sequences substantially identical thereto, or fragments comprising at least 5, 10, 15, 20, 25, 30, 35, 40, 50, 75, 100, or 150 consecutive amino acids thereof using mRNAs transcribed from a DNA construct comprising a promoter operably linked to a nucleic acid encoding the polypeptide or fragment thereof. In some embodiments, the DNA construct may be linearized prior to conducting an in vitro transcription reaction. The transcribed mRNA is then incubated with an appropriate cell-free translation extract, such as a rabbit reticulocyte extract, to produce the desired polypeptide or fragment thereof.

The invention also relates to variants of the polypeptides of Group B amino acid sequences, and sequences substantially identical thereto, or fragments comprising at least 5, 10, 15, 20, 25, 30, 35, 40, 50, 75, 100, or 150 consecutive amino acids thereof. The term "variant" includes derivatives or analogs of these polypeptides. In particular, the variants may differ in amino acid sequence from the polypeptides of Group B amino acid sequences, and sequences substantially identical thereto, by one or more substitutions, additions, deletions, fusions and truncations, which may be present in any combination.

The variants may be naturally occurring or created in vitro. In particular, such variants may be created using genetic engineering techniques such as site directed mutagenesis, random chemical mutagenesis, Exonuclease III deletion procedures, and standard cloning techniques. Alternatively, such variants, fragments, analogs, or derivatives may be created using chemical synthesis or modification procedures.

Other methods of making variants are also familiar to those skilled in the art. These include procedures in which nucleic acid sequences obtained from natural isolates are modified to generate nucleic acids which encode polypeptides having characteristics which enhance their value in industrial or laboratory applications. In such procedures, a large number of variant sequences having one or more nucleotide differences with respect to the sequence obtained from the natural isolate are generated and characterized. Typically, these nucleotide differences result in amino acid changes with respect to the polypeptides encoded by the nucleic acids from the natural isolates.

For example, variants may be created using error prone PCR. In error prone PCR, PCR is performed under conditions where the copying fidelity of the DNA polymerase is low, such that a high rate of point mutations is obtained along the entire length of the PCR product. Error prone PCR is described in Leung, D. W., et al., Technique, 1:11-15, 1989) and Caldwell, R. C. & Joyce G. F., PCR Methods Applic., 2:28-33, 1992, the disclosure of which is incorporated herein by reference in its entirety. Briefly, in such procedures, nucleic acids to be mutagenized are mixed with PCR primers, reaction buffer, MgCl2, MnCl2, Taq polymerase and an appropriate concentration of dNTPs for achieving a high rate of point mutation along the entire length of the PCR product. For example, the reaction may be performed using 20 fmoles of nucleic acid to be mutagenized, 30 pmole of each PCR primer, a reaction buffer comprising 50 mM KCl, 10 mM Tris HCl (pH 8.3) and 0.01% gelatin, 7 mM MgCl2, 0.5 mM MnCl2, 5 units of Taq polymerase, 0.2 mM dGTP, 0.2 mM dATP, 1 mM dCTP, and 1 mM dTTP. PCR may be performed for 30 cycles of 94° C. for 1 min, 45° C. for 1 min, and 72° C. for 1 min. However, it will be appreciated that these parameters may be varied as appropriate. The mutagenized nucleic acids are cloned into an appropriate vector and the activities of the polypeptides encoded by the mutagenized nucleic acids is evaluated.

Variants may also be created using oligonucleotide directed mutagenesis to generate site-specific mutations in any cloned DNA of interest. Oligonucleotide mutagenesis is described in Reidhaar-Olson, J. F. & Sauer, R. T., et al., Science, 241:53-57, 1988, the disclosure of which is incorporated herein by reference in its entirety. Briefly, in such procedures a plurality of double stranded oligonucleotides bearing one or more mutations to be introduced into the cloned DNA are synthesized and inserted into the cloned DNA to be mutagenized. Clones containing the mutagenized DNA are recovered and the activities of the polypeptides they encode are assessed.

Another method for generating variants is assembly PCR. Assembly PCR involves the assembly of a PCR product from a mixture of small DNA fragments. A large number of different PCR reactions occur in parallel in the same vial, with the products of one reaction priming the products of another reaction. Assembly PCR is described in U.S. Pat. No. 5,965,408, filed Jul. 9, 1996, entitled, "Method of DNA Reassembly by Interrupting Synthesis", the disclosure of which is incorporated herein by reference in its entirety.

Still another method of generating variants is sexual PCR mutagenesis. In sexual PCR mutagenesis, forced homologous recombination occurs between DNA molecules of different but highly related DNA sequence in vitro, as a result of random fragmentation of the DNA molecule based on sequence homology, followed by fixation of the crossover by primer extension in a PCR reaction. Sexual PCR mutagenesis is described in Stemmer, W. P., PNAS, USA, 91:10747-10751, 1994, the disclosure of which is incorporated herein by reference. Briefly, in such procedures a plurality of nucleic acids to be recombined are digested with DNAse to generate fragments having an average size of 50-200 nucleotides. Fragments of the desired average size are purified and resuspended in a PCR mixture. PCR is conducted under conditions which facilitate recombination between the nucleic acid fragments. For example, PCR may be performed by resuspending the purified fragments at a concentration of 10-30 ng/:1 in a solution of 0.2 mM of each dNTP, 2.2 mM MgCl2, 50 mM KCL, 10 mM Tris HCl, pH 9.0, and 0.1% Triton X-100. 2.5 units of Taq polymerase per 100:1 of reaction mixture is added and PCR is performed using the following regime: 94° C. for 60 seconds, 94° C. for 30 seconds, 50-55° C. for 30 seconds, 72° C. for 30 seconds (30-45 times) and 72° C. for 5 minutes. However, it will be appreciated that these parameters may be varied as appropriate. In some embodiments, oligonucleotides may be included in the PCR reactions. In other embodiments, the Klenow fragment of DNA polymerase I may be used in a first set of PCR reactions and Taq polymerase may be used in a subsequent set of PCR reactions. Recombinant sequences are isolated and the activities of the polypeptides they encode are assessed.

Variants may also be created by in vivo mutagenesis. In some embodiments, random mutations in a sequence of interest are generated by propagating the sequence of interest in a bacterial strain, such as an *E. coli* strain, which carries mutations in one or more of the DNA repair pathways. Such "mutator" strains have a higher random mutation rate than that of a wild-type parent. Propagating the DNA in one of these strains will eventually generate random mutations within the DNA. Mutator strains suitable for use for in vivo mutagenesis are described in PCT Publication No. WO 91/16427, published Oct. 31, 1991, entitled "Methods for Phenotype Creation from Multiple Gene Populations" the disclosure of which is incorporated herein by reference in its entirety.

Variants may also be generated using cassette mutagenesis. In cassette mutagenesis a small region of a double stranded DNA molecule is replaced with a synthetic oligonucleotide "cassette" that differs from the native sequence. The oligonucleotide often contains completely and/or partially randomized native sequence.

Recursive ensemble mutagenesis may also be used to generate variants. Recursive ensemble mutagenesis is an algorithm for protein engineering (protein mutagenesis) developed to produce diverse populations of phenotypically related mutants whose members differ in amino acid sequence. This method uses a feedback mechanism to control successive rounds of combinatorial cassette mutagenesis. Recursive ensemble mutagenesis is described in Arkin, A. P. and Youvan, D. C., PNAS, USA, 89:7811-7815, 1992, the disclosure of which is incorporated herein by reference in its entirety.

In some embodiments, variants are created using exponential ensemble mutagenesis. Exponential ensemble mutagenesis is a process for generating combinatorial libraries with a high percentage of unique and functional mutants, wherein small groups of residues are randomized in parallel to identify, at each altered position, amino acids which lead to functional proteins. Exponential ensemble mutagenesis is described in Delegrave, S. and Youvan, D. C., Biotechnology Research, 11:1548-1552, 1993, the disclosure of which incorporated herein by reference in its entirety. Random and site-directed mutagenesis are described in Arnold, F. H., Current Opinion in Biotechnology, 4:450-455, 1993, the disclosure of which is incorporated herein by reference in its entirety.

In some embodiments, the variants are created using shuffling procedures wherein portions of a plurality of nucleic acids which encode distinct polypeptides are fused together to create chimeric nucleic acid sequences which encode chimeric polypeptides as described in U.S. Pat. No. 5,965,408, filed Jul. 9, 1996, entitled, "Method of DNA Reassembly by Interrupting Synthesis", and U.S. Pat. No. 5,939,250, filed May 22, 1996, entitled, "Production of Enzymes Having Desired Activities by Mutagenesis", both of which are incorporated herein by reference.

The variants of the polypeptides of Group B amino acid sequences may be variants in which one or more of the amino acid residues of the polypeptides of the Group B amino acid sequences are substituted with a conserved or non-conserved amino acid residue (preferably a conserved amino acid residue) and such substituted amino acid residue may or may not be one encoded by the genetic code.

Conservative substitutions are those that substitute a given amino acid in a polypeptide by another amino acid of like characteristics. Typically seen as conservative substitutions are the following replacements: replacements of an aliphatic amino acid such as Alanine, Valine, Leucine and Isoleucine with another aliphatic amino acid; replacement of a Serine with a Threonine or vice versa; replacement of an acidic residue such as Aspartic acid and Glutamic acid with another acidic residue; replacement of a residue bearing an amide group, such as Asparagine and Glutamine, with another residue bearing an amide group; exchange of a basic residue such as Lysine and Arginine with another basic residue; and replacement of an aromatic residue such as Phenylalanine, Tyrosine with another aromatic residue.

Other variants are those in which one or more of the amino acid residues of the polypeptides of the Group B amino acid sequences includes a substituent group.

Still other variants are those in which the polypeptide is associated with another compound, such as a compound to increase the half-life of the polypeptide (for example, polyethylene glycol).

Additional variants are those in which additional amino acids are fused to the polypeptide, such as a leader sequence, a secretory sequence, a proprotein sequence or a sequence which facilitates purification, enrichment, or stabilization of the polypeptide.

In some embodiments, the fragments, derivatives and analogs retain the same biological function or activity as the polypeptides of Group B amino acid sequences, and sequences substantially identical thereto. In other embodiments, the fragment, derivative, or analog includes a proprotein, such that the fragment, derivative, or analog can be activated by cleavage of the proprotein portion to produce an active polypeptide.

Another aspect of the invention is polypeptides or fragments thereof which have at least about 50%, at least about 55%, at least about 60%, at least about 65%, at least about 70%, at least about 75%, at least about 80%, at least about 85%, at least about 90%, at least about 95%, or more than about 95% homology to one of the polypeptides of Group B amino acid sequences, and sequences substantially identical thereto, or a fragment comprising at least 5, 10, 15, 20, 25, 30, 35, 40, 50, 75, 100, or 150 consecutive amino acids thereof. Homology may be determined using any of the programs described above which aligns the polypeptides or fragments being compared and determines the extent of amino acid identity or similarity between them. It will be appreciated that amino acid "homology" includes conservative amino acid substitutions such as those described above.

The polypeptides or fragments having homology to one of the polypeptides of Group B amino acid sequences, and sequences substantially identical thereto, or a fragment comprising at least about 5, 10, 15, 20, 25, 30, 35, 40, 50, 75, 100, or 150 consecutive amino acids thereof may be obtained by isolating the nucleic acids encoding them using the techniques described above.

Alternatively, the homologous polypeptides or fragments may be obtained through biochemical enrichment or purification procedures. The sequence of potentially homologous polypeptides or fragments may be determined by proteolytic digestion, gel electrophoresis and/or microsequencing. The sequence of the prospective homologous polypeptide or fragment can be compared to one of the polypeptides of Group B amino acid sequences, and sequences substantially identical thereto, or a fragment comprising at least about 5, 10, 15, 20, 25, 30, 35, 40, 50, 75, 100, or 150 consecutive amino acids thereof using any of the programs described above.

Another aspect of the invention is an assay for identifying fragments or variants of Group B amino acid sequences, and sequences substantially identical thereto, which retain the enzymatic function of the polypeptides of Group B amino acid sequences, and sequences substantially identical thereto. For example the fragments or variants of said polypeptides, may be used to catalyze biochemical reactions, which indicate that the fragment or variant retains the enzymatic activity of the polypeptides in the Group B amino acid sequences.

The assay for determining if fragments of variants retain the enzymatic activity of the polypeptides of Group B amino acid sequences, and sequences substantially identical thereto includes the steps of: contacting the polypeptide fragment or variant with a substrate molecule under conditions which allow the polypeptide fragment or variant to function, and detecting either a decrease in the level of substrate or an increase in the level of the specific reaction product of the reaction between the polypeptide and substrate.

The polypeptides of Group B amino acid sequences, and sequences substantially identical thereto or fragments comprising at least 5, 10, 15, 20, 25, 30, 35, 40, 50, 75, 100, or 150 consecutive amino acids thereof may be used in a variety of applications. For example, the polypeptides or fragments thereof may be used to catalyze biochemical reactions. In accordance with one aspect of the invention, there is provided a process for utilizing the polypeptides of Group B amino acid sequences, and sequences substantially identical thereto or polynucleotides encoding such polypeptides for hydrolyzing glycosidic linkages. In such procedures, a substance containing a glycosidic linkage (e.g., a starch) is contacted with one of the polypeptides of Group B amino acid sequences, or sequences substantially identical thereto under conditions which facilitate the hydrolysis of the glycosidic linkage.

The polypeptides of Group B amino acid sequences, and sequences substantially identical thereto or fragments comprising at least 5, 10, 15, 20, 25, 30, 35, 40, 50, 75, 100, or 150 consecutive amino acids thereof, may also be used in the liquefaction and saccharification of starch. Using the polypeptides or fragments thereof of this invention, liquefaction may be carried out at a lower pH than with previous enzymes. In one embodiment, liquefaction is performed at a pH of 4.5. Additionally, the polypeptides or fragments thereof of this invention are less calcium dependent than enzymes previously used in these processes. In liquefaction amylases are used to hydrolyze starch. In a preferred embodiment, the polypeptides or fragments thereof of this invention are thermostable at 90-95° C.

The polypeptides of Group B amino acid sequences, and sequences substantially identical thereto or fragments comprising at least 5, 10, 15, 20, 25, 30, 35, 40, 50, 75, 100, or 150 consecutive amino acids thereof, may also be used to generate antibodies which bind specifically to the polypeptides or fragments. The resulting antibodies may be used in immunoaffinity chromatography procedures to isolate or purify the polypeptide or to determine whether the polypeptide is present in a biological sample. In such procedures, a protein preparation, such as an extract, or a biological sample is contacted with an antibody capable of specifically binding to one of the polypeptides of Group B amino acid sequences, and sequences substantially identical thereto, or fragments comprising at least 5, 10, 15, 20, 25, 30, 35, 40, 50, 75, 100, or 150 consecutive amino acids thereof.

In immunoaffinity procedures, the antibody is attached to a solid support, such as a bead or other column matrix. The protein preparation is placed in contact with the antibody under conditions in which the antibody specifically binds to one of the polypeptides of Group B amino acid sequences, and sequences substantially identical thereto, or fragment thereof. After a wash to remove non-specifically bound proteins, the specifically bound polypeptides are eluted.

The ability of proteins in a biological sample to bind to the antibody may be determined using any of a variety of procedures familiar to those skilled in the art. For example, binding may be determined by labeling the antibody with a detectable label such as a fluorescent agent, an enzymatic label, or a radioisotope. Alternatively, binding of the antibody to the sample may be detected using a secondary antibody having such a detectable label thereon. Particular assays include ELISA assays, sandwich assays, radioimmunoassays, and Western Blots.

Polyclonal antibodies generated against the polypeptides of Group B amino acid sequences, and sequences substantially identical thereto, or fragments comprising at least 5, 10, 15, 20, 25, 30, 35, 40, 50, 75, 100, or 150 consecutive amino acids thereof can be obtained by direct injection of the polypeptides into an animal or by administering the polypeptides to an animal, for example, a nonhuman. The antibody so obtained will then bind the polypeptide itself. In this manner, even a sequence encoding only a fragment of the polypeptide can be used to generate antibodies which may bind to the whole native polypeptide. Such antibodies can then be used to isolate the polypeptide from cells expressing that polypeptide.

For preparation of monoclonal antibodies, any technique which provides antibodies produced by continuous cell line cultures can be used. Examples include the hybridoma technique (Kohler and Milstein, Nature, 256:495-497, 1975, the disclosure of which is incorporated herein by reference), the trioma technique, the human B-cell hybridoma technique (Kozbor et al., Immunology Today 4:72, 1983, the disclosure of which is incorporated herein by reference), and the EBV-hybridoma technique (Cole, et al., 1985, in Monoclonal Antibodies and Cancer Therapy, Alan R. Liss, Inc., pp. 77-96, the disclosure of which is incorporated herein by reference).

Techniques described for the production of single chain antibodies (U.S. Pat. No. 4,946,778, the disclosure of which is incorporated herein by reference) can be adapted to produce single chain antibodies to the polypeptides of Group B amino acid sequences, and sequences substantially identical thereto, or fragments comprising at least 5, 10, 15, 20, 25, 30, 35, 40, 50, 75, 100, or 150 consecutive amino acids thereof. Alternatively, transgenic mice may be used to express humanized antibodies to these polypeptides or fragments thereof.

Antibodies generated against the polypeptides of Group B amino acid sequences, and sequences substantially identical thereto, or fragments comprising at least 5, 10, 15, 20, 25, 30, 35, 40, 50, 75, 100, or 150 consecutive amino acids thereof may be used in screening for similar polypeptides from other organisms and samples. In such techniques, polypeptides from the organism are contacted with the antibody and those polypeptides which specifically bind the antibody are detected. Any of the procedures described above may be used to detect antibody binding. One such screening assay is described in "Methods for Measuring Cellulase Activities", Methods in Enzymology, Vol 160, pp. 87-116, which is hereby incorporated by reference in its entirety.

As used herein the term "nucleic acid sequence as set forth in SEQ ID Nos.: 1, 3, 5, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299" encompasses the nucleotide sequences of Group A nucleic acid sequences, and sequences substantially identical thereto, as well as sequences homologous to Group A nucleic acid sequences, and fragments thereof and sequences complementary to all of the preceding sequences. The fragments include portions of SEQ ID Nos.: 1, 3, 5, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, and 299, comprising at least 10, 15, 20, 25, 30, 35, 40, 50, 75, 100, 150, 200, 300, 400, or 500 consecutive nucleotides of Group A nucleic acid sequences, and sequences substantially identical thereto. Homologous sequences and fragments of Group A nucleic acid sequences, and sequences substantially identical thereto, refer to a sequence having at least 99%, 98%, 97%, 96%, 95%, 90%, 85%, 80%, 75%, 70%, 65%, 60%, 55% or 50% homology to these sequences. Homology may be determined using any of the computer programs and parameters described herein, including FASTA version 3.0t78 with the default parameters. Homologous sequences also include RNA sequences in which uridines replace the thymines in the nucleic acid sequences as set forth in the Group A nucleic acid sequences. The homologous sequences may be obtained using any of the procedures described herein or may result from the correction of a sequencing error. It will be appreciated that the nucleic acid sequences as set forth in Group A nucleic acid sequences, and sequences substantially identical thereto, can be represented in the traditional single character format (See the inside back cover of Stryer, Lubert. Biochemistry, 3rd Ed., W. H Freeman & Co., New York) or in any other format which records the identity of the nucleotides in a sequence.

As used herein the term "a polypeptide sequence as set forth in SEQ ID Nos: 2, 4, 6, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298" encompasses the polypeptide sequence of Group B amino acid sequences, and sequences substantially identical thereto, which are encoded by a sequence as set forth in SEQ ID Nos: 2, 4, 6, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, polypeptide sequences homologous to the polypeptides of Group B amino acid sequences, and sequences substantially identical thereto, or fragments of any of the preceding sequences. Homologous polypeptide sequences refer to a polypeptide sequence having at least 99%, 98%, 97%, 96%, 95%, 90%, 85%, 80%, 75%, 70%, 65%, 60%, 55% or 50% homology to one of the polypeptide sequences of the Group B amino acid sequences. Homology may be determined using any of the computer programs and parameters described herein, including FASTA version 3.0t78 with the default parameters or with any modified parameters. The homologous sequences may be obtained using any of the procedures described herein or may result from the correction of a sequencing error. The polypeptide fragments comprise at least 5, 10, 15, 20, 25, 30, 35, 40, 50, 75, 100, or 150 consecutive amino acids of the polypeptides of Group B amino acid sequences, and sequences substantially identical thereto. It will be appreciated that the polypeptide codes as set forth in Group B amino acid sequences, and sequences substantially identical thereto, can be represented in the traditional single character format or three letter format (See the inside back cover of Stryer, Lubert. Biochemistry, 3rd Ed., W. H Freeman & Co., New York) or in any other format which relates the identity of the polypeptides in a sequence.

It will be appreciated by those skilled in the art that a nucleic acid sequence as set forth in SEQ ID No.s: 1, 3, 5, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299 and a polypeptide sequence as set forth in SEQ ID No.s: 2, 4, 6, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298 can be stored, recorded, and manipulated on any medium which can be read and accessed by a computer. As used herein, the words "recorded" and "stored" refer to a process for storing information on a computer medium. A skilled artisan can readily adopt any of the presently known methods for recording information on a computer readable medium to generate manufactures comprising one or more of the nucleic acid sequences as set forth in Group A nucleic acid sequences, and sequences substantially identical thereto, one or more of the polypeptide sequences as set forth in Group B amino acid sequences, and sequences substantially identical thereto. Another aspect of the invention is a computer readable medium having recorded thereon at least 2, 5, 10, 15, or 20 nucleic acid sequences as set forth in Group A nucleic acid sequences, and sequences substantially identical thereto.

Another aspect of the invention is a computer readable medium having recorded thereon one or more of the nucleic acid sequences as set forth in Group A nucleic acid sequences, and sequences substantially identical thereto. Another aspect of the invention is a computer readable medium having recorded thereon one or more of the polypeptide sequences as set forth in Group B amino acid sequences, and sequences substantially identical thereto. Another aspect of the invention is a computer readable medium having recorded thereon at least 2, 5, 10, 15, or 20 of the sequences as set forth above.

Computer readable media include magnetically readable media, optically readable media, electronically readable media and magnetic/optical media. For example, the computer readable media may be a hard disk, a floppy disk, a magnetic tape, CD-ROM, Digital Versatile Disk (DVD), Random Access Memory (RAM), or Read Only Memory (ROM) as well as other types of other media known to those skilled in the art.

Embodiments of the invention include systems (e.g., internet based systems), particularly computer systems which store and manipulate the sequence information described herein. One example of a computer is illustrated in block diagram form in FIG. 1. As used herein, "a computer system" refers to the hardware components, software components, and data storage components used to analyze a nucleotide sequence of a nucleic acid sequence as set forth in Group A nucleic acid sequences, and sequences substantially identical thereto, or a polypeptide sequence as set forth in the Group B amino acid sequences. The computer system 100 typically includes a processor for processing, accessing and manipulating the sequence data. The processor 105 can be any well-known type of central processing unit, such as, for example, the Pentium III from Intel Corporation, or similar processor from Sun, Motorola, Compaq, AMD or International Business Machines.

Typically the computer system 100 is a general purpose system that comprises the processor 105 and one or more internal data storage components 110 for storing data, and one or more data retrieving devices for retrieving the data stored on the data storage components. A skilled artisan can readily appreciate that any one of the currently available computer systems are suitable.

In one particular embodiment, the computer system 100 includes a processor 105 connected to a bus which is connected to a main memory 115 (preferably implemented as RAM) and one or more internal data storage devices 110, such as a hard drive and/or other computer readable media having data recorded thereon. In some embodiments, the computer system 100 further includes one or more data retrieving device 118 for reading the data stored on the internal data storage devices 110.

The data retrieving device 118 may represent, for example, a floppy disk drive, a compact disk drive, a magnetic tape drive, or a modem capable of connection to a remote data storage system (e.g., via the internet) etc. In some embodiments, the internal data storage device 110 is a removable computer readable medium such as a floppy disk, a compact disk, a magnetic tape, etc. containing control logic and/or data recorded thereon. The computer system 100 may advantageously include or be programmed by appropriate software for reading the control logic and/or the data from the data storage component once inserted in the data retrieving device.

The computer system 100 includes a display 120 which is used to display output to a computer user. It should also be noted that the computer system 100 can be linked to other computer systems 125a-c in a network or wide area network to provide centralized access to the computer system 100.

Software for accessing and processing the nucleotide sequences of a nucleic acid sequence as set forth in Group A nucleic acid sequences, and sequences substantially identical thereto, or a polypeptide sequence as set forth in Group B amino acid sequences, and sequences substantially identical thereto, (such as search tools, compare tools, and modeling tools etc.) may reside in main memory 115 during execution.

In some embodiments, the computer system 100 may further comprise a sequence comparison algorithm for comparing a nucleic acid sequence as set forth in Group A nucleic acid sequences, and sequences substantially identical thereto, or a polypeptide sequence as set forth in Group B amino acid sequences, and sequences substantially identical thereto, stored on a computer readable medium to a reference nucleotide or polypeptide sequence(s) stored on a computer readable medium. A "sequence comparison algorithm" refers to one or more programs which are implemented (locally or remotely) on the computer system 100 to compare a nucleotide sequence with other nucleotide sequences and/or compounds stored within a data storage means. For example, the sequence comparison algorithm may compare the nucleotide sequences of a nucleic acid sequence as set forth in Group A nucleic acid sequences, and sequences substantially identical thereto, or a polypeptide sequence as set forth in Group B amino acid sequences, and sequences substantially identical thereto, stored on a computer readable medium to reference sequences stored on a computer readable medium to identify homologies or structural motifs. Various sequence comparison programs identified elsewhere in this patent specification are particularly contemplated for use in this aspect of the invention. Protein and/or nucleic acid sequence homologies may be evaluated using any of the variety of sequence comparison algorithms and programs known in the art. Such algorithms and programs include, but are by no means limited to, TBLASTN, BLASTP, FASTA, TFASTA, and CLUSTALW (Pearson and Lipman, Proc. Natl. Acad. Sci. USA 85(8):2444-2448, 1988; Altschul et al., J. Mol. Biol. 215(3):403-410, 1990; Thompson et al., Nucleic Acids Res. 22(2):4673-4680, 1994; Higgins et al., Methods Enzymol. 266:383-402, 1996; Altschul et al., J. Mol. Biol. 215(3):403-410, 1990; Altschul et al., Nature Genetics 3:266-272, 1993).

Homology or identity is often measured using sequence analysis software (e.g., Sequence Analysis Software Package of the Genetics Computer Group, University of Wisconsin Biotechnology Center, 1710 University Avenue, Madison, Wis. 53705). Such software matches similar sequences by assigning degrees of homology to various deletions, substitutions and other modifications. The terms "homology" and "identity" in the context of two or more nucleic acids or polypeptide sequences, refer to two or more sequences or subsequences that are the same or have a specified percentage of amino acid residues or nucleotides that are the same when compared and aligned for maximum correspondence over a comparison window or designated region as measured using any number of sequence comparison algorithms or by manual alignment and visual inspection.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequence for comparison are well-known in the art. Optimal alignment of sequences for comparison can be conducted, e.g., by the local homology algorithm of Smith & Waterman, Adv. Appl. Math. 2:482, 1981, by the homology alignment algorithm of Needleman & Wunsch, J. Mol. Biol 48:443, 1970, by the search for similarity method of person & Lipman, Proc. Nat'l. Acad. Sci. USA 85:2444, 1988, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection. Other algorithms for determining homology or identity include, for example, in addition to a BLAST program (Basic Local Alignment Search Tool at the National Center for Biological Information), ALIGN, AMAS (Analysis of Multiply Aligned Sequences), AMPS (Protein Multiple Sequence Alignment), ASSET (Aligned Segment Statistical Evaluation Tool), BANDS, BESTSCOR, BIOSCAN (Biological Sequence Comparative Analysis Node), BLIMPS (BLocks IMProved Searcher), FASTA, Intervals & Points, BMB, CLUSTAL V, CLUSTAL W, CONSENSUS, LCONSENSUS, WCONSENSUS, Smith-Waterman algorithm, DARWIN, Las Vegas algorithm, FNAT (Forced Nucleotide Alignment Tool), Framealign, Framesearch, DYNAMIC, FILTER, FSAP (Fristensky Sequence Analysis Package), GAP (Global Alignment Program), GENAL, GIBBS, GenQuest, ISSC (Sensitive Sequence Comparison), LALIGN (Local Sequence Alignment), LCP (Local Content Program), MACAW (Multiple Alignment Construction & Analysis Workbench), MAP (Multiple Alignment Program), MBLKP, MBLKN, PIMA (Pattern-Induced Multi-sequence Alignment), SAGA (Sequence Alignment by Genetic Algorithm) and WHAT-IF. Such alignment programs can also be used to screen genome databases to identify polynucleotide sequences having substantially identical sequences. A number of genome databases are available, for example, a substantial portion of the human genome is available as part of the Human Genome Sequencing Project (J. Roach, http://weber.u.Washington.edu/~roach/human_genome_progress 2.html) (Gibbs, 1995). At least twenty-one other genomes have already been sequenced, including, for example, *M. genitalium* (Fraser et al., 1995), *M. jannaschii* (Bult et al., 1996), *H. influenzae* (Fleischmann et al., 1995), *E. coli* (Blattner et al., 1997), and yeast (*S. cerevisiae*) (Mewes et al., 1997), and *D. melanogaster* (Adams et al., 2000). Significant progress has also been made in sequencing the genomes of model organism, such as mouse, *C. elegans*, and *Arabadopsis* sp. Several databases containing genomic information annotated with some functional information are maintained by different organization, and are accessible via the internet, for example, http://wwwtigr.org/tdb; http://www.genetics.wisc.edu; http://genome-www.stanford.edu/~ball; http://hiv-web.lanl.gov; http://www.ncbi.nlm.nih.gov; http://www.ebi.ac.uk; http://Pasteur.fr/other/biology; and http://www.genome.wi.mit.edu.

One example of a useful algorithm is BLAST and BLAST 2.0 algorithms, which are described in Altschul et al., Nuc. Acids Res. 25:3389-3402, 1977, and Altschul et al., J. Mol. Biol. 215:403-410, 1990, respectively. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectations (E) of 10, and the BLOSUM62 scoring matrix (see Henikoff & Henikoff, Proc. Natl. Acad. Sci. USA 89:10915, 1989) alignments (B) of 50, expectation (E) of 10, M=5, N=−4, and a comparison of both strands.

The BLAST algorithm also performs a statistical analysis of the similarity between two sequences (see, e.g., Karlin & Altschul, Proc. Natl. Acad. Sci. USA 90:5873, 1993). One measure of similarity provided by BLAST algorithm is the smallest sum probability (P(N)), which provides an indication of the probability by which a match between two nucleotide or amino acid sequences would occur by chance. For example, a nucleic acid is considered similar to a references sequence if the smallest sum probability in a comparison of the test nucleic acid to the reference nucleic acid is less than about 0.2, more preferably less than about 0.01, and most preferably less than about 0.001.

In one embodiment, protein and nucleic acid sequence homologies are evaluated using the Basic Local Alignment Search Tool ("BLAST") In particular, five specific BLAST programs are used to perform the following task:
(1) BLASTP and BLAST3 compare an amino acid query sequence against a protein sequence database;
(2) BLASTN compares a nucleotide query sequence against a nucleotide sequence database;
(3) BLASTX compares the six-frame conceptual translation products of a query nucleotide sequence (both strands) against a protein sequence database;
(4) TBLASTN compares a query protein sequence against a nucleotide sequence database translated in all six reading frames (both strands); and
(5) TBLASTX compares the six-frame translations of a nucleotide query sequence against the six-frame translations of a nucleotide sequence database.

The BLAST programs identify homologous sequences by identifying similar segments, which are referred to herein as "high-scoring segment pairs," between a query amino or nucleic acid sequence and a test sequence which is preferably obtained from a protein or nucleic acid sequence database. High-scoring segment pairs are preferably identified (i.e., aligned) by means of a scoring matrix, many of which are known in the art. Preferably, the scoring matrix used is the BLOSUM62 matrix (Gonnet et al., Science 256:1443-1445, 1992; Henikoff and Henikoff, Proteins 17:49-61, 1993). Less preferably, the PAM or PAM250 matrices may also be used (see, e.g., Schwartz and Dayhoff, eds., 1978, Matrices for Detecting Distance Relationships: Atlas of Protein Sequence and Structure, Washington: National Biomedical Research Foundation). BLAST programs are accessible through the U.S. National Library of Medicine, e.g., at www.ncbi.nlm.nih.gov.

The parameters used with the above algorithms may be adapted depending on the sequence length and degree of homology studied. In some embodiments, the parameters may be the default parameters used by the algorithms in the absence of instructions from the user.

Figure 2:
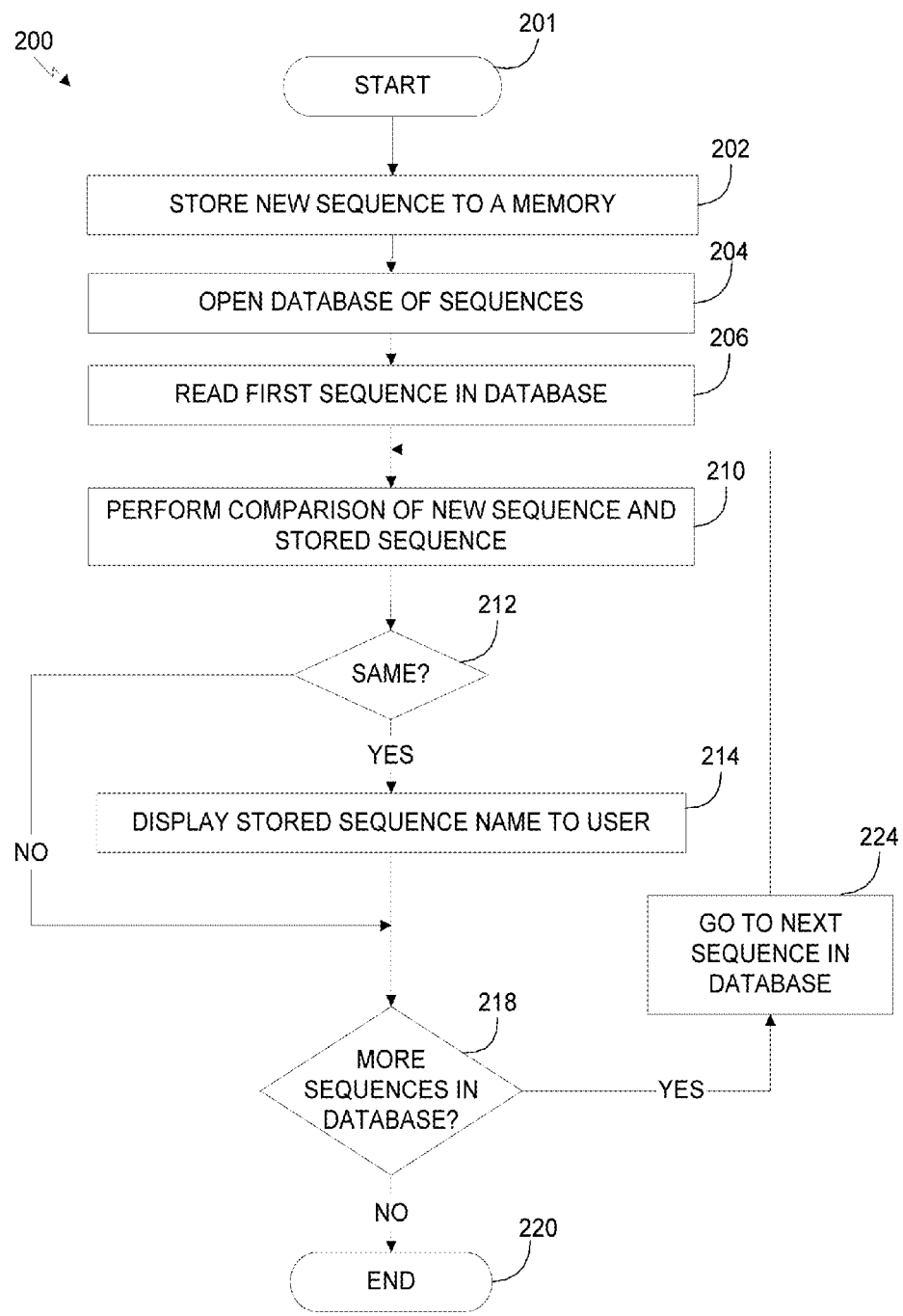
FIG. 2 is a flow diagram illustrating one embodiment of a process for comparing a new nucleotide or protein sequence with a database of sequences in order to determine the homology levels between the new sequence and the sequences in the database.

FIG. 2 is a flow diagram illustrating one embodiment of a process 200 for comparing a new nucleotide or protein sequence with a database of sequences in order to determine the homology levels between the new sequence and the sequences in the database. The database of sequences can be a private database stored within the computer system 100, or a public database such as GENBANK that is available through the Internet.

The process 200 begins at a start state 201 and then moves to a state 202 wherein the new sequence to be compared is stored to a memory in a computer system 100. As discussed above, the memory could be any type of memory, including RAM or an internal storage device.

The process 200 then moves to a state 204 wherein a database of sequences is opened for analysis and comparison. The process 200 then moves to a state 206 wherein the first sequence stored in the database is read into a memory on the computer. A comparison is then performed at a state 210 to determine if the first sequence is the same as the second sequence. It is important to note that this step is not limited to performing an exact comparison between the new sequence and the first sequence in the database. Well-known methods are known to those of skill in the art for comparing two nucleotide or protein sequences, even if they are not identical. For example, gaps can be introduced into one sequence in order to raise the homology level between the two tested sequences. The parameters that control whether gaps or other features are introduced into a sequence during comparison are normally entered by the user of the computer system.

Once a comparison of the two sequences has been performed at the state 210, a determination is made at a decision state 210 whether the two sequences are the same. Of course, the term "same" is not limited to sequences that are absolutely identical. Sequences that are within the homology parameters entered by the user will be marked as "same" in the process 200.

If a determination is made that the two sequences are the same, the process 200 moves to a state 214 wherein the name of the sequence from the database is displayed to the user. This state notifies the user that the sequence with the displayed name fulfills the homology constraints that were entered. Once the name of the stored sequence is displayed to the user, the process 200 moves to a decision state 218 wherein a determination is made whether more sequences exist in the database. If no more sequences exist in the database, then the process 200 terminates at an end state 220. However, if more sequences do exist in the database, then the process 200 moves to a state 224 wherein a pointer is moved to the next sequence in the database so that it can be compared to the new sequence. In this manner, the new sequence is aligned and compared with every sequence in the database.

It should be noted that if a determination had been made at the decision state 212 that the sequences were not homologous, then the process 200 would move immediately to the decision state 218 in order to determine if any other sequences were available in the database for comparison.

Accordingly, one aspect of the invention is a computer system comprising a processor, a data storage device having stored thereon a nucleic acid sequence as set forth in Group A nucleic acid sequences, and sequences substantially identical thereto, or a polypeptide sequence as set forth in Group B amino acid sequences, and sequences substantially identical thereto, a data storage device having retrievably stored thereon reference nucleotide sequences or polypeptide sequences to be compared to a nucleic acid sequence as set forth in Group A nucleic acid sequences, and sequences substantially identical thereto, or a polypeptide sequence as set forth in Group B amino acid sequences, and sequences substantially identical thereto, and a sequence comparer for conducting the comparison. The sequence comparer may indicate a homology level between the sequences compared or identify structural motifs in the above described nucleic acid code of Group A nucleic acid sequences, and sequences substantially identical thereto, or a polypeptide sequence as set forth in Group B amino acid sequences, and sequences substantially identical thereto, or it may identify structural motifs in sequences which are compared to these nucleic acid codes and polypeptide codes. In some embodiments, the data storage device may have stored thereon the sequences of at least 2, 5, 10, 15, 20, 25, 30 or 40 or more of the nucleic acid sequences as set forth in Group A nucleic acid sequences, and sequences substantially identical thereto, or the polypeptide sequences as set forth in Group B amino acid sequences, and sequences substantially identical thereto.

Another aspect of the invention is a method for determining the level of homology between a nucleic acid sequence as set forth in Group A nucleic acid sequences, and sequences substantially identical thereto, or a polypeptide sequence as set forth in Group B amino acid sequences, and sequences substantially identical thereto, and a reference nucleotide sequence. The method including reading the nucleic acid code or the polypeptide code and the reference nucleotide or polypeptide sequence through the use of a computer program which determines homology levels and determining homology between the nucleic acid code or polypeptide code and the reference nucleotide or polypeptide sequence with the computer program. The computer program may be any of a number of computer programs for determining homology levels, including those specifically enumerated herein, (e.g., BLAST2N with the default parameters or with any modified parameters). The method may be implemented using the computer systems described above. The method may also be performed by reading at least 2, 5, 10, 15, 20, 25, 30 or 40 or more of the above described nucleic acid sequences as set forth in the Group A nucleic acid sequences, or the polypeptide sequences as set forth in the Group B amino acid sequences through use of the computer program and determining homology between the nucleic acid codes or polypeptide codes and reference nucleotide sequences or polypeptide sequences.

Figure 3:
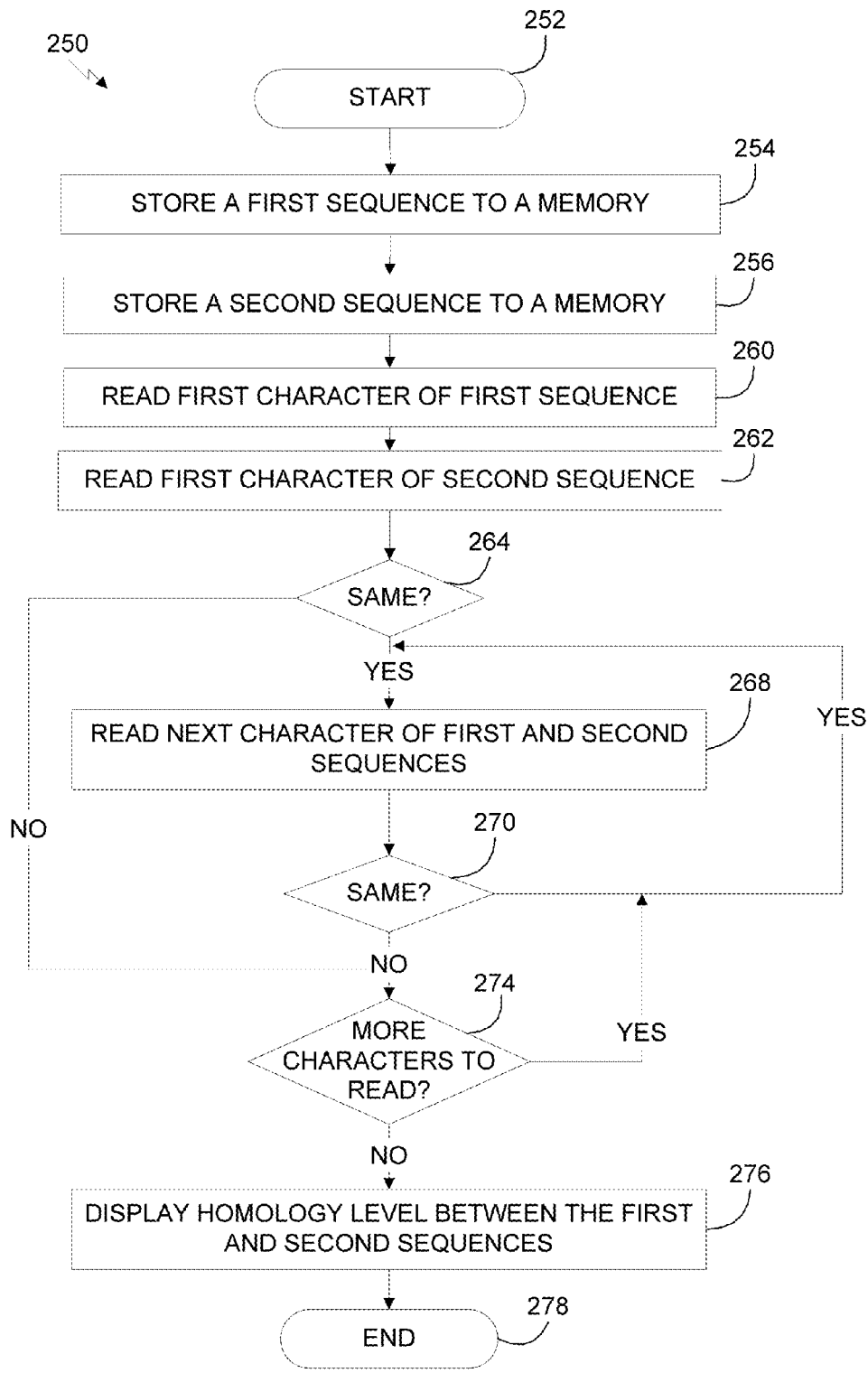
FIG. 3 is a flow diagram illustrating one embodiment of a process in a computer for determining whether two sequences are homologous.
Figure 4:
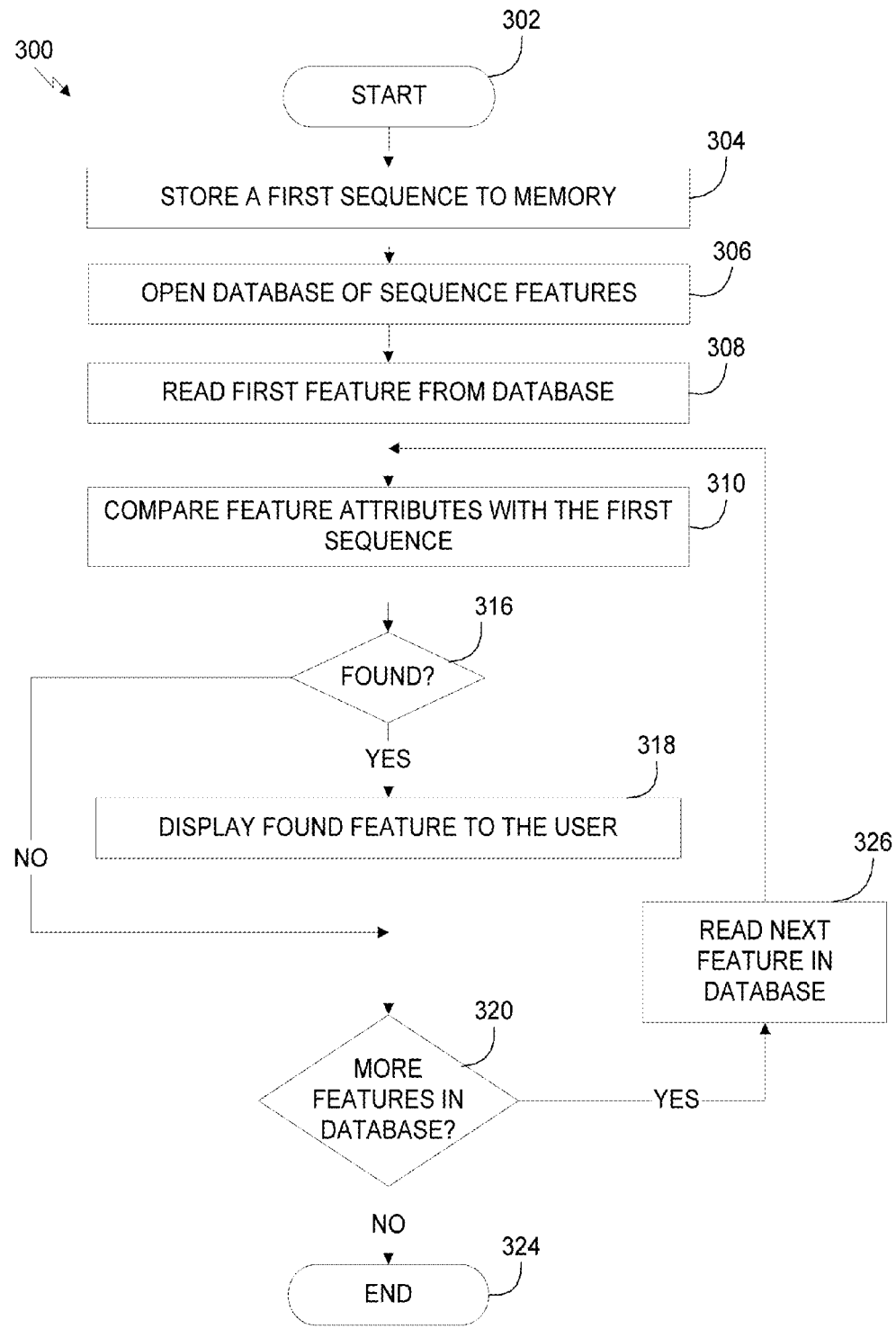
FIG. 4 is a flow diagram illustrating one embodiment of an identifier process 300 for detecting the presence of a feature in a sequence.

FIG. 3 is a flow diagram illustrating one embodiment of a process 250 in a computer for determining whether two sequences are homologous. The process 250 begins at a start state 252 and then moves to a state 254 wherein a first sequence to be compared is stored to a memory. The second sequence to be compared is then stored to a memory at a state 256. The process 250 then moves to a state 260 wherein the first character in the first sequence is read and then to a state 262 wherein the first character of the second sequence is read. It should be understood that if the sequence is a nucleotide sequence, then the character would normally be either A, T, C, G or U. If the sequence is a protein sequence, then it is preferably in the single letter amino acid code so that the first and sequence sequences can be easily compared.

A determination is then made at a decision state 264 whether the two characters are the same. If they are the same, then the process 250 moves to a state 268 wherein the next characters in the first and second sequences are read. A determination is then made whether the next characters are the same. If they are, then the process 250 continues this loop until two characters are not the same. If a determination is made that the next two characters are not the same, the process 250 moves to a decision state 274 to determine whether there are any more characters either sequence to read.

If there are not any more characters to read, then the process 250 moves to a state 276 wherein the level of homology between the first and second sequences is displayed to the user. The level of homology is determined by calculating the proportion of characters between the sequences that were the same out of the total number of sequences in the first sequence. Thus, if every character in a first 100 nucleotide sequence aligned with a every character in a second sequence, the homology level would be 100%.

Alternatively, the computer program may be a computer program which compares the nucleotide sequences of a nucleic acid sequence as set forth in the invention, to one or more reference nucleotide sequences in order to determine whether the nucleic acid code of Group A nucleic acid sequences, and sequences substantially identical thereto, differs from a reference nucleic acid sequence at one or more positions. Optionally such a program records the length and identity of inserted, deleted or substituted nucleotides with respect to the sequence of either the reference polynucleotide or a nucleic acid sequence as set forth in Group A nucleic acid sequences, and sequences substantially identical thereto. In one embodiment, the computer program may be a program which determines whether a nucleic acid sequence as set forth in Group A nucleic acid sequences, and sequences substantially identical thereto, contains a single nucleotide polymorphism (SNP) with respect to a reference nucleotide sequence.

Accordingly, another aspect of the invention is a method for determining whether a nucleic acid sequence as set forth in Group A nucleic acid sequences, and sequences substantially identical thereto, differs at one or more nucleotides from a reference nucleotide sequence comprising the steps of reading the nucleic acid code and the reference nucleotide sequence through use of a computer program which identifies differences between nucleic acid sequences and identifying differences between the nucleic acid code and the reference nucleotide sequence with the computer program. In some embodiments, the computer program is a program which identifies single nucleotide polymorphisms. The method may be implemented by the computer systems described above and the method illustrated in FIG. 3. The method may also be performed by reading at least 2, 5, 10, 15, 20, 25, 30, or 40 or more of the nucleic acid sequences as set forth in Group A nucleic acid sequences, and sequences substantially identical thereto, and the reference nucleotide sequences through the use of the computer program and identifying differences between the nucleic acid codes and the reference nucleotide sequences with the computer program.

In other embodiments the computer based system may further comprise an identifier for identifying features within a nucleic acid sequence as set forth in the Group A nucleic acid sequences or a polypeptide sequence as set forth in Group B amino acid sequences, and sequences substantially identical thereto.

An "identifier" refers to one or more programs which identifies certain features within a nucleic acid sequence as set forth in Group A nucleic acid sequences, and sequences substantially identical thereto, or a polypeptide sequence as set forth in Group B amino acid sequences, and sequences substantially identical thereto. In one embodiment, the identifier may comprise a program which identifies an open reading frame in a nucleic acid sequence as set forth in Group A nucleic acid sequences, and sequences substantially identical thereto.

Figure 5:
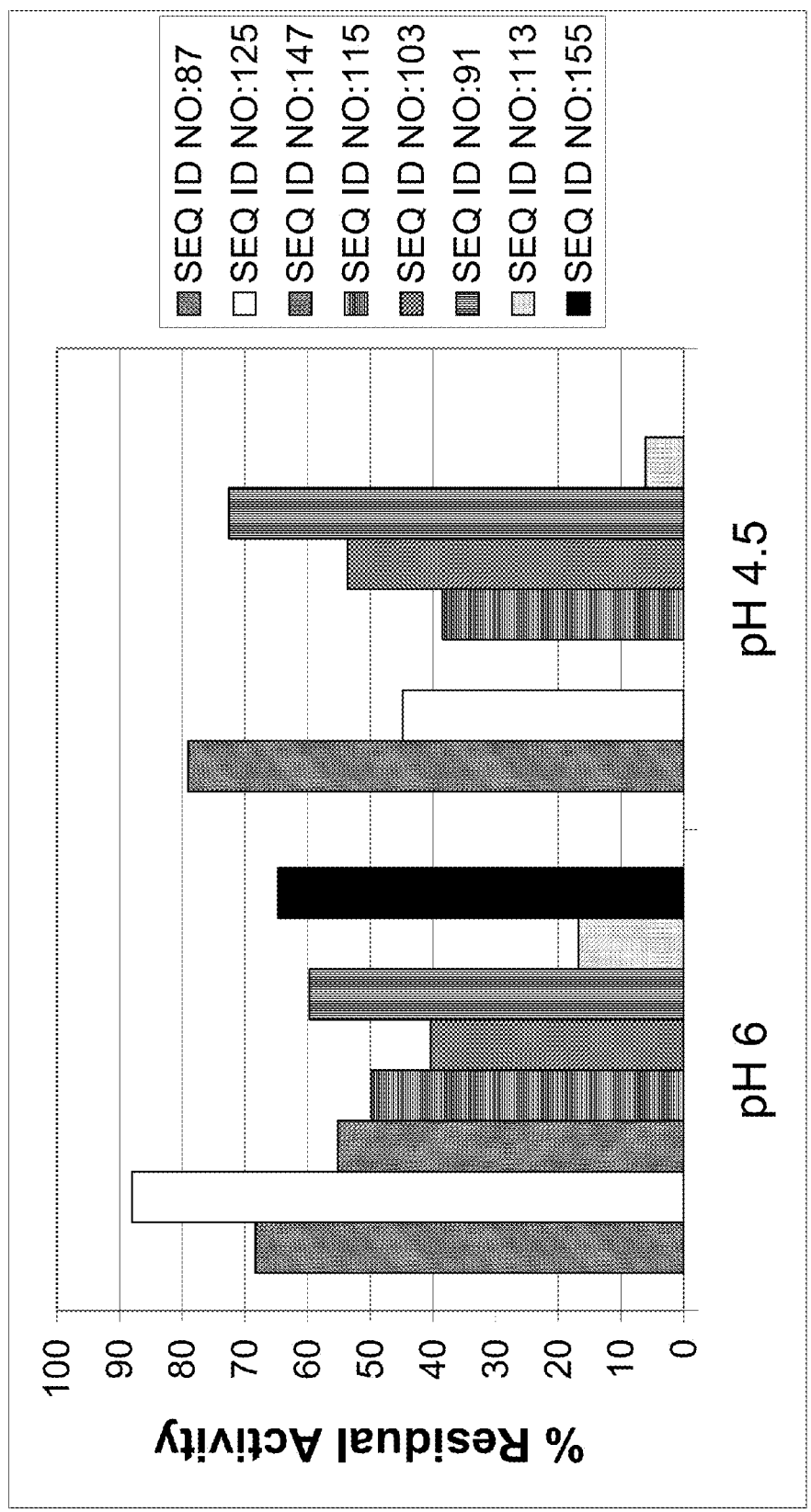
FIG. 5 is a graph showing the Residual activity of various amylases following heating to 90° C. for 10 min in Example 1.

FIG. 5 is a flow diagram illustrating one embodiment of an identifier process 300 for detecting the presence of a feature in a sequence. The process 300 begins at a start state 302 and then moves to a state 304 wherein a first sequence that is to be checked for features is stored to a memory 115 in the computer system 100. The process 300 then moves to a state 306 wherein a database of sequence features is opened. Such a database would include a list of each feature's attributes along with the name of the feature. For example, a feature name could be "Initiation Codon" and the attribute would be "ATG". Another example would be the feature name "TAATAA Box" and the feature attribute would be "TAATAA". An example of such a database is produced by the University of Wisconsin Genetics Computer Group (www.gcg.com). Alternatively, the features may be structural polypeptide motifs such as alpha helices, beta sheets, or functional polypeptide motifs such as enzymatic active sites, helix-turn-helix motifs or other motifs known to those skilled in the art.

Once the database of features is opened at the state 306, the process 300 moves to a state 308 wherein the first feature is read from the database. A comparison of the attribute of the first feature with the first sequence is then made at a state 310. A determination is then made at a decision state 316 whether the attribute of the feature was found in the first sequence. If the attribute was found, then the process 300 moves to a state 318 wherein the name of the found feature is displayed to the user.

The process 300 then moves to a decision state 320 wherein a determination is made whether move features exist in the database. If no more features do exist, then the process 300 terminates at an end state 324. However, if more features do exist in the database, then the process 300 reads the next sequence feature at a state 326 and loops back to the state 310 wherein the attribute of the next feature is compared against the first sequence.

It should be noted, that if the feature attribute is not found in the first sequence at the decision state 316, the process 300 moves directly to the decision state 320 in order to determine if any more features exist in the database.

Accordingly, another aspect of the invention is a method of identifying a feature within a nucleic acid sequence as set forth in Group A nucleic acid sequences, and sequences substantially identical thereto, or a polypeptide sequence as set forth in Group B amino acid sequences, and sequences substantially identical thereto, comprising reading the nucleic acid code(s) or polypeptide code(s) through the use of a computer program which identifies features therein and identifying features within the nucleic acid code(s) with the computer program. In one embodiment, computer program comprises a computer program which identifies open reading frames. The method may be performed by reading a single sequence or at least 2, 5, 10, 15, 20, 25, 30, or 40 of the nucleic acid sequences as set forth in Group A nucleic acid sequences, and sequences substantially identical thereto, or the polypeptide sequences as set forth in Group B amino acid sequences, and sequences substantially identical thereto, through the use of the computer program and identifying features within the nucleic acid codes or polypeptide codes with the computer program.

A nucleic acid sequence as set forth in Group A nucleic acid sequences, and sequences substantially identical thereto, or a polypeptide sequence as set forth in Group B amino acid sequences, and sequences substantially identical thereto, may be stored and manipulated in a variety of data processor programs in a variety of formats. For example, a nucleic acid sequence as set forth in Group A nucleic acid sequences, and sequences substantially identical thereto, or a polypeptide sequence as set forth in Group B amino acid sequences, and sequences substantially identical thereto, may be stored as text in a word processing file, such as MicrosoftWORD or WORDPERFECT or as an ASCII file in a variety of database programs familiar to those of skill in the art, such as DB2, SYBASE, or ORACLE. In addition, many computer programs and databases may be used as sequence comparison algorithms, identifiers, or sources of reference nucleotide sequences or polypeptide sequences to be compared to a nucleic acid sequence as set forth in Group A nucleic acid sequences, and sequences substantially identical thereto, or a polypeptide sequence as set forth in Group B amino acid sequences, and sequences substantially identical thereto. The following list is intended not to limit the invention but to provide guidance to programs and databases which are useful with the nucleic acid sequences as set forth in Group A nucleic acid sequences, and sequences substantially identical thereto, or the polypeptide sequences as set forth in Group B amino acid sequences, and sequences substantially identical thereto.

The programs and databases which may be used include, but are not limited to: MacPattern (EMBL), DiscoveryBase (Molecular Applications Group), GeneMine (Molecular Applications Group), Look (Molecular Applications Group), MacLook (Molecular Applications Group), BLAST and BLAST2 (NCBI), BLASTN and BLASTX (Altschul et al, J. Mol. Biol. 215: 403, 1990), FASTA (Pearson and Lipman, Proc. Natl. Acad. Sci. USA, 85: 2444, 1988), FASTDB (Brutlag et al. Comp. App. Biosci. 6:237-245, 1990), Catalyst (Molecular Simulations Inc.), Catalyst/SHAPE (Molecular Simulations Inc.), Cerius2.DBAccess (Molecular Simulations Inc.), HypoGen (Molecular Simulations Inc.), Insight II, (Molecular Simulations Inc.), Discover (Molecular Simulations Inc.), CHARMm (Molecular Simulations Inc.), Felix (Molecular Simulations Inc.), DelPhi, (Molecular Simulations Inc.), QuanteMM, (Molecular Simulations Inc.), Homology (Molecular Simulations Inc.), Modeler (Molecular Simulations Inc.), ISIS (Molecular Simulations Inc.), Quanta/Protein Design (Molecular Simulations Inc.), WebLab (Molecular Simulations Inc.), WebLab Diversity Explorer (Molecular Simulations Inc.), Gene Explorer (Molecular Simulations Inc.), SeqFold (Molecular Simulations Inc.), the MDL Available Chemicals Directory database, the MDL Drug Data Report data base, the Comprehensive Medicinal Chemistry database, Derwent's World Drug Index database, the BioByteMasterFile database, the Genbank database, and the Genseqn database. Many other programs and data bases would be apparent to one of skill in the art given the present disclosure.

Motifs which may be detected using the above programs include sequences encoding leucine zippers, helix-turn-helix motifs, glycosylation sites, ubiquitination sites, alpha helices, and beta sheets, signal sequences encoding signal peptides which direct the secretion of the encoded proteins, sequences implicated in transcription regulation such as homeoboxes, acidic stretches, enzymatic active sites, substrate binding sites, and enzymatic cleavage sites.

The present invention exploits the unique catalytic properties of enzymes. Whereas the use of biocatalysts (i.e., purified or crude enzymes, non-living or living cells) in chemical transformations normally requires the identification of a particular biocatalyst that reacts with a specific starting compound, the present invention uses selected biocatalysts and reaction conditions that are specific for functional groups that are present in many starting compounds, such as small molecules. Each biocatalyst is specific for one functional group, or several related functional groups, and can react with many starting compounds containing this functional group.

The biocatalytic reactions produce a population of derivatives from a single starting compound. These derivatives can be subjected to another round of biocatalytic reactions to produce a second population of derivative compounds. Thousands of variations of the original small molecule or compound can be produced with each iteration of biocatalytic derivatization.

Enzymes react at specific sites of a starting compound without affecting the rest of the molecule, a process which is very difficult to achieve using traditional chemical methods. This high degree of biocatalytic specificity provides the means to identify a single active compound within the library. The library is characterized by the series of biocatalytic reactions used to produce it, a so called "biosynthetic history". Screening the library for biological activities and tracing the biosynthetic history identifies the specific reaction sequence producing the active compound. The reaction sequence is repeated and the structure of the synthesized compound determined. This mode of identification, unlike other synthesis and screening approaches, does not require immobilization technologies, and compounds can be synthesized and tested free in solution using virtually any type of screening assay. It is important to note, that the high degree of specificity of enzyme reactions on functional groups allows for the "tracking" of specific enzymatic reactions that make up the biocatalytically produced library.

Many of the procedural steps are performed using robotic automation enabling the execution of many thousands of biocatalytic reactions and screening assays per day as well as ensuring a high level of accuracy and reproducibility. As a result, a library of derivative compounds can be produced in a matter of weeks which would take years to produce using current chemical methods.

In a particular embodiment, the invention provides a method for modifying small molecules, comprising contacting a polypeptide encoded by a polynucleotide described herein or enzymatically active fragments thereof with a small molecule to produce a modified small molecule. A library of modified small molecules is tested to determine if a modified small molecule is present within the library which exhibits a desired activity. A specific biocatalytic reaction which produces the modified small molecule of desired activity is identified by systematically eliminating each of the biocatalytic reactions used to produce a portion of the library, and then testing the small molecules produced in the portion of the library for the presence or absence of the modified small molecule with the desired activity. The specific biocatalytic reactions which produce the modified small molecule of desired activity is optionally repeated. The biocatalytic reactions are conducted with a group of biocatalysts that react with distinct structural moieties found within the structure of a small molecule, each biocatalyst is specific for one structural moiety or a group of related structural moieties; and each biocatalyst reacts with many different small molecules which contain the distinct structural moiety.

In another embodiment, the novel alkaline amylases of the invention were identified by screening for both activity at high pH and identification of amylases with stability in an automatic dish wash (ADW) formulation. Comparisons were made to the amylase derived from Bacillus lichenformis. A study of the dependence of hydrolysis on pH showed that the majority of the alkaline amylases of the invention have a pH optima of 7 or less, the exception is clone B with a pH optima of approximately 8. The alkaline amylases of the invention retain activity in ADW formulations, though clone B is sensitive to high temperatures. Preferably, when used in ADW products, the alkaline amylase of the invention will function at a pH 10-11 and at 45-60° C.

The invention will be further described with reference to the following examples; however, it is to be understood that the invention is not limited to such examples.

EXAMPLES

Example 1

Identification and Characterization of Thermostable α-Amylases

The present example shows the identification of novel acid amylases. The screening program was carried out under neutral and low pH conditions. DNA libraries generated from low pH samples were targeted for discovery. This effort afforded the discovery of hundreds of clones having the ability to degrade starch. DNA sequence and bioinformatic analyses classified many of these genes as previously unidentified amylases.

Biochemical Studies

Biochemical analysis of the amylase genomic clones showed that many had pH optima of less than pH 6. Lysates of these genomic clones were tested for thermal tolerance by incubation at 70° C., 80° C., 90° C. or 100° C. for 10 minutes and measurement of residual activity at pH 4.5. Those clones retaining >50% activity after heat treatment at 80° C. were chosen for further analysis. These clones were incubated at 90° C. for 10 minutes at pH 6.0 and 4.5 and tested for residual activity at pH 4.5 (FIG. 1). A number of clones retained >40% of their activity following this treatment. For comparative purposes, residual activity of an evolved amylase, clone c, was equivalent to the best of the second-generation enzymes; the specific activity of clone c was greater.

Thermal activity of the clones with residual activity after heat treatment at 90° C. at pH 4.5 was measured at room temperature, 70° C. and 90° C. at pH 4.5. Table 1 shows that the hydrolysis rates of SEQ ID NO.: 87 (*B. stearothermophilus* amylase) and SEQ ID NO. 113 (*B. licheniformis* amylase) decrease at higher temperatures, whereas the rate for SEQ ID NO.:125 continues to increase as the temperature is raised to 70° C. and only reduces by around 50% at 90° C.

Candidate Evaluation

Based on residual activity at pH 4.5 after a 90° C. heat treatment, specific activity and rate of starch hydrolysis at 90° C. when compared with *B. licheniformis* amylase, SEQ ID NO.:125 is compared with the evolved amylase clone c in a starch liquefaction assay.

TABLE 1

Rates of dye labeled starch hydrolysis (relative fluorescence units/s) of three genomic clones at pH 4.5 and 3 different temperatures.

|  | Room temperature | 70° C. | 90° |
|---|---|---|---|
| SEQ ID NO.: 87[1] | 1.25 | 1.43 | 0.33 |
| SEQ ID NO.: 113[2] | 3.3 | 1.9 | 0.39 |
| SEQ ID NO.: 125 | 1.9 | 47 | 19 |

[1]*B. stearothermophilus* amylase,
[2]*B. licheniformis* amylase

Example 2

Thermostable Amylases Active at Alkaline pH

The initial focus of this example was the evaluation of an existing panel of amylases in an commercial automatic dish wash (ADW) formulation. This effort identified two candidates: one with activity at high pH (SEQ ID NO.:115) and another with stability in the ADW formulation (SEQ ID NO.:207). Studies also included the identification of high pH amylases. This effort afforded the discovery of hundreds of clones having the ability to degrade starch. DNA sequence and bioinformatics analyses classified many of these genes as previously unidentified amylases. The remaining open reading frames were neopullulanases, amylopullulanases and amylomaltases. Extensive biochemical and applications studies showed that 3 candidates: clone B, SEQ ID NO.:147 and SEQ ID NO.:139) have high specific activity at pH10, but unfortunately lack stability in the ADW formulation. In summary, a panel of novel amylases each having desirable phenotypes for the ADW application has been identified.

Biochemical Studies

Biochemical analysis of the amylase genomic clones showed that many of them hydrolyzed starch at pH 10 and 50° C. To produce sufficient quantities of enzyme for further biochemical and applications testing, the amylase open reading frames of the 40 most active genomic clones were subcloned into expression vectors. This effort included making 2 constructs for those clones containing a putative signal sequence and establishing the growth and induction conditions for each subclone (plus and minus the amylase signal peptide).

Soluble, active protein was successfully purified to homogeneity from 34 subclones and specific activity (units/mg, where 1 unit=µmol reducing sugars/min) was measured at pH 8 and pH 10 (40° C. and 50° C.) using 2% starch in buffer. The amylase from *Bacillus licheniformis* (SEQ ID NO.:113) was chosen as the benchmark for these studies. Specific activity was determined by removing samples at various time points during a 30 minute reaction and analyzing for reducing sugars. The initial rate was determined by fitting the progress curves to a linear equation. A comparison of the top candidates is shown in Table 2.

A study to determine the dependence of hydrolysis rate on pH showed that only clone B is an "alkaline amylase" with a pH optimum of approximately 8; all others had pH optima of 7 or less. Nevertheless, it is clear that the panel of hits included several lead amylases with appreciable activity at pH 10 and 50° C.

TABLE 2

Specific activities (U/mg pure enzyme) of amylases

| Enzyme | Specific activity pH 8, 40° C. | Specific activity pH 10, 50° C. |
|---|---|---|
| Clone B | 682 | 20 |
| SEQ ID NO.: 139 | 430 | 33 |
| SEQ ID NO.: 127 | 250 | 47 |
| SEQ ID NO.: 137 | 230 | 3 |
| SEQ ID NO.: 113 (*B. licheniformis*) | 228 | 27 |
| SEQ ID NO.: 205 | 163 | 4 |
| Remainder | <40 | |

Stability

Stability in the presence of the ADW formulation was measured for each of the 3 top candidates identified via biochemical analysis. The benchmark for these studies was a commercial enzyme in the formulation matrix. FIG. 13 illustrates the residual activity (measured at pH 8 and 50° C.) after a 30 minute incubation at 50° C. in the presence of various components of the ADW formulation; pH 8, pH 10.8, ADW solution (with bleach) and ADW solution (without bleach). The measured activity after the incubation is expressed as a percentage of the original activity. The data show that clone B was very sensitive to high temperature, whereas the other amylases were less affected. When the enzymes were incubated at high pH and temperature, the commercial enzyme SEQ ID NO.: 139 became less stable; however, SEQ ID NO.: 127 retained full activity. The apparently anomalous behavior of SEQ ID NO.: 127 after pH 10 incubation vs pH 8 was observed in repeated trials.

Figure 6:
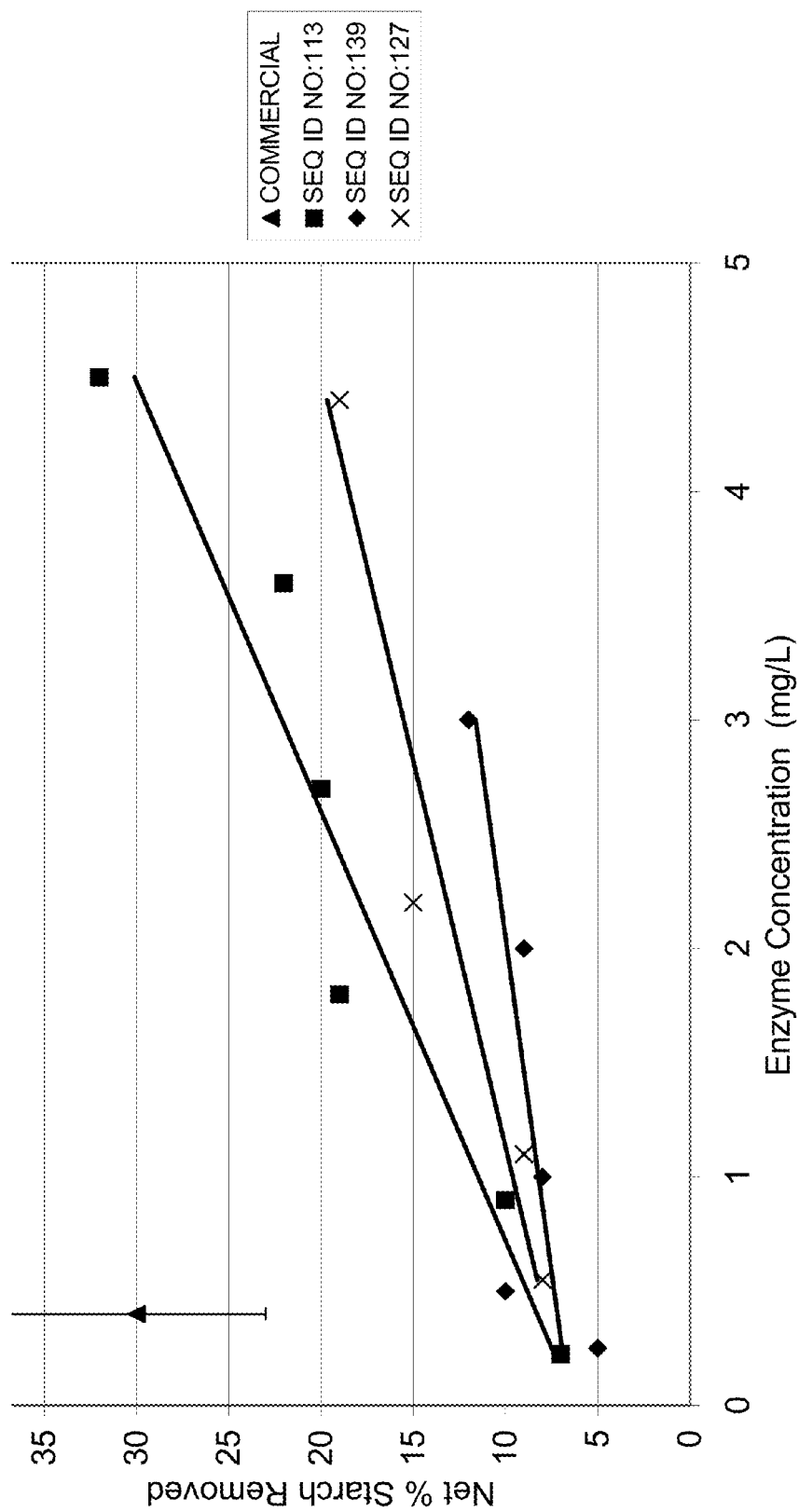
FIG. 6 is a graph showing the net percent starch removed versus enzyme concentration in ADW wash test with bleach and chelators.

When amylase activity on dye-labeled starch is measured in the ADW matrix at 50° C., the commercial amylase exhibits roughly 5% of its activity at pH 8. In the same assay, clone B, SEQ ID NO.: 139 and SEQ ID NO.: 127 exhibit <2% of their original activity measured at pH 8.
Wash Tests Wash tests using starch coated slides were carried out to gauge the performance of each of the purified enzymes as compared to the commercial amylase. The spaghetti starch coated slides were prepared according to protocol. Two pre-weighed starch coated slides were placed back to back in a 50 mL conical tube and 25 mL of ADW solution, +/− enzyme were added per tube. The tubes were incubated for 20 minutes at 50° C. with gentle rotation on a vertical carousel. Following the incubation period, the slides were immediately rinsed in water and oven dried overnight. All trials were run in duplicate and the commercial enzyme was run as a positive control. The results (FIG. 6) of these experiments are expressed as net % starch removed, e.g. % of starch removed in ADW with enzyme, minus the % of starch removed in ADW alone.

Example 3

Gene Optimization

The properties of enzymes may be improved by various evolution strategies, including GeneSiteSaturationMutagenesis (GSSM™) and GeneReassembly™ (Diversa Corporation, San Diego, Calif.). Such techniques will be applied to the discovered amylase genes in order to generate pools of variants that can be screened for improved performance.

Parental molecules for evolution will be one or all of the following: SEQ ID NO.: 113, SEQ ID NO.: 139, SEQ ID NO.:115 and SEQ ID NO.: 127 (a truncated form of SEQ ID NO.: 127).

Figure 7:
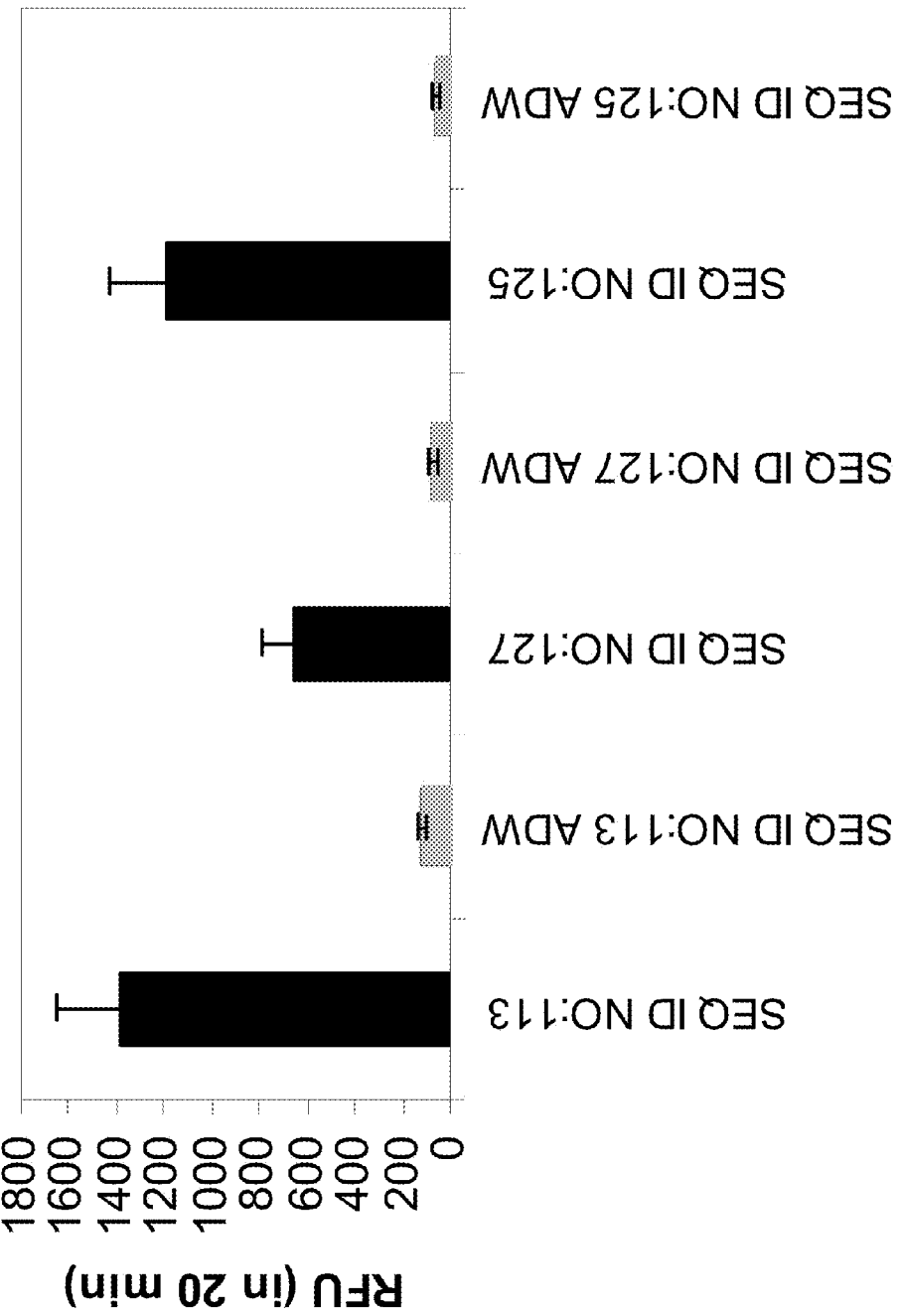
FIG. 7 is a graph showing the activity of parental amylases at pH 8, 40° C. in ADW formulation at 55° C.
Figure 8:
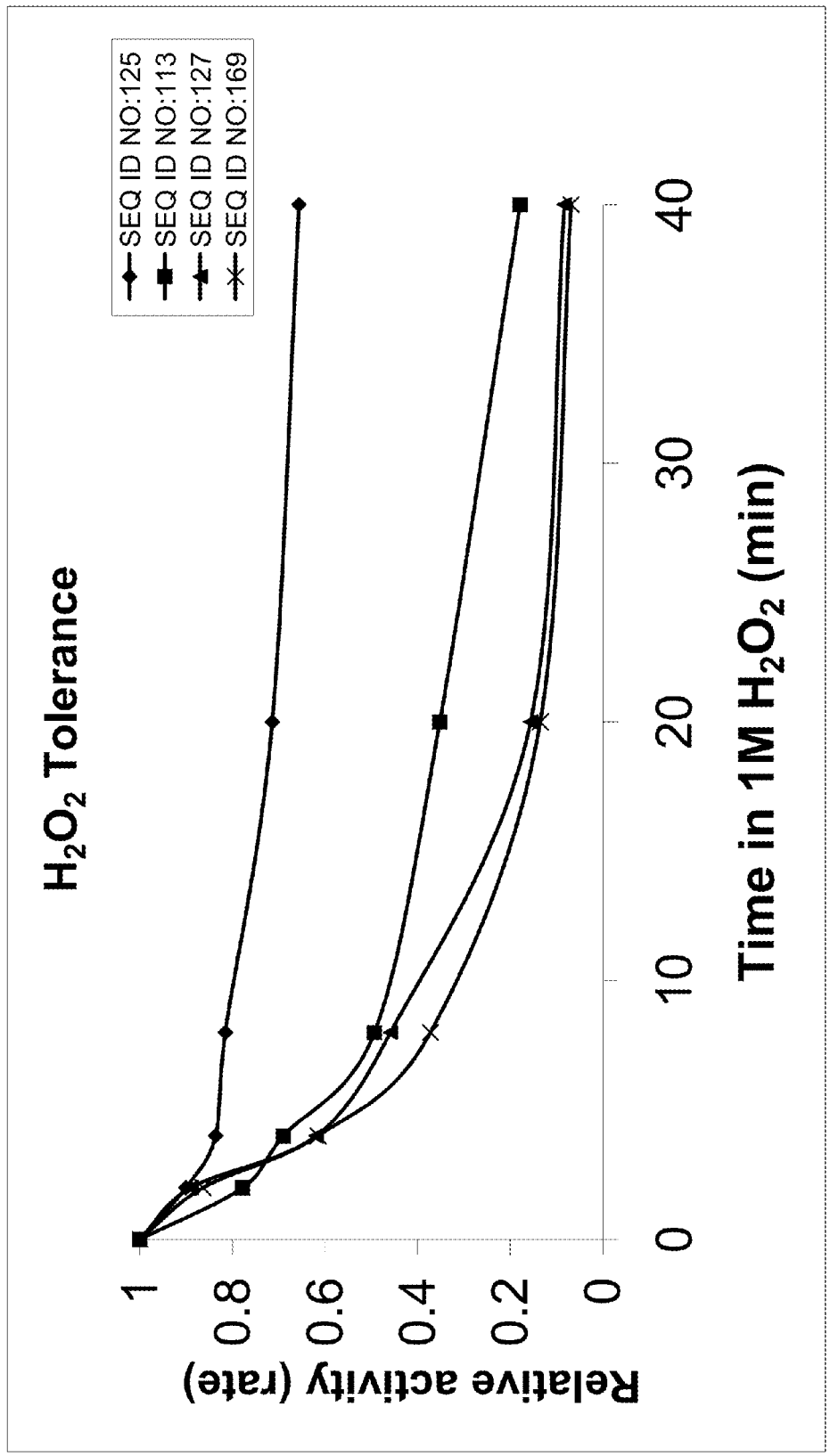
FIG. 8 is a graph of data regarding the $H_2O_2$ tolerance of the novel enzymes in Example 4.
Figure 9B:
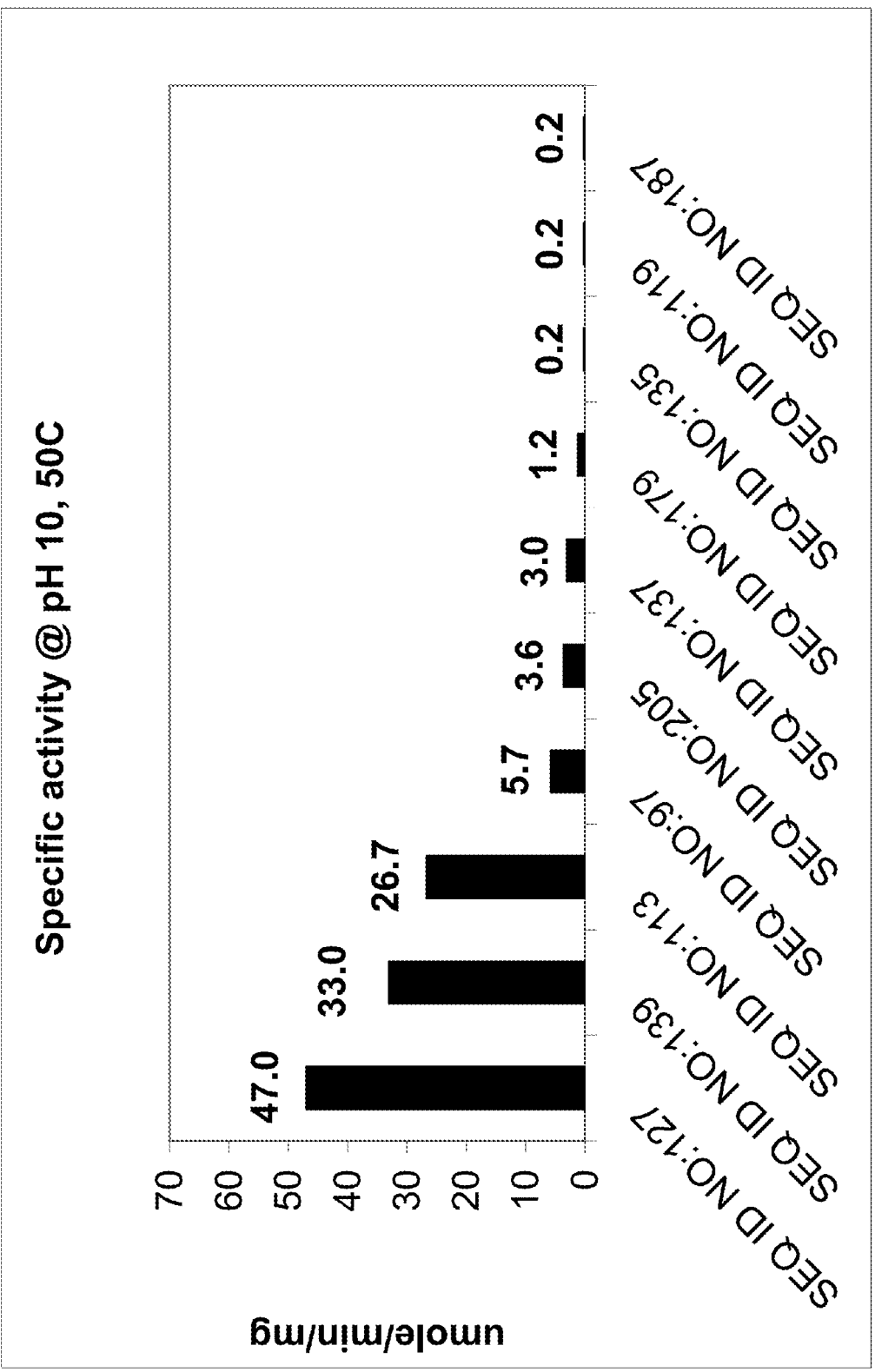
FIG. 9b is a graph showing the data at pH 10 and 50° C.
Figure 15:
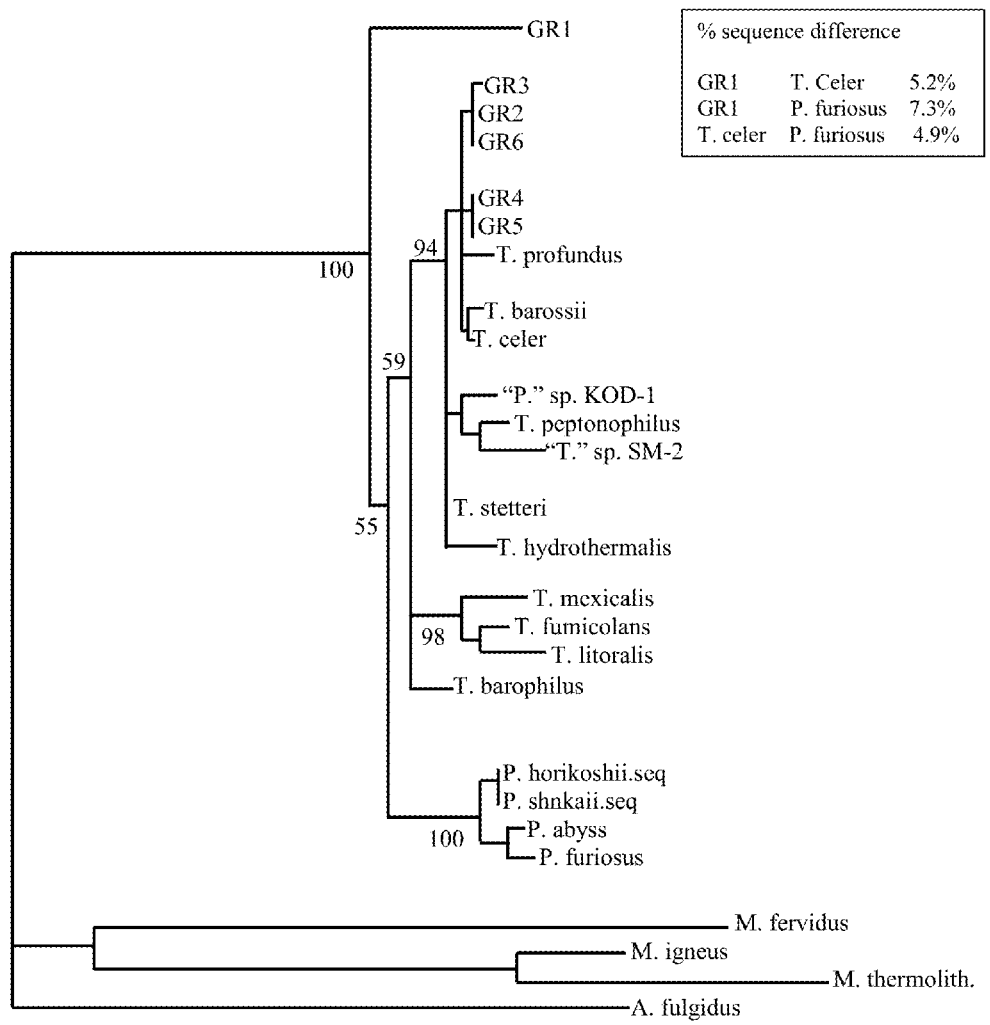
FIG. 15 is a neighbor-joining tree for Thermococcales.

A high throughput screen has been developed to assess enzyme performance in the presence of ADW performance. Development of a HTS is of paramount importance in any evolution program The HTS is automated and has showed consistent results for the parental amylases (FIG. 7). Parental amylases have measurable activity in the ADW formulation, however highly reduced relative to pH 8 activity.

Example 4

Characterization of α-Amylases Having Activity at Alkaline pH

Amylases of the invention having activity at alkaline pH were characterized further. Kinetics on 2% starch at pH 8 and 10 (40° C. and 50° C.) have been performed.

TABLE 4

| Clones, specific activities | pH 8, 40° C. | pH 10, 50° C. |
|---|---|---|
| SEQ ID NO.: 113 (*B. lichenoformis*) | 228 units/mg | 27 units/mg |
| Clone B | 682 units/mg | 31 units/mg |
| SEQ ID NO.: 139 | 430 units/mg | 33 units/mg |

TABLE 4-continued

| Clones, specific activities | pH 8, 40° C. | pH 10, 50° C. |
|---|---|---|
| SEQ ID NO.: 127 | 540 units/mg | 50 units/mg |
| control 0GL5 (*E. coli*) | 1.8 units/mg | 0 units/mg |

1 unit of activity is defined as release of 1 μmol reducing sugars per minute.

Example 5

Amylase Activity Assay: BCA Reducing Ends Assay

Amylase activity of clones of interest was determined using the following methodology.
1. Prepare 2 substrate solutions, as follows:
   a) 2% soluble starch (potato) pH 8 solution by dissolving 2 gm potato starch in 100 ml 100 mM sodium phosphate pH 8).
   b) 2% soluble starch (potato) pH 10 solution by dissolving 2 gm potato starch in 100 ml 100 mM sodium carbonate.
   Heat both solutions in a boiling water bath, while mixing, for 30-40 minutes until starch dissolves.
2. Prepare Solution A from 64 mg/ml sodium carbonate monohydrate, 24 mg/ml sodium bicarbonate and 1.95 mg/ml BCA (4,4'-dicarboxy-2,2'-biquinoline disodium salt (Sigma Chemical cat #D-8284). Added above to dH2O.
3. Prepare solution B by combining 1.24 mg/ml cupric sulfate pentahydrate and 1.26 mg/ml L-serine. Add mixture to dH2O.
4. Prepare a working reagent of a 1:1 ration of solutions A and B.
5. Prepare a Maltose standard solution of 10 mM Maltose in dH2O, where the 10 mM maltose is combined in 2% soluble starch at desired pH to a final concentration of 0, 100, 200, 300, 400, 600 μM. The standard curve will be generated for each set of time-points. Since the curve is determined by adding 10 ul of the standards to the working reagent it works out to 0, 1, 2, 3, 4, 6 nmole maltose.
6. Aliquot 1 ml of substrate solution into microcentrifuge tubes, equilibrate to desired temperature (5 min) in heat block or heated water bath. Add 50 ul of enzyme solution to the inside of the tube lid.
7. While solution is equilibrating mix 5 ml of both solution A & B. Aliquot 100 ul to 96 well PCR plate. Set plate on ice.
8. After 5 minute temperature equilibration, close lid on tubes, invert and vortex 3 times. Immediately aliquot 10 ul into plate as t=0 (zero time point). Leave enzyme mixture in heat block and aliquot 10 ul at each desired time point (e.g. 0, 5, 10, 15, 20, 30 minutes).
9. Ensure that 12 wells are left empty (only working reagent aliquoted) for the addition of 10 ul of standards, for the standard curve.
10. When all time points are collected and standards are added, cover plate and heated to 80° C. for 35 min. Cool plate on ice for 10 min. Add 100 ul $H_2O$ to all wells. Mix and aliquot 100 ul into flat bottomed 96-well plate and read absorbance at 560 nm.
11. Zero each sample's time points against its own t=0 (subtract the average t=0 A560 value from other average A560 values). Convert the $A560_{(experimental)}$ to umole (Divide $A560_{(experimental)}$ by the slope of the standard curve (A560/umole). Generate a slope of the time points and the umole (in umole/min), multiply by 100 (as the umole value only accounts for the 10 ul used in the assay, not the amount made in the 1 ml rxn). To get the specific activity divide the slope (in umole/min) by the mg of protein. All points should be done at a minimum in duplicate with three being best. An example standard curve is set forth in FIG. 11.

TABLE 5

Sample data:

| Clone | Dilution | Minutes | A560-1 | A560-2 | Avg A 560 | Zeroed A 560 | (A560exp/ std slope) umole |
|---|---|---|---|---|---|---|---|
| ENZ | 50 | 0 | 0.1711 | 0.1736 | 0.17235 | 0 | 0.0000 |
| | | 5 | 0.2104 | 0.2165 | 0.21345 | 0.0411 | 0.0005 |
| | | 10 | 0.2492 | 0.2481 | 0.24865 | 0.0763 | 0.0009 |
| | | 15 | 0.2984 | 0.2882 | 0.2933 | 0.12095 | 0.0014 |
| | | 20 | 0.3355 | 0.3409 | 0.3382 | 0.16585 | 0.0020 |
| | | 30 | 0.3942 | 0.3805 | 0.38735 | 0.215 | 0.0026 |
| | | 40 | 0.4501 | 0.4412 | 0.44565 | 0.2733 | 0.0033 |

Activity = 0.008646 umole/min
Divide protein concentration (mg/ml) by any dilution to get mg used in assay.
Divide the above slope by mg used in assay to get specific activity
Specific Activity = 24.93 umole/min/mg (See for example, Dominic W. S. Wong, Sarah B. Batt, and George H. Robertson (2000). Microassay for rapid screening of alpha-amylase activity. J. Agric. Food Chem. 48, 4540-4543 and Jeffrey D. Fox and John F. Robyt, (1991). Minituratization of three carbohydrate analyses using a micro sample plate reader. Anal. Biochem. 195, 93-96, herein incorporated by reference).

Example 6

Screening for α-Amylase Activity

Amylase activity of clones can be assessed by a number of methods known in the art. The following is the general methodology that was used in the present invention. The number of plaques screened, per plate, should be approximately 10,000 pfu's. For each DNA library: at least 50,000 plaques per isolated library and 200,000 plaques per non-isolated library should be screened depending upon the pfu titer for the λ Zap Express amplified lysate.
Titer Determination of Lambda Library
1) μL of Lambda Zap Express amplified library stock added to 600 μL E. coli MRF' cells ($OD_{600}$=1.0). To dilute MRF' stock, 10 mM $MgSO_4$ is used.
2) Incubate at 37° C. for 15 minutes.
3) Transfer suspension to 5-6 mL of NZY top agar at 50° C. and gently mix.
4) Immediately pour agar solution onto large (150 mm) NZY media plate.
5) Allow top agar to solidify completely (approximately 30 minutes), then invert plate.
6) Incubate the plate at 39° C. for 8-12 hours.
7) Number of plaques is approximated. Phage titer determined to give 10,000 pfu/plate. Dilute an aliquot of Library phage with SM buffer if needed.
Substrate Screening
1) Lambda Zap Express (50,000 pfu) from amplified library added to 600 μL of E. coli MRF' cells (OD600=1.0). For non-environment libraries, prepare 4 tubes (50,000 pfu per tube).
2) Incubate at 37° C. for 15 minutes.
3) While phage/cell suspension are incubating, 1.0 mL of red starch substrate (1.2% w/v) is added to 6.0 mL NZY top agar at 50° C. and mixed thoroughly. Keep solution at 50° C. until needed.
4) Transfer ⅕ (10,000 pfu) of the cell suspension to substrate/top agar solution and gently mixed.
5) Solution is immediately poured onto large (150 mm) NZY media plate.
6) Allow top agar to solidify completely (approximately 30 minutes), then invert plate.
7) Repeat procedures 4-6 4 times for the rest of the cell suspension (⅕ of the suspension each time).
8) Incubate plates at 39° C. for 8-12 hours.
9) Plate observed for clearing zones (halos) around plaques.
10) Plaques with halos are cored out of agar and transferred to a sterile micro tube. A large bore 200 μL pipette tip works well to remove (core) the agar plug containing the desired plaque.
11) Phages are re-suspended in 500 μL SM buffer. 20 μL Chloroform is added to inhibit any further cell growth.
12) Pure phage suspension is incubated at room temperature for 4 hours or overnight before next step.
Isolation of Pure Clones
1) 10 μL of re-suspended phage suspension is added to 500 μL of E. coli MRF' cells (OD600=1.0).
2) Incubate at 37° C. for 15 minutes.
3) While phage/cell suspension is incubating, 1 mL of red starch substrate (1.2% w/v) is added to 6.0 mL NZY top agar at 50° C. and mixed thoroughly. Keep solution at 50° C. until needed.
4) Cell suspension is transferred to substrate/top agar solution and gently mixed.
5) Solution is immediately poured onto large (150 mm) NZY media plate.
6) Allow top agar to solidify completely (approximately 30 minutes), then invert plate.
7) Plate incubated at 39° C. for 8-12 hours.
8) Plate observed for a clearing zone (halo) around a single plaque (pure clone). If a single plaque cannot be isolated, adjust titer and re-plate phage suspension.
9) Single plaque with halo is cored out of agar and transferred to a sterile micro tube. A large bore 200 μL pipette tip works well to remove (core) the agar plug containing the desired plaque. To amplify the titer, core 5 single active plaques into a micro tube.
10) Phages are re-suspended in 500 μL SM buffer. 20 μL Chloroform is added to inhibit any further cell growth.
11) Pure phage suspension is incubated at room temperature for 4 hours or overnight before next step. The pure phage suspension is stored at −80° C. by adding DMSO into the phage suspension (7% v/v).
Excision of Pure Clone
1) 100 μL of pure phage suspension is added to 200 μL E. coli MRF' cells (OD600=1.0). To this, 1.0 μL of ExAssist helper phage (>1×106 pfu/mL; Stratagene) is added. Use 2059 Falcon tube for excision.
2) Suspension is incubated at 37° C. for 15 minutes.
3) 3.0 mL of 2×YT media is added to cell suspension.
4) Incubate at 30° C. for at least 6 hours or overnight while shaking.
5) Tube transferred to 70° C. for 20 minutes. The phagemid suspension can be stored at 4° C. for 1 to 2 months.
6) 100 μL of phagemid suspension transferred to a micro tube containing 200 μL of E. coli Exp 505 cells (OD600=1.0).
7) Suspension incubated at 37° C. for 15 minutes.

8) 300 µL of SOB is added to the suspension.
9) Suspension is incubated at 37° C. for 30 to 45 minutes.
10) 100 µL of suspension is transferred to a small (90 mm) LB media plate containing Kanamycin (LB media with Kanamycin 50 m/mL) for Zap Express DNA libraries or Ampicillin (LB media with Kanamycin 100 m/mL) for Zap II DNA libraries.
11) The rest of suspension is transferred to another small LB media plate.
12) Use sterile glass beads to evenly distribute suspension on the plate.
13) Plates are incubated at 30° C. for 12 to 24 hours.
14) Plate observed for colonies.
15) Inoculate single colony into LB liquid media containing suitable antibiotic and incubate at 30° C. for 12 to 24 hours.
16) Glycerol stock can be prepared by adding 80% glycerol into liquid culture (15% v/v) and stored at −80° C.

Activity Verification
1) 50 µL of liquid culture is transferred to a micro tube. Add 500 µL of 8% pH7 Amylopectin Azure into the same tube. Prepare 2 tubes for each clone.
2) Activity is tested at 50° C. for 3 hours and overnight. Use pH 7 buffer as control.
3) Cool the test specimen at ice-water bath for 5 minutes.
4) Add 750 µL of Ethaqnol and mixed thoroughly.
5) Centrifuge at 13000 rpm (16000 g's) for 5 minutes.
6) Measure OD of the supernatant at 595 nm.

RFLP Analysis
1) 1.0 mL of liquid culture is transferred to a sterile micro tube.
2) Centrifuge at 13200 rpm (16000 g's) for 1 minute.
3) Discard the supernatant. Add another 1.0 mL of liquid culture into the same sterile micro tube.
4) Centrifuge at 13200 rpm (16000 g's) for 1 minute.
5) Discard the supernatant.
6) Follow QIAprep spin mini kit protocol for plasmid isolation.
7) Check DNA concentration using BioPhotometer.
8) Use Sac I and Kpn I for first double digestion. Incubate at 37° C. for 1 hour.
9) Use Pst I and Xho I for second double digestion. Incubate at 37° C. for 1 hour.
10) Add Loading dye into the digested sample.
11) Run the digested sample on a 1.0% agarose gel for 1-1.5 hours at 120 volts.
12) View gel with gel imager. All clones with a different digest pattern will be sent for sequence analysis.

Example 7

Assay for Amylases

Preparation of Host Cultures
1. Start an overnight culture of XL1-Blue MRF' host cells. Use a single colony from a streak plate to inoculate 10 mL LB supplemented with 20 ug/mL tetracycline. Grow overnight culture shaking at 37° C. for at least 16 hours.
2. Using aseptic technique, inoculate a fresh 100 mL of $LB_{Tet}$ day culture with XL1-Blue MRF' host from the overnight $LB_{Tet}$ culture.
3. Grow in a 37° C. shaker until the OD reaches 0.75-1.0.
4. Pellet host cells at 1000×g for 10 minutes and gently resuspend in 10 mM $MgSO_4$ at OD5.
5. Dilute a small amount of host cells to OD1 for use in titering and pintooling.
6. Host preparations can be used for up to 1 week when stored on ice or at 4° C.
Comments
To shorten growth time for the day culture, use ½× the usual Tet concentration in LB (½×=10 ug/mL), or omit the antibiotic altogether.
Do not use NZY when selecting with Tetracycline. The high $Mg^{++}$ concentration in NZY medium renders Tet inactive.

Titering Lambda Libraries
7. Place three sterile microfuge tubes in a rack.
8. Aliquot 995 uL prepared host cells in one tube and 45 uL prepared OD1 host cells into each of the two remaining tubes.
9. Add 5 uL of lambda library to the tube containing 995 uL host cells and mix by vortexing. This results in a dilution factor of 200.
10. Prepare 1/2,000 and 1/20,000 dilutions by consecutively adding 5 uL of previous dilution to the remaining two tubes containing 45 uL prepared host cells. Mix by vortexing after each dilution was made.
11. Allow phage to adsorb to host by incubating at 37° C. for 15 minutes.
12. Meanwhile, pipet 100 uL of prepared OD1 host cells to each of three Falcon 2059 tubes.
13. Add 5 uL of each dilution to a separate 2059 tube containing host cells.
14. Plate each by adding 3 mL top agar to each tube and quickly pour over 90 mm NZY plates. Ensure a smooth, even distribution before the top agar hardens.
15. Invert plates and incubate at 37° C. overnight.
16. Count plaques and calculate titer of the library stock (in plaque forming units (pfu) per uL).

Lambda Microtiter Screening for Amylases
Preparation
1. Prepare a sufficient amount of XL1-Blue MRF' host culture, as described above, for the amount of screening planned. A culture of 100 mL is usually sufficient for screening 2-3 libraries.
2. Autoclave several bottles compatible with the QFill2 dispenser. These are the wide-mouth Corning bottles, 250 mL containing a sealing ring around the lip.
3. Make sure there are sufficient amounts of plates, top agar, BODIPY starch, red starch solution, etc. available for the screen.
4. Schedule the Day 2 robot run with a representative from Automation.

Day 1
1. Label the 1536-well plates (black) with library screen and plate number. Tough-Tags™ tube stickers, cut in half width-wise, are ideal for labeling 1536 well plates.
2. Calculate volumes of library, host cells and NZY medium necessary for the screen. This is easily done with an Excel spreadsheet.
3. Combine the calculated volumes of lambda library and OD5 host cells in a sterile 250 mL wide-mouth Corning bottle (containing a sealing ring).
4. Allow adsorption to occur at 37° C. for 15 minutes.
5. Add the calculated volume of NZY medium and mix well. This is referred to as the cell-phage-medium suspension.
6. Perform a concomitant titer by combining 50 uL of the cell-phage-medium suspension with 250 uL of OD1 host cells in a Falcon 2059 tube, then plating with 9 mL of top agar onto a 150 mm NZY plate. Incubate concomitant titer plate at 37° C. overnight.
7. Load the dispenser with the remainder of the suspension and array each labeled 1536-well plate at 4 uL per well.

If the dispenser leaves air bubbles in some wells, they can be removed by centrifuging the plates at 200×g for 1 minute.
8. Add 0.5 uL of positive control phage to well position AD46 of at least two of the assay plates. Use a strong amylase-positive lambda clone for this purpose. The lambda versions of SEQ ID NO.: 113 or SEQ ID NO.: 199 are good choices for positive controls.
9. Incubate assay plates at 37° C. overnight in a humidified (95%) incubator.

Day 2
1. Count the pfu on the concomitant titer plate and determine the average seed density per well (in pfu per well).
2. Pintool at least 2 plates of each library screen (preferably the 2 containing positive controls) as follows:
   a) Prepare 2 host lawn plates to act as a surface on which to pintool: combine 250 uL of OD1 host cells with 2 mL 2% red starch and plate with 9 mL top agar onto 150 mm NZY plates. Hold each plate as level as possible as the top agar solidifies in order to produce an even hue of red across the plate.
   b) Using a twice flame-sterilized 1536 position pintool, replicate at least 2 of the screening plates onto the host lawn plates.
   c) Place the pintooled recipient plates in a laminar flow hood with the lids off for about 15-30 minutes (to vent off excess moisture).
   d) Replace the lids and incubate inverted at 37° C. overnight.
3. Prepare the 2×BODIPY starch substrate buffer as follows:
   a) Calculate the total volume of 2× substrate buffer solution needed for all screening plates at 4 uL per well (including any extra deadspace volume required by the dispenser) and measure this amount of 100 mM CAPS pH 10.4 into a vessel appropriate for the dispenser used.
   b) Retrieve enough 0.5 mg tubes of BODIPY starch to produce the required volume of 2× substrate buffer [calculated in step a) above] at a final concentration of 20-30 ug/mL.
   c) Dissolve each 0.5 mg tube in 50 uL DMSO at room temperature, protected from light, with frequent vortexing. This takes more than 15 minutes; some production lots of BODIPY starch dissolve better than others.
   d) Add 50 uL 100 mM CAPS buffer pH 10.4 to each tube and mix by vortexing.
   e) Pool the contents of all tubes and remove any undissolved aggregates by centrifuging for 1 minute at maximum speed in a microfuge.
   f) Add the supernatant to the rest of the 100 mM CAPS buffer measured in step a) above.
   g) Protect the 2× substrate buffer from light by wrapping in foil.
4. Take plates and substrate buffer to the automation room and program the robot with the following parameters:
   a) dispense 4 uL substrate buffer per well
   b) $1^{st}$ read at 1 hour post-substrate, $2^{nd}$ read at 9 hours, and third read at 17 hours; with 37° C. incubation between reads
   c) excitation filter: 485 nm; emission filter: 535 nm
   d) set the Spectrafluor gain at 70, or the optimal gain for the batch of 2× substrate buffer prepared.
   e) ensure that the incubator used will protect assay plates from light.

Day 3
1. Check pintooled plates for clearings in the bacterial lawn at all positions corresponding to wells on the associated assay plate. Also check for clearings in the red starch in any of the pin positions. If plates containing positive controls were used for pintooling, you should be able to see a large clearing zone in the red background. Be wary of contaminants that also form clearing zones in red starch (see comment "Contaminants That Form Clearing Zones in Red Starch" at end of Example 7).
2. Identify putative hits from the data file produced by the robot computer. The KANAL program produced by Engineering simplifies data analysis. As a rule of thumb, a putative hit is characterized as a well having signal intensity rising at least 1.5 fold over background.
3. For each putative, remove 2 uL from the well and add to a tube containing 500 uL SM buffer and 50 uL CHCl3. Vortex to mix and store at 4° C. This solution will be referred to hereafter as the 4e-3 stock. The original screening plates should be stored at 4° C., protected from light, at least until breakouts are complete.

This is the recommended method of breaking out putative hits. It is a liquid phase assay that relies on confirmation of activity on BODIPY starch. Alternatively, putative hits can be plated directly onto solid phase plates containing red starch such that 2,000-3,000 pfu per hit are examined for clearing zones. However, inability to observe clearing zones on red starch is not necessarily an indication that a putative hit was a false positive. It would then need to be assayed using the format in which it was originally identified (i.e., liquid phase using BODIPY starch as substrate). In addition, very weak positives are more easily identified using the method detailed below.

Day 1
1. In a sterile 50 mL conical tube, combine 0.5 mL OD5 host cells with 45.5 mL NZY. This will be referred to as the host-medium suspension.
2. For each putative hit to be analyzed, aliquot 1 mL of host-medium suspension into each of 3 three sterile microfuge tubes.
3. Set the 12-channel pipetman in multidispense mode with an aliquot size of 20 uL and an aliquot number of 2×. Mount the pipetman with a clean set of sterile tips.
4. Pour about 1 mL of host-medium suspension into a new sterile solution basin and load the multichannel pipetman.
5. Dispense 20 uL per well into the last row (row P) of a black 384-well plate (12 channels×2=24 wells). This row will be used later for the controls.
6. Expel the remaining liquid in the tips by touching the tips against the surface of the basin and pressing the RESET button on the pipetman. Lay the pipetman down in a way to prevent contamination of the tips. There is no need to change the tips at this point.
7. Pour the remainder of the fluid in the basin into a waste container (like a beaker) taking care to avoid splashback contamination.
8. For the first putative to be analyzed, take 111 uL of the 4e-3 stock (see Day 2 in Lambda Microtiter Screening for Amylases) and add it to the first in a set of three tubes containing 1 mL host-medium suspension (step 2). Vortex to mix. This is Dilution A.
9. Take 111 uL of Dilution A and add to the next tube in the set. Vortex to mix. This is Dilution B.
10. Take 111 uL of Dilution B and add to the last tube in the set. Vortex to mix. This is Dilution C. You should now have three dilutions of phage, where concentrations of each differ by a factor of 10.

11. Pour the contents of Dilution C (the most dilute of the 3 samples) into the solution basin and load the multichannel pipetman.
12. Dispense 20 uL per well into the first row of the 384-well plate (12 channels×2=24 wells).
13. Expel the remaining liquid in the tips by touching the tips against the surface of the basin and pressing the RESET button on the pipetman. Lay the pipetman down in a way to prevent contamination of the tips. There is no need to change the tips at this point.
14. Empty the basin as described above.
15. Pour the contents of Dilution B into the same basin and load the multichannel pipetman.
16. Dispense 20 uL per well into the second row of the 384-well plate.
17. Perform steps 13-16 similarly to dispense Dilution A into the third row of the plate.
18. After all three dilutions have been arrayed into the first 3 rows of the plate, discard all tips and the solution basin into the biohazardous waste container.
19. Mount the pipetman with a clean set of sterile tips and open a new sterile solution basin.
20. Repeat steps 8-19 for each remaining putative hit, using remaining rows on the plate up to row O. Five putative hits can be analyzed on one 384-well plate, with the last row (row P) saved for the controls.
21. Add 0.5 uL of each control to a separate well. Use at least 2-3 separate controls, preferably covering a range of activity.
22. Incubate assay plates at 37° C. overnight in a humidified (>_95%) incubator.

Day 2
1. Pintool all breakout plates onto a host lawn with red starch using the same method described for Day 2 in Lambda Microtiter Screening for Amylases, except that a 384 position pintool is used.
2. Prepare the 2×BODIPY starch substrate buffer as follows:
   a) Calculate the total volume of 2× substrate buffer solution needed for all breakout plates at 20 uL per well (including any extra deadspace volume required by the dispenser) and measure this amount of 100 mM CAPS pH 10.4 into a vessel appropriate for the dispenser used.
   b) Retrieve enough 0.5 mg tubes of BODIPY starch to produce the required volume of 2× substrate buffer [calculated in step a) above] at a final concentration of 20-30 ug/mL.
   c) Dissolve each 0.5 mg tube in 50 uL DMSO at room temperature, protected from light, with frequent vortexing. This takes more than 15 minutes; some production lots of BODIPY starch dissolve better than others.
   d) Add 50 uL 100 mM CAPS buffer pH 10.4 to each tube and mix by vortexing.
   e) Pool the contents of all tubes and remove any undissolved aggregates by centrifuging for 1 minute at maximum speed in a microfuge.
   f) Add the supernatant to the rest of the 100 mM CAPS buffer measured in step a) above.
   g) Protect the 2× substrate buffer from light by wrapping in foil.
3. Dispense 20 uL per well into all breakout plates.
4. Wrap all plates in aluminum foil and incubate at room temperature for 2-6 hours.
5. Read each plate in the Spectrafluor with the following settings:
   a) fluorescence read (excitation filter: 485 nm; emission filter: 535 nm)
   b) plate definition: 384 well black
   c) read from the top
   d) optimal gain
   e) number of flashes: 3
6. On the resulting Excel spreadsheet, chart each putative's 3 rows in a separate graph and check for activity. Ensure that the positives controls produced signals over background.
7. For each putative that appears to have a real signal among the wells, harvest a sample from a positive well as follows:
   a) Select a positive well from a row representing the highest initial dilution.
   b) Transfer 2 uL from that well into a tube containing 500 uL SM and 50 uL CHCl3. This is referred to as the breakout stock.
   c) Store at 4° C.
8. Using methods previously described, plate about 10 uL of each breakout stock onto 150 mm NZY plates using red starch. The objective is to obtain several (at least 20) well-separated plaques from which to core isolates.

Day 3
1. Check pintooled plates for an acceptable incidence of clearings in the bacterial lawn corresponding to wells on the associated assay plate. Also check for clearings in the red starch in the positive controls and in any tested putatives. Be wary of contaminants that also form clearing zones in red starch (see below).
2. From the solid phase plates containing dilutions of breakout stocks, core several isolated plaques, each into 500 uL SM with 50 uL CHCl3. This is referred to as the isolate stock.
3. The isolate stocks can then be individually tested on BODIPY starch using methods described above. This step can be skipped if the plaque that was cored in step 2 produced a clearing zone in the red starch background. The isolate stocks were then be individually tested on BODIPY starch using methods described above. However, this step may be skipped if the plaque that was cored in step 2 produced a clearing zone in the red starch background.

Excisions
Day 1
1. In a Falcon 2059 tube, mix 200 uL OD1 XL1-Blue MRF' host, 100 uL lambda isolate stock and 1 uL ExAssist phage stock.
2. Incubate in 37° C. shaker for 15 minutes.
3. Add 3 mL NZY medium.
4. Incubate in 30° C. shaker overnight.

Day 2
1. Heat to excision tube to 70° C. for 20 minutes.
2. Centrifuge 1000×g for 10 minutes.
3. In a Falcon 2059 tube, combine 50 uL supernatant with 200 uL EXP505 OD1 host.
4. Incubate in 37° C. shaker for 15 minutes.
5. Add 300 uL SOB medium.
6. Incubate in 37 C shaker for 30-45 minutes.
7. Plate 50 uL on large $LB_{Kan50}$ plate using sterile glass beads. If the plates are "dry", extra SOB medium can be added to help disburse the cells.
8. Incubate plate at 30° C. for at least 24 hours.
9. Culture an isolate for sequencing and/or RFLP.
Growth at 30° C. reduces plasmid copy number and is used to mitigate the apparent toxicity of some amylase clones.

Contaminants that Form Clearing Zones in Red Starch

When using red starch on solid medium to assay phage for amylase activity, it is common to see contaminating colony forming units (cfu) that form clearing zones in the red starch. For pintooled plates, it is important to distinguish amylase-positive phage clones from these contaminants whenever they align with a particular well position. The source of the contaminating microbes is presumably the 2% red starch stock solution, which cannot be sterilized by autoclaving or by filtering after preparation. It is thought that they are opportunistic organisms that survive by metabolizing the red starch. In order to reduce these contaminants, use sterile technique when making 2% red starch solutions and store the stocks either at 4° C. or on ice.

Example 8

Bioinformatic Analysis

An Initial bioinformatic analysis was made with the known hyperthermophillic α-amylase sequences. FIG. 14*a* shows an alignment of the sequences some of which have been deposited at the NCBI database. This analysis revealed the potential for designing degenerate primers to PCR the entire gene minus its signal sequence (see FIG. 14*a*), yielding potentially novel full-length alpha amylases from a library.

The following libraries were screened by PCR from genomic DNA:

TABLE 6

| Library # | Name | PCR positive | Subcloned |
|---|---|---|---|
| 5 | *A. lithotropicus* | No | |
| 13 | *Pyrodictium occultum* | No | |
| 17 | *Pyrodictium* TAG11 | No | Yes |
| 113 | Deep sea enrichment | Yes | Yes |
| 170 | Deep sea enrichment | Yes | Yes |
| 198 | Archaeglobus | No | |
| 206 | *Acidianus* sp | No | |
| 453 | Mixed iceland enrich | No | |
| 455 | Mixed iceland enrich | Yes | Yes |

FIG. 14*b* shows an alignment of the identified sequences and the table below lists their relative percent identities.

The amino acid identity ranges from about 85-98% identity. Accordingly, these sequences are useful in shuffling of genes as described herein.

FIG. 14*c* shows the nucleic acid alignment of the corresponding polypeptide sequences above. Expression of these amylases in the expression vector pSE420 and the host cell line XL1-Blue showed 1703 and 1706 to have amylase activity.

Example 9

Characterization of Library 63 GP-1 Alpha Amylase pH Optimum and Specific Activity Determination In initial experiments, the SEQ ID NO: 81 from *Thermococcus* showed that it was effective in both starch liquefaction for corn wet milling and desizing for textiles. This enzyme has a pH optimum of 4.5 to 5.0. At this lower pH, it is possible to use little or no calcium which lowers overall operating costs and less byproduct formation. In addition, at this low pH, there is decreased chemical usage and ion exchange load. The industry standard *B. licheniformis* amylase is suboptimal in both thermostability and pH optimum. The 63GP-1 amylase has a higher application specific activity compared to *B. licheniformis* amylase and therefore much less enzyme is required to hydrolyze a ton of starch (as much as 20-fold less enzyme can be used).

The pH optimum for the hydrolysis of starch was determined by reacting 50 uL of the GP-1, 0.35 U/ml, with a 100 ml of 1% soluble starch solution (0.0175 U/g of starch) for 30 minutes at 95 degrees C. The reducing ends generated in the liquefied starch solution were measured by the neocupronine assay, described herein. The percent hydrolysis of cornstarch was determined by measuring the number of sugar reducing ends produced with the neocupronine assay. Seventy grams of buffer solution (pH4-7) was weighed and 100 ppm of calcium was added. Thirty grams of cornstarch was mixed into the buffer solution to form a starch slurry. The enzyme was added and the vessels sealed and incubated at 95 degrees C. for 30 minutes with an initial heating rate of six degrees C. per minute. A 1 ml sample was extracted from the reaction beakers and analyzed by the neocupronine assay. The optimum for GP-1 was between pH 4.5 and 5, while the commercial *B. licheniformis* amylase performed optimally at about pH 6.0.

TABLE 7

| | Nucleotide sequence % identity | | | | | | | | | |
|---|---|---|---|---|---|---|---|---|---|---|
| | SEQ ID NO.: 81 | pyro | Pyro 2 | thermo | therm2 | SEQ ID NO.: 75 | SEQ ID NO.: 77 | SEQ ID NO.: 83 | SEQ ID NO.: 85 | SEQ ID NO.: 79 | Clone A |
| SEQ ID NO.: 81 | 100 | 91.7 | 75.1 | 82.1 | 80.1 | 82.5 | 82.6 | 82.1 | 82.6 | 83 | 77.8 |
| pyro | | 100 | 74.8 | 82.5 | 80.5 | 82 | 82.2 | 82.9 | 82.8 | 84 | 78.5 |
| Pyro2 | | | 100 | 71.5 | 71.1 | 74 | 74.2 | 77 | 77.1 | 73 | 70.5 |
| therm | | | | 100 | 81.7 | 83.5 | 83.8 | 82.8 | 83.2 | 83.8 | 76.4 |
| therm2 | | | | | 100 | 88.9 | 88.8 | 84.1 | 84.7 | 84 | 76.3 |
| SEQ ID NO.: 75 | | | | | | 100 | 98.3 | 84.6 | 85.2 | 85.5 | 77 |
| SEQ ID NO.: 77 | | | | | | | 100 | 84.8 | 84.9 | 85.4 | 77.4 |
| SEQ ID NO.: 83 | | | | | | | | 100 | 96 | 83.3 | 78.5 |
| SEQ ID NO.: 85 | | | | | | | | | 100 | 83 | 78.1 |
| SEQ ID NO.: 79 | | | | | | | | | | 100 | 79.8 |
| Clone A | | | | | | | | | | | 100 |

Example 10

Amylase Ligation Reassembly

Nine fragments (each about 150 bp) were amplified from each of the parent clones SEQ ID NO.: 81, SEQ ID NO.: 77, SEQ ID NO.: 79, covering the whole open reading frame. The primers are provided in Table 8.

TABLE 8

|  | SEQ ID NO: |  |
|---|---|---|
| GAACACTAGTAGGAGGTAACTTATGGCAAAGTATTCCGAGCTCGAAG | 258 | SpeI |
| GAACGGTCTCATTCCGCCAGCCAGCAAGGGGATGAGCGG | 259 | BsaI |
| GAACCGTCTCAAAACACGGCCCATGCCTACGGC | 260 | BsmBI |
| GAACGTCTCACCTCGACTTCCACCCCAACGAGGTCAAG | 261 | BsmAI |
| GAACGTCTCAGGCGCTTTGACTACGTGAAGGGC | 262 | BsmAI |
| GAACGGTCTCAACAAGATGGATGAGGCCTTTG | 263 | BsaI |
| GAACCGTCTCACGATATAATCTGGAACAAGTACCTTGC | 264 | BsmBI |
| GAACCGTCTCAGAAGCACGAGCATAGTTTACTACG | 265 | BsmBI |
| GAACCGTCTCAAAGGTGGGTTTATGTGCCG | 266 | BsmBI |
| GAACGTCTCAGGAATCCAAATGGCGGATATTCCCGC | 267 | BsmAI |
| GAACGGTCTCAGTTTATCATATTGATGAGCTCC | 268 | BsaI |
| GAACCGTCTCAGAGGTAGTTGGCAGTATATTTG | 269 | BsmBI |
| GAACGTCTCACGCCAGGCATCAACGCCGATG | 270 | BsmAI |
| GAACGTCTCATTGTAGTAGAGCGGGAAGTC | 271 | BsmAI |
| GAACGGTCTCAATCGGTGTCGTGGTTTGCTAC | 272 | BsaI |
| GAACCGTCTCACTTCCACCTGCGAGGTGGTC | 273 | BsmBI |
| GAACCGTCTCACCTTCCAACCTTGCTCGAGC | 274 | BsmBI |
| TCGAGACTGACTCTCACCCAACACCGCAATAGC | 275 |  |
| GAACACTAGTAGGAGGTAACTTATGGCCAAGTACCTGGAGCTCGAAGAGG | 276 | SpeI |
| GAACGGTCTCATTCCCCCGGCGAGCAAGGGC | 277 | BsaI |
| GAACCGTCTCAAAACACCGCCCACGCCTACGG | 278 | BsmBI |
| GAACGTCTCACCTCGACTTCCACCCCAAC | 279 | BsmAI |
| GAACGTCTCAGGCGCTTCGACTACGTCAAGG | 280 | BsmAI |
| GAACGGTCTCAACAAGATGGACGCGGCCTTTGAC | 281 | BsaI |
| GAACCGTCTCACGATATAATTTGGAACAAGTACCC | 282 | BsmBI |
| GAACCGTCTCAGAAGCACCGACATAGTCTAC | 283 | BsmBI |
| GAACCGTCTCAAAGGTGGGTCTACGTTCCG | 284 | BsmBI |
| GAACGTCTCAGGAATCCATATTGCGGAGATTCCGGC | 285 | BsmAI |
| GAACGGTCTCAGTTTATCATGTTCACGAGCTC | 286 | BsaI |
| GAACCGTCTCAGAGGTAGTTGGCCGTGTACTTG | 287 | BsmBI |
| GAACGTCTCAGCCATGCGTCAACGCCGATG | 288 | BsmAI |
| GAACGTCTCATTGTAGTAGAGCGGGAAGTCG | 289 | BsmAI |
| GAACGGTCTCAATCGGTGTCGTGGTTTGCAACG | 290 | BsaI |

TABLE 8-continued

| | SEQ ID NO: | |
|---|---|---|
| GAACCGTCTCACTTCCACCGGCGAGGTGGTCGTG | 291 | BsmBI |
| GAACCGTCTCACCTTCCGGCCTTGCTCGAGCC | 292 | BsmBI |
| TCGAGACTGACTCTCAGCCCACCCCGCAGTAGCTC | 293 | |
| GAACACTAGTAGGAGGTAACTTATGGCCAAGTACTCCGAGCTGGAAGAGG | 294 | SpeI |
| GAACGGTCTCATTCCTCCCGCGAGCAAGGG | 295 | BsaI |
| GAACCGTCTCAAAACACCGCCCACGCCTATG | 296 | BsmBI |
| GAACGTCTCACCTCGACTTCCACCCGAACGAGC | 297 | BsmAI |
| GAACGTCTCAGGCGCTTCGACTACGTCAAGG | 298 | BsmAI |
| GAACGGTCTCAACAAGATGGACGAGGCCTTCG | 299 | BsaI |
| GAACCGTCTCACGATATAATCTGGAACAAG | 300 | BsmBI |
| GAACCGTCTCAGAAGCACTGACATCGTTTACTACG | 301 | BsmBI |
| GAACCGTCTCAAAGGTGGGTTTACGTTCCG | 302 | BsmBI |
| GAACGTCTCAGGAATCCATATCGCCGAAAT | 303 | BsmAI |
| GAACGGTCTCAGTTTATCATGTTTATGAGC | 304 | BsaI |
| GAACCGTCTCAGAGGTAGTTGGCCGTGTATTTAC | 305 | BsmBI |
| GAACGTCTCACGCCAGGCATCGATGCCGAT | 306 | BsmAI |
| GAACGTCTCATTGTAGTAGAGGGCGAAGTCAAAG | 307 | BsmAI |
| GAACGGTCTCAATCGGTATCGTGGTTGGCTACAAAC | 308 | BsaI |
| GAACCGTCTCACTTCCTCCGGCGAGGTTGTCATG | 309 | BsmBI |
| GAACCGTCTCACCTTCCGGCTTTGCTTGAGGC | 310 | BsmBI |
| TCGAGACTGACTCTCACCCAACACCGCAGTAGCTCC | 311 | |
| CACACAGCAGCAACCAACCTCGAGACTGACTCTCASCC | 312 | BbvI |

Conditions used for PCR were as follows: 3 min 94° C., (30 sec 94° C.; 30 sec 55° C., 30 sec 68° C.)×30 cycles, followed by 10 min 68° C. PCR products corresponding to homologous regions from the three parents were pooled (1:1:1), cut with the appropriate restriction enzyme (see Table 8), and gel-purified. Equal amounts of fragment pools were combined and ligated (16° C.; over night). The resulting 450 bp ligation products were gel purified and ligated to yield full length amylase genes. The resulting full length products were gel-purified and PCR amplified using a mixture of F1 primers SEQ ID NO.: 81, SEQ ID NO.: 77, SEQ ID NO.: 79 and primer (SEQ ID NO: 312). Conditions used for PCR were as follows: 3 min 94° C., (30 sec 94° C.; 30 sec 50° C., 60 sec 68° C.)×30 cycles, followed by 10 min 68° C. The resulting PCR products (~1.4 kbp) were purified, cut with SpeI and BbvI, gel-purified, ligated into pMYC (vector from Mycogen, cut with SpeI/XhoI), and transformed into *E. coli* Top10. Plasmid DNA from a pool of ~21000 colonies was isolated and transformed into *Pseudomonas*.

Screening of Reassembled α-Amylase

The transformed *Pseudomonas fluorescens* (MB214) containing pMYC derived from the parent clones SEQ ID NO.: 81, SEQ ID NO.: 77, SEQ ID NO.: 79 were sorted to 96- or 384-well plates by FACS and treated with 6M urea. Primary screening using RBB-starch and/or FITC-starch as substrates was carried out as described more fully below. Elevated active clones were screened using RBB-starch as substrate using induced cultures and by liquefaction assay. Stock and sequencing new elevated active clones based on liquefaction data was performed.

The transformed reassembled amylase library (MB214 (Pf)), were collected and sorted into 96-well plates (or 384-well plates) at 1 cell/well in 50 μl of LB+Tet. The plates were incubated for 24 hours at 30° C. Replicate plates were made corresponding to each well for storage. Forty-five (45) μl of 12M urea was added to each well and the plates were shaken for 10 minutes. Plates were kept at room temp for at least 1 hour and the lysate stored at 4° C.

Assay Using RBB-Starch

75 μl of RBB-starch substrate (1% RBB-insoluble corn starch in 50 mM NaAc buffer, pH=4.5) was added into each well of a new 96-well plate (V-bottom). Five micro-liters of enzyme lysate was transferred into each well with substrate using Biomek or Zymark. The plates were sealed with aluminum sealing tape and shaken briefly on the shaker. The plates were incubated at 90° C. for 30 minutes, followed by cooling at room temperature for about 5 to 10 minutes. One hundred micro-liters of 100% ethanol was added to each well, the plates sealed and shaken briefly on the shaker. The plates were then centrifuged 4000 rpm for 20 minutes using bench-top centrifuge. 100 μl of the supernatant was transferred into a new 96-well plate (flat bottom) by Biomek and read OD595. Controls: SEQ ID NO.: 81, SEQ ID NO.: 77, SEQ ID NO.: 79.

Assay Using FITC-Starch

Added 50 ㎕ of substrate (0.01% FITC-starch in 100 mM NaAc buffer, pH=4.5) into each well of a new 384-well plate. Transferred 5 ㎕ of enzyme lysate into each well with substrate and incubated the plate at room temperature overnight. The polarization change of the substrate, excitation 485 nm, emission 535 nm, was read for each well. Controls: SEQ ID NO.: 81, SEQ ID NO.: 77, SEQ ID NO.: 79. Preferably 96 well plates are used for all assays.

Confirmation of New Active Clones

Each positive clone from screening was grown and induced using a standard protocol. Each clone was examined for growth (i.e., cell density over time), activity at per cell level (RBB-starch assay and liquefaction assay), expression (protein gel) and solubility of protein (by microscope analysis). The confirmed new elevated clones were transferred for fermentation.

TABLE 3

| SEQ ID NO. | Signal Sequence |
|---|---|
| SEQ ID NO: 87 | AA1-23 (SEQ ID NO: 213) |
| SEQ ID NO: 91 | AA1-23 (SEQ ID NO: 214) |
| SEQ ID NO: 93 | AA1-33 (SEQ ID NO: 215) |
| SEQ ID NO: 97 | AA1-31 (SEQ ID NO: 216) |
| SEQ ID NO: 99 | AA1-30 (SEQ ID NO: 217) |
| SEQ ID NO: 103 | AA1-22 (SEQ ID NO: 218) |
| SEQ ID NO: 105 | AA1-33 (SEQ ID NO: 219) |
| SEQ ID NO: 109 | AA1-25 (SEQ ID NO: 220) |
| SEQ ID NO: 111 | AA1-35 (SEQ ID NO: 221) |
| SEQ ID NO: 113 | AA1-28 (SEQ ID NO: 222) |
| SEQ ID NO: 117 | AA1-21 (SEQ ID NO: 223) |
| SEQ ID NO: 119 | AA1-30 (SEQ ID NO: 224) |
| SEQ ID NO: 123 | AA1-35 (SEQ ID NO: 225) |
| SEQ ID NO: 125 | AA1-28 (SEQ ID NO: 226) |
| SEQ ID NO: 127 | AA1-30 (SEQ ID NO: 227) |
| SEQ ID NO: 131 | AA1-30 (SEQ ID NO: 228) |
| SEQ ID NO: 133 | AA1-30 (SEQ ID NO: 229) |
| SEQ ID NO: 137 | AA1-28 (SEQ ID NO: 230) |
| SEQ ID NO: 139 | AA1-23 (SEQ ID NO: 231) |
| SEQ ID NO: 141 | AA1-23 (SEQ ID NO: 232) |
| SEQ ID NO: 143 | AA1-30 (SEQ ID NO: 233) |
| SEQ ID NO: 145 | AA1-27 (SEQ ID NO: 234) |
| SEQ ID NO: 147 | AA1-29 (SEQ ID NO: 235) |
| SEQ ID NO: 149 | AA1-28 (SEQ ID NO: 236) |
| SEQ ID NO: 69 | AA1-27 (SEQ ID NO: 237) |
| SEQ ID NO: 153 | AA1-26 (SEQ ID NO: 238) |
| SEQ ID NO: 155 | AA1-33 (SEQ ID NO: 239) |
| SEQ ID NO: 157 | AA1-25 (SEQ ID NO: 240) |
| SEQ ID NO: 159 | AA1-25 (SEQ ID NO: 241) |
| SEQ ID NO: 161 | AA1-36 (SEQ ID NO: 242) |
| SEQ ID NO: 167 | AA1-36 (SEQ ID NO: 243) |
| SEQ ID NO: 169 | AA1-23 (SEQ ID NO: 244) |
| SEQ ID NO: 173 | AA1-25 (SEQ ID NO: 245) |
| SEQ ID NO: 175 | AA1-22 (SEQ ID NO: 246) |
| SEQ ID NO: 177 | AA1-23 (SEQ ID NO: 247) |
| SEQ ID NO: 179 | AA1-23 (SEQ ID NO: 248) |
| SEQ ID NO: 185 | AA1-25 (SEQ ID NO: 249) |
| SEQ ID NO: 189 | AA1-36 (SEQ ID NO: 250) |
| SEQ ID NO: 191 | AA1-25 (SEQ ID NO: 251) |
| SEQ ID NO: 193 | AA1-25 (SEQ ID NO: 252) |
| SEQ ID NO: 197 | AA1-23 (SEQ ID NO: 253) |
| SEQ ID NO: 199 | AA1-23 (SEQ ID NO: 254) |
| SEQ ID NO: 201 | AA1-30 (SEQ ID NO: 255) |
| SEQ ID NO: 203 | AA1-25 (SEQ ID NO: 256) |
| SEQ ID NO: 205 | AA1-16 (SEQ ID NO: 257) |
| SEQ ID NO.: 73 | AA1-16 (SEQ ID NO: 7) |
| SEQ ID NO.: 79 | AA1-26 (SEQ ID NO: 8) |

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US10047350B2). An electronic copy of the "Sequence Listing" will also be available from the USPTO upon request and payment of the fee set forth in 37 CFR 1.19(b)(3).

What is claimed is:

1. A variant polypeptide comprising: an amino acid sequence having at least one amino acid substitution compared to SEQ ID NO: 126 and at least 95% sequence identity to SEQ ID NO: 126; wherein the variant polypeptide has alpha-amylase activity.

2. The polypeptide of claim 1, further comprising at least one glycosylation site or wherein the polypeptide is glycosylated.

3. A composition comprising the polypeptide of claim 1.

4. The composition of claim 3, wherein the composition is a detergent, a detergent additive, a food, a food supplement, a feed supplement, or a feed.

5. The variant polypeptide of claim 1, wherein the variant is an amino acid sequence having at least one or more conservative amino acid substitutions, deletions or insertions, wherein the variant polypeptide has alpha amylase activity.

6. A method of hydrolyzing a polysaccharide or oligosaccharide having α-1,4 glucosidic linkages comprising (a) providing the polypeptide of claim 1, and (b) contacting a substance containing the polysaccharide or oligosaccharide with the polypeptide of claim 1, under conditions which facilitate the hydrolysis of the α-1,4 glucosidic linkages of the polysaccharide or oligosaccharide linkage.

7. A method for washing an object comprising
   (a) providing the polypeptide of claim 1, and
   (b) contacting said object with the polypeptide of claim 1 under conditions sufficient for said washing.

8. A method for textile desizing comprising (a) providing the polypeptide of claim 1, and (b) contacting a textile with the polypeptide of (a) under conditions effective for said desizing.

9. A method for producing a high-maltose, a high-glucose syrup or a mixed syrup comprising (a) providing the polypeptide of claim 1, and (b) liquefying starch using an effective amount of the polypeptide of (a) to obtain a soluble starch hydrolysate; and saccharifying the soluble starch hydrolysate, thereby producing a high-maltose, a high-glucose syrup or a mixed syrup.

10. A method for making ethanol comprising (a) providing the polypeptide of claim 1, (b) contacting a starch-comprising composition with the polypeptide of (a), to produce a starch hydrolysate, and (c) fermenting the starch hydrolysate of (b) to produce ethanol.

11. A method for corn wet milling comprising
(a) providing the polypeptide of claim 1, and
(b) contacting a corn or a corn starch with the polypeptide of (a) under conditions sufficient for the polypeptide to hydrolyze an oligosaccharide or a polysaccharide in the corn or corn starch.

12. A method for dry milling comprising: (a) providing the polypeptide of claim 1, and (b) contacting a whole ground grain with the polypeptide of (a), under conditions sufficient for the polypeptide to hydrolyze starch in the whole ground grain.

13. A method for liquefying or removing starch from a composition comprising: (a) providing the polypeptide of claim 1; (b) providing a composition comprising starch; and (c) contacting the composition of (b) with the polypeptide of (a), under conditions wherein the polypeptide removes or liquefies the starch.

\* \* \* \* \*